(12) United States Patent
Ammann et al.

(10) Patent No.: US 12,121,511 B2
(45) Date of Patent: Oct. 22, 2024

(54) GLP-1R MODULATING COMPOUNDS

(71) Applicant: Gilead Sciences, Inc., Foster City, CA (US)

(72) Inventors: Stephen E. Ammann, Redwood City, CA (US); Gediminas J. Brizgys, San Carlos, CA (US); James S. Cassidy, Foster City, CA (US); Elbert Chin, San Mateo, CA (US); Chienhung Chou, Dublin, CA (US); Jeromy J. Cottell, Redwood City, CA (US); Chao-I Hung, Foster City, CA (US); Kavoos Kolahdouzan, San Francisco, CA (US); Daniel G. Shore, Redwood City, CA (US); Suzanne M. Szewczyk, San Mateo, CA (US); James G. Taylor, Burlingame, CA (US); Rhiannon Thomas-Tran, San Jose, CA (US); Nathan E. Wright, Foster City, CA (US); Zheng-Yu Yang, Palo Alto, CA (US)

(73) Assignee: Gilead Sciences, Inc., Foster City, CA (US)

(*) Notice: Subject to any disclaimer, the term of this patent is extended or adjusted under 35 U.S.C. 154(b) by 76 days.

(21) Appl. No.: 17/159,485

(22) Filed: Jan. 27, 2021

(65) Prior Publication Data

US 2022/0288030 A1    Sep. 15, 2022

Related U.S. Application Data

(60) Provisional application No. 62/967,289, filed on Jan. 29, 2020.

(51) Int. Cl.
| | |
|---|---|
| *A61K 31/4184* | (2006.01) |
| *A61K 31/4192* | (2006.01) |
| *A61K 31/4196* | (2006.01) |
| *A61K 31/422* | (2006.01) |
| *A61K 31/424* | (2006.01) |
| *A61K 31/437* | (2006.01) |
| *A61K 31/4439* | (2006.01) |
| *A61K 31/444* | (2006.01) |
| *A61K 45/06* | (2006.01) |
| *C07D 405/10* | (2006.01) |
| *C07D 405/14* | (2006.01) |
| *C07D 409/14* | (2006.01) |
| *C07D 413/10* | (2006.01) |
| *C07D 471/04* | (2006.01) |
| *C07D 493/04* | (2006.01) |
| *C07D 493/10* | (2006.01) |
| *C07D 498/04* | (2006.01) |

(52) U.S. Cl.
CPC ...... *A61K 31/4184* (2013.01); *A61K 31/4192* (2013.01); *A61K 31/4196* (2013.01); *A61K 31/422* (2013.01); *A61K 31/424* (2013.01); *A61K 31/437* (2013.01); *A61K 31/4439* (2013.01); *A61K 31/444* (2013.01); *A61K 45/06* (2013.01); *C07D 405/10* (2013.01); *C07D 405/14* (2013.01); *C07D 409/14* (2013.01); *C07D 413/10* (2013.01); *C07D 471/04* (2013.01); *C07D 493/04* (2013.01); *C07D 493/10* (2013.01); *C07D 498/04* (2013.01)

(58) Field of Classification Search
None
See application file for complete search history.

(56) References Cited

U.S. PATENT DOCUMENTS

| | | |
|---|---|---|
| 7,968,576 B2 | 6/2011 | Smith |
| 8,957,073 B2 | 2/2015 | Allen |
| 10,543,212 B2 | 1/2020 | Matsunaga et al. |
| 10,954,221 B2 | 3/2021 | Zhong et al. |
| 11,702,404 B2 | 7/2023 | Ammann |
| 11,851,419 B2 | 12/2023 | Brizgys |
| 11,858,918 B2 | 1/2024 | Armstrong |
| 2017/0035881 A1 | 2/2017 | Lannutti et al. |
| 2018/0170908 A1 | 6/2018 | Aspnes et al. |
| 2020/0325121 A1 | 10/2020 | Zhong et al. |
| 2021/0023072 A1 | 1/2021 | Freeman et al. |
| 2021/0171499 A1 | 6/2021 | Ammann et al. |
| 2022/0177449 A1 | 6/2022 | Brizgys et al. |
| 2022/0298148 A1 | 9/2022 | Brizgys et al. |
| 2022/0306614 A1 | 9/2022 | Brizgys et al. |
| 2023/0021705 A1 | 1/2023 | Armstrong et al. |
| 2024/0199580 A1 | 6/2024 | Brizgys |
| 2024/0199589 A1 | 6/2024 | Armstrong |

FOREIGN PATENT DOCUMENTS

| | | |
|---|---|---|
| CN | 112409331 A | 2/2021 |
| CN | 113480534 A | 10/2021 |
| CN | 113493447 A | 10/2021 |
| CN | 113816948 A | 12/2021 |

(Continued)

OTHER PUBLICATIONS

Chemical Abstract Registry No. 2401892-81-5, indexed in the Registry File on STN CAS Online Jan. 7, 2020.*

(Continued)

*Primary Examiner* — Po-Chih Chen
(74) *Attorney, Agent, or Firm* — Mintz, Levin, Cohn, Ferris, Glovsky and Popeo, P.C.

(57) ABSTRACT

The present disclosure provides GLP-1R agonists, and compositions, methods, and kits thereof. Such compounds are generally useful for treating a GLP-1R mediated disease or condition.

39 Claims, No Drawings

(56) References Cited

FOREIGN PATENT DOCUMENTS

| | | |
|---|---|---|
| EP | 3438095 A1 | 2/2019 |
| EP | 4057055 A1 | 9/2022 |
| TW | 201904959 A | 2/2019 |
| TW | 202015683 A | 5/2020 |
| WO | WO-2000/08015 A2 | 2/2000 |
| WO | WO-2003/026587 A2 | 4/2003 |
| WO | WO-2004/099192 A2 | 11/2004 |
| WO | 2004108672 A1 | 12/2004 |
| WO | WO-2005/014543 A1 | 2/2005 |
| WO | WO-2006/055708 A2 | 5/2006 |
| WO | WO-2006/066879 A2 | 6/2006 |
| WO | WO-2007/031791 A1 | 3/2007 |
| WO | WO-2007/115077 A2 | 10/2007 |
| WO | WO-2008/033455 A2 | 3/2008 |
| WO | WO-2010/029299 A1 | 3/2010 |
| WO | WO-2010/029300 A1 | 3/2010 |
| WO | WO-2010/046780 A2 | 4/2010 |
| WO | WO-2011/163355 A1 | 12/2011 |
| WO | WO-2013/025733 A1 | 2/2013 |
| WO | WO-2013/056679 A1 | 4/2013 |
| WO | WO-2013/186229 A1 | 12/2013 |
| WO | WO-2016/018701 A1 | 2/2016 |
| WO | WO-2016/089060 A2 | 6/2016 |
| WO | WO-2016/118638 A1 | 7/2016 |
| WO | WO-2017/161028 A1 | 9/2017 |
| WO | WO-2018/109607 A1 | 6/2018 |
| WO | WO-2018/183112 A1 | 10/2018 |
| WO | WO-2019/055540 A1 | 3/2019 |
| WO | WO-2019/239319 A1 | 12/2019 |
| WO | WO-2019/239371 A1 | 12/2019 |
| WO | WO-2020/033413 A2 | 2/2020 |
| WO | WO-2020/103815 A1 | 5/2020 |
| WO | WO-2020/207474 A1 | 10/2020 |
| WO | WO-2020/263695 A1 | 12/2020 |
| WO | 2001002369 A1 | 1/2021 |
| WO | WO-2021/018023 A1 | 2/2021 |
| WO | WO-2021/018026 A1 | 2/2021 |
| WO | WO-2021/081207 A1 | 4/2021 |
| WO | WO-2021/096284 A1 | 5/2021 |
| WO | WO-2021/096304 A1 | 5/2021 |
| WO | WO-2021/112538 A1 | 6/2021 |
| WO | WO-2021/155841 A1 | 8/2021 |
| WO | WO-2021/160127 A1 | 8/2021 |
| WO | WO-2021/187886 A1 | 9/2021 |
| WO | WO-2021/191812 A1 | 9/2021 |
| WO | WO-2021/197464 A1 | 10/2021 |
| WO | WO-2021/242817 A1 | 12/2021 |
| WO | WO-2021/244645 A1 | 12/2021 |
| WO | 2022031994 A1 | 2/2022 |
| WO | WO-2022/040600 A1 | 2/2022 |
| WO | WO-2022/068772 A1 | 4/2022 |
| WO | WO-2022/078152 A1 | 4/2022 |
| WO | WO-2022/109182 A1 | 5/2022 |
| WO | WO-2022/111624 A1 | 6/2022 |
| WO | WO-2022/192428 A1 | 9/2022 |
| WO | WO-2022/192430 A1 | 9/2022 |
| WO | 2022216094 A1 | 10/2022 |
| WO | WO-2022/225914 A1 | 10/2022 |
| WO | WO-2022/225941 A1 | 10/2022 |

OTHER PUBLICATIONS

Andersen, A et al. (2018), "Glucagon-like peptide 1 in health and disease", Nat Rev Endocrinol., Jul. 14(7):390-403.

Armstrong M J et al. (2016), "Liraglutide safety and efficacy in patients with non-alcoholic steatohepatitis (LEAN): a multicentre, double-blind, randomised, placebo-controlled phase 2 study", Lancet, 387(10019):679-690.

Armstrong, M et al. (2013), "Liraglutide efficacy and action in non-alcoholic steatohepatitis (LEAN): study protocol for a phase II multicentre, double-blinded, randomised, controlled trial", BMJ Open., 3(11):e003995, pp. 1-13.

Armstrong, M J et al. (2016), "Glucagon-like peptide 1 decreases lipotoxicity in non-alcoholic steatohepatitis", Randomized Controlled Trial J Hepatol., 64(2):399-408.

Armstrong, M. J. (2017), "Glucagon-like peptide-1 analogues in nonalcoholic steatohepatitis: From bench to bedside", Review Clin Liver Dis (Hoboken), 10(2):32-35.

Ben-Shlomo, S et al. (2011), "Glucagon-like peptide-1 reduces hepatic lipogenesis via activation of AMP-activated protein kinase", J Hepatol. 54(6):1214-23.

Bernsmeier, C et al. (2014), "Glucose-Induced Glucagon-Like Peptide 1 Secretion Is Deficient in Patients with Non-Alcoholic Fatty Liver Disease", PLoS One, 9(1):e87488, 1-7.

Bueno, A B et al. (2016), "Positive Allosteric Modulation of the Glucagon-like Peptide-1 Receptor by Diverse Electrophiles", J Biol Chem, May 13, 2016; 291(20):10700-15.

Carbone L J et al. (2016), "Incretin-based therapies for the treatment of non-alcoholic fatty liver disease: A systemic review and meta-analysis", J Gastroenterol Hepatol, 31(1):23-31.

Chen D et al. (2007), "A nonpeptidic agonist of glucagon-like peptide 1 receptors with efficacy in diabetic db/db mice", Proc Natl Acad Sci USA, 104(3):943-948.

Chen, J et al. (2017), "GLP-1/GLP-1R Signaling in Regulation of Adipocyte Differentiation and Lipogenesis", Cell Physiol Biochem, 42(3):1165-1176.

Dalsgaard N B et al. (2018), "Effects of glucagon-like peptide-1 receptor agonists on cardiovascular risk factors: A narrative review of head-to-head comparisons", Diabetes Obes Metab, 20(3):508-519.

Davies, M et al. (2017), "Effect of Oral Semaglutide Compared With Placebo and Subcutaneous Semaglutide on Glycemic Control in Patients With Type 2 Diabetes: A Randomized Clinical Trial", JAMA, 318(15):1460-1470.

De Graaf C et al. (2016), "Glucagon-Like Peptide-1 and Its Class B G Protein-Coupled Receptors: A Long March to Therapeutic Successes", Pharmacol Rev., 68(4):954-1013.

Donnelly K L et al. (2005), "Sources of fatty acids stored in liver and secreted via lipoproteins in patients with nonalcoholic fatty liver disease", J Clin Invest, 115(5):1343-1351.

Edmonds, D J et al. (2013), "Oral GLP-1 Modulators for the Treatment of Diabetes", Annual Reports in Medicinal Chemistry, Chapter Nine, 48:119-130.

Eguchi Y et al. (2015), "Pilot study of liraglutide effects in non-alcoholic steatohepatitis and non-alcoholic fatty liver disease with glucose intolerance in Japanese patients (LEAN-J)", Hepatol Res, 45(3):269-278.

Gastaldelli A et al. (2016), "Exenatide improves both hepatic and adipose tissue insulin resistance: A dynamic positron emission tomography study", Hepatology, 64(6):2028-2037.

Intl. Search Report-Written Opinion dated Apr. 9, 2021 for Intl. Appl. No. PCT/US2021/015197.

Jazayeri A et al. (2017), "Crystal structure of the GLP-1 receptor bound to a peptide agonist", Nature, 546(7657):254-258.

Jones, B et al. (2018), "Targeting GLP-1 receptor trafficking to improve agonist efficacy", Nature Communications, 9:1602, pp. 1-17.

Knudsen, L B et al. (2007), "Small-molecule agonists for the glucagon-like peptide 1 receptor", Proc Natl Acad Sci USA, 104(3):937-942.

Koole C et al. (2013), "Recent advances in understanding GLP-1R (glucagon-like peptide-1 receptor) function", Biochem Soc Trans, 41(1):172-179.

Ma H et al. (2020), "Structural insights into the activation of GLP-1R by a small molecule agonist", Cell Res 30, 1140-1142.

Mendez M et al. (2019), "Design, Synthesis and Pharmacological Evaluation of Potent Positive Allosteric Modulators of the Glucagon-like Peptide-1 Receptor (GLP-1R)", J. Med. Chem., Just Accepted Manuscript, Publication Date (Web): Oct. 9, 2019.

Nauck, M A et al. (2011), "Rapid tachyphylaxis of the glucagon-like peptide 1-induced deceleration of gastric emptying in humans", Diabetes, 60(5):1561-1565.

Nauck, M A et al. (2016), "A Phase 2, Randomized, Dose-Finding Study of the Novel Once-Weekly Human GLP-1 Analog, Semaglutide,

(56) References Cited

OTHER PUBLICATIONS

Compared With Placebo and Open-Label Liraglutide in Patients With Type 2 Diabetes", Diabetes Care, 39(2):231-241.
Petit, J-M et al. (2017), "GLP-1 receptor agonists in NAFLD", Diabetes Metab., 43 Suppl 1:2S28-2S33.
Plisson F et al. (2017), "Helixconstraints and amino acid substitution in GLP-1 increase cAMP and insulin secretion but not beta-arrestin 2 signaling", Eur J Med Chem, 127:703-714.
Portillo-Sanchez P et al. (2016), "Treatment of Nonalcoholic Fatty Liver Disease (NAFLD) in patients with Type 2 Diabetes Mellitus", Clin Diabetes Endocrinol, 2:9.
Sloop K W et al. (2010), "Novel small molecule glucagon-like peptide-1 receptor agonist stimulates insulin secretion in rodents and from human islets", Diabetes, 59(12):3099-3107.
Song G et al. (2017), "Human GLP-1 receptor transmembrane domain structure in complex with allosteric modulators", Nature, 546(7657):312-315.
Svegliati-Baroni G et al. (2011), "Glucagon-like peptide-1 receptor activation stimulates hepatic lipid oxidation and restores hepatic signalling alteration induced by a high-fat diet in nonalcoholic steatohepatitis", Liver Int., 31(9):1285-1297.
Takayanagi R et al. (2018), "Evaluation of Drug Efficacy of GLP-1 Receptor Agonists and DPP-4 Inhibitors Based on Target Molecular Binding Occupancy", Biol Pharm Bull, 41(2):153-157.
Tong W et al. (2016), "Liraglutide ameliorates non-alcoholic fatty liver disease by enhancing mitochondrial architecture and promoting autophagy through the SIRT1/SIRT3-FOXO3a pathway", Hepatol Res., 46(9):933-943.
Umapathysivam M M et al. (2014), "Comparative effects of prolonged and intermittent stimulation of the glucagon-like peptide 1 receptor on gastric emptying and glycemia", Diabetes, 63(2):785-790.
Vendrell J et al. (2011), "Study of the potential association of adipose tissue GLP-1 receptor with obesity and insulin resistance", Endocrinology, 152(11):4072-4079.
Vilar-Gomez E et al. (2015), "Weight Loss Through Lifestyle Modification Significantly Reduces Features of Nonalcoholic Steatohepatitis", Gastroenterology, 149(2):367-378.e5.
Villanueva-Penacarrillo M L et al. (2001), "Effect of GLP-1 on lipid metabolism in human adipocytes", Horm Metab Res, 33(2):73-77.
VTv Therapeutics (2016), "Oral Small Molecule GLP-1 Receptor (GLP-1R) Agonists for Type 2 Diabetes (T2DM) with Negligible Nausea and Vomiting", Presentation from Keystone Symposia 2016.
Wang X-C et al. (2014), "Effects of glucagon-like peptide-1 receptor agonists on non-alcoholic fatty liver disease and inflammation", World J Gastroenterol, 20(40):14821-14830.
Wootten D et al. (2013), "Differential activation and modulation of the glucagon-like peptide-1 receptor by small molecule ligands", Mol Pharmacol, 83(4):822-834.
Wootten D et al. (2016), "A Hydrogen-Bonded Polar Network in the Core of the Glucagon-Like Peptide-1 Receptor Is a Fulcrum for Biased Agonism: Lessons from Class B Crystal Structures", Mol Pharmacol, 89(3):335-347.
Yang D et al. (2015), "Landmark studies on the glucagon subfamily of GPCRs: from small molecule modulators to a crystal structure", Acta Pharmacol Sin, 36(9):1033-42.
Office Action dated Feb. 23, 2022 for Taiwanese Appl. No. 110103228.
Intl. Preliminary Report on Patentability dated Aug. 11, 2022 for Intl. Appl. No. PCT/US2021/015197.
Notice of Allowance dated Oct. 18, 2022 for Taiwanese Appl. No. 110103228.
JP Office Action, Application No. 2022-542391, Jul. 27, 2023.
AU Examination Report 1, Application No. 2021212669, Mar. 6, 2023.
Ratziu et al., Journal of Hepatology 62:S65-S75, 2015.
N. Foloppe, Potter, Bioorganic & Medicinal Chemistry, 2006, 14, 1792-1804.

\* cited by examiner

GLP-1R MODULATING COMPOUNDS

CROSS REFERENCE TO RELATED APPLICATIONS

This application claims the benefit of U.S. Provisional Application 62/967,289 filed on Jan. 29, 2020. The entire contents of this application are incorporated herein by reference in its entirety.

FIELD

The present disclosure relates to compounds that bind to and act as agonists or modulators of the glucagon-like peptide-1 receptor (GLP-1R) and act as agonists or modulators of GLP-1R. The disclosure further relates to the use of the compounds for the treatment and/or prevention of diseases and/or conditions by said compounds.

BACKGROUND

Glucagon-like peptide-1 (GLP-1) is a peptide hormone that is secreted from the enteroendocrine cells in the gut in response to a meal. GLP-1 is believed to play a role in regulation of post-prandial glycemia, via directly augmenting meal-induced insulin secretion from the pancreatic beta-cells, as well as in promoting satiety by delaying the transit of food through the gut. GLP-1 mediates intracellular signaling via the GLP-1 receptor (GLP-1R) which belongs to a family of G-protein coupled receptors that are present on the cell membrane and can result in accumulation of the secondary messenger cyclic adenosine monophosphate (cAMP) upon activation. Non-alcoholic steatohepatitis (NASH) can be associated with features of metabolic syndrome, including obesity, type 2 diabetes, insulin resistance and cardiovascular disease.

GLP-1R agonists are currently being investigated in connection with diabetes, obesity, and NASH. GLP-1R agonists include peptides, such as exenatide, liraglutide, and dulaglutide, that have been approved for the management of type 2 diabetes. Such peptides are predominantly administered by subcutaneous injection. Oral GLP-1 agonists are also under investigation for treatment of type 2 diabetes. Some GLP-1R agonists, such as liraglutide, dulaglutide, and exenatide, are resistant to rapid degradation by dipeptidyl peptidase 4, resulting in longer half-lives than endogenous GLP-1.

There remains a need for compounds, such as agonists of GLP-1R, with desirable therapeutic properties, metabolic properties, and/or easy administration in the treatment of metabolic diseases and related diseases, including but not limited to NASH, obesity, and Type 2 diabetes.

SUMMARY

In one embodiment, the present disclosure provides a compound of Formula (I):

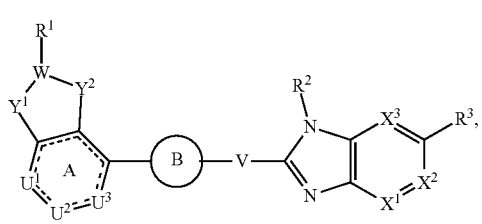

(I)

or a pharmaceutically acceptable salt thereof, wherein
$R^1$ is $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{6-10}$ aryl, heteroaryl, —C(O)N($R^{1b}$)($R^{1c}$), —C(O)$R^{1b}$, or —C(O)O$R^{1c}$, wherein the alkyl, haloalkyl, cycloalkyl, aryl, heteroaryl, or heterocyclyl is each optionally substituted with one to four $Z^1$;

ring A is an aromatic ring in which $U^1$, $U^2$, $U^3$, are each independently —C(H)═, —C($Z^{1a}$)═, or —N═;

ring B is $C_{6-10}$ aryl or heteroaryl, which is each optionally substituted with one to four $R^4$;

$R^2$ is H, $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{6-10}$ aryl, heteroaryl, —S—$R^{2a}$, —S(O)$R^{2a}$, —S(O)(NH)$R^{2a}$, —S(O)$_2R^{2a}$, —S(O)$_2$N($R^{2a}$)($R^{2b}$), or —S(O)(N$R^{2a}$)$R^{2b}$, wherein the alkyl, cycloalkyl, heterocyclyl, aryl, or heteroaryl is each optionally substituted with one to four $Z^1$;

$X^1$, $X^2$, and $X^3$ are each independently —N═, —C(H)═, or —C($R^8$)═;

$Y^1$ and $Y^2$ are each —C($R^{y1}$)($R^{y2}$)—, —N($R^{y1}$)—, —O—, —S—, —S(O)$_2$—, or —C(O)—;

W is —C($R^5$)═, or —N—, wherein when W is —N, one of $Y^1$ and $Y^2$ is —C($R^{y1}$)($R^{y2}$)— or —C(O)— and the other of $Y^1$ and $Y^2$ is —C($R^{y1}$)($R^{y2}$)—, —C(O)—, or —S(O)$_2$—;

$R^3$ is H, $C_{1-6}$ alkyl, $C_{1-6}$ haloalkyl, $C_{2-6}$ alkenyl, $C_{2-6}$ alkynyl, halogen, $C_{3-10}$ cycloalkyl, heterocyclyl, $C_{6-10}$ aryl, heteroaryl, —CN, —NO$_2$, —O$R^{3a}$, —C(O)$R^{3a}$, —C(O)O$R^{3a}$, —C(O)N($R^{3a}$)($R^{3b}$), —N($R^{3a}$)C(O)$R^{3b}$, —N($R^{3a}$)C(O)O$R^{3b}$, —N($R^{3a}$)C(O)N($R^{3b}$)$_2$, —C(O)NHS(O)$_2R^{3a}$, —C(O)N$R^{3a}$S(O)$_2R^{3b}$, —C(O)N$R^{3a}$S(O)$_2$N$R^{3b}R^{3c}$, —C(O)N$R^{3a}$—S(O)(═N$R^{3b}$)$R^{3c}$—S(O)$_2R^{3a}$, —S(O)$_2$O$R^{3a}$, —S(O)$_2$N($R^{3a}$)($R^{3b}$), —N($R^{3a}$)S(O)$_2R^{3b}$, —S(O)$_2$NHC(O)$R^{3a}$, —S(O)(═N$R^{3a}$)$R^{3b}$, —S(O)(═N$R^{3a}$)N$R^{3b}$, —S(═N$R^{3a}$)(═N$R^{3b}$)$R^{3c}$, —P(O)(O$R^{3a}$)($R^{3b}$), —P(O)(O$R^{3a}$)(O$R^{3b}$), or —B(O$R^{3a}$)(O$R^{3b}$), wherein the alkyl, haloalkyl, alkenyl, alkynyl, cycloalkyl, heterocyclyl, aryl, or heteroaryl is each optionally substituted with one to four $R^{3d}$;

each $R^{3a}$, $R^{3b}$, and $R^{3c}$ is independently H, $C_{1-6}$ alkyl, $C_{1-6}$ haloalkyl, $C_{2-8}$ alkoxyalkyl, —$C_{1-4}$ alkyl-N($R^{9a}$)($R^{9b}$), —$C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$alkyl, —$C_{1-4}$ alkyl-O—C(O)—$C_{1-4}$ alkyl-N($R^{9a}$)($R^{9b}$), —$C_{1-4}$ alkyl-$C_{3-8}$ cycloalkyl, —$C_{1-4}$ alkyl-heterocyclyl, $C_{2-6}$ alkenyl, $C_{2-6}$ alkynyl, $C_{3-10}$ cycloalkyl, heterocyclyl, $C_{6-10}$ aryl, heteroaryl, —P(O)(O$R^{9c}$)$_2$, —OP(O)(O$R^{9c}$)$_2$, —CH$_2$P(O)(O$R^{9c}$)$_2$, —OCH$_2$P(O)(O$R^{9c}$)$_2$, —C(O)OCH$_2$P(O)(O$R^{9c}$)$_2$, —P(O)($R^{9c}$)(O$R^{9d}$), —OP(O)($R^{9c}$)(O$R^{9d}$), —CH$_2$P(O)($R^{9c}$)(O$R^{9d}$), —OCH$_2$P(O)($R^{9c}$)(O$R^{9d}$), —C(O)OCH$_2$P(O)($R^{9c}$)(O$R^{9d}$), —P(O)(N($R^{9c}$)$_2$)$_2$, —OP(O)(N($R^{9c}$)$_2$)$_2$, —CH$_2$P(O)(N($R^{9c}$)$_2$)$_2$, —OCH$_2$P(O)(N($R^{9c}$)$_2$)$_2$, —C(O)OCH$_2$P(O)(N($R^{9c}$)$_2$)$_2$, —P(O)(N($R^{9c}$)$_2$)(O$R^{9d}$), —OP(O)(N($R^{9c}$)$_2$)(O$R^{9d}$), —CH$_2$P(O)(N($R^{9c}$)$_2$)(O$R^{9d}$), —OCH$_2$P(O)(N($R^{9c}$)$_2$)(O$R^{9d}$), —C(O)OCH$_2$P(O)(N($R^{9c}$)$_2$)(O$R^{9d}$), —P(O)($R^{9c}$)(N($R^{9d}$)$_2$), —OP(O)($R^{9c}$)(N($R^{9d}$)$_2$), —CH$_2$P(O)($R^{9c}$)(N($R^{9d}$)$_2$), —OCH$_2$P(O)($R^{9c}$)(N($R^{9d}$)$_2$), or —C(O)OCH$_2$P(O)($R^{9c}$)(N($R^{9d}$)$_2$);

wherein the alkyl, alkenyl, cycloalkyl, heterocyclyl, aryl, or heteroaryl is each optionally substituted with one to four $Z^{1b}$, each $R^4$ is independently $C_{1-9}$ alkyl, $C_{1-8}$ haloalkyl, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —CN, —$N_3$, —O—$R^{4a}$, —C(O)$R^{4a}$, —C(O)O—$R^{4a}$, —C(O)N($R^{4a}$)($R^{4b}$), —N($R^{4a}$)($R^{4b}$), —N($R^{4a}$)$_2$($R^{4b}$)$^+$, —N($R^{4a}$)—C(O)$R^{4b}$, —N($R^{4a}$)C(O)O($R^{4b}$), —N($R^{4a}$)C(O)N($R^{4b}$)($R^{4c}$), —N($R^{4a}$)S(O)$_2$($R^{4b}$), —N($R^{4a}$)S(O)$_2$—N($R^{4b}$)($R^{4c}$), —N($R^{4a}$)S(O)$_2$O($R^{4b}$), —OC(O)$R^{4a}$, —OC(O)O$R^{4a}$, —OC(O)—N($R^{4a}$)($R^{4b}$), —S—$R^{4a}$, —S(O)$R^{4a}$, —S(O)(NH)$R^{4a}$, —S(O)$_2$$R^{4a}$, —S(O)$_2$N($R^{4a}$)($R^{4b}$), —S(O)(N$R^{4a}$)$R^{4b}$, or —Si($R^{4a}$)$_3$;

wherein the alkyl, haloalkyl, alkenyl, alkynyl, cycloalkyl, heterocyclyl, aryl, or heteroaryl is each optionally substituted with one to four $Z^{1b}$;

or two $R^4$ groups attached to adjacent ring atoms are combined with the atoms to which they are attached to form a $C_{5-10}$ cycloalkyl or heterocyclyl, which is each optionally substituted with one to four $Z^{1b}$;

$R^5$ is H, cyclopropyl, or $C_{1-3}$alkyl, wherein the $C_{1-3}$alkyl is optionally substituted with one, two or three groups selected from halogen, —OH, —OCH$_3$, —CN, oxo, and —N($R^{x1}$)($R^{x2}$);

or $R^5$ and $R^{y1}$ are combined with the atoms to which they are attached to form a $C_{3-10}$ cycloalkyl or heterocyclyl optionally substituted with oxo;

$R^{x1}$ and $R^{x2}$ are each independently H, $C_{1-6}$ alkyl, $C_{3-10}$ cycloalkyl, heterocyclyl, —S(O)$_2$$R^{6a1}$, or —S(O)$_2$N($R^{6a1}$)(N$R^{6a2}$), wherein the $C_{1-6}$ alkyl, cycloalkyl or heterocyclyl is each optionally substituted with F, —CN, oxo, or $C_{3-6}$ cycloalkyl;

or $R^{x1}$ and $R^{x2}$ are combined with the atom to which they are attached to form a heterocyclyl, which is optionally substituted with one to four $R^{6b1}$;

V is —C(O)—, —O—, —N($R^{6a}$)—, or —C($R^{6b}$)($R^{6c}$)—;

$R^{6a}$ is H, $C_{1-6}$ alkyl, $C_{3-10}$ cycloalkyl, heterocyclyl, —S(O)$_2$$R^{6a1}$, or —S(O)$_2$N($R^{6a1}$)(N$R^{6a2}$), wherein the cycloalkyl or heterocyclyl is each optionally substituted with $C_{1-6}$ alkyl, F, or —CN;

each $R^{6b}$ and $R^{6c}$ is independently H, $C_{1-6}$ alkyl, $C_{1-6}$ haloalkyl, $C_{2-6}$ alkoxyalkyl, halogen, $C_{3-10}$ cycloalkyl, heterocyclyl, —$C_{1-6}$ alkyl-N($R^{9a}$)($R^{9b}$), —CN, —O$R^{6c1}$, or —N($R^{6c2}$)($R^{6c3}$), wherein the alkyl, cycloalkyl, or heterocyclyl is each optionally substituted with one to four $R^{6b1}$;

or $R^{6b}$ and $R^{6c}$ are combined with the atom to which they are attached to form $C_{3-10}$ cycloalkyl or heterocyclyl, which is each optionally substituted with one to four $R^{6b1}$;

or $R^{6a}$ or $R^{6c}$ is combined with one $R^4$ group and the atoms to which they are attached to form a $C_{5-10}$ cycloalkyl or heterocyclyl, which is each optionally substituted with one to four $R^{10}$;

each $R^{y1}$ and $R^{y2}$ is independently H, halo, $C_{1-6}$ alkyl, $C_{1-6}$ haloalkyl, wherein the alkyl and haloalkyl are each optionally substituted with oxo;

each $R^{3d}$, $R^{6b1}$, and $R^{10}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —OH, —CN, —$NO_2$, or —C(O)N($R^{2a}$)($R^{2b}$), wherein the heterocyclyl or heteroaryl is optionally substituted with $C_{1-6}$ alkyl, $C_{1-6}$ haloalkyl, or $C_{1-6}$ haloalkoxy; and each $R^{6a1}$, $R^{6a2}$, $R^{6c1}$, $R^{6c2}$, and $R^{6c3}$ is independently H, $C_{1-6}$ alkyl or $C_{3-10}$ cycloalkyl;

each $R^{9a}$ and $R^{9b}$ is independently H, $C_{1-6}$ alkyl, or $C_{1-6}$ haloalkyl;

each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —$N_3$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —N$R^{12a}$S(O)$_2$N($R^{12b}$)($R^{12c}$), —N$R^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$$R^{12a}$, —S(O)$_2$N($R^{12a}$)($R^{12b}$), —S(O)(N$R^{12a}$)$R^{12b}$, or —Si($R^{12a}$)$_3$;

wherein the alkyl, haloalkyl, alkenyl, alkynyl, cycloalkyl, heterocyclyl, aryl, or heteroaryl is each optionally substituted with one to four $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —CN, —$N_3$, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$)$^+$, —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$$R^{12a}$, —S(O)$_2$N($R^{12a}$)($R^{12b}$), —S(O)(N$R^{12a}$)$R^{12b}$, or —Si($R^{12a}$)$_3$;

wherein the alkyl, haloalkyl, alkenyl, alkynyl, cycloalkyl, heterocyclyl, aryl, or heteroaryl is each optionally substituted with one to four $Z^{1b}$;

each $R^8$ or $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)

(heterocyclyl), —NHC(O)(C$_{6-10}$ aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkenyl), —NHC(O)O (C$_{2-6}$ alkynyl), —NHC(O)O(C$_{3-15}$ cycloalkyl), —NHC (O)O(heterocyclyl), —NHC(O)O(C$_{6-10}$ aryl), —NHC (O)O(heteroaryl), —NHC(O)NH(C$_{1-9}$ alkyl), —NHC (O)NH(C$_{1-8}$ haloalkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(heterocyclyl), —NHC(O) NH(C$_{6-10}$ aryl), —NHC(O)NH(heteroaryl), —NHS(O) (C$_{1-9}$ alkyl), —N(C$_{1-9}$ alkyl)(S(O)(C$_{1-9}$ alkyl), —S(C$_{1-9}$ alkyl), —S(C$_{1-8}$ haloalkyl), —S(C$_{2-6}$ alkenyl), —S(C$_{2-6}$ alkynyl), —S(C$_{3-15}$ cycloalkyl), —S(heterocyclyl), —S(C$_{6-10}$ aryl), —S(heteroaryl), —S(O)N(C$_{1-9}$ alkyl)$_2$, —S(O)(C$_{1-9}$ alkyl), —S(O)(C$_{1-8}$ haloalkyl), —S(O)(C$_{2-6}$ alkenyl), —S(O)(C$_{2-6}$ alkynyl), —S(O)(C$_{3-15}$ cycloalkyl), —S(O)(heterocyclyl), —S(O)(C$_{6-10}$ aryl), —S(O)(heteroaryl), —S(O)$_2$(C$_{1-9}$ alkyl), —S(O)$_2$(C$_{1-8}$ haloalkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(heterocyclyl), —S(O)$_2$(C$_{6-10}$ aryl), —S(O)$_2$ (heteroaryl), —S(O)(NH)(C$_{1-9}$ alkyl), —S(O)$_2$NH (C$_{1-9}$ alkyl), or —S(O)$_2$N(C$_{1-9}$ alkyl)$_2$;
  wherein the alkyl, cycloalkyl, heterocyclyl, aryl, or heteroaryl in each instance is optionally substituted with one to three C$_{1-9}$ alkyl, C$_{1-8}$ haloalkyl, halogen, —OH, —NH$_2$, —O(C$_{1-9}$ alkyl), —O(C$_{1-8}$ haloalkyl), —O(C$_{3-15}$ cycloalkyl), —O(heterocyclyl), —O(aryl), —O(heteroaryl), —NH(C$_{1-9}$ alkyl), —NH(C$_{1-8}$ haloalkyl), —NH(C$_{3-15}$ cycloalkyl), —NH(heterocyclyl), —NH(aryl), —NH(heteroaryl), —N(C$_{1-9}$ alkyl)$_2$, —N(C$_{3-5}$ cycloalkyl)$_2$, —NHC(O)(C$_{1-8}$ haloalkyl), —NHC(O)(C$_{3-15}$ cycloalkyl), —NHC(O)(heterocyclyl), —NHC(O) (aryl), —NHC(O)(heteroaryl), —NHC(O)O(C$_{1-9}$ alkyl), —NHC(O)O(C$_{1-8}$ haloalkyl), —NHC(O)O (C$_{2-6}$ alkynyl), —NHC(O)O(C$_{3-15}$ cycloalkyl), —NHC(O)O(heterocyclyl), —NHC(O)O(aryl), —NHC(O)O(heteroaryl), —NHC(O)NH(C$_{1-9}$ alkyl), S(O)$_2$(C$_{1-9}$ alkyl), —S(O)$_2$(C$_{1-8}$ haloalkyl), —S(O)$_2$(C$_{3-15}$ cycloalkyl), —S(O)$_2$(heterocyclyl), —S(O)$_2$(aryl), —S(O)$_2$(heteroaryl), —S(O)(NH) (C$_{1-9}$ alkyl), —S(O)$_2$NH(C$_{1-9}$ alkyl), or —S(O)$_2$N (C$_{1-9}$ alkyl)$_2$; and
each R$^{1b}$, R$^{1c}$, R$^{2a}$, R$^{2b}$, R$^{4a}$, R$^{4b}$, R$^{4c}$, R$^{9c}$, R$^{9d}$, R$^{12a}$, R$^{12b}$, and R$^{12c}$ is independently H, C$_{1-9}$ alkyl, C$_{2-6}$ alkenyl, C$_{2-6}$ alkynyl, C$_{3-15}$ cycloalkyl, heterocyclyl, C$_{6-10}$ aryl, or heteroaryl wherein the alkyl, alkenyl, alkynyl, cycloalkyl, heterocyclyl, aryl, or heteroaryl is each optionally substituted with one to four Z$^{1b}$;
wherein each heteroaryl has 5 to 12 ring members and has one to four heteroatoms each independently N, O, or S; and
wherein each heterocyclyl has 3 to 12 ring members and has one to four heteroatoms each independently N, O, or S.

The present disclosure further provides pharmaceutical compositions, methods, and uses comprising the compound of Formula (I) or pharmaceutically acceptable salts thereof. For example, the compounds of the present disclosure are generally useful in a method of treating a GLP-1R-mediated disease or condition.

DETAILED DESCRIPTION

I. Definitions

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning. A prefix such as "C$_{u-v}$" or "C$_u$-C$_v$" indicates that the following group has from u to v carbon atoms, where u and v are integers. For example, "C$_{1-6}$ alkyl" or "C$_1$-C$_6$ alkyl" indicates that the alkyl group has from 1 to 6 carbon atoms.

"Alkyl" is a monovalent or divalent linear or branched saturated hydrocarbon radical. For example, an alkyl group can have 1 to 10 carbon atoms (i.e., C$_{1-10}$ alkyl) or 1 to 8 carbon atoms (i. e., C$_{1-8}$ alkyl) or 1 to 6 carbon atoms (i. e., C$_{1-6}$ alkyl) or 1 to 4 carbon atoms (i.e., C$_{1-4}$ alkyl). Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$) CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$) CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$) CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), 3,3-dimethyl-2-butyl (—CH(CH$_3$)C (CH$_3$)$_3$, and octyl (—(CH$_2$)$_7$CH$_3$). Alkyl groups can be unsubstituted or substituted.

"Alkoxy" refers to the group —O-alkyl, where alkyl is as defined above. For example, C$_{1-4}$ alkoxy refers to an —O-alkyl group having 1 to 4 carbons. Alkoxy groups can be unsubstituted or substituted.

"Alkoxyalkyl" is an alkoxy group attached to an alkyl as defined above, such that the alkyl is divalent. For example, C$_{2-6}$ alkoxyalkyl includes —CH$_2$—OMe, —CH$_2$—O-iPr, —CH$_2$—CH$_2$—OMe, —CH$_2$—CH$_2$—O—CH$_2$—CH$_3$, and —CH$_2$—CH$_2$—O-tBu. Alkoxyalkyl groups can be unsubstituted or substituted.

"Alkenyl" is a monovalent or divalent linear or branched hydrocarbon radical with at least one carbon-carbon double bond. For example, an alkenyl group can have 2 to 8 carbon atoms (i. e., C$_{2-8}$ alkenyl) or 2 to 6 carbon atoms (i. e., C$_{2-6}$ alkenyl) or 2 to 4 carbon atoms (i. e., C$_{2-4}$ alkenyl). Examples of alkenyl groups include, but are not limited to, ethenyl (—CH=CH$_2$), allyl (—CH$_2$CH=CH$_2$), and —CH$_2$—CH=CH—CH$_3$. Alkenyl groups can be unsubstituted or substituted.

"Alkynyl" is a monovalent or divalent linear or branched hydrocarbon radical with at least one carbon-carbon triple bond. For example, an alkynyl group can have 2 to 8 carbon atoms (i. e., C$_{2-8}$ alkynyl) or 2 to 6 carbon atoms (i. e., C$_{2-6}$ alkynyl) or 2 to 4 carbon atoms (i. e., C$_{2-4}$ alkynyl). Examples of alkynyl groups include, but are not limited to, acetylenyl (—C≡CH), propargyl (—CH$_2$C≡CH), and —CH$_2$—C≡C—CH$_3$. Alkynyl groups can be unsubstituted or substituted.

"Halogen" refers to fluoro (—F), chloro (—Cl), bromo (—Br) and iodo (—I).

"Haloalkyl" is an alkyl as defined herein, wherein one or more hydrogen atoms of the alkyl are independently replaced by a halogen, which may be the same or different, such that the alkyl is divalent. The alkyl group and the halogen can be any of those described above. In some embodiments, the haloalkyl defines the number of carbon atoms in the alkyl portion, e.g., $C_{1-4}$ haloalkyl includes $CF_3$, $CH_2F$, $CHF_2$, $CH_2CF_3$, $CH_2CH_2CF_3$, $CCl_2CH_2CH_2CH_3$, and $C(CH_3)_2(CF_2H)$. Haloalkyl groups can be unsubstituted or substituted.

"Haloalkoxy" is an alkoxy as defined herein, wherein one or more hydrogen atoms of the alkyl in the alkyoxy are independently replaced by a halogen, which may be the same or different, such that the alkyl is divalent. The alkoxy group and the halogen can be any of those described above. In some embodiments, the haloalkoxy defines the number of carbon atoms in the alkyl portion, e.g., $C_{1-4}$ haloalkoxy includes $OCF_3$, $OCH_2F$, $OCH_2CF_3$, $OCH_2CH_2CF_3$, $OCCl_2CH_2CH_2CH_3$, and $OC(CH_3)_2(CF_2H)$. Haloalkoxy groups can be unsubstituted or substituted.

"Cycloalkyl" is a monovalent or divalent single all carbon ring or a multiple condensed all carbon ring system wherein the ring in each instance is a non-aromatic saturated or unsaturated ring. For example, in some embodiments, a cycloalkyl group has 3 to 12 carbon atoms, 3 to 10 carbon atoms, 3 to 8 carbon atoms, 3 to 6 carbon atoms, 3 to 5 carbon atoms, or 3 to 4 carbon atoms. Exemplary single ring cycloalkyl groups include cyclopropyl, cyclobutyl, cyclopentyl, cyclohexyl, cyclohexenyl, cycloheptyl, cycloheptenyl, and cyclooctyl. Cycloalkyl also includes multiple condensed ring systems (e.g., ring systems comprising 2 rings) having about 7 to 12 carbon atoms. The rings of the multiple condensed ring system can be connected to each other via fused, spiro, or bridged bonds when allowed by valency requirements. Exemplary multiple ring cycloalkyl groups include octahydropentalene, bicyclo[2. 2. 1]heptane, bicyclo[2. 2. 2]octane, bicyclo[2. 2. 2]oct-2-ene, and spiro[2. 5]octane. Cycloalkyl groups can be unsubstituted or substituted.

"Alkylcycloalkyl" refers to an alkyl as defined herein, wherein one or more hydrogen atoms of the alkyl are independently replaced by a cycloalkyl group, which may be the same or different. The alkyl group and the cycloalkyl group can be any of those described above. In some embodiments, the number of carbon atoms in the alkyl and cycloalkyl portion can be designated separately, e.g., $C_{1-6}$ alkyl-$C_{3-12}$ cycloalkyl. Alkylcycloalkyl groups can be unsubstituted or substituted.

"Aryl" as used herein refers to a monovalent or divalent single all carbon aromatic ring or a multiple condensed all carbon ring system wherein the ring is aromatic. For example, in some embodiments, an aryl group has 6 to 20 carbon atoms, 6 to 14 carbon atoms, 6 to 12 carbon atoms, or 6 to 10 carbon atoms. Aryl includes a phenyl radical. Aryl also includes multiple condensed ring systems (e.g., ring systems comprising 2, 3 or 4 rings) having about 9 to 20 carbon atoms in which multiple rings are aromatic. The rings of the multiple condensed ring system can be connected to each other via fused bonds when allowed by valency requirements. It is also understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl. Non-limiting examples of aryl groups include, but are not limited to, phenyl, naphthyl, anthracenyl, and the like. Aryl groups can be unsubstituted or substituted.

"Alkylaryl" refers to an alkyl as defined herein, wherein one or more hydrogen atoms of the alkyl are independently replaced by an aryl group, which may be the same or different. The alkyl group and the aryl group can be any of those described above, such that the alkyl is divalent. In some embodiments, an alkylaryl group has 7 to 24 carbon atoms, 7 to 16 carbon atoms, 7 to 13 carbon atoms, or 7 to 11 carbon atoms. An alkylaryl group defined by the number of carbon atoms refers to the total number of carbon atoms present in the constitutive alkyl and aryl groups combined. For example, $C_7$ alkylaryl refers to benzyl, while $C_{11}$ alkylaryl includes 1-methylnaphthyl and n-pentylphenyl. In some embodiments the number of carbon atoms in the alkyl and aryl portion can be designated separately, e.g., $C_{1-6}$ alkyl-$C_{6-10}$ aryl. Non-limiting examples of alkylaryl groups include, but are not limited to, benzyl, 2,2-dimethylphenyl, n-pentylphenyl, 1-methylnaphthyl, 2-ethylnaphthyl, and the like. Alkylaryl groups can be unsubstituted or substituted.

"Heterocyclyl" or "heterocycle" or "heterocycloalkyl" as used herein refers to a single saturated or partially unsaturated non-aromatic ring or a non-aromatic multiple ring system that has at least one heteroatom in the ring (i. e., at least one annular (i.e., ring-shaped) heteroatom selected from oxygen, nitrogen, and sulfur). Unless otherwise specified, a heterocyclyl group has from 3 to about 20 annular atoms, for example from 3 to 12 annular atoms, for example from 4 to 12 annular atoms, 4 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring (e.g. bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3. 3]heptan-6-yl, 6-oxa-1-azaspiro[3. 3]heptan-1-yl, 2-thia-6-azaspiro[3. 3]heptan-6-yl, 2,6-diazaspiro[3. 3]heptan-2-yl, 2-azabicyclo[3. 1. 0]hexan-2-yl, 3-azabicyclo[3. 1. 0]hexanyl, 2-azabicyclo[2. 1. 1]hexanyl, 2-azabicyclo[2. 2. 1]heptan-2-yl, 4-azaspiro[2. 4]heptanyl, 5-azaspiro[2. 4]heptanyl, and the like. Heterocyclyl groups can be unsubstituted or substituted.

"Alkylheterocyclyl" refers to an alkyl as defined herein, wherein one or more hydrogen atoms of the alkyl are independently replaced by a heterocyclyl group, which may be the same or different. The alkyl group and the heterocyclyl group can be any of those described above, such that the alkyl is divalent. In some embodiments, the number of atoms in the alkyl and heterocyclyl portion can be designated separately, e.g., $C_{1-6}$ alkyl-3 to 12 membered heterocyclyl having one to three heteroatoms each independently N, O, or S. Alkylheterocyclyl groups can be unsubstituted or substituted.

"Heteroaryl" refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl) and aryls (to form, for example, benzimidazolyl or indazolyl) to form the multiple condensed ring system. Thus, a heteroaryl (a single aromatic ring or multiple condensed ring system) can have about 1-20 carbon atoms and about 1-6 heteroatoms within the heteroaryl ring. For example, tetrazolyl has 1 carbon atom and 4 nitrogen heteroatoms within the ring. The rings of the multiple condensed ring system can be connected to each other via fused bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. It is also to be understood that the rings of the multiple condensed ring system may include an aryl ring fused to a heterocyclic ring with saturated or partially unsaturated bonds (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. For example, a 5-membered heteroaryl includes thiazolyl and a 10-membered heteroaryl includes quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, benzofuranyl, benzimidazolyl, thianaphthenyl, pyrrolo[2,3-b]pyridinyl, quinazolinyl-4 (3H)-one, triazolyl, and tetrazolyl. Heteroaryl groups can be unsubstituted or substituted.

"Alkylheteroaryl" refers to an alkyl as defined herein, wherein one or more hydrogen atoms of the alkyl are independently replaced by a heteroaryl group, which may be the same or different, such that the alkyl is divalent. The alkyl group and the heteroaryl group can be any of those described above. In some embodiments, the number of atoms in the alkyl and heteroaryl portion are designated separately, e.g., $C_{1-6}$ alkyl-5 to 10 membered heteroaryl having one to four heteroatoms each independently N, O, or S. Alkylheteroaryl groups can be unsubstituted or substituted.

"Oxo" as used herein refers to =O.

"Substituted" as used herein refers to wherein one or more hydrogen atoms of the group are independently replaced by one or more substituents (e.g., 1, 2, 3, or 4 or more) as indicated.

A "compound of the present disclosure" includes compounds disclosed herein, for example a compound of the present disclosure includes compounds of Formula (I), (Ia), (Ib), (Ic), (Id), (Ie), and (If) including the compounds of the Examples.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Therapeutically effective amount" or "effective amount" as used herein refers to an amount that is effective to elicit the desired biological or medical response, including the amount of a compound that, when administered to a subject for treating a disease, is sufficient to affect such treatment for the disease. The effective amount will vary depending on the compound, the disease, and its severity and the age, weight, etc., of the subject to be treated. The effective amount can include a range of amounts. As is understood in the art, an effective amount may be in one or more doses, i. e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the subject.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds described herein may be prepared and/or formulated as pharmaceutically acceptable salts or when appropriate as a free base. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Wiliams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $N(C_1-C_4 \text{ alkyl})_4^+$. Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium. In some embodiments, a compound of formula (I), (Ia), (Ib), (Ic), (Id), (Ie), or (If) includes one or more deuterium atoms.

Examples of isotopes that can be incorporated into the disclosed compounds also include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$ respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I) can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

"Stereoisomer" as used herein refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

"Tautomer" as used herein refers to a proton shift from one atom of a molecule to another atom of the same molecule. In some embodiments, the present disclosure includes tautomers of said compounds.

"Solvate" as used herein refers to the result of the interaction of a solvent and a compound. Solvates of salts of the compounds described herein are also provided. Hydrates of the compounds described herein are also provided.

"Hydrate" as used herein refers to a compound of the disclosure that is chemically associated with one or more molecules of water.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Prodrug" as used herein refers to a derivative of a drug that upon administration to the human body is converted to the parent drug according to some chemical or enzymatic pathway. In some embodiments, a prodrug is a biologically inactive derivative of a drug that upon administration to the human body is converted to the biologically active parent drug according to some chemical or enzymatic pathway.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

"At risk individual" as used herein refers to an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

II. Compounds

In some embodiments, the compound of the present disclosure is a compound of Formula (I):

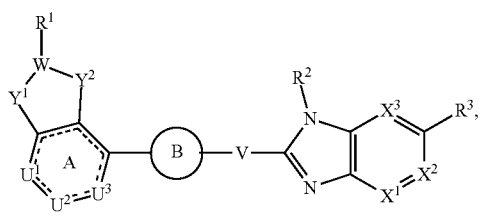

(I)

or other formula described herein,
or a pharmaceutically acceptable salt thereof, wherein
$R^1$ is $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{1-10}$ aryl, heteroaryl, —C(O)N($R^{1b}$)($R^{1c}$), —C(O)$R^{1b}$, or —C(O)O$R^{1c}$,
  wherein the alkyl, haloalkyl, cycloalkyl, aryl, heteroaryl, or heterocyclyl is each optionally substituted with one to four $Z^1$;
ring A is an aromatic ring in which $U^1$, $U^2$, $U^3$, are each independently —C(H)═, —C($Z^{1a}$)═, or —N═;
ring B is $C_{6-10}$ aryl or heteroaryl, which is each optionally substituted with one to four $R^4$;
$R^2$ is H, $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{6-10}$ aryl, heteroaryl, —S—$R^{2a}$, —S(O)$R^{2a}$, —S(O)(NH)$R^{2a}$, —S(O)$_2R^{2a}$, —S(O)$_2$N($R^{2a}$)($R^{2b}$), or —S(O)(N$R^{2a}$)$R^{2b}$,
  wherein the alkyl, cycloalkyl, heterocyclyl, aryl, or heteroaryl is each optionally substituted with one to four $Z^1$;
$X^1$, $X^2$, and $X^3$ are each independently —N═, —C(H)═, or —C($R^8$)═;

$Y^1$ and $Y^2$ are each —C($R^{y1}$)($R^{y2}$)—, —N($R^{y1}$)—, —O—, —S—, —S(O)$_2$—, or —C(O)—;
W is —C($R^5$)—, or —N—,
  wherein when W is —N, one of $Y^1$ and $Y^2$ is —C($R^{y1}$)($R^{y2}$)— or —C(O)— and the other of $Y^1$ and $Y^2$ is —C($R^{y1}$)($R^{y2}$)—, —C(O)—, or —S(O)$_2$—;
$R^3$ is H, $C_{1-6}$ alkyl, $C_{1-6}$ haloalkyl, $C_{2-6}$ alkenyl, $C_{2-6}$ alkynyl, halogen, $C_{3-10}$ cycloalkyl, heterocyclyl, $C_{6-10}$ aryl, heteroaryl, —CN, —NO$_2$, —O$R^{3a}$, —C(O)$R^{3a}$, —C(O)O$R^{3a}$, —C(O)N($R^{3a}$)($R^{3b}$), —N($R^{3a}$)C(O)$R^{3b}$, —N($R^{3a}$)C(O)O$R^{3b}$, —N($R^{3a}$)C(O)N($R^{3b}$)$_2$, —C(O)NHS(O)$_2R^{3a}$, —C(O)N$R^{3a}$S(O)$_2R^{3b}$, —C(O)N$R^{3a}$S(O)$_2$N$R^{3b}R^{3c}$, —C(O)N$R^{3a}$—S(O)(═N$R^{3b}$)$R^{3c}$—S(O)$_2R^{3a}$, —S(O)$_2$O$R^{3a}$, —S(O)$_2$N($R^{3a}$)($R^{3b}$), —N($R^{3a}$)S(O)$_2R^{3b}$, —S(O)$_2$NHC(O)$R^{3a}$, —S(O)(═N$R^{3a}$)$R^{3b}$, —S(O)(═N$R^{3a}$)N$R^{3b}$, —S(═N$R^{3a}$)(═N$R^{3b}$)$R^{3c}$, —P(O)(O$R^{3a}$)($R^{3b}$), —P(O)(O$R^{3a}$)(O$R^{3b}$), or —B(O$R^{3a}$)(O$R^{3b}$), wherein the alkyl, haloalkyl, alkenyl, alkynyl, cycloalkyl, heterocyclyl, aryl, or heteroaryl is each optionally substituted with one to four $R^{3d}$;
each $R^{3a}$, $R^{3b}$, and $R^{3c}$ is independently H, $C_{1-6}$ alkyl, $C_{1-6}$ haloalkyl, $C_{2-8}$ alkoxyalkyl, —$C_{1-4}$ alkyl-N($R^{9a}$)($R^{9b}$), —$C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$alkyl, —$C_{1-4}$ alkyl-O—C(O)—$C_{1-4}$ alkyl-N($R^{9a}$)($R^{9b}$), —$C_{1-4}$ alkyl-$C_{3-8}$ cycloalkyl, —$C_{1-4}$ alkyl-heterocyclyl, $C_{2-6}$ alkenyl, $C_{2-6}$ alkynyl, $C_{3-10}$ cycloalkyl, heterocyclyl, $C_{6-10}$ aryl, heteroaryl, —P(O)(O$R^{9c}$)$_2$, —OP(O)(O$R^{9c}$)$_2$, —CH$_2$P(O)(O$R^{9c}$)$_2$, —OCH$_2$P(O)(O$R^{9c}$)$_2$, —C(O)OCH$_2$P(O)(O$R^{9c}$)$_2$, —P(O)($R^{9c}$)(O$R^{9d}$), —OP(O)($R^{9c}$)(O$R^{9d}$), —CH$_2$P(O)($R^{9c}$)(O$R^{9d}$), —OCH$_2$P(O)($R^{9c}$)(O$R^{9d}$), —C(O)OCH$_2$P(O)($R^{9c}$)(O$R^{9d}$), —P(O)(N($R^{9c}$)$_2$)$_2$, —OP(O)(N($R^{9c}$)$_2$)$_2$, —CH$_2$P(O)(N($R^{9c}$)$_2$)$_2$, —OCH$_2$P(O)(N($R^{9c}$)$_2$)$_2$, —C(O)OCH$_2$P(O)(N($R^{9c}$)$_2$)$_2$, —P(O)(N($R^{9c}$)$_2$)(O$R^{9d}$), —OP(O)(N($R^{9c}$)$_2$)(O$R^{9d}$), —CH$_2$P(O)(N($R^{9c}$)$_2$)(O$R^{9d}$), —OCH$_2$P(O)(N($R^{9c}$)$_2$)(O$R^{9d}$), —C(O)OCH$_2$P(O)(N($R^{9c}$)$_2$)(O$R^{9d}$), —P(O)($R^{9c}$)(N($R^9$)$_2$), —OP(O)($R^{9c}$)(N($R^{9d}$)$_2$), —CH$_2$P(O)($R^{9c}$)(N($R^{9d}$)$_2$), —OCH$_2$P(O)($R^{9c}$)(N($R^9$)$_2$), or —C(O)OCH$_2$P(O)($R^{9c}$)(N($R^{9d}$)$_2$);
  wherein the alkyl, alkenyl, cycloalkyl, heterocyclyl, aryl, or heteroaryl is each optionally substituted with one to four $Z^{1b}$,
each $R^4$ is independently $C_{1-9}$ alkyl, $C_{1-8}$ haloalkyl, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—$R^{4a}$, —C(O)$R^{4a}$, —C(O)O—$R^{4a}$, —C(O)N($R^{4a}$)($R^{4b}$), —N($R^{4a}$)($R^{4b}$), —N($R^{4a}$)$_2$($R^{4b}$)$^+$, —N($R^{4a}$)—C(O)$R^{4b}$, —N($R^{4a}$)C(O)O($R^{4b}$), —N($R^{4a}$)C(O)N($R^{4b}$)($R^{4c}$), —N($R^{4a}$)S(O)$_2$($R^{4b}$), —N($R^{4a}$)S(O)$_2$—N($R^{4b}$)($R^{4c}$), —N($R^{4a}$)S(O)$_2$O($R^{4b}$), —OC(O)$R^{4a}$, —OC(O)O$R^{4a}$, —OC(O)—N($R^{4a}$)($R^{4b}$), —S—$R^{4a}$, —S(O)$R^{4a}$, —S(O)(NH)$R^{4a}$, —S(O)$_2R^{4a}$, —S(O)$_2$N($R^{4a}$)($R^{4b}$), —S(O)(N$R^{4a}$)$R^{4b}$, or —Si($R^{4a}$)$_3$;
  wherein the alkyl, haloalkyl, alkenyl, alkynyl, cycloalkyl, heterocyclyl, aryl, or heteroaryl is each optionally substituted with one to four $Z^{1b}$;
or two $R^4$ groups attached to adjacent ring atoms are combined with the atoms to which they are attached to form a $C_{5-10}$ cycloalkyl or heterocyclyl, which is each optionally substituted with one to four $Z^{1b}$;
$R^5$ is H, cyclopropyl, or $C_{1-3}$alkyl, wherein the $C_{1-3}$alkyl is optionally substituted with one, two or three groups selected from halogen, —OH, —OCH$_3$, —CN, oxo, and —N($R^{x1}$)($R^{x2}$);

or $R^5$ and $R^{y1}$ are combined with the atoms to which they are attached to form a $C_{3-10}$ cycloalkyl or heterocyclyl optionally substituted with oxo;

$R^{x1}$ and $R^{x2}$ are each independently H, $C_{1-6}$ alkyl, $C_{3-10}$ cycloalkyl, heterocyclyl, —S(O)$_2$R$^{6a1}$, or —S(O)$_2$N(R$^{6a1}$)(NR$^{6a2}$), wherein the $C_{1-6}$ alkyl, cycloalkyl or heterocyclyl is each optionally substituted with F, —CN, oxo, or $C_{3-6}$ cycloalkyl;

or $R^{x1}$ and $R^{x2}$ are combined with the atom to which they are attached to form a heterocyclyl, which is optionally substituted with one to four $R^{6b1}$;

V is —C(O)—, —O—, —N(R$^{6a}$)—, or —C(R$^{6b}$)(R$^{6c}$)—;

$R^{6a}$ is H, $C_{1-6}$ alkyl, $C_{3-10}$ cycloalkyl, heterocyclyl, —S(O)$_2$R$^{6a1}$, or —S(O)$_2$N(R$^{6a1}$)(NR$^{6a2}$), wherein the cycloalkyl or heterocyclyl is each optionally substituted with $C_{1-6}$ alkyl, F, or —CN;

each $R^{6b}$ and $R^{6c}$ is independently H, $C_{1-6}$ alkyl, $C_{1-6}$ haloalkyl, $C_{2-6}$ alkoxyalkyl, halogen, $C_{3-10}$ cycloalkyl, heterocyclyl, —C$_{1-6}$ alkyl-N(R$^{9a}$)(R$^{9b}$), —CN, —OR$^{6c1}$, or —N(R$^{6c2}$)(R$^{6c3}$), wherein the alkyl, cycloalkyl, or heterocyclyl is each optionally substituted with one to four $R^{6b1}$;

or $R^{6b}$ and $R^{6c}$ are combined with the atom to which they are attached to form $C_{3-10}$ cycloalkyl or heterocyclyl, which is each optionally substituted with one to four $R^{6b1}$;

or $R^{6a}$ or $R^{6c}$ is combined with one $R^4$ group and the atoms to which they are attached to form a $C_{5-10}$ cycloalkyl or heterocyclyl, which is each optionally substituted with one to four $R^{10}$;

each $R^{y1}$ and $R^{y2}$ is independently H, halo, $C_{1-6}$ alkyl, $C_{1-6}$ haloalkyl, wherein the alkyl and haloalkyl are each optionally substituted with oxo;

each $R^{3d}$, $R^{6b1}$, and $R^{10}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —OH, —CN, —NO$_2$, or —C(O)N(R$^{2a}$)(R$^{2b}$), wherein the heterocyclyl or heteroaryl is optionally substituted with $C_{1-6}$ alkyl, $C_{1-6}$ haloalkyl, or $C_{1-6}$ haloalkoxy; and each $R^{6a1}$, $R^{6a2}$, $R^{6c1}$, $R^{6c2}$, and $R^{6c3}$ is independently H, $C_{1-6}$ alkyl or $C_{3-10}$ cycloalkyl;

each $R^{9a}$ and $R^{9b}$ is independently H, $C_{1-6}$ alkyl, or $C_{1-6}$ haloalkyl;

each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —N$_3$, —CN, —O—R$^{12a}$, —C(O)—R$^{12a}$, —C(O)O—R$^{12a}$, —C(O)—N(R$^{12a}$)(R$^{12b}$), —N(R$^{12a}$)(R$^{12b}$), —N(R$^{12a}$)$_2$(R$^{12b}$)$^+$, —N(R$^{12a}$)C(O)—R$^{12b}$, —N(R$^{12a}$)C(O)O—R$^{12b}$, —N(R$^{12a}$)C(O)N(R$^{12b}$)(R$^{12c}$), —N(R$^{12a}$)S(O)$_2$(R$^{12b}$), —NR$^{12a}$S(O)$_2$N(R$^{12b}$)(R$^{12c}$), —NR$^{12a}$S(O)$_2$O(R$^{12b}$), —OC(O)R$^{12a}$, —OC(O)OR$^{12a}$, —OC(O)—N(R$^{12a}$)(R$^{12b}$), —R$^{12a}$, —S(O)R$^{12a}$, —S(O)(NH)R$^{12a}$, —S(O)$_2$R$^{12a}$, —S(O)$_2$N(R$^{12a}$)(R$^{12b}$), —S(O)(NR$^{12a}$)R$^{12b}$, or —Si(R$^{12a}$)$_3$;

wherein the alkyl, haloalkyl, alkenyl, alkynyl, cycloalkyl, heterocyclyl, aryl, or heteroaryl is each optionally substituted with one to four $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—R$^{12a}$, —C(O)R$^{12a}$, —C(O)O—R$^{12a}$, —C(O)N(R$^{12a}$)(R$^{12b}$), —N(R$^{12a}$)(R$^{12b}$), —N(R$^{12a}$)$_2$(R$^{12b}$)$^+$, —N(R$^{12a}$)—C(O)R$^{12b}$, —N(R$^{12a}$)C(O)O(R$^{12b}$), —N(R$^{12a}$)C(O)N(R$^{12b}$)(R$^{12c}$), —N(R$^{12a}$)S(O)$_2$(R$^{12b}$), —N(R$^{12a}$)S(O)$_2$—N(R$^{12b}$)(R$^{12c}$), —N(R$^{12a}$)S(O)$_2$O(R$^{12b}$), —OC(O)R$^{12a}$, —OC(O)OR$^{12a}$, —OC(O)—N(R$^{12a}$)(R$^{12b}$), —S—R$^{12a}$, —S(O)R$^{12a}$, —S(O)(NH)R$^{12a}$, —S(O)$_2$R$^{12a}$, —S(O)$_2$N(R$^{12a}$)(R$^{12b}$), —S(O)(NR$^{12a}$)R$^{12b}$, or —Si(R$^{12a}$)$_3$;

wherein the alkyl, haloalkyl, alkenyl, alkynyl, cycloalkyl, heterocyclyl, aryl, or heteroaryl is each optionally substituted with one to four $Z^{1b}$;

each $R^8$ or $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —NO$_2$, —NH$_2$, —N$_3$, —SH, —O(C$_{1-9}$ alkyl), —O(C$_{1-8}$ haloalkyl), —O(C$_{2-6}$ alkenyl), —O(C$_{2-6}$ alkynyl), —O(C$_{3-15}$ cycloalkyl), —O(heterocyclyl), —O(C$_{6-10}$ aryl), —O(heteroaryl), —NH(C$_{1-9}$ alkyl), —NH(C$_{1-8}$ haloalkyl), —NH(C$_{2-6}$ alkenyl), —NH(C$_{2-6}$ alkynyl), —NH(C$_{3-15}$ cycloalkyl), —NH(heterocyclyl), —NH(C$_{6-10}$ aryl), —NH(heteroaryl), —N(C$_{1-9}$ alkyl)$_2$, —N(C$_{1-8}$ haloalkyl)$_2$, —N(C$_{2-6}$ alkenyl)$_2$, —N(C$_{2-6}$ alkynyl)$_2$, —N(C$_{3-15}$ cycloalkyl)$_2$, —N(heterocyclyl)$_2$, —N(C$_{6-10}$ aryl)$_2$, —N(heteroaryl)$_2$, —N(C$_{1-9}$ alkyl)(C$_{1-8}$ haloalkyl), —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(heterocyclyl), —N(C$_{1-9}$ alkyl)(C$_{6-10}$ aryl), —N(C$_{1-9}$ alkyl)(heteroaryl), —C(O)(C$_{1-9}$ alkyl), —C(O)(C$_{1-8}$ haloalkyl), —C(O)(C$_{2-6}$ alkenyl), —C(O)(C$_{2-6}$ alkynyl), —C(O)(C$_{3-15}$ cycloalkyl), —C(O)(heterocyclyl), —C(O)(C$_{6-10}$ aryl), —C(O)(heteroaryl), —C(O)O(C$_{1-9}$ alkyl), —C(O)O(C$_{1-8}$ haloalkyl), —C(O)O(C$_{2-6}$ alkenyl), —C(O)O(C$_{2-6}$ alkynyl), —C(O)O(C$_{3-15}$ cycloalkyl), —C(O)O(heterocyclyl), —C(O)O(C$_{6-10}$ aryl), —C(O)O(heteroaryl), —C(O)NH$_2$, —C(O)NH(C$_{1-9}$ alkyl), —C(O)NH(C$_{1-8}$ haloalkyl), —C(O)NH(C$_{2-6}$ alkenyl), —C(O)NH(C$_{2-6}$ alkynyl), —C(O)NH(C$_{3-15}$ cycloalkyl), —C(O)NH(heterocyclyl), —C(O)NH(C$_{6-10}$ aryl), —C(O)NH(heteroaryl), —C(O)N(C$_{1-9}$ alkyl)$_2$, —C(O)N(C$_{1-8}$ haloalkyl)$_2$, —C(O)N(C$_{2-6}$ alkenyl)$_2$, —C(O)N(C$_{2-6}$ alkynyl)$_2$, —C(O)N(C$_{3-5}$ cycloalkyl)$_2$, —C(O)N(heterocyclyl)$_2$, —C(O)N(C$_{6-10}$ aryl)$_2$, —C(O)N(heteroaryl)$_2$, —NHC(O)(C$_{1-9}$ alkyl), —NHC(O)(C$_{1-8}$ haloalkyl), —NHC(O)(C$_{2-6}$ alkenyl), —NHC(O)(C$_{2-6}$ alkynyl), —NHC(O)(C$_{3-15}$ cycloalkyl), —NHC(O)(heterocyclyl), —NHC(O)(C$_{6-10}$ aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(heterocyclyl), —NHC(O)O(C$_{6-10}$ aryl), —NHC(O)O(heteroaryl), —NHC(O)NH(C$_{1-9}$ alkyl), —NHC(O)NH(C$_{1-8}$ haloalkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(heterocyclyl), —NHC(O)NH(C$_{6-10}$ aryl), —NHC(O)NH(heteroaryl), —NHS(O)(C$_{1-9}$ alkyl), —N(C$_{1-9}$ alkyl)(S(O)(C$_{1-9}$ alkyl), —S(C$_{1-9}$ alkyl), —S(C$_{1-8}$ haloalkyl), —S(C$_{2-6}$ alkenyl), —S(C$_{2-6}$ alkynyl), —S(C$_{3-15}$ cycloalkyl), —S(heterocyclyl), —S(C$_{6-10}$ aryl), —S(heteroaryl), —S(O)N(C$_{1-9}$ alkyl)$_2$, —S(O)(C$_{1-9}$ alkyl), —S(O)(C$_{1-8}$ haloalkyl), —S(O)(C$_{2-6}$ alkenyl), —S(O)(C$_{2-6}$ alkynyl), —S(O)(C$_{3-15}$ cycloalkyl), —S(O)(heterocyclyl), —S(O)(C$_{6-10}$ aryl), —S(O)(heteroaryl), —S(O)$_2$(C$_{1-9}$ alkyl), —S(O)$_2$(C$_{1-8}$ haloalkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(heterocyclyl), —S(O)$_2$(C$_{6-10}$ aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$;

wherein the alkyl, cycloalkyl, heterocyclyl, aryl, or heteroaryl in each instance is optionally substituted with one to three $C_{1-9}$ alkyl, $C_{1-8}$ haloalkyl, halogen, —OH, —NH$_2$, —O(C$_{1-9}$ alkyl), —O(C$_{1-8}$ haloalkyl), —O(C$_{3-15}$ cycloalkyl), —O(heterocyclyl), —O(aryl), —O(heteroaryl), —NH(C$_{1-9}$ alkyl), —NH(C$_{1-8}$ haloalkyl), —NH(C$_{3-15}$ cycloalkyl), —NH(heterocyclyl), —NH(aryl), —NH(heteroaryl), —N(C$_{1-9}$ alkyl)$_2$, —N(C$_{3-15}$ cycloalkyl)$_2$, —NHC(O)(C$_{1-8}$ haloalkyl), —NHC(O)(C$_{3-15}$ cycloalkyl), —NHC(O)(heterocyclyl), —NHC(O)(aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkynyl), —NHC(O)O(C$_{3-15}$ cycloalkyl), —NHC(O)O(heterocyclyl), —NHC(O)O(aryl), —NHC(O)O(heteroaryl), —NHC(O)NH(C$_{1-9}$ alkyl), S(O)$_2$(C$_{1-9}$ alkyl), —S(O)$_2$(C$_{1-8}$ haloalkyl), —S(O)$_2$(C$_{3-15}$ cycloalkyl), —S(O)$_2$(heterocyclyl), —S(O)$_2$(aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$; and each $R^{1b}$, $R^{1c}$, $R^{2a}$, $R^{2b}$, $R^{4a}$, $R^{4b}$, $R^{4c}$, $R^{9c}$, $R^{9d}$, $R^{12a}$, $R^{12b}$, and $R^{12c}$ is independently H, C$_{1-9}$ alkyl, C$_{2-6}$ alkenyl, C$_{2-6}$ alkynyl, C$_{3-15}$ cycloalkyl, heterocyclyl, C$_{6-10}$ aryl, or heteroaryl wherein the alkyl, alkenyl, alkynyl, cycloalkyl, heterocyclyl, aryl, or heteroaryl is each optionally substituted with one to four $Z^{1b}$;

wherein each heteroaryl has 5 to 12 ring members and has one to four heteroatoms each independently N, O, or S; and wherein each heterocyclyl has 3 to 12 ring members and has one to four heteroatoms each independently N, O, or S.

In some embodiments, the compound of the present disclosure is a compound of Formula (Ia):

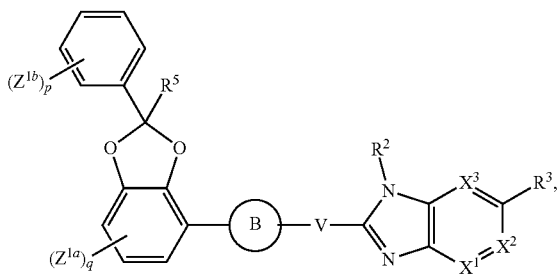

(Ia)

or a pharmaceutically acceptable salt thereof, wherein
ring B is C$_{6-10}$ aryl or heteroaryl, which is each optionally substituted with one to four $R^4$.

$R^2$ is H, C$_{1-6}$ alkyl, C$_{1-6}$ haloalkyl, C$_{2-6}$ alkenyl, C$_{2-6}$ alkynyl, C$_{3-10}$ cycloalkyl, heterocyclyl, C$_{6-10}$ aryl, heteroaryl, —S—R$^{2a}$, —S(O)R$^{2a}$, —S(O)(NH)R$^{2a}$, —S(O)$_2$R$^{2a}$, —S(O)$_2$N(R$^{2a}$)(R$^{2b}$), or —S(O)(NR$^{2a}$)R$^{2b}$, wherein the alkyl, cycloalkyl, heterocyclyl, aryl, or heteroaryl is each optionally substituted with one to four $Z^1$;

$X^1$, $X^2$, and $X^3$ are each independently —N=, —C(H)=, or —C(R$^8$)=;

$R^3$ is H, C$_{1-6}$ alkyl, C$_{1-6}$ haloalkyl, C$_{2-6}$ alkenyl, C$_{2-6}$ alkynyl, halogen, C$_{3-10}$ cycloalkyl, heterocyclyl, C$_{6-10}$ aryl, heteroaryl, —CN, —NO$_2$, —OR$^{3a}$, —C(O)R$^{3a}$, —C(O)OR$^{3a}$, —C(O)N(R$^{3a}$)(R$^{3b}$), —N(R$^{3a}$)C(O)R$^{3b}$, —N(R$^{3a}$)C(O)OR$^{3b}$, —N(R$^{3a}$)C(O)N(R$^{3b}$)$_2$, —C(O)NHS(O)$_2$R$^{3a}$, —C(O)NR$^{3a}$S(O)$_2$R$^{3b}$, —C(O)NR$^{3a}$S(O)$_2$NR$^{3b}$R$^{3c}$, —C(O)NR$^{3a}$—S(O)(=NR$^{3b}$)R$^{3c}$—S(O)$_2$R$^{3a}$, —S(O)$_2$OR$^{3a}$, —S(O)$_2$N(R$^{3a}$)(R$^{3b}$), —N(R$^{3a}$)S(O)$_2$R$^{3b}$, —S(O)$_2$NHC(O)R$^{3a}$, —S(O)(=NR$^{3a}$)R$^{3b}$, —S(O)(=NR$^{3a}$)NR$^{3b}$, —S(=NR$^{3a}$)(=NR$^{3b}$)R$^{3c}$, —P(O)(OR$^{3a}$)(R$^{3b}$), —P(O)(OR$^{3a}$)(OR$^{3b}$), or —B(OR$^{3a}$)(OR$^{3b}$), wherein the alkyl, haloalkyl, alkenyl, alkynyl, cycloalkyl, heterocyclyl, aryl, or heteroaryl is each optionally substituted with one to four $R^{3d}$;

each $R^{3a}$, $R^{3b}$, and $R^{3c}$ is independently H, C$_{1-6}$ alkyl, C$_{1-6}$ haloalkyl, C$_{2-8}$ alkoxyalkyl, —C$_{1-4}$ alkyl-N(R$^{9a}$)(R$^{9b}$), —C$_{1-4}$ alkyl-C(O)N(R$^{9a}$)(R$^{9b}$), —C$_{1-4}$ alkyl-O—C(O)—C$_{1-4}$ alkyl, —C$_{1-4}$ alkyl-O—C(O)—O—C$_{1-4}$alkyl, —C$_{1-4}$ alkyl-O—C(O)—C$_{1-4}$ alkyl-N(R$^{9a}$)(R$^{9b}$), —C$_{1-4}$ alkyl-C$_{3-8}$ cycloalkyl, —C$_{1-4}$ alkyl-heterocyclyl, C$_{2-6}$ alkenyl, C$_{2-6}$ alkynyl, C$_{3-10}$ cycloalkyl, heterocyclyl, C$_{6-10}$ aryl, heteroaryl, —P(O)(OR$^{9c}$)$_2$, —OP(O)(OR$^{9c}$)$_2$, —CH$_2$P(O)(OR$^{9c}$)$_2$, —OCH$_2$P(O)(OR$^{9c}$)$_2$, —C(O)OCH$_2$P(O)(OR$^{9c}$)$_2$, —P(O)(R$^{9c}$)(OR$^{9d}$), —OP(O)(R$^{9c}$)(OR$^{9d}$), —CH$_2$P(O)(R$^{9c}$)(OR$^{9d}$), —OCH$_2$P(O)(R$^{9c}$)(OR$^{9d}$), —C(O)OCH$_2$P(O)(R$^{9c}$)(OR$^{9d}$), —P(O)(N(R$^{9c}$)$_2$)$_2$, —OP(O)(N(R$^{9c}$)$_2$)$_2$, —CH$_2$P(O)(N(R$^{9c}$)$_2$)$_2$, —OCH$_2$P(O)(N(R$^{9c}$)$_2$)$_2$, —C(O)OCH$_2$P(O)(N(R$^{9c}$)$_2$)$_2$, —P(O)(N(R$^{9c}$)$_2$)(OR$^{9d}$), —OP(O)(N(R$^{9c}$)$_2$)(OR$^{9d}$), —CH$_2$P(O)(N(R$^{9c}$)$_2$)(OR$^{9d}$), —OCH$_2$P(O)(N(R$^{9c}$)$_2$)(OR$^{9d}$), —C(O)OCH$_2$P(O)(N(R$^{9c}$)$_2$)(OR$^{9d}$), —P(O)(R$^{9c}$)(N(R$^{9d}$)$_2$), —OP(O)(R$^{9c}$)(N(R$^{9d}$)$_2$), —CH$_2$P(O)(R$^{9c}$)(N(R$^{9d}$)$_2$), —OCH$_2$P(O)(R$^{9c}$)(N(R$^{9d}$)$_2$), or —C(O)OCH$_2$P(O)(R$^{9c}$)(N(R$^{9d}$)$_2$);

wherein the alkyl, alkenyl, cycloalkyl, heterocyclyl, aryl, or heteroaryl is each optionally substituted with one to four $Z^{1b}$, each $R^4$ is independently C$_{1-9}$ alkyl, C$_{1-8}$ haloalkyl, C$_{1-6}$ haloalkoxy, C$_{2-6}$ alkoxyalkyl, C$_{2-6}$ alkenyl, C$_{2-6}$ alkynyl, halogen, C$_{3-15}$ cycloalkyl, heterocyclyl, C$_{6-10}$ aryl, heteroaryl, oxo, —NO$_2$, —CN, —N$_3$, —O—R$^{4a}$, —C(O)R$^{4a}$, —C(O)O—R$^{4a}$, —C(O)N(R$^{4a}$)(R$^{4b}$), —N(R$^{4a}$)(R$^{4b}$), —N(R$^{4a}$)$_2$(R$^{4b}$)$^+$, —N(R$^{4a}$)—C(O)R$^{4b}$, —N(R$^{4a}$)C(O)O(R$^{4b}$), —N(R$^{4a}$)C(O)N(R$^{4b}$)(R$^{4c}$), —N(R$^{4a}$)S(O)$_2$(R$^{4b}$), —N(R$^{4a}$)S(O)$_2$—N(R$^{4b}$)(R$^{4c}$), —N(R$^{4a}$)S(O)$_2$O(R$^{4b}$), —OC(O)R$^{4a}$, —OC(O)OR$^{4a}$, —OC(O)—N(R$^{4a}$)(R$^{4b}$), —S—R$^{4a}$, —S(O)R$^{4a}$, —S(O)(NH)R$^{4a}$, —S(O)$_2$R$^{4a}$, —S(O)$_2$N(R$^{4a}$)(R$^{4b}$), —S(O)(NR$^{4a}$)R$^{4b}$, or —Si(R$^{4a}$)$_3$;

wherein the alkyl, haloalkyl, alkenyl, alkynyl, cycloalkyl, heterocyclyl, aryl, or heteroaryl is each optionally substituted with one to four $Z^{1b}$;

or two $R^4$ groups attached to adjacent ring atoms are combined with the atoms to which they are attached to form a C$_{5-10}$ cycloalkyl or heterocyclyl, which is each optionally substituted with one to four $Z^{1b}$;

$R^5$ is H, cyclopropyl, or C$_{1-3}$alkyl, wherein the C$_{1-3}$alkyl is optionally substituted with one, two or three groups selected from halogen, —OH, —OCH$_3$, —CN, oxo, and —N(R$^{x1}$)(R$^{x2}$);

or $R^5$ and R$^{y1}$ are combined with the atoms to which they are attached to form a C$_{3-10}$ cycloalkyl or heterocyclyl optionally substituted with oxo;

$R^{x1}$ and $R^{x2}$ are each independently H, C$_{1-6}$ alkyl, C$_{3-10}$ cycloalkyl, heterocyclyl, —S(O)$_2$R$^{6a1}$, or —S(O)$_2$N(R$^{6a1}$)(NR$^{6a2}$), wherein the C$_{1-6}$ alkyl, cycloalkyl or heterocyclyl is each optionally substituted with F, —CN, oxo, or C$_{3-6}$ cycloalkyl;

or R$^{x1}$ and R$^{x2}$ are combined with the atom to which they are attached to form a heterocyclyl, which is optionally substituted with one to four R$^{6b1}$;

V is —C(O)—, —O—, —N(R$^{6a}$)—, or —C(R$^{6b}$)(R$^{6c}$)—;

R$^{6a}$ is H, C$_{1-6}$ alkyl, C$_{3-10}$ cycloalkyl, heterocyclyl, —S(O)$_2$R$^{6a1}$, or —S(O)$_2$N(R$^{6a1}$)(NR$^{6a2}$), wherein the cycloalkyl or heterocyclyl is each optionally substituted with C$_{1-6}$ alkyl, F, or —CN;

each $R^{6b}$ and $R^{6c}$ is independently H, $C_{1-6}$ alkyl, $C_{1-6}$ haloalkyl, $C_{2-6}$ alkoxyalkyl, halogen, $C_{3-10}$ cycloalkyl, heterocyclyl, —$C_{1-6}$ alkyl-N($R^{9a}$)($R^{9b}$), —CN, —O$R^{6c1}$, or —N($R^{6c2}$)($R^{6c3}$), wherein the alkyl, cycloalkyl, or heterocyclyl is each optionally substituted with one to four $R^{6b1}$;

or $R^{6b}$ and $R^{6c}$ are combined with the atom to which they are attached to form $C_{3-10}$ cycloalkyl or heterocyclyl, which is each optionally substituted with one to four $R^{6b1}$;

or $R^{6a}$ or $R^{6c}$ is combined with one $R^4$ group and the atoms to which they are attached to form a $C_{5-10}$ cycloalkyl or heterocyclyl, which is each optionally substituted with one to four $R^{10}$;

each $R^{y1}$ and $R^{y2}$ is independently H, halo, $C_{1-6}$ alkyl, $C_{1-6}$ haloalkyl, wherein the alkyl and haloalkyl are each optionally substituted with oxo;

each $R^{3d}$, $R^{6b1}$, and $R^{10}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —OH, —CN, —NO$_2$, or —C(O)N($R^{2a}$)($R^{2b}$), wherein the heterocyclyl or heteroaryl is optionally substituted with $C_{1-6}$ alkyl, $C_{1-6}$ haloalkyl, or $C_{1-6}$ haloalkoxy; and each $R^{6a1}$, $R^{6a2}$, $R^{6c1}$, $R^{6c2}$, and $R^{6c3}$ is independently H, $C_{1-6}$ alkyl or $C_{3-15}$ cycloalkyl;

each $R^{9a}$ and $R^{9b}$ is independently H, $C_{1-6}$ alkyl, or $C_{1-6}$ haloalkyl;

each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —N$_3$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —N$R^{12a}$S(O)$_2$N($R^{12b}$)($R^{12c}$), —N$R^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$$R^{12a}$, —S(O)$_2$N($R^{12a}$)($R^{12b}$), —S(O)(N$R^{12a}$)$R^{12b}$, or —Si($R^{12a}$)$_3$;

wherein the alkyl, haloalkyl, alkenyl, alkynyl, cycloalkyl, heterocyclyl, aryl, or heteroaryl is each optionally substituted with one to four $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$)$^+$, —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$$R^{12a}$, —S(O)$_2$N($R^{12a}$)($R^{12b}$), —S(O)(N$R^{12a}$)$R^{12b}$, or —Si($R^{12a}$)$_3$;

wherein the alkyl, haloalkyl, alkenyl, alkynyl, cycloalkyl, heterocyclyl, aryl, or heteroaryl is each optionally substituted with one to four $Z^{1b}$;

each $R^8$ or $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —NO$_2$, —NH$_2$, —N$_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein the alkyl, cycloalkyl, heterocyclyl, aryl, or heteroaryl in each instance is optionally substituted with one to three $C_{1-9}$ alkyl, $C_{1-8}$ haloalkyl, halogen, —OH, —NH$_2$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$; and each $R^{1b}$, $R^{1c}$, $R^{2a}$, $R^{2b}$, $R^{4a}$, $R^{4b}$, $R^{4c}$, $R^{9c}$, $R^{9d}$, $R^{12a}$, $R^{12b}$, and $R^{12c}$ is independently H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl wherein the alkyl, alkenyl, alkynyl, cycloalkyl, heterocyclyl, aryl, or heteroaryl is each optionally substituted with one to four $Z^{1b}$;

subscript p is 1, 2, or 3; and subscript q is 0, 1, or 2;

wherein each heteroaryl has 5 to 12 ring members and has one to four heteroatoms each independently N, O, or S; and wherein each heterocyclyl has 3 to 12 ring members and has one to four heteroatoms each independently N, O, or S.

In some embodiments, the compound of the present disclosure is a compound of Formula (Ib):

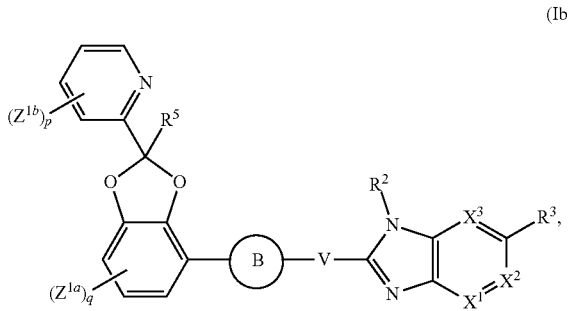

(Ib)

or a pharmaceutically acceptable salt thereof, wherein ring B is $C_{6-10}$ aryl or heteroaryl, which is each optionally substituted with one to four $R^4$.

$R^2$ is H, $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{6-10}$ aryl, heteroaryl, —S—$R^{2a}$, —S(O)$R^{2a}$, —S(O)(NH)$R^{2a}$, —S(O)$_2R^{2a}$, —S(O)$_2$N($R^{2a}$)($R^{2b}$), or —S(O)(N$R^{2a}$)$R^{2b}$, wherein the alkyl, cycloalkyl, heterocyclyl, aryl, or heteroaryl is each optionally substituted with one to four $Z^1$;

$X^1$, $X^2$, and $X^3$ are each independently —N=, —C(H)=, or —C($R^8$)=;

$Y^1$ and $Y^2$ are each —C($R^{y1}$)($R^{y2}$)—, —N($R^{y1}$)—, —O—, —S—, —S(O)$_2$—, or —C(O)—;

$R^3$ is H, $C_{1-6}$ alkyl, $C_{1-6}$ haloalkyl, $C_{2-6}$ alkenyl, $C_{2-6}$ alkynyl, halogen, $C_{3-10}$ cycloalkyl, heterocyclyl, $C_{6-10}$ aryl, heteroaryl, —CN, —NO$_2$, —O$R^{3a}$, —C(O)$R^{3a}$, —C(O)O$R^{3a}$, —C(O)N($R^{3a}$)($R^{3b}$), —N($R^{3a}$)C(O)$R^{3b}$, —N($R^{3a}$)C(O)O$R^{3b}$, —N($R^{3a}$)C(O)N($R^{3b}$)$_2$, —C(O)NHS(O)$_2R^{3a}$, —C(O)N$R^{3a}$S(O)$_2R^{3b}$, —C(O)N$R^{3a}$S(O)$_2$N$R^{3b}R^{3c}$, —C(O)N$R^{3a}$—S(O)(=N$R^{3b}$)$R^{3c}$—S(O)$_2R^{3a}$, —S(O)$_2$O$R^{3a}$, —S(O)$_2$N($R^{3a}$)($R^{3b}$), —N($R^{3a}$)S(O)$_2R^{3b}$, —S(O)$_2$NHC(O)$R^{3a}$, —S(O)(=N$R^{3a}$)$R^{3b}$, —S(O)(=N$R^{3a}$)N$R^{3b}$, —S(=N$R^{3a}$)(=N$R^{3b}$)$R^{3c}$, —P(O)(O$R^{3a}$)($R^{3b}$), —P(O)(O$R^{3a}$)(O$R^{3b}$), or —B(O$R^{3a}$)(O$R^{3b}$), wherein the alkyl, haloalkyl, alkenyl, alkynyl, cycloalkyl, heterocyclyl, aryl, or heteroaryl is each optionally substituted with one to four $R^{3d}$;

each $R^{3a}$, $R^{3b}$, and $R^{3c}$ is independently H, $C_{1-6}$ alkyl, $C_{1-6}$ haloalkyl, $C_{2-8}$ alkoxyalkyl, —$C_{1-4}$ alkyl-N($R^{9a}$)($R^{9b}$), —$C_{1-4}$ alkyl-C(O)N($R^{9a}$)($R^{9b}$), —$C_{1-4}$ alkyl-O—C(O)—$C_{1-4}$alkyl, —$C_{1-4}$ alkyl-O—C(O)—O—$C_{1-4}$alkyl, —$C_{1-4}$ alkyl-O—C(O)—$C_{1-4}$ alkyl-N($R^{9a}$)($R^{9b}$), —$C_{1-4}$ alkyl-$C_{3-8}$ cycloalkyl, —$C_{1-4}$ alkyl-heterocyclyl, $C_{2-6}$ alkenyl, $C_{2-6}$ alkynyl, $C_{3-10}$ cycloalkyl, heterocyclyl, $C_{6-10}$ aryl, heteroaryl, —P(O)(O$R^{9c}$)$_2$, —OP(O)(O$R^{9c}$)$_2$, —CH$_2$P(O)(O$R^{9c}$)$_2$, —OCH$_2$P(O)(O$R^{9c}$)$_2$, —C(O)OCH$_2$P(O)(O$R^{9c}$)$_2$, —P(O)($R^{9c}$)(O$R^{9d}$), —OP(O)($R^{9c}$)(O$R^{9d}$), —CH$_2$P(O)($R^{9c}$)(O$R^{9d}$), —OCH$_2$P(O)($R^{9c}$)(O$R^{9d}$), —C(O)OCH$_2$P(O)($R^{9c}$)(O$R^{9d}$), —P(O)(N($R^{9c}$)$_2$)$_2$, —OP(O)(N($R^{9c}$)$_2$)$_2$, —CH$_2$P(O)(N($R^{9c}$)$_2$)$_2$, —OCH$_2$P(O)(N($R^{9c}$)$_2$)$_2$, —C(O)OCH$_2$P(O)(N($R^{9c}$)$_2$)$_2$, —P(O)(N($R^{9c}$)$_2$)(O$R^{9d}$), —OP(O)(N($R^{9c}$)$_2$)(O$R^{9d}$), —CH$_2$P(O)(N($R^{9c}$)$_2$)(O$R^{9d}$), —OCH$_2$P(O)(N($R^{9c}$)$_2$)(O$R^{9d}$), —C(O)OCH$_2$P(O)(N($R^{9c}$)$_2$)(O$R^{9d}$), —P(O)($R^{9c}$)(N($R^{9d}$)$_2$), —OP(O)($R^{9c}$)(N($R^{9d}$)$_2$), —CH$_2$P(O)($R^{9c}$)(N($R^{9d}$)$_2$), —OCH$_2$P(O)($R^{9c}$)(N($R^{9d}$)$_2$), or —C(O)OCH$_2$P(O)($R^{9c}$)(N($R^{9d}$)$_2$);

wherein the alkyl, alkenyl, cycloalkyl, heterocyclyl, aryl, or heteroaryl is each optionally substituted with one to four $Z^{1b}$, each $R^4$ is independently $C_{1-9}$ alkyl, $C_{1-8}$ haloalkyl, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—$R^{4a}$, —C(O)$R^{4a}$, —C(O)O—$R^{4a}$, —C(O)N($R^{4a}$)($R^{4b}$), —N($R^{4a}$)($R^{4b}$), —N($R^{4a}$)$_2$($R^{4b}$)$^+$, —N($R^{4a}$)—C(O)$R^{4b}$, —N($R^{4a}$)C(O)O($R^{4b}$), —N($R^{4a}$)C(O)N($R^{4b}$)($R^{4c}$), —N($R^{4a}$)S(O)$_2$($R^{4b}$), —N($R^{4a}$)S(O)$_2$—N($R^{4b}$)($R^{4c}$), —N($R^{4a}$)S(O)$_2$O($R^{4b}$), —OC(O)$R^{4a}$, —OC(O)O$R^{4a}$, —OC(O)—N($R^{4a}$)($R^{4b}$), —S—$R^{4a}$, —S(O)$R^{4a}$, —S(O)(NH)$R^{4a}$, —S(O)$_2R^{4a}$, —S(O)$_2$N($R^{4a}$)($R^{4b}$), —S(O)(N$R^{4a}$)$R^{4b}$, or —Si($R^{4a}$)$_3$;

wherein the alkyl, haloalkyl, alkenyl, alkynyl, cycloalkyl, heterocyclyl, aryl, or heteroaryl is each optionally substituted with one to four $Z^{1b}$;

or two $R^4$ groups attached to adjacent ring atoms are combined with the atoms to which they are attached to form a $C_{5-10}$ cycloalkyl or heterocyclyl, which is each optionally substituted with one to four $Z^{1b}$;

$R^5$ is H, cyclopropyl, or $C_{1-3}$alkyl, wherein the $C_{1-3}$alkyl is optionally substituted with one, two or three groups selected from halogen, —OH, —OCH$_3$, —CN, oxo, and —N($R^{x1}$)($R^{x2}$);

or $R^5$ and $R^{y1}$ are combined with the atoms to which they are attached to form a $C_{3-10}$ cycloalkyl or heterocyclyl optionally substituted with oxo;

$R^{x1}$ and $R^{x2}$ are each independently H, $C_{1-6}$ alkyl, $C_{3-10}$ cycloalkyl, heterocyclyl, —S(O)$_2R^{6a1}$, or —S(O)$_2$N($R^{6a1}$)(N$R^{6a2}$), wherein the $C_{1-6}$ alkyl, cycloalkyl or heterocyclyl is each optionally substituted with F, —CN, oxo, or $C_{3-6}$ cycloalkyl;

or $R^{x1}$ and $R^{x2}$ are combined with the atom to which they are attached to form a heterocyclyl, which is optionally substituted with one to four $R^{6b1}$;

V is —C(O)—, —O—, —N($R^{6a}$)—, or —C($R^{6b}$)($R^{6c}$)—;

$R^{6a}$ is H, $C_{1-6}$ alkyl, $C_{3-10}$ cycloalkyl, heterocyclyl, —S(O)$_2R^{6a1}$, or —S(O)$_2$N($R^{6a1}$)(N$R^{6a2}$), wherein the cycloalkyl or heterocyclyl is each optionally substituted with $C_{1-6}$ alkyl, F, or —CN;

each $R^{6b}$ and $R^{6c}$ is independently H, $C_{1-6}$ alkyl, $C_{1-6}$ haloalkyl, $C_{2-6}$ alkoxyalkyl, halogen, $C_{3-10}$ cycloalkyl, heterocyclyl, —$C_{1-6}$ alkyl-N($R^{9a}$)($R^{9b}$), —CN, —O$R^{6c1}$, or —N($R^{6c2}$)($R^{6c3}$), wherein the alkyl, cycloalkyl, or heterocyclyl is each optionally substituted with one to four $R^{6b1}$;

or $R^{6b}$ and $R^{6c}$ are combined with the atom to which they are attached to form $C_{3-10}$ cycloalkyl or heterocyclyl, which is each optionally substituted with one to four $R^{6b1}$;

or $R^{6a}$ or $R^{6c}$ is combined with one $R^4$ group and the atoms to which they are attached to form a $C_{5-10}$ cycloalkyl or heterocyclyl, which is each optionally substituted with one to four $R^{10}$;

each $R^{y1}$ and $R^{y2}$ is independently H, halo, $C_{1-6}$ alkyl, $C_{1-6}$ haloalkyl, wherein the alkyl and haloalkyl are each optionally substituted with oxo;

each $R^{3d}$, $R^{6b1}$, and $R^{10}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —OH, —CN, —$NO_2$, or
—C(O)N($R^{2a}$)($R^{2b}$), wherein the heterocyclyl or heteroaryl is optionally substituted with $C_{1-6}$ alkyl, $C_{1-6}$ haloalkyl, or $C_{1-6}$ haloalkoxy; and each $R^{6a1}$, $R^{6a2}$, $R^{6c1}$, $R^{6c2}$, and $R^{6c3}$ is independently H, $C_{1-6}$ alkyl or $C_{3-10}$ cycloalkyl;

each $R^{9a}$ and $R^{9b}$ is independently H, $C_{1-6}$ alkyl, or $C_{1-6}$ haloalkyl;

each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —$N_3$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —N$R^{12a}$S(O)$_2$N($R^{12b}$)($R^{12c}$), —N$R^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$$R^{12a}$, —S(O)$_2$N($R^{12a}$)($R^{12b}$), —S(O)(N$R^{12a}$)$R^{12b}$, or —Si($R^{12a}$)$_3$;
wherein the alkyl, haloalkyl, alkenyl, alkynyl, cycloalkyl, heterocyclyl, aryl, or heteroaryl is each optionally substituted with one to four $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —CN, —$N_3$, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$)$^+$, —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O ($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$$R^{12a}$, —S(O)$_2$N($R^{12a}$)($R^{12b}$), —S(O)(N$R^{12a}$) $R^{12b}$, or —Si($R^{12a}$)$_3$;
wherein the alkyl, haloalkyl, alkenyl, alkynyl, cycloalkyl, heterocyclyl, aryl, or heteroaryl is each optionally substituted with one to four $Z^{1b}$;

each $R^8$ or $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH ($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl) ($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heterocyclyl), —C(O)($C_{1-9}$ alkyl), —C(O)($C_{1-8}$ haloalkyl), —C(O)($C_{2-6}$ alkenyl), —C(O) ($C_{2-6}$ alkynyl), —C(O)($C_{3-15}$ cycloalkyl), —C(O)(heterocyclyl), —C(O)($C_{6-10}$ aryl), —C(O)(heteroaryl), —C(O) O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH ($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{2-6}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O) N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O (heterocyclyl), —NHC(O)O($C_{6-10}$ aryl), —NHC(O)O (heteroaryl), —NHC(O)NH($C_{1-9}$ alkyl), —NHC(O)NH ($C_{1-8}$ haloalkyl), —NHC(O)NH($C_{2-6}$ alkenyl), —NHC (O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O) ($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$ ($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;
wherein the alkyl, cycloalkyl, heterocyclyl, aryl, or heteroaryl in each instance is optionally substituted with one to three $C_{1-9}$ alkyl, $C_{1-8}$ haloalkyl, halogen, —OH, —$NH_2$, —O($C_{1-9}$ alkyl), —O($C_{1-8}$ haloalkyl), —O ($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O (aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$; and each $R^{1b}$, $R^{1c}$, $R^{2a}$, $R^{2b}$, $R^{4a}$, $R^{4b}$, $R^{4c}$, $R^{9c}$, $R^{9d}$, $R^{12a}$, $R^{12b}$, and $R^{12c}$ is independently H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl wherein the alkyl, alkenyl, alkynyl, cycloalkyl, heterocyclyl, aryl, or heteroaryl is each optionally substituted with one to four $Z^{1b}$;

subscript p is 1, 2, or 3; and subscript q is 0, 1, or 2;

wherein each heteroaryl has 5 to 12 ring members and has one to four heteroatoms each independently N, O, or S; and wherein each heterocyclyl has 3 to 12 ring members and has one to four heteroatoms each independently N, O, or S.

In some embodiments, the compound of the present disclosure is a compound of Formula (Ic):

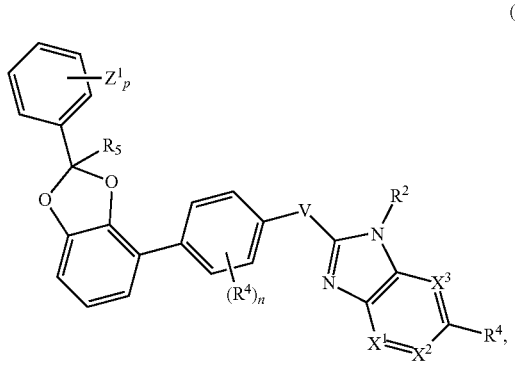

(Ic)

or a pharmaceutically acceptable salt thereof, wherein
$R^2$ is H, $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{6-10}$ aryl, heteroaryl, —S—$R^{2a}$, —S(O)$R^{2a}$, —S(O)(NH)$R^{2a}$, —S(O)$_2R^{2a}$, —S(O)$_2$N($R^{2a}$)($R^{2b}$), or —S(O)(N$R^{2a}$)$R^{2b}$,
  wherein the alkyl, cycloalkyl, heterocyclyl, aryl, or heteroaryl is each optionally substituted with one to four $Z^1$;
$X^1$, $X^2$, and $X^3$ are each independently —N=, —C(H)=, or —C($R^8$)=;
$R^3$ is H, $C_{1-6}$ alkyl, $C_{1-6}$ haloalkyl, $C_{2-6}$ alkenyl, $C_{2-6}$ alkynyl, halogen, $C_{3-10}$ cycloalkyl, heterocyclyl, $C_{6-10}$ aryl, heteroaryl, —CN, —NO$_2$, —O$R^{3a}$, —C(O)$R^{3a}$, —C(O)O$R^{3a}$, —C(O)N($R^{3a}$)($R^{3b}$), —N($R^{3a}$)C(O)$R^{3b}$, —N($R^{3a}$)C(O)O$R^{3b}$, —N($R^{3a}$)C(O)N($R^{3b}$)$_2$, —C(O)NHS(O)$_2R^{3a}$, —C(O)N$R^{3a}$S(O)$_2R^{3b}$, —C(O)N$R^{3a}$S(O)$_2$N$R^{3b}R^{3c}$, —C(O)N$R^{3a}$—S(O)(=N$R^{3b}$)$R^{3c}$—S(O)$_2R^{3a}$, —S(O)$_2$O$R^{3a}$, —S(O)$_2$N($R^{3a}$)($R^{3b}$), —N($R^{3a}$)S(O)$_2R^{3b}$, —S(O)$_2$NHC(O)$R^{3a}$, —S(O)(=N$R^{3a}$)$R^{3b}$, —S(O)(=N$R^{3a}$)N$R^{3b}$, —S(=N$R^{3a}$)(=N$R^{3b}$)$R^{3c}$, —P(O)(O$R^{3a}$)($R^{3b}$), —P(O)(O$R^{3a}$)(O$R^{3b}$), or —B(O$R^{3a}$)(O$R^{3b}$), wherein the alkyl, haloalkyl, alkenyl, alkynyl, cycloalkyl, heterocyclyl, aryl, or heteroaryl is each optionally substituted with one to four $R^{3d}$;
each $R^{3a}$, $R^{3b}$, and $R^{3c}$ is independently H, $C_{1-6}$ alkyl, $C_{1-6}$ haloalkyl, $C_{2-8}$ alkoxyalkyl, —$C_{1-4}$ alkyl-N($R^{9a}$)($R^{9b}$), —$C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$alkyl, —$C_{1-4}$ alkyl-O—C(O)—$C_{1-4}$ alkyl-N($R^{9a}$)($R^{9b}$), —$C_{1-4}$ alkyl-$C_{3-8}$ cycloalkyl, —$C_{1-4}$ alkyl-heterocyclyl, $C_{2-6}$ alkenyl, $C_{2-6}$ alkynyl, $C_{3-10}$ cycloalkyl, heterocyclyl, $C_{6-10}$ aryl, heteroaryl, —P(O)(O$R^{9c}$)$_2$, —OP(O)(O$R^{9c}$)$_2$, —CH$_2$P(O)(O$R^{9c}$)$_2$, —OCH$_2$P(O)(O$R^{9c}$)$_2$, —C(O)OCH$_2$P(O)(O$R^{9c}$)$_2$, —P(O)($R^{9c}$)(O$R^{9d}$), —OP(O)($R^{9c}$)(O$R^{9d}$), —CH$_2$P(O)($R^{9c}$)(O$R^{9d}$), —OCH$_2$P(O)($R^{9c}$)(O$R^{9d}$), —C(O)OCH$_2$P(O)($R^{9c}$)(O$R^{9d}$), —P(O)(N($R^{9c}$)$_2$)$_2$, —OP(O)(N($R^{9c}$)$_2$)$_2$, —CH$_2$P(O)(N($R^{9c}$)$_2$)$_2$, —OCH$_2$P(O)(N($R^{9c}$)$_2$)$_2$, —C(O)OCH$_2$P(O)(N($R^{9c}$)$_2$)$_2$, —P(O)(N($R^{9c}$)$_2$)(O$R^{9d}$), —OP(O)(N($R^{9c}$)$_2$)(O$R^{9d}$), —CH$_2$P(O)(N($R^{9c}$)$_2$)(O$R^{9d}$), —OCH$_2$P(O)(N($R^{9c}$)$_2$)(O$R^{9d}$), —C(O)OCH$_2$P(O)(N($R^{9c}$)$_2$)(O$R^{9d}$), —P(O)($R^{9c}$)(N($R^{9d}$)$_2$), —OP(O)($R^{9c}$)(N($R^{9d}$)$_2$), —CH$_2$P(O)($R^{9c}$)(N($R^{9d}$)$_2$), —OCH$_2$P(O)($R^{9c}$)(N($R^{9d}$)$_2$), or —C(O)OCH$_2$P(O)($R^{9c}$)(N($R^{9d}$)$_2$);
wherein the alkyl, alkenyl, cycloalkyl, heterocyclyl, aryl, or heteroaryl is each optionally substituted with one to four $Z^{1b}$;
each $R^4$ is independently $C_{1-9}$ alkyl, $C_{1-8}$ haloalkyl, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—$R^{4a}$, —C(O)$R^{4a}$, —C(O)O—$R^{4a}$, —C(O)N($R^{4a}$)($R^{4b}$), —N($R^{4a}$)($R^{4b}$), —N($R^{4a}$)$_2$($R^{4b}$)$^+$, —N($R^{4a}$)—C(O)$R^{4b}$, —N($R^{4a}$)C(O)O($R^{4b}$), —N($R^{4a}$)C(O)N($R^{4b}$)($R^{4c}$), —N($R^{4a}$)S(O)$_2$($R^{4b}$), —N($R^{4a}$)S(O)$_2$—N($R^{4b}$)($R^{4c}$), —N($R^{4a}$)S(O)$_2$O($R^{4b}$), —OC(O)$R^{4a}$, —OC(O)O$R^{4a}$, —OC(O)—N($R^{4a}$)($R^{4b}$), —S—$R^{4a}$, —S(O)$R^{4a}$, —S(O)(NH)$R^{4a}$, —S(O)$_2R^{4a}$, —S(O)$_2$N($R^{4a}$)($R^{4b}$), —S(O)(N$R^{4a}$)$R^{4b}$, or —Si($R^{4a}$)$_3$;
  wherein the alkyl, haloalkyl, alkenyl, alkynyl, cycloalkyl, heterocyclyl, aryl, or heteroaryl is each optionally substituted with one to four $Z^{1b}$;
or two $R^4$ groups attached to adjacent ring atoms are combined with the atoms to which they are attached to form a $C_{5-10}$ cycloalkyl or heterocyclyl, which is each optionally substituted with one to four $Z^{1b}$;
$R^5$ is H, cyclopropyl, or $C_{1-3}$alkyl, wherein the $C_{1-3}$alkyl is optionally substituted with one, two or three groups selected from halogen, —OH, —OCH$_3$, —CN, oxo, and —N($R^{x1}$)($R^{x2}$);
or $R^5$ and $R^{y1}$ are combined with the atoms to which they are attached to form a $C_{3-10}$ cycloalkyl or heterocyclyl optionally substituted with oxo;
$R^{x1}$ and $R^{x2}$ are each independently H, $C_{1-6}$ alkyl, $C_{3-10}$ cycloalkyl, heterocyclyl, —S(O)$_2R^{6a1}$, or —S(O)$_2$N($R^{6a1}$)(N$R^{6a2}$), wherein the $C_{1-6}$ alkyl, cycloalkyl or heterocyclyl is each optionally substituted with F, —CN, oxo, or $C_{3-6}$ cycloalkyl;
or $R^{x1}$ and $R^{x2}$ are combined with the atom to which they are attached to form a heterocyclyl, which is optionally substituted with one to four $R^{6b1}$;
V is —C(O)—, —O—, —N($R^{6a}$)—, or —C($R^{6b}$)($R^{6c}$)—;
$R^{6a}$ is H, $C_{1-6}$ alkyl, $C_{3-10}$ cycloalkyl, heterocyclyl, —S(O)$_2R^{6a1}$, or —S(O)$_2$N($R^{6a1}$)(N$R^{6a2}$), wherein the cycloalkyl or heterocyclyl is each optionally substituted with $C_{1-6}$ alkyl, F, or —CN;
each $R^{6b}$ and $R^{6c}$ is independently H, $C_{1-6}$ alkyl, $C_{1-6}$ haloalkyl, $C_{2-6}$ alkoxyalkyl, halogen, $C_{3-10}$ cycloalkyl, heterocyclyl, —$C_{1-6}$ alkyl-N($R^{9a}$)($R^{9b}$), —CN, —O$R^{6c1}$, or —N($R^{6c2}$)($R^{6c3}$), wherein the alkyl, cycloalkyl, or heterocyclyl is each optionally substituted with one to four $R^{6b1}$;
or $R^{6b}$ and $R^{6c}$ are combined with the atom to which they are attached to form $C_{3-10}$ cycloalkyl or heterocyclyl, which is each optionally substituted with one to four $R^{6b1}$;
or $R^{6a}$ or $R^{6c}$ is combined with one $R^4$ group and the atoms to which they are attached to form a $C_{5-10}$ cycloalkyl or heterocyclyl, which is each optionally substituted with one to four $R^{10}$;
each $R^{y1}$ and $R^{y2}$ is independently H, halo, $C_{1-6}$ alkyl, $C_{1-6}$ haloalkyl, wherein the alkyl and haloalkyl are each optionally substituted with oxo;
each $R^{3d}$, $R^{6b1}$, and $R^{10}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —OH, —CN, —NO$_2$, or —C(O)N($R^{2a}$)($R^{2b}$), wherein the heterocyclyl or heteroaryl is optionally substituted with $C_{1-6}$ alkyl, $C_{1-6}$ haloalkyl, or $C_{1-6}$ haloalkoxy; and
each $R^{6a1}$, $R^{6a2}$, $R^{6c1}$, $R^{6c2}$, and $R^{6c3}$ is independently H, $C_{1-6}$ alkyl or $C_{3-10}$ cycloalkyl;

each $R^{9a}$ and $R^{9b}$ is independently H, $C_{1-6}$ alkyl, or $C_{1-6}$ haloalkyl;

each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —$N_3$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$($R^{12b}$)$^+$, —N($R^{12a}$)C(O)—$R^{12b}$, —N($R^{12a}$)C(O)O—$R^{12b}$), —N($R^{12a}$)C(O)N($R^{12b}$)($R^{12c}$), —N($R^{12a}$)S(O)$_2$($R^{12b}$), —N$R^{12a}$S(O)$_2$N($R^{12b}$)($R^{12c}$), —N$R^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2R^{12a}$, —S(O)$_2$N($R^{12a}$)($R^{12b}$), —S(O)(N$R^{12a}$)$R^{12b}$, or —Si($R^{12a}$)$_3$;

wherein the alkyl, haloalkyl, alkenyl, alkynyl, cycloalkyl, heterocyclyl, aryl, or heteroaryl is each optionally substituted with one to four $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —CN, —$N_3$, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$)$^+$, —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2R^{12a}$, —S(O)$_2$N($R^{12a}$)($R^{12b}$), —S(O)(N$R^{12a}$)$R^{12b}$, or —Si($R^{12a}$)$_3$;

wherein the alkyl, haloalkyl, alkenyl, alkynyl, cycloalkyl, heterocyclyl, aryl, or heteroaryl is each optionally substituted with one to four $Z^{1b}$;

each $R^8$ or $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein the alkyl, cycloalkyl, heterocyclyl, aryl, or heteroaryl in each instance is optionally substituted with one to three $C_{1-9}$ alkyl, $C_{1-8}$ haloalkyl, halogen, —OH, —$NH_2$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$; and each $R^{1b}$, $R^{1c}$, $R^{2a}$, $R^{2b}$, $R^{4a}$, $R^{4b}$, $R^{4c}$, $R^{9c}$, $R^{9d}$, $R^{12a}$, $R^{12b}$, and $R^{12c}$ is independently H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl wherein the alkyl, alkenyl, alkynyl, cycloalkyl, heterocyclyl, aryl, or heteroaryl is each optionally substituted with one to four $Z^{1b}$;

subscript p is 1, 2, or 3;
subscript q is 0, 1, or 2; and
subscript n is 0, 1, 2, or 3; and
wherein each heteroaryl has 5 to 12 ring members and has one to four heteroatoms each independently N, O, or S; and
wherein each heterocyclyl has 3 to 12 ring members and has one to four heteroatoms each independently N, O, or S.

In some embodiments, the compound of the present disclosure is a compound of Formula (Id):

(Id)

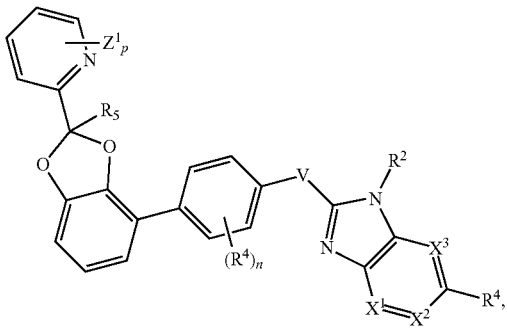

or a pharmaceutically acceptable salt thereof, wherein
$R^2$ is H, $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{6-10}$ aryl, heteroaryl, —S—$R^{2a}$, —S(O)$R^{2a}$, —S(O)(NH)$R^{2a}$, —S(O)$_2R^{2a}$, —S(O)$_2$N($R^{2a}$)($R^{2b}$), or —S(O)(N$R^{2a}$)$R^{2b}$,
  wherein the alkyl, cycloalkyl, heterocyclyl, aryl, or heteroaryl is each optionally substituted with one to four $Z^1$;
$X^1$, $X^2$, and $X^3$ are each independently —N=, —C(H)=, or —C($R^8$)=;
$R^3$ is H, $C_{1-6}$ alkyl, $C_{1-6}$ haloalkyl, $C_{2-6}$ alkenyl, $C_{2-6}$ alkynyl, halogen, $C_{3-10}$ cycloalkyl, heterocyclyl, $C_{6-10}$ aryl, heteroaryl, —CN, —NO$_2$, —O$R^{3a}$, —C(O)$R^{3a}$, —C(O)O$R^{3a}$, —C(O)N($R^{3a}$)($R^{3b}$), —N($R^{3a}$)C(O)$R^{3b}$, —N($R^{3a}$)C(O)O$R^{3b}$, —N($R^{3a}$)C(O)N($R^{3b}$)$_2$, —C(O)NHS(O)$_2R^{3a}$, —C(O)N$R^{3a}$S(O)$_2R^{3b}$, —C(O)N$R^{3a}$S(O)$_2$N$R^{3b}R^{3c}$, —C(O)N$R^{3a}$—S(O)(=N$R^{3b}$)$R^{3c}$—S(O)$_2R^{3a}$, —S(O)$_2$O$R^{3a}$, —S(O)$_2$N($R^{3a}$)($R^{3b}$), —N($R^{3a}$)S(O)$_2R^{3b}$, —S(O)$_2$NHC(O)$R^{3a}$, —S(O)(=N$R^{3a}$)$R^{3b}$, —S(O)(=N$R^{3a}$)N$R^{3b}$, —S(=N$R^{3a}$)(=N$R^{3b}$)$R^{3c}$, —P(O)(O$R^{3a}$)($R^{3b}$), —P(O)(O$R^{3a}$)(O$R^{3b}$), or —B(O$R^{3a}$)(O$R^{3b}$), wherein the alkyl, haloalkyl, alkenyl, alkynyl, cycloalkyl, heterocyclyl, aryl, or heteroaryl is each optionally substituted with one to four $R^{3d}$;
each $R^{3a}$, $R^{3b}$, and $R^{3c}$ is independently H, $C_{1-6}$ alkyl, $C_{1-6}$ haloalkyl, $C_{2-8}$ alkoxyalkyl, —$C_{1-4}$ alkyl-N($R^{9a}$)($R^{9b}$), —$C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$alkyl, —$C_{1-4}$ alkyl-O—C(O)—$C_{1-4}$ alkyl-N($R^{9a}$)($R^{9b}$), —$C_{1-4}$ alkyl-$C_{3-8}$ cycloalkyl, —$C_{1-4}$ alkyl-heterocyclyl, $C_{2-6}$ alkenyl, $C_{2-6}$ alkynyl, $C_{3-10}$ cycloalkyl, $C_{6-10}$ aryl, heteroaryl, —P(O)(O$R^{9c}$)$_2$, —OP(O)(O$R^{9c}$)$_2$, —CH$_2$P(O)(O$R^{9c}$)$_2$, —OCH$_2$P(O)(O$R^{9c}$)$_2$, —C(O)OCH$_2$P(O)(O$R^{9c}$)$_2$, —P(O)($R^{9c}$)(O$R^{9d}$), —OP(O)($R^{9c}$)(O$R^{9d}$), —CH$_2$P(O)($R^{9c}$)(O$R^{9d}$), —OCH$_2$P(O)($R^{9c}$)(O$R^{9d}$), —C(O)OCH$_2$P(O)($R^{9c}$)(O$R^{9d}$), —P(O)(N($R^{9c}$)$_2$)$_2$, —OP(O)(N($R^{9c}$)$_2$)$_2$, —CH$_2$P(O)(N($R^{9c}$)$_2$)$_2$, —OCH$_2$P(O)(N($R^{9c}$)$_2$)$_2$, —C(O)OCH$_2$P(O)(N($R^{9c}$)$_2$)$_2$, —P(O)(N($R^{9c}$)$_2$)(O$R^{9d}$), —OP(O)(N($R^{9c}$)$_2$)(O$R^{9d}$), —CH$_2$P(O)(N($R^{9c}$)$_2$)(O$R^{9d}$), —OCH$_2$P(O)(N($R^{9c}$)$_2$)(O$R^{9d}$), —C(O)OCH$_2$P(O)(N($R^{9c}$)$_2$)(O$R^{9d}$), —P(O)($R^{9c}$)(N($R^{9d}$)$_2$), —OP(O)($R^{9c}$)(N($R^{9d}$)$_2$), —CH$_2$P(O)($R^{9c}$)(N($R^{9d}$)$_2$), —OCH$_2$P(O)($R^{9c}$)(N($R^{9d}$)$_2$), or —C(O)OCH$_2$P(O)($R^{9c}$)(N($R^{9d}$)$_2$);
  wherein the alkyl, alkenyl, cycloalkyl, heterocyclyl, aryl, or heteroaryl is each optionally substituted with one to four $Z^{1b}$,
each $R^4$ is independently $C_{1-9}$ alkyl, $C_{1-8}$ haloalkyl, $C_{1-6}$ haloalkoxy, $C_{2-6}$ alkoxyalkyl, $C_{2-6}$ alkenyl, halogen, $C_{3-15}$ cycloalkyl, heterocyclyl, $C_{6-10}$ aryl, heteroaryl, oxo, —NO$_2$, —CN, —N$_3$, —O—$R^{4a}$, —C(O)$R^{4a}$, —C(O)O—$R^{4a}$, —C(O)N($R^{4a}$)($R^{4b}$), —N($R^{4a}$)($R^{4b}$), —N($R^{4a}$)$_2$($R^{4b}$)$^+$, —N($R^{4a}$)—C(O)$R^{4b}$, —N($R^{4a}$)C(O)O($R^{4b}$), —N($R^{4a}$)C(O)N($R^{4b}$)($R^{4c}$), —N($R^{4a}$)S(O)$_2$($R^{4b}$), —N($R^{4a}$)S(O)$_2$—N($R^{4b}$)($R^{4c}$), —N($R^{4a}$)S(O)$_2$O($R^{4b}$), —OC(O)$R^{4a}$, —OC(O)O$R^{4a}$, —OC(O)—N($R^{4a}$)($R^{4b}$), —S—$R^{4a}$, —S(O)$R^{4a}$, —S(O)(NH)$R^{4a}$, —S(O)$_2R^{4a}$, —S(O)$_2$N($R^{4a}$)($R^{4b}$), —S(O)(N$R^{4a}$)$R^{4b}$, or —Si($R^{4a}$)$_3$;
  wherein the alkyl, haloalkyl, alkenyl, alkynyl, cycloalkyl, heterocyclyl, aryl, or heteroaryl is each optionally substituted with one to four $Z^{1b}$;
  or two $R^4$ groups attached to adjacent ring atoms are combined with the atoms to which they are attached to form a $C_{5-10}$ cycloalkyl or heterocyclyl, which is each optionally substituted with one to four $Z^{1b}$;
$R^5$ is H, cyclopropyl, or $C_{1-3}$alkyl, wherein the $C_{1-3}$alkyl is optionally substituted with one, two or three groups selected from halogen, —OH, —OCH$_3$, —CN, oxo, and —N($R^{x1}$)($R^{x2}$);
or $R^5$ and $R^{y1}$ are combined with the atoms to which they are attached to form a $C_{3-10}$ cycloalkyl or heterocyclyl optionally substituted with oxo;
$R^{x1}$ and $R^{x2}$ are each independently H, $C_{1-6}$ alkyl, $C_{3-10}$ cycloalkyl, heterocyclyl, —S(O)$_2R^{6a1}$, or —S(O)$_2$N($R^{6a1}$)(N$R^{6a2}$), wherein the $C_{1-6}$ alkyl, cycloalkyl or heterocyclyl is each optionally substituted with F, —CN, oxo, or $C_{3-6}$ cycloalkyl;
or $R^{x1}$ and $R^{x2}$ are combined with the atom to which they are attached to form a heterocyclyl, which is optionally substituted with one to four $R^{6b1}$;
V is —C(O)—, —O—, —N($R^{6a}$)—, or —C($R^{6b}$)($R^{6c}$)—;
$R^{6a}$ is H, $C_{1-6}$ alkyl, $C_{3-10}$ cycloalkyl, heterocyclyl, —S(O)$_2R^{6a1}$, or —S(O)$_2$N($R^{6a1}$)(N$R^{6a2}$), wherein the cycloalkyl or heterocyclyl is each optionally substituted with $C_{1-6}$ alkyl, F, or —CN;
each $R^{6b}$ and $R^{6c}$ is independently H, $C_{1-6}$ alkyl, $C_{1-6}$ haloalkyl, $C_{2-6}$ alkoxyalkyl, halogen, $C_{3-10}$ cycloalkyl, heterocyclyl, —$C_{1-6}$ alkyl-N($R^{9a}$)($R^{9b}$), —CN, —O$R^{6c1}$, or —N($R^{6c2}$)($R^{6c3}$), wherein the alkyl, cycloalkyl, or heterocyclyl is each optionally substituted with one to four $R^{6b1}$;
or $R^{6b}$ and $R^{6c}$ are combined with the atom to which they are attached to form $C_{3-10}$ cycloalkyl or heterocyclyl, which is each optionally substituted with one to four $R^{6b1}$;
or $R^{6a}$ or $R^{6c}$ is combined with one $R^4$ group and the atoms to which they are attached to form a $C_{5-10}$ cycloalkyl or heterocyclyl, which is each optionally substituted with one to four $R^{10}$;
each $R^{y1}$ and $R^{y2}$ is independently H, halo, $C_{1-6}$ alkyl, $C_{1-6}$ haloalkyl, wherein the alkyl and haloalkyl are each optionally substituted with oxo;
each $R^{3d}$, $R^{6b1}$, and $R^{10}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —OH, —CN, —NO$_2$, or
  —C(O)N($R^{2a}$)($R^{2b}$), wherein the heterocyclyl or heteroaryl is optionally substituted with $C_{1-6}$ alkyl, $C_{1-6}$ haloalkyl, or $C_{1-6}$ haloalkoxy; and
each $R^{6a1}$, $R^{6a2}$, $R^{6c1}$, $R^{6c2}$, and $R^{6c3}$ is independently H, $C_{1-6}$ alkyl or $C_{3-10}$ cycloalkyl;
each $R^{9a}$ and $R^{9b}$ is independently H, $C_{1-6}$ alkyl, or $C_{1-6}$ haloalkyl;
each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, halogen, $C_{3-15}$ cycloalkyl, heterocyclyl, $C_{6-10}$ aryl, heteroaryl, oxo, —$NO_2$, —$N_3$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —N$R^{12a}$S(O)$_2$N($R^{12b}$)($R^{12c}$), —N$R^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$$R^{12a}$, —S(O)$_2$N($R^{12a}$)($R^{12b}$), —S(O)(N$R^{12a}$)$R^{12b}$, or —Si($R^{12a}$)$_3$;

wherein the alkyl, haloalkyl, alkenyl, alkynyl, cycloalkyl, heterocyclyl, aryl, or heteroaryl is each optionally substituted with one to four $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —$NO_2$, —CN, —$N_3$, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$)$^+$, —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$$R^{12a}$, —S(O)$_2$N($R^{12a}$)($R^{12b}$), —S(O)(N$R^{12a}$)$R^{12b}$, or —Si($R^{12a}$)$_3$;

wherein the alkyl, haloalkyl, alkenyl, alkynyl, cycloalkyl, heterocyclyl, aryl, or heteroaryl is each optionally substituted with one to four $Z^{1b}$;

each $R^8$ or $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —$NO_2$, —$NH_2$, —$N_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)$NH_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein the alkyl, cycloalkyl, heterocyclyl, aryl, or heteroaryl in each instance is optionally substituted with one to three $C_{1-9}$ alkyl, $C_{1-8}$ haloalkyl, halogen, —OH, —$NH_2$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$; and each $R^{1b}$, $R^{1c}$, $R^{2a}$, $R^{2b}$, $R^{4a}$, $R^{4b}$, $R^{4c}$, $R^{9c}$, $R^{9d}$, $R^{12a}$, $R^{12b}$, and $R^{12c}$ is independently H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl wherein the alkyl, alkenyl, alkynyl, cycloalkyl, heterocyclyl, aryl, or heteroaryl is each optionally substituted with one to four $Z^{1b}$;

subscript p is 1, 2, or 3;

subscript q is 0, 1, or 2; and subscript n is 0, 1, 2, or 3; and wherein each heteroaryl has 5 to 12 ring members and has one to four heteroatoms each independently N, O, or S; and wherein each heterocyclyl has 3 to 12 ring members and has one to four heteroatoms each independently N, O, or S.

In some embodiments, the compound of the present disclosure is a compound of Formula (Ie):

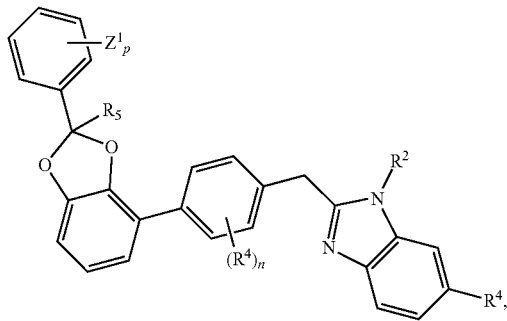

(Ie)

or a pharmaceutically acceptable salt thereof, wherein
  $R^2$ is H, $C_{1-6}$ alkyl, $C_{1-6}$haloalkyl, $C_{2-6}$ alkenyl, $C_{2-6}$ alkynyl, $C_{3-10}$ cycloalkyl, heterocyclyl, $C_{6-10}$ aryl, heteroaryl, —S—$R^{2a}$, —S(O)$R^{2a}$, —S(O)(NH)$R^{2a}$, —S(O)$_2R^{2a}$, —S(O)$_2$N($R^{2a}$)($R^{2b}$), or —S(O)(N$R^{2a}$)$R^{2b}$,
    wherein the alkyl, cycloalkyl, heterocyclyl, aryl, or heteroaryl is each optionally substituted with one to four $Z^1$;
  $R^3$ is H, $C_{1-6}$ alkyl, $C_{1-6}$haloalkyl, $C_{2-6}$ alkenyl, $C_{2-6}$ alkynyl, halogen, $C_{3-10}$ cycloalkyl, heterocyclyl, $C_{6-10}$ aryl, heteroaryl, —CN, —NO$_2$, —O$R^{3a}$, —C(O)$R^{3a}$, —C(O)O$R^{3a}$, —C(O)N($R^{3a}$)($R^{3b}$), —N($R^{3a}$)C(O)$R^{3b}$, —N($R^{3a}$)C(O)O$R^{3b}$, —N($R^{3a}$)C(O)N($R^{3b}$)$_2$, —C(O)NHS(O)$_2R^{3a}$, —C(O)N$R^{3a}$S(O)$_2R^{3b}$, —C(O)N$R^{3a}$S(O)$_2$N$R^{3b}R^{3c}$, —C(O)N$R^{3a}$—S(O)(=N$R^{3b}$)$R^{3c}$—S(O)$_2R^{3a}$, —S(O)$_2$O$R^{3a}$, —S(O)$_2$N($R^{3a}$)($R^{3b}$), —N($R^{3a}$)S(O)$_2R^{3b}$, —S(O)$_2$NHC(O)$R^{3a}$, —S(O)(=N$R^{3a}$)$R^{3b}$, —S(O)(=N$R^{3a}$)N$R^{3b}$, —S(=N$R^{3a}$)(=N$R^{3b}$)$R^{3c}$, —P(O)(O$R^{3a}$)($R^{3b}$), —P(O)(O$R^{3a}$)(O$R^{3b}$), or —B(O$R^{3a}$)(O$R^{3b}$), wherein the alkyl, haloalkyl, alkenyl, alkynyl, cycloalkyl, heterocyclyl, aryl, or heteroaryl is each optionally substituted with one to four $R^{3d}$;
  each $R^{3a}$, $R^{3b}$, and $R^{3c}$ is independently H, $C_{1-6}$ alkyl, $C_{1-6}$ haloalkyl, $C_{2-8}$ alkoxyalkyl, —$C_{1-4}$ alkyl-N($R^{9a}$)($R^{9b}$), —$C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$alkyl, —$C_{1-4}$ alkyl-O—C(O)—$C_{1-4}$ alkyl-N($R^{9a}$)($R^{9b}$), —$C_{1-4}$ alkyl-$C_{3-8}$ cycloalkyl, —$C_{1-4}$ alkyl-heterocyclyl, $C_{2-6}$ alkenyl, $C_{2-6}$ alkynyl, $C_{3-10}$ cycloalkyl, heterocyclyl, $C_{6-10}$ aryl, heteroaryl, —P(O)(O$R^{9c}$)$_2$, —OP(O)(O$R^{9c}$)$_2$, —CH$_2$P(O)(O$R^{9c}$)$_2$, —OCH$_2$P(O)(O$R^{9c}$)$_2$, —C(O)OCH$_2$P(O)(O$R^{9c}$)$_2$, —P(O)($R^{9c}$)(O$R^{9d}$), —OP(O)($R^{9c}$)(O$R^{9d}$), —CH$_2$P(O)($R^{9c}$)(O$R^{9d}$), —OCH$_2$P(O)($R^{9c}$)(O$R^{9d}$), —C(O)OCH$_2$P(O)($R^{9c}$)(O$R^{9d}$), —P(O)(N($R^{9c}$)$_2$)$_2$, —OP(O)(N($R^{9c}$)$_2$)$_2$, —CH$_2$P(O)(N($R^{9c}$)$_2$)$_2$, —OCH$_2$P(O)(N($R^{9c}$)$_2$)$_2$, —C(O)OCH$_2$P(O)(N($R^{9c}$)$_2$)$_2$, —P(O)(N($R^{9c}$)$_2$)(O$R^{9d}$), —OP(O)(N($R^{9c}$)$_2$)(O$R^{9d}$), —CH$_2$P(O)(N($R^{9c}$)$_2$)(O$R^{9d}$), —OCH$_2$P(O)(N($R^{9c}$)$_2$)(O$R^{9d}$), —C(O)OCH$_2$P(O)(N($R^{9c}$)$_2$)(O$R^{9d}$), —P(O)($R^{9c}$)(N($R^{9d}$)$_2$), —OP(O)($R^{9c}$)(N($R^{9d}$)$_2$), —CH$_2$P(O)($R^{9c}$)(N($R^{9d}$)$_2$), —OCH$_2$P(O)($R^{9c}$)(N($R^{9d}$)$_2$), or —C(O)OCH$_2$P(O)($R^{9c}$)(N($R^{9d}$)$_2$);
    wherein the alkyl, alkenyl, cycloalkyl, heterocyclyl, aryl, or heteroaryl is each optionally substituted with one to four $Z^{1b}$,
  each $R^4$ is independently $C_{1-9}$ alkyl, $C_{1-8}$ haloalkyl, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—$R^{4a}$, —C(O)$R^{4a}$, —C(O)O—$R^{4a}$, —C(O)N($R^{4a}$)($R^{4b}$), —N($R^{4a}$)($R^{4b}$), —N($R^{4a}$)$_2$($R^{4b}$)$^+$, —N($R^{4a}$)—C(O)$R^{4b}$, —N($R^{4a}$)C(O)O($R^{4b}$), —N($R^{4a}$)C(O)N($R^{4b}$)($R^{4c}$), —N($R^{4a}$)S(O)$_2$($R^{4b}$), —N($R^{4a}$)S(O)$_2$—N($R^{4b}$)($R^{4c}$), —N($R^{4a}$)S(O)$_2$O ($R^{4b}$), —OC(O)$R^{4a}$, —OC(O)O$R^{4a}$, —OC(O)—N($R^{4a}$)($R^{4b}$), —S—$R^{4a}$, —S(O)$R^{4a}$, —S(O)(NH)$R^{4a}$, —S(O)$_2R^{4a}$, —S(O)$_2$N($R^{4a}$)($R^{4b}$), —S(O)(N$R^{4a}$)$R^{4b}$, or —Si($R^{4a}$)$_3$;
    wherein the alkyl, haloalkyl, alkenyl, alkynyl, cycloalkyl, heterocyclyl, aryl, or heteroaryl is each optionally substituted with one to four $Z^{1b}$;
  or two $R^4$ groups attached to adjacent ring atoms are combined with the atoms to which they are attached to form a $C_{5-10}$ cycloalkyl or heterocyclyl, which is each optionally substituted with one to four $Z^{1b}$;
  $R^5$ is H, cyclopropyl, or $C_{1-3}$alkyl, wherein the $C_{1-3}$alkyl is optionally substituted with one, two or three groups selected from halogen, —OH, —OCH$_3$, —CN, oxo, and —N($R^{x1}$)($R^{x2}$);
  or $R^5$ and $R^{y1}$ are combined with the atoms to which they are attached to form a $C_{3-10}$ cycloalkyl or heterocyclyl optionally substituted with oxo;
  $R^{x1}$ and $R^{x2}$ are each independently H, $C_{1-6}$ alkyl, $C_{3-10}$ cycloalkyl, heterocyclyl, —S(O)$_2R^{6a1}$, or —S(O)$_2$N($R^{6a1}$)(N$R^{6a2}$), wherein the $C_{1-6}$ alkyl, cycloalkyl or heterocyclyl is each optionally substituted with F, —CN, oxo, or $C_{3-6}$ cycloalkyl;
  or $R^{x1}$ and $R^{x2}$ are combined with the atom to which they are attached to form a heterocyclyl, which is optionally substituted with one to four $R^{6b1}$;
  $R^{6a}$ is H, $C_{1-6}$ alkyl, $C_{3-10}$ cycloalkyl, heterocyclyl, —S(O)$_2R^{6a1}$, or —S(O)$_2$N($R^{6a1}$)(N$R^{6a2}$), wherein the cycloalkyl or heterocyclyl is each optionally substituted with $C_{1-6}$ alkyl, F, or —CN;
  each $R^{6b}$ and $R^{6c}$ is independently H, $C_{1-6}$ alkyl, $C_{1-6}$ haloalkyl, $C_{2-6}$ alkoxyalkyl, halogen, $C_{3-10}$ cycloalkyl, heterocyclyl, —$C_{1-6}$ alkyl-N($R^{9a}$)($R^{9b}$), —CN, —O$R^{6c1}$, or —N($R^{6c2}$)($R^{6c3}$), wherein the alkyl, cycloalkyl, or heterocyclyl is each optionally substituted with one to four $R^{6b1}$;
  or $R^{6b}$ and $R^{6c}$ are combined with the atom to which they are attached to form $C_{3-10}$ cycloalkyl or heterocyclyl, which is each optionally substituted with one to four $R^{6b1}$;
  or $R^{6a}$ or $R^{6c}$ is combined with one $R^4$ group and the atoms to which they are attached to form a $C_{5-10}$ cycloalkyl or heterocyclyl, which is each optionally substituted with one to four $R^{10}$;
  each $R^{y1}$ and $R^{y2}$ is independently H, halo, $C_{1-6}$ alkyl, $C_{1-6}$ haloalkyl, wherein the alkyl and haloalkyl are each optionally substituted with oxo;
  each $R^{3d}$, $R^{6b1}$, and $R^{10}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —OH, —CN, —NO$_2$, or —C(O)N($R^{2a}$)($R^{2b}$), wherein the heterocyclyl or heteroaryl is optionally substituted with $C_{1-6}$ alkyl, $C_{1-6}$ haloalkyl, or $C_{1-6}$ haloalkoxy; and
  each $R^{6a1}$, $R^{6a2}$, $R^{6c1}$, $R^{6c2}$, and $R^{6c3}$ is independently H, $C_{1-6}$ alkyl or $C_{3-10}$ cycloalkyl;
  each $R^{9a}$ and $R^{9b}$ is independently H, $C_{1-6}$ alkyl, or $C_{1-6}$ haloalkyl;
  each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —N$_3$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$($R^{12b}$)$^+$, —N(R$^{12a}$)C(O)—R$^{12b}$, —N(R$^{12a}$)C(O)O—R$^{12b}$, —N(R$^{12a}$)C(O)N(R$^{12b}$)(R$^{12c}$), —N(R$^{12a}$)S(O)$_2$(R$^{12b}$), —NR$^{12a}$S(O)$_2$N(R$^{12b}$)(R$^{12c}$), —NR$^{12a}$S(O)$_2$O(R$^{12b}$), —OC(O)R$^{12a}$, —OC(O)OR$^{12a}$, —OC(O)—N(R$^{12a}$)(R$^{12b}$), —S—R$^{12a}$, —S(O)R$^{12a}$, —S(O)(NH)R$^{12a}$, —S(O)$_2$R$^{12a}$, —S(O)$_2$N(R$^{12a}$)(R$^{12b}$), —S(O)(NR$^{12a}$)R$^{12b}$, or —Si(R$^{12a}$)$_3$;

wherein the alkyl, haloalkyl, alkenyl, alkynyl, cycloalkyl, heterocyclyl, aryl, or heteroaryl is each optionally substituted with one to four $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—R$^{12a}$, —C(O)R$^{12a}$, —C(O)O—R$^{12a}$, —C(O)N(R$^{12a}$)(R$^{12b}$), —N(R$^{12a}$)(R$^{12b}$), —N(R$^{12a}$)$_2$(R$^{12b}$)$^+$, —N(R$^{12a}$)—C(O)R$^{12b}$, —N(R$^{12a}$)C(O)O(R$^{12b}$), —N(R$^{12a}$)C(O)N(R$^{12b}$)(R$^{12c}$), —N(R$^{12a}$)S(O)$_2$(R$^{12b}$), —N(R$^{12a}$)S(O)$_2$—N(R$^{12b}$)(R$^{12c}$), —N(R$^{12a}$)S(O)$_2$O(R$^{12b}$), —OC(O)R$^{12a}$, —OC(O)OR$^{12a}$, —OC(O)—N(R$^{12a}$)(R$^{12b}$), —S—R$^{12a}$, —S(O)R$^{12a}$, —S(O)(NH)R$^{12a}$, —S(O)$_2$R$^{12a}$, —S(O)$_2$N(R$^{12a}$)(R$^{12b}$), —S(O)(NR$^{12a}$)R$^{12b}$, or —Si(R$^{12a}$)$_3$;

wherein the alkyl, haloalkyl, alkenyl, alkynyl, cycloalkyl, heterocyclyl, aryl, or heteroaryl is each optionally substituted with one to four $Z^{1b}$;

each $R^8$ or $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —NO$_2$, —NH$_2$, —N$_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O)($C_{3-15}$ cycloalkyl), —C(O)(heterocyclyl), —C(O)($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O)($C_{1-9}$ alkyl), —N($C_{1-9}$ alkyl)(S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$(heterocyclyl), —S(O)$_2$($C_{6-10}$ aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$;

wherein the alkyl, cycloalkyl, heterocyclyl, aryl, or heteroaryl in each instance is optionally substituted with one to three $C_{1-9}$ alkyl, $C_{1-8}$ haloalkyl, halogen, —OH, —NH$_2$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O)(aryl), —NHC(O)(heteroaryl), —NHC(O)O($C_{1-9}$ alkyl), —NHC(O)O($C_{1-8}$ haloalkyl), —NHC(O)O($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$(heterocyclyl), —S(O)$_2$(aryl), —S(O)$_2$(heteroaryl), —S(O)(NH)($C_{1-9}$ alkyl), —S(O)$_2$NH($C_{1-9}$ alkyl), or —S(O)$_2$N($C_{1-9}$ alkyl)$_2$; and each $R^{1b}$, $R^{1c}$, $R^{2a}$, $R^{2b}$, $R^{4a}$, $R^{4b}$, $R^{4c}$, $R^{9c}$, $R^{9d}$, $R^{12a}$, $R^{12b}$, and $R^{12c}$ is independently H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl wherein the alkyl, alkenyl, alkynyl, cycloalkyl, heterocyclyl, aryl, or heteroaryl is each optionally substituted with one to four $Z^{1b}$;

subscript p is 1, 2, or 3;

subscript q is 0, 1, or 2; and subscript n is 0, 1, 2, or 3; and wherein each heteroaryl has 5 to 12 ring members and has one to four heteroatoms each independently N, O, or S; and wherein each heterocyclyl has 3 to 12 ring members and has one to four heteroatoms each independently N, O, or S.

In some embodiments, the compound of the present disclosure is a compound of Formula (If):

(If)

or a pharmaceutically acceptable salt thereof, wherein $R^2$ is H, $C_{1-6}$ alkyl, $C_{1-6}$haloalkyl, $C_{2-6}$ alkenyl, $C_{2-6}$ alkynyl, $C_{3-10}$ cycloalkyl, heterocyclyl, $C_{6-10}$ aryl, heteroaryl, —S—$R^{2a}$, —S(O)$R^{2a}$, —S(O)(NH)$R^{2a}$, —S(O)$_2R^{2a}$, —S(O)$_2$N($R^{2a}$)($R^{2b}$), or —S(O)(N$R^{2a}$)$R^{2b}$, wherein the alkyl, cycloalkyl, heterocyclyl, aryl, or heteroaryl is each optionally substituted with one to four $Z^1$;

$R^3$ is H, $C_{1-6}$ alkyl, $C_{1-6}$haloalkyl, $C_{2-6}$ alkenyl, $C_{2-6}$ alkynyl, halogen, $C_{3-10}$ cycloalkyl, heterocyclyl, $C_{6-10}$ aryl, heteroaryl, —CN, —NO$_2$, —O$R^{3a}$, —C(O)$R^{3a}$, —C(O)O$R^{3a}$, —C(O)N($R^{3a}$)($R^{3b}$), —N($R^{3a}$)C(O)$R^{3b}$, —N($R^{3a}$)C(O)O$R^{3b}$, —N($R^{3a}$)C(O)N($R^{3b}$)$_2$, —C(O)NHS(O)$_2R^{3a}$, —C(O)N$R^{3a}$S(O)$_2R^{3b}$, —C(O)N$R^{3a}$S(O)$_2$N$R^{3b}R^{3c}$, —C(O)N$R^{3a}$—S(O)(=N$R^{3b}$)$R^{3c}$—S(O)$_2R^{3a}$, —S(O)$_2$O$R^{3a}$, —S(O)$_2$N($R^{3a}$)($R^{3b}$), —N($R^{3a}$)S(O)$_2R^{3b}$, —S(O)$_2$NHC(O)$R^{3a}$, —S(O)(=N$R^{3a}$)$R^{3b}$, —S(O)(=N$R^{3a}$)N$R^{3b}$, —S(=N$R^{3a}$)(=N$R^{3b}$)$R^{3c}$, —P(O)(O$R^{3a}$)($R^{3b}$), —P(O)(O$R^{3a}$)(O$R^{3b}$), or —B(O$R^{3a}$)(O$R^{3b}$), wherein the alkyl, haloalkyl, alkenyl, alkynyl, cycloalkyl, heterocyclyl, aryl, or heteroaryl is each optionally substituted with one to four $R^{3d}$;

each $R^{3a}$, $R^{3b}$, and $R^{3c}$ is independently H, $C_{1-6}$ alkyl, $C_{1-6}$ haloalkyl, $C_{2-8}$ alkoxyalkyl, —$C_{1-4}$ alkyl-N($R^{9a}$)($R^{9b}$), —$C_{1-4}$ alkyl-C(O)N($R^{9a}$)($R^{9b}$), —$C_{1-4}$ alkyl-O—C(O)—$C_{1-4}$ alkyl, —$C_{1-4}$ alkyl-O—C(O)—O—$C_{1-4}$alkyl, —$C_{1-4}$ alkyl-O—C(O)—$C_{1-4}$ alkyl-N($R^{9a}$)($R^{9b}$), —$C_{1-4}$ alkyl-$C_{3-8}$ cycloalkyl, —$C_{1-4}$ alkyl-heterocyclyl, $C_{2-6}$ alkenyl, $C_{2-6}$ alkynyl, $C_{3-10}$ cycloalkyl, heterocyclyl, $C_{6-10}$ aryl, heteroaryl, —P(O)(O$R^{9c}$)$_2$, —OP(O)(O$R^{9c}$)$_2$, —CH$_2$P(O)(O$R^{9c}$)$_2$, —OCH$_2$P(O)(O$R^{9c}$)$_2$, —C(O)OCH$_2$P(O)(O$R^{9c}$)$_2$, —P(O)($R^{9c}$)(O$R^{9d}$), —OP(O)($R^{9c}$)(O$R^{9d}$), —CH$_2$P(O)($R^{9c}$)(O$R^{9d}$), —OCH$_2$P(O)($R^{9c}$)(O$R^{9d}$), —C(O)OCH$_2$P(O)($R^{9c}$)(O$R^{9d}$), —P(O)(N($R^{9c}$)$_2$)$_2$, —OP(O)(N($R^{9c}$)$_2$)$_2$, —CH$_2$P(O)(N($R^{9c}$)$_2$)$_2$, —OCH$_2$P(O)(N($R^{9c}$)$_2$)$_2$, —C(O)OCH$_2$P(O)(N($R^{9c}$)$_2$)$_2$, —P(O)(N($R^{9c}$)$_2$)(O$R^{9d}$), —OP(O)(N($R^{9c}$)$_2$)(O$R^{9d}$), —CH$_2$P(O)(N($R^{9c}$)$_2$)(O$R^{9d}$), —OCH$_2$P(O)(N($R^{9c}$)$_2$)(O$R^{9d}$), —C(O)OCH$_2$P(O)(N($R^{9c}$)$_2$)(O$R^{9d}$), —P(O)($R^{9c}$)(N($R^{9d}$)$_2$), —OP(O)($R^{9c}$)(N($R^{9d}$)$_2$), —CH$_2$P(O)($R^{9c}$)(N($R^{9d}$)$_2$), —OCH$_2$P(O)($R^{9c}$)(N($R^{9d}$)$_2$), or —C(O)OCH$_2$P(O)($R^{9c}$)(N($R^{9d}$)$_2$);

wherein the alkyl, alkenyl, cycloalkyl, heterocyclyl, aryl, or heteroaryl is each optionally substituted with one to four $Z^{1b}$;

each $R^4$ is independently $C_{1-9}$ alkyl, $C_{1-8}$ haloalkyl, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, $C_{6-10}$ aryl, heteroaryl, oxo, —NO$_2$, —CN, —N$_3$, —O—$R^{4a}$, —C(O)$R^{4a}$, —C(O)O—$R^{4a}$, —C(O)N($R^{4a}$)($R^{4b}$), —N($R^{4a}$)($R^{4b}$), —N($R^{4a}$)$_2$($R^{4b}$)$^+$, —N($R^{4a}$)—C(O)$R^{4b}$, —N($R^{4a}$)C(O)O($R^{4b}$), —N($R^{4a}$)C(O)N($R^{4b}$)($R^{4c}$), —N($R^{4a}$)S(O)$_2$($R^{4b}$), —N($R^{4a}$)S(O)$_2$—N($R^{4b}$)($R^{4c}$), —N($R^{4a}$)S(O)$_2$O($R^{4b}$), —OC(O)$R^{4a}$, —OC(O)O$R^{4a}$, —OC(O)—N($R^{4a}$)($R^{4b}$), —S—$R^{4a}$, —S(O)$R^{4a}$, —S(O)(NH)$R^{4a}$, —S(O)$_2R^{4a}$, —S(O)$_2$N($R^{4a}$)($R^{4b}$), —S(O)(N$R^{4a}$)$R^{4b}$, or —Si($R^{4a}$)$_3$;

wherein the alkyl, haloalkyl, alkenyl, alkynyl, cycloalkyl, heterocyclyl, aryl, or heteroaryl is each optionally substituted with one to four $Z^{1b}$;

or two $R^4$ groups attached to adjacent ring atoms are combined with the atoms to which they are attached to form a $C_{5-10}$ cycloalkyl or heterocyclyl, which is each optionally substituted with one to four $Z^{1b}$;

$R^5$ is H, cyclopropyl, or $C_{1-3}$alkyl, wherein the $C_{1-3}$alkyl is optionally substituted with one, two or three groups selected from halogen, —OH, —OCH$_3$, —CN, oxo, and —N($R^{x1}$)($R^{x2}$);

or $R^5$ and $R^{y1}$ are combined with the atoms to which they are attached to form a $C_{3-10}$ cycloalkyl or heterocyclyl optionally substituted with oxo;

$R^{x1}$ and $R^{x2}$ are each independently H, $C_{1-6}$ alkyl, $C_{3-10}$ cycloalkyl, heterocyclyl, —S(O)$_2R^{6a1}$, or —S(O)$_2$N($R^{6a1}$)(N$R^{6a2}$), wherein the $C_{1-6}$ alkyl, cycloalkyl or heterocyclyl is each optionally substituted with F, —CN, oxo, or $C_{3-6}$ cycloalkyl;

or $R^{x1}$ and $R^{x2}$ are combined with the atom to which they are attached to form a heterocyclyl, which is optionally substituted with one to four $R^{6b1}$.

$R^{6a}$ is H, $C_{1-6}$ alkyl, $C_{3-10}$ cycloalkyl, heterocyclyl, —S(O)$_2R^{6a1}$, or —S(O)$_2$N($R^{6a1}$)(N$R^{6a2}$), wherein the cycloalkyl or heterocyclyl is each optionally substituted with $C_{1-6}$ alkyl, F, or —CN;

each $R^{6b}$ and $R^{6c}$ is independently H, $C_{1-6}$ alkyl, $C_{1-6}$ haloalkyl, $C_{2-6}$ alkoxyalkyl, halogen, $C_{3-10}$ cycloalkyl, heterocyclyl, —$C_{1-6}$ alkyl-N($R^{9a}$)($R^{9b}$), —CN, —O$R^{6c}$, or —N($R^{6c2}$)($R^{6c3}$), wherein the alkyl, cycloalkyl, or heterocyclyl is each optionally substituted with one to four $R^{6b1}$;

or $R^{6b}$ and $R^{6c}$ are combined with the atom to which they are attached to form $C_{3-10}$ cycloalkyl or heterocyclyl, which is each optionally substituted with one to four $R^{6b1}$;

or $R^{6a}$ or $R^{6c}$ is combined with one $R^4$ group and the atoms to which they are attached to form a $C_{5-10}$ cycloalkyl or heterocyclyl, which is each optionally substituted with one to four $R^{10}$;

each $R^{y1}$ and $R^{y2}$ is independently H, halo, $C_{1-6}$ alkyl, $C_{1-6}$ haloalkyl, wherein the alkyl and haloalkyl are each optionally substituted with oxo;

each $R^{3d}$, $R^{6b1}$, and $R^{10}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —OH, —CN, —NO$_2$, or —C(O)N($R^{2a}$)($R^{2b}$), wherein the heterocyclyl or heteroaryl is optionally substituted with $C_{1-6}$ alkyl, $C_{1-6}$ haloalkyl, or $C_{1-6}$ haloalkoxy; and each $R^{6a1}$, $R^{6a2}$, $R^{6c1}$, $R^{6c2}$, and $R^{6c3}$ is independently H, $C_{1-6}$ alkyl or $C_{3-10}$ cycloalkyl;

each $R^{9a}$ and $R^{9b}$ is independently H, $C_{1-6}$ alkyl, or $C_{1-6}$ haloalkyl;

each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —N$_3$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —N$R^{12a}$S(O)$_2$N($R^{12b}$)($R^{12c}$), —N$R^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2R^{12a}$, —S(O)$_2$N($R^{12a}$)($R^{12b}$), —S(O)(N$R^{12a}$)$R^{12b}$, or —Si($R^{12a}$)$_3$;

wherein the alkyl, haloalkyl, alkenyl, alkynyl, cycloalkyl, heterocyclyl, aryl, or heteroaryl is each optionally substituted with one to four $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—R$^{12a}$, —C(O)R$^{12a}$, —C(O)O—R$^{12a}$, —C(O)N(R$^{12a}$)(R$^{12b}$), —N(R$^{12a}$)(R$^{12b}$), —N(R$^{12a}$)$_2$(R$^{12b}$)$^+$, —N(R$^{12a}$)—C(O)R$^{12b}$, —N(R$^{12a}$)C(O)O(R$^{12b}$), —N(R$^{12a}$)C(O)N(R$^{12b}$)(R$^{12c}$), —N(R$^{12a}$)S(O)$_2$(R$^{12b}$), —N(R$^{12a}$)S(O)$_2$—N(R$^{12b}$)(R$^{12c}$), —N(R$^{12a}$)S(O)$_2$O (R$^{12b}$), —OC(O)R$^{12a}$, —OC(O)OR$^{12a}$, —OC(O)—N(R$^{12a}$)(R$^{12b}$), —S—R$^{12a}$, —S(O)R$^{12a}$, —S(O)(NH)R$^{12a}$, —S(O)$_2$R$^{12a}$, —S(O)$_2$N(R$^{12a}$)(R$^{12b}$), —S(O)(NR$^{12a}$)R$^{12b}$, or —Si(R$^{12a}$)$_3$;

wherein the alkyl, haloalkyl, alkenyl, alkynyl, cycloalkyl, heterocyclyl, aryl, or heteroaryl is each optionally substituted with one to four Z$^{1b}$;

each R$^8$ or Z$^{1b}$ is independently C$_{1-9}$ alkyl, C$_{1-8}$ haloalkyl, C$_{2-6}$ alkenyl, C$_{2-6}$ alkynyl, halogen, C$_{3-15}$ cycloalkyl, heterocyclyl, C$_{6-10}$ aryl, heteroaryl, oxo, —OH, —CN, —NO$_2$, —NH$_2$, —N$_3$, —SH, —O(C$_{1-9}$ alkyl), —O(C$_{1-8}$ haloalkyl), —O(C$_{2-6}$ alkenyl), —O(C$_{2-6}$ alkynyl), —O(C$_{3-15}$ cycloalkyl), —O(heterocyclyl), —O(C$_{6-10}$ aryl), —O(heteroaryl), —NH(C$_{1-9}$ alkyl), —NH(C$_{1-8}$ haloalkyl), —NH(C$_{2-6}$ alkenyl), —NH(C$_{2-6}$ alkynyl), —NH(C$_{3-15}$ cycloalkyl), —NH(heterocyclyl), —NH(C$_{6-10}$ aryl), —NH(heteroaryl), —N(C$_{1-9}$ alkyl)$_2$, —N(C$_{1-8}$ haloalkyl)$_2$, —N(C$_{2-6}$ alkenyl)$_2$, —N(C$_{2-6}$ alkynyl)$_2$, —N(C$_{3-15}$ cycloalkyl)$_2$, —N(heterocyclyl)$_2$, —N(C$_{6-10}$ aryl)$_2$, —N(heteroaryl)$_2$, —N(C$_{1-9}$ alkyl)(C$_{1-8}$ haloalkyl), —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(heterocyclyl), —N(C$_{1-9}$ alkyl)(C$_{6-10}$ aryl), —N(C$_{1-9}$ alkyl)(heteroaryl), —C(O)(C$_{1-9}$ alkyl), —C(O)(C$_{1-8}$ haloalkyl), —C(O)(C$_{2-6}$ alkenyl), —C(O)(C$_{2-6}$ alkynyl), —C(O)(C$_{3-15}$ cycloalkyl), —C(O)(heterocyclyl), —C(O)(C$_{6-10}$ aryl), —C(O)(heteroaryl), —C(O)O(C$_{1-9}$ alkyl), —C(O)O(C$_{1-8}$ haloalkyl), —C(O)O(C$_{2-6}$ alkenyl), —C(O)O(C$_{2-6}$ alkynyl), —C(O)O(C$_{3-15}$ cycloalkyl), —C(O)O(heterocyclyl), —C(O)O(C$_{6-10}$ aryl), —C(O)O(heteroaryl), —C(O)NH$_2$, —C(O)NH(C$_{1-9}$ alkyl), —C(O)NH(C$_{1-8}$ haloalkyl), —C(O)NH(C$_{2-6}$ alkenyl), —C(O)NH(C$_{2-6}$ alkynyl), —C(O)NH(C$_{3-15}$ cycloalkyl), —C(O)NH(heterocyclyl), —C(O)NH(C$_{6-10}$ aryl), —C(O)NH(heteroaryl), —C(O)N(C$_{1-9}$ alkyl)$_2$, —C(O)N(C$_{1-8}$ haloalkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(heterocyclyl)$_2$, —C(O)N(C$_{6-10}$ aryl)$_2$, —C(O)N(heteroaryl)$_2$, —NHC(O)(C$_{1-9}$ alkyl), —NHC(O)(C$_{1-8}$ haloalkyl), —NHC(O)(C$_{2-6}$ alkenyl), —NHC(O)(C$_{2-6}$ alkynyl), —NHC(O)(C$_{3-15}$ cycloalkyl), —NHC(O)(heterocyclyl), —NHC(O)(C$_{6-10}$ aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(heterocyclyl), —NHC(O)O(C$_{6-10}$ aryl), —NHC(O)O(heteroaryl), —NHC(O)NH(C$_{1-9}$ alkyl), —NHC(O)NH(C$_{1-8}$ haloalkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(heterocyclyl), —NHC(O)NH(C$_{6-10}$ aryl), —NHC(O)NH(heteroaryl), —NHS(O)(C$_{1-9}$ alkyl), —N(C$_{1-9}$ alkyl)(S(O)(C$_{1-9}$ alkyl), —S(C$_{1-9}$ alkyl), —S(C$_{1-8}$ haloalkyl), —S(C$_{2-6}$ alkenyl), —S(C$_{2-6}$ alkynyl), —S(C$_{3-15}$ cycloalkyl), —S(heterocyclyl), —S(C$_{6-10}$ aryl), —S(heteroaryl), —S(O)N(C$_{1-9}$ alkyl)$_2$, —S(O)(C$_{1-9}$ alkyl), —S(O)(C$_{1-8}$ haloalkyl), —S(O)(C$_{2-6}$ alkenyl), —S(O)(C$_{2-6}$ alkynyl), —S(O)(C$_{3-15}$ cycloalkyl), —S(O)(heterocyclyl), —S(O)(C$_{6-10}$ aryl), —S(O)(heteroaryl), —S(O)$_2$(C$_{1-9}$ alkyl), —S(O)$_2$(C$_{1-8}$ haloalkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(heterocyclyl), —S(O)$_2$(C$_{6-10}$ aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$;

wherein the alkyl, cycloalkyl, heterocyclyl, aryl, or heteroaryl in each instance is optionally substituted with one to three C$_{1-9}$ alkyl, C$_{1-8}$ haloalkyl, halogen, —OH, —NH$_2$, —O(C$_{1-9}$ alkyl), —O(C$_{1-8}$ haloalkyl), —O(C$_{3-15}$ cycloalkyl), —O(heterocyclyl), —O(aryl), —O(heteroaryl), —NH(C$_{1-9}$ alkyl), —NH(C$_{1-8}$ haloalkyl), —NH(C$_{3-15}$ cycloalkyl), —NH(heterocyclyl), —NH(aryl), —NH(heteroaryl), —N(C$_{1-9}$ alkyl)$_2$, —N(C$_{3-15}$ cycloalkyl)$_2$, —NHC(O)(C$_{1-8}$ haloalkyl), —NHC(O)(C$_{3-15}$ cycloalkyl), —NHC(O)(heterocyclyl), —NHC(O)(aryl), —NHC(O)(heteroaryl), —NHC(O)O(C$_{1-9}$ alkyl), —NHC(O)O(C$_{1-8}$ haloalkyl), —NHC(O)O(C$_{2-6}$ alkynyl), —NHC(O)O(C$_{3-15}$ cycloalkyl), —NHC(O)O(heterocyclyl), —NHC(O)O (aryl), —NHC(O)O(heteroaryl), —NHC(O)NH(C$_{1-9}$ alkyl), S(O)$_2$(C$_{1-9}$ alkyl), —S(O)$_2$(C$_{1-8}$ haloalkyl), —S(O)$_2$(C$_{3-15}$ cycloalkyl), —S(O)$_2$(heterocyclyl), —S(O)$_2$(aryl), —S(O)$_2$(heteroaryl), —S(O)(NH)(C$_{1-9}$ alkyl), —S(O)$_2$NH(C$_{1-9}$ alkyl), or —S(O)$_2$N(C$_{1-9}$ alkyl)$_2$; and each R$^{1b}$, R$^{1c}$, R$^{2a}$, R$^{2b}$, R$^{4a}$, R$^{4b}$, R$^{4c}$, R$^{9c}$, R$^{9d}$, R$^{12a}$, R$^{12b}$, and R$^{12c}$ is independently H, C$_{1-9}$ alkyl, C$_{2-6}$ alkenyl, C$_{2-6}$ alkynyl, C$_{3-15}$ cycloalkyl, heterocyclyl, C$_{6-10}$ aryl, or heteroaryl wherein the alkyl, alkenyl, alkynyl, cycloalkyl, heterocyclyl, aryl, or heteroaryl is each optionally substituted with one to four Z$^{1b}$;

subscript p is 1, 2, or 3;
subscript q is 0, 1, or 2; and
subscript n is 0, 1, 2, or 3; and
wherein each heteroaryl has 5 to 12 ring members and has one to four heteroatoms each independently N, O, or S; and
wherein each heterocyclyl has 3 to 12 ring members and has one to four heteroatoms each independently N, O, or S.

In some embodiments of the compound of Formula (I), or pharmaceutically acceptable salt thereof, R$^1$ is C$_{1-6}$ alkyl, C$_{1-6}$ haloalkyl, C$_{3-10}$ cycloalkyl, heterocyclyl, C$_{6-10}$ aryl, or heteroaryl; wherein the alkyl, haloalkyl, cycloalkyl, aryl, heteroaryl, or heterocyclyl is each optionally substituted with one to four Z$^1$.

In some embodiments of the compound of Formula (I), or pharmaceutically acceptable salt thereof, R$^1$ is C$_{6-10}$ aryl, or heteroaryl, which is each optionally substituted with one to three Z$^1$.

In some embodiments of the compound of Formula (I), or pharmaceutically acceptable salt thereof, R$^1$ is a 6 membered aryl or a 5 or 6 membered heteroaryl substituted with one, two, or three groups selected from C$_{1-8}$ haloalkyl, halogen, C$_{1-6}$ alkoxy, —CN, and —C(O)—N(R$^{12a}$)(R$^{12b}$).

In some embodiments of the compound of Formula (I), or pharmaceutically acceptable salt thereof, R$^1$ is a 6 membered aryl or a 5 or 6 membered heteroaryl substituted with one or two —Cl, —F, or —CN.

In some embodiments of the compound of Formula (I), (Ia), (Ib), (Ic), (Id), (Ie), (If), and/or (Ig), or pharmaceutically acceptable salt thereof, R$^5$ is hydrogen or methyl. In some embodiments, R$^5$ is methyl.

In some embodiments of the compound of Formula (I), or pharmaceutically acceptable salt thereof, at least one of Y$^1$ and Y$^2$ is —O—. In some embodiments, Y$^1$ and Y$^2$ are both —O—.

In some embodiments, the disclosure provides a compound, or a pharmaceutically acceptable salt thereof, having the structure of Formula (Ia) or (Ib):

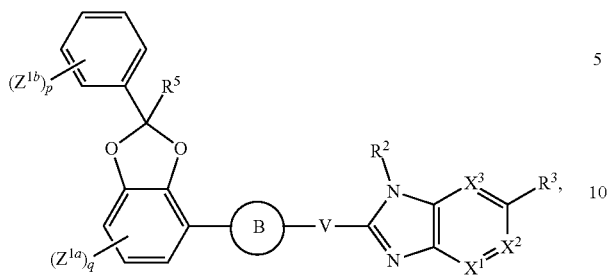

(Ia)

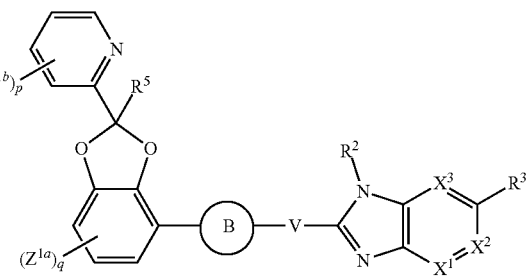

(Ib)

wherein $R^2$, $R^3$, $R^5$, ring B, V, $X^1$, $X^2$, $X^3$, $Z^{1a}$, $Z^{1b}$, p, and q are as set forth herein.

In some embodiments of the compound of Formula (I), (Ia), (Ib), (Ic), (Id), (Ie), (If), and/or (Ig), or pharmaceutically acceptable salt thereof, each $Z^{1a}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —OH, —CN, —$NO_2$, —$OR^{12a}$, —$C(O)N(R^{12a})(R^{12b})$, each of which is optionally substituted with $Z^{1b}$.

In some embodiments of the compound of Formula (I), (Ia), and/or (Ib), or pharmaceutically acceptable salt thereof, ring B is phenyl or 5 to 6 membered heteroaryl, wherein the phenyl or heteroaryl is optionally substituted with one to four $R^4$. In some embodiments, ring B is

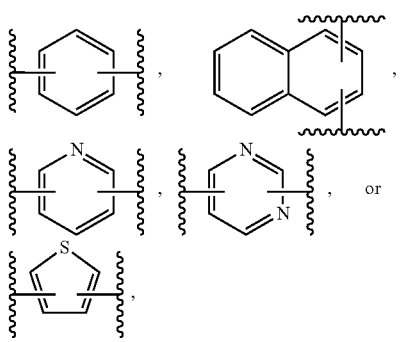

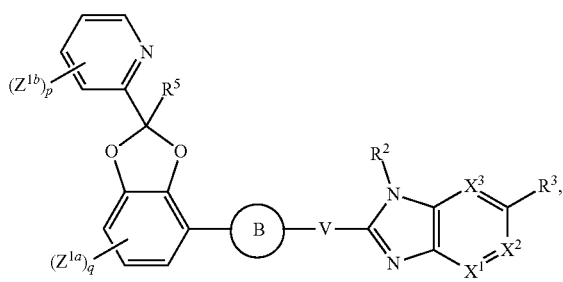

(Ib)

wherein:
subscript p is 1, 2, or 3;
subscript q is 0, 1, or 2; and
wherein $R^2$, $R^3$, $R^5$, ring B, V, $X^1$, $X^2$, $X^3$, $Z^{1a}$, and $Z^{1b}$ are as set forth herein.

In some embodiments, the disclosure provides a compound, or a pharmaceutically acceptable salt thereof, having the structure of Formula (Ia)

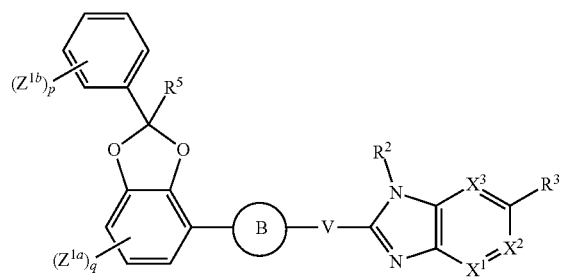

(Ia)

wherein $R^2$, $R^3$, $R^5$, ring B, V, $X^1$, $X^2$, $X^3$, $Z^{1a}$, $Z^{1b}$, p, and q are as set forth herein.

In some embodiments, the disclosure provides a compound, or a pharmaceutically acceptable salt thereof, having the structure of Formula (Ib)

which are each optionally substituted with one to three $R^4$.

In some embodiments of the compound of Formula (I), (Ia), and/or (Ib), or pharmaceutically acceptable salt thereof, ring B is

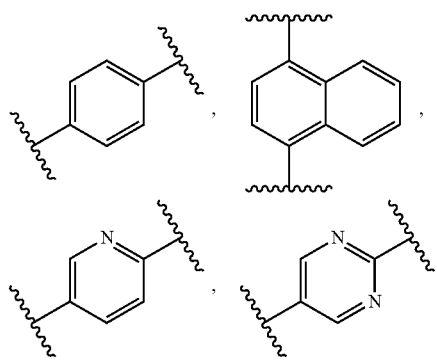

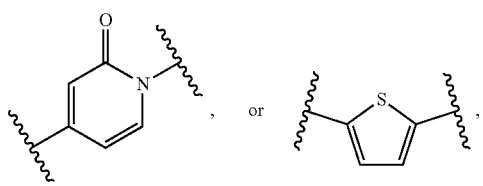

which are each optionally substituted with one or two $R^4$.

In some embodiments, a compound of the disclosure, or a pharmaceutically acceptable salt thereof, has the structure of Formula (Ic) or (Id):

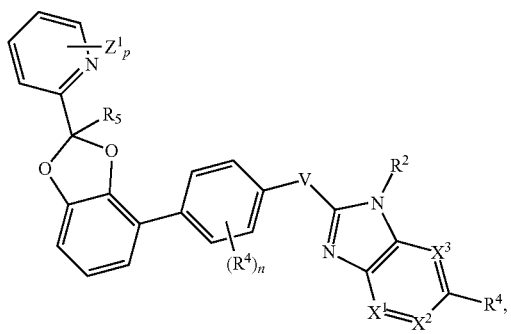

wherein
subscript n is 0, 1, 2, or 3;
subscript p is 1, 2, or 3; and
wherein $R^2$, $R^3$, $R^4$, $R^5$, V, $X^1$, $X^2$, $X^3$, and $Z^1$ are as defined herein.

In some embodiments of the compound of Formula (I), (Ia), (Ib), (Ic), and/or (Id), or pharmaceutically acceptable salt thereof, $X^1$, $X^2$, and $X^3$ are each independently —CH=, —C(F)=, —C(Cl)=, —C(Br)=, or —C(CN)=.

In some embodiments of the compound of Formula (I), (Ia), (Ib), (Ic), and/or (Id), or pharmaceutically acceptable salt thereof, V is —O—, —NH—, or —CH$_2$—.

In some embodiments, a compound of the disclosure, or a pharmaceutically acceptable salt thereof, has the structure of Formula (Ie) or (If):

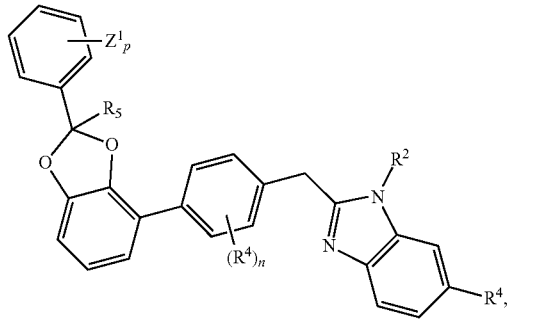

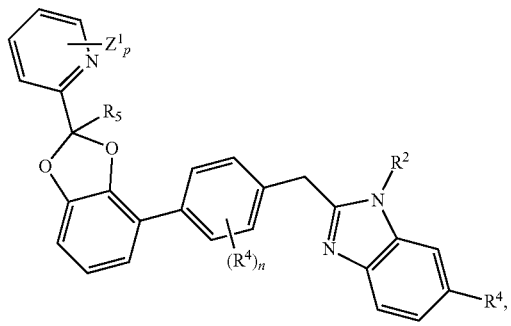

wherein
subscript n is 0, 1, 2, or 3;
subscript p is 1, 2, or 3; and
wherein $R^2$, $R^3$, $R^4$, $R^5$, and $Z^1$ are as defined herein.

In some embodiments, a compound of the disclosure, or a pharmaceutically acceptable salt thereof, has the structure of Formula (Ig):

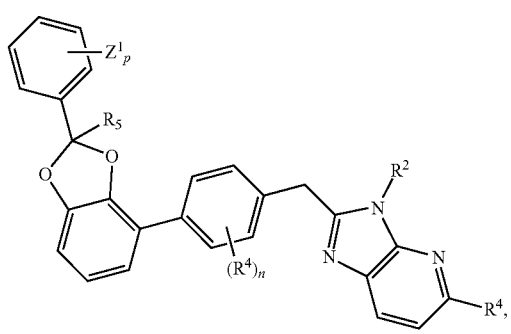

wherein
subscript n is 0, 1, 2, or 3; and
subscript p is 1, 2, or 3.

In some embodiments of the compound of Formula (I), (Ia), (Ib), (Ic), (Id), (Ie), (If), and/or (Ig), or pharmaceutically acceptable salt thereof, each $Z^1$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, heterocyclyl-$C_{1-6}$ alkyl, heterocyclyl-$C_{1-6}$ haloalkyl, heteroaryl-$C_{1-6}$ alkyl, heteroaryl-$C_{1-6}$ haloalkyl, oxo, —OH, —CN, —NO$_2$, or —C(O)N($R^{12a}$)($R^{12b}$), wherein the heteroaryl or heterocyclyl is each optionally substituted with one to four halogen, $C_{1-6}$ haloalkyl, $C_{3-6}$ cycloalkyl, 4-6 membered heterocyclyl, or —CN.

In some embodiments of the compound of Formula (I), (Ia), (Ib), (Ic), (Id), (Ie), (If), and/or (Ig), or pharmaceutically acceptable salt thereof, each $Z^1$ is independently $C_{1-6}$ alkyl, $C_{1-6}$ haloalkyl, $C_{1-6}$ alkoxy, $C_{1-6}$ haloalkoxy, halogen, oxo, —OH, —CN, or —NO$_2$, $C_{3-10}$ cycloalkyl, 3 to 12 membered heterocyclyl having one to three heteroatoms, or 5 to 10 membered heteroaryl having one to three heteroatoms. In some embodiments, each $Z^1$ is independently $C_{1-6}$ haloalkyl, $C_{1-6}$ haloalkoxy, halogen, —CN, or 5 to 6 membered heteroaryl having one to three heteroatoms. In some embodiments, each $Z^1$ is independently halogen, $C_{1-6}$ haloalkyl, $C_{1-3}$ alkoxy, $C_{3-10}$ cycloalkyl, or —CN.

In some embodiments of the compound of Formula (I), (Ia), (Ib), (Ic), (Id), (Ie), (If), and/or (Ig), or pharmaceutically acceptable salt thereof, $R^2$ is H, $C_{1-6}$ alkyl, $C_{1-6}$ haloalkyl, $C_{2-6}$ alkoxyalkyl, $C_{2-6}$ alkenyl, $C_{2-6}$ alkynyl, $C_{3-10}$ cycloalkyl, heterocyclyl, $C_{6-10}$ aryl, heteroaryl, $C_{1-6}$ alkyl-$C_{3-10}$ cycloalkyl, $C_{1-6}$ alkyl-heterocyclyl, $C_{1-6}$ alkyl-$C_{6-10}$ aryl, $C_{1-6}$ alkyl-heteroaryl, $C_{1-6}$ alkyl-$C_{3-10}$ cycloalkyl-$C_{1-6}$ alkyl, $C_{1-6}$ alkyl-heterocyclyl-$C_{1-6}$ alkyl, —C(O)$R^{2a}$, —C(O)O$R^{2a}$, —C(O)N($R^{2a}$)($R^{2b}$), —C(O)N$R^{2c}$S(O)$_2R^{2a}$, —S(O)$_2R^{2a}$, —S(O)$_2$N($R^{2a}$)($R^{2b}$), or —S(O)$_2$N$R^{2c}$C(O)$R^{2a}$, wherein the alkyl, cycloalkyl, aryl, heteroaryl, and heterocyclyl are each optionally substituted with one to four $Z^{1b}$, wherein each $Z^{1b}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, heterocyclyl-$C_{1-6}$ alkyl, heterocyclyl-$C_{1-6}$ haloalkyl, heteroaryl-$C_{1-6}$ alkyl, heteroaryl-$C_{1-6}$ haloalkyl, oxo, —OH, —CN, —NO$_2$, or —C(O)N($R^{12a}$)($R^{12b}$).

In some embodiments of the compound of Formula (I), (Ia), (Ib), (Ic), (Id), (Ie), (If), and/or (Ig), or pharmaceutically acceptable salt thereof, $R^2$ is $C_{1-6}$ alkyl, $C_{3-10}$ cycloalkyl, heterocyclyl, heteroaryl, $C_{1-6}$ alkyl-$C_{3-10}$ cycloalkyl, $C_{1-6}$ alkyl-heteroaryl, $C_{1-6}$ alkyl-$C_{3-10}$ cycloalkyl-$C_{1-6}$ alkyl, $C_{1-6}$ alkyl-heterocyclyl-$C_{1-6}$ alkyl, or $C_{1-6}$ alkyl-heteroaryl, each of which is optionally substituted with one to four $Z^{1b}$. In some embodiments, $R^2$ is $C_{1-6}$ alkyl-$C_{3-10}$ cycloalkyl or $C_{1-6}$ alkyl-$C_{3-10}$ cycloalkyl-$C_{1-6}$ alkyl, which is each optionally substituted with one to four $Z^{1b}$.

In some embodiments, wherein $R^2$ is:

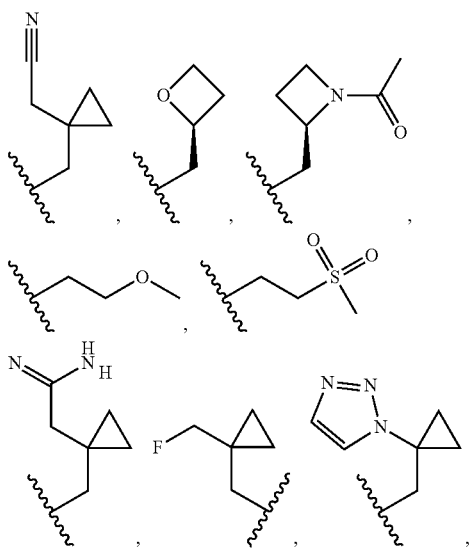

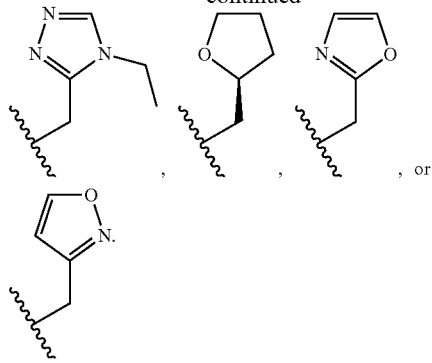

In some embodiments, $R^2$ is:

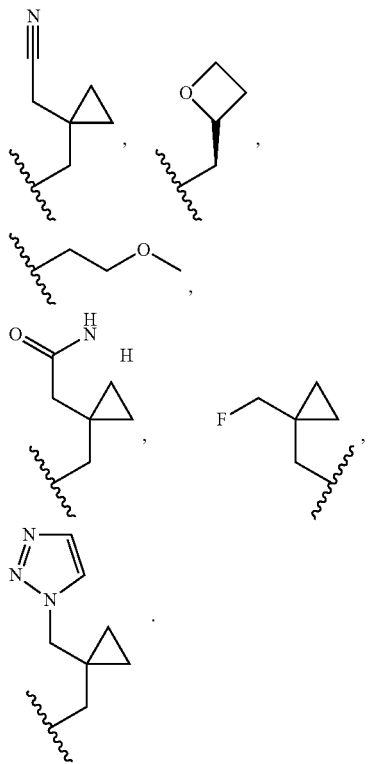

In some embodiments of the compound of Formula (I), (Ia), (Ib), (Ic), (Id), (Ie), (If), and/or (Ig), or pharmaceutically acceptable salt thereof, $R^3$ is heteroaryl, —C(O)OH, —C(O)O$R^{3a}$, —C(O)N($R^{3a}$)S(O)$_2$($R^{3b}$), —S(O)$_2$NHC(O)$R^{3a}$, or —C(O)N($R^{3a}$)S(O)$_2$N($R^{3b}$)($R^{3c}$), wherein the heteroaryl is optionally substituted with one to four $R^{3d}$. In some embodiments, $R^3$ is 5 to 6 membered heteroaryl, optionally substituted with one to four $R^{3d}$. In some embodiments, $R^3$ is —C(O)O$R^{3a}$. In some embodiments, $R^3$ is —C(O)OH.

In some embodiments of the compound of Formula (I), (Ia), (Ib), (Ic), (Id), (Ie), (If), and/or (Ig), or pharmaceutically acceptable salt thereof, each $R^4$ is independently $C_{1-6}$ alkyl, $C_{1-6}$ haloalkoxy, $C_{2-6}$ alkoxyalkyl, halogen, oxo, —CN, or —OR$^{4a}$. In some embodiments, each $R^4$ is independently $C_{1-6}$ alkyl, halogen, oxo, —CN, or —OR$^{4a}$. In some embodiments, each $R^4$ is independently $C_{1-6}$ alkyl, halogen, oxo, —OH, or —CN. In some embodiments, each $R^4$ is independently F, oxo, or —CN.

In some embodiments of the compound of Formula (I), (Ia), (Ib), (Ic), (Id), (Ie), (If), and/or (Ig), or pharmaceutically acceptable salt thereof, $R^{6a}$ is H, $C_{1-6}$ alkyl, $C_{3-10}$ cycloalkyl, or heterocyclyl. In some embodiments, each $R^{6b}$ and $R^{6c}$ is independently H, $C_{1-3}$ alkyl, F, Cl, or —CN.

In some embodiments of the compound of Formula (I), (Ic), (Id), (Ie), (If), and/or (Ig), or pharmaceutically acceptable salt thereof, or pharmaceutically acceptable salt thereof, subscript n is 0, 1, or 2.

In some embodiments of the compound of Formula (I), (Ia), (Ib), (Ic), (Id), (Ie), (If), and/or (Ig), or pharmaceutically acceptable salt thereof, subscript p is 1 or 2.

In some embodiments, a compound of Formula (I), (Ia), (Ib), (Ic), (Id), (Ie), (If), and/or (Ig), or pharmaceutically acceptable salt thereof, has a formula:

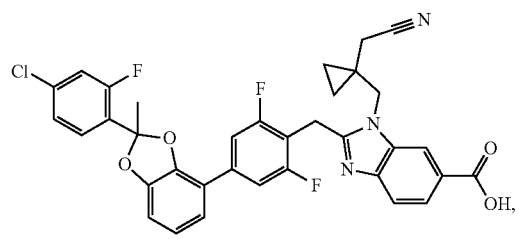

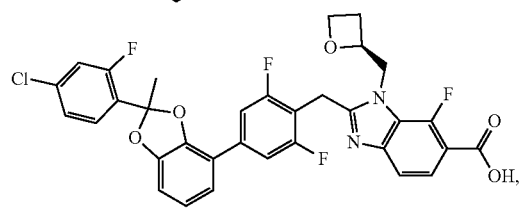

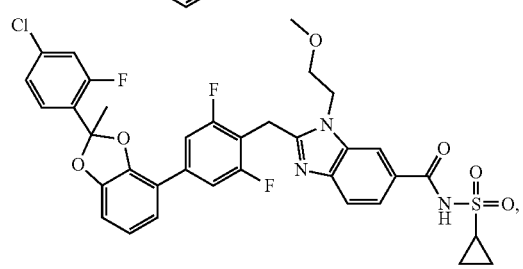

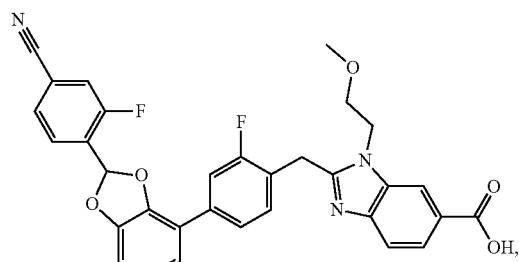

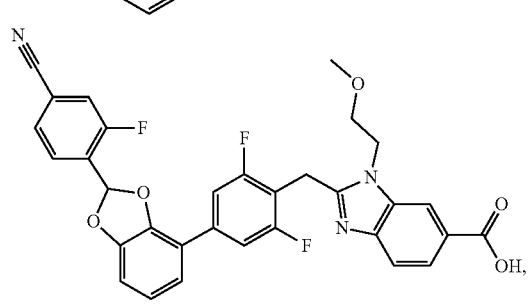

-continued

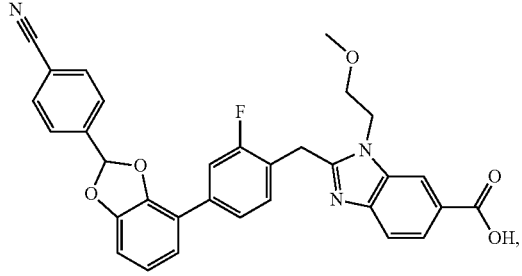

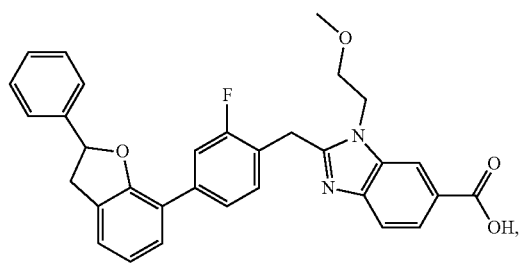

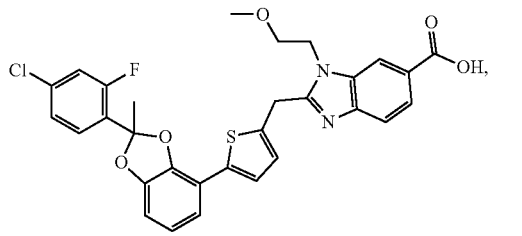

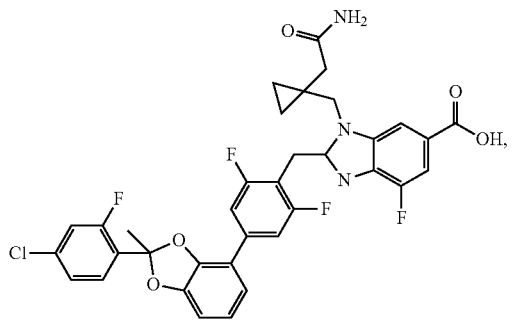

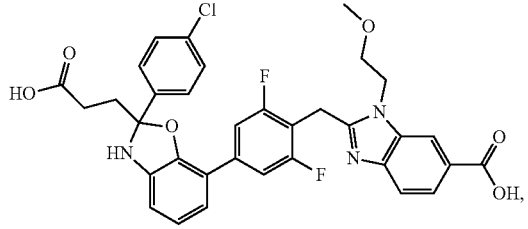

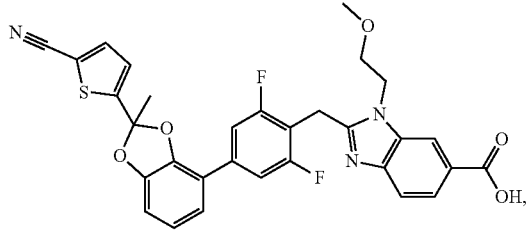

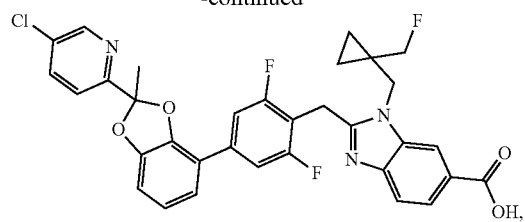
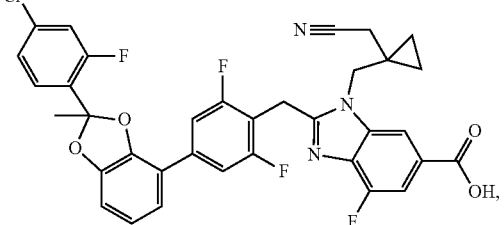
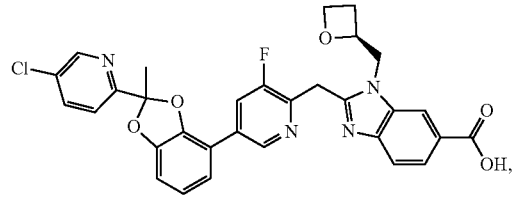
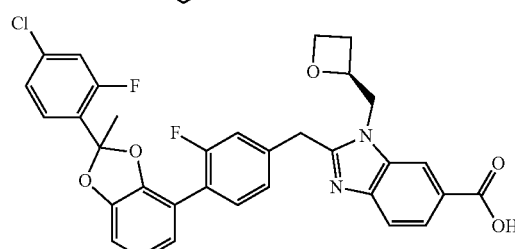
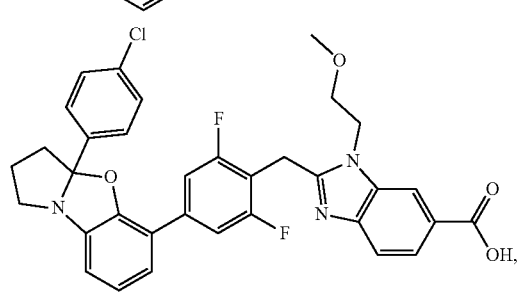
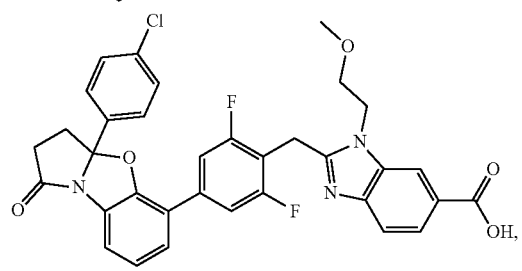
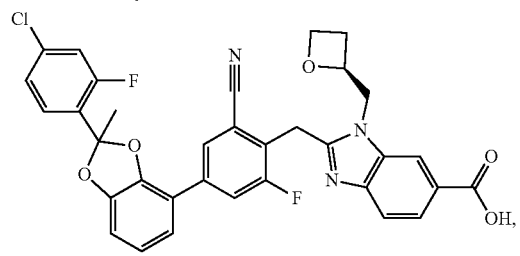
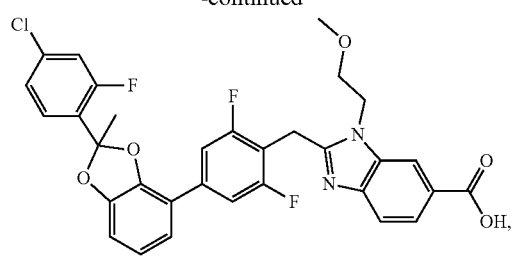
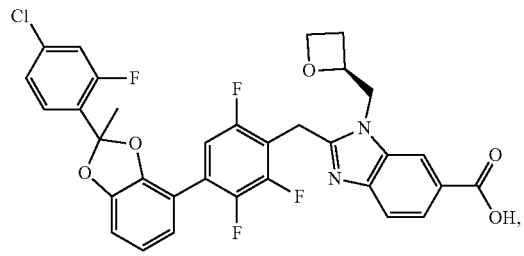
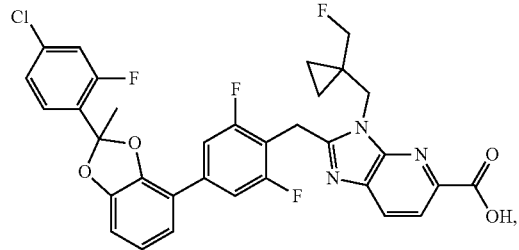
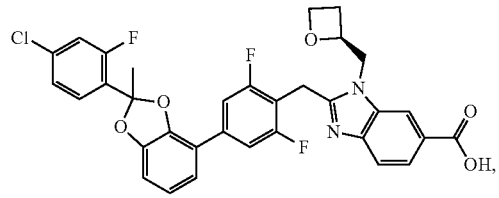
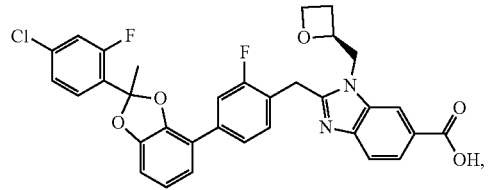
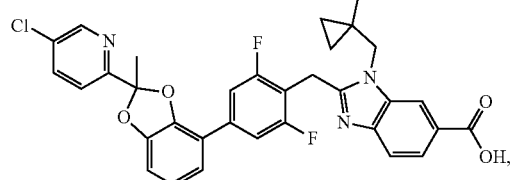
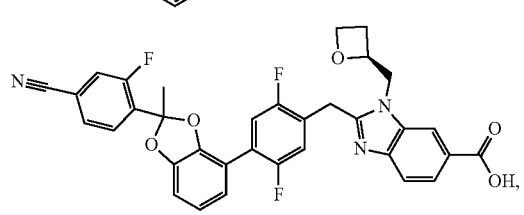

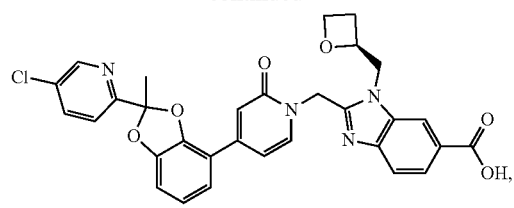
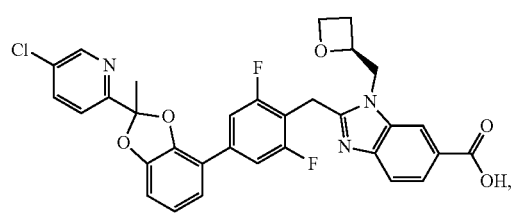
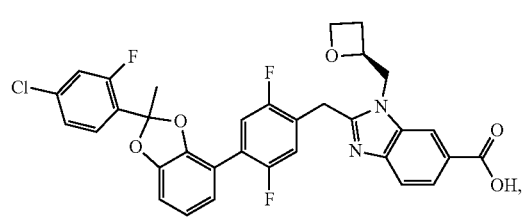
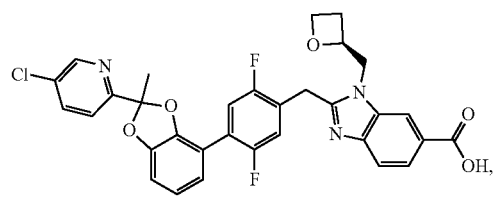
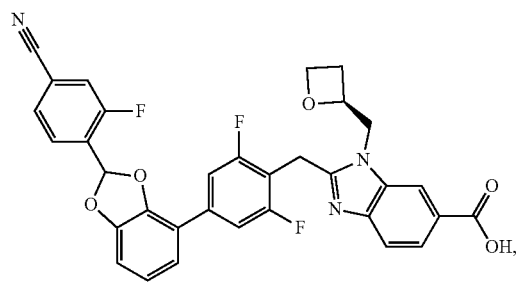
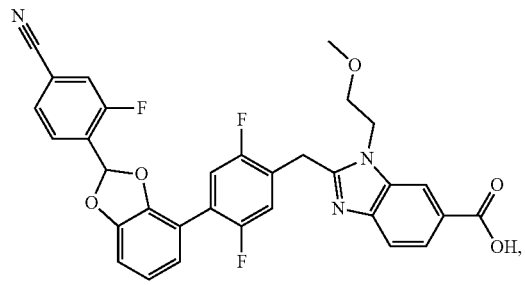
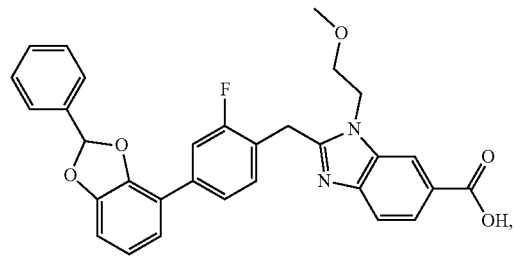
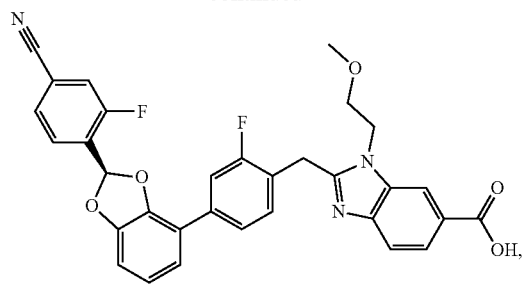
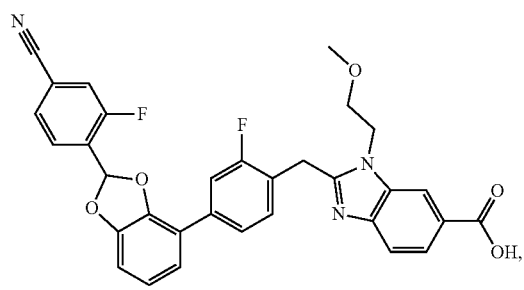
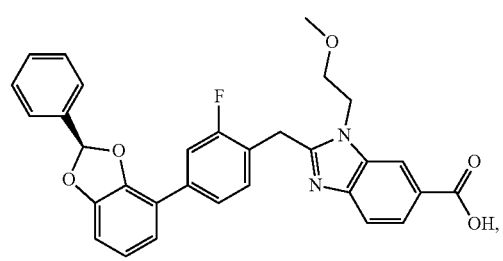
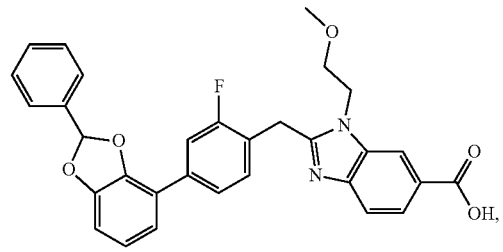
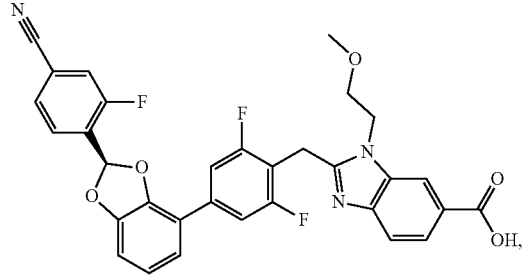
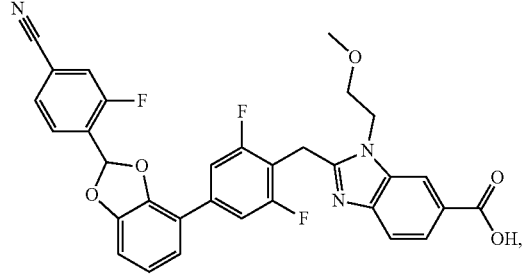

-continued

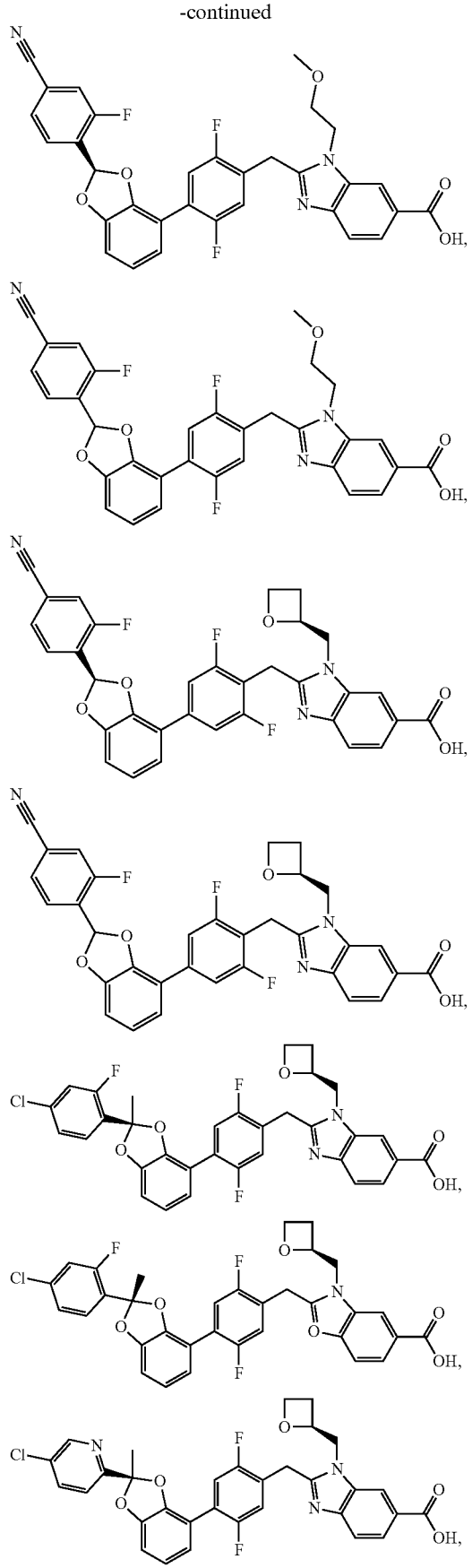

-continued

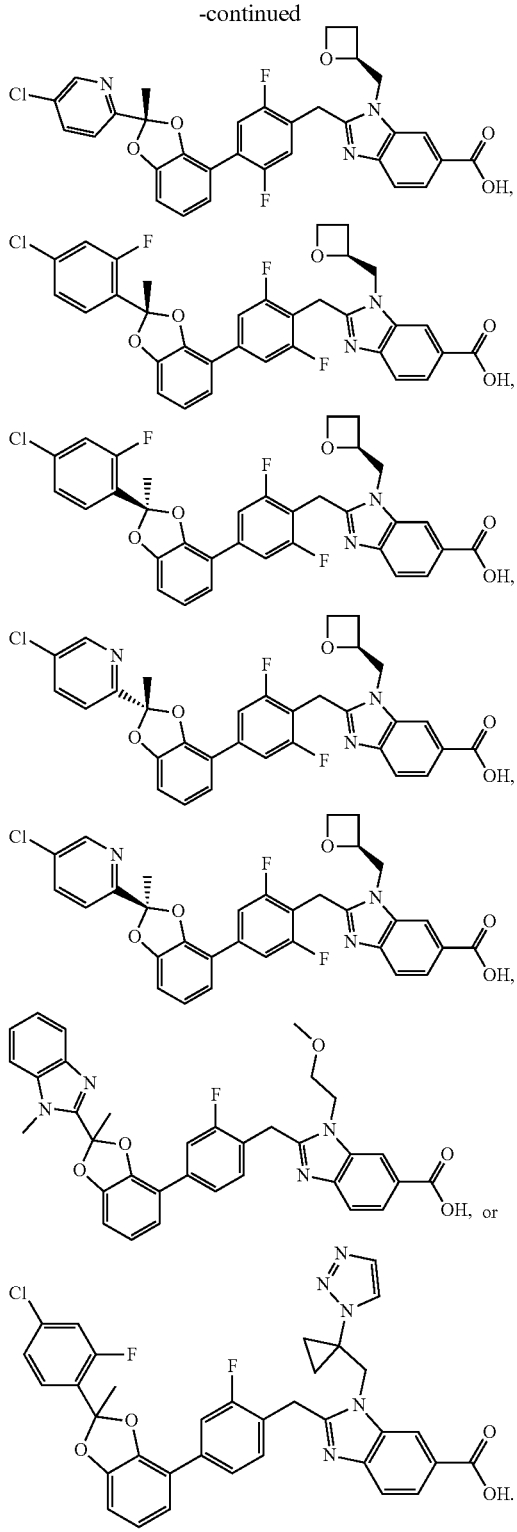

Also disclosed herein are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, included are novel and unobvious compounds produced by a process comprising contacting a compound with a mammal for a period of time sufficient to yield a metabolic product thereof. Such products typically are identified by preparing a radiolabeled (e.g. $^{14}C$ or $^{3}H$) compound, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products can be easily isolated since they are labeled (others are isolated by the use of antibodies capable of binding epitopes surviving in the metabolite). The metabolite structures are determined in conventional fashion, e.g. by MS or NMR analysis. In general, analysis of metabolites can be done in the same way as conventional drug metabolism studies well-known to those skilled in the art. The conversion products, so long as they are not otherwise found in vivo, can be useful in diagnostic assays for therapeutic dosing of the compounds even if they possess no GLP-1R activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs typically will be stable in the digestive system but may be substantially hydrolyzed to the parental drug in the digestive lumen, liver, lung or other metabolic organ, or within cells in general. As used herein, a prodrug is understood to be a compound that is chemically designed to efficiently liberate the parent drug after overcoming biological barriers to oral delivery.

III. Methods of Preparing Compounds

The compounds of the present disclosure can be prepared by any method known in the art. The following exemplary general methods illustrate routes that may be used to obtain a compound of the present disclosure.

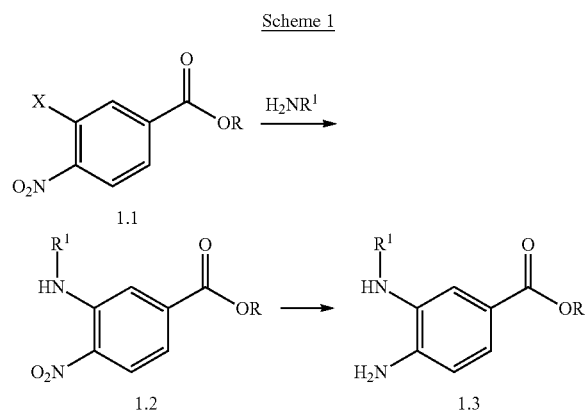

Compounds of formula 1.3 may be assembled by first reacting an amine with intermediate 1.1 in the presence of a suitable base (e.g. DIPEA, KOtBu, etc.) to give intermediate 1.2. This can then be converted to the intermediate 1.3 using suitable reducing conditions (e.g. $H_2$ and Pd/C, Fe and HCl, etc.).

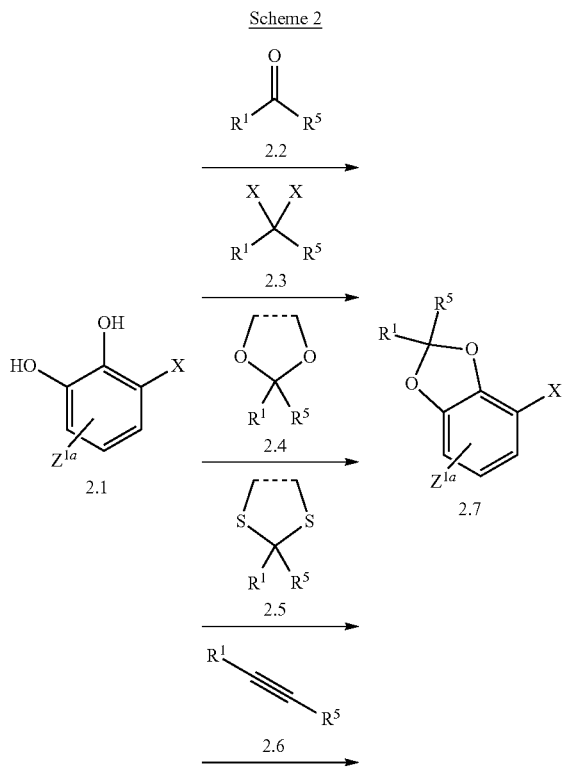

Compounds of formula 2.7 may be assembled by reacting substituted diols of general structure 2.1 with ketones or aldehydes of general structure 2.2 with a catalytic quantity of a mild acid catalyst such as para-toluene sulfonic acid at reflux in aprotic solvent such as benzene, toluene, or xylenes. During the course of this reaction, water may be removed azeotropically via a Dean-Stark trap or with molecular sieves. Catechols of formula 2.1 may also be reacted with bis-halides of formula 2.3 in the presence of organic bases such as pyridine to form compounds of general structure 2.7. Additionally, acetals or ketals of acyclic (dotted line does not exist) or cyclic (dotted line exists) structure 2.4 may be reacted with catechols of formula 2.1 in the presence of either acid or base to furnish compounds of structure 2.7. In a similar fashion, thioacetals or thioketals of acyclic (dotted line does not exist) or cyclic (dotted line exists) structure 2.5 may be reacted with catechols of formula 2.1 in the presence of mercury salts, mild oxidants, or alkylating agents to furnish compounds of structure 2.7. Additionally, alkynes of the formula 2.6, where $R^1$ is aryl or heteroaryl, may be reacted with catechols of formula 2.1 in the presence of triruthenium dodecacarbonyl in an aprotic solvent such as toluene to form compounds of formula 2.7. The reaction is degassed with an inert gas like argon or nitrogen and stirred at 100° C.

Scheme 3

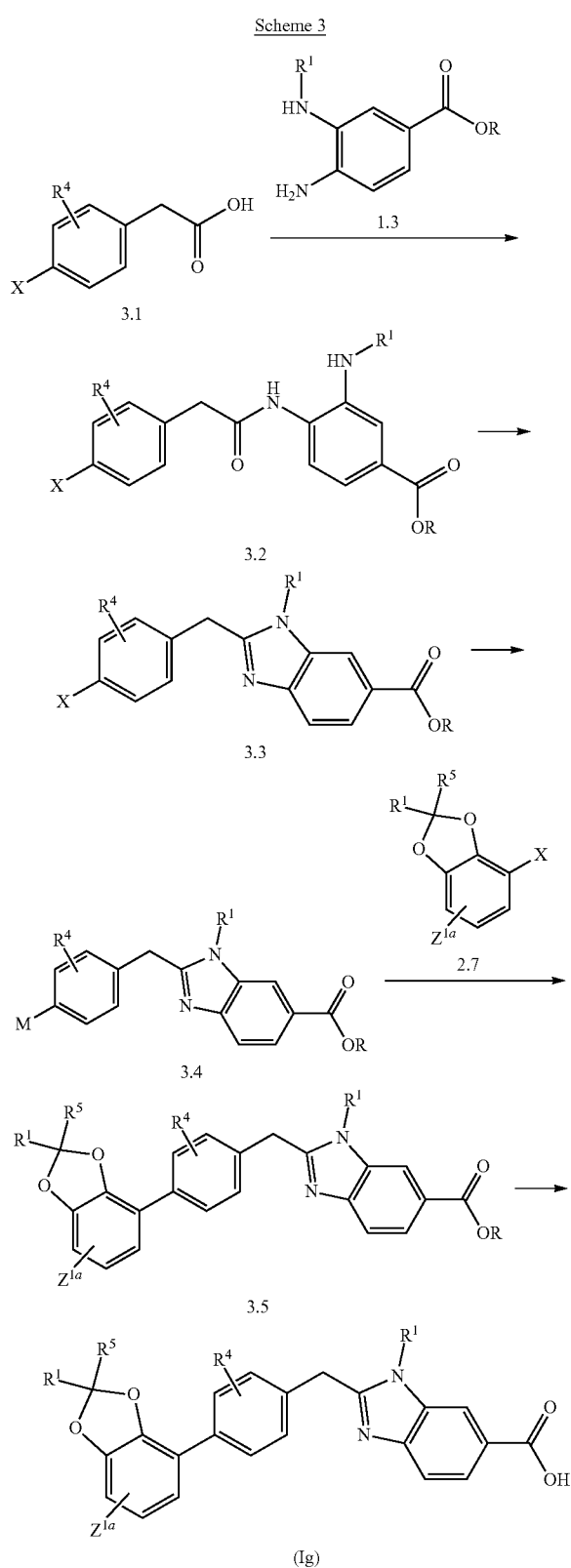

with HATU, etc.). Treatment with a suitable acid catalyst (e.g. HCl, AcOH, etc.) can deliver intermediate 3.3. Halogen metal exchange of —X to -M can then be achieved using a suitable reagent (e.g. iPrMgBr, etc.) or transition metal coupling using a suitable palladium catalyst and metal source (e.g. $B_2Pin_2$, $Bu_6Sn_2$, etc.) to give intermediate 3.4. This can then be coupled to intermediate 2.7 using a suitable palladium catalyst to deliver intermediate 3.5. If R=methyl or ethyl, compound 3.5 can be converted to formula (Ig) using standard ester hydrolysis conditions (e.g. LiOH, LiI and pyridine, $Me_3SnOH$, etc.). If R=tert-butyl, compound 3.5 can be converted to formula (Ig) in the presence of protic acid (e.g. trifluoroacetic acid, etc.).

Scheme 4

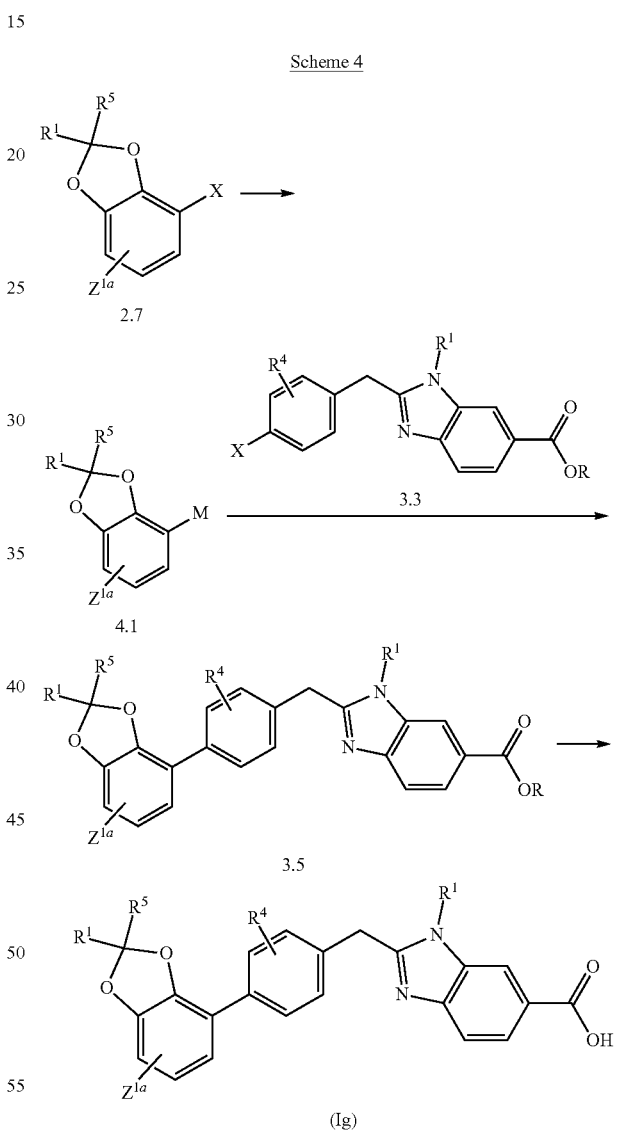

Exemplary compounds of formula (I), such as compounds of formula (Ig) as depicted above, can be assembled first by the combination of intermediate 3.1 with intermediate 1.3 under standard amide bond forming conditions (e.g. DIPEA Exemplary compounds of formula (I), including compounds of formula (Ig) above, can be formed by first conversion of intermediate 2.7 to the metallated variant intermediate 4.1 using a suitable palladium catalyst and metal source (e.g. bis(neopentyl glycolato)diboron, $B_2Pin_2$, $Bu_6Sn_2$, etc.). This can then be coupled to intermediate 3.3 using a suitable palladium catalyst to deliver intermediate 3.5. If R is methyl or ethyl, compound 3.5 can be converted to formula (Ig) using standard ester hydrolysis conditions (e.g. LiOH, LiI and pyridine, Me₃SnOH, etc.). If R is tert-butyl, compound 3.5 can be converted to formula (Ig) in the presence of protic acid (e.g. trifluoroacetic acid, etc.).

Scheme 5

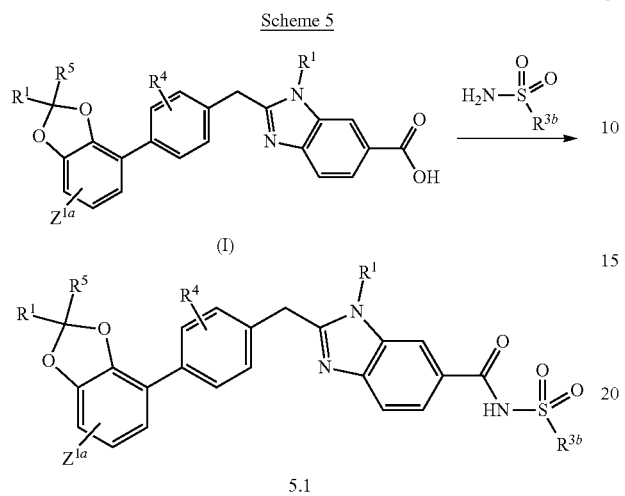

Compounds of the formula 5.1 can be obtained through the reaction of formula (I) with a sulfonamide under suitable coupling conditions (e.g. EDC and DMAP, etc.).

Scheme 6

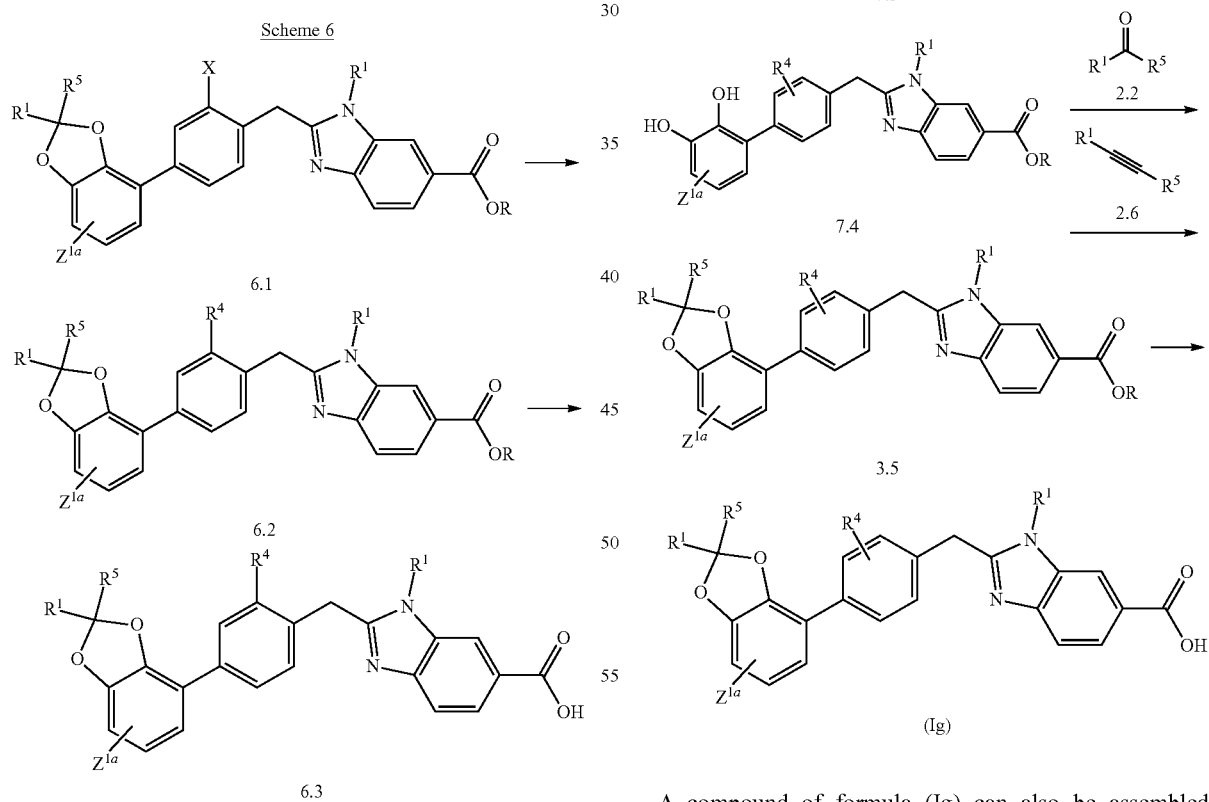

A compound of the formula 6.3 can be assembled via first coupling to the halogen —X of intermediate 6.1 using a suitable coupling partner and palladium catalyst to deliver intermediate 6.2 which can be converted to compound 6.3 using standard ester hydrolysis conditions (e.g. LiOH, LiI and pyridine, etc.).

Scheme 7

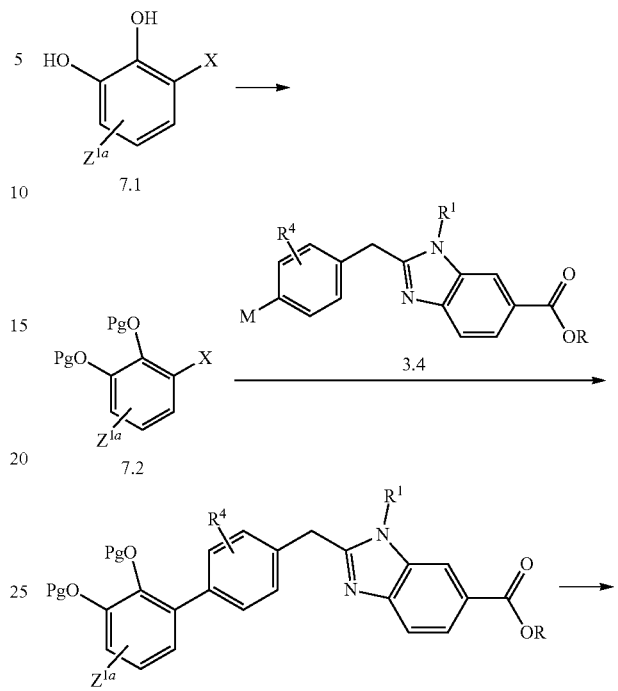

A compound of formula (Ig) can also be assembled through protecting the alcohol groups of intermediate 7.1 (protecting group Pg may be benzyl or trimethylsilylethoxymethyl) to furnish intermediate 7.2. Cross-coupling intermediate of the type 3.4 with intermediate 7.2 using a suitable transition metal catalyst (e.g. palladium, etc.) may furnish intermediate 7.3. This can then be deprotected (e.g. using a metal catalyst and H₂ gas when Pg is benzyl, or by using HCl or TFA when Pg is trimethylsilylethoxymethyl) to furnish intermediate 7.4. Intermediate 7.4 can be reacted with carbonyl-containing intermediates 2.2 or alkyne intermediates 2.6 to access intermediates 3.5 in manner similar to the procedures described in Scheme 2. This can then be converted to formula (Ig) using standard ester hydrolysis conditions (e.g. LiOH, LiI and pyridine, etc.).

Scheme 8

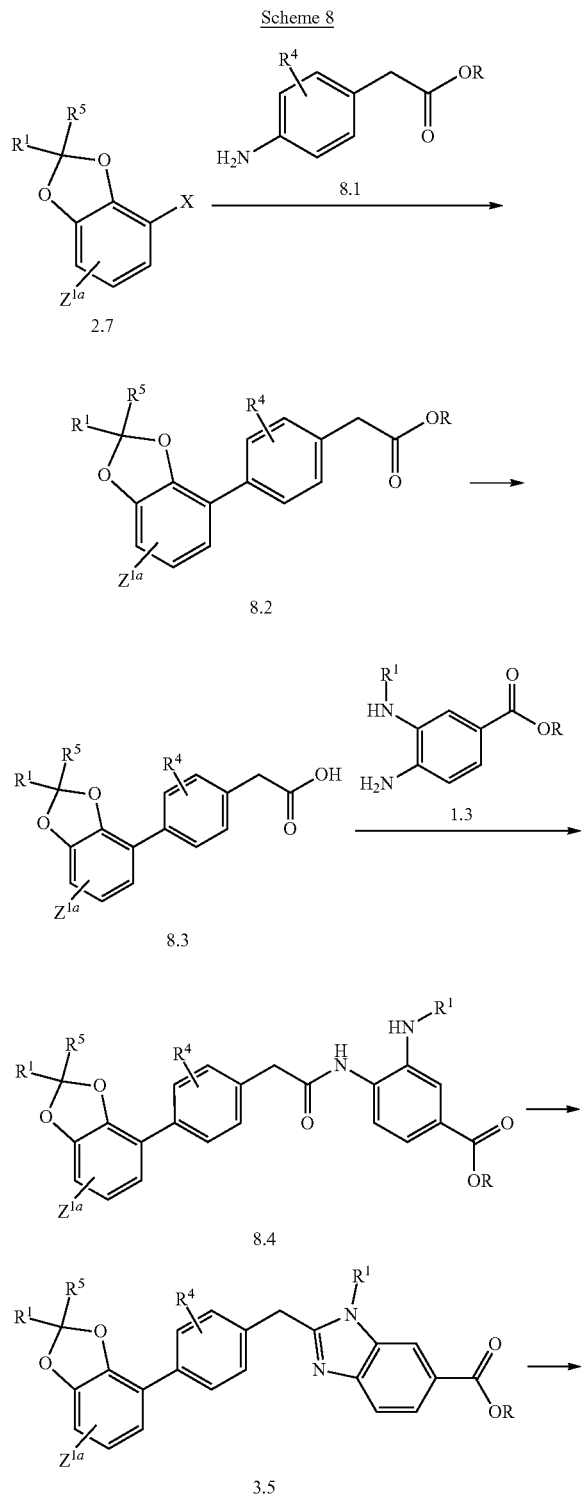

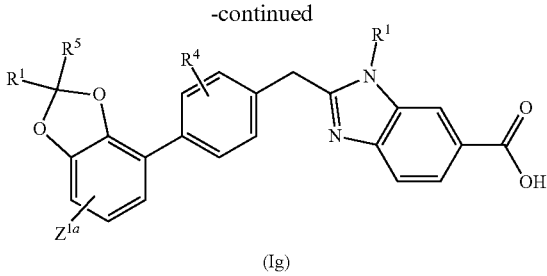

Compounds of formula (Ig) may also be assembled by first coupling an intermediate 2.7 with an intermediate 8.1 (purchased commercially or obtained through metalation of a corresponding halide) using a suitable palladium catalyst to deliver intermediate 8.2. Following conversion to the acid 8.3 using standard conditions (e.g. LiOH, LiI and pyridine, etc.), the intermediate 1.3 can be coupled using standard amide bond forming conditions (e.g. DIPEA with HATU, etc.) to give intermediate 8.4. This can then be converted to the corresponding benzimidazole 3.5 under the influence of an acid catalyst (e.g. HCl, AcOH, TFA, etc.) after which it can be converted to formula (Ig) using standard ester hydrolysis conditions (e.g. LiOH, LiI and pyridine, etc.).

Scheme 9

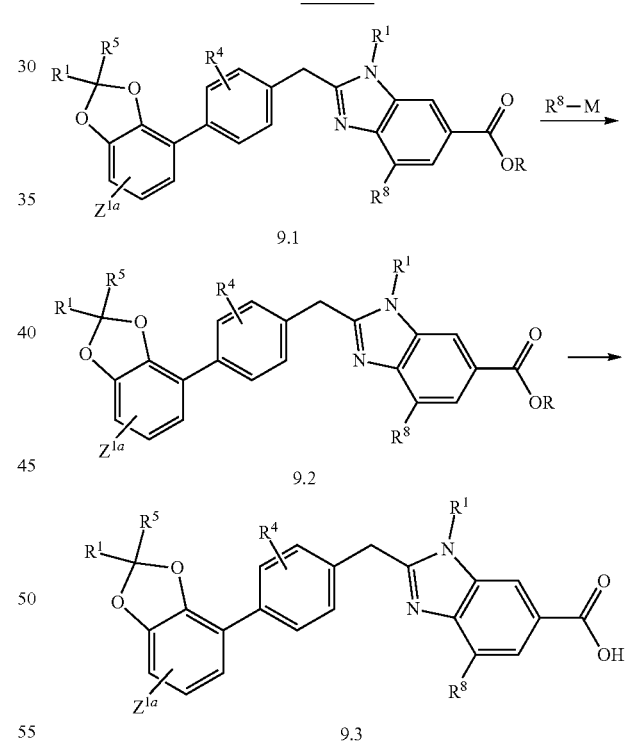

A compound of the formula 9.3 can be assembled via first coupling to the halogen —X of intermediate 9.1 using a suitable coupling partner and metal catalyst (e.g. palladium, etc.) to deliver intermediate 9.2 which can be converted to compound 9.3 using standard ester hydrolysis conditions (e.g. LiOH, LiI and pyridine, etc.).

IV. Pharmaceutical Formulations

In some embodiments, the present disclosure provides a pharmaceutical composition comprising a compound of the present disclosure (e.g. a compound of Formula (I), (Ia), (Ib), (Ic), (Id), (Ie), (If), and/or (Ig), or a pharmaceutically acceptable salt thereof), and a pharmaceutically acceptable excipient.

In some embodiments, the pharmaceutical composition comprises a compound of Formula (I), (Ia), (Ib), (Ic), (Id), (Ie), (If), and/or (Ig), or a pharmaceutically acceptable salt thereof, and one or more additional therapeutic agents, as more fully set forth below.

Pharmaceutical compositions comprising the compounds disclosed herein, or pharmaceutically acceptable salts thereof, may be prepared with one or more pharmaceutically acceptable excipients which may be selected in accord with ordinary practice. Tablets may contain excipients including glidants, fillers, binders and the like. Aqueous compositions may be prepared in sterile form, and when intended for delivery by other than oral administration generally may be isotonic. In some embodiments, compositions may contain excipients such as those set forth in the Rowe et al, Handbook of Pharmaceutical Excipients, $6^{th}$ edition, American Pharmacists Association, 2009. Excipients can include ascorbic acid and other antioxidants, chelating agents such as EDTA, carbohydrates such as dextrin, hydroxyalkylcellulose, hydroxyalkylmethylcellulose, stearic acid and the like. In some embodiments, the composition is provided as a solid dosage form, including a solid oral dosage form.

The compositions include those suitable for various administration routes, including oral administration. The compositions may be presented in unit dosage form and may be prepared by any of the methods well known in the art of pharmacy. Such methods include the step of bringing into association the active ingredient (e.g., a compound of the present disclosure or a pharmaceutical salt thereof) with one or more pharmaceutically acceptable excipients. The compositions may be prepared by uniformly and intimately bringing into association the active ingredient with liquid excipients or finely divided solid excipients or both, and then, if desired, shaping the product. Techniques and formulations generally are found in Remington: The Science and Practice of Pharmacy, $21^{st}$ Edition, Lippincott Wiliams and Wilkins, Philadelphia, Pa., 2006.

Compositions described herein that are suitable for oral administration may be presented as discrete units (a unit dosage form) including but not limited to capsules, sachets or tablets each containing a predetermined amount of the active ingredient. In one embodiment, the pharmaceutical composition of the disclosure is a tablet.

Pharmaceutical compositions disclosed herein comprise one or more compounds disclosed herein, or a pharmaceutically acceptable salt thereof, together with a pharmaceutically acceptable excipient and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more excipients including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the mode of administration. For example, in some embodiments, a dosage form for oral administration to humans may contain approximately 1 to 1000 mg of active material formulated with an appropriate and convenient amount of a pharmaceutically acceptable excipient. In some embodiments, the pharmaceutically acceptable excipient varies from about 5 to about 95% of the total compositions (weight:weight).

In some embodiments, a composition comprising a compound of the present disclosure, or a pharmaceutically acceptable salt thereof in one variation does not contain an agent that affects the rate at which the active ingredient is metabolized. Thus, it is understood that compositions comprising a compound of the present disclosure in one aspect do not comprise an agent that would affect (e.g., slow, hinder or retard) the metabolism of a compound of the present disclosure or any other active ingredient administered separately, sequentially or simultaneously with a compound of the present disclosure. It is also understood that any of the methods, kits, articles of manufacture and the like detailed herein in one aspect do not comprise an agent that would affect (e.g., slow, hinder or retard) the metabolism of a compound of the present disclosure or any other active ingredient administered separately, sequentially or simultaneously with a compound of the present disclosure.

In some embodiments, the pharmaceutical compositions described above are for use in a human or an animal.

The disclosure further includes a compound of the present disclosure for administration as a single active ingredient of a pharmaceutically acceptable composition which can be prepared by conventional methods known in the art, for example by binding the active ingredient to a pharmaceutically acceptable, therapeutically inert organic and/or inorganic carrier or excipient, or by mixing therewith. In one aspect, provided herein is the use of a compound of the present disclosure as a second or other active ingredient having a synergistic effect with other active ingredients in known drugs, or administration of the compound of the present disclosure together with such drugs.

The compound of the present disclosure may also be used in the form of a prodrug or other suitably modified form which releases the active ingredient in vivo.

V. Routes of Administration

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intratumoral, intrathecal and epidural), and the like. It will be appreciated that the preferred route may vary with for example the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in an effective amount. In some embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

A compound of the present disclosure may be combined with one or more additional therapeutic agents in any dosage amount of the compound of the present disclosure (e.g., from 1 mg to 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, 125, 150, 175, 200, 225, 250, 275, 300, 325, 350, 375, 400, 425, 450, 475, or about 500 mg per dose. Other therapeutically effective amounts of the compound of the present disclosure are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In some embodiments, a single dose can be administered once every week. A single dose can also be administered once every month.

Kits that comprise a compound of the present disclosure, or an enantiomer, or pharmaceutically acceptable salt thereof, or a pharmaceutical composition containing any of the above, are also included in the present disclosure. In one embodiment, a kit further includes instructions for use. In one aspect, a kit includes a compound of the disclosure, or a pharmaceutically acceptable salt, tautomer, stereoisomer, mixture of stereoisomers, prodrug, or deuterated analog thereof, and a label and/or instructions for use of the compounds in the treatment of the indications, such as the diseases or conditions, described herein. In one embodiment, kits comprising a compound of the present disclosure, or a pharmaceutically acceptable salt thereof, in combination with one or more (e.g., one, two, three, four, one or two, or one to three, or one to four) additional therapeutic agents are provided.

Provided herein are also articles of manufacture that include a compound of the present disclosure or a pharmaceutically acceptable salt, tautomer, stereoisomer, mixture of stereoisomers, prodrug, or deuterated analog thereof in a suitable container. The container may be a vial, jar, ampoule, preloaded syringe, and intravenous bag.

VI. Combination Therapy

In some embodiments, a compound of the present disclosure, or a pharmaceutically acceptable salt thereof, can be combined with a therapeutically effective amount of one or more (e.g., one, two, three, four, one or two, one to three, or one to four) additional therapeutic agents. In some embodiments, the additional therapeutic agent comprises an apoptotic signal-regulating kinase (ASK-1) inhibitor, a farnesoid X receptor (FXR) agonist, a peroxisome proliferator-activated receptor alpha (PPARα) agonist, fish oil, an acetyl-coA carboxylase (ACC) inhibitor, or a TGFβ antagonist, or a combination thereof.

In some embodiments, the therapeutic agent, or combination of therapeutic agents, are a(n) ACE inhibitor, 2-Acylglycerol O-acyltransferase 2 (DGAT2) inhibitor, Acetaldehyde dehydrogenase inhibitor, Alstrom syndrome protein 1 (ALMS1)/PKC alpha protein interaction inhibitor, Apelin receptor agonist, Acetyl CoA carboxylase inhibitor, Diacylglycerol O acyltransferase 2 inhibitor, Adenosine A3 receptor agonist, Adiponectin receptor agonist, Aldehyde dehydrogenase 2 stimulator, AKT protein kinase inhibitor, AMP-activated protein kinases (AMPK), AMP kinase activator, ATP citrate lyase inhibitor, AMP activated protein kinase stimulator, Endothelial nitric oxide synthase stimulator, NAD-dependent deacetylase sirtuin-1 stimulator, Adrenergic receptor antagonist, Androgen receptor agonist, Amylin receptor agonist, Angiotensin II AT-1 receptor antagonist, Autophagy protein modulator, Autotaxin inhibitors, Axl tyrosine kinase receptor inhibitor, Bax protein stimulator, Beta-catenin inhibitor, Bioactive lipid, Calcitonin agonist, Cannabinoid receptor modulator, Caspase inhibitor, Caspase-3 stimulator, Cathepsin inhibitor, Caveolin 1 inhibitor, CCL26 gene inhibitor, CCR2 chemokine antagonist, CCR2 chemokine antagonist, Angiotensin II AT-1 receptor antagonist, CCR3 chemokine antagonist, CCR5 chemokine antagonist, CD3 antagonist, Chloride channel stimulator, CNR1 inhibitor, Connective tissue growth factor ligand inhibitor, Cyclin D1 inhibitor, Cytochrome P450 7A1 inhibitor, DGAT1/2 inhibitor, Diacylglycerol O acyltransferase 1 inhibitor (DGAT1), Cytochrome P450 2E1 inhibitor (CYP2E1), CXCR4 chemokine antagonist, Dihydroceramide delta 4 desaturase inhibitor, Dihydroorotate dehydrogenase inhibitor, Dipeptidyl peptidase IV inhibitor, Endosialin modulator, Eotaxin ligand inhibitor, Extracellular matrix protein modulator, Farnesoid X receptor agonist, Fatty acid synthase inhibitors, FGF1 receptor agonist, Fibroblast growth factor (FGF-15, FGF-19, FGF-21) ligands, fibroblast activation protein inhibitor, Galectin-3 inhibitor, GDNF family receptor alpha like agonist Glucagon receptor agonist, Glucagon-like peptide 1 agonist, Glucocorticoid receptor antagonist, Glucose 6-phosphate 1-dehydrogenase inhibitor, G-protein coupled bile acid receptor 1 agonist, G-protein coupled receptor 84 antagonist, Hedgehog (Hh) modulator, Hepatitis C virus NS3 protease inhibitor, Hepatocyte nuclear factor 4 alpha modulator (HNF4A), Hepatocyte growth factor modulator, Histone deacetylase inhibitor, STAT-3 modulator, HMG CoA reductase inhibitor, HSD17B13 gene inhibitor, hydrolase inhibitor, Hypoxia inducible factor-2 alpha inhibitor, IL-10 agonist, IL-17 antagonist, IL-22 agonist, Ileal sodium bile acid cotransporter inhibitor, Insulin sensitizer, Insulin ligand agonist, Insulin receptor agonist, integrin modulator, Integrin Antagonist, Integrin alpha-V/beta-1 antagonist, Integrin alpha-V/beta-6 antagonist, intereukin-1 receptor-associated kinase 4 (IRAK4) inhibitor, IL-6 receptor agonist, interleukin 17 ligand inhibitor, Jak2 tyrosine kinase inhibitor, Jun N terminal kinase-1 inhibitor, Kelch like ECH associated protein 1 modulator, Ketohexokinase (KHK) inhibitor, Klotho beta stimulator, 5-Lipoxygenase inhibitor, Lipoprotein lipase inhibitor, Liver X receptor, LPL gene stimulator, Lysophosphatidate-1 receptor antagonist, Lysyl oxidase homolog 2 inhibitor, LXR inverse agonists, Macrophage mannose receptor 1 modulator, Matrix metalloproteinases (MMPs) inhibitor, MEKK-5 protein kinase inhibitor, MCH receptor-1 antagonist, Membrane copper amine oxidase (VAP-1) inhibitor, Methionine aminopeptidase-2 inhibitor, Methyl CpG binding protein 2 modulator, MicroRNA-132 (miR-132) antagonist, MicroRNA-21 (miR-21) inhibitor, Mitochondrial uncoupler, Mixed lineage kinase-3 inhibitor, Myelin basic protein stimulator, NACHT LRR PYD domain protein 3 (NLRP3) inhibitor, NAD-dependent deacetylase sirtuin stimulator, NADPH oxidase inhibitor (NOX), Nicotinic acid receptor 1 agonist, P2Y13 purinoceptor stimulator, Nuclear erythroid 2-related factor 2 stimulator, Nuclear receptor modulators, P2X7 purinoceptor modulator, PACAP type I receptor agonist, PDE 3 inhibitor, PDE 4 inhibitor, PDE 5 inhibitor, PDGF receptor beta modulator, Phenylalanine hydroxylase stimulator, Phospholipase C inhibitor, PPAR alpha agonist, PPAR delta agonist, PPAR gamma agonist, Peptidyl-prolyl cis-trans isomerase A inhibitor, PPAR gamma modulator, Protease-activated receptor-2 antagonist, Protein kinase modulator, PTGS2 gene inhibitor, Resistin/CAP1 (adenylyl cyclase associated protein 1) interaction inhibitor, Rho associated protein kinase inhibitor, Snitrosoglutathione reductase (GSNOR) enzyme inhibitor, Sodium glucose transporter-2 inhibitor, SREBP transcription factor inhibitor, STAT-1 inhibitor, Stearoyl CoA desaturase-1 inhibitor, STK25 inhibitor, Suppressor of cytokine signalling-1 stimulator, Suppressor of cytokine signalling-3 stimulator, Telomerase stimulator, TERT gene modulator, TGF beta (TGFB1) ligand inhibitor, TNF antagonist, Transforming growth factor β (TGF-β), Transforming growth factor β activated Kinase 1 (TAK1), Thyroid hormone receptor beta agonist, TLR-4 antagonist, TLR-9 antagonist, VDR agonist, Transglutaminase inhibitor, Tyrosine kinase receptor modulator, GPCR modulator, nuclear hormone receptor modulator, WNT modulators, or YAP/TAZ modulator and Zonulin inhibitor.

Non-limiting examples of the one or more additional therapeutic agents include:
 ACE inhibitors, such as enalapril;
 Acetaldehyde dehydrogenase inhibitors, such as ADX-629;
 Acetyl CoA carboxylase (ACC) inhibitors, such as NDI-010976 (firsocostat), DRM-01, gemcabene, PF-05175157, QLT-091382, PF-05221304;
 Acetyl CoA carboxylase/Diacylglycerol 0 acyltransferase 2 inhibitors, such as PF-07055341;
 Adenosine receptor agonists, such as CF-102 (namodenoson), CF-101, CF-502, CGS21680;
 Adenosine A3 receptor antagonist, such as FM-101;
 Adiponectin receptor agonists, such as ADP-355, ADP-399;
 Adrenergic receptor antagonist, such as bromocriptine, VI-0521
 Aldehyde dehydrogenase 2 stimulators, such as FP-045;
 Alpha glucosidase inhibitors (e.g. voglibose, acarbose, or miglitol);
 Amylin/calcitonin receptor agonists, such as KBP-042, KBP-089;
 AMP activated protein kinase stimulators, such as, PXL-770, O-304;
 AMP kinase activators/ATP citrate lyase inhibitors, such as as bempedoic acid (ETC-1002, ESP-55016)
 AMP activated protein kinase/Endothelial nitric oxide synthase/NAD-dependent deacetylase sirtuin-1 stimulators, such as NS-0200 (leucine+metformin+sildenafil);
 Androgen receptor agonists, such as LPCN-1144, LPCN-1148;
 Angiotensin II AT-1 receptor antagonists, such as irbesartan;
 Angiopoietin-related protein-3 inhibitors, such as IONIS-ANGPTL3-LRx;
 Apelin receptor agonist, such as CB-5064;
 Anti-lysyl oxidase homologue 2 (LOXL2) monoclonal antibody (e.g., simtuzumab);
 Autophagy protein modulators, such as A-2906;
 Autotaxin inhibitors, such as PAT-505, PAT-048, GLPG-1690, X-165, PF-8380, TJC-0265, TJC-0316, AM-063, BBT-877;
 Axl tyrosine kinase receptor inhibitors, such as bemcentinib (BGB-324, R-428);
 Bax protein stimulators, such as CBL-514;
 Bioactive lipids, such as DS-102;
 Biguanides, such as metformin;
 Cannabinoid receptor modulators, such as namacizumab (nimacimab), GWP-42004, REV-200, CRB-4001, SCN-002;
 Caspase inhibitors, such as emricasan;
 Pan cathepsin B inhibitors, such as VBY-376;
 Pan cathepsin inhibitors, such as VBY-825;
 CCL26 gene inhibitor, such as KDDF-201410-10;
 CCR2/CCR5 chemokine antagonists, such as cenicriviroc, maraviroc, CCX-872, WXSH-0213;
 CCR2/CCR5 chemokine antagonists and FXR agonists, such as LJC-242 (tropifexor+cenivriviroc);
 CCR2 chemokine antagonists, such as propagermanium;
 CCR2 chemokine/Angiotensin II AT-1 receptor antagonists, such as DMX-200, DMX-250;
 CCR3 chemokine antagonists, such as bertilimumab;
 CD3 antagonists, such as NI-0401 (foralumab);
 Chloride channel stimulators, such as cobiprostone, and lubiprostone;
 Casein kinase-1 (CK1) delta/epsilon inhibitors, such as PF-05006739;
 Connective tissue growth factor ligand inhibitor, such as PBI-4050;
 CXCR4 chemokine antagonists, such as AD-214;
 Diglyceride acyltransferase 2 (DGAT2) inhibitors, such as IONIS-DGAT2Rx, PF-06865571;
 Diglyceride acyltransferase 1 (DGAT1) inhibitors, such as GSK-3008356;

Diacylglycerol O acyltransferase 1 (DGAT1)/Cytochrome P450 2E1 inhibitors (CYP2E1), such as SNP-610;

Dihydroorotate dehydrogenase inhibitor, such as vidofludimus;

Dipeptidyl peptidase IV inhibitors, such as linagliptin, evogliptin, sitagliptin, vildagliptin, saxagliptin, gemigliptin, anagliptin, teneligliptin, alogliptin, trelagliptin, dutogliptin, or omarigliptin;

Eotaxin ligand inhibitors, such as bertilimumab, CM-101;

Extracellular matrix protein modulators, such as CNX-024;

Farnesoid X receptor (FXR) agonists, such as AGN-242266, AGN-242256, EP-024297, RDX-023, BWL-200, AKN-083, EDP-305, GNF-5120, GS-9674, HPG-1860, LMB-763, obeticholic acid, Px-102, Px-103, M790, M780, M450, M-480, MET-409, PX20606, EYP-001, TERN-101, TC-100, INT-2228, ZG-5266, or cilofexor;

Farnesoid X receptor (FXR)/G-protein coupled bile acid receptor 1 (TGR5) agonists, such as INT-767;

Fatty acid synthase inhibitors, such as TVB-2640, FT-8225;

Fibroblast growth factor 19 (rhFGF19)/cytochrome P450 (CYP) 7A1 inhibitors, such as NGM-282;

Fibroblast growth factor 21 (FGF-21) ligand, such as BMS-986171, BIO89-100, BMS-986036, B-1344;

Fibroblast growth factor 21 (FGF-21)/glucagon like peptide 1 (GLP-1) agonists, such as YH-25723 (YH-25724; YH-22241), AKR-001;

FGF receptor agonists/Klotho beta stimulators, such as BFKB-8488A (RG-7992);

Galectin-3 inhibitors, such as GR-MD-02, GB-1107 (Gal-300), GB1211 (Gal-400);

GDNF family receptor alpha like agonist, such as NGM-395

Glitazars, such as saroglitazar, aleglitazar, muraglitazar or tesaglitazar;

Glitazones (e.g., pioglitazone, rosiglitazone, balaglitazone, rivoglitazone, or lobeglitazone), Glucagon-like peptide 1 (GLP-1R) agonists, such as ALT-801, AC-3174, liraglutide, cotadutide (MEDI-0382), SAR-425899, LY-3305677, HM-15211, YH-25723, YH-GLP1, RPC-8844, PB-718, semaglutide;

Gastric inhibitory polypeptide/Glucagon-like peptide-1 (GIP/GLP-1) receptor co-agonist, such as tirzepatide (LY-3298176);

PEGylated long-acting glucagon-like peptide-1/glucagon (GLP-1R/GCGR) receptor dual agonist, such as DD-01;

Glucocorticoid receptor antagonists, such as CORT-118335 (miricorilant);

Glucose 6-phosphate 1-dehydrogenase inhibitors, such as ST001;

Glucokinase stimulator, such as sinogliatin (RO-5305552);

G-protein coupled bile acid receptor 1 (TGR5) agonists, such as RDX-009, INT-777;

GPR40 agonists (FFAR1/FFA1 agonist, e.g. fasiglifam);

Glucose-dependent insulinotropic peptide (GIP) and analogues thereof;

Heat shock protein 47 (HSP47) inhibitors, such as ND-L02-s0201;

Hedgehog protein and/or TGF beta ligand inhibitors, such as Oxy-210;

Histone deacetylase inhibitors/STAT-3 modulators, such as SFX-01;

HMG CoA reductase inhibitors, such as atorvastatin, fluvastatin, pitavastatin, pravastatin, rosuvastatin, simvastatin;

$HSD17B_{13}$ gene inhibitor, such as ARO-HSD;

Hydrolase inhibitor, such as ABD-X;

Hypoxia inducible factor-2 alpha inhibitors, such as PT-2567;

IL-10 agonists, such as peg-ilodecakin;

Ileal sodium bile acid cotransporter inhibitors, such as odevixibat (A-4250), volixibat potassium ethanolate hydrate (SHP-262), GSK2330672, CJ-14199, elobixibat (A-3309);

Insulin sensitizers, such as, KBP-042, MSDC-0602K, MSDC-5514, Px-102, RG-125 (AZD4076), tolimidone, VVP-100X, CB-4211, ETI-101;

Insulin ligand/dsInsulin receptor agonists, such as ORMD-0801;

Insulins or insulin analogues;

Integrin antagonists, such as IDL-2965;

IL-6 receptor agonists, such as KM-2702;

Integrin alpha-V/beta-6 and alpha-V/beta-1 dual inhibitor; such as PLN-74809;

Interleukin 17 ligand inhibitor, such as netakimab;

Jak1/2 tyrosine kinase inhibitor, such as baricitinib;

Jun N terminal kinase-1 inhibitor, such as CC-90001;

Ketohexokinase (KHK) inhibitors, such as PF-06835919;

beta Klotho (KLB)-FGF1c agonists, such as MK-3655 (NGM-313);

5-Lipoxygenase inhibitors, such as tipelukast (MN-001), DS-102 (AF-102);

Lipoprotein lipase inhibitors, such as CAT-2003;

LPL gene stimulators, such as alipogene tiparvovec;

Liver X receptor (LXR) inhibitors, such as PX-L603, PX-L493, BMS-852927, T-0901317, GW-3965, SR-9238;

Lysophosphatidate-1 receptor antagonists, such as BMT-053011, UD-009 (CP-2090), AR-479, ITMN-10534, BMS-986020, KI-16198;

Lysyl oxidase homolog 2 inhibitors, such as simtuzumab, PXS-5382A (PXS-5338);

Macrophage mannose receptor 1 modulators, such as tilmanocept-Cy3 (technetium Tc 99m tilmanocept);

Meglitinides, such as nateglinide, repaglinide;

Membrane copper amine oxidase (VAP-1) inhibitors, such as TERN-201;

MEKK-5 protein kinase (ASK-1) inhibitors, such as CJ-16871, selonsertib (GS-4997), SRT-015, GS-444217, GST-HG-151;

MCH receptor-1 antagonists, such as CSTI-100 (ALB-127158);

Semicarbazide-Sensitive Amine Oxidase/Vascular Adhesion Protein-1 (SSAO/VAP-1) Inhibitors, such as PXS-4728A (BI-1467335);

Sulfonylureas, such as tolbutamide, glibenclamide, gliclazide, chlorpropamide, tolazamide, acetohexamide. glyclopyramide, glimepiride, or glipizide;

Methionine aminopeptidase-2 inhibitors, such as ZGN-1061, ZGN-839, ZN-1345;

Methyl CpG binding protein 2 modulators, such as mercaptamine;

Mineralocorticoid receptor antagonists (MCRA), such as MT-3995 (apararenone);

Mitochondrial uncouplers, such as 2,4-dinitrophenol, Mito-99-0053, and HU6;

Mixed lineage kinase-3 inhibitors, such as URMC-099-C;

Myelin basic protein stimulators, such as olesoxime;
Myeloperoxidase inhibitors, such as PF-06667272, AZM-198;
NADPH oxidase inhibitors, such as GKT-831, GenKyoTex, APX-311, setanaxib-Nicotinic acid receptor 1 agonists, such as ARI-3037MO;
NACHT LRR PYD domain protein 3 (NLRP3) inhibitors, such as KDDF-201406-03, NBC-6, IFM-514, JT-194 (JT-349);
NFE2L2 gene inhibitor, such as GeRP-amiR-144;
Nuclear receptor modulators, such as DUR-928 (DV-928);
P2X7 purinoceptor modulators, such as SGM-1019;
P2Y13 purinoceptor stimulators, such as CER-209;
PDE 3/4 inhibitors, such as tipelukast (MN-001);
PDE 5 inhibitors, such as sildenafil, MSTM-102;
PDGF receptor beta modulators, such as BOT-191, BOT-509;
Peptidyl-prolyl cis-trans isomerase inhibitors, such as CRV-431 (CPI-432-32), NVP-018, NV-556 (NVP-025);
Phenylalanine hydroxylase stimulators, such as HepaStem;
PPAR agonists, such as chiglitazar, elafibranor (GFT-505), seladelpar lysine (MBX-8025), deuterated pioglitazone R-enantiomer, pioglitazone, DRx-065, saroglitazar, lanifibranor (IVA-337), CHS-131, pemafibrate (K-877), ZSP-0678;
Protease-activated receptor-2 antagonists, such as PZ-235;
Protein kinase modulators, such as CNX-014;
PTGS2 gene inhibitors, such as STP-705, STP-707;
Resistin/CAP1 (adenylyl cyclase associated protein 1) interaction inhibitors, such as DWJ-211;
Rev protein modulator, such as ABX-464;
Rho associated protein kinase (ROCK) inhibitors, such as REDX-10178 (REDX-10325), KD-025, TDI-01;
Snitrosoglutathione reductase (GSNOR) enzyme inhibitors, such as SL-891;
Sodium glucose transporter-2 (SGLT2) inhibitors, such as ipragliflozin, remogliflozin etabonate, ertugliflozin, dapagliflozin, tofogliflozin, sotagliflozin, empagliflozin, canagliflozin, Ipraglrflozin, tofogliflozin, sergliflozin etabonate,
Sodium glucose transporter-1/2 (SGLT 1/2) inhibitors, such as licogliflozin bis(prolinate) (LIK-066);
SREBP transcription factor inhibitors, such as CAT-2003, MDV-4463;
Stearoyl CoA desaturase-1 inhibitors, such as aramchol;
Thiazolidinediones, such as pioglitazone, rosiglitazone, or lobeglitazone;
Thyroid hormone receptor beta agonists, such as ALG-009, ASC-41, CNPT-101101; CNPT-101207, resmetirom (MGL-3196), MGL-3745, VK-2809;
TLR-2/TLR-4 antagonists, such as VB-201 (CI-201);
TLR-4 antagonists, such as JKB-121, JKB-122;
Tyrosine kinase receptor modulators, such as CNX-025, GFE-2137 (repurposed nitazoxanide);
TLR-9 antagonist, such as GNKS-356;
TNF antagonist, such as ALF-421;
GPCR modulators, such as CNX-023;
Nuclear hormone receptor modulators, such as Px-102;
VDR agonist, such as CK-15;
Xanthine oxidase/Urate anion exchanger 1 (URAT1) inhibitors, such as RLBN-1001, RLBN-1127; and
Zonulin Inhibitors, such as lorazotide acetate (INN-202).

In some embodiments, the one or more additional therapeutic agents are selected from A-4250, AC-3174, acetylsalicylic acid, AK-20, alipogene tiparvovec, AMX-342, AN-3015, aramchol, ARI-3037MO, ASP-8232, AZD-2693, bertilimumab, Betaine anhydrous, BI-1467335, BMS-986036, BMS-986171, BMT-053011, BOT-191, BTT-1023, budenoside, BX-003, CAT-2003, cenicriviroc, CBW-511, CER-209, CF-102, CGS21680, CNX-014, CNX-023, CNX-024, CNX-025, cobiprostone, colesevelam, dapagliflozin, DCR-LIV1, deuterated pioglitazone R-enantiomer, 2,4-dinitrophenol, DRx-065, DS-102, DUR-928, EDP-305, elafibranor (GFT-505), emricasan, enalapril, ertugliflozin, evogliptin, F-351, fluasterone (ST-002), FT-4101, GDD-3898, GH-509, GKT-831, GNF-5120, GRI-0621, GR-MD-02, GS-300, GS-4997, GS-9674, HEC-96719, HTD-1801, HSG-4112, HST-202, HST-201, hydrochlorothiazide, icosabutate (PRC-4016), icosapent ethyl ester, IMM-124-E, INT-767, INV-240, IONIS-DGAT2Rx, ipragliflozin, Irbesarta, propagermanium, IVA-337, JKB-121, KB-GE-001, KBP-042, KD-025, M790, M780, M450, metformin, sildenafil, LB-700, LC-280126, linagliptin, liraglutide, LJN-452 (tropifexor), LM-011, LM-002 (CVI-LM-002), LMB-763, LYN-100, MBX-8025, MDV-4463, mercaptamine, MGL-3196, MGL-3745, MP-301, MSDC-0602K, namacizumab, NC-101, NDI-010976, ND-L02-s0201 (BMS-986263), NGM-282, NGM-313, NGM-386, NGM-395, NP-011, NP-135, NP-160, norursodeoxycholic acid, NVP-022, 0-304, obeticholic acid (OCA), 25HC3S, olesoxime, PAT-505, PAT-048, PBI-4547, peg-ilodecakin, PF-05221304, pioglitazone, pirfenidone, PRI-724, PX20606, Px-102, PX-L603, PX-L493, PXS-4728A, PZ-235, RCYM-001, RDX-009, remogliflozin etabonate, RG-125 (AZD4076), RPI-500, saroglitazar, semaglutide, SH-2442, simtuzumab, solithromycin, sotagliflozin, statins (atorvastatin, fluvastatin, pitavastatin, pravastatin, rosuvastatin, simvastatin), symbiotic, TCM-606F, TEV-45478, TQA-3526, TQA-3563, tipelukast (MN-001), TLY-012, TRx-318, TVB-2640, UD-009, ursodeoxycholic acid, VBY-376, VBY-825, VK-2809, vismodegib, volixibat potassium ethanolate hydrate (SHP-626), VVP-100X, WAV-301, WNT-974, XEN-103, XRx-117, ZGN-839, ZG-5216, ZSYM-008, ZYSM-007.

In some embodiments, the compound of present disclosure is combined with an anti-obesity agent including but not limited to peptide YY or an analogue thereof, a neuropeptide Y receptor type 2 (NPYR2) agonist, a NPYR1 or NPYR5 antagonist, a cannabinoid receptor type 1 (CB1 R) antagonist, a lipase inhibitor (e.g., orlistat), a human proislet peptide (HIP), a melanocortin receptor 4 agonist (e.g., setmelanotide), a melanin concentrating hormone receptor 1 antagonist, a farnesoid X receptor (FXR) agonist (e.g. obeticholic acid), zonisamide, phentermine (alone or in combination with topiramate), a norepinephrine/dopamine reuptake inhibitor (e.g., buproprion), an opioid receptor antagonist (e.g., naltrexone), a combination of norepinephrine/dopamine reuptake inhibitor and opioid receptor antagonist (e.g., a combination of bupropion and naltrexone), a GDF-15 analog, sibutramine, a cholecystokinin agonist, amylin and analogues thereof (e.g., pramlintide), leptin and analogues thereof (e.g., metroleptin), a serotonergic agent (e.g., lorcaserin), a methionine aminopeptidase 2 (MetAP2) inhibitor (e.g., beloranib or ZGN-1061), phendimetrazine, diethylpropion, benzphetamine, an SGLT2 inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a dual SGLT2/SGLT1 inhibitor, a fibroblast growth factor receptor (FGFR) modulator, an AMP-activated protein kinase (AMPK) activator, biotin, a MAS receptor modulator, or a glucagon receptor agonist (alone or in combination with another GLP-1 R agonist, e.g., liraglutide, exenatide, dulaglutide, albiglutide, lixisenatide, or semaglutide), including the pharmaceutically acceptable salts of the specifically named agents and the pharmaceutically acceptable solvates of said agents and salts.

In some embodiments, methods and compositions include a therapeutically effective amount of a compound of Formula (I), (Ia), (Ib), (Ic), (Id), (Ie), (If), and/or (Ig), or a pharmaceutically acceptable salt thereof, and a therapeutically effective amount of a Farnesoid X Receptor (FXR) agonist. In some embodiments, the FXR agonist is a compound of Formula (II) or (III):

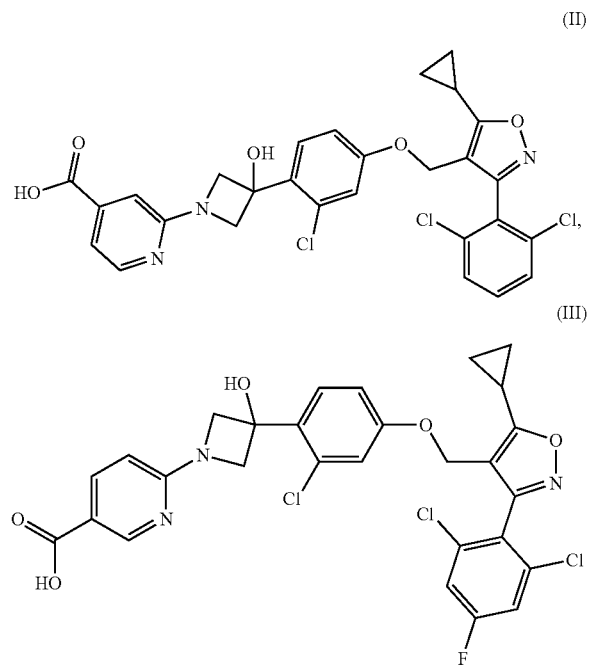

or a pharmaceutically acceptable salt, a stereoisomer, a mixture of stereoisomers, or a tautomer thereof.

In some embodiments, methods and compositions include a therapeutically effective amount of a compound of Formula (I), (Ia), (Ib), (Ic), (Id), (Ie), (If), and/or (Ig), or a pharmaceutically acceptable salt thereof, and a therapeutically effective amount of an ASK1 inhibitor. In some embodiments, the ASK1 inhibitor is a compound of Formula (IV):

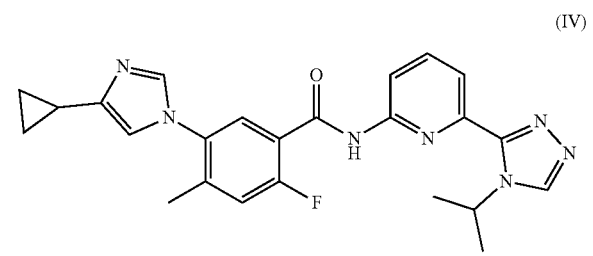 [SMILES: Cc1cc(F)c(C(=O)Nc2cccc(-c3nncn3C(C)C)n2)cc1-n1cnc(C2CC2)c1]

or a pharmaceutically acceptable salt, a stereoisomer, a mixture of stereoisomers, or a tautomer thereof.

In some embodiments, methods and compositions include a therapeutically effective amount of a compound of Formula (I), (Ia), (Ib), (Ic), (Id), (Ie), (If), and/or (Ig), or a pharmaceutically acceptable salt thereof, and a therapeutically effective amount of an Acetyl CoA Carboxylase (ACC) inhibitor. In certain embodiments, the ACC inhibitor is a compound of Formula (V):

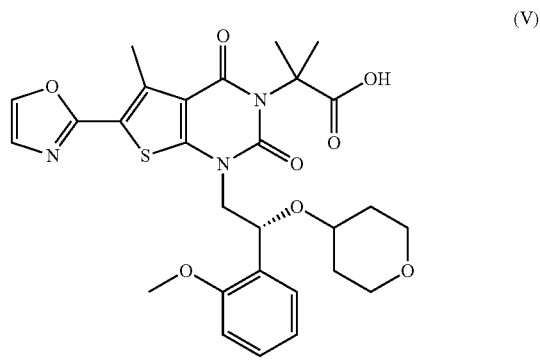 [SMILES: COc1ccccc1[C@H](Cn1c(=O)n(C(C)(C)C(=O)O)c(=O)c2c(C)c(-c3ncco3)sc21)OC1CCOCC1]

or a pharmaceutically acceptable salt thereof.

In some embodiments, methods and compositions include a therapeutically effective amount of a compound of Formula (I), (Ia), (Ib), (Ic), (Id), (Ie), (If), and/or (Ig), or a pharmaceutically acceptable salt thereof, and a therapeutically effective amount of a Thyroid Hormone Receptor (THR) R agonist. In certain embodiments, the THR R agonist is a compound of Formula (VI):

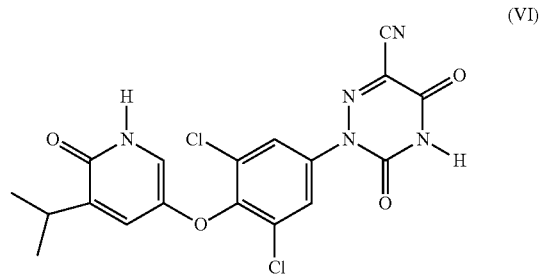 [SMILES: CC(C)c1cc(Oc2c(Cl)cc(-n3nc(C#N)c(=O)[nH]c3=O)cc2Cl)c[nH]c1=O]

or a pharmaceutically acceptable salt, a stereoisomer, a mixture of stereoisomers, or a tautomer thereof.

VII. Methods of Treatment

In some embodiments, compounds of the present disclosure are useful in a method of treating and/or preventing a GLP-1R mediated disease or condition. In some embodiments, a method for treating and/or preventing a GLP-1R mediated disease or condition includes administering to a subject in need thereof a pharmaceutically effective amount of a compound of the present disclosure or pharmaceutically acceptable salt thereof.

In some embodiments, the disease or condition comprises a liver disease or related diseases or conditions, e.g., liver fibrosis, non-alcoholic fatty liver disease (NAFLD), non-alcoholic steatohepatitis (NASH), liver cirrhosis, compensated liver fibrosis, decompensated liver fibrosis, hepatocellular carcinoma, Primary Biliary Cirrhosis (PBC), or Primary Sclerosing Cholangitis (PSC). In some embodiments, the disease or condition comprises a metabolic disease or related diseases or conditions, such as diabetes mellitus, obesity, or cardiometabolic diseases.

GLP-1R agonists are currently being investigated in connection with certain disorders and conditions, including for example diabetes. GLP-1 analogs that are DPP4 resistant and have longer half-lives than endogenous GLP-1 have been reported to be associated with weight loss and improved insulin action. Liraglutide, a peptide GLP-1R agonist approved in connection with treatment of diabetes, has been reported to show favorable improvements in outcomes in NASH subjects.

In some embodiments, the present disclosure relates to the use of compounds of Formula (I), or other formula described herein, or a pharmaceutically acceptable salt thereof in the preparation of a medicament for the prevention and/or treatment of a disease or condition mediated by GLP-1R, such as a liver disease or metabolic disease. For example, some embodiments provide a compound of Formula (I) or other formula described herein, or a pharmaceutically acceptable salt thereof, or a use thereof, for treatment and/or prevention of chronic intrahepatic or some forms of extrahepatic cholestatic conditions, of liver fibrosis, of acute intrahepatic cholestatic conditions, of obstructive or chronic inflammatory disorders that arise out of improper bile composition, of gastrointestinal conditions with a reduced uptake of dietary fat and fat-soluble dietary vitamins, of inflammatory bowel diseases, of lipid and lipoprotein disorders, of type II diabetes and clinical complications of type I and type II diabetes, of conditions and diseases which result from chronic fatty and fibrotic degeneration of organs due to enforced lipid and specifically triglyceride accumulation and subsequent activation of profibrotic pathways, of obesity and metabolic syndrome (combined conditions of dyslipidemia, diabetes and abnormally high body-mass index), of acute myocardial infarction, of acute stroke, of thrombosis which occurs as an endpoint of chronic obstructive atherosclerosis, of persistent infections by intracellular bacteria or parasitic protozoae, of non-malignant hyperproliferative disorders, of malignant hyperproliferative disorders, of colon adenocarcinoma and hepatocellular carcinoma for instance, of liver steatosis and associated syndromes, of liver failure or liver malfunction as an outcome of chronic liver diseases or of surgical liver resection, of Hepatitis B infection, of Hepatitis C infection and/or of cholestatic and fibrotic effects that are associated with alcohol-induced cirrhosis or with viral-borne forms of hepatitis, of type I diabetes, pre-diabetes, idiopathic type 1 diabetes, latent autoimmune diabetes, maturity onset diabetes of the young, early onset diabetes, malnutrition-related diabetes, gestational diabetes, hyperglycemia, insulin resistance, hepatic insulin resistance, impaired glucose tolerance, diabetic neuropathy, diabetic nephropathy, kidney disease, diabetic retinopathy, adipocyte dysfunction, visceral adipose deposition, obesity, eating disorders, sleep apnea, weight gain, sugar craving, dyslipidemia, hyperinsulinemia, congestive heart failure, myocardial infarction, stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, left ventricular hypertrophy, Parkinson's Disease, peripheral arterial disease, macular degeneration, cataract, glomerulosclerosis, chronic renal failure, metabolic syndrome, angina pectoris, premenstrual syndrome, thrombosis, atherosclerosis, impaired glucose metabolism, or vascular restenosis.

In some embodiments, a method of treating and/or preventing a non-alcoholic fatty liver disease (NAFLD), comprises administering to a subject in need thereof a compound of the present disclosure or a pharmaceutically acceptable salt thereof.

The disclosure also relates to a compound according to Formula (I) or other formula described herein, or a pharmaceutical composition comprising said compound for preventive and posttraumatic treatment of a cardiovascular disorder, such as acute myocardial infarction, acute stroke, or thrombosis which occur as an endpoint of chronic obstructive atherosclerosis. In some embodiments, a method for treating and/or preventing cardiovascular disorder comprises administering a compounds of Formula (I) or other formula described herein, to a subject in need thereof.

The disclosure further relates to a compound or pharmaceutical composition for the treatment and/or prevention of obesity and associated disorders such as metabolic syndrome (combined conditions of dyslipidemias, diabetes and abnormally high body-mass index) which can be overcome by GLP1R-mediated lowering of serum triglycerides, blood glucose and increased insulin sensitivity and GLP1R-mediated weight loss. In some embodiments, a method for treating and/or preventing a metabolic disease comprises administering a compounds of Formula (I) or other formula described herein, to a subject in need thereof.

In a further embodiment, the compounds or pharmaceutical composition of the present disclosure are useful in preventing and/or treating clinical complications of Type I and Type II Diabetes. Examples of such complications include diabetic nephropathy, diabetic retinopathy, diabetic neuropathies, or Peripheral Arterial Occlusive Disease (PAOD). Other clinical complications of diabetes are also encompassed by the present disclosure. In some embodiments, a method for treating and/or preventing complications of Type I and Type II Diabetes comprises administering a compounds of Formula (I) or other formula described herein, to a subject in need thereof.

Furthermore, conditions and diseases which result from chronic fatty and fibrotic degeneration of organs due to enforced lipid and/or triglyceride accumulation and subsequent activation of profibrotic pathways may also be prevented and/or treated by administering the compounds or pharmaceutical composition of the present disclosure. Such conditions and diseases can include NASH and chronic cholestatic conditions in the liver, Glomerulosclerosis and Diabetic Nephropathy in the kidney, Macular Degeneration and Diabetic Retinopathy in the eye and neurodegenerative diseases, such as Alzheimer's Disease in the brain, or Diabetic Neuropathies in the peripheral nervous system. In some embodiments, a method for treating and/or preventing conditions and diseases which result from chronic fatty and fibrotic degeneration of organs due to enforced lipid and/or triglyceride accumulation and subsequent activation of profibrotic pathways comprises administering a compounds of Formula (I) to a subject in need thereof. In some embodiments, a method for treating and/or preventing NASH comprises administering a compounds of Formula (I) or other formula described herein, to a subject in need thereof.

Further provided herein is a pharmaceutical composition for use in treating a GLP-1R mediated disease or condition described herein, comprising a compound of the present disclosure or a pharmaceutically acceptable salt thereof.

The present disclosure also describes a use for the manufacture of a medicament in treating a GLP-1R mediated disease or condition comprising a compound of the present disclosure or a pharmaceutically acceptable salt thereof. Medicaments as referred to herein may be prepared by conventional processes, including the combination of a compound according to the present disclosure and a pharmaceutically acceptable carrier.

Also disclosed is a compound of the present disclosure or a pharmaceutically acceptable salt thereof for the treatment of a GLP-1R mediated disease or condition. Also disclosed is a compound of the present disclosure or a pharmaceutically acceptable salt thereof for the prevention of a GLP-1R mediated disease or condition.

VIII. Examples

Many general references providing commonly known chemical synthetic schemes and conditions useful for synthesizing the disclosed compounds are available (see, e.g., Smith, March's Advanced Organic Chemistry: Reactions, Mechanisms, and Structure, $7^{th}$ edition, Wiley-Interscience, 2013.)

Compounds as described herein can be purified by any of the means known in the art, including chromatographic means, such as high-performance liquid chromatography (HPLC), preparative thin layer chromatography, flash column chromatography and ion exchange chromatography. Any suitable stationary phase can be used, including normal and reversed phases as well as ionic resins. For example, the disclosed compounds can be purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4th ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the pendant groups. Each of the reactions depicted in the general schemes can be run at a temperature from about 0° C. to the reflux temperature of the organic solvent used.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The embodiments are also directed to processes and intermediates useful for preparing the subject compounds or pharmaceutically acceptable salts thereof. The following description is, therefore, not intended to limit the scope of the present disclosure.

In some embodiments, the present disclosure generally provides a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or diastereomerically pure.

Representative syntheses of compounds of the present disclosure are described in schemes below, and the examples that follow.

The compounds detailed in the Examples were synthesized according to the general synthetic methods described below. Compounds were named using ChemDraw version 18. 1. 0. 535 (PerkinElmer Informatics, Inc.) unless otherwise indicated.

Abbreviations

Certain abbreviations and acronyms are used in describing the experimental details. Although most of these would be understood by one skilled in the art, Table 1 contains a list of many of these abbreviations and acronyms.

TABLE 1

| List of abbreviations and acronyms. | |
|---|---|
| Abbreviation | Meaning |
| Ac | acetate |
| ACN | acetonitrile |
| AmPhos | di-tert-butyl(4-dimethylaminophenyl)phosphine |
| Bn | benzyl |
| Bpin | (pinacolato)boron |
| $B_2Pin_2$ | bis(pinacolato)diboron |
| Bu | butyl |
| Bz | benzoyl |
| BzCl | benzoyl chloride |
| cataCXium ® A Pd G3 | Mesylate[(di(1-adamantyl)-n-butylphosphine)-2-(2'-amino-1,1'-biphenyl)]palladium(II) |
| DBU | 1,8-Diazabicyclo[5.4.0]undec-7-ene |
| DCM | dichloromethane |
| DEA | diethylamine |

TABLE 1-continued

List of abbreviations and acronyms.

| Abbreviation | Meaning |
|---|---|
| Deoxofluor | Bis(2-methoxyethyl)aminosulfur trifluoride |
| DIPEA | diisopropylethylamine |
| DME | dimethoxyethane |
| DMEM | Dulbecco's Modified Eagle Medium |
| DMF | dimethylformamide |
| DMSO | dimethylsulfoxide |
| dppf | 1,1'-Ferrocenediyl-bis(diphenylphosphine) |
| EDCI | N-(3-dimethylaminopropyl)-N'-ethylcarbodiimide hydrochloride |
| ES/MS | electron spray mass spectrometry |
| Et | ethyl |
| FBS | fetal bovine serum |
| HATU | 1-[Bis(dimethylamino)methylene]-1H-1,2,3-triazolo[4,5-b]pyridinium 3-oxide hexafluorophosphate |
| IPA | isopropanol |
| JohnPhos | (2-Biphenyl)di-tert-butylphosphine |
| KOtBu | potassium tert-butoxide |
| LC | liquid chromatography |
| LCMS | liquid chromatography/mass spectrometry |
| MCPBA | meta-chloroperbenzoic acid |
| Me | methyl |
| m/z | mass to charge ratio |
| MS or ms | mass spectrum |
| NMP | N-methyl-2-pyrrolidone |
| Pd Rockphos G3 | [(2-Di-tert-butylphosphino-3-methoxy-6-methyl-2',4',6'-triisopropyl-1,1'-biphenyl)-2-(2-aminobiphenyl)]palladium(II) methanesulfonate |
| Ph | phenyl |
| $Ph_3P$ | triphenylphosphine |
| pin | pinacol |
| Pyr | pyridine |
| RBF | round bottom flask |
| RP-HPLC | reverse phase high performance liquid chromatography |
| RT | room temperature |
| SFC | supercritical fluid chromatography |
| tBuXPhos Pd G3 | [(2-Di-tert-butylphosphino-2',4',6'-triisopropyl-1,1'-biphenyl)-2-(2'-amino-1,1'-biphenyl)] palladium(II) methanesulfonate |
| TEA | triethylamine |
| TFA | trifluoroacetic acid |
| THF | tetrahydrofuran |
| Ts | 4-toluenesulfonyl |
| XPhos Pd G2 | Chloro(2-dicyclohexylphosphino-2',4',6'-triisopropyl-1,1'-biphenyl)[2-(2'-amino-1,1'-biphenyl)]palladium(II) |
| δ | parts per million referenced to residual solvent peak |

A. Synthesis of Intermediates

Preparation of Intermediate I-1

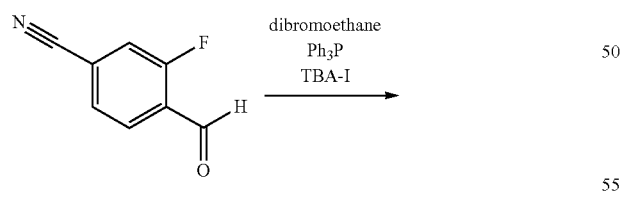

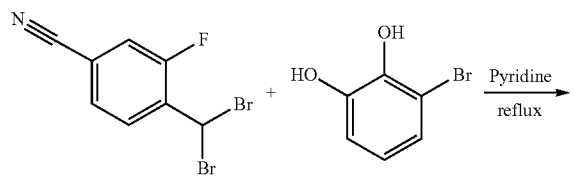

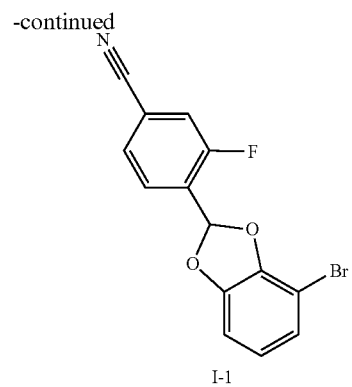

4-(dibromomethyl)-3-fluorobenzonitrile: To a 40 mL vial was added 3-fluoro-4-formylbenzonitrile (500 mg, 3.35 mmol), triphenylphosphine (1.76 g, 6.71 mmol), tetrabutylammonium iodide (1.24 g, 3.35 mmol) and 1,2-dibromoethane (7 mL). The solution was heated at 60° C. overnight. LCMS showed formation of the product by UV. The mixture was concentrated under reduced pressure, and purified by silica chromatography (eluent: EtOAc/hexanes) to afford the desired product 4-(dibromomethyl)-3-fluorobenzonitrile which was carried forward to the next step. 1H NMR (400

MHz, Chloroform-d) δ 8.00 (dd, J=8.1, 7.4 Hz, 1H), 7.58 (ddd, J=8.2, 1.5, 0.8 Hz, 1H), 7.38 (dd, J=9.4, 1.6 Hz, 1H), 6.91 (s, 1H).

4-(4-bromobenzo[d][1,3]dioxol-2-yl)-3-fluorobenzonitrile: To a 40 mL vial was added 4-(dibromomethyl)-3-fluorobenzonitrile (744 mg, 2.54 mmol) and 3-bromobenzene-1,2-diol (400 mg, 2.12 mmol). The mixture was dissolved in pyridine (2 mL), and the vial was sealed with a Teflon cap. The solution was heated at 90° C. overnight. LCMS showed formation of the product by UV. The mixture was concentrated under reduced pressure, and purified by silica chromatography (eluent: EtOAc/hexanes) to afford the desired product I-1. 1H NMR (400 MHz, Chloroform-d) δ 7.76 (dd, J=8.0, 6.8 Hz, 1H), 7.56 (dd, J=8.1, 1.5 Hz, 1H), 7.50 (dd, J=9.3, 1.5 Hz, 1H), 7.33 (s, 1H), 7.06 (dd, J=7.7, 1.6 Hz, 1H), 6.87-6.75 (m, 2H).

Preparation of Intermediate I-2

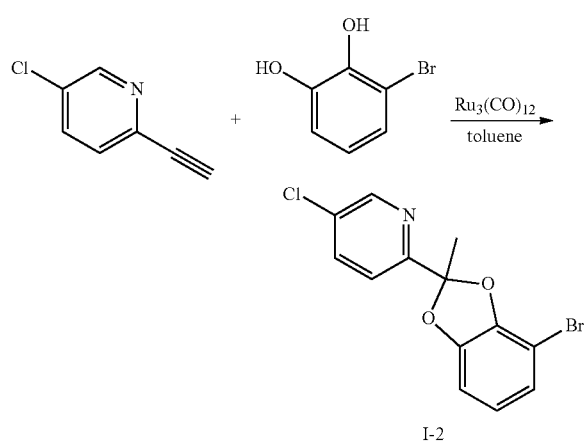

2-(4-bromo-2-methylbenzo[d][1,3]dioxol-2-yl)-5-chloropyridine: To a 40 mL vial was added 5-chloro-2-ethynylpyridine (1 g, 7.27 mmol), 3-bromobenzene-1,2-diol (1.37 g, 7.27 mmol), and triruthenium dodecacarbonyl (139 mg, 0.218 mmol). The mixture was dissolved in dry toluene (15 mL), and the mixture was degassed for 2 minutes with argon. The vial was sealed with a teflon cap. The solution was heated at 100° C. overnight. LCMS showed formation of the product by UV. The mixture was cooled and then diluted with EtOAc (30 mL). The mixture was filtered through celite (rinsing with EtOAc), and the filtrate was concentrated under reduced pressure. The crude material was purified by silica chromatography (eluent: EtOAc/hexanes) to afford the desired product I-2. ES/MS: 328.1 (M+H⁺). 1H NMR (400 MHz, Chloroform-d) δ 8.66 (dd, J=2.4, 0.7 Hz, 1H), 7.73 (dd, J=8.4, 2.4 Hz, 1H), 7.63 (dd, J=8.4, 0.8 Hz, 1H), 6.99 (dd, J=7.9, 1.4 Hz, 1H), 6.82-6.69 (m, 2H), 2.13 (s, 3H).

Preparation of Intermediate I-3

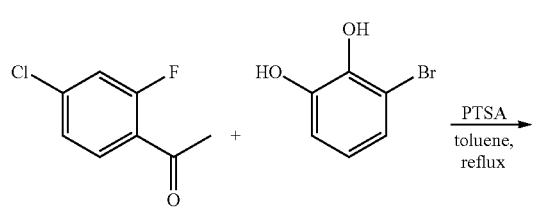

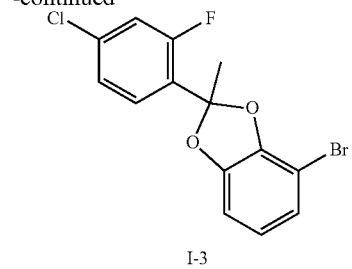

4-bromo-2-(4-chloro-2-fluorophenyl)-2-methylbenzo[d][1,3]dioxole: To a 250 mL RBF was added 1-(4-chloro-2-fluoro-phenyl)ethanone (9.59 g, 55.6 mmol), 3-bromobenzene-1,2-diol (10 g, 52.9 mmol), and p-toluenesulfonic acid monohydrate (500 mg, 2.65 mmol). The mixture was dissolved in dry toluene (50 mL). The solution was refluxed for 48 hours under Dean-Stark conditions. The mixture was subsequently cooled and then dry-loaded onto silica. The crude material was purified by silica chromatography (eluent: EtOAc/hexanes) to afford the desired product I-3. 1H NMR (400 MHz, Chloroform-d) δ 7.57 (t, J=8.4 Hz, 1H), 7.20-7.09 (m, 2H), 6.98 (dd, J=8.0, 1.4 Hz, 1H), 6.80-6.68 (m, 2H), 2.13 (s, 3H).

Preparation of Intermediate I-4

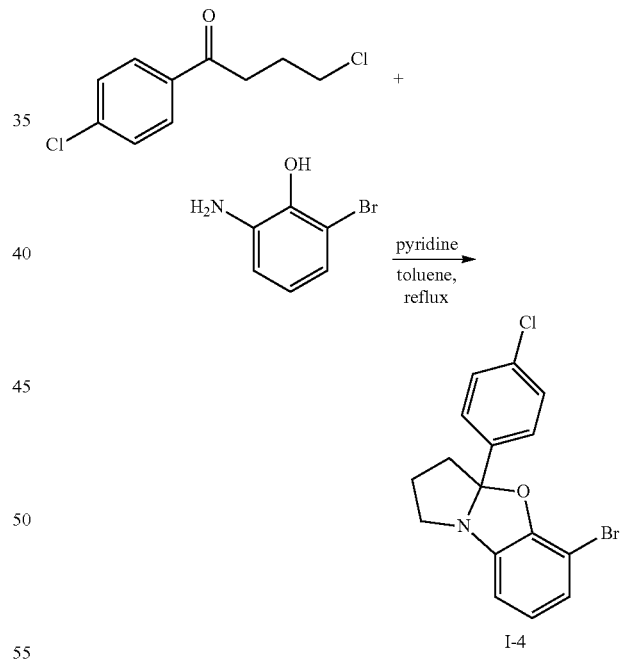

5-Bromo-3a-(4-chlorophenyl)-1,2,3,3a-tetrahydrobenzo[d]pyrrolo[2,1-b]oxazole: To a 40 mL vial was added 4-chloro-1-(4-chlorophenyl)butan-1-one (462 mg, 2.13 mmol) and 2-amino-6-bromophenol (400 mg, 2.13 mmol). The mixture was dissolved in pyridine (5 mL). The vial was sealed, stirred for 4 h at 50° C., and then subsequently for 16 h at at 90° C. The mixture was concentrated under reduced pressure, and the crude material was purified by silica chromatography (eluent: EtOAc/hexanes) to afford the desired product I-4. ES/MS: 350.2 (M⁺). 1H NMR (400 MHz, Chloroform-d) δ 7.65-7.56 (m, 2H), 7.38-7.31 (m, 2H), 6.98 (dd, J=8.1, 1.2 Hz, 1H), 6.78 (dd, J=7.6, 1.2 Hz, 1H), 6.75-6.65 (m, 1H), 3.62 (ddd, J=10.7, 8.6, 6.1 Hz, 1H), 3.33 (ddd, J=10.9, 7.1, 4.3 Hz, 1H), 2.76-2.59 (m, 1H), 2.29 (ddd, J=13.7, 9.0, 6.7 Hz, 1H), 2.07-1.88 (m, 2H).

Preparation of Intermediate I-5

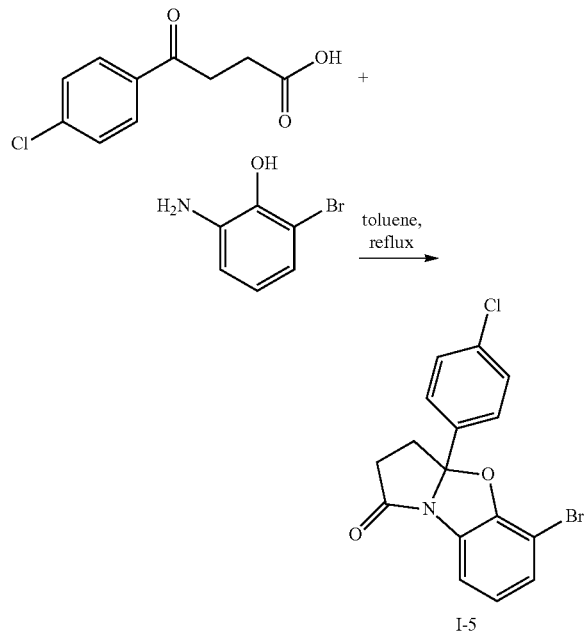

5-bromo-3a-(4-chlorophenyl)-3,3a-dihydrobenzo[d]pyrrolo[2,1-b]oxazol-1 (2H)-one: To a 100 mL RBF was added 4-(4-chlorophenyl)-4-oxobutanoic acid (1.13 g, 5.32 mmol) and 2-amino-6-bromophenol (1 g, 5.32 mmol). The mixture was dissolved in dry toluene (15 mL). The solution was refluxed for 48 hours under Dean-Stark conditions. The mixture was subsequently cooled and then dry-loaded onto silica. The crude material was purified by silica chromatography (eluent: EtOAc/hexanes) to afford the desired product I-5. ES/MS: 364.2 (M⁺). 1H NMR (400 MHz, Chloroform-d) δ 8.03-7.96 (m, 2H), 7.60 (dd, J=8.0, 1.0 Hz, 1H), 7.54-7.45 (m, 3H), 7.21 (t, J=8.0 Hz, 1H), 3.66 (dd, J=7.7, 6.6 Hz, 2H), 3.45 (t, J=7.0 Hz, 2H).

Preparation of Intermediate I-6

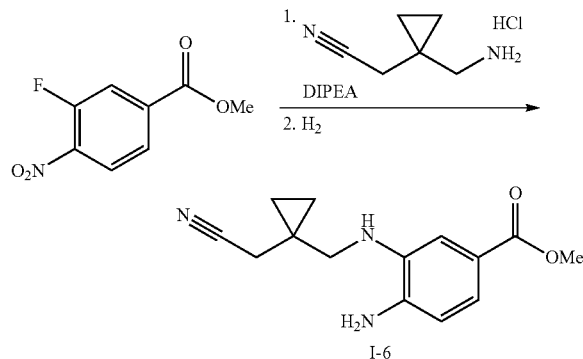

Methyl 4-amino-3-(((1-(cyanomethyl)cyclopropyl)methyl)amino)benzoate: To a solution methyl 3-fluoro-4-nitrobenzoate (700 mg, 3.52 mmol) in THF (10 mL) and DMF (5 mL) was added diisoproylethylamine (3.1 mL, 17.6 mmol) and 2-(1-(aminomethyl)cyclopropyl)acetonitrile hydrochloride (567 mg, 3.87 mmol). The resulting solution was heated to 70° C. for 24 hrs. Upon completion the solvent was removed, the resulting residue taken up in EtOAc (50 mL), washed with brine (10 mL), concentrated and carried forward without further purification. Methyl 3-(((1-(cyanomethyl)cyclopropyl)methyl)amino)-4-nitrobenzoate (1.0 g, 3.46 mmol) was then dissolved in EtOAc:THF (2:1, 15 mL) after which 10% palladium on carbon (368 mg, 0.346 mmol) was added. The resulting suspension was stirred under a hydrogen balloon at room temperature for 16 hrs. The mixture was filtered through celite washing with EtOAc (50 mL) and concentrated to give the desired product I-6 without further purification. ES/MS: 260.2 (M+H⁺).

Preparation of Intermediate I-7

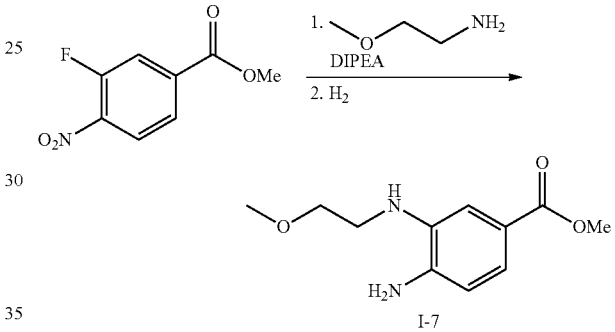

Methyl 4-amino-3-(2-methoxyethylamino)benzoate: To a solution of methyl 3-fluoro-4-nitro-benzoate (50.0 g, 251 mmol) in THF (400 mL) was added diisoproylethylamine (70.0 mL, 402 mmol) and 2-methoxyethylamine (34.9 mL, 402 mmol). The resulting solution was heated to 55° C. for 6 hrs. Upon completion, the solvent was removed and the resulting residue was taken up in EtOAc (150 mL), washed with brine (30 mL), concentrated and carried forward without further purification. Methyl 3-(2-methoxyethylamino)-4-nitro-benzoate (20.0 g, 78.7 mmol) was then dissolved in EtOAc:EtOH (1:1, 140 mL) after which 10% palladium on carbon (5.02 g, 4.72 mmol) was added. The resulting suspension was stirred under a hydrogen balloon at room temperature for 16 hrs. The reaction mixture was filtered through celite washing with EtOAc (100 mL) and concentrated to give the desired product I-7 without further purification. ES/MS: 225.2 (M+H⁺)

Preparation of Intermediate I-8

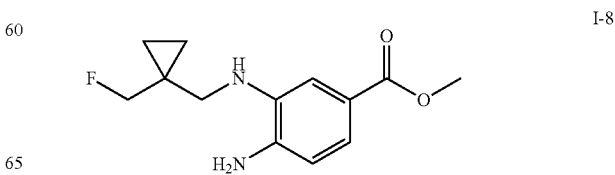

Methyl 4-amino-3-(((1-(fluoromethyl)cyclopropyl)methyl)amino)benzoate (I-8): Methyl 4-amino-3-(((1-(fluoromethyl)cyclopropyl)methyl)amino)benzoate was prepared as described for I-7 substituting methoxyethylamine with (1-(fluoromethyl)cyclopropyl)methanamine;2,2,2-trifluoroacetic acid. ES/MS: 253.3 (M+H$^+$)

Preparation of Intermediate I-9

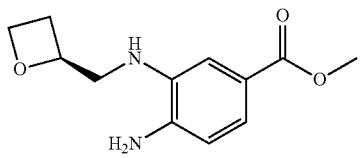

Methyl 4-amino-3-((oxetan-2-ylmethyl)amino)benzoate (I-9): Methyl 4-amino-3-((oxetan-2-ylmethyl)amino)benzoate was prepared as described for I-7 substituting methoxyethylamine with (S)-oxetan-2-ylmethanamine. ES/MS: 237.0 (M+H$^+$)

Preparation of Intermediate I-10

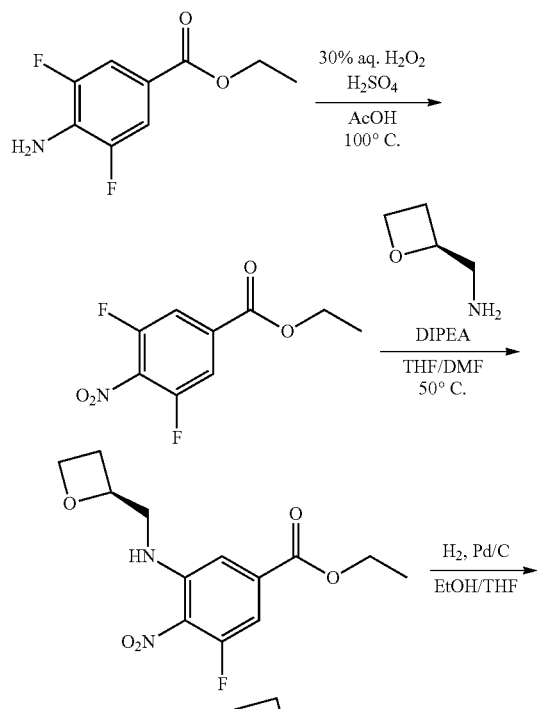

Ethyl 3,5-difluoro-4-nitrobenzoate: Ethyl 4-amino-3,5-difluorobenzoate (5.00 g, 24.9 mmol) was taken up in acetic acid (50.0 mL). Sulfuric acid (12.1 M, 2.05 mL, 24.9 mmol) and hydrogen peroxide (30% aqueous solution, 46.7 mL, 74.6 mmol) were added sequentially and the reaction was heated to 100° C. for 1 hour. Following this time, the reaction was cooled to room temperature and then slowly poured into 300 mL of ice water while swirling. The mixture was then diluted with EtOAc (200 mL), transferred to a separatory funnel, and the organic phase collected. The aqueous phase was extracted with 2×100 mL EtOAc and the combined organics were dried over MgSO$_4$ and concentrated in vacuo. The residue was purified by column chromatography (EtOAc/Hexanes gradient) to afford the product.

Ethyl (S)-3-fluoro-4-nitro-5-((oxetan-2-ylmethyl)amino)benzoate: Ethyl 3,5-difluoro-4-nitro-benzoate (2.50 g, 10.8 mmol) and (S)-oxetan-2-ylmethanamine (989 mg, 11.4 mol) were taken up in tetrahydrofuran (12.0 mL) and N,N-dimethylformamide (6.0 mL) and N,N-diisopropylethylamine (9.42 mL, 54.1 mmol) was added. The reaction was heated to 50° C. for 16 hours. Following this time, the reaction was concentrated in vacuo and the residue purified by column chromatography (0-25% EtOAc/Hexanes) to afford the product. ES/MS: 299.2 (M+H$^+$).

Ethyl (S)-4-amino-3-fluoro-5-((oxetan-2-ylmethyl)amino)benzoate (I-10): Ethyl (S)-3-fluoro-4-nitro-5-((oxetan-2-ylmethyl)amino)benzoate (2.20 g, 7.38 mmol) was taken up in ethanol (10 mL) and tetrahydrofuran (5 mL) and the mixture sparged with nitrogen for 5 minutes. Palladium on carbon (10 wt. % loading, 785 mg, 0.74 mmol) was then added and sparging continued for 5 minutes. Hydrogen was then bubbled through the solution for one minute and then the reaction was set up under balloon hydrogen atmosphere for 21 hours. Following this time, the reaction was stopped and the mixture was filtered through celite. The filter was washed with EtOAc (2×20 mL) and methanol (2×10 mL) and the filtrate concentrated in vacuo to afford ethyl (S)-4-amino-3-fluoro-5-((oxetan-2-ylmethyl)amino)benzoate (I-10). ES/MS: 269.2 (M+H$^+$). 1H NMR (400 MHz, chloroform) δ 7.44-7.30 (m, 2H), 5.13 (qd, J=7.1, 3.4 Hz, 1H), 4.72 (ddd, J=8.7, 7.4, 6.0 Hz, 1H), 4.62 (dt, J=9.1, 6.1 Hz, 1H), 4.33 (q, J=7.1 Hz, 2H), 3.58-3.30 (m, 2H), 2.76 (dtd, J=11.4, 8.0, 6.1 Hz, 1H), 2.56 (ddt, J=11.3, 9.0, 7.1 Hz, 1H), 1.37 (t, J=7.1 Hz, 3H).

Preparation of Intermediate I-11

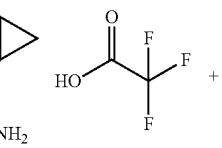

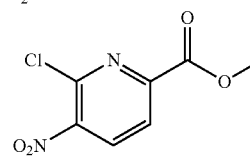

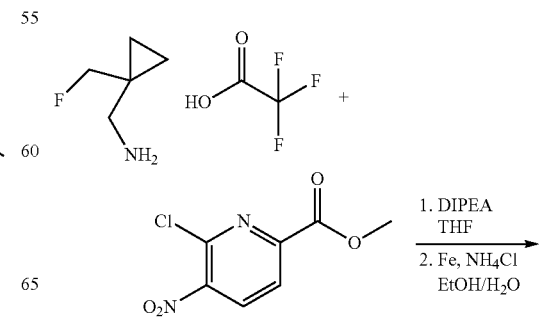

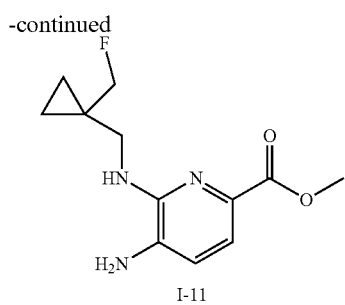

I-11

Methyl 5-amino-6-(((1-(fluoromethyl)cyclopropyl)methyl)amino)picolinate: To a solution of methyl 6-chloro-5-nitro-pyridine-2-carboxylate (1.5 g, 6.93 mmol) in 10 mL of THF, was added N-ethyldiisopropylamine (5.87 mL, 34.6 mmol). Followed by addition of [1-(fluoromethyl)cyclopropyl]methanamine;2,2,2-trifluoroacetic acid (1.5 g, 6.93 mmol) at RT. The mixture was stirred overnight, diluted with 50 mL of EtOAc, and washed with 20 mL of brine and water. The organic layer was dried and concentrated. The mixture was dissolved in 10 mL ethanol and 5 mL of water. Iron (2.4 g, 43.2 mmol) and ammonium chloride (3.3 g, 61.8 mmol) were added to the solution. The mixture was heated to 80° C. for 1 hour. The mixture was cooled and filtered by celite. The filtrate was diluted with 50 mL of EtOAc and washed with 20 mL of brine. The organic layer was dried and concentrated to furnish I-11, which was used without further purification. ES/MS: 254.2 (M+H$^+$).

Preparation of Intermediate I-12

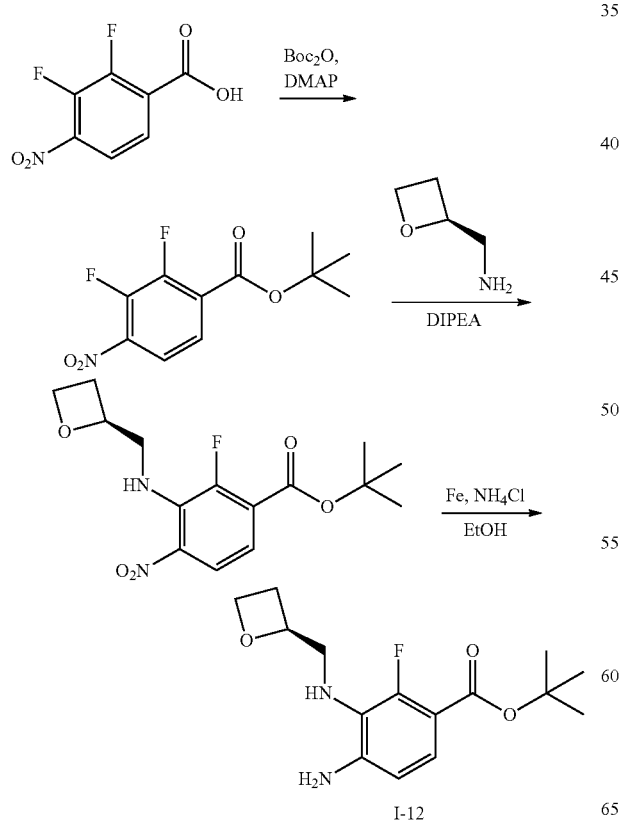

Tert-butyl 2,3-difluoro-4-nitrobenzoate: To a solution of 2,3-difluoro-4-nitrobenzoic acid (1.00 g, 4.92 mmol) in THF (15 mL) was added di-tert-butyl decarbonate (2.15 g, 9.85 mmol) and 4-dimethylaminopyridine (180 mg, 1.48 mmol) and the resulting solution stirred at 40° C. for 3 hrs. Upon completion the solvent was removed by rotary evaporation, and the resulting residue was diluted with EtOAc (100 mL), washed with water (25 mL), brine (25 mL), dried over MgSO$_4$, filtered, and concentrated. The crude residue was purified by column chromatography (0-50% EtOAc in hexane) to give the titled compound.

Tert-butyl (S)-2-fluoro-4-nitro-3-((oxetan-2-ylmethyl)amino)benzoate: To a solution of tert-butyl 2,3-difluoro-4-nitrobenzoate (300 mg, 1.16 mmol) in THF (4 mL) was added diisoproylethylamine (0.61 mL, 3.47 mmol) and (S)-oxetan-2-ylmethanamine (0.12 mL, 1.2 mmol). The resulting solution was heated to 60° C. for 4 hrs. Upon completion, the solvent was removed, the resulting residue taken up in EtOAc (50 mL), washed with water (10 mL) then brine (10 mL), concentrated, and carried forward without further purification. ES/MS: 327.9 (M+H$^+$)

Tert-butyl (S)-4-amino-2-fluoro-3-((oxetan-2-ylmethyl)amino)benzoate: tert-butyl (S)-2-fluoro-4-nitro-3-((oxetan-2-ylmethyl)amino)benzoate (378 mg, 1.16 mmol) was taken up in ethanol (5 mL) and saturated aqueous ammonium chloride (1.5 mL) was added. Iron powder (323 mg, 5.79 mmol) was then added to the reaction mixture and the reaction heated to 60° C. After 3 hours, the mixture was cooled to room temperature, filtered through celite washing with water (10 mL), MeOH (10 mL, and EtOAc (25 mL), and concentrated in vacuo. To the resulting mixture was added EtOAc (50 mL). The organic solution was washed with water (25 mL), brine (25 mL), dried over MgSO$_4$, filtered and concentrated. The product I-12 was used without further purification. ES/MS: 298.0 (M+H$^+$)

Preparation of Intermediate I-13

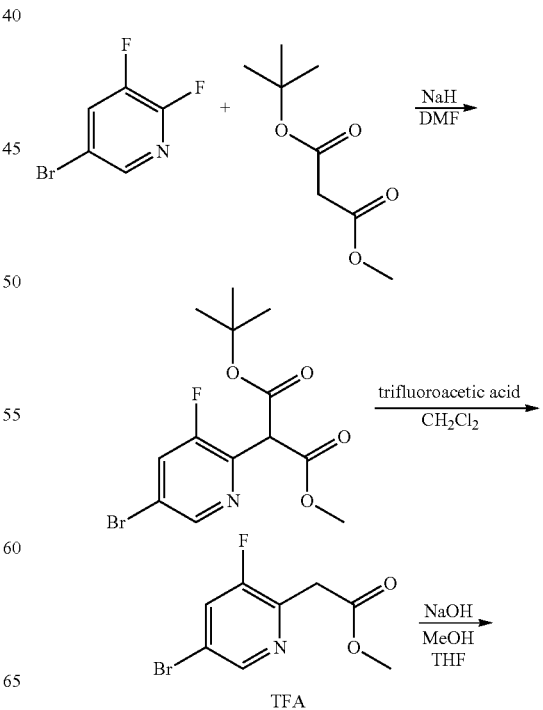

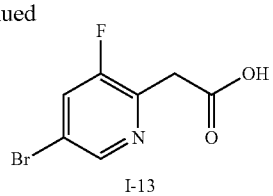

I-13

1-(tert-butyl) 3-methyl 2-(5-bromo-3-fluoropyridin-2-yl) malonate: To a 40 mL vial was added tert-butyl methyl malonate (898 mg, 5.16 mmol) and DMF (10 mL). The solution was cooled to 0° C., and NaH (60% in mineral oil, 237 mg, 6.19 mmol) was added. The reaction mixture was stirred for 20 min at RT, and gas evolution was observed. The reaction was then cooled to 0° C. and 5-bromo-2,3-difluoropyridine (1.0 g, 5.16 mmol) was added, and the reaction was stirred overnight. LCMS showed formation of the product. The mixture was partitioned between EtOAc (50 mL) and water (20 mL) and the organic layer was separated, dried over MgSO₄, and concentrated under reduced pressure to afford 1-(tert-butyl) 3-methyl 2-(5-bromo-3-fluoropyridin-2-yl)malonate which was carried directly forward to the next step. ES/MS: 348.5 (M+H⁺)

Methyl 2-(5-bromo-3-fluoropyridin-2-yl)acetate: To a 100 mL RBF was added 1-(tert-butyl) 3-methyl 2-(5-bromo-3-fluoropyridin-2-yl)malonate (1.4 g, 4.02 mmol), and trifluoroacetic acid (10 mL) and CH₂Cl₂ (10 mL) were added. The mixture was stirred at RT overnight. LCMS showed formation of the product. The solvents were evaporated under reduced pressure to afford the product as a TFA salt. ES/MS: 248.3 (M+H⁺)

2-(5-bromo-3-fluoro-2-pyridyl)acetic acid (I-13): To a 40 mL RBF was added methyl 2-(5-bromo-3-fluoropyridin-2-yl)acetate (trifluoroacetate salt) (1.2 g, 3.31 mmol). Methanol (10 mL) and THF (5 mL) were added, and then 1M NaOH (6.63 mL, 6.63 mmol) was added. The reaction mixture was stirred at 70 degrees overnight. The mixture was concentrated under reduced pressure, and the residue was dissolved in water and acidified with 1N HCl. The resulting mixture was extracted 3× with a mixture of DCM and methanol. The combined organic layers were dried over MgSO₄, filtered, and concentrated under reduced pressure. The crude material I-13 was carried forward without further purification.

ES/MS: 234.159 (M+H⁺)

Preparation of Intermediate I-14

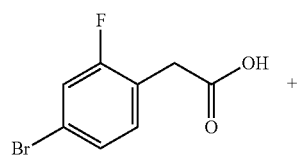

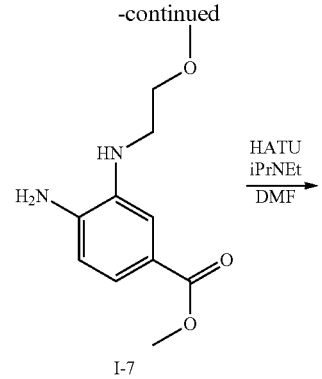

I-7

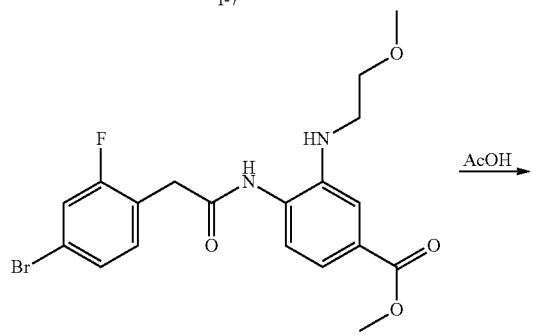

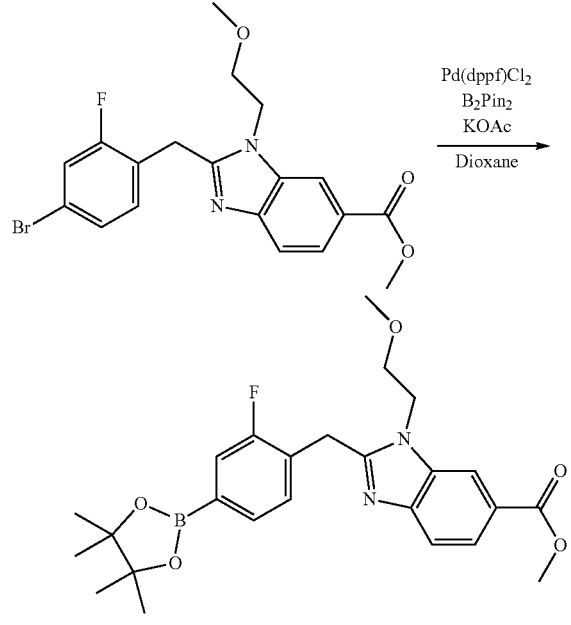

I-14

Methyl 4-[[2-(4-bromo-2-fluoro-phenyl)acetyl]amino]-3-(2-methoxyethylamino)benzoate: To a solution of 2-(4-bromo-2-fluoro-phenyl)acetic acid (1.00 g, 4.29 mmol) in DMF (20.0 mL) was added methyl 4-amino-3-(2-methoxyethylamino)benzoate (I-7) (1.18 g, 5.28 mmol) and O-(7-azabenzotriazol-1-yl)-N,N,N',N'-tetramethyluronium hexafluorophosphate (1.96 g, 5.15 mmol) followed by N,N-diisopropylethylamine (3.74 mL, 21.5 mmol), and the reaction mixture was stirred for 2 h at room temperature. The reaction was concentrated in vacuo and the residue was taken up in EtOAc and washed with water (1×) and brine (1×). The organic layer was dried over sodium sulfate, filtered, and concentrated in vacuo. The crude residue was taken forward without further purification. ES/MS m/z: 583.5 (M+H⁺)

Methyl 2-[(4-bromo-2-fluoro-phenyl)methyl]-3-(2-methoxyethyl)benzimidazole-5-carboxylate: The crude product from the previous step, methyl 4-[[2-(4-bromo-2-fluoro-phenyl)acetyl]amino]-3-(2-methoxyethylamino)benzoate (1.89 g, 4.29 mmol), was dissolved in AcOH (40.0 mL) and the reaction mixture was heated to 60° C. for 2 h. The reaction mixture was then concentrated in vacuo and the crude residue was taken up in DCM and washed with saturated aqueous sodium bicarbonate. The layers were separated and the aqueous layer was extracted with DCM (2×). The combined organic extracts were dried over sodium sulfate, filtered and the filtrate was concentrated in vacuo. The crude residue was purified by column chromatography (0-100% EtOAc in hexane) to give the titled compound. ES/MS m/z: 421.9 (M+H$^+$).

Methyl 2-[[2-fluoro-4-(4,4,5,5-tetramethyl-1,3,2-dioxaborolan-2-yl)phenyl]methyl]-3-(2-methoxyethyl)benzimidazole-5-carboxylate: To a vial was added methyl 2-[(4-bromo-2-fluoro-phenyl)methyl]-3-(2-methoxyethyl)benzimidazole-5-carboxylate (200 mg, 0.475 mmol), 4,4,5,5-tetramethyl-2-(4,4,5,5-tetramethyl-1,3,2-dioxaborolan-2-yl)-1,3,2-dioxaborolane (145 mg, 0.570 mmol), (1,1'-bis(diphenylphosphino)ferrocene)-dichloropalladium(II) (33.6 mg, 0.0475 mmol) and potassium acetate (0.140 g, 1.42 mmol). 1,4-dioxane (4.80 mL) was added and the reaction was heated to 100° C. for 24 h. The reaction mixture was filtered through celite, eluting with DCM and the filtrate was concentrated in vacuo. The crude residue was purified by column chromatography (0-100% EtOAc in hexane) to give compound I-14. ES/MS m/z: 469.4 (M+H$^+$).

Preparation of Intermediate I-15

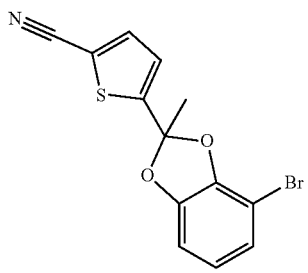

I-15

5-(4-bromo-2-methylbenzo[d][1,3]dioxol-2-yl)thiophene-2-carbonitrile (I-15): 5-(4-bromo-2-methylbenzo[d][1,3]dioxol-2-yl)thiophene-2-carbonitrile was prepared in a manner as described for Intermediate I-2 substituting 5-chloro-2-ethynylpyridine with 5-ethynylthiophene-2-carbonitrile. 1H NMR (400 MHz, Chloroform-d) δ 7.54 (d, J=3.9 Hz, 1H), 7.26 (d, J=3.9 Hz, 1H), 7.02 (dd, J=7.2, 2.2 Hz, 1H), 6.84-6.74 (m, 2H), 2.16 (s, 3H).

Preparation of Intermediate I-16

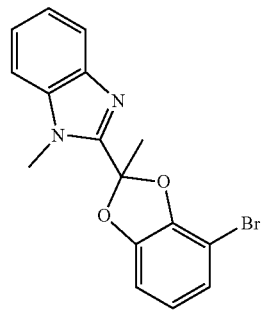

I-16

2-(4-bromo-2-methylbenzo[d][1,3]dioxol-2-yl)-1-methyl-1H-benzo[d]imidazole (I-16): 2-(4-bromo-2-methylbenzo[d][1,3]dioxol-2-yl)-1-methyl-1H-benzo[d]imidazole was prepared in a manner as described for Intermediate I-2 substituting 5-chloro-2-ethynylpyridine with 2-ethynyl-1-methyl-1H-benzo[d]imidazole. ES/MS: 346.2 (M+H$^+$).

Preparation of Intermediate I-17

Methyl 2-(4-bromo-2,6-difluorophenyl)acetate: To 2-(4-bromo-2,6-difluoro-phenyl)acetic acid (5.00 g, 1.99 mmol) was added 31.9 mL of HCl in methanol (1.25 M, 2 equiv). The mixture was heated to 70° C. overnight. After cooling to rt, the mixture was concentrated under reduced pressure. The residue was purified by silica gel flash column chromatography, eluting with 0-10% EtOAc in hexanes to yield methyl 2-(4-bromo-2,6-difluoro-phenyl)acetate. 1H NMR (400 MHz, Chloroform-d) δ 7.16-7.08 (m, 2H), 3.74 (s, 3H), 3.69 (s, 2H).

Methyl 2-(4-(2-(4-chloro-2-fluorophenyl)-2-methylbenzo[d][1,3]dioxol-4-yl)-2,6-difluorophenyl)acetate: 2-(4-bromo-2,6-difluoro-phenyl)acetate (2.83 g, 0.0107 mol) were taken up in 1,4-dioxane (30 mL), along with potassium propionate (3.59 g, 0.0320 mol), bis(diphenylphosphino)ferrocene)dichloropalladium(II) (1.19 g, 0.00160 mol) and bis(pinacolato)diboron (3.52 g, 0.0139 mol). The mixture was capped and sparged with nitrogen for five minutes. Then, the mixture was heated for 1 hr at 110° C. Following this time, the reaction cap was opened, followed by an addition of bis(diphenylphosphino)ferrocene)dichloropalladium(II) (0.594 g, 0.0008 mol) and aqueous 2M sodium bicarbonate solution (10.7 mL, 0.0214 mol). The mixture was stirred at room temperature for two minutes before the addition of 4-bromo-2-(4-chloro-2-fluoro-phenyl)-2-methyl-1,3-benzodioxole (5.5 grams, 0.0160 mol). Then, the mixture was capped and heated for 3 hours at 95° C. LCMS showed full conversion of the boronate. Then, the mixture was cooled to r.t., filtered through celite, and concentrated in vacuo. The mixture was directly loaded onto a column, eluting with a slow gradient of 0-30% EtOAc in hexanes to yield an oil. LC-MS (ESI) m/z 449.0 (M+H).

2-(4-(2-(4-chloro-2-fluorophenyl)-2-methylbenzo[d][1,3]dioxol-4-yl)-2,6-difluorophenyl)acetic acid (I-17): Methyl 2-[4-[2-(4-chloro-2-fluoro-phenyl)-2-methyl-1,3-benzodioxol-4-yl]-2,6-difluoro-phenyl]acetate (1.50 g, 0.00334 mol) was taken up in 15 mL of acetonitrile. Then, a 0.3 M lithium hydroxide solution was added (0.0167 mol, 16.7 mL) and the mixture was heated at a 100° C. for 1 hour. LCMS showed quantitative conversion to the desired starting material. The reaction mixture was acidified to a pH of 6 via the addition of 1.0 M solution of citric acid, followed by the addition of water and EtOAc. The mixture was extracted 3 times with EtOAc, dried with magnesium sulfate and concentrated under reduced pressure to yield 2-[4-[2-(4-chloro-2-fluoro-phenyl)-2-methyl-1,3-benzodioxol-4-yl]-2,6-difluoro-phenyl]acetic acid. 1H NMR (400 MHz, Chloroform-d) δ 11.53 (s, 1H), 7.56 (t, J=8.2 Hz, 1H), 7.48-7.37 (m, 2H), 7.25-7.11 (m, 2H), 7.06 (dd, J=7.9, 1.5 Hz, 1H), 6.99-6.86 (m, 2H), 3.86 (s, 2H), 2.16 (s, 3H). ES/MS: 436.0 (M+H).

Preparation of Intermediate I-18

Methyl 4-amino-3-((2-(methylsulfonyl)ethyl)amino)benzoate: I-18 was prepared in an identical manner as described for I-7 substituting methoxyethylamine with 2-(methylsulfonyl)ethan-1-amine. ES/MS: 273.2 (M+H+).

Preparation of Intermediate I-19

Methyl 4-amino-3-((2-(difluoromethoxy)ethyl)amino)benzoate: I-19 was prepared in an identical manner as described for I-7 substituting methyoxyethylamine with 2-(difluoromethoxy)ethan-1-amine. ES/MS: 261.2 (M+H+).

Preparation of Intermediates I-20 and I-21

2-(4-(2-(4-chloro-2-fluorophenyl)-2-methylbenzo[d][1,3]dioxol-4-yl)-2,6-difluorophenyl)acetic acid I-17 as a mixture of two stereoisomers was separated by chiral SFC (OJ-H column with 5% MeOH cosolvent) to give two distinct stereoisomers.
2-(4-(2-(4-chloro-2-fluorophenyl)-2-methylbenzo[d][1,3]dioxol-4-yl)-2,6-difluorophenyl)acetic acid: ES/MS: 436.1.
2-(4-(2-(4-chloro-2-fluorophenyl)-2-methylbenzo[d][1,3]dioxol-4-yl)-2,6-difluorophenyl)acetic acid: ES/MS: 436.1.

Preparation of Intermediate I-22

3-(2-methoxyethylamino)-4-nitro-benzonitrile: A solution of 3-fluoro-4-nitro-benzonitrile (2 g, 12.04 mmol), 2-methoxyethanamine (1.25 ml, 14.79 mmol), and N,N-Diisopropylethylamine (3.2 ml, 18.37 mmol) in DMF was stirred at rt for 3 days. The mixture was diluted with EtOAc, washed with 5% LiCl 2× and brine. The organic extract was dried over sodium sulfate to give title product. ES/MS m/z: 222 (M+H+); 1H NMR (400 MHz, CDCl3) δ 8.26 (dd, J=8.7, 1.7 Hz, 1H), 8.23 (s, 1H), 7.21 (d, J=1.7 Hz, 1H), 6.89 (dt, J=8.8, 1.5 Hz, 1H), 3.71 (dd, J=5.6, 4.8 Hz, 2H), 3.51 (q, J=5.2 Hz, 2H), 3.45 (d, J=1.0 Hz, 3H).

N-(2-methoxyethyl)-2-nitro-5-(2H-tetrazol-5-yl)aniline: In a 200 ml round bottomed flask, a suspension of 3-(2-methoxyethylamino)-4-nitro-benzonitrile (2.563 g, 11.6 mmol), sodium azide (1.51 g, 23.2 mmol), and ammonium chloride (1.24 g, 23.2 mmol) in DMF (50 mL) was heated at 110 deg overnight. The mixture was diluted with EtOAc and washed with 5% LiCl 3×50 mL. The aqueous layer was extracted 2× with EtOAc 100 mL. The combined organic extracts were dried over sodium sulfate to give title product as an oil. ES/MS m/z: 265.2 (M+H+); 1H NMR (400 MHz, MeOD) δ 8.32 (d, J=8.8 Hz, 1H), 7.77 (d, J=1.8 Hz, 1H), 7.35 (dd, J=8.9, 1.8 Hz, 1H), 3.82-3.69 (m, 2H), 3.66 (t, J=5.2 Hz, 2H), 3.46 (s, 3H), 3.01 (d, J=0.5 Hz, 4H).

N2-(2-methoxyethyl)-4-(2H-tetrazol-5-yl)benzene-1,2-diamine (I-22): A solution of N-(2-methoxyethyl)-2-nitro-5-(2H-tetrazol-5-yl)aniline (93 mg, 352 μmol) in EtOH (25 mL) was degassed with Ar/Vac 3×. To the mixture was added Pd/C (10%, 37.7 mg, 0.0354 mmol) and the mixture was stirred at rt with a balloon of hydrogen overnight. The mixture was filtered over a Celite plug and rinsed with EtOAc. The mixture was concentrated to give title product, which was used in subsequent steps without further purification. ES/MS m/z: 235.2 (M+H+).

Preparation of Intermediate I-23

Tert-butyl 2-(6-chloro-2-methoxypyridin-3-yl)acetate: In a 40 mL reaction vial, a mixture of 3-bromo-6-chloro-2-methoxy-pyridine (1000 mg, 4.50 mmol), Pd2(dba)3 (103 mg, 0.112 mmol), and 9,9-dimethyl-4,5-bis(diphenylphosphino)xanthene (130 mg, 0.225 mmol) was degassed with Ar/vac 3×. Added THF (10 mL) and degassed with Ar/vac 3×. To this was added bromo-(2-tert-butoxy-2-oxo-ethyl)zinc (0.500 M, 13.5 mL, 6.74 mmol) and the mixture was heated at 65 deg for 3 hr. The reaction was diluted with EtOAc and brine. The organic extract was dried over sodium sulfate and purified by flash chromatography (eluent: EtOAc/hexanes) to give the title compound. ES/MS m/z: 258.2 (M+H+); 1H NMR (400 MHz, CDCl3) δ 7.43 (dt, J=7.6, 0.7 Hz, 1H), 6.89 (d, J=7.6 Hz, 1H), 3.97 (s, 3H), 3.48 (s, 2H), 1.46 (s, 9H).

2-(6-chloro-2-methoxypyridin-3-yl)acetic acid: To a solution of tert-butyl 2-(6-chloro-2-methoxy-3-pyridyl)acetate (250 mg, 0.970 mmol) in DCM (5 mL) was added TFA (0.750 mL). The reaction was stirred at rt overnight, concentrated to dryness, and carried onto next without further purification. ES/MS m/z: 202.2 (M+H+)

Methyl 4-(2-(6-chloro-2-methoxypyridin-3-yl)acetamido)-3-((2-methoxyethyl)amino)benzoate: To a solution of 2-(6-chloro-2-methoxy-3-pyridyl)acetic acid (196 mg, 0.972 mmol), methyl 4-amino-3-(2-methoxyethylamino)benzoate (262 mg, 1.17 mmol), and methyl 4-amino-3-(2-methoxyethylamino)benzoate (262 mg, 1.17 mmol), and o-(7-azabenzotriazol-1-yl)-N,N,N',N'-tetramethyluronium hexafluorophosphate (626 mg, 1.65 mmol) in DMF (4 mL), was added N,N-diisopropylethylamine (0.800 mL, 4.59 mmol. Stirred at rt overnight. The reaction was diluted with EtOAc washed with 5% LiCl, saturated NaHCO3, and brine. The organic extract was dried over sodium sulfate and concentrated. The crude residue was taken forward without further purification, assuming full conversion. ES/MS m/z: 408.2 (M+H+).

Methyl 2-[(4-bromo-2,6-difluoro-phenyl)methyl]-3-(2-methoxyethyl)benzimidazole-5-carboxylate (I-23): A solution of methyl 4-[[2-(6-chloro-2-methoxy-3-pyridyl)acetyl]amino]-3-(2-methoxyethylamino)benzoate (397 mg, 0.973 mmol) and acetic acid glacial (3.5 mL, 61.2 mmol) in DCE (4 mL) was heated at 60 deg for 7 hr. The mixture was concentrated and chromatographed (eluent: EtOAc/hexanes) to give the title compound. ES/MS m/z: 390.2 (M+H+); 1H NMR (400 MHz, CDCl3) δ 8.11 (dd, J=1.6, 0.7 Hz, 1H), 7.99 (dd, J=8.5, 1.6 Hz, 1H), 7.73 (dd, J=8.5, 0.6 Hz, 1H), 7.46-7.38 (m, 1H), 6.87 (d, J=7.7 Hz, 1H), 4.39 (t, J=5.4 Hz, 2H), 4.30-4.25 (m, 2H), 4.00 (s, 3H), 3.97 (s, 3H), 3.65 (t, J=5.4 Hz, 2H), 3.26 (s, 3H).

Preparation of Intermediate I-24

2-chloro-5,5-dimethoxy-6,7,8,9-tetrahydro-5H-benzo[7]annulene: To a 100 mL vial was added 3-2-chloro-6,7,8,9-tetrahydro-5H-benzo[7]annulen-5-one (1 g, 5.14 mmol, methanol (10 mL), HCl (2.5M methanolic solution, 2.05 mL, 1.03 mmol), and trimethyl orthoformate (1.69 mL, 12.5 mmol). The solution was heated at 70° C. for 24 hours. The mixture was subsequently cooled to room temperature and concentrated under reduced pressure. The crude material was diluted with diethyl ether (50 mL), and washed with 50% aq. NaHCO$_3$ (1x 20 mL). The aqueous layer was back-extracted with diethyl ether (1x 50 mL), and the combined organic layers were dried over MgSO$_4$, filtered, and concentrated under reduced pressure to afford the desired product 2-chloro-5,5-dimethoxy-6,7,8,9-tetrahydro-5H-benzo[7]annulene which was carried forward to the next step.

4-bromo-2'-chloro-6', 7', 8', 9'-tetrahydrospiro[benzo[d][1,3]dioxole-2,5'-benzo[7]annulene]: To a 100 mL vial was added 2-chloro-5,5-dimethoxy-6,7,8,9-tetrahydro-5H-benzo[7]annulene (800 mg, 3.32 mmol) and 3-bromobenzene-1,2-diol (691 mg, 3.66 mmol), and para-toluenesulfonic acid monohydrate (63 mg, 0.33 mmol). The mixture was dissolved in toluene (10 mL), and the solution was heated at reflux overnight under Dean-Stark conditions. The mixture was subsequently cooled, dry-loaded onto silica, and purified by silica chromatography (eluent: EtOAc/hexanes) to afford the desired product I-24. 1H NMR (400 MHz, Chloroform-d) δ 7.62-7.54 (m, 1H), 7.28 (s, 1H), 7.17 (d, J=7.7 Hz, 1H), 6.96 (dd, J=8.1, 1.3 Hz, 1H), 6.77 (dd, J=7.8, 1.2 Hz, 1H), 6.71 (t, J=7.9 Hz, 1H), 3.06 (dt, J=7.1, 2.3 Hz, 2H), 2.41-2.26 (m, 2H), 2.18-2.05 (m, 2H), 1.87-1.65 (m, 2H).

Preparation of Intermediate I-25

4'-bromo-8-chloro-3,4-dihydro-2H-spiro[benzo[b]oxepine-5,2'-benzo[d][1,3]dioxole] (I-25): 4'-bromo-8-chloro-3,4-dihydro-2H-spiro[benzo[b]oxepine-5,2'-benzo[d][1,3]dioxole] was prepared identically as described for I-24 substituting 3-2-chloro-6,7,8,9-tetrahydro-5H-benzo[7]annulen-5-one with 8-chloro-3,4-dihydrobenzo[b]oxepin-5(2H)-one. ES/MS: 367.0 (M+H+). 1H NMR (400 MHz, Chloroform-d) δ 7.54 (d, J=8.4 Hz, 1H), 7.16-6.99 (m, 3H), 6.87-6.63 (m, 2H), 4.33 (ddd, J=12.2, 6.2, 3.9 Hz, 1H), 4.24-4.09 (m, 1H), 2.58-2.36 (m, 2H), 2.31 (ddp, J=17.8, 9.0, 4.5 Hz, 1H), 2.15 (tq, J=11.4, 4.2 Hz, 1H).

Preparation of Intermediate I-26

4'-bromo-8-chloro-3,4-dihydro-2H-spiro[benzo[b]oxepine-5,2'-benzo[d][1,3]dioxole] (I-26): 4-bromo-6'-chloro-3', 4'-dihydro-2'H-spiro[benzo[d][1,3]dioxole-2,1'-naphthalene] was prepared identically as described for I-24 substituting 3-2-chloro-6,7,8,9-tetrahydro-5H-benzo[7]annulen-5-one with 6-chloro-3,4-dihydronaphthalen-1(2H)-one. ES/MS: 353.1 (M+H+). 1H NMR (400 MHz, Chloroform-d) δ 7.51 (d, J=8.4 Hz, 1H), 7.26-7.19 (m, 2H), 7.04-6.96 (m, 1H), 6.79-6.75 (m, 2H), 2.89 (t, J=6.3 Hz, 2H), 2.43-2.22 (m, 2H), 2.19-2.06 (m, 2H).

Preparation of Intermediate I-27

4-bromo-2-(4-chloro-2-fluorophenyl)-2-ethylbenzo[d][1,3]dioxole (I-27): 4-bromo-2-(4-chloro-2-fluorophenyl)-2-ethylbenzo[d][1,3]dioxole was prepared identically as described for I-24 substituting 3-2-chloro-6,7,8,9-tetrahydro-5H-benzo[7]annulen-5-one with 1-(4-chloro-2-fluorophenyl)propan-1-one.

Preparation of Intermediate I-28

4-bromo-2-(2-fluoro-4-(trifluoromethyl)phenyl)-2-methylbenzo[d][1,3]dioxole (I-28): 4-bromo-2-(2-fluoro-4-(trifluoromethyl)phenyl)-2-methylbenzo[d][1,3]dioxole was prepared identically as described for I-3 substituting 1-(4-chloro-2-fluorophenyl)ethan-1-one with 1-(2-fluoro-4-(trifluoromethyl)phenyl)ethan-1-one. 1H NMR (400 MHz, Chloroform-d) δ 7.83-7.73 (m, 1H), 7.49-7.36 (m, 2H), 7.05-6.84 (m, 2H), 6.83-6.67 (m, 1H), 2.25-2.09 (m, 3H).

Preparation of Intermediate I-29

4-chloro-1-(diethoxyphosphorylmethyl)-2-fluoro-benzene: To a 40 mL vial (vented to the atmosphere) was added 1-(bromomethyl)-4-chloro-2-fluoro-benzene (3.3 g, 14.8 mmol), and triethyl phosphite (2.53 mL, 14.8 mmol) (gas evolution). The mixture was heated at 100° C. for 3 hours.) The mixture was cooled and taken directly forward to the next step.

(E)-1-bromo-3-(4-chloro-2-fluorostyryl)-2-fluorobenzene: To a 250 mL vial containing 4-chloro-1-(diethoxyphosphorylmethyl)-2-fluoro-benzene (4 g, 14.3 mmol) was added THF (100 mL), and the mixture was cooled to 0° C. Solid potassium tert-butoxide (2.4 g, 21.4 mmol) was added, and the mixture was stirred 30 minutes at 0° C. 3-Bromo-2-fluoro-benzaldehyde (2.89 g, 14.3 mmol) was added, and the mixture was stirred at room temperature for 48 hours. The mixture was diluted with EtOAc (100 mL), and washed with sat. aq. NH$_4$Cl (1x 50 mL). The organic layer was dried over MgSO$_4$, filtered, and concentrated under reduced pressure. The crude material was purified by silica chromatography (eluent: EtOAc/hexanes) to afford the desired product. 1H NMR (400 MHz, Chloroform-d) δ 7.61-7.55 (m, 2H), 7.49 (ddd, J=8.1, 6.5, 1.6 Hz, 1H), 7.29 (d, J=6.2 Hz, 2H), 7.17 (ddd, J=12.3, 10.4, 2.1 Hz, 2H), 7.06 (td, J=7.9, 1.0 Hz, 1H).

1-(3-bromo-2-fluorophenyl)-2-(4-chloro-2-fluorophenyl)ethane-1,2-diol: To a 100 mL vial containing (E)-1-bromo-3-(4-chloro-2-fluorostyryl)-2-fluorobenzene (1 g, 3.03 mmol) was added tert-butanol (12 mL), water (10 mL), acetone (10 mL), citric acid (50% solution in water, 2.3 mL), potassium osmate(IV) dihydrate (5.6 mg, 0.015 mmol), and 4-methylmorpholine N-oxide (390 mg, 3.3 mmol). The solution was stirred overnight at 40° C. LCMS indicated consumption of the starting material. The mixture was diluted with EtOAc (50 mL), and 2 mL sat. aq. NH$_4$Cl was added. The layers were separated, and the aqueous layer was extracted with EtOAc (2x50 mL). The combined organic layer was dried over MgSO$_4$, filtered, and concentrated under reduced pressure. The crude material was purified by silica chromatography (eluent: EtOAc/hexanes) to afford the desired product. 1H NMR (400 MHz, Chloroform-d) δ 7.57-7.38 (m, 3H), 7.24-6.89 (m, 3H), 5.16 (s, 2H).

1-bromo-7-chloro-4b,9b-dihydrobenzofuro[3,2-b]benzofuran (I-29): To a 40 mL vial containing 1-(3-bromo-2-fluorophenyl)-2-(4-chloro-2-fluorophenyl)ethane-1,2-diol (100 mg, 0.275 mmol) was added THF (5 mL), and the mixture was cooled to 0° C. under a nitrogen atmosphere. Potassium tert-butoxide (1M THF, 0.825 mL, 0.825 mmol) was added, and the mixture was stirred 1 hour warming to room temperature. The mixture was quenched with water (2 mL) and diluted with EtOAc (20 mL). The layers were separated, and the aqueous layer was extracted with EtOAc (2×10 mL). The combined organic layer was dried over MgSO$_4$, filtered, and concentrated under reduced pressure. The crude material was purified by silica chromatography (eluent: EtOAc/hexanes) to afford the desired product.

Preparation of Intermediate I-30

Methyl 5-amino-6-(((1-(cyanomethyl)cyclopropyl)methyl)amino)picolinate (I-30): Methyl 5-amino-6-(((1-

(cyanomethyl)cyclopropyl)methyl)amino)picolinate was prepared in a manner analogous to I-11, substituting 2-(1-(aminomethyl)cyclopropyl)acetonitrile hydrochloride for [1-(fluoromethyl)cyclopropyl]methanamine;2,2,2-trifluoro-acetic acid. ES/MS: 261.2 (M+H+).

Preparation of Intermediates I-31 and I-32

2-(4-bromo-2-methyl-1,3-benzodioxol-2-yl)-5-chloro-pyridine (I-31 and I-32): 2-(4-bromo-2-methyl-1,3-benzodioxol-2-yl)-5-chloro-pyridine (I-2) was separated by chiral SFC (AD-H column with 5% IPA-NH3 cosolvent) to give two distinct stereoisomers.
Peak 1: 2-(4-bromo-2-methyl-1,3-benzodioxol-2-yl)-5-chloro-pyridine (I-31): ES/MS: 328.1 (M+H+). 1H NMR (400 MHz, Chloroform-d) δ 8.66 (d, J=2.4 Hz, 1H), 7.74 (dd, J=8.4, 2.4 Hz, 1H), 7.63 (dd, J=8.4, 0.7 Hz, 1H), 6.99 (dd, J=8.0, 1.4 Hz, 1H), 6.81-6.70 (m, 2H), 2.13 (s, 3H).
Peak 2: 2-(4-bromo-2-methyl-1,3-benzodioxol-2-yl)-5-chloro-pyridine (I-32): ES/MS: 328.1 (M+H+). 1H NMR (400 MHz, Chloroform-d) δ 8.66 (d, J=2.4 Hz, 1H), 7.74 (dd, J=8.4, 2.4 Hz, 1H), 7.63 (dd, J=8.4, 0.7 Hz, 1H), 6.99 (dd, J=8.0, 1.4 Hz, 1H), 6.81-6.70 (m, 2H), 2.13 (s, 3H).

Preparation of Intermediate I-33

Methyl 4-amino-3-(((4-ethyl-4H-1,2,4-triazol-3-yl)methyl)amino)benzoate: methyl 4-amino-3-(((4-ethyl-4H-1,2,4-triazol-3-yl)methyl)amino)benzoate was prepared identically as described for I-6 substituting 2-(1-(aminomethyl)cyclopropyl)acetonitrile hydrochloride with (4-ethyl-4H-1,2,4-triazol-3-yl)methanamine. ES/MS: 276.2 (M+H+).

Preparation of Intermediate I-34

Methyl 4-amino-3-((oxazol-2-ylmethyl)amino)benzoate: methyl 4-amino-3-(((4-ethyl-4H-1,2,4-triazol-3-yl)methyl)amino)benzoate was prepared identically as described for I-6 substituting 2-(1-(aminomethyl)cyclopropyl)acetonitrile hydrochloride with oxazol-2-ylmethanamine hydrochloride. ES/MS: 248.2 (M+H+).

Preparation of Intermediates I-35 and I-36

4-Bromo-2-(4-chloro-2-fluorophenyl)isoindolin-1-one: To a solution of 4-chloro-2-fluoroaniline (100 g, 0.69 mmol) in acetic acid (1.37 mL) was added methyl 3-bromo-2-(bromomethyl)benzoate (216 mg, 0.70 mmol). The resulting mixture was heated to 100° C. for 18 h and then cooled to room temperature and concentrated to dryness. The crude material was then purified by SiO$_2$ column chromatography (eluent: EtOAc/hexanes) to provide 4-bromo-2-(4-chloro-2-fluorophenyl)isoindolin-1-one (I-35). ES/MS m/z: 341.954 (M+H+).
4-Bromo-2-(4-chloro-2-fluorophenyl)isoindoline: To 4-bromo-2-(4-chloro-2-fluorophenyl)isoindolin-1-one (36 mg, 0.10 mmol) was added borane-tetrahydrofuran complex (1M in THF, 1 mL, 1 mmol). The resulting mixture was stirred at room temperature for 3 days and then diluted with methanol. The mixture was then concentrated to dryness and the crude material was then purified by SiO$_2$ column chromatography (eluent: EtOAc/hexanes) to provide 4-bromo-2-(4-chloro-2-fluorophenyl)isoindoline (I-36). ES/MS m/z: 326.019 (M+H+).

Preparation of Intermediate I-37

7-Bromo-2-(4-chloro-2-fluorophenyl)isoindolin-1-one: To a solution of 4-chloro-2-fluoroaniline (106 g, 0.73 mmol) in acetic acid (1.5 mL) was added methyl 2-bromo-6-(bromomethyl)benzoate (270 mg, 0.88 mmol). The resulting mixture was heated to 100° C. for 6 h and then cooled to room temperature and concentrated to dryness. The crude material was then purified by SiO$_2$ column chromatography (eluent: EtOAc/hexanes) to provide 7-bromo-2-(4-chloro-2-fluorophenyl)isoindolin-1-one (I-37). ES/MS m/z: 342.074 (M+H+).

Preparation of Intermediate I-38

2-(4-chloro-2-fluorophenyl)-2-methylbenzo[d][1,3]dioxol-4-ol: To a solution of benzene-1,2,3-triol (2.5 g, 19.8 mmol) and 1-(4-chloro-2-fluorophenyl)ethan-1-one (3.5 g, 20.3 mmol) in toluene (19.8 mL) was added p-toluenesulfonic acid (190 mg, 1.0 mmol). The resulting mixture was heated to reflux with a Dean-Stark trap for 2.5 days. The resulting mixture was concentrated to dryness and the crude material was then purified by SiO$_2$ column chromatography (eluent: EtOAc/hexanes) to provide 2-(4-chloro-2-fluorophenyl)-2-methylbenzo[d][1,3]dioxol-4-ol. 1H NMR (400 MHz, CDCl3) δ 7.61-7.52 (m, 1H), 7.20-7.10 (m, 2H), 6.73 (t, J=8.1 Hz, 1H), 6.54-6.47 (m, 2H), 5.09 (s, 1H), 2.10 (d, J=1.2 Hz, 3H).
2-(4-chloro-2-fluorophenyl)-2-methylbenzo[d][1,3]dioxol-4-yl trifluoromethanesulfonate: To a solution of 2-(4-chloro-2-fluorophenyl)-2-methylbenzo[d][1,3]dioxol-4-ol (60 mg, 0.21 mmol) in dichloromethane (2 mL) at −78° C. (external temperature, acetone/Cl$_2$ bath) was added trifluoromethanesulfonic anhydride (1M in CH$_2$Cl$_2$, 0.24 mL, 0.24 mmol) and triethylamine (0.06 mL, 0.43 mmol). The resulting mixture was stirred at −78° C. for 20 min and slowly warmed to room temperature for 40 min. The resulting mixture was diluted with CH$_2$Cl$_2$ and washed with aqueous bicarbonate. The aqueous layer was back-extracted with CH$_2$Cl$_2$ and concentrated to dryness. The crude material was then purified by SiO$_2$ column chromatography (eluent: EtOAc/hexanes) to provide 2-(4-chloro-2-fluorophenyl)-2-methylbenzo[d][1,3]dioxol-4-yl trifluoromethanesulfonate (I-38). 1H NMR (400 MHz, CDCl3) δ 7.59 (t, J=8.4 Hz, 1H), 7.18 (ddd, J=9.6, 6.2, 2.1 Hz, 2H), 6.89-6.84 (m, 2H), 6.81 (dd, J=6.9, 2.9 Hz, 1H), 2.13 (d, J=1.1 Hz, 3H).

Preparation of Intermediate I-39

4-(1,1-dimethoxyethyl)-3-fluorobenzonitrile: To a solution of 4-acetyl-3-fluorobenzonitrile (110 mg, 0.67 mmol) and p-toluenesulfonic acid (6 mg, 0.05 mmol) in methanol (0.79 mL) was added trimethyl orthoformate (0.1 mL, 0.91 mmol). The resulting mixture was heated to 50° C. for 24 h and cooled to room temperature. The resulting mixture was diluted with diethyl ether and washed with dilute aqueous bicarbonate. The aqueous layer was back-extracted, dried over magnesium sulfate and concentrated to dryness to provide 4-(1,1-dimethoxyethyl)-3-fluorobenzonitrile. 1H NMR (400 MHz, CDCl3) δ 7.82 (t, J=7.9 Hz, 1H), 7.47 (dd, J=8.2, 1.6 Hz, 1H), 7.37 (dd, J=10.6, 1.6 Hz, 1H), 3.22 (s, 6H), 1.66 (d, J=0.7 Hz, 3H).
4-(4-bromo-2-methylbenzo[d][1,3]dioxol-2-yl)-3-fluorobenzonitrile: To a solution of 4-(1,1-dimethoxyethyl)-3-fluorobenzonitrile (141 mg, 0.67 mmol) and 3-bromobenzene-1,2-diol (133 mg, 0.70 mmol) in toluene (1.5 mL) was added p-toluenesulfonic acid (12 mg, 0.06 mmol). The resulting mixture was heated to 75° C. for 4 days and concentrated to dryness. The crude material was then purified by SiO$_2$ column chromatography (eluent: EtOAc/hexanes) to provide -(4-bromo-2-methylbenzo[d][1,3]dioxol-2-yl)-3-fluorobenzonitrile (I-39). 1H NMR (400 MHz, MeOD) δ 7.81 (t, J=7.7 Hz, 1H), 7.69 (dd, J=10.6, 1.5 Hz, 1H), 7.63 (dd, J=8.0, 1.6 Hz, 1H), 7.02 (dd, J=8.2, 1.2 Hz, 1H), 6.87 (dd, J=7.8, 1.2 Hz, 1H), 6.80 (t, J=8.0 Hz, 1H), 2.13 (d, J=1.1 Hz, 3H).

Preparation of Intermediate I-40

Methyl 2-(2,5-difluoro-4-(4,4,5,5-tetramethyl-1,3,2-dioxaborolan-2-yl)benzyl)-1-(2-methoxyethyl)-1H-benzo[d]imidazole-6-carboxylate: Methyl 2-(2,5-difluoro-4-(4,4,5,5-tetramethyl-1,3,2-dioxaborolan-2-yl)benzyl)-1-(2-methoxyethyl)-1H-benzo[d]imidazole-6-carboxylate was prepared following the preparation of Intermediate I-14, substituting 2-(4-bromo-2,5-difluorophenyl)acetic acid for 2-(4-bromo-2-fluorophenyl)acetic acid. ES/MS m/z: 487.257 (M+H+). 1H NMR (400 MHz, CDCl3) δ 8.10 (d, J=1.6 Hz, 1H), 8.00 (dt, J=8.5, 1.4 Hz, 1H), 7.77 (d, J=8.4 Hz, 1H), 7.45 (dd, J=9.4, 4.6 Hz, 1H), 6.98-6.88 (m, 1H), 4.40 (d, J=3.2 Hz, 2H), 4.32 (t, J=5.2 Hz, 2H), 3.97 (d, J=1.1 Hz, 3H), 3.64 (t, J=5.2 Hz, 2H), 3.25 (d, J=1.8 Hz, 3H), 1.36 (s, 12H).

Preparation of Intermediate I-41

2-(4-(2-(4-chloro-2-fluorophenyl)-2-methylbenzo[d][1,3]dioxol-4-yl)-2-fluorophenyl)acetic acid: 4-Bromo-2-(4-chloro-2-fluoro-phenyl)-2-methyl-1,3-benzodioxole (500 mg, 1.46 mmol) and ethyl 2-[2-fluoro-4-(4,4,5,5-tetramethyl-1,3,2-dioxaborolan-2-yl)phenyl]acetate (538 mg, 1.75 mmol) were dissolved in 1,4-dioxane (3.0 mL) and the solution was degassed by bubbling in N2 for 10 minutes. [1,1'-Bis(diphenylphosphino)ferrocene]dichloropalladium (II) (107 mg, 0.146 mmol) and aq. NaHCO3 (2.0 M, 2.18 mL, 4.37 mmol) were added to the flask and the mixture was heated to 90° C. for 1 hour. The reaction was cooled to ambient temperature and diluted with EtOAc (5 mL) and water (2 mL) and the organic layer was separated. The aqueous layer was extracted with EtOAc (5×2 mL) and the organic layers were combined, washed with brine (5 mL), dried with sodium sulfate, filtered and concentrated in vacuo. The product was purified through a silica plug to remove residual palladium (50% EtOAc in hexanes). ES/MS: 445.0 (M+H+).

The residue was dissolved in ACN (5.0 mL) and aq. LiOH (1.0 M, 2 mL) was added. The reaction was heated to 80° C. for 2 hours. The reaction was cooled to ambient temperature and quenched with aq. HCl (1 M) until just mildly acidic as determined using pH paper. The reaction was diluted with EtOAc (3 mL) and the organic layer was separated. The aqueous layer was extracted with EtOAc (2×5 mL) and the organic layers were combined, washed with brine (3 mL), dried with sodium sulfate, filtered and concentrated in vacuo and used without further purification. The titled product was obtained. ES/MS: 439.0 (M+Na+).

Preparation of Intermediate I-42

Methyl (S)-4-amino-3-(((tetrahydrofuran-2-yl)methyl)amino)benzoate: Methyl (S)-4-amino-3-(((tetrahydrofuran-2-yl)methyl)amino)benzoate (I-42) was prepared as described for I-7 substituting methoxyethylamine with [(2S)-tetrahydrofuran-2-yl]methanamine. ES/MS m/z: 251.2 (M+H+).

B. Compound Examples

Procedure 1: Example 1

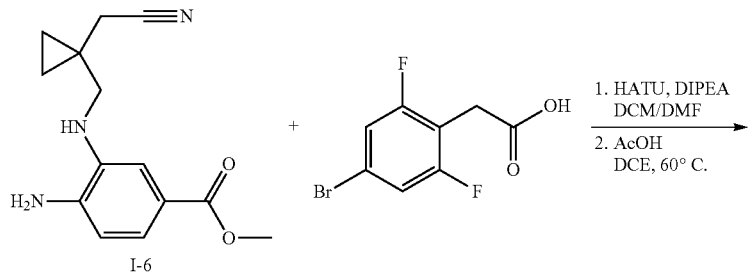

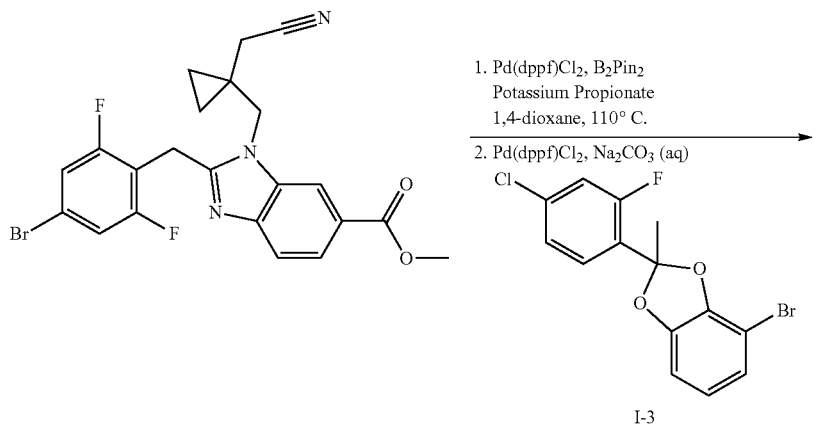

-continued

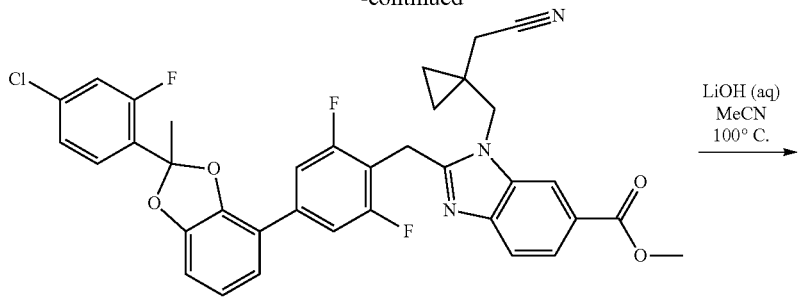

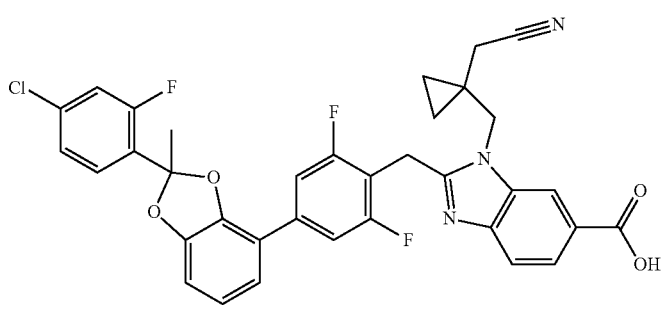

Example 1

Methyl 2-(4-bromo-2,6-difluorobenzyl)-1-((1-(cyanomethyl)cyclopropyl)methyl)-1H-benzo[d]imidazole-6-carboxylate: To a solution of 2-(4-bromo-2,6-difluorophenyl)acetic acid (150 mg, 0.58 mmol), methyl 4-amino-3-(((1-(cyanomethyl)cyclopropyl)methyl)amino)benzoate (I-6) (174 mg, 0.69 mmol), and HATU (177 mg, 0.75 mmol) in DCM (3.0 mL) and DMF (1.5 mL) was added DIPEA (0.50 mL, 2.90 mmol). The reaction mixture was stirred at RT for 16 hours, then diluted with saturated aqueous ammonium chloride and EtOAc. The aqueous layer was extracted with two additional portions of EtOAc. The combined organic layers were washed with brine, dried over sodium sulfate, isolated by vacuum filtration, and concentrated in vacuo. The crude material was taken up in dichloroethane (1.0 mL) and acetic acid (3.0 mL) and stirred at 60° C. for 4 hours. The reaction mixture was concentrated in vacuo and purified by silica gel column chromatography (eluent: EtOAc/Hex) to provide the desired product. ES/MS: 474.0, 476.0 (M+H$^+$).

Methyl 2-(4-(2-(4-chloro-2-fluorophenyl)-2-methylbenzo[d][1,3]dioxol-4-yl)-2,6-difluorobenzyl)-1-((1-(cyanomethyl)cyclopropyl)methyl)-1H-benzo[d]imidazole-6-carboxylate: A solution of methyl 2-(4-bromo-2,6-difluorobenzyl)-1-((1-(cyanomethyl)cyclopropyl)methyl)-1H-benzo[d]imidazole-6-carboxylate (40.0 mg, 0.084 mmol), bis(pinacolato)diboron (27.8 mg, 0.11 mmol), potassium propionate (28.4 mg, 0.25 mmol), and [1,1'-Bis(diphenylphosphino)ferrocene]dichloropalladium(II) (9.4 mg, 0.013 mmol) in 1,4-dioxane (1.0 mL) was degassed by bubbling argon for 60 seconds, then heated in a sealed tube at 110° C. for 45 minutes. The reaction mixture was cooled, then 2 M aqueous sodium carbonate (84 µL, 0.17 mmol), [1,1'-Bis(diphenylphosphino)ferrocene]dichloropalladium (II) (4.7 mg, 0.0063 mmol), and 4-bromo-2-(4-chloro-2-fluorophenyl)-2-methylbenzo[d][1,3]dioxole (I-3) (29.0 mg, 0.084 mmol) were added. The solution was degassed by bubbling argon for 60 seconds, then heated in a sealed tube at 80° C. for 2 hours. The reaction mixture was cooled, filtered through Celite (eluent: EtOAc), and concentrated. The resulting residue was purified by silica gel column chromatography (eluent: EtOAc/Hex) to provide the desired product. ES/MS: 658.2 (M+H$^+$)

2-(4-(2-(4-chloro-2-fluorophenyl)-2-methylbenzo[d][1,3]dioxol-4-yl)-2,6-difluorobenzyl)-1-((1-(cyanomethyl)cyclopropyl)methyl)-1H-benzo[d]imidazole-6-carboxylic acid (Example 1): To a solution of methyl 2-(4-(2-(4-chloro-2-fluorophenyl)-2-methylbenzo[d][1,3]dioxol-4-yl)-2,6-difluorobenzyl)-1-((1-(cyanomethyl)cyclopropyl)methyl)-1H-benzo[d]imidazole-6-carboxylate (48.5 mg, 0.074 mmol) in MeCN (0.75 mL) was added 0.3 M aqueous lithium hydroxide (0.49 mL, 0.15 mmol). The reaction mixture was heated in a sealed tube at 100° C. for 2 minutes. The cooled reaction mixture was purified by RP-HPLC (eluent: water/MeCN*0.1% TFA) to provide the product Example 1 as a trifluoroacetate salt. ES/MS: 644.2 (M+H$^+$). 1H NMR (400 MHz, MeOD) δ 8.56 (dd, J=1.4, 0.7 Hz, 1H), 8.14 (dd, J=8.6, 1.4 Hz, 1H), 7.71 (dd, J=8.5, 0.6 Hz, 1H), 7.64-7.53 (m, 3H), 7.31 (dd, J=10.9, 2.0 Hz, 1H), 7.23 (ddd, J=8.4, 2.0, 0.8 Hz, 1H), 7.20 (dd, J=7.8, 1.5 Hz, 1H), 7.03-6.93 (m, 2H), 4.76 (s, 2H), 4.73 (s, 2H), 2.64 (s, 2H), 2.12 (d, J=1.0 Hz, 3H), 1.03-0.96 (m, 2H), 0.96-0.88 (m, 2H).

Procedure 2, Example 2

2-(4-(2-(4-chloro-2-fluorophenyl)-2-methylbenzo[d][1,3]dioxol-4-yl)-2,6-difluorobenzyl)-7-fluoro-1-(((S)-oxetan-2-yl)methyl)-1H-benzo[d]imidazole-6-carboxylic Acid (Example 2)

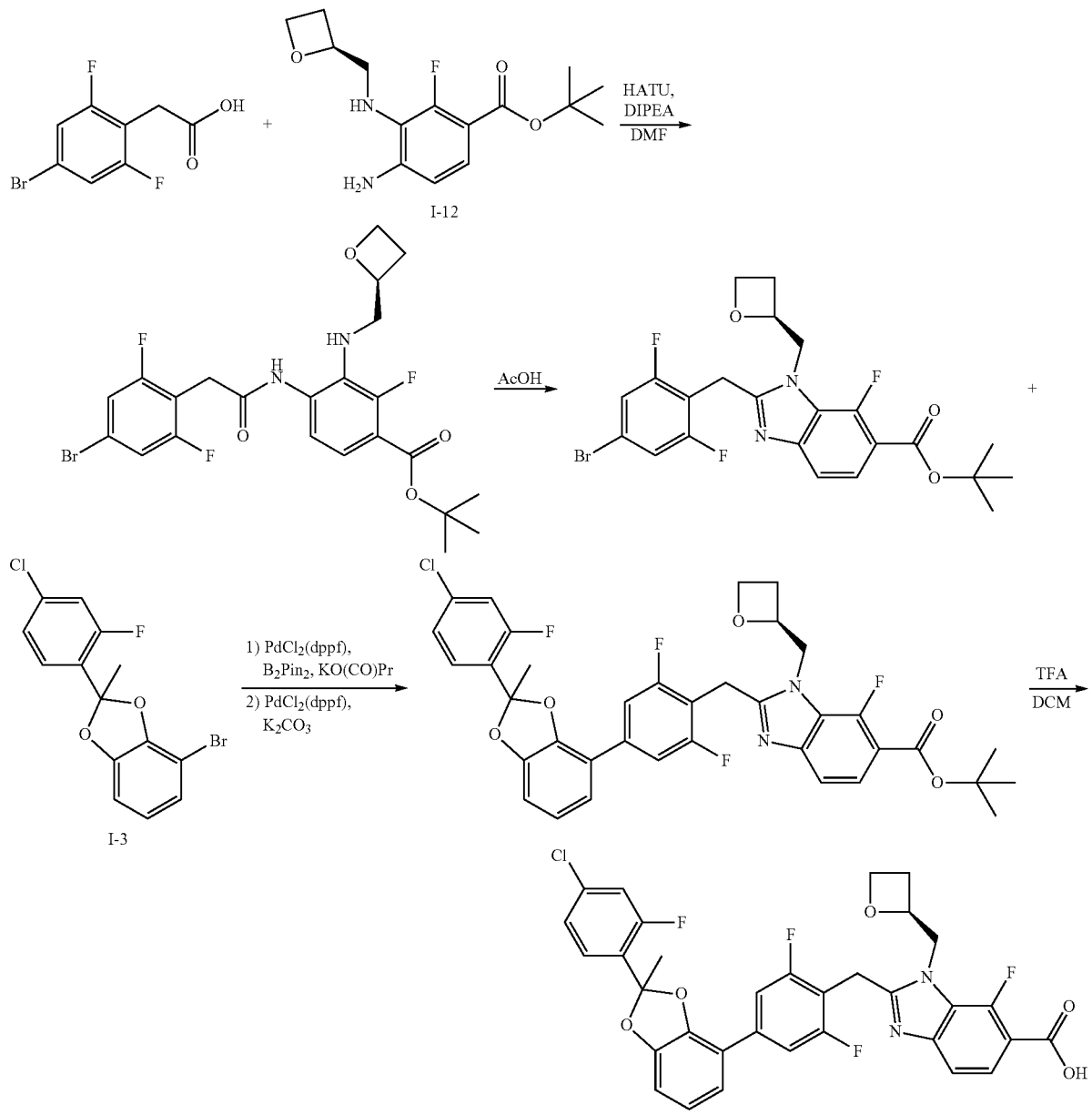

up in EtOAc (40 mL) and washed with water (10 mL) and brine (10 mL). The organic layer was dried over MgSO$_4$, filtered and concentrated in vacuo. The crude residue was taken forward without further purification. ES/MS: 529.5 (M+H$^+$).

Tert-butyl (S)-4-(2-(4-bromo-2,6-difluorophenyl)acetamido)-3-((oxetan-2-ylmethyl)amino)benzoate: To a solution of 2-(4-bromo-2,6-difluoro-phenyl)acetic acid (100 mg, 0.40 mmol) in DMF (2 mL) was added tert-butyl (S)-4-amino-2-fluoro-3-((oxetan-2-ylmethyl)amino)benzoate (I-12) (106 mg, 0.36 mmol) and O-(7-azabenzotriazol-1-yl)-N,N,N',N'-tetramethyluronium hexafluorophosphate (227 mg, 0.60 mmol) followed by N,N-diisopropylethylamine (0.35 mL, 1.99 mmol) and the reaction mixture was stirred for 1 h at room temperature. The reaction mixture was taken (S)-2-(4-bromo-2,6-difluorobenzyl)-7-fluoro-1-(oxetan-2-ylmethyl)-1H-benzo[d]imidazole-6-carboxylic acid: The crude product from the previous step, tert-butyl (S)-4-(2-(4-bromo-2,6-difluorophenyl)acetamido)-3-((oxetan-2-ylmethyl)amino)benzoate (211 mg, 0.40 mmol) was dissolved in AcOH (2 mL) and the reaction mixture was heated to 100° C. for 30 minutes. The reaction mixture was concentrated in vacuo and the crude residue was taken up in EtOAc (40 mL) and washed with saturated aqueous sodium bicarbonate (4×10 mL) followed by water (10 mL) and brine (10 mL).

The organic layer was dried over MgSO$_4$, filtered and concentrated in vacuo. The crude residue was purified by column chromatography (0-100% EtOAc in hexane) to give the titled compound. ES/MS: 511.9 (M+H$^+$).

tert-butyl 2-(4-(2-(4-chloro-2-fluorophenyl)-2-methyl-benzo[d][1,3]dioxol-4-yl)-2,6-difluorobenzyl)-7-fluoro-1-(((S)-oxetan-2-yl)methyl)-1H-benzo[d]imidazole-6-carboxylate: To a vial was added S)-2-(4-bromo-2,6-difluorobenzyl)-7-fluoro-1-(oxetan-2-ylmethyl)-1H-benzo[d]imidazole-6-carboxylic acid (67 mg, 0.13 mmol), potassium propionate (44 mg, 0.39 mmol), bis(pinacolato) diboron (43 mg, 0.17 mmol), 1,1'-Bis(diphenylphosphino) ferrocene] dichloropalladium(II) (15 mg, 0.020 mmol) and dioxane (1.5 mL). The resulting mixture was degassed by bubbling argon below the liquid surface for 1 minute after which the vial was sealed and placed in a 110° C. heating block for 30 minutes. Upon cooling the vial was opened and to the reaction mixture was added 4-bromo-2-(4-chloro-2-fluorophenyl)-2-methylbenzo[d][1,3]dioxole (54 mg, 0.16 mmol) (I-3), 1,1'-Bis(diphenylphosphino)ferrocene] dichloropalladium(II) (7.3 mg, 0.010 mmol) and potassium carbonate (2M aq. solution, 0.13 mL, 0.26 mmol). The resulting mixture was degassed by bubbling argon below the liquid surface for 1 minute after which the vial was sealed and placed in a 0° C. heating block for 2 hours. Upon completion the reaction mixture was cooled to room temperature, poured into water (15 mL) and extracted with EtOAc (2×25 mL). The organic layer was washed with brine (10 mL), dried over MgSO$_4$, filtered and concentrated. The crude residue was purified by column chromatography (20-100% EtOAc in hexane) to give the titled compound. ES/MS: 695.3 (M+H$^+$)

2-(4-(2-(4-chloro-2-fluorophenyl)-2-methylbenzo[d][1,3]dioxol-4-yl)-2,6-difluorobenzyl)-7-fluoro-1-(((S)-oxetan-2-yl)methyl)-1H-benzo[d]imidazole-6-carboxylic acid (Example 2): To a solution of tert-butyl 2-(4-(2-(4-chloro-2-fluorophenyl)-2-methylbenzo[d][1,3]dioxol-4-yl)-2,6-difluorobenzyl)-7-fluoro-1-(((S)-oxetan-2-yl)methyl)-1H-benzo[d]imidazole-6-carboxylate (40 mg, 0.057 mmol) in DCM (2 mL) was added 0.25 mL TFA and the resulting solution stirred at 40° C. for 1 hour. The reaction mixture was diluted with EtOAc (30 mL), washed with water (3×5 mL), concentrated and purified by RP-HPLC (eluent: water/MeCN 0.1% TFA). The combined fractions were then diluted with EtOAc (50 mL), washed with water (3×20 mL), brine (1×15 mL) and dried over MgSO$_4$. The EtOAc was removed by rotary evaporation and the crude residue taken up in acetonitrile (20 mL) and concentrated to dryness twice after which the residue was dissolved in acetonitrile:water (2:1, 20 mL), frozen and placed on a lyopholizer to provide the final compound Example 2. ES/MS: 639.6 (M+H$^+$). 1H NMR (400 MHz, DMSO-d6) δ 7.67-7.53 (m, 5H), 7.44-7.35 (m, 2H), 7.31 (dd, J=8.0, 1.3 Hz, 1H), 7.07 (dd, 7.8, 1.3 Hz, 1H), 7.01 (t, J=7.9 Hz, 1H), 5.18-5.10 (m, 1 Hz), 4.85 (dd, J=15.6, 7.1 Hz, 1H), 4.69 (dd, J=15.7, 2.8 Hz, 1H), 4.62-4.51 (m, 2H), 4.49-4.35 (m, 2H), 2.90-2.70 (m, 1H), 2.47-2.37 (m, 1H), 2.12 (s, 3H).

Procedure 3: Example 3

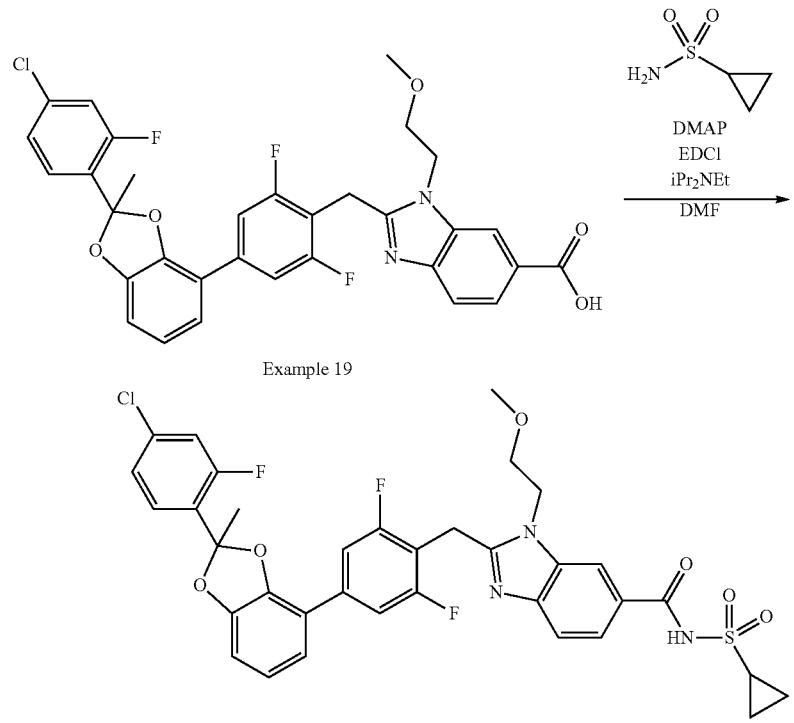

Example 19

Example 3

2-(4-(2-(4-chloro-2-fluorophenyl)-2-methylbenzo[d][1,3]dioxol-4-yl)-2,6-difluorobenzyl)-N-(cyclopropylsulfonyl)-1-(2-methoxyethyl)-1H-benzo[d]imidazole-6-carboxamide (Example 3): To a mixture of 2-[[4-[2-(4-chloro-2-fluorophenyl)-2-methyl-1,3-benzodioxol-4-yl]-2,6-difluoro-phenyl]methyl]-3-(2-methoxyethyl)benzimidazole-5-carboxylic acid (Example 19) (20.0 mg, 0.0328 mmol), cyclopropane sulfonamide (11.9 mg, 0.0985 mmol), 4-(dimethylamino)-pyridine (16.9 mg, 0.138 mmol) and N-(3- dimethylaminopropyl)-N'-ethylcarbodiimide hydrochloride (26.4 mg, 0.138 mmol) in DMF (1.00 mL) was added N,N-diisopropylethylamine (0.0515 mL, 0.296 mmol) and the reaction mixture was stirred at room temperature for 16 h. The reaction was quenched by the addition of 50 μL of TFA and the crude reaction mixture was purified directly by RP-HPLC (15-76.84% 0.1% TFA-ACN in 0.1% TFA Water, 15 min gradient, Column: Gemini 5 uM, NX—C18 110 Angstrom, 250×21.2 mm) to give the title compound, Example 3, as a racemic mixture of trifluoroacetate salts. ES/MS m/z: 712.3 (M+H$^+$). $^1$H NMR (400 MHz, Methanol-d4) δ 8.41-8.37 (m, 1H), 8.01 (dd, J=8.6, 1.6 Hz, 1H), 7.76 (dd, J=8.6, 0.7 Hz, 1H), 7.65-7.54 (m, 3H), 7.34 (dd, J=11.0, 2.0 Hz, 1H), 7.29-7.24 (m, 1H), 7.21 (dd, J=7.8, 1.5 Hz, 1H), 7.05-6.95 (m, 2H), 4.85 (s, 3H), 4.78 (t, J=5.0 Hz, 2H), 4.73 (s, 2H), 3.87 (t, J=4.9 Hz, 2H), 3.25-3.17 (m, 1H), 2.14 (s, 3H), 1.41-1.28 (m, 2H), 1.23-1.10 (m, 2H).

Procedure 4: Example 4

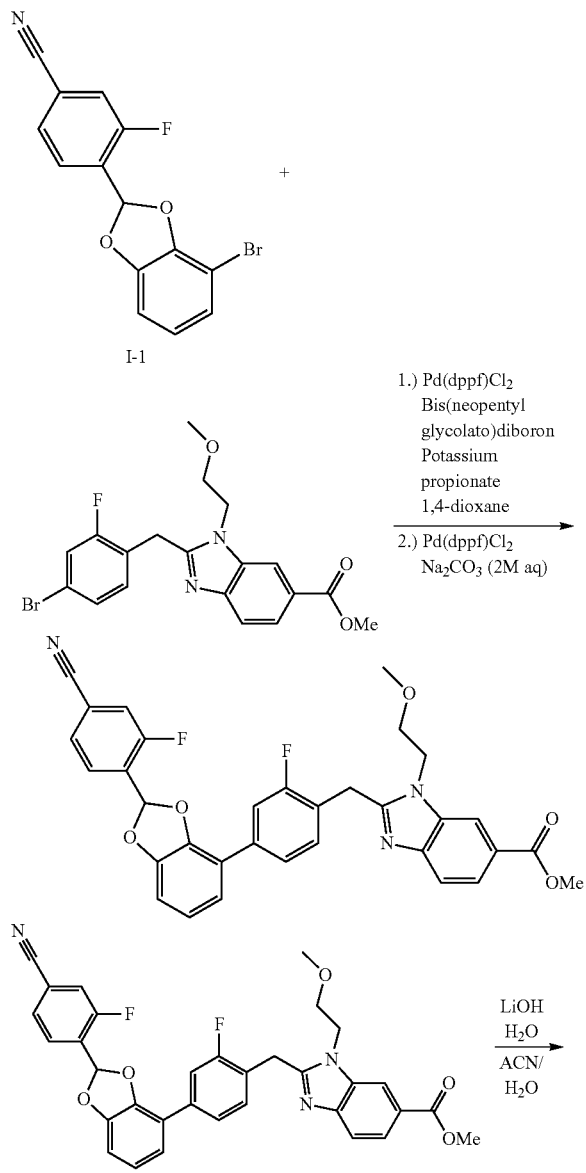

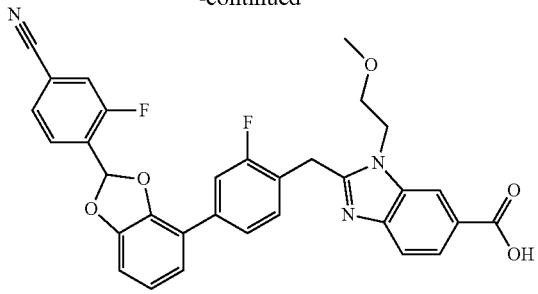

Example 4

Methyl 2-(4-(2-(4-cyano-2-fluorophenyl)benzo[d][1,3]dioxol-4-yl)-2-fluorobenzyl)-1-(2-methoxyethyl)-1H-benzo[d]imidazole-6-carboxylate: To a vial was added methyl 2-(4-bromo-2-fluorobenzyl)-1-(2-methoxyethyl)-1H-benzo[d]imidazole-6-carboxylate (prepared in a similar fashion to the first step of Procedure 1) (60 mg, 0.142 mmol), bis(neopentyl glycolato)diboron (64.3 mg, 0.285 mmol), Pd(dppf)Cl$_2$ (16 mg, 0.0214 mmol), and potassium propionate (48 mg, 0.43 mmol). 1,4-Dioxane (1.0 mL) was added, and the mixture was degassed with argon for 30 seconds. The vial was sealed, and the mixture was heated for 1 hour at 120° C. The vial was cooled, and LCMS showed conversion of the starting aryl bromide to the intermediate boronic acid. Pd(dppf)Cl$_2$ (8 mg, 0.012 mmol) and 4-(4-bromobenzo[d][1,3]dioxol-2-yl)-3-fluorobenzonitrile (I-1) (41 mg, 0.128 mmol) were added, and sodium carbonate (2M aqueous, 0.18 mL, 0.356 mmol) was added. The flask was sealed and stirred 1 hour at 90° C. LCMS showed conversion to the desired product, and the flask was cooled to RT. The organic layer was transferred directly to a loading column, and the crude material was purified by silica gel chromatography (eluent: EtOAc/hexanes) to afford the desired product. ES/MS: 582.4 (M+H$^+$).

2-(4-(2-(4-cyano-2-fluorophenyl)benzo[d][1,3]dioxol-4-yl)-2-fluorobenzyl)-1-(2-methoxyethyl)-1H-benzo[d]imidazole-6-carboxylic acid: To a 40 mL vial was added methyl 2-(4-(2-(4-cyano-2-fluorophenyl)benzo[d][1,3]dioxol-4-yl)-2-fluorobenzyl)-1-(2-methoxyethyl)-1H-benzo[d]imidazole-6-carboxylate (32.5 mg, 0.0559 mmol), and acetonitrile (1 mL) was added. To the mixture was added LiOH H$_2$O (3.3 mg, 0.06 mmol) dissolved in water (0.2 mL), and the mixture was stirred 3 hours at 55° C. LCMS showed conversion of the starting material to the product. The mixture was acidified with 50% citric acid (0.2 mL) and 2 drops of trifluoroacetic acid were added. The material was purified by RP-HPLC (eluent: water/MeCN*0.1% TFA) to yield the product Example 4 as a trifluoroacetate salt. ES/MS: 568.5 (M+H$^+$). 1H NMR (400 MHz, Methanol-d4) δ 8.53 (d, J=1.4 Hz, 1H), 8.20 (dd, J=8.6, 1.5 Hz, 1H), 7.85-7.78 (m, 1H), 7.78-7.63 (m, 4H), 7.49 (t, J=8.0 Hz, 1H), 7.46 (s, 1H), 7.23 (dd, J=8.0, 1.3 Hz, 1H), 7.06 (t, J=7.9 Hz, 1H), 6.99 (dd, J=7.8, 1.2 Hz, 1H), 4.78 (t, J=5.0 Hz, 2H), 4.73 (s, 2H), 3.85-3.73 (m, 2H), 3.30 (s, 3H).

Procedure 5: Example 5

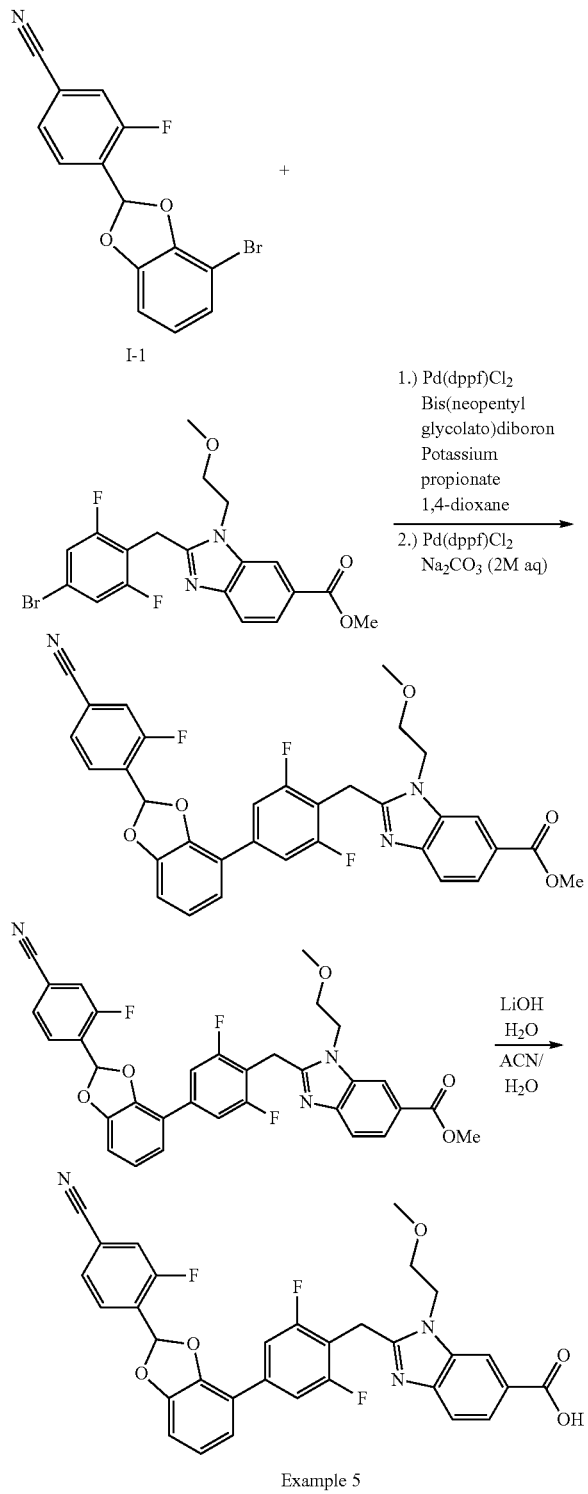

Methyl 2-(4-(2-(4-cyano-2-fluorophenyl)benzo[d][1,3]dioxol-4-yl)-2,6-difluorobenzyl)-1-(2-methoxyethyl)-1H-benzo[d]imidazole-6-carboxylate: To a vial was added bromobenzo[d][1,3]dioxol-2-yl)-3-fluorobenzonitrile (I-1) (65 mg, 0.203 mmol), bis(neopentyl glycolato)diboron (60 mg, 0.264 mmol), Pd(dppf)Cl$_2$ (22.6 mg, 0.03 mmol), and potassium propionate (68 mg, 0.609 mmol). 1,4-Dioxane (1.0 mL) was added, and the mixture was degassed with argon for 30 seconds. The vial was sealed, and the mixture was heated for 30 minutes at 120° C. The vial was cooled, and LCMS showed conversion of the starting aryl bromide to the intermediate boronic acid. Pd(dppf)Cl$_2$ (12 mg, 0.018 mmol) and methyl 2-(4-bromo-2,6-difluorobenzyl)-1-(2-methoxyethyl)-1H-benzo[d]imidazole-6-carboxylate (prepared in a similar fashion to the first step of Procedure 1) (93 mg, 0.212 mmol) were added, and sodium carbonate (2M aqueous, 0.2 mL, 0.406 mmol) was added. The flask was sealed and stirred 1 hour at 90° C. LCMS showed conversion to the desired product, and the flask was cooled to rt. The organic layer was transferred directly to a loading column, and the crude material was purified by silica gel chromatography (eluent: EtOAc/hexanes) to afford the desired product. ES/MS: 600.3 (M+H$^+$).

2-(4-(2-(4-cyano-2-fluorophenyl)benzo[d][1,3]dioxol-4-yl)-2,6-difluorobenzyl)-1-(2-methoxyethyl)-1H-benzo[d]imidazole-6-carboxylic acid: To a 40 mL vial was added methyl 2-(4-(2-(4-cyano-2-fluorophenyl)benzo[d][1,3]dioxol-4-yl)-2,6-difluorobenzyl)-1-(2-methoxyethyl)-1H-benzo[d]imidazole-6-carboxylate (70 mg, 0.117 mmol), and acetonitrile (1 mL) was added. To the mixture was added LiOH H$_2$O (4.2 mg, 0.18 mmol) dissolved in water (0.2 mL), and the mixture was stirred 5 hours at 55° C. LCMS showed conversion of the starting material to the product. The mixture was acidified with 50% citric acid (0.2 mL) and 2 drops of trifluoroacetic acid were added. The material was purified by RP-HPLC (eluent: water/MeCN*0.1% TFA) to yield the product Example 5 as a trifluoroacetate salt. ES/MS: 586.291 (M+H$^+$). 1H NMR (400 MHz, Methanol-d4) δ 8.54 (d, J=1.5 Hz, 1H), 8.21 (dd, J=8.5, 1.6 Hz, 1H), 7.86-7.62 (m, 4H), 7.51-7.40 (m, 2H), 7.35 (dd, J=10.0, 6.2 Hz, 1H), 7.12-6.98 (m, 3H), 4.80 (t, J=5.0 Hz, 2H), 4.74 (s, 2H), 3.83 (t, J=4.9 Hz, 2H), 3.30 (s, 3H).

Procedure 6: Example 32

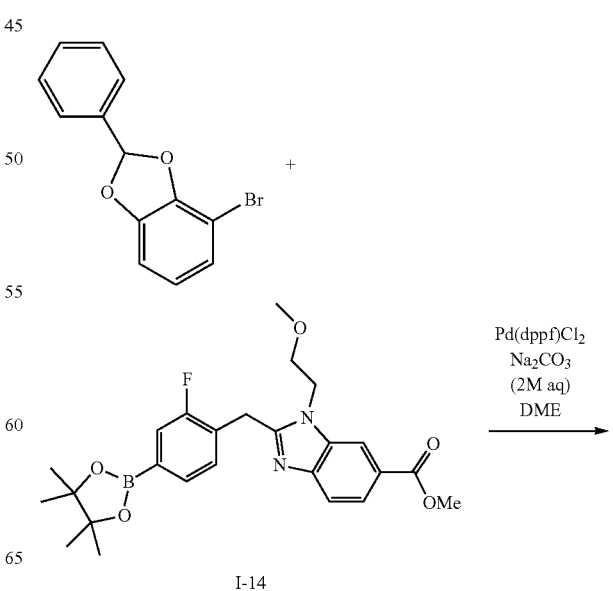

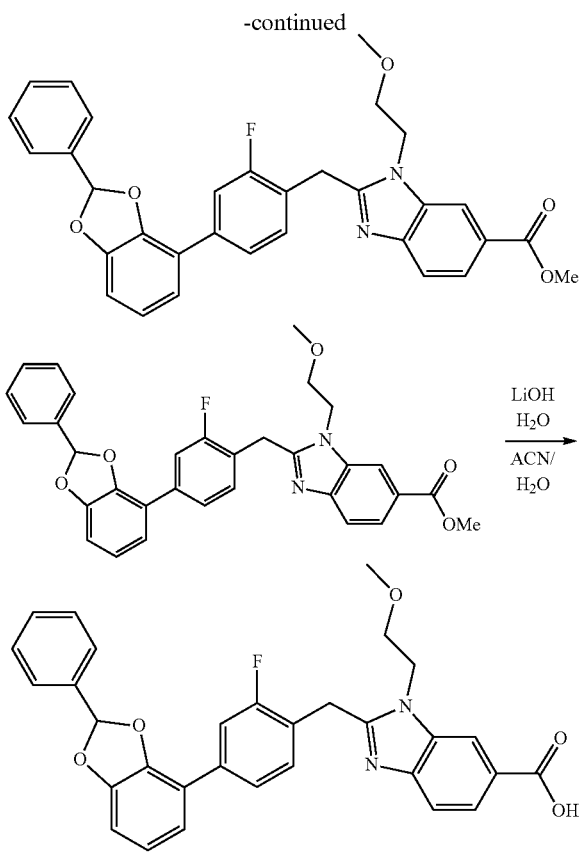

Methyl 2-(2-fluoro-4-(2-phenylbenzo[d][1,3]dioxol-4-yl)benzyl)-1-(2-methoxyethyl)-1H-benzo[d]imidazole-6-carboxylate: To a vial was added 4-bromo-2-phenylbenzo[d][1,3]dioxole (synthesized in the same manner as I-1, starting from benzal bromide) (59 mg, 0.214 mmol), Pd(dppf)Cl$_2$ (23.8 mg, 0.024 mmol), methyl 2-(2-fluoro-4-(4,4,5,5-tetramethyl-1,3,2-dioxaborolan-2-yl)benzyl)-1-(2-methoxyethyl)-1H-benzo[d]imidazole-6-carboxylate (I-14) (100 mg, 0.214 mmol), DME (1 mL), and sodium carbonate (2M aqueous, 0.21 mL, 0.427 mmol). The flask was degassed 30 seconds with argon, sealed and stirred 1 hour at 90° C. LCMS showed conversion to the desired product, and the flask was cooled to RT. The organic layer was transferred directly to a loading column, and the crude material was purified by silica gel chromatography (eluent: EtOAc/hexanes) to afford the desired product. ES/MS: 539.568 (M+H$^+$).

2-(2-fluoro-4-(2-phenylbenzo[d][1,3]dioxol-4-yl)benzyl)-1-(2-methoxyethyl)-1H-benzo[d]imidazole-6-carboxylic acid: To a 40 mL vial was added methyl 2-(2-fluoro-4-(2-phenylbenzo[d][1,3]dioxol-4-yl)benzyl)-1-(2-methoxyethyl)-1H-benzo[d]imidazole-6-carboxylate (100 mg, 0.186 mmol), and acetonitrile (2 mL) was added. To the mixture was added LiOH (11.1 mg, 0.464 mmol) dissolved in water (0.5 mL), and the mixture was stirred 24 hours at 55° C. LCMS showed conversion of the starting material to the product. The mixture was acidified with 50% citric acid (0.2 mL) and 2 drops of trifluoroacetic acid were added. The material was purified by RP-HPLC (eluent: water/MeCN*0.1% TFA) to yield the product Example 32 as a trifluoroacetate salt. ES/MS: 525.581 (M+H$^+$). 1H NMR (400 MHz, Methanol-d4) δ 8.55 (s, 1H), 8.23 (dd, J=8.6, 1.4 Hz, 1H), 7.76 (d, J=8.6 Hz, 1H), 7.74-7.64 (m, 2H), 7.60 (dd, J=7.4, 2.4 Hz, 2H), 7.56-7.42 (m, 4H), 7.19 (d, J=8.1 Hz, 1H), 7.13 (s, 1H), 7.01 (t, J=7.9 Hz, 1H), 6.94 (d, J=7.7 Hz, 1H), 4.81 (t, J=5.0 Hz, 2H), 4.76 (s, 2H), 3.80 (t, J=4.9 Hz, 2H), 3.30 (s, 3H).

Procedure 7: Example 7

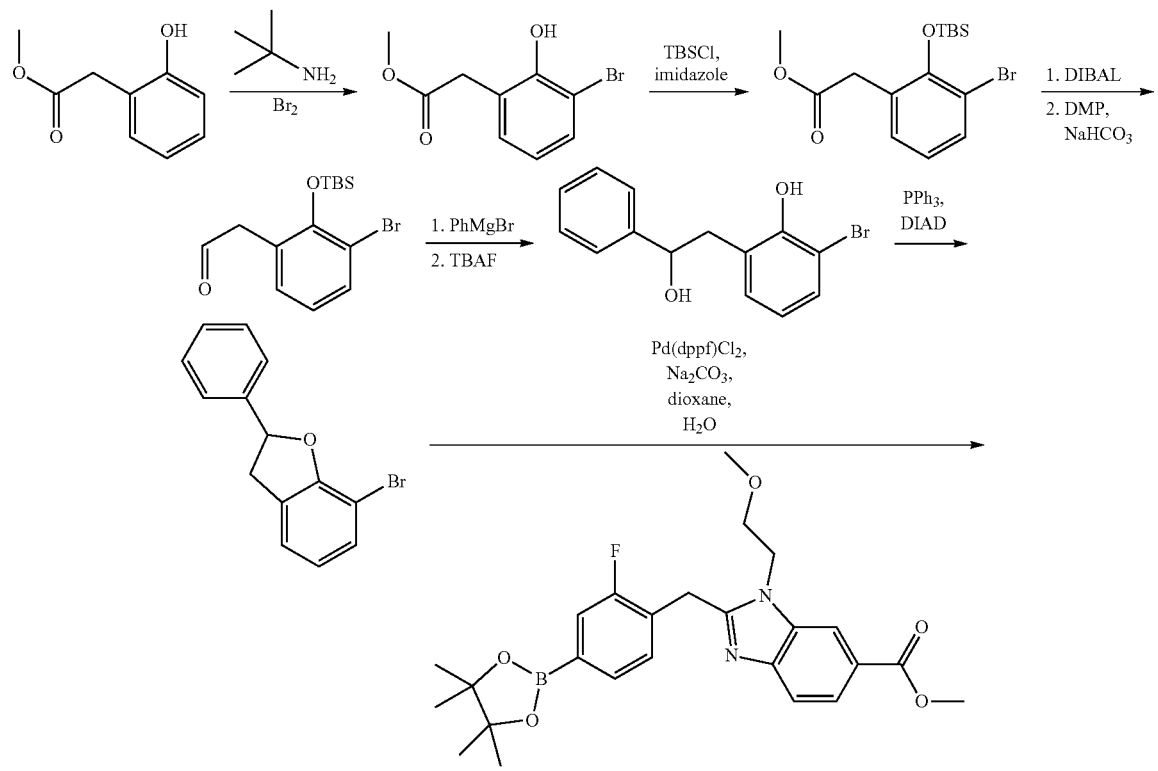

I-14

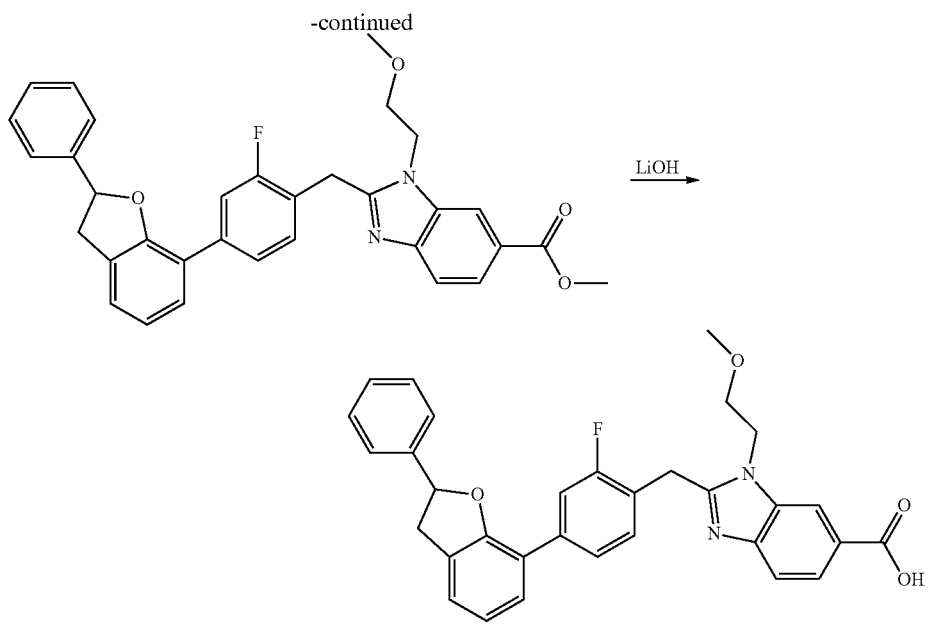

Example 7

Methyl 2-(3-bromo-2-hydroxyphenyl)acetate: To a solution of tert-butylamine (940 mg, 12.9 mmol) in PhMe (10 mL) at −30° C. was added bromine (1.08 g, 6.74 mmol) dropwise. The solution was stirred at −30° C. for 1 h before cooling to −78° C. A solution of methyl 2-(2-hydroxyphenyl)acetate (1.40 g, 8.42 mmol) in DCM (6 mL) was added slowly. The resulting mixture was slowly warmed to RT over 16 h with rapid stirring. $H_2O$ (50 mL) and EtOAc (50 mL) were added, and the resulting mixture was poured into a separatory funnel. The layers were separated, and the aqueous phase was extracted with EtOAc (2×50 mL). The combined organic extracts were washed with brine (50 mL), dried over $MgSO_4$, filtered, and concentrated in vacuo. The residue was purified by silica gel chromatography (eluent: EtOAc/hexanes). ES/MS: 245.2 (M+H⁺).

Methyl 2-(3-bromo-2-((tert-butyldimethylsilyl)oxy)phenyl)acetate: To a solution of methyl 2-(3-bromo-2-hydroxyphenyl)acetate (1.29 g, 5.26 mmol) in DCM (10 mL) at RT was added imidazole (720 mg, 10.5 mmol) and tert-butylchlorodimethylsilane (1.20 g, 7.90 mmol), respectively. The mixture stirred at rt for 1.5 h before diluting with $H_2O$ (50 mL) and DCM (50 mL) and poured into a separatory funnel. The layers were separated, and the aqueous phase was extracted with DCM (2×50 mL). The combined organic extracts were washed with brine (50 mL), dried over $MgSO_4$, filtered, and concentrated in vacuo. The residue was purified by silica gel chromatography (eluent: EtOAc/hexanes). 1H NMR (400 MHz, Chloroform-d) δ 7.51-7.40 (m, 1H), 7.21-7.14 (m, 1H), 6.85 (t, J=7.8 Hz, 1H), 3.72 (s, 3H), 3.69 (s, 2H), 1.06 (s, 9H), 0.30 (s, 6H).

2-(3-bromo-2-((tert-butyldimethylsilyl)oxy)phenyl)acetaldehyde: To a solution of methyl 2-(3-bromo-2-((tert-butyldimethylsilyl)oxy)phenyl)acetate (150 mg, 0.417 mmol) in DCM (10 mL) at 0° C. was added diisobutylaluminium hydride (1M solution in hexanes) (1.04 mL, 1.04 mmol) dropwise. The mixture was warmed to RT over 1 h with rapid stirring before quenching with saturated aqueous sodium potassium tartrate (50 mL) and diluting with EtOAc (50 mL). The resulting slurry was filtered through a plug of Celite and the cake was washed with EtOAc (50 mL). The filtrate was poured into a separatory funnel, and the layers were separated. The aqueous phase was extracted with EtOAc (2×50 mL), and the combined organic extracts were washed with brine (50 mL), dried over $MgSO_4$, filtered, and concentrated in vacuo.

The crude mixture was dissolved in DCM (10 mL). $NaHCO_3$ (76 mg, 1.25 mmol) and Dess-Martin Periodinane (270 mg) were added at RT. The mixture was stirred at RT for 1 h before filtering through a Celite and the cake was washed with DCM (20 mL). The filtrate was concentrated in vacuo and purified by silica gel chromatography (eluent: EtOAc/hexanes). 1H NMR (400 MHz, Chloroform-d) δ 9.68 (t, J=2.1 Hz, 1H), 7.51 (dd, J=8.0, 1.7 Hz, 1H), 7.09 (dd, J=7.5, 1.7 Hz, 1H), 6.88 (t, J=7.8 Hz, 1H), 3.71 (d, J=2.1 Hz, 2H), 1.06 (s, 9H), 0.30 (s, 6H).

2-bromo-6-(2-hydroxy-2-phenylethyl)phenol: To a solution of 2-(3-bromo-2-((tert-butyldimethylsilyl)oxy)phenyl)acetaldehyde (100 mg, 0.30 mmol) in THF (5 mL) was added phenylmagnesium bromide (1M solution in THF) (0.46 mL, 0.46 mmol) dropwise at 0° C. The resulting mixture was stirred at 0° C. for 1 h before quenching with saturated aqueous $NH_4Cl$ (10 mL) with rapid stirring and warmed to RT. The mixture was poured into a separatory funnel, and the layers were separated. The aqueous phase was extracted with EtOAc (2×20 mL), and the combined organic extracts were washed with brine (50 mL), dried over $MgSO_4$, filtered, and concentrated in vacuo.

The crude mixture was re-dissolved in THF (5 mL). Tetrabutylammonium fluoride (1M solution in THF) (0.46 mL, 0.46 mmol) was added dropwise at RT, and the resulting mixture was stirred for 1 h before diluting with EtOAc (20 mL) and saturated aqueous $NaHCO_3$ (20 mL). The mixture was poured into a separatory funnel, and the layers were separated. The aqueous phase was extracted with EtOAc (2×20 mL), and the combined organic extracts were washed with brine (50 mL), dried over $MgSO_4$, filtered, and concentrated in vacuo. The residue was purified by silica gel chromatography (eluent: EtOAc/hexanes). 1H NMR (400

MHz, Chloroform-d) δ 9.29 (s, 1H), 7.37-7.26 (m, 5H), 7.25-7.19 (m, 1H), 6.82 (dd, J=7.5, 1.6 Hz, 1H), 6.62 (t, J=7.7 Hz, 1H), 5.49 (s, 1H), 5.10 (dd, J=8.2, 3.1 Hz, 1H), 3.14 (dd, J=14.4, 8.2 Hz, 1H), 3.02 (dd, J=14.4, 3.1 Hz, 1H).

7-bromo-2-phenyl-2,3-dihydrobenzofuran: To a solution of 2-bromo-6-(2-hydroxy-2-phenylethyl)phenol (48 mg, 0.164 mmol) in THF (6 mL) at RT was added triphenylphosphine (52 mg, 0.20 mmol) and diisopropyl azodicarboxylate (50 mg, 0.25 mmol), respectively. The mixture was stirred at rt for 15 min before concentrating in vacuo. The residue was purified by silica gel chromatography (eluent: EtOAc/hexanes). 1H NMR (400 MHz, Chloroform-d) δ 7.51-7.37 (m, 4H), 7.37-7.32 (m, 2H), 7.13 (dt, J=7.2, 1.1 Hz, 1H), 6.79 (t, J=7.6 Hz, 1H), 3.96-3.67 (m, 1H), 3.33 (ddt, J=15.8, 7.9, 1.0 Hz, 1H).

Methyl 2-(2-fluoro-4-(2-phenyl-2,3-dihydrobenzofuran-7-yl)benzyl)-1-(2-methoxyethyl)-1H-benzo[d]imidazole-6-carboxylate: A 5-mL microwave vial was charged with methyl 2-(2-fluoro-4-(4,4,5,5-tetramethyl-1,3,2-dioxaborolan-2-yl)benzyl)-1-(2-methoxyethyl)-1H-benzo[d]imidazole-6-carboxylate (I-14) (61 mg, 0.13 mmol), 7-bromo-2-phenyl-2,3-dihydrobenzofuran (30 mg, 0.11 mmol), and Pd(dppf)Cl$_2$ (10 mg, 0.0135 mmol). Dioxane (3 mL) and Na$_2$CO$_3$ (1.5M in H$_2$O) (0.22 mL, 0.33 mmol) were added, and the resulting mixture was purged with argon for 2 min. The mixture was heated to 85° C. and stirred for 2 h before cooling to RT. After diluting with H$_2$O (20 mL) and EtOAc (20 mL), the mixture was poured into a separatory funnel. The layers were separated, and the aqueous phase was extracted with EtOAc (2×20 mL). The combined organic extracts were washed with brine (50 mL), dried over MgSO$_4$, filtered, and concentrated in vacuo. The residue was purified by silica gel chromatography (eluent: EtOAc/hexanes). ES/MS: 537.20 (M+H$^+$).

2-(2-fluoro-4-(2-phenyl-2,3-dihydrobenzofuran-7-yl)benzyl)-1-(2-methoxyethyl)-1H-benzo[d]imidazole-6-carboxylic acid: methyl 2-(2-fluoro-4-(2-phenyl-2,3-dihydrobenzofuran-7-yl)benzyl)-1-(2-methoxyethyl)-1H-benzo[d]imidazole-6-carboxylate (43 mg, 0.080 mmol) was dissolved in acetonitrile (0.9 mL) after which LiOH (2 M in H$_2$O) (0.2 mL, 0.40 mmol) was added and the resulting mixture was stirred at 50° C. for 3 hr. The reaction mixture was adjusted to pH 2 using citric acid (1M in H$_2$O) (1 mL) and extracted with EtOAc (2×10 mL). The combined organics was concentrated and purified by RP-HPLC (eluent: H$_2$O/MeCN 0.1% TFA) to yield the product (Example 7) as a trifluoroacetate salt. ES/MS: 523.2 (M+H$^+$). 1H NMR (400 MHz, DMSO-d6) δ 8.31 (d, J=1.5 Hz, 1H), 7.89 (dd, J=8.5, 1.5 Hz, 1H), 7.67 (d, J=8.5 Hz, 1H), 7.65-7.58 (m, 2H), 7.49-7.37 (m, 6H), 7.37-7.31 (m, 1H), 7.28 (dd, J=7.3, 1.3 Hz, 1H), 7.01 (t, J=7.6 Hz, 1H), 5.92 (dd, J=9.4, 8.1 Hz, 1H), 4.64 (t, J=5.2 Hz, 2H), 4.51 (s, 2H), 3.75 (dd, J=15.9, 9.4 Hz, 1H), 3.66 (t, J=5.0 Hz, 2H), 3.25-3.14 (m, 4H).

Procedure 8: Example 8

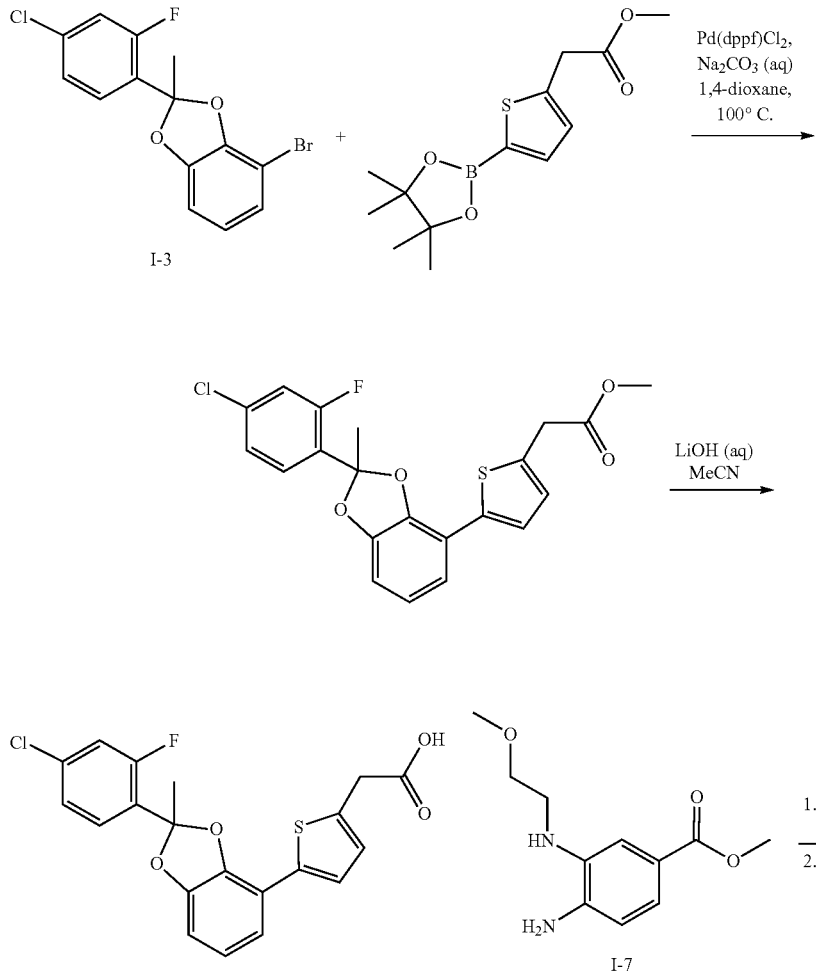

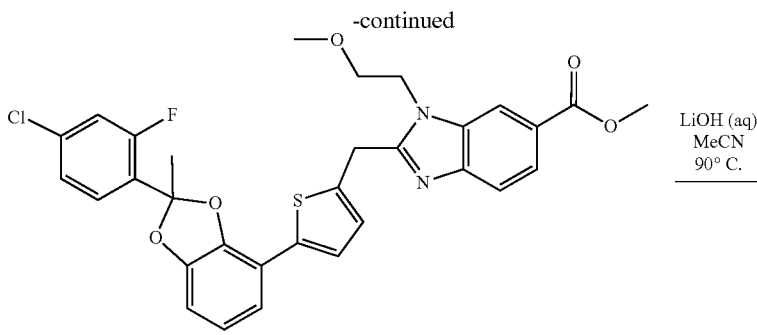

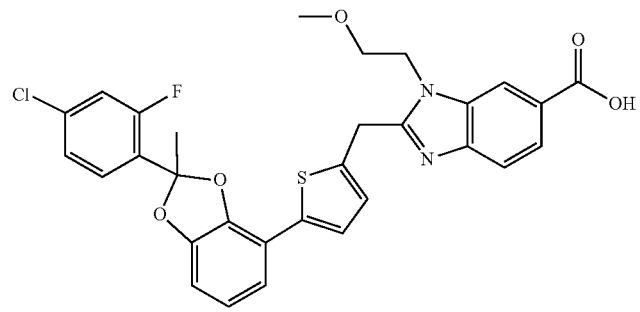

Example 8

Methyl 2-(5-(2-(4-chloro-2-fluorophenyl)-2-methylbenzo[d][1,3]dioxol-4-yl)thiophen-2-yl)acetate: In an 8 ml reaction vial, a suspension of methyl 2-[5-(4,4,5,5-tetramethyl-1,3,2-dioxaborolan-2-yl)-2-thienyl]acetate (150 mg, 0.532 mmol), 4-bromo-2-(4-chloro-2-fluorophenyl)-2-methyl-benzo[d][1,3]dioxole I-3 (198 mg, 0.575 mmol), (1,1'-bis(diphenylphosphino)ferrocene)-dichloropalladium(II) (30.1 mg, 0.0425 mmol) and sodium carbonate (2.00 M, 0.550 mL, 1.10 mmol) in dioxane (2 mL) was degassed with Ar for 5 min. The reaction was heated at 100° C. for 6 hr. The reaction was diluted with EtOAc and washed with brine. The organic extract was dried over sodium sulfate and purified by silica gel chromatography (eluent: EtOAc/hexanes). 1H NMR (400 MHz, CDCl3) δ 7.58 (t, J=8.3 Hz, 1H), 7.48 (d, J=3.7 Hz, 1H), 7.18 (dd, J=10.5, 2.0 Hz, 1H), 7.13 (ddd, J=8.4, 2.0, 0.8 Hz, 1H), 7.09 (dd, J=8.1, 1.2 Hz, 1H), 6.98 (dd, J=3.7, 1.0 Hz, 1H), 6.84 (t, J=7.9 Hz, 1H), 6.75 (dd, J=7.7, 1.1 Hz, 1H), 3.89 (d, J=0.9 Hz, 2H), 3.78 (s, 3H), 2.15 (d, J=1.1 Hz, 3H).

2-(5-(2-(4-chloro-2-fluorophenyl)-2-methylbenzo[d][1,3]dioxol-4-yl)thiophen-2-yl)acetic acid: A solution of methyl 2-[5-[2-(4-chloro-2-fluoro-phenyl)-2-methyl-1,3-benzodioxol-4-yl]-2-thienyl]acetate (69.0 mg, 0.165 mmol) and lithium hydroxide monohydrate (19.3 mg, 0.461 mmol) in CH₃CN (3 mL) and water (1 mL) was stirred at RT overnight. The reaction was diluted with EtOAc and adjusted to pH~6 with 1N HCl (500 uL). The organic extract was dried over sodium sulfate to give the desired product. ES/MS: 405.0 (M⁺).

Methyl 2-((5-(2-(4-chloro-2-fluorophenyl)-2-methyl-benzo[d][1,3]dioxol-4-yl)thiophen-2-yl)methyl)-1-(2-methoxyethyl)-1H-benzo[d]imidazole-6-carboxylate: To a solution of 2-[5-[2-(4-chloro-2-fluoro-phenyl)-2-methyl-1,3-benzodioxol-4-yl]-2-thienyl]acetic acid (66.7 mg, 0.165 mmol), methyl 4-amino-3-(2-methoxyethylamino)benzoate I-7 (44.3 mg, 0.198 mmol), and o-(7-azabenzotriazol-1-yl)-N,N,N',N'-tetramethyluronium hexafluorophosphate (106 mg, 0.279 mmol) in DMF (3 mL), was added N,N-diisopropylethylamine (0.135 mL, 0.776 mmol). The mixture was stirred at RT overnight. The mixture was diluted with EtOAc and washed with 5% LiCl, saturated NaHCO₃, and brine. The organic extract was dried over sodium sulfate to give crude product, which was carried onto the step below.

A solution of methyl 4-[[2-[5-[2-(4-chloro-2-fluoro-phenyl)-2-methyl-1,3-benzodioxol-4-yl]-2-thienyl]acetyl]amino]-3-(2-methoxyethylamino)benzoate (101 mg, 0.165 mmol) in AcOH (0.650 mL) and DCE (4 mL) was heated at 60° C. for 18 hr. The reaction mixture was concentrated and purified by silica gel chromatography (eluent: EtOAc/hexanes). ES/MS: 593.2 (M⁺). Multiplet Report 1H NMR (400 MHz, CDCl3) δ 8.11 (t, J=1.0 Hz, 1H), 8.07-7.96 (m, 1H), 7.83 (d, J=8.5 Hz, 1H), 7.55 (t, J=8.2 Hz, 1H), 7.46 (d, J=3.7 Hz, 1H), 7.15 (dd, J=10.6, 2.0 Hz, 1H), 7.11 (ddd, J=8.3, 2.0, 0.7 Hz, 1H), 7.03 (dd, J=8.1, 1.1 Hz, 1H), 6.96 (d, J=3.6 Hz, 1H), 6.82 (t, J=7.9 Hz, 1H), 6.74 (dd, J=7.8, 1.2 Hz, 1H), 4.67 (s, 2H), 4.40 (t, J=5.3 Hz, 2H), 3.98 (s, 3H), 3.66 (t, J=5.3 Hz, 2H), 3.29 (s, 3H), 2.13 (d, J=1.0 Hz, 3H).

2-((5-(2-(4-chloro-2-fluorophenyl)-2-methylbenzo[d][1,3]dioxol-4-yl)thiophen-2-yl)methyl)-1-(2-methoxyethyl)-1H-benzo[d]imidazole-6-carboxylic acid: A mixture of methyl 2-[[5-[2-(4-chloro-2-fluoro-phenyl)-2-methyl-1,3-benzodioxol-4-yl]-2-thienyl]methyl]-3-(2-methoxyethyl)benzimidazole-5-carboxylate (32.3 mg, 0.0545 mmol) and lithium hydroxide, monohydrate (0.300 M, 0.545 mL, 0.163 mmol) in CH₃CN (1 mL) in a 40 ml reaction vial was heated at 90° C. for 15 min. The mixture was diluted with EtOAc and water and neutralized with 0.160 mL 1M citric acid. The organic extract was dried over sodium sulfate and purified by RP-HPLC (eluent: H₂O/MeCN 0.1% TFA) to yield the product (Example 8) as a trifluoroacetate salt. ES/MS: 593.2 (M⁺). Multiplet Report 1H NMR (400 MHz, DMSO) δ 12.83 (s, 1H), 8.21 (d, J=1.6 Hz, 1H), 7.66 (d, J=8.5 Hz, 1H), 7.60-7.54 (m, 2H), 7.51 (d, J=3.7 Hz, 1H), 7.35 (dd, J=8.4, 2.1 Hz, 1H), 7.18-7.12 (m, 1H), 7.11 (d, J=3.7 Hz, 1H), 6.94-6.79 (m, 2H), 4.64 (s, 2H), 4.56 (t, J=5.0 Hz, 2H), 3.61 (t, J=5.1 Hz, 2H), 3.19 (s, 3H), 2.10 (s, 3H).

Procedure 9: Example 9 and Example 13

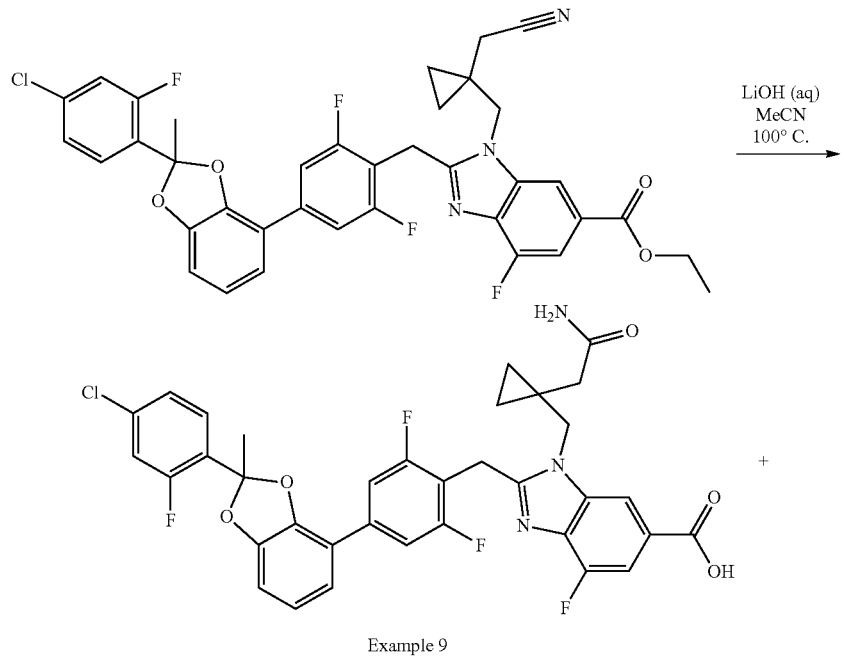

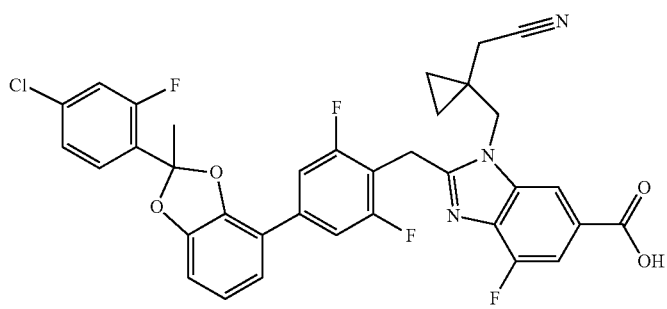

Example 9

Example 13

1-((1-(2-amino-2-oxoethyl)cyclopropyl)methyl)-2-(4-(2-(4-chloro-2-fluorophenyl)-2-methylbenzo[d][1,3]dioxol-4-yl)-2,6-difluorobenzyl)-4-fluoro-1H-benzo[d]imidazole-6-carboxylic acid (Example 9) and 2-(4-(2-(4-chloro-2-fluorophenyl)-2-methylbenzo[d][1,3]dioxol-4-yl)-2,6-difluorobenzyl)-1-((1-(cyanomethyl)cyclopropyl)methyl)-4-fluoro-1H-benzo[d]imidazole-6-carboxylic acid (Example 13): To a solution of ethyl 2-(4-(2-(4-chloro-2-fluorophenyl)-2-methylbenzo[d][1,3]dioxol-4-yl)-2,6-difluorobenzyl)-1-((1-(cyanomethyl)cyclopropyl)methyl)-1H-benzo[d]imidazole-6-carboxylate (synthesized as in Procedure 1) (70 mg, 0.1 mmol) in MeCN (1 mL) was added 0.3 M aqueous lithium hydroxide (0.49 mL, 0.15 mmol). The reaction mixture was heated in a sealed tube at 70° C. for 2 hours. The cooled reaction mixture was purified by RP-HPLC (eluent: water/MeCN*0.1% TFA) to provide the products Example 9 and Example 13 as trifluoroacetate salts.

Example 9: ES/MS: 680.0 (M+H$^+$). 1H NMR (400 MHz, Methanol-d4) δ 8.24 (d, J=1.2 Hz, 1H), 7.70-7.55 (m, 2H), 7.51 (d, J=9.0 Hz, 2H), 7.33 (dd, J=10.9, 2.0 Hz, 1H), 7.27-7.14 (m, 2H), 7.07-6.87 (m, 2H), 4.69 (s, 2H), 4.57 (s, 2H), 2.26 (s, 2H), 2.13 (d, J=1.0 Hz, 3H), 0.96-0.80 (m, 1H).

Example 13: ES/MS: 662.2 (M+H$^+$). 1H NMR (400 MHz, Methanol-d4) δ 8.24 (d, J=1.2 Hz, 1H), 7.73-7.57 (m, 2H), 7.57-7.46 (m, 2H), 7.32 (dd, J=10.9, 2.0 Hz, 1H), 7.28-7.15 (m, 2H), 7.06-6.81 (m, 2H), 4.66 (s, 2H), 4.55 (s, 2H), 2.61 (s, 2H), 2.13 (d, J=1.0 Hz, 3H), 0.98-0.79 (m, 4H).

Procedure 10: Example 10 and Example 17

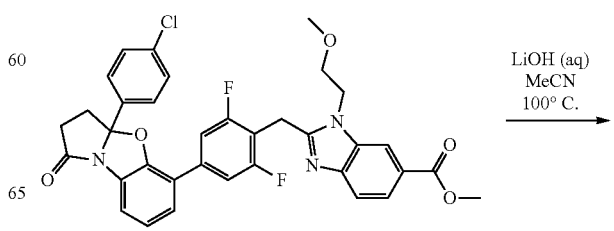

121
-continued

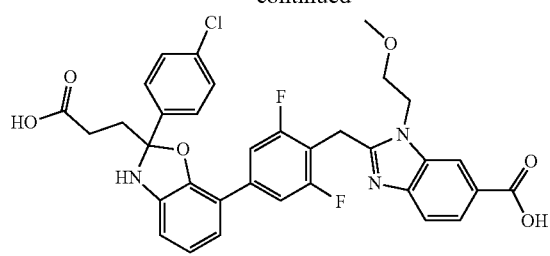

Example 10

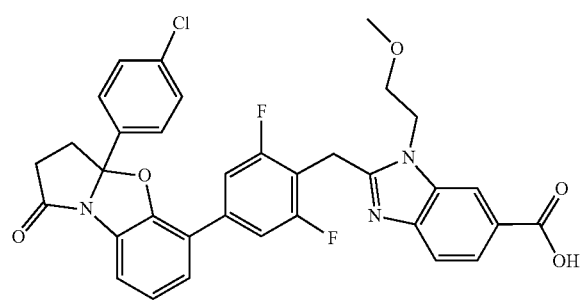

Example 17

2-(4-(2-(2-carboxyethyl)-2-(4-chlorophenyl)-2,3-dihydrobenzo[d]oxazol-7-yl)-2,6-difluorobenzyl)-1-(2-methoxyethyl)-1H-benzo[d]imidazole-6-carboxylic acid (Example 10) and 2-(4-(3a-(4-chlorophenyl)-1-oxo-1,2,3,3a-tetrahydrobenzo[d]pyrrolo[2,1-b]oxazol-5-yl)-2,6-difluorobenzyl)-1-(2-methoxyethyl)-1H-benzo[d]imidazole-6-carboxylic acid (Example 17): To a solution of methyl 2-(4-(3a-(4-chlorophenyl)-1-oxo-1,2,3,3a-tetrahydrobenzo[d]pyrrolo[2,1-b]oxazol-5-yl)-2,6-difluorobenzyl)-1-(2-methoxyethyl)-1H-benzo[d]imidazole-6-carboxylate (synthesized as in Procedure 1) (112 mg, 0.174 mmol) in MeCN (1 mL) was added lithium hydroxide monohydrate (11 mg, 0.26 mmol) dissolved in water (0.5 mL). The reaction mixture was heated in a sealed tube at 100° C. for 3 minutes. The cooled reaction mixture was purified by RP-HPLC (eluent: water/MeCN*0.1% TFA) to provide the products Example 10 and Example 17 as trifluoroacetate salts.

Example 10: ES/MS: 648.2 (M+). 1H NMR (400 MHz, Methanol-d4) δ 8.54 (t, J=1.0 Hz, 1H), 8.21 (dd, J=8.6, 1.4 Hz, 1H), 8.08-8.00 (m, 2H), 7.76 (d, J=8.6 Hz, 1H), 7.57-7.50 (m, 2H), 7.41-7.33 (m, 2H), 7.33-7.21 (m, 2H), 7.00 (t, J=7.8 Hz, 1H), 4.85-4.81 (m, 2H), 4.78 (s, 2H), 3.88-3.81 (m, 2H), 3.47 (t, J=6.4 Hz, 2H), 3.32 (s, 3H), 2.94 (t, J=6.4 Hz, 2H).

Example 17: ES/MS: 630.2 (M+). 1H NMR (400 MHz, Methanol-d4) δ 8.58 (s, 1H), 8.28-8.22 (m, 1H), 8.12-8.01 (m, 2H), 7.78 (d, J=8.6 Hz, 1H), 7.71 (t, J=8.6 Hz, 4H), 7.59-7.44 (m, 3H), 4.86-4.83 (m, 4H), 3.87 (t, J=4.9 Hz, 2H), 3.74 (t, J=6.6 Hz, 2H), 3.46 (t, J=6.5 Hz, 2H), 3.32 (s, 3H).

122
Procedure 11: 2-(4-(2-(4-cyano-2-fluorophenyl)benzo[d][1,3]dioxol-4-yl)-2-fluorobenzyl)-1-(2-methoxyethyl)-1H-benzo[d]imidazole-6-carboxylic Acid (Example 33 and Example 34)

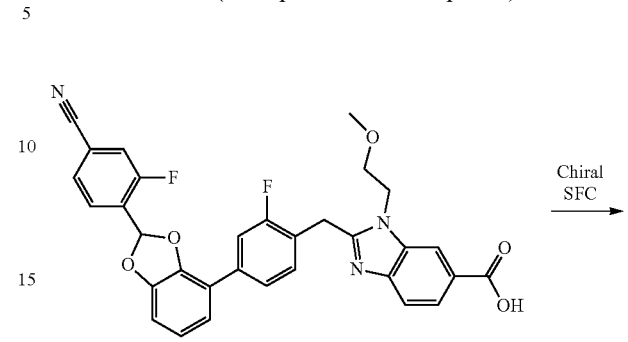

Example 4

Chiral SFC →

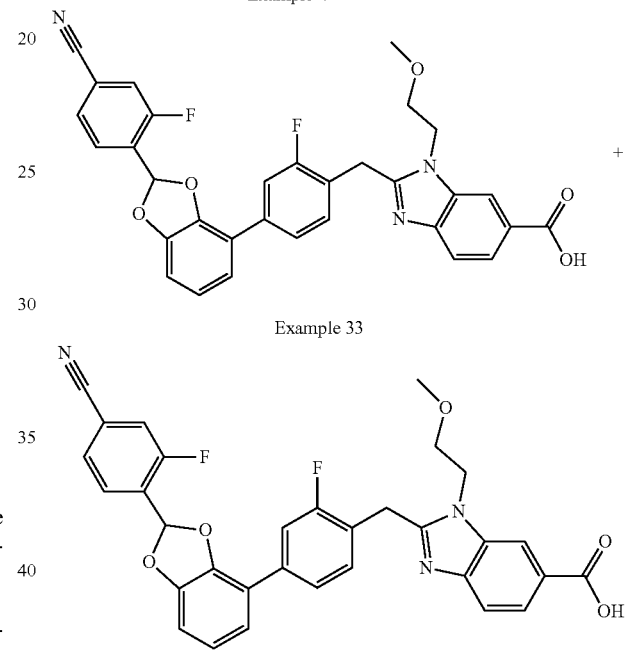

Example 33

Example 34

2-(4-(2-(4-cyano-2-fluorophenyl)benzo[d][1,3]dioxol-4-yl)-2-fluorobenzyl)-1-(2-methoxyethyl)-1H-benzo[d]imidazole-6-carboxylic acid: 2-(4-(2-(4-cyano-2-fluorophenyl)benzo[d][1,3]dioxol-4-yl)-2-fluorobenzyl)-1-(2-methoxyethyl)-1H-benzo[d]imidazole-6-carboxylic acid (Example 4 obtained as described in procedure 4) as a mixture of 2 stereoisomers was separated by chiral SFC (CELL-2 column with 30% EtOH-TFA cosolvent) to give two distinct stereoisomers.

2-(4-(2-(4-cyano-2-fluorophenyl)benzo[d][1,3]dioxol-4-yl)-2-fluorobenzyl)-1-(2-methoxyethyl)-1H-benzo[d]imidazole-6-carboxylic acid (Example 33): ES/MS: 568.4 (M+H+). 1H NMR (400 MHz, Methanol-d4) δ 8.41 (s, 1H), 8.13-8.06 (m, 1H), 7.84-7.77 (m, 1H), 7.77-7.59 (m, 5H), 7.43 (d, J=14.0 Hz, 2H), 7.25-7.17 (m, 1H), 7.04 (t, J=7.9 Hz, 1H), 6.97 (dd, J=7.6, 1.1 Hz, 1H), 4.67 (t, J=5.0 Hz, 2H), 4.62 (s, 2H), 3.75 (t, J=4.9 Hz, 2H), 3.28 (s, 3H).

2-(4-(2-(4-cyano-2-fluorophenyl)benzo[d][1,3]dioxol-4-yl)-2-fluorobenzyl)-1-(2-methoxyethyl)-1H-benzo[d]imidazole-6-carboxylic acid (Example 34). ES/MS: 568.4 (M+H+). 1H NMR (400 MHz, Methanol-d4) δ 8.41 (s, 1H), 8.11 (dd, J=8.6, 1.5 Hz, 1H), 7.80 (t, J=7.5 Hz, 1H), 7.77-7.57 (m, 5H), 7.43 (d, J=12.3 Hz, 2H), 7.22 (dd, J=8.0, 1.2 Hz, 1H), 7.04 (t, J=7.9 Hz, 1H), 6.97 (dd, J=7.8, 1.2 Hz, 1H), 4.67 (t, J=5.0 Hz, 2H), 4.63 (s, 2H), 3.75 (t, J=5.0 Hz, 2H), 3.28 (s, 3H).

Procedure 12: 2-(2-fluoro-4-(2-phenylbenzo[d][1,3]dioxol-4-yl)benzyl)-1-(2-methoxyethyl)-1H-benzo[d]imidazole-6-carboxylic Acid (Example 35 and Example 36)

2-(2-fluoro-4-(2-phenylbenzo[d][1,3]dioxol-4-yl)benzyl)-1-(2-methoxyethyl)-1H-benzo[d]imidazole-6-carboxylic acid: 2-(2-fluoro-4-(2-phenylbenzo[d][1,3]dioxol-4-yl)benzyl)-1-(2-methoxyethyl)-1H-benzo[d]imidazole-6-carboxylic acid (Example 32 obtained as described in procedure 6) as a mixture of 2 stereoisomers was separated by chiral SFC (AD-H column with 30% MeOH cosolvent) to give two distinct stereoisomers.

2-(2-fluoro-4-(2-phenylbenzo[d][1,3]dioxol-4-yl)benzyl)-1-(2-methoxyethyl)-1H-benzo[d]imidazole-6-carboxylic acid (Example 35): ES/MS: 525.3 (M+H⁺). 1H NMR (400 MHz, Methanol-d4) δ 8.52-8.48 (m, 1H), 8.19 (dd, J=8.6, 1.4 Hz, 1H), 7.75 (d, J=8.6 Hz, 1H), 7.72-7.64 (m, 2H), 7.64-7.56 (m, 2H), 7.52-7.42 (m, 4H), 7.19 (dd, J=8.1, 1.2 Hz, 1H), 7.13 (s, 1H), 7.01 (t, J=7.9 Hz, 1H), 6.93 (dd, J=7.7, 1.2 Hz, 1H), 4.76 (t, J=5.0 Hz, 2H), 4.71 (s, 2H), 3.79 (t, J=4.9 Hz, 2H), 3.29 (s, 3H).

2-(2-fluoro-4-(2-phenylbenzo[d][1,3]dioxol-4-yl)benzyl)-1-(2-methoxyethyl)-1H-benzo[d]imidazole-6-carboxylic acid (Example 36): ES/MS: 525.3 (M+H⁺). 1H NMR (400 MHz, Methanol-d4) δ 8.50 (t, J=1.0 Hz, 1H), 8.18 (dd, J=8.6, 1.4 Hz, 1H), 7.75 (d, J=8.6 Hz, 1H), 7.71-7.64 (m, 2H), 7.63-7.57 (m, 2H), 7.51-7.40 (m, 4H), 7.19 (dd, J=8.1, 1.2 Hz, 1H), 7.13 (s, 1H), 7.01 (t, J=7.9 Hz, 1H), 6.93 (dd, J=7.7, 1.2 Hz, 1H), 4.76 (t, J=5.0 Hz, 2H), 4.71 (s, 2H), 3.78 (t, J=4.9 Hz, 2H), 3.29 (s, 3H).

Procedure 13: 2-(4-(2-(4-cyano-2-fluorophenyl)benzo[d][1,3]dioxol-4-yl)-2,6-difluorobenzyl)-1-(2-methoxyethyl)-1H-benzo[d]imidazole-6-carboxylic Acid (Example 37 and Example 38)

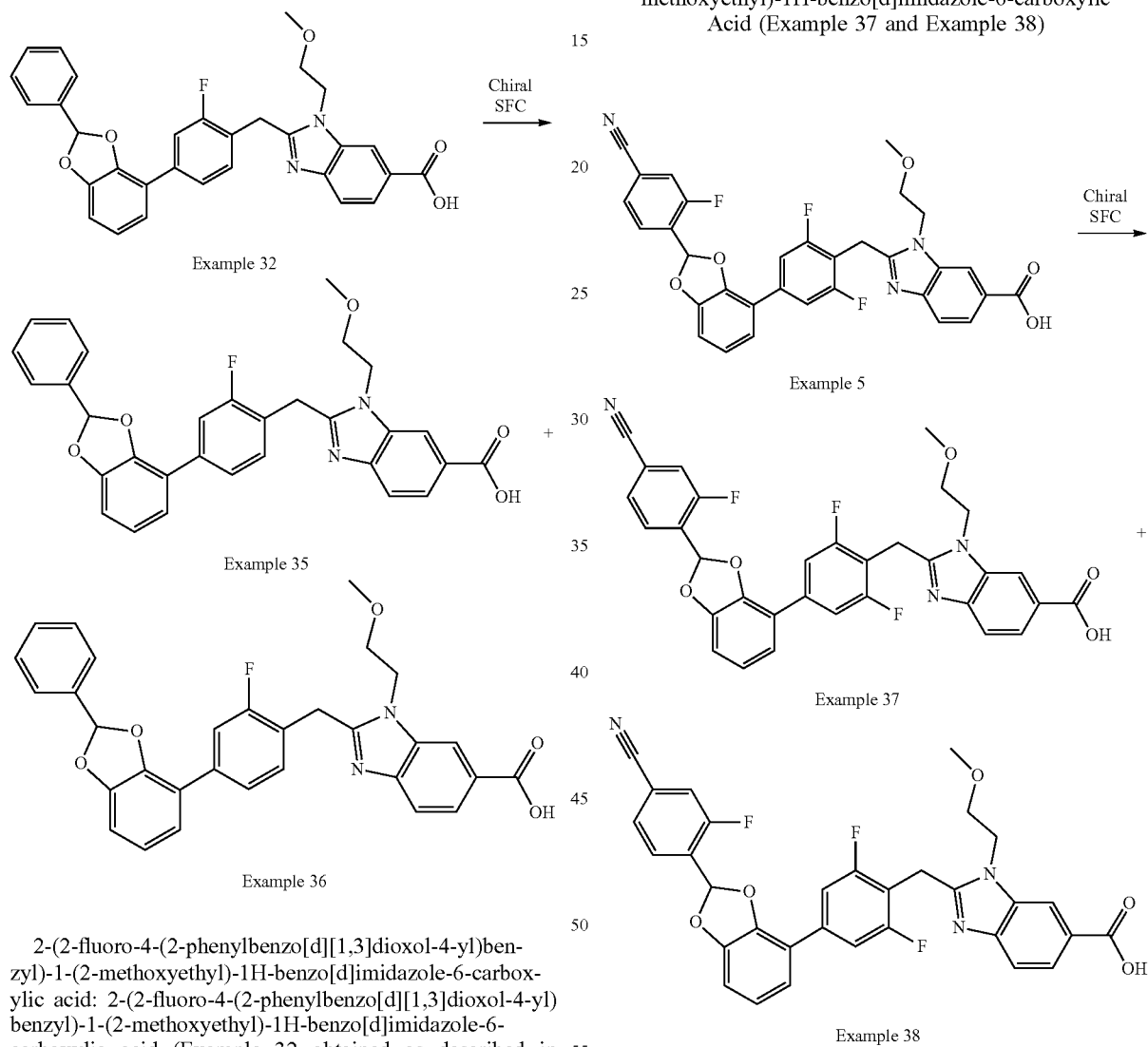

2-(4-(2-(4-cyano-2-fluorophenyl)benzo[d][1,3]dioxol-4-yl)-2,6-difluorobenzyl)-1-(2-methoxyethyl)-1H-benzo[d]imidazole-6-carboxylic acid: 2-(4-(2-(4-cyano-2-fluorophenyl)benzo[d][1,3]dioxol-4-yl)-2,6-difluorobenzyl)-1-(2-methoxyethyl)-1H-benzo[d]imidazole-6-carboxylic acid (Example 5 obtained as described in procedure 5) as a mixture of 2 stereoisomers was separated by chiral SFC (AD-H column with 40% MeOH cosolvent) to give two distinct stereoisomers.

2-(4-(2-(4-cyano-2-fluorophenyl)benzo[d][1,3]dioxol-4-yl)-2,6-difluorobenzyl)-1-(2-methoxyethyl)-1H-benzo[d]

imidazole-6-carboxylic acid (Example 37): ES/MS: 586.2 (M+H⁺). 1H NMR (400 MHz, Methanol-d4) δ 8.59-8.34 (m, 1H), 8.21-8.02 (m, 1H), 7.93-7.53 (m, 4H), 7.41 (d, J=8.8 Hz, 2H), 7.37-7.21 (m, 1H), 7.15-6.89 (m, 3H), 4.79-4.71 (m, 2H), 4.67 (s, 2H), 3.86-3.73 (m, 2H), 3.28 (s, 3H).

2-(4-(2-(4-cyano-2-fluorophenyl)benzo[d][1,3]dioxol-4-yl)-2,6-difluorobenzyl)-1-(2-methoxyethyl)-1H-benzo[d]imidazole-6-carboxylic acid (Example 38): ES/MS: 586.2 (M+H⁺). 1H NMR (400 MHz, Methanol-d4) δ 8.45 (s, 1H), 8.14 (dd, J=8.4, 1.5 Hz, 1H), 7.81 (t, J=7.5 Hz, 1H), 7.76-7.70 (m, 2H), 7.67 (dd, J=8.0, 1.6 Hz, 1H), 7.48-7.37 (m, 2H), 7.28 (dd, J=10.1, 6.2 Hz, 1H), 7.12-6.97 (m, 3H), 4.73 (t, J=5.0 Hz, 2H), 4.66 (s, 2H), 3.79 (t, J=4.9 Hz, 2H), 3.29 (s, 3H).

Procedure 14: 2-(4-(2-(4-cyano-2-fluorophenyl)benzo[d][1,3]dioxol-4-yl)-2,5-difluorobenzyl)-1-(2-methoxyethyl)-1H-benzo[d]imidazole-6-carboxylic Acid (Example 39 and Example 40)

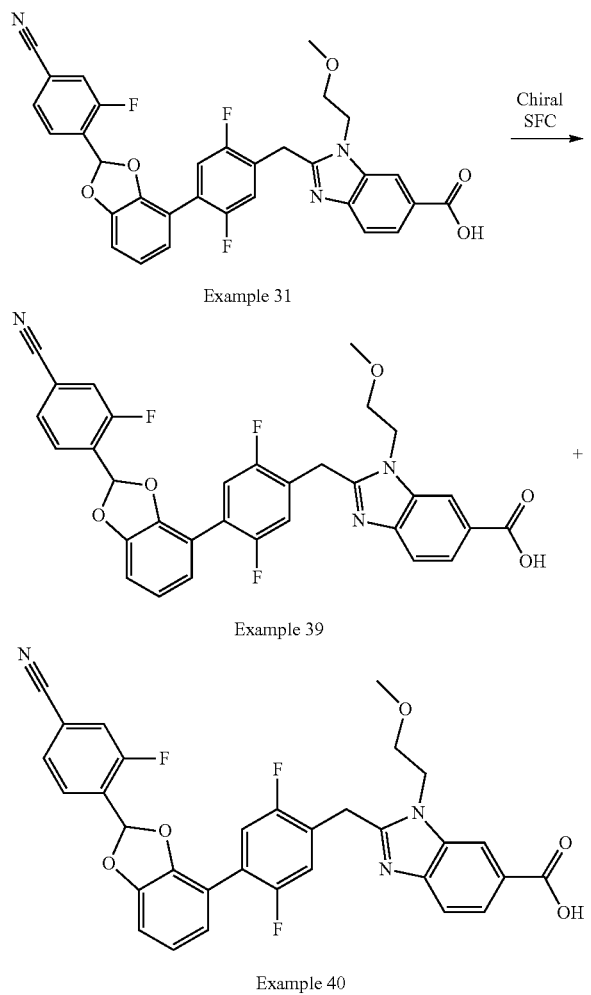

2-(4-(2-(4-cyano-2-fluorophenyl)benzo[d][1,3]dioxol-4-yl)-2,5-difluorobenzyl)-1-(2-methoxyethyl)-1H-benzo[d]imidazole-6-carboxylic acid: 2-(4-(2-(4-cyano-2-fluorophenyl)benzo[d][1,3]dioxol-4-yl)-2,5-difluorobenzyl)-1-(2-methoxyethyl)-1H-benzo[d]imidazole-6-carboxylic acid (Example 31 obtained as described in procedure 1) as a mixture of 2 stereoisomers was separated by chiral SFC (CELL-2 column with 45% MeOH cosolvent) to give two distinct stereoisomers.

2-(4-(2-(4-cyano-2-fluorophenyl)benzo[d][1,3]dioxol-4-yl)-2,5-difluorobenzyl)-1-(2-methoxyethyl)-1H-benzo[d]imidazole-6-carboxylic acid (Example 39): ES/MS: 586.2 (M+H⁺). 1H NMR (400 MHz, Methanol-d4) δ 8.50 (s, 1H), 8.18 (dd, J=8.6, 1.6 Hz, 1H), 7.82 (t, J=7.5 Hz, 1H), 7.78-7.64 (m, 3H), 7.49-7.40 (m, 2H), 7.31 (dd, J=10.1, 6.2 Hz, 1H), 7.10-6.98 (m, 3H), 4.77 (t, J=5.0 Hz, 2H), 4.70 (s, 2H), 3.81 (t, J=5.0 Hz, 2H), 3.30 (s, 3H).

2-(4-(2-(4-cyano-2-fluorophenyl)benzo[d][1,3]dioxol-4-yl)-2,5-difluorobenzyl)-1-(2-methoxyethyl)-1H-benzo[d]imidazole-6-carboxylic acid (Example 40): ES/MS: 586.2 (M+H⁺). 1H NMR (400 MHz, Methanol-d4) δ 8.47 (s, 1H), 8.16 (dd, J=8.5, 1.5 Hz, 1H), 7.82 (t, J=7.4 Hz, 1H), 7.77-7.64 (m, 3H), 7.48-7.39 (m, 2H), 7.30 (dd, J=10.0, 6.0 Hz, 1H), 7.10-6.98 (m, 3H), 4.75 (t, J=5.1 Hz, 2H), 4.68 (s, 2H), 3.81 (t, J=5.1 Hz, 2H), 3.29 (s, 3H).

Procedure 15: 2-(4-(2-(4-cyano-2-fluorophenyl)benzo[d][1,3]dioxol-4-yl)-2,6-difluorobenzyl)-1-(((S)-oxetan-2-yl)methyl)-1H-benzo[d]imidazole-6-carboxylic Acid (Example 41 and Example 42)

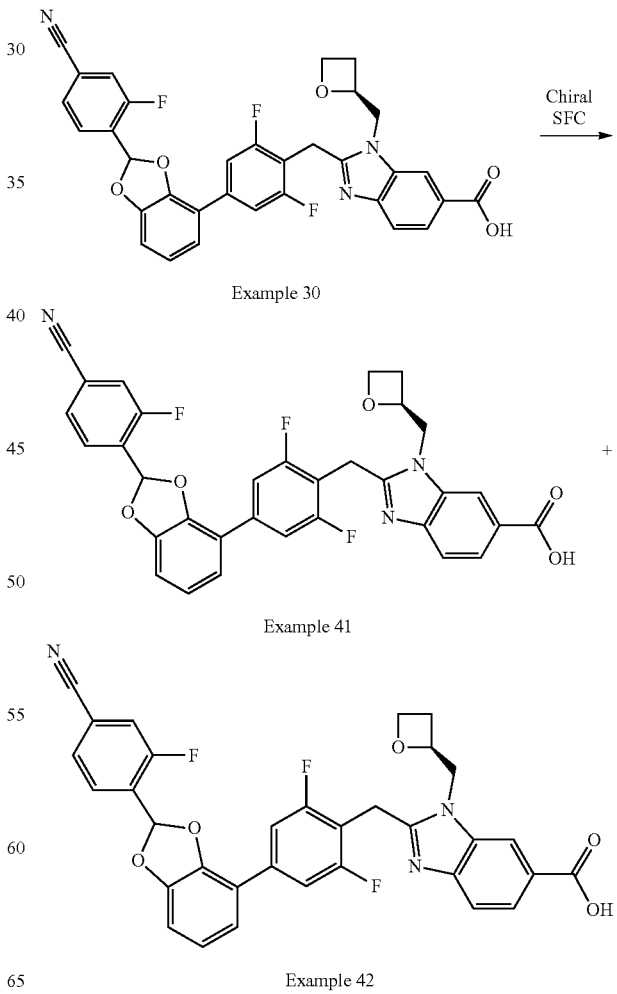

2-(4-(2-(4-cyano-2-fluorophenyl)benzo[d][1,3]dioxol-4-yl)-2,6-difluorobenzyl)-1-(((S)-oxetan-2-yl)methyl)-1H-benzo[d]imidazole-6-carboxylic acid: 2-(4-(2-(4-cyano-2-fluorophenyl)benzo[d][1,3]dioxol-4-yl)-2,6-difluorobenzyl)-1-(((S)-oxetan-2-yl)methyl)-1H-benzo[d]imidazole-6-carboxylic acid (Example 30 obtained as described in procedure 1) as a mixture of 2 stereoisomers was separated by chiral SFC (IG column with 50% MeOH cosolvent) to give two distinct stereoisomers.

2-(4-(2-(4-cyano-2-fluorophenyl)benzo[d][1,3]dioxol-4-yl)-2,6-difluorobenzyl)-1-(((S)-oxetan-2-yl)methyl)-1H-benzo[d]imidazole-6-carboxylic acid (Example 41): ES/MS: 598.1 (M+H$^+$). 1H NMR (400 MHz, Methanol-d4) δ 8.44 (s, 1H), 8.09 (d, J=8.5 Hz, 1H), 7.82 (t, J=7.4 Hz, 1H), 7.72 (dd, J=24.1, 9.1 Hz, 3H), 7.55 (d, J=8.9 Hz, 2H), 7.49 (s, 1H), 7.26 (d, J=7.8 Hz, 1H), 7.12-6.98 (m, 2H), 5.31-5.21 (m, 1H), 4.93-4.61 (m, 5H), 4.54-4.44 (m, 1H), 2.84 (t, J=9.4 Hz, 1H), 2.61-2.47 (m, 1H).

2-(4-(2-(4-cyano-2-fluorophenyl)benzo[d][1,3]dioxol-4-yl)-2,6-difluorobenzyl)-1-(((S)-oxetan-2-yl)methyl)-1H-benzo[d]imidazole-6-carboxylic acid (Example 42): ES/MS: 598.2 (M+H$^+$). 1H NMR (400 MHz, Methanol-d4) δ 8.47 (s, 1H), 8.11 (d, J=8.5 Hz, 1H), 7.82 (t, J=7.5 Hz, 1H), 7.77-7.67 (m, 3H), 7.55 (d, J=8.9 Hz, 2H), 7.48 (s, 1H), 7.26 (d, J=7.9 Hz, 1H), 7.11-6.98 (m, 2H), 5.26 (qd, J=7.3, 2.4 Hz, 1H), 4.84-4.62 (m, 5H), 4.50 (dt, J=9.1, 6.0 Hz, 1H), 2.85 (dq, J=14.6, 7.7 Hz, 1H), 2.64-2.50 (m, 1H).

Procedure 16: 2-(4-(2-(4-chloro-2-fluorophenyl)-2-methylbenzo[d][1,3]dioxol-4-yl)-2,5-difluorobenzyl)-1-(((S)-oxetan-2-yl)methyl)-1H-benzo[d]imidazole-6-carboxylic Acid (Example 43 and Example 44)

2-(4-(2-(4-chloro-2-fluorophenyl)-2-methylbenzo[d][1,3]dioxol-4-yl)-2,5-difluorobenzyl)-1-(((S)-oxetan-2-yl)methyl)-1H-benzo[d]imidazole-6-carboxylic acid: 2-(4-(2-(4-chloro-2-fluorophenyl)-2-methylbenzo[d][1,3]dioxol-4-yl)-2,5-difluorobenzyl)-1-(((S)-oxetan-2-yl)methyl)-1H-benzo[d]imidazole-6-carboxylic acid (Example 28 obtained as described in procedure 1) as a mixture of 2 stereoisomers was separated by chiral SFC (AZ-H column with 25% IPA-NH3 cosolvent) to give two distinct stereoisomers.

2-(4-(2-(4-chloro-2-fluorophenyl)-2-methylbenzo[d][1,3]dioxol-4-yl)-2,5-difluorobenzyl)-1-(((S)-oxetan-2-yl)methyl)-1H-benzo[d]imidazole-6-carboxylic acid (Example 43): ES/MS: 621.3 (M$^+$). 1H NMR (400 MHz, Methanol-d4) δ 8.32 (s, 1H), 7.99 (d, J=8.5 Hz, 1H), 7.68 (d, J=8.5 Hz, 1H), 7.62 (t, J=8.3 Hz, 1H), 7.32 (ddd, J=19.8, 10.5, 4.0 Hz, 2H), 7.26-7.10 (m, 2H), 7.03-6.86 (m, 3H), 5.24-5.12 (m, 1H), 4.74 (dd, J=15.7, 6.9 Hz, 1H), 4.69-4.56 (m, 3H), 4.55-4.40 (m, 2H), 2.79 (dq, J=16.7, 7.8, 5.9 Hz, 1H), 2.58-2.41 (m, 1H), 2.06 (s, 3H).

2-(4-(2-(4-chloro-2-fluorophenyl)-2-methylbenzo[d][1,3]dioxol-4-yl)-2,5-difluorobenzyl)-1-(((S)-oxetan-2-yl)methyl)-1H-benzo[d]imidazole-6-carboxylic acid (Example 44): ES/MS: 621.4 (M$^+$). 1H NMR (400 MHz, Methanol-d4) δ 8.31 (dd, J=1.5, 0.7 Hz, 1H), 7.99 (dd, J=8.5, 1.5 Hz, 1H), 7.67 (dd, J=8.5, 0.6 Hz, 1H), 7.61 (t, J=8.3 Hz, 1H), 7.40-7.26 (m, 2H), 7.26-7.15 (m, 2H), 7.02-6.87 (m, 3H), 5.19 (qd, J=7.0, 2.6 Hz, 1H), 4.78-4.39 (m, 7H), 2.80 (dtd, J=11.4, 8.2, 6.1 Hz, 1H), 2.49 (ddt, J=11.4, 9.2, 7.2 Hz, 1H), 2.06 (d, J=1.1 Hz, 3H).

Procedure 17: 2-(4-(2-(5-chloropyridin-2-yl)-2-methylbenzo[d][1,3]dioxol-4-yl)-2,5-difluorobenzyl)-1-(((S)-oxetan-2-yl)methyl)-1H-benzo[d]imidazole-6-carboxylic Acid (Example 45 and Example 46)

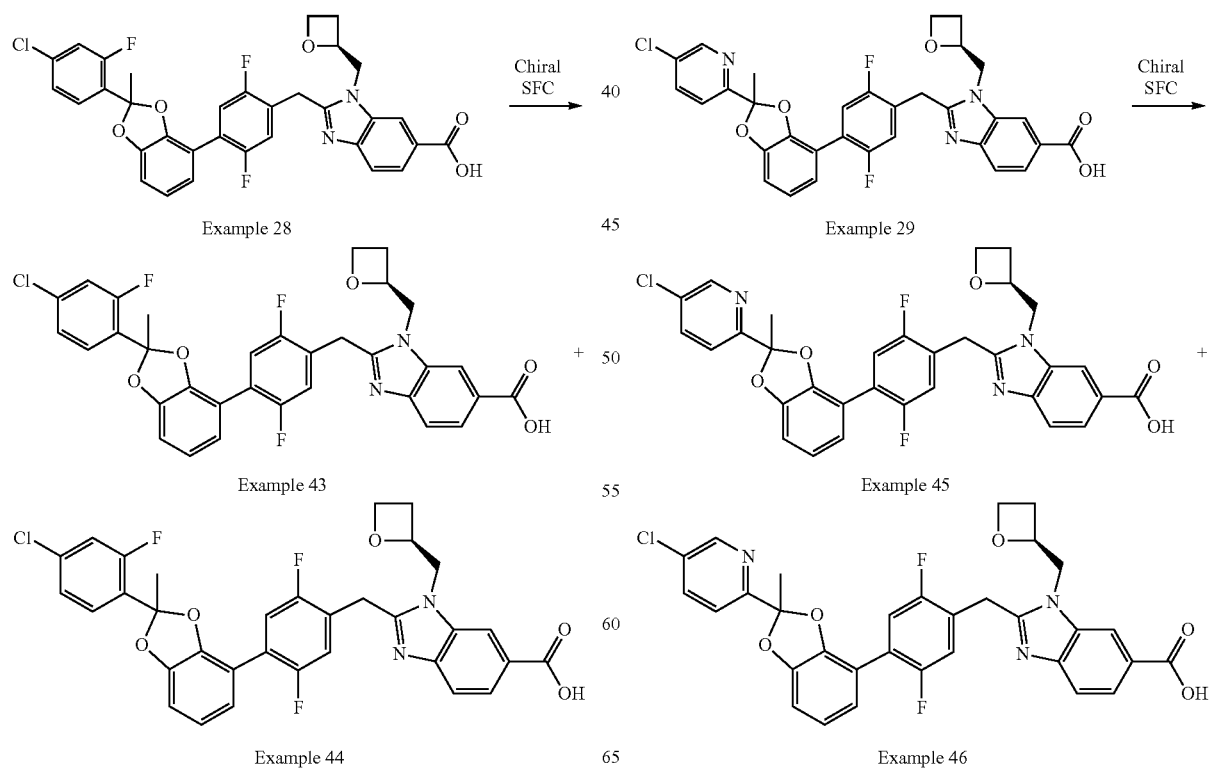

Example 28 → Chiral SFC → Example 29 → Chiral SFC →

Example 43 +  Example 45 +

Example 44  Example 46

2-(4-(2-(5-chloropyridin-2-yl)-2-methylbenzo[d][1,3]dioxol-4-yl)-2,5-difluorobenzyl)-1-(((S)-oxetan-2-yl)methyl)-1H-benzo[d]imidazole-6-carboxylic acid: 2-(4-(2-(5-chloropyridin-2-yl)-2-methylbenzo[d][1,3]dioxol-4-yl)-2,5-difluorobenzyl)-1-(((S)-oxetan-2-yl)methyl)-1H-benzo[d]imidazole-6-carboxylic acid (Example 29 obtained as described in procedure 1) as a mixture of 2 stereoisomers was separated by chiral SFC (AD-H column with 35% MeOH-DEA cosolvent) to give two distinct stereoisomers.

2-(4-(2-(5-chloropyridin-2-yl)-2-methylbenzo[d][1,3]dioxol-4-yl)-2,5-difluorobenzyl)-1-(((S)-oxetan-2-yl)methyl)-1H-benzo[d]imidazole-6-carboxylic acid (Example 45): ES/MS: 604.2 (M+). 1H NMR (400 MHz, Methanol-d4) δ 8.63 (dd, J=2.4, 0.7 Hz, 1H), 8.52 (t, J=1.0 Hz, 1H), 8.17 (dd, J=8.6, 1.4 Hz, 1H), 7.92 (dd, J=8.5, 2.4 Hz, 1H), 7.76 (dd, J=8.6, 0.7 Hz, 1H), 7.71 (dd, J=8.5, 0.7 Hz, 1H), 7.44 (dd, J=10.0, 6.0 Hz, 1H), 7.33 (dd, J=10.0, 6.2 Hz, 1H), 7.04-6.92 (m, 3H), 5.25 (qd, J=7.4, 2.4 Hz, 1H), 4.99-4.64 (m, 5H), 4.52 (dt, J=9.1, 5.9 Hz, 1H), 2.95-2.77 (m, 1H), 2.63-2.44 (m, 1H), 2.07 (s, 3H).

2-(4-(2-(5-chloropyridin-2-yl)-2-methylbenzo[d][1,3]dioxol-4-yl)-2,5-difluorobenzyl)-1-(((S)-oxetan-2-yl)methyl)-1H-benzo[d]imidazole-6-carboxylic acid (Example 46): ES/MS: 604.2 (M+). 1H NMR (400 MHz, Methanol-d4) δ 8.63 (dd, J=2.5, 0.7 Hz, 1H), 8.54-8.46 (m, 1H), 8.15 (dd, J=8.5, 1.4 Hz, 1H), 7.92 (dd, J=8.5, 2.4 Hz, 1H), 7.75 (d, J=8.5 Hz, 1H), 7.71 (dd, J=8.5, 0.7 Hz, 1H), 7.43 (dd, J=10.0, 6.0 Hz, 1H), 7.31 (dd, J=10.0, 6.1 Hz, 1H), 7.04-6.93 (m, 3H), 5.23 (dd, J=8.1, 5.8 Hz, 1H), 4.86-4.64 (m, 5H), 4.51 (dt, J=9.2, 6.0 Hz, 1H), 2.93-2.76 (m, 1H), 2.64-2.44 (m, 1H), 2.07 (s, 3H).

Procedure 18: 2-(4-(2-(4-chloro-2-fluorophenyl)-2-methylbenzo[d][1,3]dioxol-4-yl)-2,6-difluorobenzyl)-1-(((S)-oxetan-2-yl)methyl)-1H-benzo[d]imidazole-6-carboxylic Acid (Example 47 and Example 48)

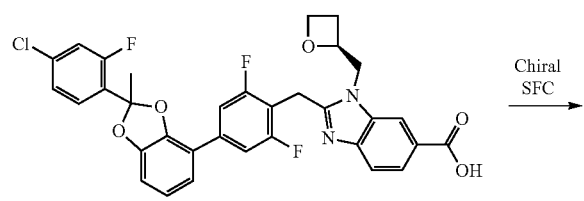

Example 22

Chiral SFC →

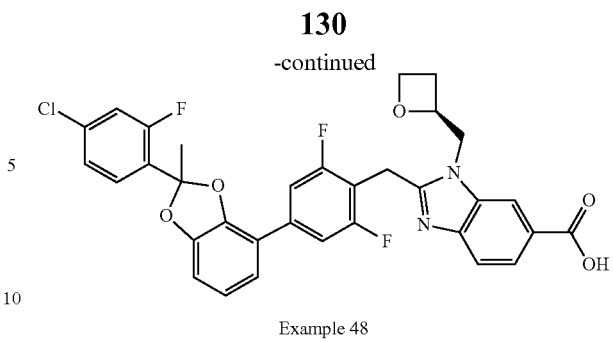

Example 48

2-(4-(2-(4-chloro-2-fluorophenyl)-2-methylbenzo[d][1,3]dioxol-4-yl)-2,6-difluorobenzyl)-1-(((S)-oxetan-2-yl)methyl)-1H-benzo[d]imidazole-6-carboxylic acid: 2-(4-(2-(4-chloro-2-fluorophenyl)-2-methylbenzo[d][1,3]dioxol-4-yl)-2,6-difluorobenzyl)-1-(((S)-oxetan-2-yl)methyl)-1H-benzo[d]imidazole-6-carboxylic acid (Example 22 obtained as described in procedure 1) as a mixture of 2 stereoisomers was separated by chiral SFC (AD-H column with 25% IPA-NH3 cosolvent) to give two distinct stereoisomers.

2-(4-(2-(4-chloro-2-fluorophenyl)-2-methylbenzo[d][1,3]dioxol-4-yl)-2,6-difluorobenzyl)-1-(((S)-oxetan-2-yl)methyl)-1H-benzo[d]imidazole-6-carboxylic acid (Example 47): ES/MS: 621.2 (M+). 1H NMR (400 MHz, DMSO) δ 12.79 (s, 1H), 8.26 (d, J=1.6 Hz, 1H), 7.78 (dd, J=8.4, 1.6 Hz, 1H), 7.67-7.47 (m, 5H), 7.39 (dd, J=8.4, 2.1 Hz, 1H), 7.31 (dd, J=7.9, 1.4 Hz, 1H), 7.10-6.95 (m, 2H), 5.12 (qd, J=6.9, 2.7 Hz, 1H), 4.81 (dd, J=15.6, 6.8 Hz, 1H), 4.68 (dd, J=15.6, 2.7 Hz, 1H), 4.61-4.39 (m, 3H), 4.35 (dt, J=9.1, 5.9 Hz, 1H), 2.82-2.71 (m, 1H), 2.44-2.36 (m, 1H), 2.12 (s, 3H).

2-(4-(2-(4-chloro-2-fluorophenyl)-2-methylbenzo[d][1,3]dioxol-4-yl)-2,6-difluorobenzyl)-1-(((S)-oxetan-2-yl)methyl)-1H-benzo[d]imidazole-6-carboxylic acid (Example 48): ES/MS: 621.2 (M+). 1H NMR (400 MHz, DMSO) δ 12.77 (s, 1H), 8.25 (d, J=1.6 Hz, 1H), 7.77 (dd, J=8.4, 1.6 Hz, 1H), 7.69-7.50 (m, 5H), 7.39 (dd, J=8.4, 2.1 Hz, 1H), 7.31 (dd, J=7.9, 1.4 Hz, 1H), 7.16-6.93 (m, 2H), 5.12 (tt, J=6.9, 3.3 Hz, 1H), 4.80 (dd, J=15.7, 6.8 Hz, 1H), 4.67 (dd, J=15.6, 2.7 Hz, 1H), 4.60-4.39 (m, 3H), 4.35 (dt, J=9.0, 5.9 Hz, 1H), 2.78-2.71 (m, 1H), 2.45-2.35 (m, 1H), 2.12 (s, 3H).

Procedure 19: 2-(4-(2-(5-chloropyridin-2-yl)-2-methylbenzo[d][1,3]dioxol-4-yl)-2,6-difluorobenzyl)-1-(((S)-oxetan-2-yl)methyl)-1H-benzo[d]imidazole-6-carboxylic Acid (Example 49 and Example 50)

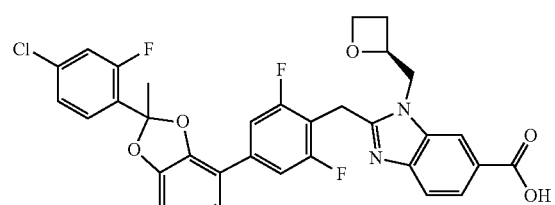

Example 47

+

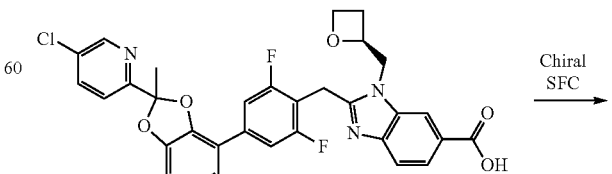

Example 27

Chiral SFC →

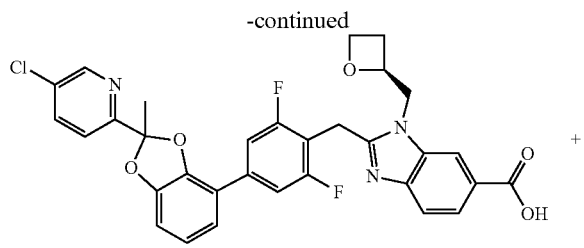

Example 49

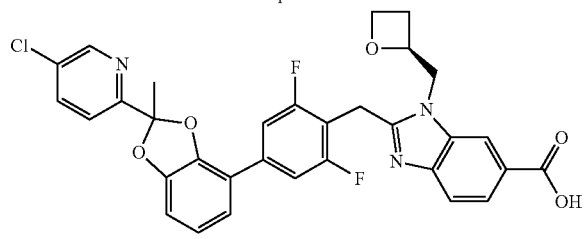

Example 50

2-(4-(2-(5-chloropyridin-2-yl)-2-methylbenzo[d][1,3]dioxol-4-yl)-2,6-difluorobenzyl)-1-(((S)-oxetan-2-yl)methyl)-1H-benzo[d]imidazole-6-carboxylic acid: 2-(4-(2-(5-chloropyridin-2-yl)-2-methylbenzo[d][1,3]dioxol-4-yl)-2,6-difluorobenzyl)-1-(((S)-oxetan-2-yl)methyl)-1H-benzo[d]imidazole-6-carboxylic acid (Example 27 obtained as described in procedure 1) as a mixture of 2 stereoisomers was separated by chiral SFC (AD-H column with 35% EtOH cosolvent) to give two distinct stereoisomers.

2-(4-(2-(5-chloropyridin-2-yl)-2-methylbenzo[d][1,3]dioxol-4-yl)-2,6-difluorobenzyl)-1-(((S)-oxetan-2-yl)methyl)-1H-benzo[d]imidazole-6-carboxylic acid (Example 49): ES/MS: 604.2 (M⁺). 1H NMR (400 MHz, DMSO) δ 12.81 (s, 1H), 8.75 (d, J=2.4 Hz, 1H), 8.27 (d, J=1.5 Hz, 1H), 8.04 (dd, J=8.5, 2.5 Hz, 1H), 7.78 (dd, J=8.5, 1.6 Hz, 1H), 7.71 (d, J=8.5 Hz, 1H), 7.57 (dd, J=10.5, 8.5 Hz, 4H), 7.29 (dd, J=7.4, 1.9 Hz, 1H), 7.22-6.91 (m, 3H), 5.11 (tt, J=7.1, 3.7 Hz, 1H), 4.81 (dd, J=15.6, 6.8 Hz, 1H), 4.68 (dd, J=15.5, 2.7 Hz, 1H), 4.60-4.38 (m, 4H), 4.35 (dt, J=9.1, 5.9 Hz, 1H), 2.74 (dq, J=11.1, 7.6 Hz, 1H), 2.45-2.35 (m, 1H), 2.12 (s, 4H).

2-(4-(2-(5-chloropyridin-2-yl)-2-methylbenzo[d][1,3]dioxol-4-yl)-2,6-difluorobenzyl)-1-(((S)-oxetan-2-yl)methyl)-1H-benzo[d]imidazole-6-carboxylic acid (Example 50): ES/MS: 604.2 (M⁺). 1H NMR (400 MHz, DMSO) δ 12.79 (s, 1H), 8.75 (d, J=2.4 Hz, 1H), 8.26 (d, J=1.5 Hz, 1H), 8.04 (dd, J=8.5, 2.5 Hz, 1H), 7.78 (dd, J=8.5, 1.6 Hz, 1H), 7.71 (d, J=8.6 Hz, 1H), 7.56 (t, J=8.9 Hz, 4H), 7.29 (dd, J=7.4, 2.0 Hz, 1H), 7.16-6.92 (m, 2H), 5.12 (qd, J=6.9, 2.7 Hz, 1H), 4.81 (dd, J=15.6, 6.8 Hz, 1H), 4.67 (dd, J=15.6, 2.7 Hz, 1H), 4.61-4.40 (m, 4H), 4.35 (dt, J=9.0, 5.9 Hz, 1H), 2.97-2.62 (m, 1H), 2.39 (ddt, J=11.3, 9.1, 6.9 Hz, 1H), 2.12 (s, 4H).

Procedure 20: Example 82

Methyl 2-[[4-[6-[(4-cyano-2-fluoro-phenyl)methoxy]-2-pyridyl]-2-fluoro-phenyl]methyl]-3-(2-methoxyethyl)benzimidazole-5-carboxylate: To a solution of 2-(4-(2-(4-chloro-2-fluorophenyl)-2-methylbenzo[d][1,3]dioxol-4-yl)-2,6-difluorophenyl)acetic acid I-17 (113 mg, 0.144 mmol), Methyl 4-amino-3-((2-(methylsulfonyl)ethyl)amino)benzoate I-18 (46.5 mg, 0.154 mmol), and o-(7-azabenzotriazol-1-yl)-N,N,N',N'-tetramethyluronium hexafluorophosphate (49 mg, 0.116 mmol) in DMF (3 mL), was added N,N-diisopropylethylamine (0.085 mL, 0.776 mmol). The mixture was stirred at RT overnight. The mixture was diluted with EtOAc and washed with 5% LiCl, saturated NaHCO₃, and brine. The organic extract was dried over sodium sulfate to give crude product. Then, acetic acid was added to the intermediate and the mixture was heated at 80° C. for 4 hours. Upon completion of the reaction, the compound was purified by silica gel chromatography and carried on to the next step. ES/MS: 672.2 (M+H+).

2-[[4-[2-(4-chloro-2-fluoro-phenyl)-2-methyl-1,3-benzodioxol-4-yl]-2,6-difluoro-phenyl]methyl]-3-(2-methylsulfonylethyl)benzimidazole-5-carboxylic acid (Example 82): A solution of methyl 2-[[4-[6-[(4-cyano-2-fluoro-phenyl)methoxy]-2-pyridyl]-2-fluoro-phenyl]methyl]-3-(2-methoxyethyl)benzimidazole-5-carboxylate (40.0 mg, 0.0.05 mmol) and aqueous lithium hydroxide monohydrate solution (0.3 M, 4.2 mg, 0.17 mmol) in CH₃CN (1 mL) was stirred at 100° C. for 5 minutes. Upon completion, the reaction was diluted with EtOAc and adjusted to pH6 with 1N HCl. The organic extract was dried over sodium sulfate, filtered, concentrate and purified by RP-HPLC (eluent: water/MeCN*0.1% TFA) to yield the desired product. ES/MS: 658.2. 1H NMR (400 MHz, DMSO-d6) δ 8.25 (d, J=1.5 Hz, 1H), 7.95-7.86 (m, 2H), 7.83-7.71 (m, 4H), 7.61 (d, J=8.4 Hz, 1H), 7.53 (dd, J=7.6, 1.7 Hz, 1H), 7.38 (dd, J=11.6, 6.1 Hz, 1H), 6.99 (d, J=8.2 Hz, 1H), 6.65 (t, J=75.3 Hz, 1H), 5.61 (s, 2H), 4.72 (t, J=5.1 Hz, 2H), 4.44 (s, 2H), 4.21 (t, J=5.1 Hz, 2H).

Procedure 21: Example 84

2-(4-(2-(4-chloro-2-fluorophenyl)-2-methylbenzo[d][1,3]dioxol-4-yl)-2,6-difluorophenyl)-N-(2-((2-methoxyethyl)amino)-4-(2H-tetrazol-5-yl)phenyl)acetamide: To a solution of 2-(4-(2-(4-chloro-2-fluorophenyl)-2-methylbenzo[d][1,3]dioxol-4-yl)-2,6-difluorophenyl)acetic (I-17, 61.0 mg, 0.140 mmol), N2-(2-methoxyethyl)-4-(2H-tetrazol-5-yl)benzene-1,2-diamine (I-22, 35.7 mg, 0.152 mmol), and o-(7-azabenzotriazol-1-yl)-N,N,N',N'-tetramethyluronium hexafluorophosphate (79.2 mg, 0.208 mmol) in DMF (3 mL), was added N,N-diisopropylethylamine (0.133 mL, 0.766 mmol). The reaction was stirred at rt overnight. The reaction mixture was diluted with EtOAc and washed with 5% LiCl solution and brine. The aqueous was extracted 2× with EtOAc and the combined organic extracts were dried over sodium sulfate. The crude residue was carried onto the next step without purification. ES/MS m/z: 651.2 (M+)

2-(4-(2-(4-chloro-2-fluorophenyl)-2-methylbenzo[d][1,3]dioxol-4-yl)-2,5-difluorobenzyl)-1-(2-methoxyethyl)-6-(2H-tetrazol-5-yl)-1H-benzo[d]imidazole (Example 84): A solution of 2-(4-(2-(4-chloro-2-fluorophenyl)-2-methylbenzo[d][1,3]dioxol-4-yl)-2,6-difluorophenyl)-N-(2-((2-methoxyethyl)amino)-4-(2H-tetrazol-5-yl)phenyl)acetamide (91.3 mg, 0.140 mmol) and glacial acetic acid (0.521 mL, 9.12 mmol) in DCE (3 mL) was heated at 60 deg overnight. The reaction was concentrated to dryness and purified by RP-HPLC (eluent: MeCN/H2O) to yield the product as a trifluoroacetate salt. ES/MS: 633.2 (M+H+); 1H NMR (400 MHz, DMSO) δ 8.32 (d, J=1.6 Hz, 1H), 7.84 (dd, J=8.4, 1.6 Hz, 1H), 7.73 (d, J=8.4 Hz, 1H), 7.67-7.53 (m, 4H), 7.39 (dd, J=8.4, 2.1 Hz, 1H), 7.32 (dd, J=8.0, 1.4 Hz, 1H), 7.10-6.98 (m, 2H), 4.65 (d, J=5.3 Hz, 2H), 4.47 (d, J=6.9 Hz, 2H), 3.77 (t, J=5.1 Hz, 2H), 3.26 (s, 3H), 2.13 (s, 3H).

Procedure 22: Example 85

Methyl 2-((6-(2-(4-chloro-2-fluorophenyl)-2-methylbenzo[d][1,3]dioxol-4-yl)-2-methoxypyridin-3-yl)methyl)-

1-(2-methoxyethyl)-1H-benzo[d]imidazole-6-carboxylate: In a 20 mL rxn vial, a suspension of 4-bromo-2-(4-chloro-2-fluoro-phenyl)-2-methyl-1,3-benzodioxole (Intermediate I-3, 100 mg, 0.291 mmol), [1,1'-Bis(diphenylphosphino)ferrocene]dichloropalladium(II) (32.4 mg, 0.0437 mmol), potassium propionate (97.9 mg, 0.873 mmol), and Bis(pinacolato)diboron (86.1 mg, 0.339 mmol) in dioxane (3 mL) was degassed with Ar for 5 min. The reaction was sealed and heated at 120 deg thermally for 50 min. The reaction was cooled to rt, then added sodium carbonate (2.00 M, 0.291 mL, 0.582 mmol). Stirred at rt for 2 min. Added [1,1'-Bis(diphenylphosphino)ferrocene] dichloropalladium (II) (15.0 mg, 0.0202 mmol) and methyl 2-[[6-chloro-2-methoxy-3-pyridyl)methyl]-3-(2-methoxyethyl)benzimidazole-5-carboxylate (intermediate I-23, 113 mg, 0.291 mmol). The reaction mixture was degassed for 5 min with argon, then heated at 90° C. overnight. The reaction mixture was diluted with EtOAc and washed with brine and saturated sodium bicarbonate solution. The organic extract was dried over sodium sulfate, filtered and concentrated. The crude residue was purified by flash chromatography (20-40% EtOAc in hexane) to yield desired product. ES/MS m/z: 618.0 (M+H+); 1H NMR (400 MHz, CDCl3) δ 8.13 (d, J=1.5 Hz, 1H), 8.00 (dd, J=8.5, 1.6 Hz, 1H), 7.81 (dd, J=8.1, 1.3 Hz, 1H), 7.77 (d, J=8.5 Hz, 1H), 7.70 (d, J=7.6 Hz, 1H), 7.61-7.48 (m, 2H), 7.14 (dd, J=10.6, 2.0 Hz, 1H), 7.11-7.02 (m, 1H), 6.94 (t, J=7.9 Hz, 1H), 6.86 (d, J=7.7, 1.3 Hz, 1H), 4.41 (t, J=5.5 Hz, 2H), 4.37 (s, 2H), 4.10 (s, 3H), 3.98 (s, 3H), 3.64 (t, J=5.5 Hz, 2H), 3.26 (s, 3H), 2.12 (d, J=1.1 Hz, 3H).

2-((6-(2-(4-chloro-2-fluorophenyl)-2-methylbenzo[d][1,3]dioxol-4-yl)-2-methoxypyridin-3-yl)methyl)-1-(2-methoxyethyl)-1H-benzo[d]imidazole-6-carboxylic acid (Example 85): A suspension of methyl 2-[[6-[2-(4-chloro-2-fluoro-phenyl)-2-methyl-1,3-benzodioxol-4-yl]-2-methoxy-3-pyridyl]methyl]-3-(2-methoxyethyl)benzimidazole-5-carboxylate (64.4 mg, 0.104 mmol) and lithium hydroxide, monohydrate (0.300 M, 1.05 mL, 0.316 mmol) in CH3CN (1.5 mL) in a 40 ml reaction vial was heated at 90 deg for 12 min. The reaction mixture was diluted with EtOAc and brine. Added 0.350 mL of 1M citric acid. The organic extract was dried over sodium sulfate, filtered and concentrated. The crude residue was purified by RP-HPLC (eluent: MeCN/H2O) to give title product. ES/MS m/z: 604.2 (M+H+); 1H NMR (400 MHz, DMSO) δ 8.32 (s, 1H), 7.89 (d, J=8.5 Hz, 1H), 7.78-7.71 (m, 2H), 7.69 (d, J=7.9 Hz, 1H), 7.65 (d, J=8.3 Hz, 2H), 7.58 (dd, J=11.1, 2.0 Hz, 1H), 7.36 (dd, J=8.4, 2.1 Hz, 1H), 7.07-6.95 (m, 2H), 4.65 (d, J=5.4 Hz, 2H), 4.41 (s, 2H), 3.96 (s, 3H), 3.69 (t, J=5.1 Hz, 2H), 3.21 (s, 3H), 2.12 (s, 3H).

Procedure 23: Example 86

2-((6-(2-(4-chloro-2-fluorophenyl)-2-methylbenzo[d][1,3]dioxol-4-yl)-2-oxo-1,2-dihydropyridin-3-yl)methyl)-1-(2-methoxyethyl)-1H-benzo[d]imidazole-6-carboxylic acid (Example 86): A solution of 2-[[6-[2-(4-chloro-2-fluoro-phenyl)-2-methyl-1,3-benzodioxol-4-yl]-2-methoxy-3-pyridyl]methyl]-3-(2-methoxyethyl)benzimidazole-5-carboxylic acid (39.2 mg, 0.0649 mmol), p-toluenesulfonic acid monohydrate (0.06 g, 0 mol) (24.7 mg, 0.130 mmol), and lithium chloride (5.50 mg, 0.130 mmol) in NMP (1.5 mL) was heated at 180 deg for 40 min with a microwave. The crude residue was purified by RP-HPLC (eluent: MeCN/H2O) to give title product. ES/MS m/z: 590.2 (M+H+); 1H NMR (400 MHz, DMSO) δ 12.98 (s, 1H), 11.78 (s, 1H), 8.32 (s, 1H), 7.98-7.82 (m, 1H), 7.68 (d, J=8.5 Hz, 1H), 7.65-7.50 (m, 3H), 7.36 (dd, J=8.4, 2.1 Hz, 1H), 7.27 (s, 1H), 7.08 (dd, J=7.8, 1.2 Hz, 1H), 6.98 (t, J=8.0 Hz, 1H), 6.73 (s, 1H), 4.70 (t, J=5.2 Hz, 2H), 4.25 (s, 2H), 3.72 (t, J=5.1 Hz, 2H), 3.21 (s, 3H), 2.09 (s, 3H).

Procedure 24: Example 87

2-((6-(2-(4-chloro-2-fluorophenyl)-2-methylbenzo[d][1,3]dioxol-4-yl)-1-methyl-2-oxo-1,2-dihydropyridin-3-yl)methyl)-1-(2-methoxyethyl)-1H-benzo[d]imidazole-6-carboxylic acid (Example 87): A solution of 2-[[6-[2-(4-chloro-2-fluoro-phenyl)-2-methyl-1,3-benzodioxol-4-yl]-2-oxo-1H-pyridin-3-yl]methyl]-3-(2-methoxyethyl)benzimidazole-5-carboxylic acid (17.7 mg, 0.0300 mmol) in DMF (2 mL) at 0 deg, was added sodium hydride, 60% disp. in oil (8.30 mg, 0.217 mmol). After 10 min, added iodomethane (0.0200 mL, 0.321 mmol). The reaction was diluted with EtOAc and washed with 5% LiCl and brine. The organic extract was dried with sodium sulfate and purified by RP-HPLC (eluent: MeCN/H2O) to give title product. ES/MS m/z: 604.2 (M+H+); 1H NMR (400 MHz, DMSO) δ 11.76 (s, 1H), 8.33 (s, 1H), 7.91 (d, J=8.5 Hz, 1H), 7.70 (d, J=8.5 Hz, 1H), 7.65-7.51 (m, 3H), 7.36 (dd, J=8.4, 2.1 Hz, 1H), 7.26 (s, 1H), 7.07 (d, J=7.8 Hz, 1H), 6.98 (t, J=8.0 Hz, 1H), 6.68 (s, 1H), 4.70 (d, J=5.9 Hz, 2H), 4.24 (s, 2H), 3.90 (s, 3H), 3.71 (t, J=5.1 Hz, 2H), 3.21 (s, 3H), 2.09 (s, 3H).

Procedure 25: Example 90

Methyl 2-(4-(2-(4-cyano-2-fluorophenyl)-2-methylbenzo[d][1,3]dioxol-4-yl)-2,3,6-trifluorobenzyl)-1-(((S)-oxetan-2-yl)methyl)-1H-benzo[d]imidazole-6-carboxylate: To a solution of methyl 2-(4-(2-(4-chloro-2-fluorophenyl)-2-methylbenzo[d][1,3]dioxol-4-yl)-2,3,6-trifluorobenzyl)-1-(((S)-oxetan-2-yl)methyl)-1H-benzo[d]imidazole-6-carboxylate (prepared in an analogous fashion to Procedure 1) (400 mg, 2.45 mmol), zinc cyanide (288 mg, 0.2.45 mmol), Bis(tri-tert-butylphosphine)palladium(0) (48 mg, 0.123 mmol) in NMP (1.0 mL) was degassed by bubbling argon for 30 seconds, then heated under microwave conditions at 120° C. for 30 minutes. The crude mixture was directly purified by silica gel column chromatography (eluent: EtOAc/Hex) to provide the desired product. ES/MS: 644.2 (M+H+).

2-(4-(2-(4-cyano-2-fluorophenyl)-2-methylbenzo[d][1,3]dioxol-4-yl)-2,3,6-trifluorobenzyl)-1-(((S)-oxetan-2-yl)methyl)-1H-benzo[d]imidazole-6-carboxylic acid (Example 90): To a solution of methyl 2-(4-(2-(4-cyano-2-fluorophenyl)-2-methylbenzo[d][1,3]dioxol-4-yl)-2,3,6-trifluorobenzyl)-1-(((S)-oxetan-2-yl)methyl)-1H-benzo[d]imidazole-6-carboxylate (150 mg, 0.23 mmol) in MeCN (1.5 mL) was added lithium hydroxide monohydrate (11.7 mg, 0.28 mmol) dissolved in water (0.5 mL). The reaction mixture was heated in a sealed tube at 100° C. for 5 minutes. The cooled reaction mixture was purified by RP-HPLC (eluent: water/MeCN*0.1% TFA) to provide the product Example 90 as a trifluoroacetate salt. ES/MS: 630.3 (M+H+). 1H NMR (400 MHz, Methanol-d4) δ 8.51 (s, 1H), 8.15 (dd, J=8.7, 1.4 Hz, 1H), 7.84 (t, J=7.7 Hz, 1H), 7.74 (d, J=8.6 Hz, 1H), 7.69 (dd, J=10.6, 1.5 Hz, 1H), 7.63 (dd, J=8.1, 1.5 Hz, 1H), 7.30 (ddd, J=10.0, 5.4, 2.1 Hz, 1H), 7.09-6.96 (m, 3H), 5.30 (dt, J=7.1, 3.6 Hz, 1H), 5.00-4.91 (m, 1H), 4.86-4.65 (m, 4H), 4.51 (dt, J=10.7, 5.9 Hz, 1H), 2.89 (dq, J=14.6, 7.6 Hz, 1H), 2.62-2.47 (m, 1H), 2.12 (s, 3H).

Procedure 26: Example 92 and Example 93

2-(4-(2-(4-cyano-2-fluorophenyl)-2-methylbenzo[d][1,3]dioxol-4-yl)-2,6-difluorobenzyl)-1-(((S)-oxetan-2-yl)

methyl)-1H-benzo[d]imidazole-6-carboxylic acid (Example 92 and Example 93): 2-(4-(2-(4-cyano-2-fluorophenyl)-2-methylbenzo[d][1,3]dioxol-4-yl)-2,6-difluorobenzyl)-1-(((S)-oxetan-2-yl)methyl)-1H-benzo[d]imidazole-6-carboxylic acid (obtained as described in Procedure 25) as a mixture of 2 stereoisomers was separated by chiral SFC (OJ-H column with 25% MeOH cosolvent) to give two distinct stereoisomers.

2-(4-(2-(4-cyano-2-fluorophenyl)-2-methylbenzo[d][1,3]dioxol-4-yl)-2,6-difluorobenzyl)-1-(((S)-oxetan-2-yl)methyl)-1H-benzo[d]imidazole-6-carboxylic acid (Example 92): ES/MS: 612.3 (M+H+). 1H NMR (400 MHz, Methanol-d4) δ 8.48 (t, J=1.0 Hz, 1H), 8.12 (dd, J=8.6, 1.5 Hz, 1H), 7.82 (t, J=7.8 Hz, 1H), 7.75-7.66 (m, 2H), 7.66-7.52 (m, 3H), 7.23 (dd, J=7.5, 1.7 Hz, 1H), 7.06-6.94 (m, 2H), 5.27 (tt, J=7.1, 3.7 Hz, 1H), 5.00-4.90 (m, 2H), 4.82-4.44 (m, 4H), 2.95-2.81 (m, 1H), 2.56 (dd, J=11.6, 8.9 Hz, 1H), 2.17 (s, 3H).

2-(4-(2-(4-cyano-2-fluorophenyl)-2-methylbenzo[d][1,3]dioxol-4-yl)-2,6-difluorobenzyl)-1-(((S)-oxetan-2-yl)methyl)-1H-benzo[d]imidazole-6-carboxylic acid (Example 93): ES/MS: 612.3 (M+H+). 1H NMR (400 MHz, Methanol-d4) δ 8.48 (t, J=1.0 Hz, 1H), 8.12 (dd, J=8.5, 1.5 Hz, 1H), 7.82 (t, J=7.8 Hz, 1H), 7.75-7.66 (m, 2H), 7.65-7.54 (m, 3H), 7.23 (dd, J=7.6, 1.7 Hz, 1H), 7.08-6.95 (m, 2H), 5.27 (tt, J=7.2, 3.7 Hz, 1H), 4.97-4.91 (m, 1H), 4.84-4.64 (m, 4H), 4.51 (dt, J=9.2, 6.0 Hz, 1H), 2.93-2.81 (m, 1H), 2.64-2.50 (m, 1H), 2.17 (s, 3H).

Procedure 27: Example 94 and Example 95

2-(4-(2-(4-cyano-2-fluorophenyl)-2-methylbenzo[d][1,3]dioxol-4-yl)-2,3,6-trifluorobenzyl)-1-(((S)-oxetan-2-yl)methyl)-1H-benzo[d]imidazole-6-carboxylic acid (Example 94 and Example 95): 2-(4-(2-(4-cyano-2-fluorophenyl)-2-methylbenzo[d][1,3]dioxol-4-yl)-2,3,6-trifluorobenzyl)-1-(((S)-oxetan-2-yl)methyl)-1H-benzo[d]imidazole-6-carboxylic acid (obtained as described in Procedure 25) as a mixture of 2 stereoisomers was separated by chiral SFC (AD-H column with 20% EtOH—NH3 cosolvent) to give two distinct stereoisomers.

2-(4-(2-(4-cyano-2-fluorophenyl)-2-methylbenzo[d][1,3]dioxol-4-yl)-2,3,6-trifluorobenzyl)-1-(((S)-oxetan-2-yl)methyl)-1H-benzo[d]imidazole-6-carboxylic acid (Example 94): ES/MS: 630.3 (M+H+). 1H NMR (400 MHz, Methanol-d4) δ 8.51 (dd, J=1.4, 0.7 Hz, 1H), 8.15 (dd, J=8.6, 1.5 Hz, 1H), 7.84 (t, J=7.8 Hz, 1H), 7.77-7.66 (m, 2H), 7.63 (dd, J=8.0, 1.6 Hz, 1H), 7.30 (ddd, J=9.8, 5.3, 2.1 Hz, 1H), 7.04 (d, J=1.7 Hz, 3H), 5.30 (td, J=7.2, 4.7 Hz, 1H), 5.04-4.92 (m, 1H), 4.87-4.63 (m, 4H), 4.51 (dt, J=9.2, 6.0 Hz, 1H), 2.98-2.81 (m, 1H), 2.69-2.50 (m, 1H), 2.12 (s, 3H).

2-(4-(2-(4-cyano-2-fluorophenyl)-2-methylbenzo[d][1,3]dioxol-4-yl)-2,3,6-trifluorobenzyl)-1-(((S)-oxetan-2-yl)methyl)-1H-benzo[d]imidazole-6-carboxylic acid (Example 95): ES/MS: 630.3 (M+H+). 1H NMR (400 MHz, Methanol-d4) δ 8.50 (t, J=1.0 Hz, 1H), 8.15 (dd, J=8.5, 1.5 Hz, 1H), 7.84 (t, J=7.7 Hz, 1H), 7.77-7.66 (m, 2H), 7.63 (dd, J=8.1, 1.6 Hz, 1H), 7.30 (ddd, J=9.9, 5.3, 2.1 Hz, 1H), 7.04 (d, J=1.7 Hz, 3H), 5.30 (qd, J=7.1, 2.5 Hz, 1H), 5.03-4.91 (m, 1H), 4.87-4.67 (m, 4H), 4.51 (dt, J=9.2, 6.0 Hz, 1H), 2.97-2.82 (m, 1H), 2.57 (ddd, J=16.2, 11.5, 7.3 Hz, 1H), 2.12 (s, 3H).

Procedure 28: Example 96 and Example 97

2-(4-(2-(4-cyano-2-fluorophenyl)-2-methylbenzo[d][1,3]dioxol-4-yl)-2,3,6-trifluorobenzyl)-1-(2-methoxyethyl)-1H-benzo[d]imidazole-6-carboxylic acid (Example 96 and Example 97): 2-(4-(2-(4-cyano-2-fluorophenyl)-2-methylbenzo[d][1,3]dioxol-4-yl)-2,3,6-trifluorobenzyl)-1-(2-methoxyethyl)-1H-benzo[d]imidazole-6-carboxylic acid (obtained as described in Procedure 25) as a mixture of 2 stereoisomers was separated by chiral SFC (IC column with 30% IPA-NH3 cosolvent) to give two distinct stereoisomers.

2-(4-(2-(4-cyano-2-fluorophenyl)-2-methylbenzo[d][1,3]dioxol-4-yl)-2,3,6-trifluorobenzyl)-1-(2-methoxyethyl)-1H-benzo[d]imidazole-6-carboxylic acid (Example 96): ES/MS: 618.5 (M+H+). 1H NMR (400 MHz, Methanol-d4) δ 8.45 (d, J=1.4 Hz, 1H), 8.12 (dd, J=8.5, 1.5 Hz, 1H), 7.84 (t, J=7.8 Hz, 1H), 7.75-7.66 (m, 2H), 7.62 (dd, J=8.1, 1.5 Hz, 1H), 7.28 (ddd, J=9.9, 5.3, 2.1 Hz, 1H), 7.08-6.95 (m, 3H), 4.82-4.69 (m, 4H), 3.85 (t, J=4.9 Hz, 2H), 3.33 (s, 3H), 2.14-2.09 (m, 3H).

2-(4-(2-(4-cyano-2-fluorophenyl)-2-methylbenzo[d][1,3]dioxol-4-yl)-2,3,6-trifluorobenzyl)-1-(2-methoxyethyl)-1H-benzo[d]imidazole-6-carboxylic acid (Example 97): ES/MS: 618.5 (M+H+). 1H NMR (400 MHz, Methanol-d4) δ 8.51 (d, J=1.4 Hz, 1H), 8.18 (dd, J=8.6, 1.5 Hz, 1H), 7.84 (t, J=7.8 Hz, 1H), 7.75 (d, J=8.6 Hz, 1H), 7.69 (dd, J=10.6, 1.5 Hz, 1H), 7.63 (dd, J=8.1, 1.6 Hz, 1H), 7.31 (ddd, J=9.9, 5.3, 2.2 Hz, 1H), 7.08-7.02 (m, 3H), 4.85-4.78 (m, 4H), 3.91-3.83 (m, 2H), 3.32 (s, 3H), 2.15-2.09 (m, 3H).

Procedure 29: Example 98 and Example 99

2-(4-(2-(4-cyano-2-fluorophenyl)-2-methylbenzo[d][1,3]dioxol-4-yl)-2,6-difluorobenzyl)-1-(2-methoxyethyl)-1H-benzo[d]imidazole-6-carboxylic acid (Example 98 and Example 99): 2-(4-(2-(4-cyano-2-fluorophenyl)-2-methylbenzo[d][1,3]dioxol-4-yl)-2,6-difluorobenzyl)-1-(2-methoxyethyl)-1H-benzo[d]imidazole-6-carboxylic acid (obtained as described in Procedure 25) as a mixture of 2 stereoisomers was separated by chiral SFC (CELL-2 column with 35% MeOH-DEA cosolvent) to give two distinct stereoisomers.

2-(4-(2-(4-cyano-2-fluorophenyl)-2-methylbenzo[d][1,3]dioxol-4-yl)-2,6-difluorobenzyl)-1-(2-methoxyethyl)-1H-benzo[d]imidazole-6-carboxylic acid (Example 99): ES/MS: 600.4 (M+H+). 1H NMR (400 MHz, Methanol-d4) δ 8.45-8.38 (m, 1H), 8.09 (dd, J=8.5, 1.5 Hz, 1H), 7.82 (t, J=7.8 Hz, 1H), 7.74-7.66 (m, 2H), 7.62 (dd, J=8.0, 1.5 Hz, 1H), 7.56 (d, J=9.0 Hz, 2H), 7.23 (dd, J=7.6, 1.7 Hz, 1H), 7.08-6.94 (m, 2H), 4.75 (t, J=5.0 Hz, 2H), 4.67 (s, 2H), 3.83 (t, J=4.9 Hz, 2H), 3.32 (s, 3H), 2.22-2.09 (m, 3H).

2-(4-(2-(4-cyano-2-fluorophenyl)-2-methylbenzo[d][1,3]dioxol-4-yl)-2,6-difluorobenzyl)-1-(2-methoxyethyl)-1H-benzo[d]imidazole-6-carboxylic acid (Example 98): ES/MS: 600.3 (M+H+). 1H NMR (400 MHz, Methanol-d4) δ 8.46-8.41 (m, 1H), 8.12 (dd, J=8.6, 1.5 Hz, 1H), 7.82 (t, J=7.8 Hz, 1H), 7.74-7.67 (m, 2H), 7.62 (dd, J=8.0, 1.5 Hz, 1H), 7.57 (d, J=9.0 Hz, 2H), 7.23 (dd, J=7.6, 1.7 Hz, 1H), 7.06-6.97 (m, 2H), 4.76 (t, J=5.0 Hz, 2H), 4.69 (s, 2H), 3.84 (t, J=4.9 Hz, 2H), 3.32 (s, 3H), 2.17 (d, J=1.0 Hz, 3H).

Procedure 30: Example 100

2-(4-(2-(5-chloropyridin-2-yl)-5-fluoro-2-methylbenzo[d][1,3]dioxol-4-yl)-2,6-difluorobenzyl)-1-(2-methoxyethyl)-1H-benzo[d]imidazole-6-carboxylic acid: 2-(4-(2-(5-chloropyridin-2-yl)-5-fluoro-2-methylbenzo[d][1,3]dioxol-4-yl)-2,6-difluorobenzyl)-1-(2-methoxyethyl)-1H-benzo[d]imidazole-6-carboxylic acid (Example 100): 2-(4-(2-(5-chloropyridin-2-yl)-5-fluoro-2-methylbenzo[d][1,3]dioxol-4-yl)-2,6-difluorobenzyl)-1-(2-methoxyethyl)-1H-benzo[d]

imidazole-6-carboxylic acid was synthesized in a manner analogous to Procedure 4: Example 4 substituting methyl 2-(4-bromo-2,6-difluorobenzyl)-1-(2-methoxyethyl)-1H-benzo[d]imidazole-6-carboxylate (prepared in a manner analogous to Intermediate I-14 Steps 1-2) for methyl 2-(4-bromo-2-fluorobenzyl)-1-(2-methoxyethyl)-1H-benzo[d]imidazole-6-carboxylate and 2-(4-bromo-5-fluoro-2-methylbenzo[d][1,3]dioxol-2-yl)-5-chloropyridine (synthesized in a manner analogous to Intermediate I-2) for 4-(4-bromobenzo[d][1,3]dioxol-2-yl)-3-fluorobenzonitrile. ES/MS: 610.0 (M+H+). 1H NMR (400 MHz, DMSO) δ 8.74 (d, J=2.1 Hz, 1H), 8.22 (d, J=1.6 Hz, 1H), 8.05 (dd, J=8.5, 2.5 Hz, 1H), 7.78 (dd, J=8.4, 1.6 Hz, 1H), 7.72 (d, J=8.7 Hz, 1H), 7.60 (d, J=8.5 Hz, 1H), 7.39-7.33 (m, 2H), 7.03 (dd, J=8.6, 4.2 Hz, 1H), 6.88 (dd, J=11.4, 8.6 Hz, 1H), 4.65 (t, J=5.0 Hz, 2H), 4.47 (s, 2H), 3.71 (t, J=5.0 Hz, 2H), 3.22 (s, 3H), 2.09 (s, 3H).

Procedure 31: Example 102 and Example 103

2-(4-(2-(4-chloro-2-fluorophenyl)-2-methylbenzo[d][1,3]dioxol-4-yl)-2,6-difluorobenzyl)-1-(2-methoxyethyl)-1H-benzo[d]imidazole-6-carboxylic acid (Example 102 and Example 103): 2-(4-(2-(4-chloro-2-fluorophenyl)-2-methylbenzo[d][1,3]dioxol-4-yl)-2,6-difluorobenzyl)-1-(2-methoxyethyl)-1H-benzo[d]imidazole-6-carboxylic acid (Example 19) was separated by chiral SFC (AD-H column with 25% IPA-NH3 cosolvent) to give two distinct stereoisomers.

Peak 2: 2-(4-(2-(4-chloro-2-fluorophenyl)-2-methylbenzo[d][1,3]dioxol-4-yl)-2,6-difluorobenzyl)-1-(2-methoxyethyl)-1H-benzo[d]imidazole-6-carboxylic acid (Example 102): ES/MS: 609.8 (M+H+). 1H NMR (400 MHz, Methanol-d4) δ 8.50 (t, J=1.0 Hz, 1H), 8.17 (dd, J=8.6, 1.5 Hz, 1H), 7.73 (d, J=8.6 Hz, 1H), 7.65-7.56 (m, 3H), 7.34 (dd, J=10.9, 2.0 Hz, 1H), 7.28-7.19 (m, 2H), 7.01 (t, J=7.8 Hz, 1H), 6.97 (dd, J=7.8, 1.5 Hz, 1H), 4.80 (t, J=5.0 Hz, 2H), 4.75 (s, 2H), 3.85 (t, J=4.9 Hz, 2H), 2.14 (s, 3H).

Peak 1: 2-(4-(2-(4-chloro-2-fluorophenyl)-2-methylbenzo[d][1,3]dioxol-4-yl)-2,6-difluorobenzyl)-1-(2-methoxyethyl)-1H-benzo[d]imidazole-6-carboxylic acid (Example 103): ES/MS: 609.7 (M+H+). 1H NMR (400 MHz, Methanol-d4) δ 8.49 (t, J=1.0 Hz, 1H), 8.16 (dd, J=8.5, 1.5 Hz, 1H), 7.73 (d, J=8.5 Hz, 1H), 7.66-7.55 (m, 3H), 7.34 (dd, J=10.9, 2.0 Hz, 1H), 7.28-7.19 (m, 2H), 7.01 (t, J=7.8 Hz, 1H), 6.97 (dd, J=7.8, 1.5 Hz, 1H), 4.80 (t, J=5.0 Hz, 2H), 4.74 (s, 2H), 3.84 (t, J=4.9 Hz, 2H), 2.14 (s, 3H).

Procedure 32: Example 104

2-(5-Chloro-2-pyridyl)-2-methyl-1,3-benzodioxole-4-carbaldehyde: Methyl 2-[[4-(6-chloro-2-pyridyl)-1-piperidyl]methyl]-3-(2-methoxyethyl)benzimidazole-5-carboxylate (200 mg, 0.61 mmol) in THF (5.0 mL) was added nBuLi (1.9 M, 0.40 mL, 0.61 mmol) at −78° C. The reaction was stirred at −78° C. for 1 h followed by dropwise addition of DMF (0.47 mL, 6.1 mmol). The reaction mixture was then warmed up to 0° C. and stirred for 30 min before quenching with sat. aqueous NH4Cl (50 mL) and diluted with EtOAc (50 mL). The organic phase was collected, and the aqueous phase was extracted with EtOAc (2×50 mL). The combined organics were dried over MgSO4, concentrated in vacuo, and purified by silica gel column chromatography (eluent: EtOAc/hexanes) to afford the product: ES/MS: 276.2 (M+H+).

5-Chloro-2-(4-ethynyl-2-methyl-1,3-benzodioxol-2-yl)pyridine: 2-(5-Chloro-2-pyridyl)-2-methyl-1,3-benzodiox-ole-4-carbaldehyde (40 mg. 0.15 mmol) in MeOH (1.5 mL) was added Bestmann-Ohira reagent (56 mg, 0.29 mmol) and K2CO3 (60 mg, 0.44 mmol) at rt. The mixture was stirred at rt for 2 h before quenching with sat. aqueous NH4Cl (10 mL) and diluted with EtOAc (10 mL). The organic phase was collected, and the aqueous phase was extracted with EtOAc (2×10 mL). The combined organics were dried over MgSO4, concentrated in vacuo, and purified by silica gel column chromatography (eluent: EtOAc/hexanes) to afford the product: ES/MS: 272.2 (M+H+).

Methyl 2-[[4-[2-(5-chloro-2-pyridyl)-2-methyl-1,3-benzodioxol-4-yl]triazol-1-yl]methyl]-3-(2-methoxyethyl)benzimidazole-5-carboxylate: 5-Chloro-2-(4-ethynyl-2-methyl-1,3-benzodioxol-2-yl)pyridine (20 mg. 0.074 mmol) and methyl 2-(chloromethyl)-3-(2-methoxyethyl)benzimidazole-5-carboxylate (27 mg. 0.096 mmol) in DMF (1.5 mL) was added to sodium azide (6.2 mg, 0.096 mmol), $K_2CO_3$ (20 mg, 0.15 mmol), and CuI (2.8 mg, 0.015 mmol). The mixture was stirred at 70° C. for 2 h before concentrating in vacuo. The residue was purified by silica gel column chromatography (eluent: EtOAc/hexanes) to afford the product: ES/MS: 561.2 (M+H+).

2-[[4-[2-(5-Chloro-2-pyridyl)-2-methyl-1,3-benzodioxol-4-yl]triazol-1-yl]methyl]-3-(2-methoxyethyl)benzimidazole-5-carboxylic acid (Example 104): Methyl 2-[[4-[2-(5-chloro-2-pyridyl)-2-methyl-1,3-benzodioxol-4-yl]triazol-1-yl]methyl]-3-(2-methoxyethyl)benzimidazole-5-carboxylate (15 mg. 0.027 mmol) was taken up in acetonitrile (0.6 mL) and aqueous lithium hydroxide (2.0 M, 0.07 mL, 0.13 mmol) was added. The mixture was heated to 60° C. for 1 hour. Following this time, the mixture was diluted with water (5 mL), the pH adjusted to 5 with 1M aqueous citric acid solution and the mixture extracted with EtOAc (3×5 mL). The combined organics were dried over MgSO4, concentrated in vacuo, and purified by RP-HPLC (eluent: MeCN/water) to yield the product as a mono TFA salt (Example 104): ES/MS: 547.2 (M+H+); 1H NMR (400 MHz, Methanol-d4) δ 8.60 (dd, J=2.4, 0.7 Hz, 1H), 8.53 (s, 1H), 8.39 (s, 1H), 8.06 (dd, J=8.5, 1.5 Hz, 1H), 7.88 (dd, J=8.5, 2.4 Hz, 1H), 7.81-7.68 (m, 2H), 7.60 (dd, J=8.1, 1.2 Hz, 1H), 6.99 (t, J=7.9 Hz, 1H), 6.89 (dd, J=7.8, 1.1 Hz, 1H), 6.19 (s, 2H), 4.76 (t, J=5.0 Hz, 2H), 3.75 (t, J=4.9 Hz, 2H), 3.28 (s, 3H), 2.10 (s, 3H).

Procedure 33: Example 105 and Example 106

2-(4-(2-(4-chloro-2-fluorophenyl)-2-methylbenzo[d][1,3]dioxol-4-yl)-2,6-difluorobenzyl)-1-((1-(cyanomethyl)cyclopropyl)methyl)-4-fluoro-1H-benzo[d]imidazole-6-carboxylic acid (Example 105 and Example 106): The titled products were obtained by separation of Example 1 via chiral SFC.

Example 105: ES/MS: 662.2 (M+H+). 1H NMR (400 MHz, Methanol-d4) δ 8.19 (s, 1H), 7.71-7.56 (m, 2H), 7.52 (d, J=9.0 Hz, 2H), 7.33 (dd, J=10.9, 2.1 Hz, 1H), 7.28-7.15 (m, 2H), 7.05-6.82 (m, 2H), 4.64 (s, 2H), 4.52 (s, 2H), 2.13 (s, 3H), 0.87 (s, 4H).

Example 106: ES/MS: 662.2 (M+H+). 1H NMR (400 MHz, Methanol-d4) δ 8.19 (s, 1H), 7.71-7.56 (m, 2H), 7.52 (d, J=9.0 Hz, 2H), 7.33 (dd, J=10.9, 2.1 Hz, 1H), 7.28-7.15 (m, 2H), 7.05-6.82 (m, 2H), 4.64 (s, 2H), 4.52 (s, 2H), 2.13 (s, 3H), 0.87 (s, 4H).

Procedure 34: Example 107

2-(4-(2-(4-chloro-2-fluorophenyl)-2-methylbenzo[d][1,3]dioxol-4-yl)-2-fluorobenzyl)-1-(isoxazol-3-ylmethyl)-3a, 7a-dihydro-1H-benzo[d]imidazole-6-carboxylic acid (Example 107): 2-[4-[2-(4-chloro-2-fluoro-phenyl)-2-methyl-1,3-benzodioxol-4-yl]-2-fluoro-phenyl]acetic acid (250 mg, 0.600 mmol) and methyl 4-amino-3-(isoxazol-3-ylmethyl-amino)benzoate (163 mg, 0.660 mmol) were dissolved in DMF (3.0 mL). 2-(7-Aza-1H-benzotriazole-1-yl)-1,1,3,3-tetramethyluronium hexafluorophosphate (HATU), (274 mg, 0.720 mmol) was added followed by DIPEA (0.313 mL, 1.80 mmol). The reaction was stirred at ambient temperature overnight. The reaction was quenched with the addition of water (5 mL) and extracted with EtOAc (3×5 mL). The combined organic layers were washed with brine (10 mL), dried with sodium sulfate, filtered and concentrated in vacuo. The residue was dissolved in AcOH (2.0 mL) and heated at 100° C. for 1.25 hours. The reaction was cooled to ambient temperature and concentrated. The residue was dissolved in acetonitrile (1.0 mL) and aq. LiOH (1.0 M, 1.0 mL) was added. The reaction was heated to 60° C. and stirred until starting material was consumed as shown by LCMS after about 2 hours. The reaction was cooled to ambient temperature, quenched with the addition of excess trifluoroacetic acid (TFA) (100 μL), and purified by reverse phase preparatory HPLC (10-100% ACN:H2O). The titled product was obtained. ES/MS: 614.0 (M+H+). 1H NMR (400 MHz, Methanol-d4) δ 8.62 (d, J=1.7 Hz, 1H), 8.45-8.33 (m, 1H), 8.16 (dd, J=8.5, 1.5 Hz, 1H), 7.79 (d, J=8.6 Hz, 1H), 7.67-7.55 (m, 4H), 7.46 (t, J=8.0 Hz, 1H), 7.32 (dd, J=10.9, 2.0 Hz, 1H), 7.28-7.19 (m, 1H), 7.14 (dd, J=8.0, 1.3 Hz, 1H), 7.05-6.87 (m, 1H), 6.39 (d, J=1.8 Hz, 1H), 5.91 (s, 2H), 4.69 (s, 2H), 2.11 (d, J=1.0 Hz, 3H).

Procedure 35: Example 108

3-[[(2R)-1-acetylazetidin-2-yl]methyl]-2-[[4-[2-(4-chloro-2-fluoro-phenyl)-2-methyl-1,3-benzodioxol-4-yl]-2-fluoro-phenyl]methyl]benzimidazole-5-carboxylic acid (Example 108): 2-[4-[2-(4-Chloro-2-fluoro-phenyl)-2-methyl-1,3-benzodioxol-4-yl]-2-fluoro-phenyl]acetic acid (250 mg, 0.600 mmol) and tert-butyl (2R)-2-[(2-amino-5-tert-butoxycarbonyl-anilino)methyl]azetidine-1-carboxylate (226 mg, 0.600 mmol) were dissolved in DMF (3.0 mL). 2-(7-Aza-1H-benzotriazole-1-yl)-1,1,3,3-tetramethyluronium hexafluorophosphate (HATU) (274 mg, 0.720 mmol) followed by DIPEA (0.313 mL, 1.80 mmol) were added and the reaction was stirred at ambient temperature for 4 hours. The reaction was quenched with the addition of water (5 mL) and extracted with EtOAc (3×5 mL). The combined organic layers were washed with brine (10 mL), dried with sodium sulfate, filtered and concentrated in vacuo. The residue was dissolved in AcOH (2.0 mL) and heated at 100° C. overnight. Excess trifluoroacetic anhydride (TFA) (0.2 mL) was added and the reaction was stirred for 4 hours at 100° C. until the starting material was converted to the desired product as determined by LCMS. The reaction was cooled to ambient temperature and purified by reverse phase preparatory HPLC (10-100% ACN:H2O). The titled product was obtained. ES/MS: 644.2 (M+H+). 1H NMR (400 MHz, Methanol-d4) δ 8.67-8.58 (m, 1H), 8.23 (dd, J=8.6, 1.4 Hz, 1H), 7.81-7.74 (m, 1H), 7.74-7.65 (m, 2H), 7.65-7.53 (m, 2H), 7.36-7.27 (m, 1H), 7.23 (dd, J=8.4, 2.1 Hz, 1H), 7.17 (dd, J=7.9, 1.4 Hz, 1H), 7.08-6.87 (m, 2H), 5.04 (dd, J=15.5, 9.6 Hz, 1H), 4.74 (d, J=22.7 Hz, 1H), 4.26-4.05 (m, 2H), 2.70-2.48 (m, 1H), 2.24 (dq, J=15.4, 6.1 Hz, 1H), 2.10 (s, 3H), 1.67 (s, 2H).

Procedure 36: Example 110

2-[[4-[2-(4-chloro-2-fluoro-phenyl)-2-methyl-1,3-benzodioxol-4-yl]-2,6-difluoro-phenyl]methyl]-3-[[(2S)-tetrahydrofuran-2-yl]methyl]benzimidazole-5-carboxylic acid (Example 110): 2-[[4-[2-(4-chloro-2-fluoro-phenyl)-2-methyl-1,3-benzodioxol-4-yl]-2,6-difluoro-phenyl]methyl]-3-[[(2S)-tetrahydrofuran-2-yl]methyl]benzimidazole-5-carboxylic acid (I-42) was made analogous to Example 1 Procedure 1 replacing I-6 with I-42. Example 110. ES/MS m/z: 636.2 (M+H+); 11H NMR (400 MHz, Acetonitrile-d3) δ 8.42 (dd, J=1.5, 0.7 Hz, 1H), 8.06 (dd, J=8.6, 1.5 Hz, 1H), 7.72 (dd, J=8.6, 0.7 Hz, 1H), 7.61 (td, J=8.4, 1.3 Hz, 1H), 7.56-7.46 (m, 2H), 7.32 (ddd, J=11.0, 2.0, 1.0 Hz, 1H), 7.25 (dt, J=8.4, 1.3 Hz, 1H), 7.17-7.07 (m, 1H), 7.06-6.92 (m, 2H), 4.70-4.59 (m, 3H), 4.44 (dd, J=15.1, 8.7 Hz, 1H), 4.33-4.21 (m, 1H), 3.87 (dtd, J=7.9, 6.7, 1.1 Hz, 1H), 3.71 (dt, J=7.8, 6.6 Hz, 1H), 2.27-2.14 (m, 1H), 2.13 (d, J=1.1 Hz, 3H), 1.98-1.84 (m, 2H), 1.72 (ddt, J=12.4, 8.5, 7.3 Hz, 1H).

Procedure 37: Example 111 and Example 112

2-[[4-[2-(4-chloro-2-fluoro-phenyl)-2-methyl-1,3-benzodioxol-4-yl]-2,5-difluoro-phenyl]methyl]-3-[[(2S)-tetrahydrofuran-2-yl]methyl]benzimidazole-5-carboxylic acid: 2-[[4-[2-(4-chloro-2-fluoro-phenyl)-2-methyl-1,3-benzodioxol-4-yl]-2,5-difluoro-phenyl]methyl]-3-[[(2S)-tetrahydrofuran-2-yl]methyl]benzimidazole-5-carboxylic acid (Example 110, obtained as described in procedure 36) as a mixture of 2 stereoisomers was separated by chiral SFC (CELL-2 column with 35% MeOH TFA cosolvent) to give two distinct stereoisomers.

2-[[4-[2-(4-chloro-2-fluoro-phenyl)-2-methyl-1,3-benzodioxol-4-yl]-2,5-difluoro-phenyl]methyl]-3-[[(2S)-tetrahydrofuran-2-yl]methyl]benzimidazole-5-carboxylic acid (Example 111): ES/MS m/z: 635.1 (M+); 1H NMR (400 MHz, Acetonitrile-d3) δ 8.21 (d, J=1.6 Hz, 1H), 7.85 (dd, J=8.4, 1.6 Hz, 1H), 7.62 (t, J=8.4 Hz, 1H), 7.54 (d, J=8.5 Hz, 1H), 7.49 (d, J=8.8 Hz, 2H), 7.32 (dd, J=11.0, 2.0 Hz, 1H), 7.25 (ddd, J=8.4, 2.0, 0.8 Hz, 1H), 7.16 (dd, J=7.4, 1.9 Hz, 1H), 7.03-6.91 (m, 2H), 4.50 (dd, J=15.0, 2.6 Hz, 1H), 4.46-4.43 (m, 2H), 4.39-4.23 (m, 2H), 3.87 (dt, J=8.3, 6.8 Hz, 1H), 3.72 (dt, J=8.2, 6.7 Hz, 1H), 2.22-2.09 (m, 4H), 1.94-1.85 (m, 2H), 1.68 (dq, J=12.3, 7.7 Hz, 1H).

2-[[4-[2-(4-chloro-2-fluoro-phenyl)-2-methyl-1,3-benzodioxol-4-yl]-2,5-difluoro-phenyl]methyl]-3-[[(2S)-tetrahydrofuran-2-yl]methyl]benzimidazole-5-carboxylic acid (Example 112): ES/MS m/z: 635.1 (M+); 1H NMR (400 MHz, Acetonitrile-d3) δ 8.21 (d, J=1.6 Hz, 1H), 7.85 (dd, J=8.4, 1.6 Hz, 1H), 7.62 (t, J=8.4 Hz, 1H), 7.54 (d, J=8.5 Hz, 1H), 7.49 (d, J=8.8 Hz, 2H), 7.32 (dd, J=11.0, 2.0 Hz, 1H), 7.25 (ddd, J=8.4, 2.0, 0.8 Hz, 1H), 7.16 (dd, J=7.4, 1.9 Hz, 1H), 7.03-6.91 (m, 2H), 4.50 (dd, J=15.0, 2.6 Hz, 1H), 4.46-4.43 (m, 2H), 4.39-4.23 (m, 2H), 3.87 (dt, J=8.3, 6.8 Hz, 1H), 3.72 (dt, J=8.2, 6.7 Hz, 1H), 2.22-2.09 (m, 4H), 1.94-1.85 (m, 2H), 1.68 (dq, J=12.3, 7.7 Hz, 1H).

Procedure 38: Example 113

2-[[4-[2-(4-chloro-2-fluoro-phenyl)-2-methyl-1,3-benzodioxol-4-yl]-2,5-difluoro-phenyl]methyl]-3-(2-methoxyethyl)benzimidazole-5-carboxylic acid (Example 113): 2 2-[[4-[2-(4-chloro-2-fluoro-phenyl)-2-methyl-1,3-benzodioxol-4-yl]-2,5-difluoro-phenyl]methyl]-3-(2-methoxyethyl)benzimidazole-5-carboxylic acid (Example 113) was made analogous to Example 1 Procedure 1 replacing I-7 for I-6 and 2-(4-bromo-2,5-difluorophenyl)acetic acid for 2-(4-bromo-2,6-difluorophenyl)acetic acid. ES/MS m/z: 609.2 (M+H+); 11H NMR (400 MHz, Acetonitrile-d3) δ 8.41 (dd, J=1.5, 0.7 Hz, 1H), 8.10 (dd, J=8.6, 1.5 Hz, 1H), 7.81 (dd, J=8.5, 0.7 Hz, 1H), 7.62 (t, J=8.4 Hz, 1H), 7.39 (dd, J=10.2, 6.1 Hz, 1H), 7.35-7.21 (m, 3H), 6.99 (s, 3H), 4.68-4.59 (m, 4H), 3.79-3.71 (m, 2H), 3.25 (s, 3H), 2.08 (d, J=1.0 Hz, 3H).

Procedure 39: Example 114

2-[[4-[2-(5-chloro-2-pyridyl)-2-methyl-1,3-benzodioxol-4-yl]-2,5-difluoro-phenyl]methyl]-3-(2-methoxyethyl)benzimidazole-5-carboxylic acid (Example 114): 2-[[4-[2-(5-chloro-2-pyridyl)-2-methyl-1,3-benzodioxol-4-yl]-2,5-difluoro-phenyl]methyl]-3-(2-methoxyethyl) benzimidazole-5-carboxylic acid (Example 114) was made analogous to Example 1 Procedure 1 replacing I-6 with I-7 and 2-(4-bromo-2,5-difluorophenyl)acetic acid with 2-(4-bromo-2,6-difluorophenyl)acetic acid, and I-3 with I-2. ES/MS m/z: 592.2 (M+H+); 11H NMR (400 MHz, Acetonitrile-d3) δ 8.64 (dd, J=2.5, 0.7 Hz, 1H), 8.46 (dd, J=1.5, 0.7 Hz, 1H), 8.15 (dd, J=8.6, 1.5 Hz, 1H), 7.89-7.78 (m, 2H), 7.67 (dd, J=8.5, 0.7 Hz, 1H), 7.42 (dd, J=10.2, 6.1 Hz, 1H), 7.31 (dd, J=10.2, 6.2 Hz, 1H), 7.05-6.94 (m, 3H), 4.80-4.52 (m, 4H), 3.77 (dd, J=5.4, 4.4 Hz, 2H), 3.25 (s, 3H), 2.07 (s, 3H).

Compounds of the disclosure prepared using the general routes described herein include the following Examples in Table 2.

TABLE 2

| Structure | Example | Name | Procedure | ES/MS m/z |
|---|---|---|---|---|
| 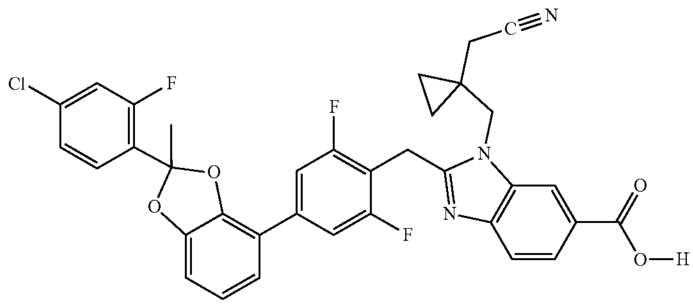 [SMILES: CC1(c2ccc(Cl)cc2F)Oc2cccc(-c3cc(F)c(Cc4nc5ccc(C(=O)O)cc5n4CC4(CC#N)CC4)c(F)c3)c2O1] | 1 | 2-(4-(2-(4-chloro-2-fluorophenyl)-2-methylbenzo[d][1,3]dioxol-4-yl)-2,6-difluorobenzyl)-1-((1-(cyanomethyl)cyclopropyl)methyl)-1H-benzo[d]imidazole-6-carboxylic acid | 1 | 644.2 |
| 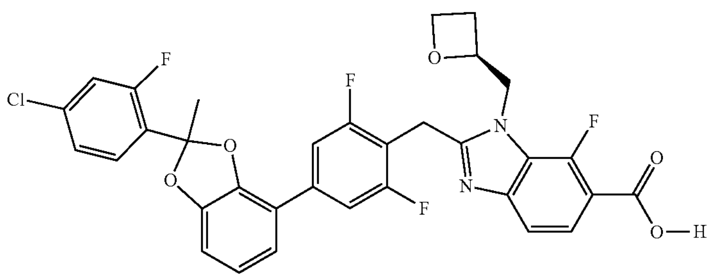 [SMILES: CC1(c2ccc(Cl)cc2F)Oc2cccc(-c3cc(F)c(Cc4nc5ccc(C(=O)O)c(F)c5n4C[C@@H]4CCO4)c(F)c3)c2O1] | 2 | 2-(4-(2-(4-chloro-2-fluorophenyl)-2-methylbenzo[d][1,3]dioxol-4-yl)-2,6-difluorobenzyl)-7-fluoro-1-(((S)-oxetan-2-yl)methyl)-1H-benzo[d]imidazole-6-carboxylic acid | 2 | 639.6 |
| 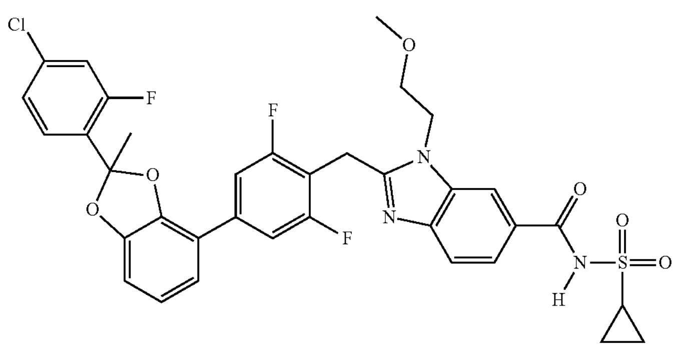 [SMILES: COCCn1c(Cc2c(F)cc(-c3cccc4c3OC(C)(c3ccc(Cl)cc3F)O4)cc2F)nc2ccc(C(=O)NS(=O)(=O)C3CC3)cc21] | 3 | 2-(4-(2-(4-chloro-2-fluorophenyl)-2-methylbenzo[d][1,3]dioxol-4-yl)-2,6-difluorobenzyl)-N-(cyclopropylsulfonyl)-1-(2-methoxyethyl)-1H-benzo[d]imidazole-6-carboxamide | 3 | 712.3 |
| 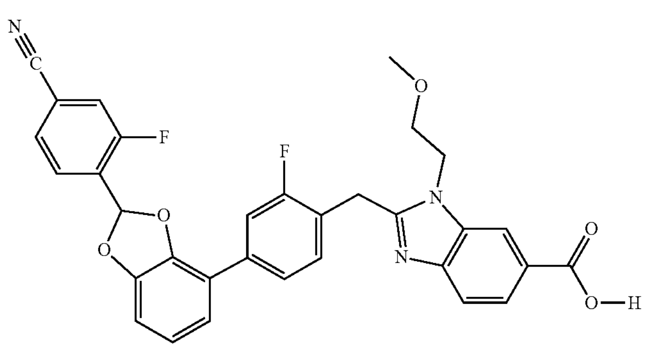 [SMILES: COCCn1c(Cc2ccc(-c3cccc4c3OC(c3ccc(C#N)cc3F)O4)cc2F)nc2ccc(C(=O)O)cc21] | 4 | 2-(4-(2-(4-cyano-2-fluorophenyl)benzo[d][1,3]dioxol-4-yl)-2-fluorobenzyl)-1-(2-methoxyethyl)-1H-benzo[d]imidazole-6-carboxylic acid | 4 | 568.5 |

TABLE 2-continued

| Structure | Example | Name | Procedure | ES/MS m/z |
|---|---|---|---|---|
| 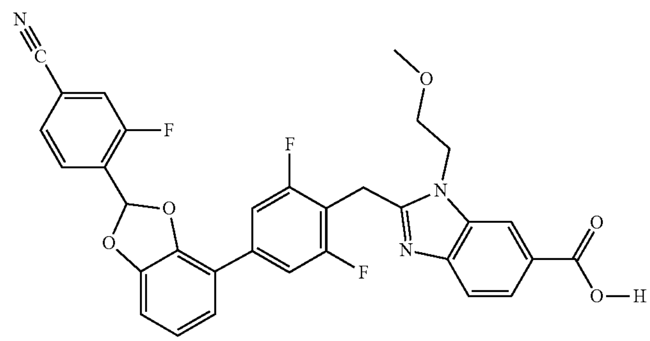 [SMILES: COCCn1c(Cc2c(F)cc(-c3cccc4c3OC(c3ccc(C#N)cc3F)O4)cc2F)nc2ccc(C(=O)O)cc21] | 5 | 2-(4-(2-(4-cyano-2-fluorophenyl)benzo[d][1,3]dioxol-4-yl)-2,6-difluorobenzyl)-1-(2-methoxyethyl)-1H-benzo[d]imidazole-6-carboxylic acid | 5 | 586.3 |
| 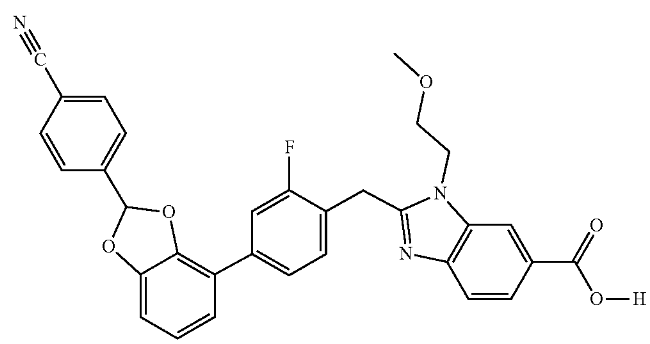 [SMILES: COCCn1c(Cc2ccc(-c3cccc4c3OC(c3ccc(C#N)cc3)O4)cc2F)nc2ccc(C(=O)O)cc21] | 6 | 2-(4-(2-(4-cyanophenyl)benzo[d][1,3]dioxol-4-yl)-2-fluorobenzyl)-1-(2-methoxyethyl)-1H-benzo[d]imidazole-6-carboxylic acid | 6 | 550.5 |
| 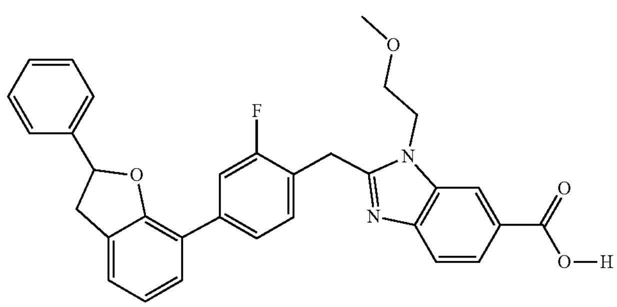 [SMILES: COCCn1c(Cc2ccc(-c3cccc4c3OC(c3ccccc3)C4)cc2F)nc2ccc(C(=O)O)cc21] | 7 | 2-(2-fluoro-4-(2-phenyl-2,3-dihydrobenzofuran-7-yl)benzyl)-1-(2-methoxyethyl)-1H-benzo[d]imidazole-6-carboxylic acid | 7 | 523.2 |
| 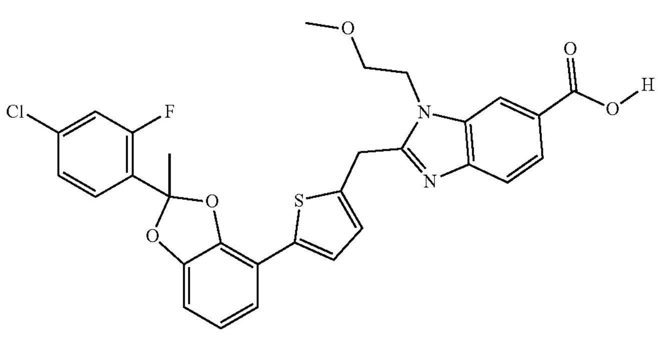 [SMILES: COCCn1c(Cc2ccc(-c3cccc4c3OC(C)(c3ccc(Cl)cc3F)O4)s2)nc2ccc(C(=O)O)cc21] | 8 | 2-((5-(2-(4-chloro-2-fluorophenyl)-2-methylbenzo[d][1,3]dioxol-4-yl)thiophen-2-yl)methyl)-1-(2-methoxyethyl)-1H-benzo[d]imidazole-6-carboxylic acid | 8 | 579 |

TABLE 2-continued

| Structure | Example | Name | Procedure | ES/MS m/z |
|---|---|---|---|---|
| 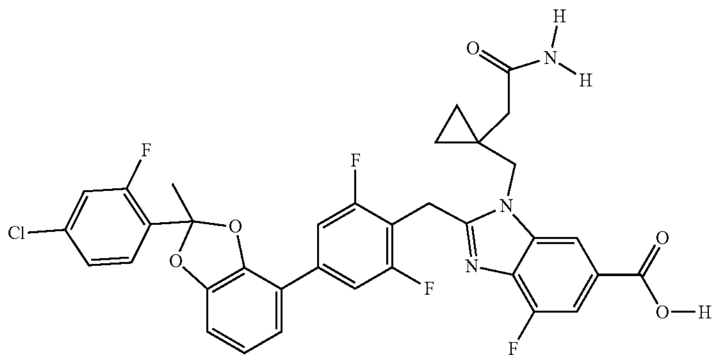 [SMILES: CC1(c2ccc(Cl)cc2F)Oc2cccc(-c3cc(F)c(Cc4nc5c(F)cc(C(=O)O)cc5n4CC4(CC(N)=O)CC4)c(F)c3)c2O1] | 9 | 1-((1-(2-amino-2-oxoethyl)cyclopropyl)methyl)-2-(4-(2-(4-chloro-2-fluorophenyl)-2-methylbenzo[d][1,3]dioxol-4-yl)-2,6-difluorobenzyl)-4-fluoro-1H-benzo[d]imidazole-6-carboxylic acid | 9 | 680.0 |
| 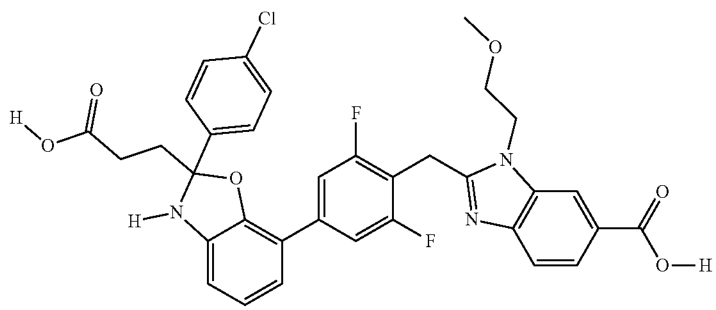 [SMILES: COCCn1c(Cc2c(F)cc(-c3cccc4c3OC(CCC(=O)O)(c3ccc(Cl)cc3)N4)cc2F)nc2ccc(C(=O)O)cc21] | 10 | 2-(4-(2-(2-carboxyethyl)-2-(4-chlorophenyl)-2,3-dihydrobenzo[d]oxazol-7-yl)-2,6-difluorobenzyl)-1-(2-methoxyethyl)-1H-benzo[d]imidazole-6-carboxylic acid | 10 | 648.2 |
| 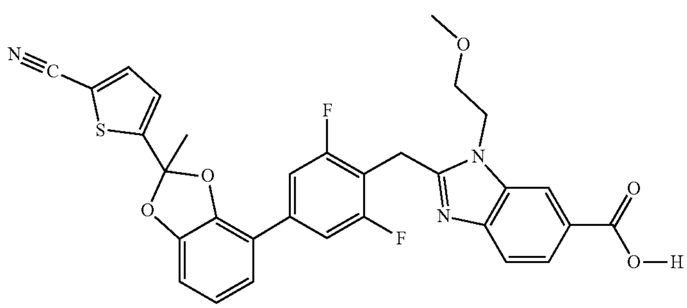 [SMILES: COCCn1c(Cc2c(F)cc(-c3cccc4c3OC(C)(c3ccc(C#N)s3)O4)cc2F)nc2ccc(C(=O)O)cc21] | 11 | 2-(4-(2-(5-cyanothiophen-2-yl)-2-methylbenzo[d][1,3]dioxol-4-yl)-2,6-difluorobenzyl)-1-(2-methoxyethyl)-1H-benzo[d]imidazole-6-carboxylic acid | 1 | 588.3 |
| 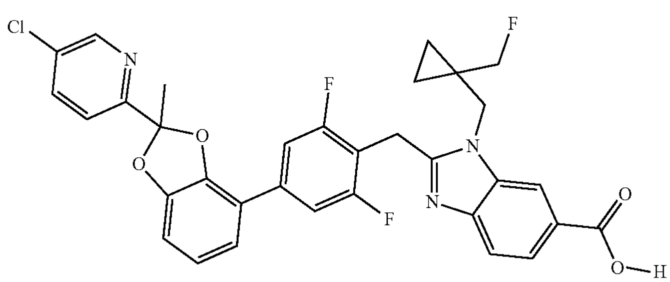 [SMILES: CC1(c2ccc(Cl)cn2)Oc2cccc(-c3cc(F)c(Cc4nc5ccc(C(=O)O)cc5n4CC4(CF)CC4)c(F)c3)c2O1] | 12 | 2-(4-(2-(5-chloropyridin-2-yl)-2-methylbenzo[d][1,3]dioxol-4-yl)-2,6-difluorobenzyl)-1-((1-(fluoromethyl)cyclopropyl)methyl)-1H-benzo[d]imidazole-6-carboxylic acid | 2 | 620.2 |
| 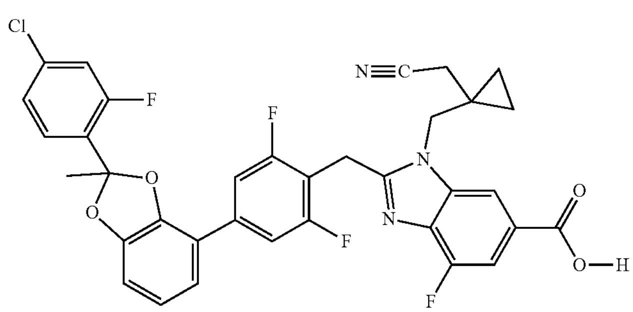 [SMILES: CC1(c2ccc(Cl)cc2F)Oc2cccc(-c3cc(F)c(Cc4nc5c(F)cc(C(=O)O)cc5n4CC4(CC#N)CC4)c(F)c3)c2O1] | 13 | 2-(4-(2-(4-chloro-2-fluorophenyl)-2-methylbenzo[d][1,3]dioxol-4-yl)-2,6-difluorobenzyl)-1-((1-(cyanomethyl)cyclopropyl)methyl)-4-fluoro-1H-benzo[d]imidazole-6-carboxylic acid | 9 | 662.2 |

TABLE 2-continued

| Structure | Example | Name | Procedure | ES/MS m/z |
|---|---|---|---|---|
| 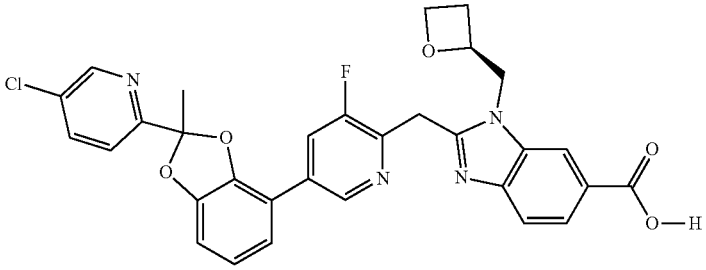 [SMILES: CC1(c2ccc(Cl)cn2)Oc2cccc(-c3cnc(Cc4nc5ccc(C(=O)O)cc5n4C[C@@H]4CCO4)c(F)c3)c2O1] | 14 | 2-((5-(2-(5-chloropyridin-2-yl)-2-methylbenzo[d][1,3]dioxol-4-yl)-3-fluoropyridin-2-yl)methyl)-1-(((S)-oxetan-2-yl)methyl)-1H-benzo[d]imidazole-6-carboxylic acid | 1 | 587.5 |
| 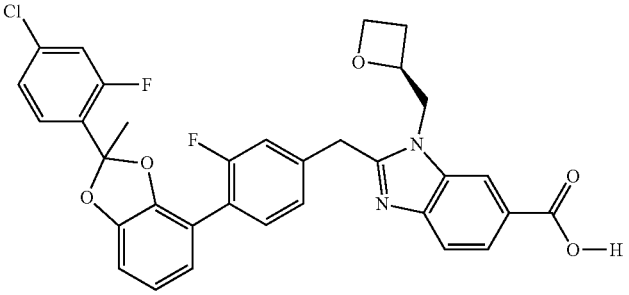 [SMILES: CC1(c2ccc(Cl)cc2F)Oc2cccc(-c3ccc(Cc4nc5ccc(C(=O)O)cc5n4C[C@@H]4CCO4)cc3F)c2O1] | 15 | 2-(4-(2-(4-chloro-2-fluorophenyl)-2-methylbenzo[d][1,3]dioxol-4-yl)-3-fluorobenzyl)-1-(((S)-oxetan-2-yl)methyl)-1H-benzo[d]imidazole-6-carboxylic acid | 1 | 603.2 |
| 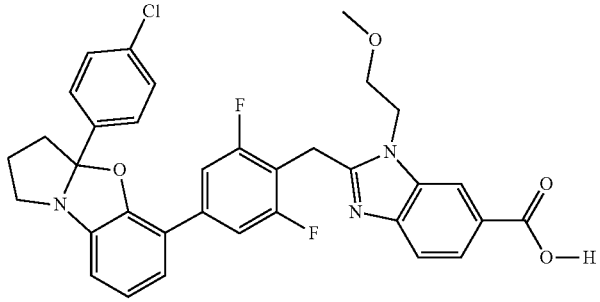 [SMILES: COCCn1c(Cc2c(F)cc(-c3cccc4c3OC3(c5ccc(Cl)cc5)CCCN43)cc2F)nc2ccc(C(=O)O)cc21] | 16 | 2-(4-(3a-(4-chlorophenyl)-1,2,3,3a-tetrahydrobenzo[d]pyrrolo[2,1-b]oxazol-5-yl)-2,6-difluorobenzyl)-1-(2-methoxyethyl)-1H-benzo[d]imidazole-6-carboxylic acid | 1 | 616.5 |
| 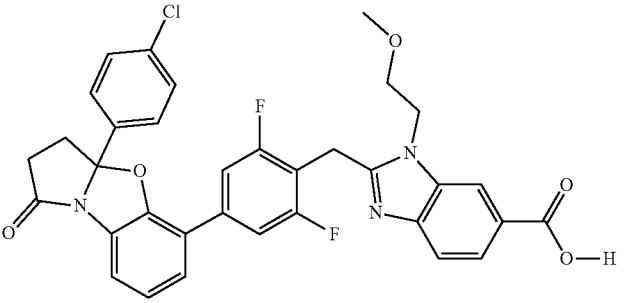 [SMILES: COCCn1c(Cc2c(F)cc(-c3cccc4c3OC3(c5ccc(Cl)cc5)CCC(=O)N43)cc2F)nc2ccc(C(=O)O)cc21] | 17 | 2-(4-(3a-(4-chlorophenyl)-1-oxo-1,2,3,3a-tetrahydrobenzo[d]pyrrolo[2,1-b]oxazol-5-yl)-2,6-difluorobenzyl)-1-(2-methoxyethyl)-1H-benzo[d]imidazole-6-carboxylic acid | 10 | 630.2 |
| 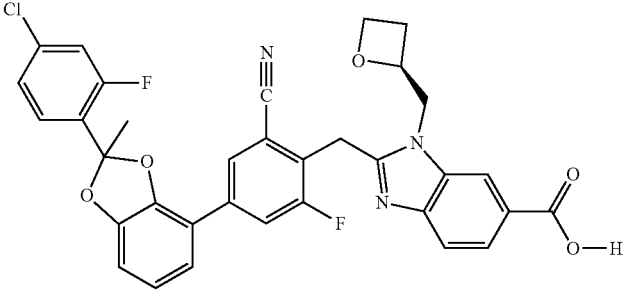 [SMILES: CC1(c2ccc(Cl)cc2F)Oc2cccc(-c3cc(F)c(Cc4nc5ccc(C(=O)O)cc5n4C[C@@H]4CCO4)c(C#N)c3)c2O1] | 18 | 2-(4-(2-(4-chloro-2-fluorophenyl)-2-methylbenzo[d][1,3]dioxol-4-yl)-2-cyano-6-fluorobenzyl)-1-(((S)-oxetan-2-yl)methyl)-1H-benzo[d]imidazole-6-carboxylic acid | 1 | 628.2 |

TABLE 2-continued

| Structure | Example | Name | Procedure | ES/MS m/z |
|---|---|---|---|---|
| 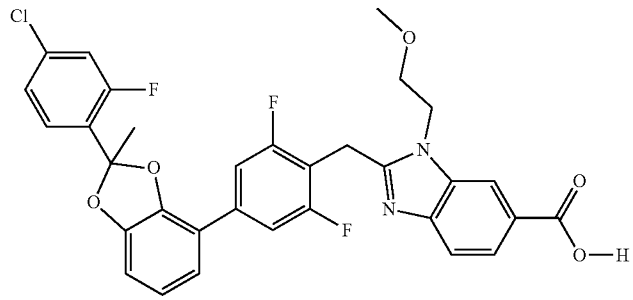 [SMILES: COCCn1c(Cc2c(F)cc(-c3cccc4c3OC(C)(c3ccc(Cl)cc3F)O4)cc2F)nc2ccc(C(=O)O)cc21] | 19 | 2-(4-(2-(4-chloro-2-fluorophenyl)-2-methylbenzo[d][1,3]dioxol-4-yl)-2,6-difluorobenzyl)-1-(2-methoxyethyl)-1H-benzo[d]imidazole-6-carboxylic acid | 1 | 609.5 |
| 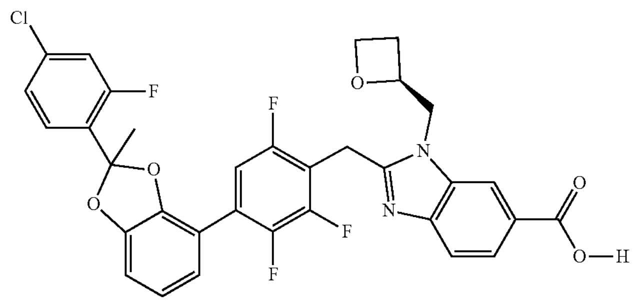 [SMILES: CC1(c2ccc(Cl)cc2F)Oc2cccc(-c3cc(F)c(Cc4nc5ccc(C(=O)O)cc5n4C[C@@H]4CCO4)c(F)c3F)c2O1] | 20 | 2-(4-(2-(4-chloro-2-fluorophenyl)-2-methylbenzo[d][1,3]dioxol-4-yl)-2,3,6-trifluorobenzyl)-1-(((S)-oxetan-2-yl)methyl)-1H-benzo[d]imidazole-6-carboxylic acid | 1 | 639.0 |
| 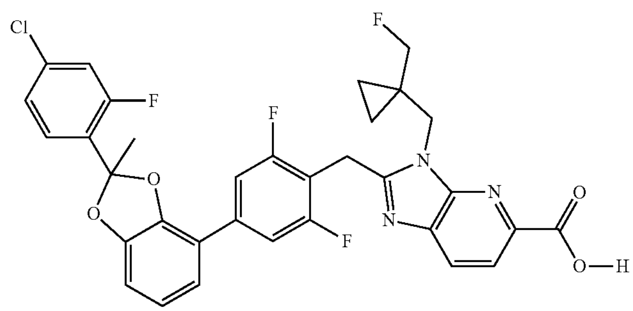 [SMILES: CC1(c2ccc(Cl)cc2F)Oc2cccc(-c3cc(F)c(Cc4nc5ccc(C(=O)O)nc5n4CC4(CF)CC4)c(F)c3)c2O1] | 21 | 2-(4-(2-(4-chloro-2-fluorophenyl)-2-methylbenzo[d][1,3]dioxol-4-yl)-2,6-difluorobenzyl)-3-((1-(fluoromethyl)cyclopropyl)methyl)-3H-imidazo[4,5-b]pyridine-5-carboxylic acid | 1 | 638.3 |
| 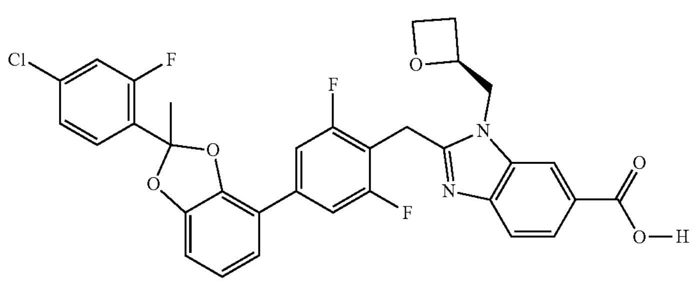 [SMILES: CC1(c2ccc(Cl)cc2F)Oc2cccc(-c3cc(F)c(Cc4nc5ccc(C(=O)O)cc5n4C[C@@H]4CCO4)c(F)c3)c2O1] | 22 | 2-(4-(2-(4-chloro-2-fluorophenyl)-2-methylbenzo[d][1,3]dioxol-4-yl)-2,6-difluorobenzyl)-1-(((S)-oxetan-2-yl)methyl)-1H-benzo[d]imidazole-6-carboxylic acid | 1 | 621.2 |
| 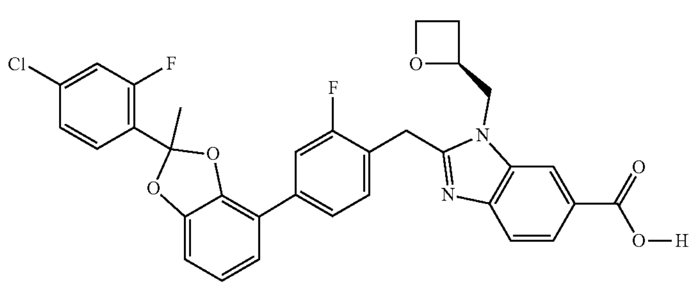 [SMILES: CC1(c2ccc(Cl)cc2F)Oc2cccc(-c3ccc(Cc4nc5ccc(C(=O)O)cc5n4C[C@@H]4CCO4)c(F)c3)c2O1] | 23 | 2-(4-(2-(4-chloro-2-fluorophenyl)-2-methylbenzo[d][1,3]dioxol-4-yl)-2-fluorobenzyl)-1-(((S)-oxetan-2-yl)methyl)-1H-benzo[d]imidazole-6-carboxylic acid | 1 | 603.2 |

TABLE 2-continued

| Structure | Example | Name | Procedure | ES/MS m/z |
|---|---|---|---|---|
| 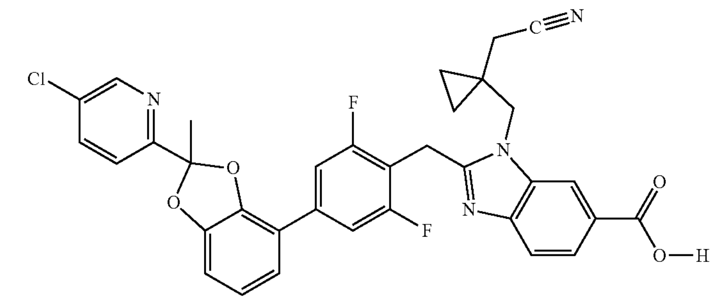 [SMILES: CC1(c2ccc(Cl)cn2)Oc2cccc(-c3cc(F)c(Cc4nc5ccc(C(=O)O)cc5n4CC4(CC#N)CC4)c(F)c3)c2O1] | 24 | 2-(4-(2-(5-chloropyridin-2-yl)-2-methylbenzo[d][1,3]dioxol-4-yl)-2,6-difluorobenzyl)-1-(((1-(cyanomethyl)cyclopropyl)methyl)-1H-benzo[d]imidazole 6-carboxylic acid | 1 | 627.2 |
| 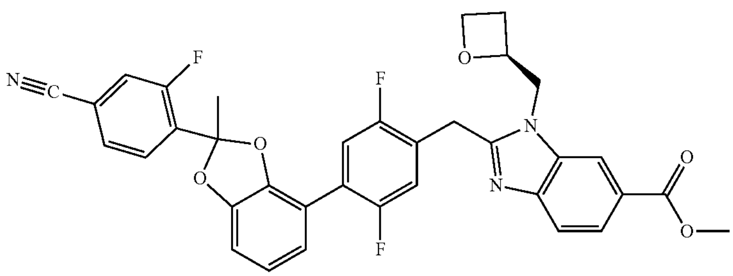 [SMILES: COC(=O)c1ccc2nc(Cc3cc(F)c(-c4cccc5c4OC(C)(c4ccc(C#N)cc4F)O5)cc3F)n(C[C@@H]3CCO3)c2c1] | 25 | 2-(4-(2-(4-cyano-2-fluorophenyl)-2-methylbenzo[d][1,3]dioxol-4-yl)-2,5-difluorobenzyl)-1-(((S)-oxetan-2-yl)methyl)-1H-benzo[d]imidazole-6-carboxylic acid | 1 | 612.2 |
| 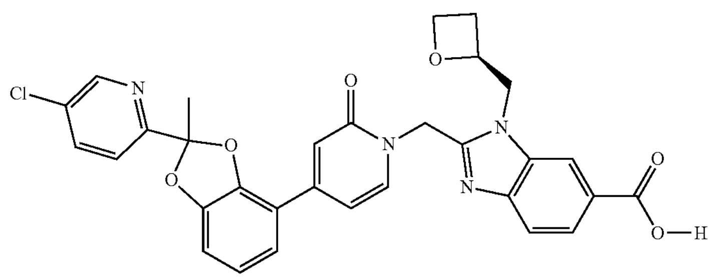 [SMILES: CC1(c2ccc(Cl)cn2)Oc2cccc(-c3ccn(Cc4nc5ccc(C(=O)O)cc5n4C[C@@H]4CCO4)c(=O)c3)c2O1] | 26 | 2-((4-(2-(5-chloropyridin-2-yl)-2-methylbenzo[d][1,3]dioxol-4-yl)-2-oxopyridin-1(2H)-yl)methyl)-1-(((S)-oxetan-2-yl)methyl)-1H-benzo[d]imidazole-6-carboxylic acid | 1 | 585.2 |
| 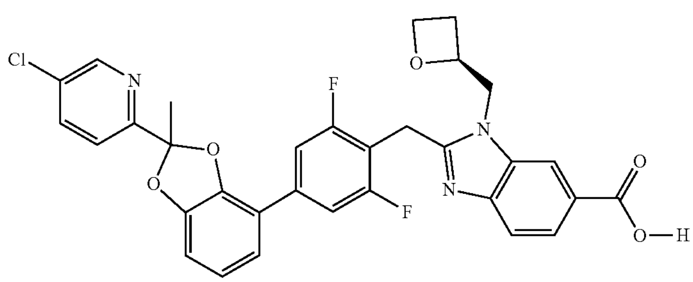 [SMILES: CC1(c2ccc(Cl)cn2)Oc2cccc(-c3cc(F)c(Cc4nc5ccc(C(=O)O)cc5n4C[C@@H]4CCO4)c(F)c3)c2O1] | 27 | 2-(4-(2-(5-chloropyridin-2-yl)-2-methylbenzo[d][1,3]dioxol-4-yl)-2,6-difluorobenzyl)-1-(((S)-oxetan-2-yl)methyl)-1H-benzo[d]imidazole-6-carboxylic acid | 1 | 604.2 |
| 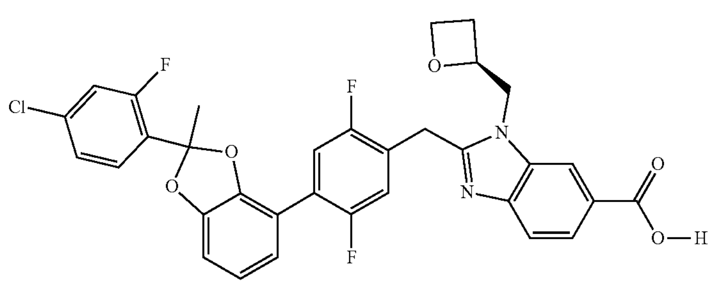 [SMILES: CC1(c2ccc(Cl)cc2F)Oc2cccc(-c3cc(F)c(Cc4nc5ccc(C(=O)O)cc5n4C[C@@H]4CCO4)cc3F)c2O1] | 28 | 2-(4-(2-(4-chloro-2-fluorophenyl)-2-methylbenzo[d][1,3]dioxol-4-yl)-2,5-difluorobenzyl)-1-(((S)-oxetan-2-yl)methyl)-1H-benzo[d]imidazole-6-carboxylic acid | 1 | 621.4 |

TABLE 2-continued

| Structure | Example | Name | Procedure | ES/MS m/z |
|---|---|---|---|---|
| 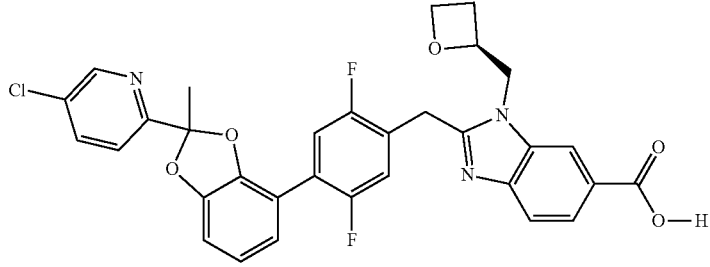 [SMILES: CC1(c2ccc(Cl)cn2)Oc2cccc(-c3cc(F)c(Cc4nc5ccc(C(=O)O)cc5n4C[C@@H]4CCO4)cc3F)c2O1] | 29 | 2-(4-(2-(5-chloropyridin-2-yl)-2-methylbenzo[d][1,3]dioxol-4-yl)-2,5-difluorobenzyl)-1-(((S)-oxetan-2-yl)methyl)-1H-benzo[d]imidazole-6-carboxylic acid | 1 | 604.8 |
| 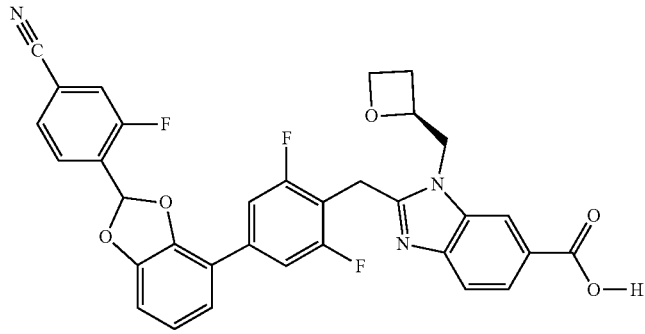 [SMILES: N#Cc1ccc(C2Oc3cccc(-c4cc(F)c(Cc5nc6ccc(C(=O)O)cc6n5C[C@@H]5CCO5)c(F)c4)c3O2)c(F)c1] | 30 | (S)-2-(4-(2-(4-cyano-2-fluorophenyl)benzo[d][1,3]dioxol-4-yl)-2,6-difluorobenzyl)-1-(oxetan-2-ylmethyl)-1H-benzo[d]imidazole-6-carboxylic acid | 1 | 598.3 |
| 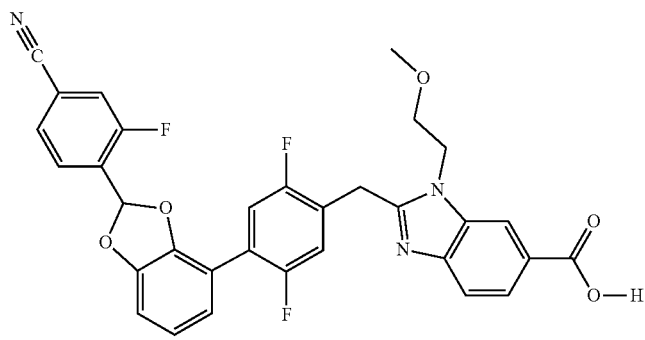 [SMILES: COCCn1c(Cc2cc(F)c(-c3cccc4c3OC(c3ccc(C#N)cc3F)O4)cc2F)nc2ccc(C(=O)O)cc21] | 31 | 2-(4-(2-(4-cyano-2-fluorophenyl)benzo[d][1,3]dioxol-4-yl)-2,5-difluorobenzyl)-1-(2-methoxyethyl)-1H-benzo[d]imidazole-6-carboxylic acid | 1 | 586.3 |
| 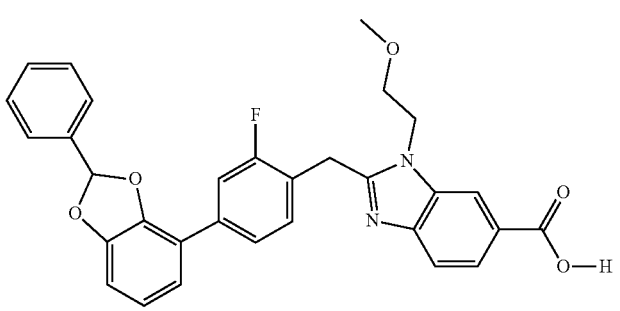 | 32 | 2-(2-fluoro-4-(2-phenylbenzo[d][1,3]dioxol-4-yl)benzyl)-1-(2-methoxyethyl)-1H-benzo[d]imidazole-6-carboxylic acid | 6 | 525.6 |

TABLE 2-continued

| Structure | Example | Name | Procedure | ES/MS m/z |
|---|---|---|---|---|
| 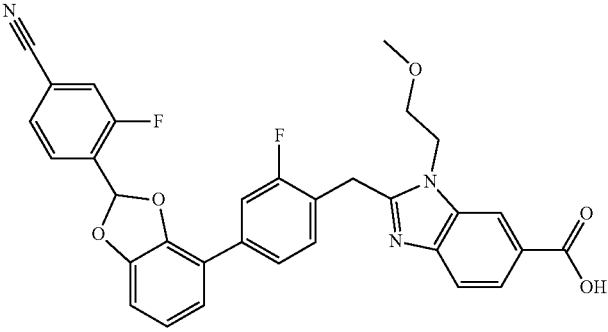 [SMILES: COCCn1c(Cc2ccc(-c3cccc4c3OC(c3ccc(C#N)cc3F)O4)cc2F)nc2ccc(C(=O)O)cc21] Isomer 1 | 33 | 2-(4-(2-(4-cyano-2-fluorophenyl)benzo[d][1,3]dioxol-4-yl)-2-fluorobenzyl)-1-(2-methoxyethyl)-1H-benzo[d]imidazole-6-carboxylic acid | 11 | 568.4 |
| 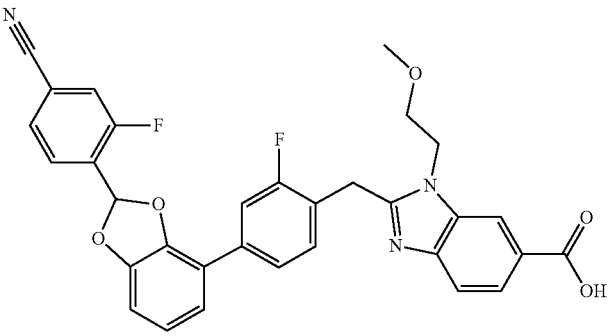 [SMILES: COCCn1c(Cc2ccc(-c3cccc4c3OC(c3ccc(C#N)cc3F)O4)cc2F)nc2ccc(C(=O)O)cc21] Isomer 2 | 34 | 2-(4-(2-(4-cyano-2-fluorophenyl)benzo[d][1,3]dioxol-4-fluorobenzyl)-1-(2-methoxyethyl)-1H-benzo[d]imidazole-6-carboxylic acid | 11 | 568.4 |
| 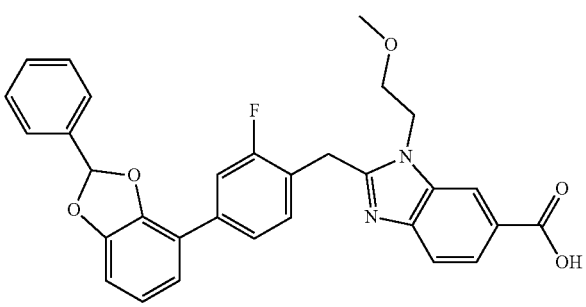 [SMILES: COCCn1c(Cc2ccc(-c3cccc4c3OC(c3ccccc3)O4)cc2F)nc2ccc(C(=O)O)cc21] Isomer 1 | 35 | 2-(2-fluoro-4-(2-phenylbenzo[d][1,3]dioxol-4-yl)benzyl)-1-(2-methoxyethyl)-1H-benzo[d]imidazole-6-carboxylic acid | 12 | 525.3 |
| 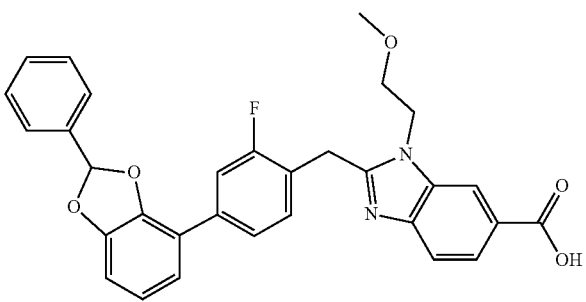 [SMILES: COCCn1c(Cc2ccc(-c3cccc4c3OC(c3ccccc3)O4)cc2F)nc2ccc(C(=O)O)cc21] Isomer 2 | 36 | 2-(2-fluoro-4-(2-phenylbenzo[d][1,3]dioxol-4-yl)benzyl)-1-(2-methoxyethyl)-1H-benzo[d]imidazole-6-carboxylic acid | 12 | 525.3 |

TABLE 2-continued

| Structure | Example | Name | Procedure | ES/MS m/z |
|---|---|---|---|---|
| Isomer 1 | 37 | 2-(4-(2-(4-cyano-2-fluorophenyl)benzo[d][1,3]dioxol-4-yl)-2,6-difluorobenzyl)-1-(2-methoxyethyl)-1H-benzo[d]imidazole-6-carboxylic acid | 13 | 586.2 |
| Isomer 2 | 38 | 2-(4-(2-(4-cyano-2-fluorophenyl)benzo[d][1,3]dioxol-4-yl)-2,6-difluorobenzyl)-1-(2-methoxyethyl)-1H-benzo[d]imidazole-6-carboxylic acid | 13 | 586.2 |
| Isomer 1 | 39 | 2-(4-(2-(4-cyano-2-fluorophenyl)benzo[d][1,3]dioxol-4-yl)-2,5-difluorobenzyl)-1-(2-methoxyethyl)-1H-benzo[d]imidazole-6-carboxylic acid | 14 | 586.2 |
| Isomer 2 | 40 | 2-(4-(2-(4-cyano-2-fluorophenyl)benzo[d][1,3]dioxol-4-yl)-2,5-difluorobenzyl)-1-(2-methoxyethyl)-1H-benzo[d]imidazole-6-carboxylic acid | 14 | 586.2 |

TABLE 2-continued

| Structure | Example | Name | Procedure | ES/MS m/z |
|---|---|---|---|---|
| Isomer 1 | 41 | 2-(4-(2-(4-cyano-2-fluorophenyl)benzo[d][1,3]dioxol-4-yl)-2,6-difluorobenzyl)-1-(((S)-oxetan-2-yl)methyl)-1H-benzo[d]imidazole-6-carboxylic acid | 15 | 598.1 |
| Isomer 2 | 42 | 2-(4-(2-(4-cyano-2-fluorophenyl)benzo[d][1,3]dioxol-4-yl)-2,6-difluorobenzyl)-1-(((S)-oxetan-2-yl)methyl)-1H-benzo[d]imidazole-6-carboxylic acid | 15 | 598.2 |
| Isomer 1 | 43 | 2-(4-(2-(4-chloro-2-fluorophenyl)-2-methylbenzo[d][1,3]dioxol-4-yl)-2,5-difluorobenzyl)-1-(((S)-oxetan-2-yl)methyl)-1H-benzo[d]imidazole-6-carboxylic acid | 16 | 621.3 |
| Isomer 2 | 44 | 2-(4-(2-(4-chloro-2-fluorophenyl)-2-methylbenzo[d][1,3]dioxol-4-yl)-2,5-difluorobenzyl)-1-(((S)-oxetan-2-yl)methyl)-1H-benzo[d]imidazole-6-carboxylic acid | 16 | 621.4 |

TABLE 2-continued

| Structure | Example | Name | Procedure | ES/MS m/z |
|---|---|---|---|---|
| Isomer 1 | 45 | 2-(4-(2-(5-chloropyridin-2-yl)-2-methylbenzo[d][1,3]dioxol-4-yl)-2,5-difluorobenzyl)-1-(((S)-oxetan-2-yl)methyl)-1H-benzo[d]imidazole-6-carboxylic acid | 17 | 604.2 |
| Isomer 2 | 46 | 2-(4-(2-(5-chloropyridin-2-yl)-2-methylbenzo[d][1,3]dioxol-4-yl)-2,5-difluorobenzyl)-1-(((S)-oxetan-2-yl)methyl)-1H-benzo[d]imidazole-6-carboxylic acid | 17 | 604.2 |
| Isomer 1 | 47 | 2-(4-(2-(4-chloro-2-fluorophenyl)-2-methylbenzo[d][1,3]dioxol-4-yl)-2,6-difluorobenzyl)-1-(((S)-oxetan-2-yl)methyl)-1H-benzo[d]imidazole-6-carboxylic acid | 18 | 621.2 |
| Isomer 2 | 48 | 2-(4-(2-(4-chloro-2-fluorophenyl)-2-methylbenzo[d][1,3]dioxol-4-yl)-2,6-difluorobenzyl)-1-(((S)-oxetan-2-yl)methyl)-1H-benzo[d]imidazole-6-carboxylic acid | 18 | 621.2 |
| Isomer 1 | 49 | 2-(4-(2-(5-chloropyridin-2-yl)-2-methylbenzo[d][1,3]dioxol-4-yl)-2,6-difluorobenzyl)-1-(((S)-oxetan-2-yl)methyl)-1H-benzo[d]imidazole-6-carboxylic acid | 19 | 604.2 |

TABLE 2-continued

| Structure | Example | Name | Procedure | ES/MS m/z |
|---|---|---|---|---|
| (Isomer 2) | 50 | 2-(4-(2-(5-chloropyridin-2-yl)-2-methylbenzo[d][1,3]dioxol-4-yl)-2,6-difluorobenzyl)-1-(((S)-oxetan-2-yl)methyl)-1H-benzo[d]imidazole-6-carboxylic acid | 19 | 604.2 |
| 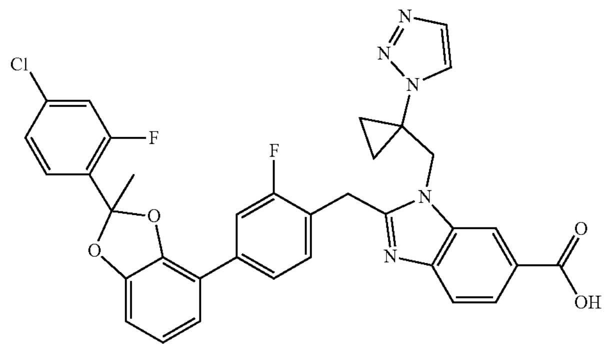 [SMILES: CC1(c2ccc(Cl)cc2F)Oc2cccc(-c3ccc(Cc4nc5ccc(C(=O)O)cc5n4CC4(n5ccnn5)CC4)c(F)c3)c2O1] | 51 | 1-((1-(1H-1,2,3-triazol-1-yl)cyclopropyl)methyl)-2-(4-(2-(4-chloro-2-fluorophenyl)-2-methylbenzo[d][1,3]dioxol-4-yl)-2-fluorobenzyl)-1H-benzo[d]imidazole-6-carboxylic acid | 8 | 654.2 |
| 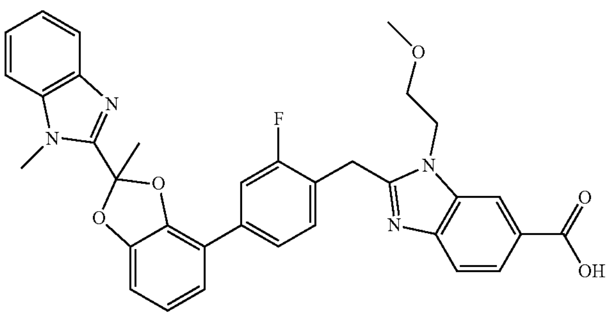 [SMILES: COCCn1c(Cc2ccc(-c3cccc4c3OC(C)(c3nc5ccccc5n3C)O4)cc2F)nc2ccc(C(=O)O)cc21] | 52 | 2-[[2-fluoro-4-[2-methyl-2-(1-methylbenzimidazol-2-yl)-1,3-benzodioxol-4-yl]phenyl]methyl]-3-(2-methoxyethyl)benzimidazole-5-carboxylic acid | 6 | 593.2 |
| 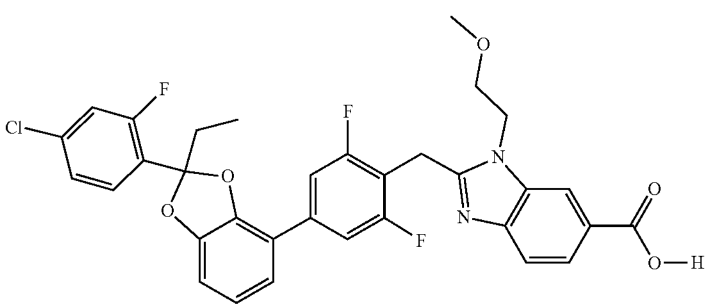 [SMILES: CCC1(c2ccc(Cl)cc2F)Oc2cccc(-c3cc(F)c(Cc4nc5ccc(C(=O)O)cc5n4CCOC)c(F)c3)c2O1] | 53 | 2-(4-(2-(4-chloro-2-fluorophenyl)-2-ethylbenzo[d][1,3]dioxol-4-yl)-2,6-difluorobenzyl)-1-(2-methoxyethyl)-1H-benzo[d]imidazole-6-carboxylic acid | 1 | 623.8 |
| 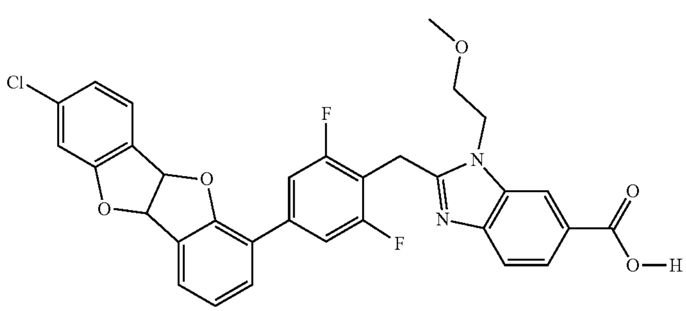 [SMILES: COCCn1c(Cc2c(F)cc(-c3cccc4c3OC3c5ccc(Cl)cc5OC43)cc2F)nc2ccc(C(=O)O)cc21] | 54 | 2-(4-(7-chloro-4b,9b-dihydrobenzofuro[3,2-b]benzofuran-1-yl)-2,6-difluorobenzyl)-1-(2-methoxyethyl)-1H-benzo[d]imidazole-6-carboxylic acid | 1 | 589.2 |

TABLE 2-continued

| Structure | Example | Name | Procedure | ES/MS m/z |
|---|---|---|---|---|
| 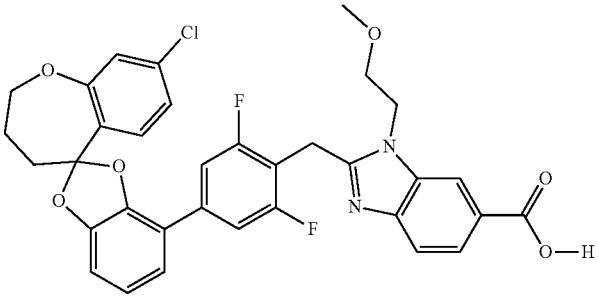 [SMILES: COCCn1c(Cc2c(F)cc(-c3cccc4c3OC3(CCCOc5cc(Cl)ccc53)O4)cc2F)nc2ccc(C(=O)O)cc21] | 55 | 2-(4-(8-chloro-3,4-dihydro-2H-spiro[benzo[b]oxepine-5,2'-benzo[d][1,3]dioxol]-4'-yl)-2,6-difluorobenzyl)-1-(2-methoxyethyl)-1H-benzo[d]imidazole-6-carboxylic acid | 1 | 633.5 |
| 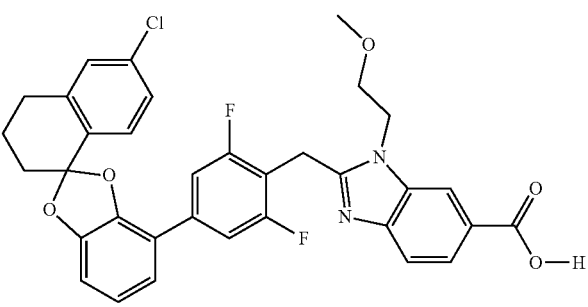 [SMILES: COCCn1c(Cc2c(F)cc(-c3cccc4c3OC3(CCCc5cc(Cl)ccc53)O4)cc2F)nc2ccc(C(=O)O)cc21] | 56 | 2-(4-(6'-chloro-3',4'-dihydro-2'H-spiro[benzo[d][1,3]dioxole-2,1'-naphthalen]-4-yl)-2,6-difluorobenzyl)-1-(2-methoxyethyl)-1H-benzo[d]imidazole-6-carboxylic acid | 1 | 617.4 |
| 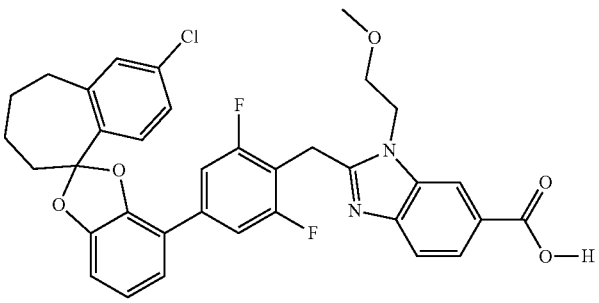 [SMILES: COCCn1c(Cc2c(F)cc(-c3cccc4c3OC3(CCCCc5cc(Cl)ccc53)O4)cc2F)nc2ccc(C(=O)O)cc21] | 57 | 2-(4-(2'-chloro-6',7',8',9'-tetrahydrospiro[benzo[d][1,3]dioxole-2,5'-benzo[7]annulen]-4-yl)-2,6-difluorobenzyl)-1-(2-methoxyethyl)-1H-benzo[d]imidazole-6-carboxylic acid | 1 | 630.4 |
| 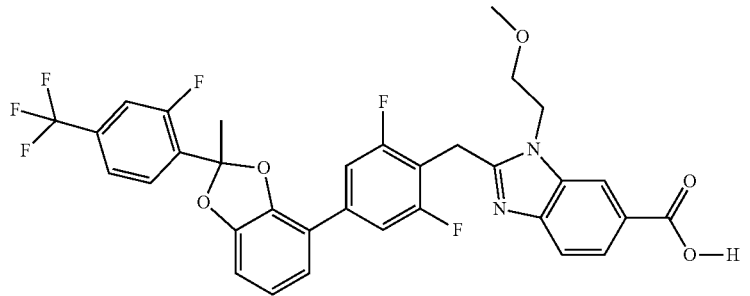 [SMILES: COCCn1c(Cc2c(F)cc(-c3cccc4c3OC(C)(c3ccc(C(F)(F)F)cc3F)O4)cc2F)nc2ccc(C(=O)O)cc21] | 58 | 2-(2,6-difluoro-4-(2-(2-fluoro-4-(trifluoromethyl)phenyl)-2-methylbenzo[d][1,3]dioxol-4-yl)benzyl)-1-(2-methoxyethyl)-1H-benzo[d]imidazole-6-carboxylic acid | 1 | 643.3 |
| 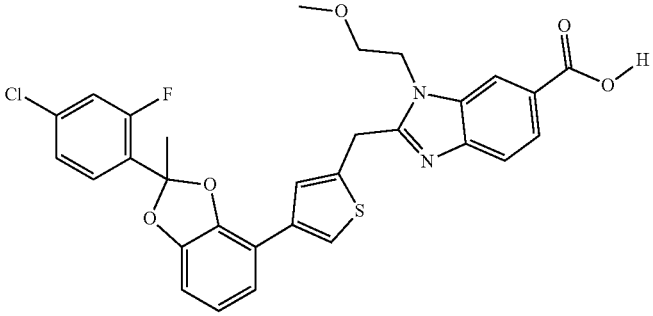 [SMILES: COCCn1c(Cc2cc(-c3cccc4c3OC(C)(c3ccc(Cl)cc3F)O4)cs2)nc2ccc(C(=O)O)cc21] | 59 | 2-((4-(2-(4-chloro-2-fluorophenyl)-2-methylbenzo[d][1,3]dioxol-4-yl)thiophen-2-yl)methyl)-1-(2-methoxyethyl)-1H-benzo[d]imidazole-6-carboxylic acid | 1 | 579 |

TABLE 2-continued

| Structure | Example | Name | Procedure | ES/MS m/z |
|---|---|---|---|---|
| 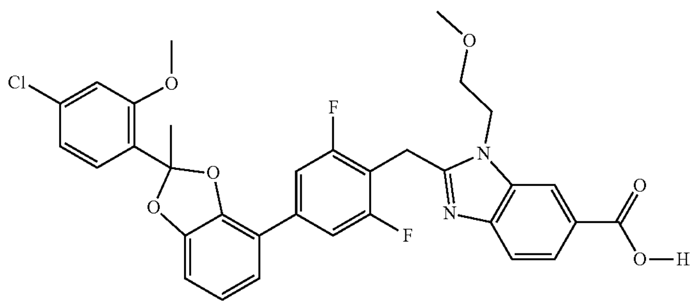 [SMILES: COCCn1c(Cc2c(F)cc(-c3cccc4c3OC(C)(c3ccc(Cl)cc3OC)O4)cc2F)nc2ccc(C(=O)O)cc21] | 60 | 2-(4-(2-(4-chloro-2-methoxyphenyl)-2-methylbenzo[d][1,3]dioxol-4-yl)-2,6-difluorobenzyl)-1-(2-methoxyethyl)-1H-benzo[d]imidazole-6-carboxylic acid | 1 | 621 |
| 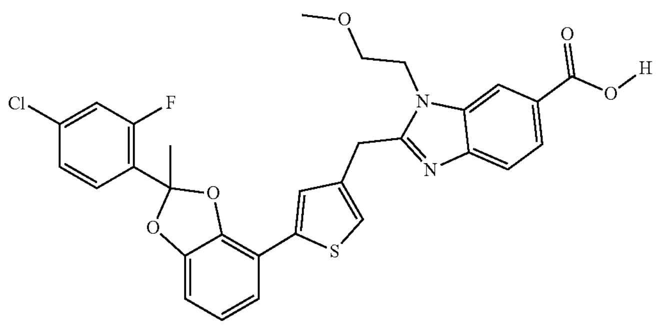 [SMILES: COCCn1c(Cc2csc(-c3cccc4c3OC(C)(c3ccc(Cl)cc3F)O4)c2)nc2ccc(C(=O)O)cc21] | 61 | 2-((5-(2-(4-chloro-2-fluorophenyl)-2-methylbenzo[d][1,3]dioxol-4-yl)thiophen-3-yl)methyl)-1-(2-methoxyethyl)-1H-benzo[d]imidazole-6-carboxylic acid | 1 | 579 |
| 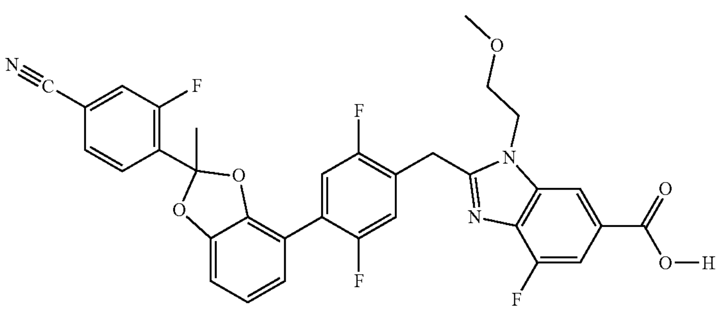 [SMILES: COCCn1c(Cc2cc(F)c(-c3cccc4c3OC(C)(c3ccc(C#N)cc3F)O4)cc2F)nc2c(F)cc(C(=O)O)cc21] | 62 | 2-(4-(2-(4-cyano-2-fluorophenyl)-2-methylbenzo[d][1,3]dioxol-4-yl)-2,5-difluorobenzyl)-4-fluoro-1-(2-methoxyethyl)-1H-benzo[d]imidazole-6-carboxylic acid | 1 | 618.2 |
| 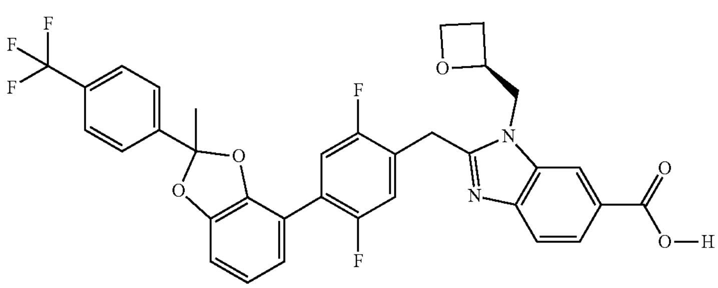 [SMILES: CC1(c2ccc(C(F)(F)F)cc2)Oc2cccc(-c3cc(F)c(Cc4nc5ccc(C(=O)O)cc5n4C[C@@H]4CCO4)cc3F)c2O1] | 63 | 2-(2,5-difluoro-4-(2-methyl-2-(4-(trifluoromethyl)phenyl)benzo[d][1,3]dioxol-4-yl)benzyl)-1-(((S)-oxetan-2-yl)methyl)-1H-benzo[d]imidazole-6-carboxylic acid | 1 | 637.2 |
| 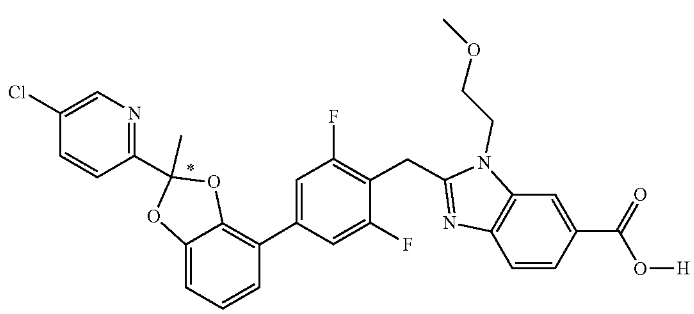 [SMILES: COCCn1c(Cc2c(F)cc(-c3cccc4c3OC(C)(c3ccc(Cl)cn3)O4)cc2F)nc2ccc(C(=O)O)cc21] | 64 | 2-(4-(2-(5-chloropyridin-2-yl)-2-methylbenzo[d][1,3]dioxol-4-yl)-2,6-difluorobenzyl)-1-(2-methoxyethyl)-1H-benzo[d]imidazole-6-carboxylic acid | 1 | 592.7 |

TABLE 2-continued

| Structure | Example | Name | Procedure | ES/MS m/z |
|---|---|---|---|---|
| 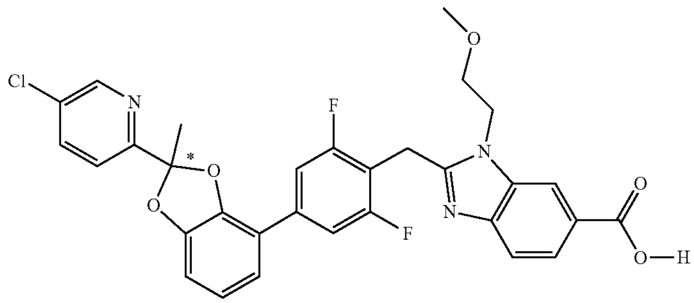 [SMILES: COCCn1c(Cc2c(F)cc(-c3cccc4c3OC(C)(c3ccc(Cl)cn3)O4)cc2F)nc2ccc(C(=O)O)cc21] | 65 | 2-(4-(2-(5-chloropyridin-2-yl)-2-methylbenzo[d][1,3]dioxol-4-yl)-2,6-difluorobenzyl)-1-(2-methoxyethyl)-1H-benzo[d]imidazole-6-carboxylic acid | 1 | 592.4 |
| 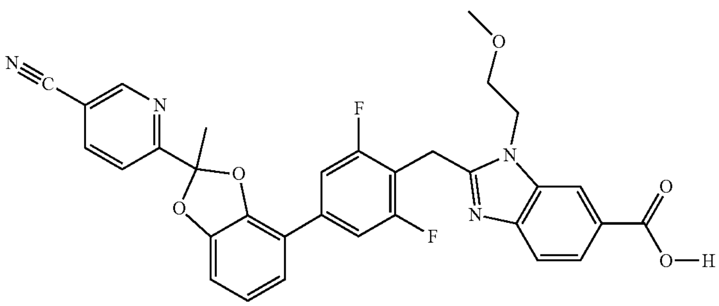 [SMILES: COCCn1c(Cc2c(F)cc(-c3cccc4c3OC(C)(c3ccc(C#N)cn3)O4)cc2F)nc2ccc(C(=O)O)cc21] | 66 | 2-(4-(2-(5-cyanopyridin-2-yl)-2-methylbenzo[d][1,3]dioxol-4-yl)-2,6-difluorobenzyl)-1-(2-methoxyethyl)-1H-benzo[d]imidazole-6-carboxylic acid | 1 | 583.2 |
| 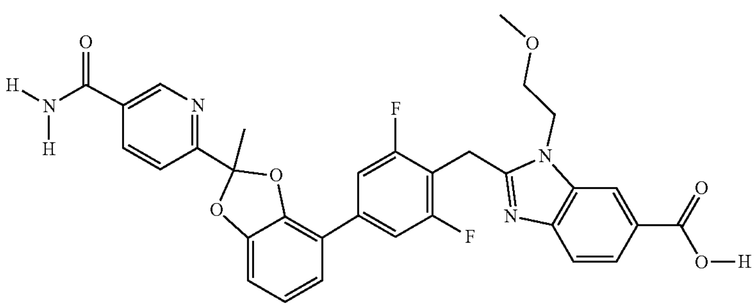 [SMILES: COCCn1c(Cc2c(F)cc(-c3cccc4c3OC(C)(c3ccc(C(N)=O)cn3)O4)cc2F)nc2ccc(C(=O)O)cc21] | 67 | 2-(4-(2-(5-carbamoylpyridin-2-yl)-2-methylbenzo[d][1,3]dioxol-4-yl)-2,6-difluorobenzyl)-1-(2-methoxyethyl)-1H-benzo[d]imidazole-6-carboxylic acid | 1 | 601.2 |
| 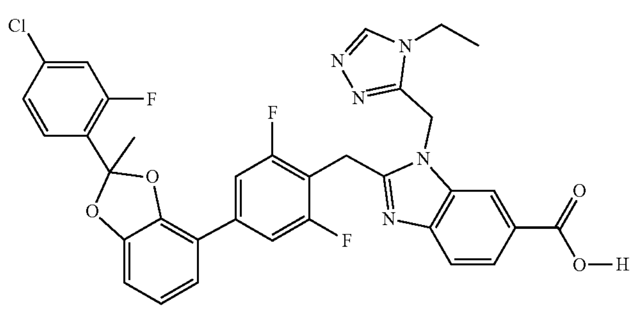 [SMILES: CCn1cnnc1Cn1c(Cc2c(F)cc(-c3cccc4c3OC(C)(c3ccc(Cl)cc3F)O4)cc2F)nc2ccc(C(=O)O)cc21] | 68 | 2-(4-(2-(4-chloro-2-fluorophenyl)-2-methylbenzo[d][1,3]dioxol-4-yl)-2,6-difluorobenzyl)-1-((4-ethyl-4H-1,2,4-triazol-3-yl)methyl)-1H-benzo[d]imidazole-6-carboxylic acid | 1 | 660.2 |
| 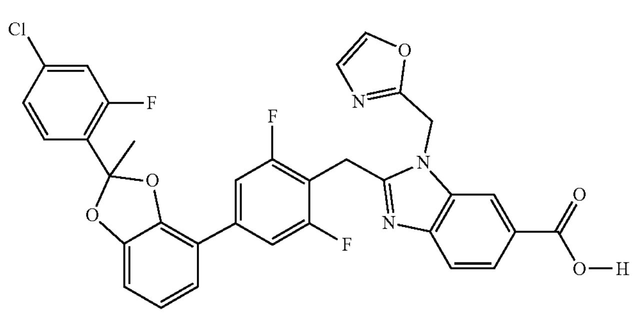 [SMILES: CC1(c2ccc(Cl)cc2F)Oc2cccc(-c3cc(F)c(Cc4nc5ccc(C(=O)O)cc5n4Cc4ncco4)c(F)c3)c2O1] | 69 | 2-(4-(2-(4-chloro-2-fluorophenyl)-2-methylbenzo[d][1,3]dioxol-4-yl)-2,6-difluorobenzyl)-1-(oxazol-2-ylmethyl)-1H-benzo[d]imidazole-6-carboxylic acid | 1 | 632.2 |

TABLE 2-continued

| Structure | Example | Name | Procedure | ES/MS m/z |
|---|---|---|---|---|
| 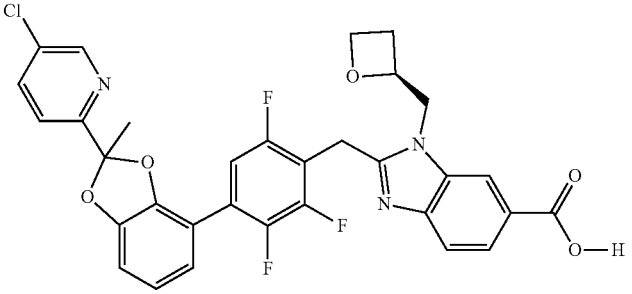 [SMILES: CC1(c2ccc(Cl)cn2)Oc2cccc(-c3cc(F)c(Cc4nc5ccc(C(=O)O)cc5n4C[C@@H]4CCO4)c(F)c3F)c2O1] | 70 | 2-(4-(2-(5-chloropyridin-2-yl)-2-methylbenzo[d][1,3]dioxol-4-yl)-2,3,6-trifluorobenzyl)-1-(((S)-oxetan-2-yl)methyl)-1H-benzo[d]imidazole-6-carboxylic acid | 1 | 622 |
| 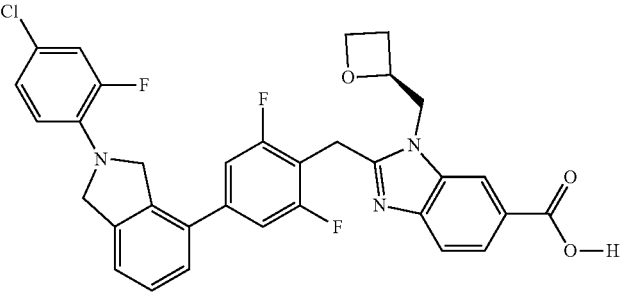 [SMILES: O=C(O)c1ccc2nc(Cc3c(F)cc(-c4cccc5c4CN(c4ccc(Cl)cc4F)C5)cc3F)n(C[C@@H]3CCO3)c2c1] | 71 | (S)-2-(4-(2-(4-chloro-2-fluorophenyl)isoindolin-4-yl)-2,6-difluorobenzyl)-1-(oxetan-2-ylmethyl)-1H-benzo[d]imidazole-6-carboxylic acid | 1 | 604.4 |
| 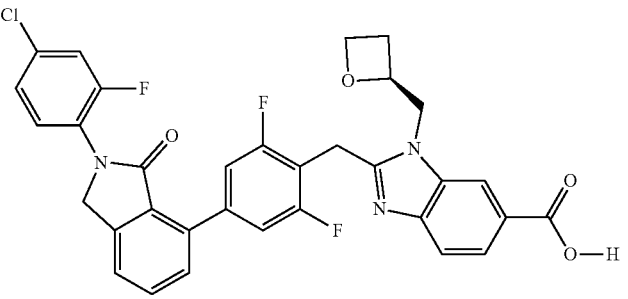 [SMILES: O=C(O)c1ccc2nc(Cc3c(F)cc(-c4cccc5c4C(=O)N(c4ccc(Cl)cc4F)C5)cc3F)n(C[C@@H]3CCO3)c2c1] | 72 | (S)-2-(4-(2-(4-chloro-2-fluorophenyl)-3-oxoisoindolin-4-yl)-2,6-difluorobenzyl)-1-(oxetan-2-ylmethyl)-1H-benzo[d]imidazole-6-carboxylic acid | 1 | 618.8 |
| 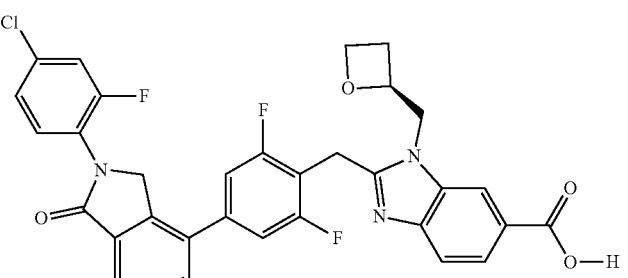 | 73 | (S)-2-(4-(2-(4-chloro-2-fluorophenyl)-1-oxoisoindolin-4-yl)-2,6-difluorobenzyl)-1-(oxetan-2-ylmethyl)-1H-benzo[d]imidazole-6-carboxylic acid | 1 | 618.3 |
| 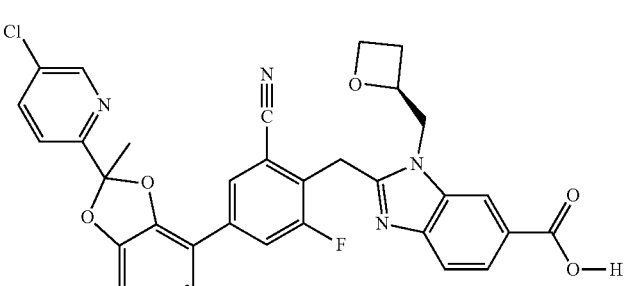 | 74 | 2-(4-(2-(5-chloropyridin-2-yl)-2-methylbenzo[d][1,3]dioxol-4-yl)-2-cyano-6-fluorobenzyl)-1-(((S)-oxetan-2-yl)methyl)-1H-benzo[d]imidazole-6-carboxylic acid | 1 | 611.3 |

TABLE 2-continued

| Structure | Example | Name | Procedure | ES/MS m/z |
|---|---|---|---|---|
| 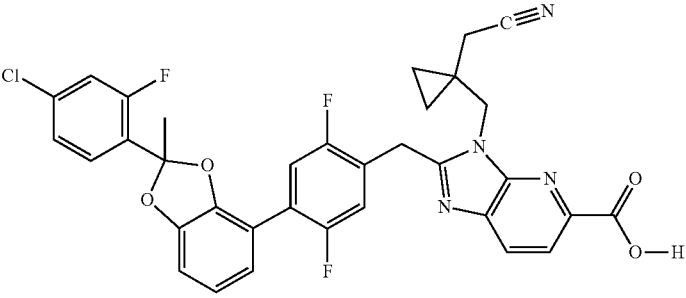 [SMILES: CC1(c2ccc(Cl)cc2F)Oc2cccc(-c3cc(F)c(Cc4nc5ccc(C(=O)O)nc5n4CC4(CC#N)CC4)cc3F)c2O1] | 75 | 2-(4-(2-(4-chloro-2-fluorophenyl)-2-methylbenzo[d][1,3]dioxol-4-yl)-2,5-difluorobenzyl)-3-((1-(cyanomethyl)cyclopropyl)methyl)-3H-imidazo[4,5-b]pyridine-5-carboxylic acid | 1 | 645.2 |
| 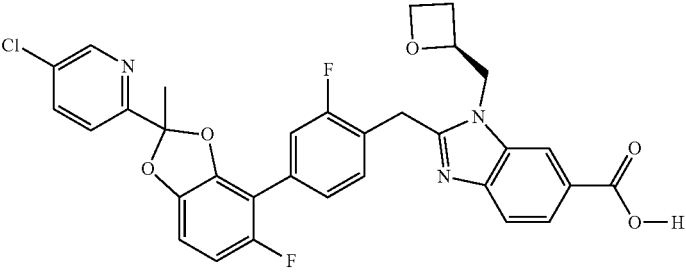 [SMILES: CC1(c2ccc(Cl)cn2)Oc2ccc(F)c(-c3ccc(Cc4nc5ccc(C(=O)O)cc5n4C[C@@H]4CCO4)c(F)c3)c2O1] | 76 | 2-(4-(2-(5-chloropyridin-2-yl)-5-fluoro-2-methylbenzo[d][1,3]dioxol-4-yl)-2-fluorobenzyl)-1-(((S)-oxetan-2-yl)methyl)-1H-benzo[d]imidazole-6-carboxylic acid | 5 | 604.2 |
| 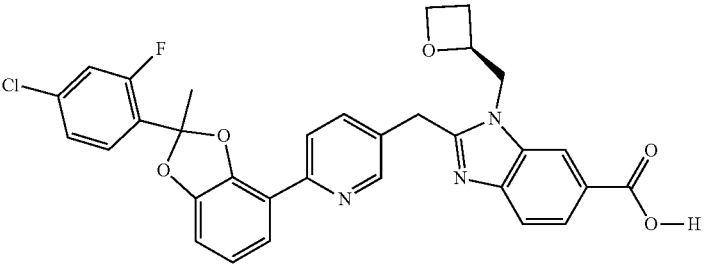 [SMILES: CC1(c2ccc(Cl)cc2F)Oc2cccc(-c3ccc(Cc4nc5ccc(C(=O)O)cc5n4C[C@@H]4CCO4)cn3)c2O1] | 77 | 2-((6-(2-(4-chloro-2-fluorophenyl)-2-methylbenzo[d][1,3]dioxol-4-yl)pyridin-3-yl)methyl)-1-(((S)-oxetan-2-yl)methyl)-1H-benzo[d]imidazole-6-carboxylic acid | 5 | 586.2 |
| 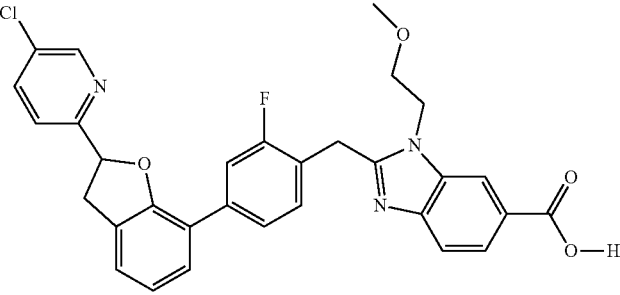 [SMILES: COCCn1c(Cc2ccc(-c3cccc4c3OC(c3ccc(Cl)cn3)C4)cc2F)nc2ccc(C(=O)O)cc21] | 78 | 2-(4-(2-(5-chloropyridin-2-yl)-2,3-dihydrobenzofuran-7-yl)-2-fluorobenzyl)-1-(2-methoxyethyl)-1H-benzo[d]imidazole-6-carboxylic acid | 7 | 558.2 |
| 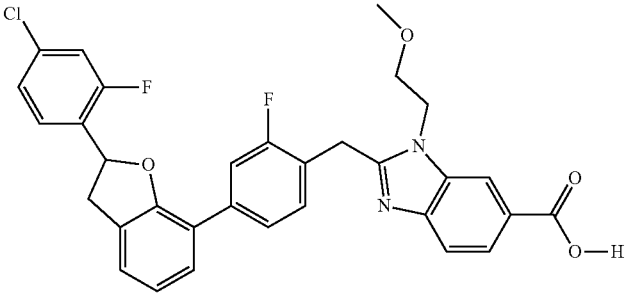 [SMILES: COCCn1c(Cc2ccc(-c3cccc4c3OC(c3ccc(Cl)cc3F)C4)cc2F)nc2ccc(C(=O)O)cc21] | 79 | 2-(4-(2-(4-chloro-2-fluorophenyl)-2,3-dihydrobenzofuran-7-yl)-2-fluorobenzyl)-1-(2-methoxyethyl)-1H-benzo[d]imidazole-6-carboxylic acid | 7 | 575 |

TABLE 2-continued

| Structure | Example | Name | Procedure | ES/MS m/z |
|---|---|---|---|---|
| 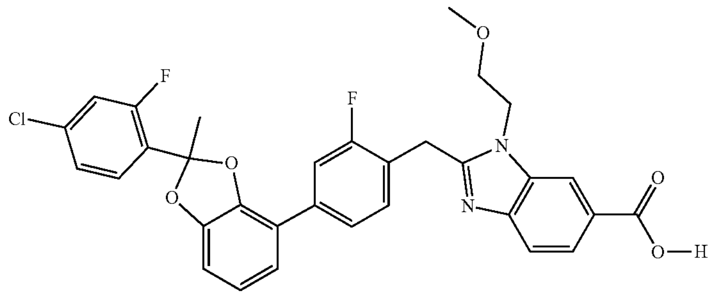 [SMILES: COCCn1c(Cc2ccc(-c3cccc4c3OC(C)(c3ccc(Cl)cc3F)O4)cc2F)nc2ccc(C(=O)O)cc21] | 80 | 2-(4-(2-(4-chloro-2-fluorophenyl)-2-methylbenzo[d][1,3]dioxol-4-yl)-2-fluorobenzyl)-1-(2-methoxyethyl)-1H-benzo[d]imidazole-6-carboxylic acid | 7 | 591.4 |
| 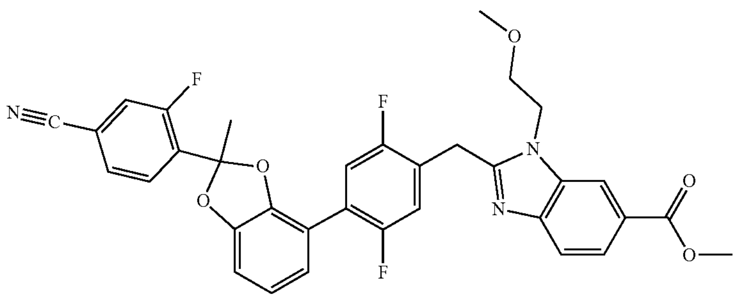 [SMILES: COCCn1c(Cc2cc(F)c(-c3cccc4c3OC(C)(c3ccc(C#N)cc3F)O4)cc2F)nc2ccc(C(=O)OC)cc21] | 81 | 2-(4-(2-(4-cyano-2-fluorophenyl)-2-methylbenzo[d][1,3]dioxol-4-yl)-2,5-difluorobenzyl)-1-(2-methoxyethyl)-1H-benzo[d]imidazole-6-carboxylic acid | 7 | 600.4 |
| 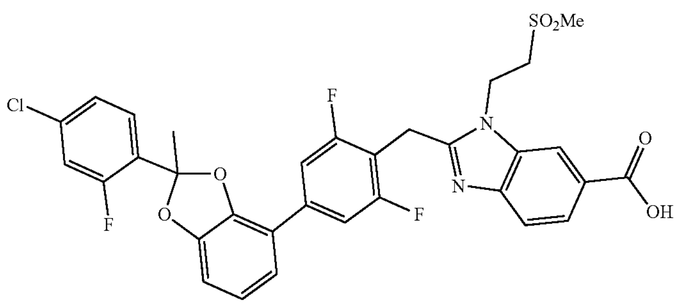 [SMILES: CC1(c2ccc(Cl)cc2F)Oc2cccc(-c3cc(F)c(Cc4nc5ccc(C(=O)O)cc5n4CCS(C)(=O)=O)c(F)c3)c2O1] | 82 | 2-[[4-[2-(4-chloro-2-fluoro-phenyl)-2-methyl-1,3-benzodioxol-4-yl]-2,6-difluoro-phenyl]methyl]-3-(2-methylsulfonylethyl)benzimidazole-5-carboxylic acid | 20 | 658.2 |
| 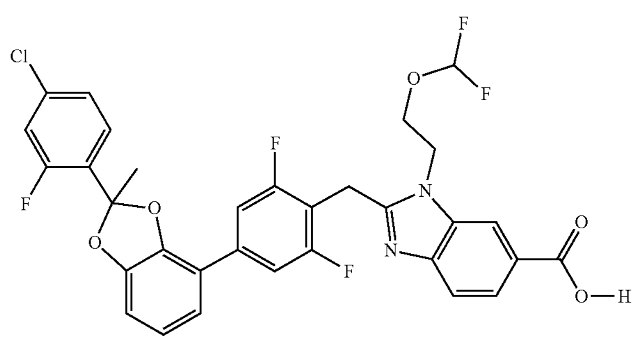 [SMILES: CC1(c2ccc(Cl)cc2F)Oc2cccc(-c3cc(F)c(Cc4nc5ccc(C(=O)O)cc5n4CCOC(F)F)c(F)c3)c2O1] | 83 | 2-(4-(2-(4-chloro-2-fluorophenyl)-2-methylbenzo[d][1,3]dioxol-4-yl)-2,6-difluorobenzyl)-1-(2-(difluoromethoxy)ethyl)-1H-benzo[d]imidazole-6-carboxylic acid | 20 | 645.2 |
| 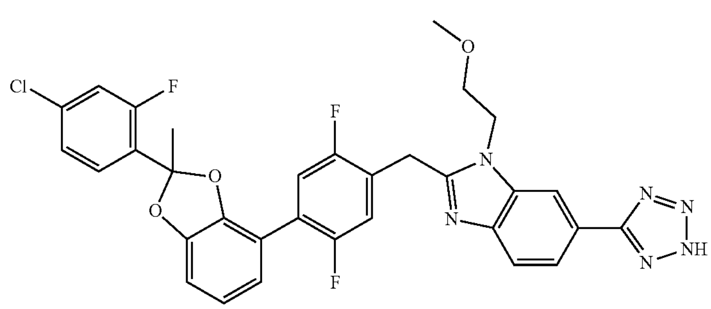 [SMILES: COCCn1c(Cc2cc(F)c(-c3cccc4c3OC(C)(c3ccc(Cl)cc3F)O4)cc2F)nc2ccc(-c3nn[nH]n3)cc21] | 84 | 2-(4-(2-(4-chloro-2-fluorophenyl)-2-methylbenzo[d][1,3]dioxol-4-yl)-2,5-difluorobenzyl)-1-(2-methoxyethyl)-6-(2H-tetrazol-5-yl)-1H-benzo[d]imidazole | 21 | 633.2 |

TABLE 2-continued

| Structure | Example | Name | Procedure | ES/MS m/z |
|---|---|---|---|---|
| 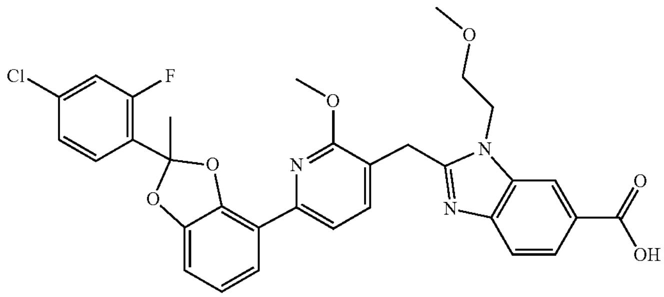 [SMILES: COCCn1c(Cc2ccc(-c3cccc4c3OC(C)(c3ccc(Cl)cc3F)O4)nc2OC)nc2ccc(C(=O)O)cc21] | 85 | 2-((6-(2-(4-chloro-2-fluorophenyl)-2-methylbenzo[d][1,3]dioxol-4-yl)-2-methoxypyridin-3-yl)methyl)-1-(2-methoxyethyl)-1H-benzo[d]imidazole-6-carboxylic acid | 22 | 604.2 |
| 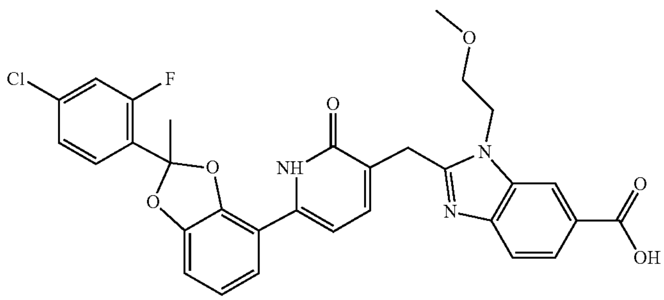 [SMILES: COCCn1c(Cc2ccc(-c3cccc4c3OC(C)(c3ccc(Cl)cc3F)O4)[nH]c2=O)nc2ccc(C(=O)O)cc21] | 86 | 2-((6-(2-(4-chloro-2-fluorophenyl)-2-methylbenzo[d][1,3]dioxol-4-yl)-2-oxo-1,2-dihydropyridin-3-yl)methyl)-1-(2-methoxyethyl)-1H-benzo[d]imidazole-6-carboxylic acid | 23 | 590.2 |
| 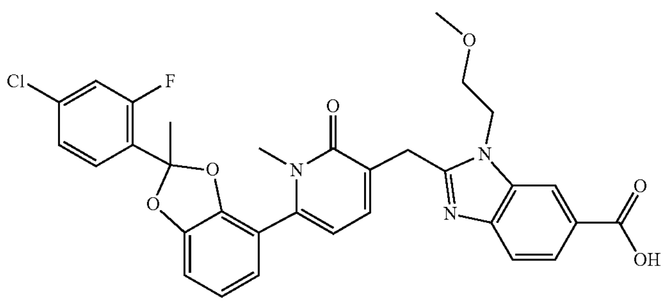 [SMILES: COCCn1c(Cc2ccc(-c3cccc4c3OC(C)(c3ccc(Cl)cc3F)O4)n(C)c2=O)nc2ccc(C(=O)O)cc21] | 87 | 2-((6-(2-(4-chloro-2-fluorophenyl)-2-methylbenzo[d][1,3]dioxol-4-yl)-1-methyl-2-oxo-1,2-dihydropyridin-3-yl)methyl)-1-(2-methoxyethyl)-1H-benzo[d]imidazole-6-carboxylic acid | 24 | 604.2 |
| 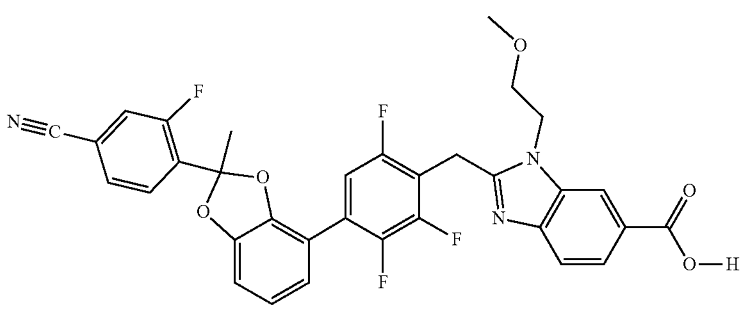 [SMILES: COCCn1c(Cc2c(F)cc(-c3cccc4c3OC(C)(c3ccc(C#N)cc3F)O4)c(F)c2F)nc2ccc(C(=O)O)cc21] | 88 | 2-(4-(2-(4-cyano-2-fluorophenyl)-2-methylbenzo[d][1,3]dioxol-4-yl)-2,3,6-trifluorobenzyl)-1-(2-methoxyethyl)-1H-benzo[d]imidazole-6-carboxylic acid | 25 | 618.3 |
| 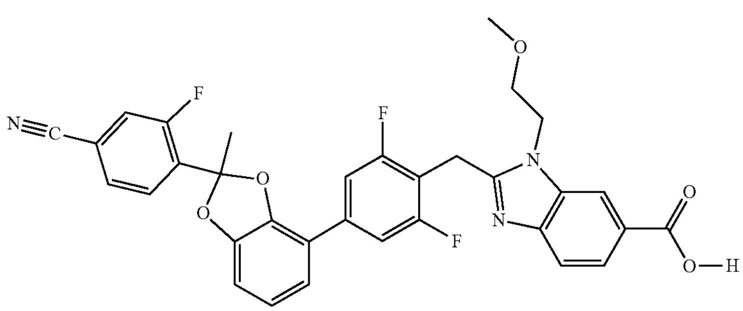 [SMILES: COCCn1c(Cc2c(F)cc(-c3cccc4c3OC(C)(c3ccc(C#N)cc3F)O4)cc2F)nc2ccc(C(=O)O)cc21] | 89 | 2-(4-(2-(4-cyano-2-fluorophenyl)-2-methylbenzo[d][1,3]dioxol-4-yl)-2,6-difluorobenzyl)-1-(2-methoxyethyl)-1H-benzo[d]imidazole-6-carboxylic acid | 25 | 600.2 |

TABLE 2-continued

| Structure | Example | Name | Procedure | ES/MS m/z |
|---|---|---|---|---|
| 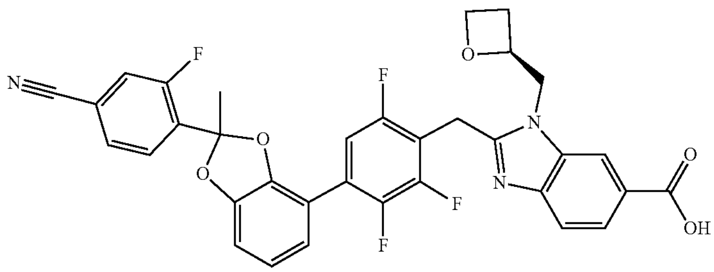 [SMILES: CC1(c2ccc(C#N)cc2F)Oc2cccc(-c3cc(F)c(Cc4nc5ccc(C(=O)O)cc5n4C[C@@H]4CCO4)c(F)c3F)c2O1] | 90 | 2-(4-(2-(4-cyano-2-fluorophenyl)-2-methylbenzo[d][1,3]dioxol-4-yl)-2,3,6-trifluorobenzyl)-1-(((S)-oxetan-2-yl)methyl)-1H-benzo[d]imidazole-6-carboxylic acid | 25 | 630.3 |
| 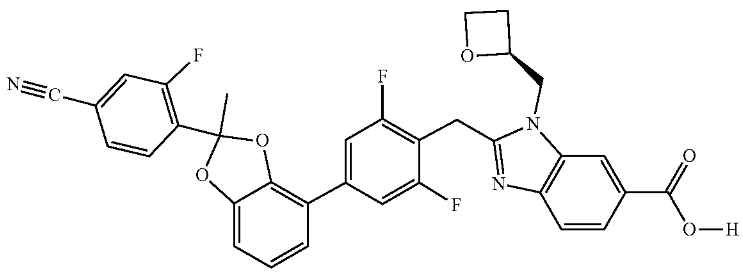 [SMILES: CC1(c2ccc(C#N)cc2F)Oc2cccc(-c3cc(F)c(Cc4nc5ccc(C(=O)O)cc5n4C[C@@H]4CCO4)c(F)c3)c2O1] | 91 | 2-(4-(2-(4-cyano-2-fluorophenyl)-2-methylbenzo[d][1,3]dioxol-4-yl)-2,6-difluorobenzyl)-1-(((S)-oxetan-2-yl)methyl)-1H-benzo[d]imidazole-6-carboxylic acid | 25 | 612.3 |
| 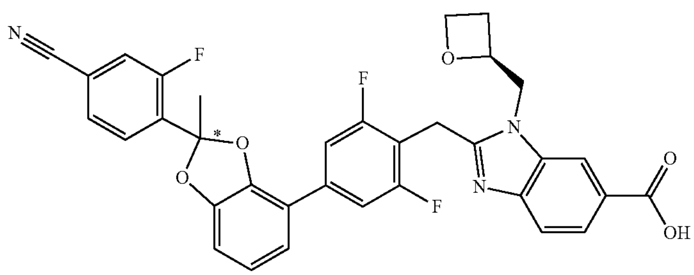 [SMILES: CC1(c2ccc(C#N)cc2F)Oc2cccc(-c3cc(F)c(Cc4nc5ccc(C(=O)O)cc5n4C[C@@H]4CCO4)c(F)c3)c2O1] | 92 | 2-(4-(2-(4-cyano-2-fluorophenyl)-2-methylbenzo[d][1,3]dioxol-4-yl)-2,6-difluorobenzyl)-1-(((S)-oxetan-2-yl)methyl)-1H-benzo[d]imidazole-6-carboxylic acid | 26 | 612.3 |
| 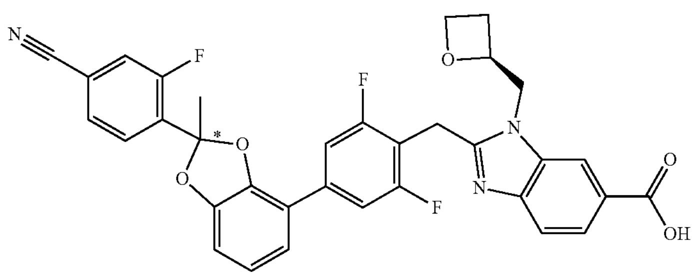 [SMILES: CC1(c2ccc(C#N)cc2F)Oc2cccc(-c3cc(F)c(Cc4nc5ccc(C(=O)O)cc5n4C[C@@H]4CCO4)c(F)c3)c2O1] | 93 | 2-(4-(2-(4-cyano-2-fluorophenyl)-2-methylbenzo[d][1,3]dioxol-4-yl)-2,6-difluorobenzyl)-1-(((S)-oxetan-2-yl)methyl)-1H-benzo[d]imidazole-6-carboxylic acid | 26 | 612.3 |
| 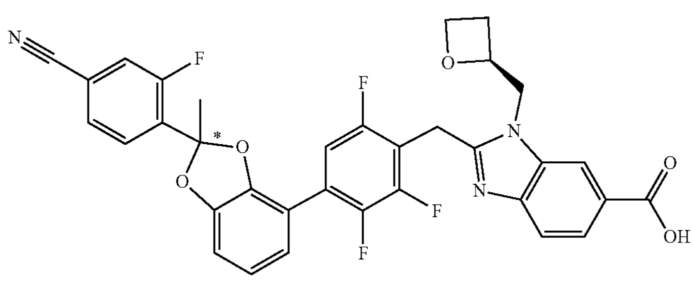 [SMILES: CC1(c2ccc(C#N)cc2F)Oc2cccc(-c3cc(F)c(Cc4nc5ccc(C(=O)O)cc5n4C[C@@H]4CCO4)c(F)c3F)c2O1] | 94 | 2-(4-(2-(4-cyano-2-fluorophenyl)-2-methylbenzo[d][1,3]dioxol-4-yl)-2,3,6-trifluorobenzyl)-1-(((S)-oxetan-2-yl)methyl)-1H-benzo[d]imidazole-6-carboxylic acid | 27 | 630.3 |

TABLE 2-continued

| Structure | Example | Name | Procedure | ES/MS m/z |
|---|---|---|---|---|
| 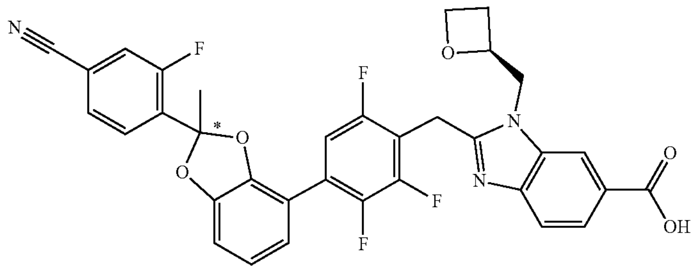 [SMILES: CC1(c2ccc(C#N)cc2F)Oc2cccc(-c3cc(F)c(Cc4nc5ccc(C(=O)O)cc5n4C[C@@H]4CCO4)c(F)c3F)c2O1] | 95 | 2-(4-(2-(4-cyano-2-fluorophenyl)-2-methylbenzo[d][1,3]dioxol-4-yl)-2,3,6-trifluorobenzyl)-1-(((S)-oxetan-2-yl)methyl)-1H-benzo[d]imidazole-6-carboxylic acid | 27 | 630.3 |
| 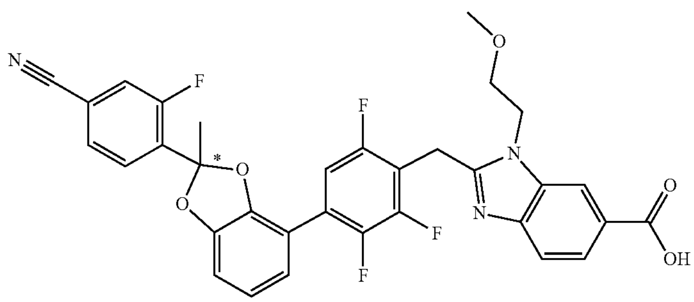 [SMILES: COCCn1c(Cc2c(F)cc(-c3cccc4c3OC(C)(c3ccc(C#N)cc3F)O4)c(F)c2F)nc2ccc(C(=O)O)cc21] | 96 | 2-(4-(2-(4-cyano-2-fluorophenyl)-2-methylbenzo[d][1,3]dioxol-4-yl)-2,3,6-trifluorobenzyl)-1-(2-methoxyethyl)-1H-benzo[d]imidazole-6-carboxylic acid | 28 | 618.5 |
| 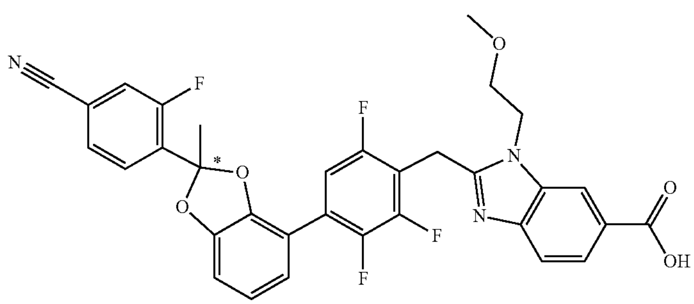 [SMILES: COCCn1c(Cc2c(F)cc(-c3cccc4c3OC(C)(c3ccc(C#N)cc3F)O4)c(F)c2F)nc2ccc(C(=O)O)cc21] | 97 | 2-(4-(2-(4-cyano-2-fluorophenyl)-2-methylbenzo[d][1,3]dioxol-4-yl)-2,3,6-trifluorobenzyl)-1-(2-methoxyethyl)-1H-benzo[d]imidazole-6-carboxylic acid | 28 | 618.5 |
| 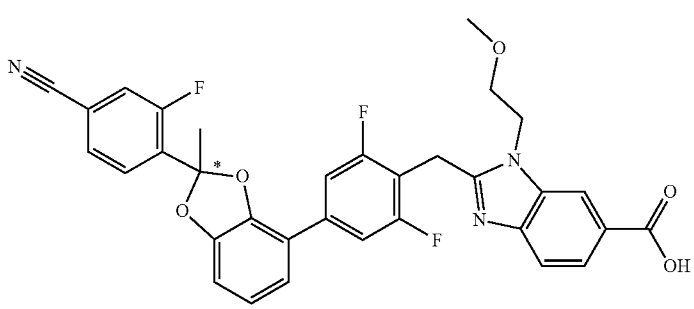 [SMILES: COCCn1c(Cc2c(F)cc(-c3cccc4c3OC(C)(c3ccc(C#N)cc3F)O4)cc2F)nc2ccc(C(=O)O)cc21] | 98 | 2-(4-(2-(4-cyano-2-fluorophenyl)-2-methylbenzo[d][1,3]dioxol-4-yl)-2,6-difluorobenzyl)-1-(2-methoxyethyl)-1H-benzo[d]imidazole-6-carboxylic acid | 29 | 600.3 |
| 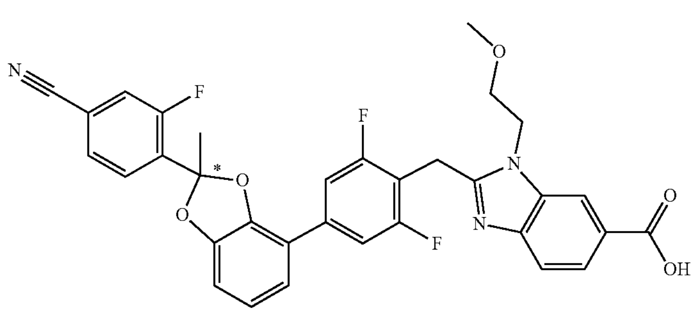 [SMILES: COCCn1c(Cc2c(F)cc(-c3cccc4c3OC(C)(c3ccc(C#N)cc3F)O4)cc2F)nc2ccc(C(=O)O)cc21] | 99 | 2-(4-(2-(4-cyano-2-fluorophenyl)-2-methylbenzo[d][1,3]dioxol-4-yl)-2,6-difluorobenzyl)-1-(2-methoxyethyl)-1H-benzo[d]imidazole-6-carboxylic acid | 29 | 600.4 |

TABLE 2-continued

| Structure | Example | Name | Procedure | ES/MS m/z |
|---|---|---|---|---|
| 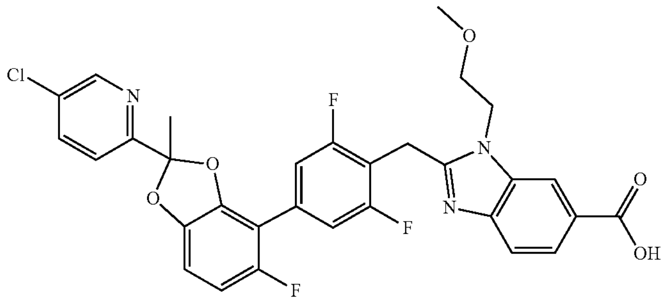 [SMILES: COCCn1c(Cc2c(F)cc(-c3c(F)ccc4c3OC(C)(c3ccc(Cl)cn3)O4)cc2F)nc2ccc(C(=O)O)cc21] | 100 | 2-(4-(2-(5-chloropyridin-2-yl)-5-fluoro-2-methylbenzo[d][1,3]dioxol-4-yl)-2,6-difluorobenzyl)-1-(2-methoxyethyl)-1H-benzo[d]imidazole-6-carboxylic acid | 30 | 610 |
| 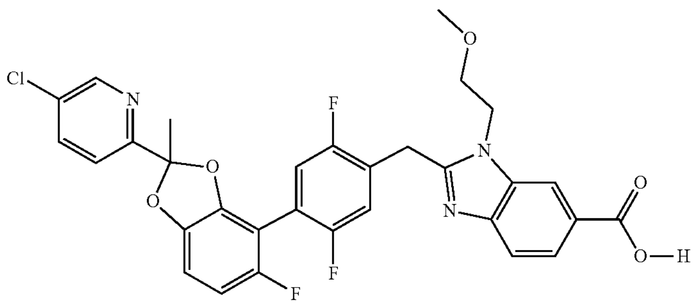 [SMILES: COCCn1c(Cc2cc(F)c(-c3c(F)ccc4c3OC(C)(c3ccc(Cl)cn3)O4)cc2F)nc2ccc(C(=O)O)cc21] | 101 | 2-(4-(2-(5-chloropyridin-2-yl)-5-fluoro-2-methylbenzo[d][1,3]dioxol-4-yl)-2,5-difluorobenzyl)-1-(2-methoxyethyl)-1H-benzo[d]imidazole-6-carboxylic acid | 30 | 610.2 |
| 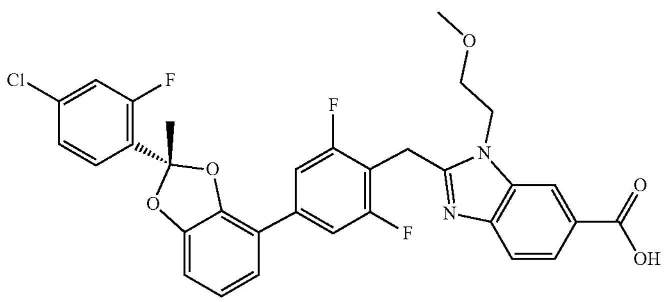 [SMILES: COCCn1c(Cc2c(F)cc(-c3cccc4c3O[C@@](C)(c3ccc(Cl)cc3F)O4)cc2F)nc2ccc(C(=O)O)cc21] | 102 | 2-(4-(2-(4-chloro-2-fluorophenyl)-2-methylbenzo[d][1,3]dioxol-4-yl)-2,6-difluorobenzyl)-1-(2-methoxyethyl)-1H-benzo[d]imidazole-6-carboxylic acid | 31 | 609.8 |
| 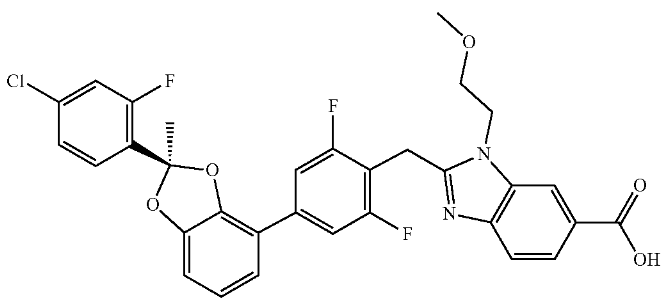 [SMILES: COCCn1c(Cc2c(F)cc(-c3cccc4c3O[C@](C)(c3ccc(Cl)cc3F)O4)cc2F)nc2ccc(C(=O)O)cc21] | 103 | 2-(4-(2-(4-chloro-2-fluorophenyl)-2-methylbenzo[d][1,3]dioxol-4-yl)-2,6-difluorobenzyl)-1-(2-methoxyethyl)-1H-benzo[d]imidazole-6-carboxylic acid | 31 | 609.7 |
| 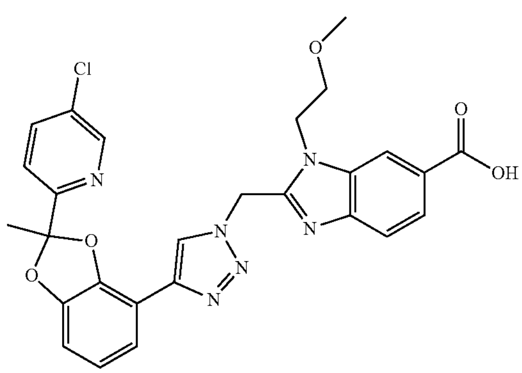 | 104 | 2-[[4-[2-(5-Chloro-2-pyridyl)-2-methyl-1,3-benzodioxol-4-yl]triazol-1-yl]methyl]-3-(2-methoxyethyl)bencarboxylic acid | 32 | 547.2 |

TABLE 2-continued

| Structure | Example | Name | Procedure | ES/MS m/z |
|---|---|---|---|---|
| 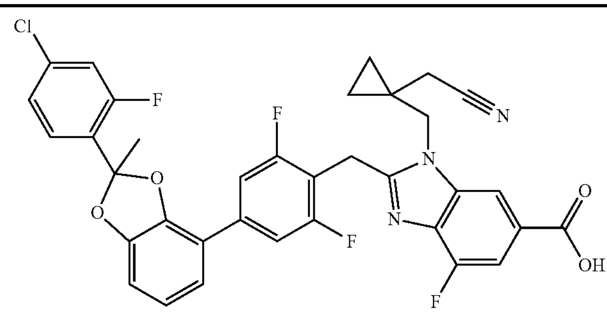 | 105 | 2-(4-(2-(4-chloro-2-fluorophenyl)-2-methylbenzo[d][1,3]dioxol-4-yl)-2,6-difluorobenzyl)-1-((1-(cyanomethyl)cyclopropyl)methyl)-4-fluoro-1H-benzo[d]imidazole-6-carboxylic acid | 33 | 662.2 |
| 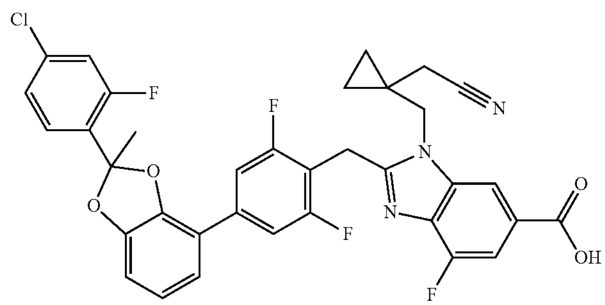 [SMILES: CC1(c2ccc(Cl)cc2F)Oc2cccc(-c3cc(F)c(Cc4nc5c(F)cc(C(=O)O)cc5n4CC4(CC#N)CC4)c(F)c3)c2O1] | 106 | 2-(4-(2-(4-chloro-2-fluorophenyl)-2-methylbenzo[d][1,3]dioxol-4-yl)-2,6-difluorobenzyl)-1-((1-(cyanomethyl)cyclopropyl)methyl)-4-fluoro-1H-benzo[d]imidazole-6-carboxylic acid | 33 | 662.2 |
| 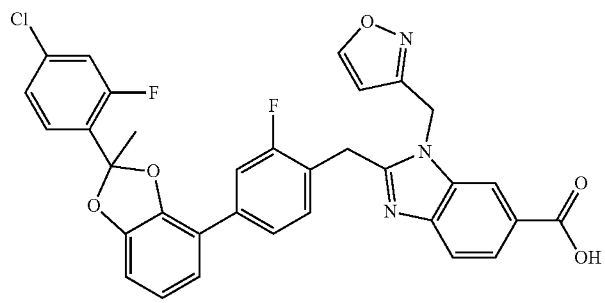 [SMILES: CC1(c2ccc(Cl)cc2F)Oc2cccc(-c3ccc(Cc4nc5ccc(C(=O)O)cc5n4Cc4ccon4)c(F)c3)c2O1] | 107 | 2-(4-(2-(4-chloro-2-fluorophenyl)-2-methylbenzo[d][1,3]dioxol-4-yl)-2-fluorobenzyl)-1-(isoxazol-3-ylmethyl)-3a,7a-dihydro-1H-benzo[d]imidazole-6-carboxylic acid | 34 | 614 |
| 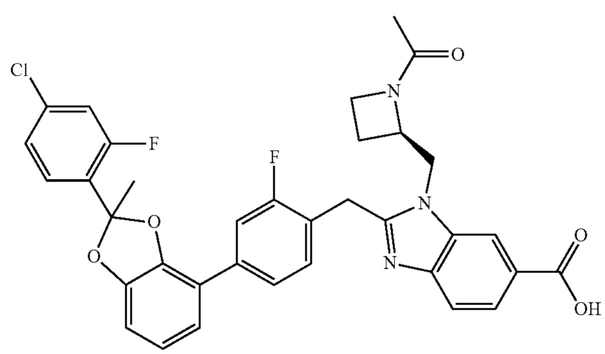 [SMILES: CC(=O)N1CC[C@@H]1Cn1c(Cc2ccc(-c3cccc4c3OC(C)(c3ccc(Cl)cc3F)O4)cc2F)nc2ccc(C(=O)O)cc21] | 108 | 3-[[(2R)-1-acetylazetidin-2-yl]methyl]-2-[[4-[2-(4-chloro-2-fluoro-phenyl)-2-methyl-1,3-benzodioxol-4-yl]-2-fluoro-phenyl]methyl]benzimidazole-5-carboxylic acid | 35 | 644.2 |
| 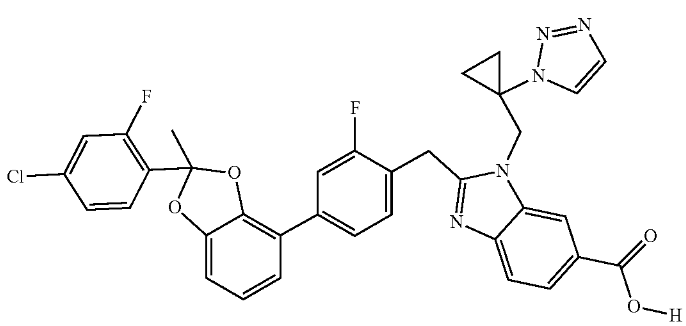 [SMILES: CC1(c2ccc(Cl)cc2F)Oc2cccc(-c3ccc(Cc4nc5ccc(C(=O)O)cc5n4CC4(n5ccnn5)CC4)c(F)c3)c2O1] | 109 | 1-((1-(1H-1,2,3-triazol-1-yl)cyclopropyl)methyl)-2-(4-(2-(4-chloro-2-fluorophenyl)-2-methylbenzo[d][1,3]dioxol-4-yl)-2-fluorobenzyl)-1H-benzo[d]imidazole-6-carboxylic acid | 35 | 654 |

TABLE 2-continued

| Structure | Example | Name | Procedure | ES/MS m/z |
|---|---|---|---|---|
| 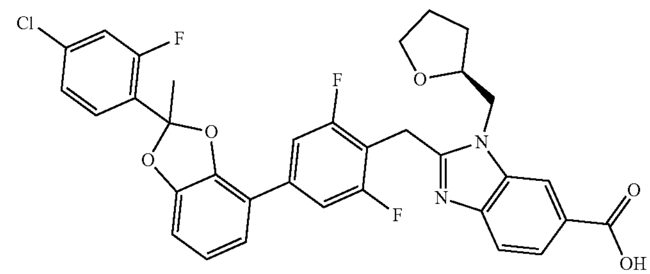 [SMILES: CC1(c2ccc(Cl)cc2F)Oc2cccc(-c3cc(F)c(Cc4nc5ccc(C(=O)O)cc5n4C[C@@H]4CCCO4)c(F)c3)c2O1] | 110 | 2-[[4-[2-(4-chloro-2-fluoro-phenyl)-2-methyl-1,3-benzodioxol-4-yl]-2,5-difluoro-phenyl]methyl]-3-[[(2S)-tetrahydrofuran-2-yl]methyl]benzimidazole-5-carboxylic acid | 36 | 636.2 |
| 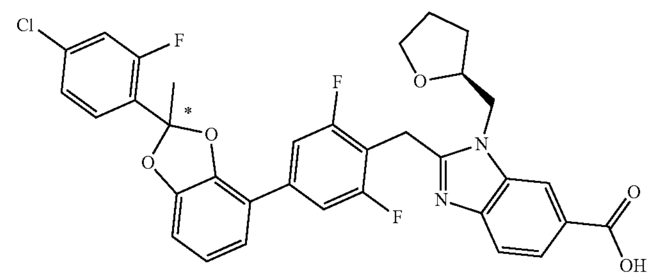 [SMILES: CC1(c2ccc(Cl)cc2F)Oc2cccc(-c3cc(F)c(Cc4nc5ccc(C(=O)O)cc5n4C[C@@H]4CCCO4)c(F)c3)c2O1] | 111 | 2-[[4-[2-(4-chloro-2-fluoro-phenyl)-2-methyl-1,3-benzodioxol-4-yl]-2,5-difluoro-phenyl]methyl]-3-[[(2S)-tetrahydrofuran-2-yl]methyl]benzimidazole-5-carboxylic acid | 37 | 635.1 |
| 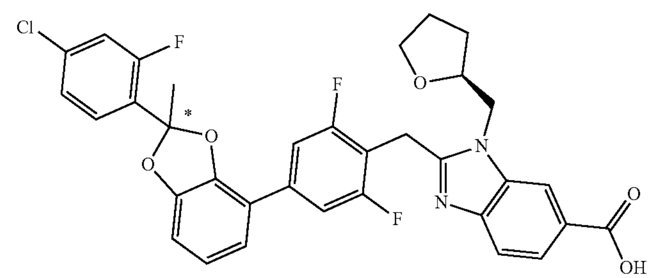 [SMILES: CC1(c2ccc(Cl)cc2F)Oc2cccc(-c3cc(F)c(Cc4nc5ccc(C(=O)O)cc5n4C[C@@H]4CCCO4)c(F)c3)c2O1] | 112 | 2-[[4-[2-(4-chloro-2-fluoro-phenyl)-2-methyl-1,3-benzodioxol-4-yl]-2,5-difluoro-phenyl]methyl]-3-[[(2S)-tetrahydrofuran-2-yl]methyl]benzimidazole-5-carboxylic acid | 37 | 635.1 |
| 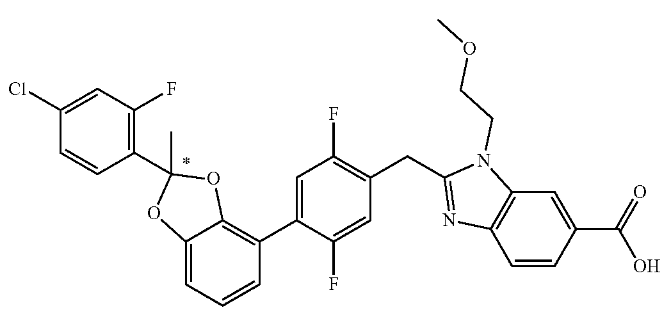 [SMILES: COCCn1c(Cc2cc(F)c(-c3cccc4c3OC(C)(c3ccc(Cl)cc3F)O4)cc2F)nc2ccc(C(=O)O)cc21] | 113 | 2-[[4-[2-(4-chloro-2-fluoro-phenyl)-2-methyl-1,3-benzodioxol-4-yl]-2,5-difluoro-phenyl]methyl]-3-(2-methoxyethyl)benzimidazole-5-carboxylic acid | 38 | 609.2 |
| 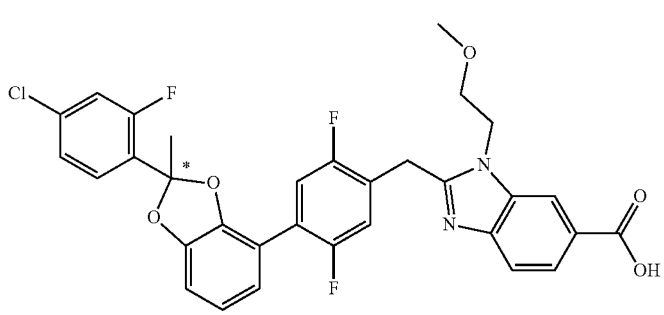 [SMILES: COCCn1c(Cc2cc(F)c(-c3cccc4c3OC(C)(c3ccc(Cl)cc3F)O4)cc2F)nc2ccc(C(=O)O)cc21] | 114 | 2-[[4-[2-(5-chloro-2-pyridyl)-2-methyl-1,3-benzodioxol-4-yl]-2,5-difluoro-phenyl]methyl]-3-(2-methoxyethyl)benzimidazole-5-carboxylic acid | 39 | 592.2 |

Characterization data obtained for compounds synthesized according to the disclosure is included in Table 3, below.

TABLE 3

| Example | 1H-NMR |
|---|---|
| 1 | 1H NMR (400 MHz, MeOD) δ 8.56 (dd, J = 1.4, 0.7 Hz, 1H), 8.14 (dd, J = 8.6, 1.4 Hz, 1H), 7.71 (dd, J = 8.5, 0.6 Hz, 1H), 7.64-7.53 (m, 3H), 7.31 (dd, J = 10.9, 2.0 Hz, 1H), 7.23 (ddd, J = 8.4, 2.0, 0.8 Hz, 1H), 7.20 (dd, J = 7.8, 1.5 Hz, 1H), 7.03-6.93 (m, 2H), 4.76 (s, 2H), 4.73 (s, 2H), 2.64 (s, 2H), 2.12 (d, J = 1.0 Hz, 3H), 1.03-0.96 (m, 2H), 0.96-0.88 (m, 2H). |
| 2 | 1H NMR (400 MHz, DMSO-d6) δ 7.67-7.53 (m, 5H), 7.44-7.35 (m, 2H), 7.31 (dd, J = 8.0, 1.3 Hz, 1H), 7.07 (dd, J = 7.8, 1.3 Hz, 1H), 7.01 (t, J = 7.9 Hz, 1H), 5.18-5.10 (m, 1H), 4.85 (dd, J = 15.6, 7.1 Hz, 1H), 4.69 (dd, J = 15.7, 2.8 Hz, 1H), 4.62-4.51 (m, 2H), 4.49-4.35 (m, 2H), 2.90-2.70 (m, 1H), 2.47-2.37 (m, 1H), 2.12 (s, 3H). |
| 3 | 1H NMR (400 MHz, Methanol-d4) δ 8.41-8.37 (m, 1H), 8.01 (dd, J = 8.6, 1.6 Hz, 1H), 7.76 (dd, J = 8.6, 0.7 Hz, 1H), 7.65-7.54 (m, 3H), 7.34 (dd, J = 11.0, 2.0 Hz, 1H), 7.29-7.24 (m, 1H), 7.21 (dd, J = 7.8, 1.5 Hz, 1H), 7.05-6.95 (m, 2H), 4.85 (s, 3H), 4.78 (t, J = 5.0 Hz, 2H), 4.73 (s, 2H), 3.87 (t, J = 4.9 Hz, 2H), 3.25-3.17 (m, 1H), 2.14 (s, 3H), 1.41-1.28 (m, 2H), 1.23-1.10 (m, 2H). |
| 4 | 1H NMR (400 MHz, Methanol-d4) δ 8.53 (d, J = 1.4 Hz, 1H), 8.20 (dd, J = 8.6, 1.5 Hz, 1H), 7.85-7.78 (m, 1H), 7.78-7.63 (m, 4H), 7.49 (t, J = 8.0 Hz, 1H), 7.46 (s, 1H), 7.23 (dd, J = 8.0, 1.3 Hz, 1H), 7.06 (t, J = 7.9 Hz, 1H), 6.99 (dd, J = 7.8, 1.2 Hz, 1H), 4.78 (t, J = 5.0 Hz, 2H), 4.73 (s, 2H), 3.85-3.73 (m, 2H), 3.30 (s, 3H). |
| 5 | 1H NMR (400 MHz, Methanol-d4) δ 8.54 (d, J = 1.5 Hz, 1H), 8.21 (dd, J = 8.5, 1.6 Hz, 1H), 7.86-7.62 (m, 4H), 7.51-7.40 (m, 2H), 7.35 (dd, J = 10.0, 6.2 Hz, 1H), 7.12-6.98 (m, 3H), 4.80 (t, J = 5.0 Hz, 2H), 4.74 (s, 2H), 3.83 (t, J = 4.9 Hz, 2H), 3.30 (s, 3H). |
| 6 | 1H NMR (400 MHz, Methanol-d4) δ 8.55 (d, J = 1.3 Hz, 1H), 8.22 (dd, J = 8.6, 1.4 Hz, 1H), 7.86 (d, J = 8.4 Hz, 2H), 7.83-7.63 (m, 5H), 7.51 (t, J = 8.0 Hz, 1H), 7.26-7.20 (m, 2H), 7.03 (d, J = 8.0 Hz, 1H), 6.98 (dd, J = 7.8, 1.2 Hz, 1H), 4.80 (t, J = 5.0 Hz, 2H), 4.75 (s, 2H), 3.81 (t, J = 4.9 Hz, 2H), 3.31 (s, 3H). |
| 7 | 1H NMR (400 MHz, DMSO-d6) δ 8.31 (d, J = 1.5 Hz, 1H), 7.89 (dd, J = 8.5, 1.5 Hz, 1H), 7.67 (d, J = 8.5 Hz, 1H), 7.65-7.58 (m, 2H), 7.49-7.37 (m, 6H), 7.37-7.31 (m, 1H), 7.28 (dd, J = 7.3, 1.3 Hz, 1H), 7.01 (t, J = 7.6 Hz, 1H), 5.92 (dd, J = 9.4, 8.1 Hz, 1H), 4.64 (t, J = 5.2 Hz, 2H), 4.51 (s, 2H), 3.75 (dd, J = 15.9, 9.4 Hz, 1H), 3.66 (t, J = 5.0 Hz, 2H), 3.25-3.14 (m, 4H). |
| 8 | 1H NMR (400 MHz, DMSO) δ 12.83 (s, 1H), 8.21 (d, J = 1.6 Hz, 1H), 7.66 (d, J = 8.5 Hz, 1H), 7.60-7.54 (m, 2H), 7.51 (d, J = 3.7 Hz, 1H), 7.35 (dd, J = 8.4, 2.1 Hz, 1H), 7.18-7.12 (m, 1H), 7.11 (d, J = 3.7 Hz, 1H), 6.94-6.79 (m, 2H), 4.64 (s, 2H), 4.56 (t, J = 5.0 Hz, 2H), 3.61 (t, J = 5.1 Hz, 2H), 3.19 (s, 3H), 2.10 (s, 3H). |
| 9 | 1H NMR (400 MHz, Methanol-d4) δ 8.24 (d, J = 1.2 Hz, 1H), 7.70-7.55 (m, 2H), 7.51 (d, J = 9.0 Hz, 2H), 7.33 (dd, J = 10.9, 2.0 Hz, 1H), 7.27-7.14 (m, 2H), 7.07-6.87 (m, 2H), 4.69 (s, 2H), 4.57 (s, 2H), 2.26 (s, 2H), 2.13 (d, J = 1.0 Hz, 3H), 0.96-0.80 (m, 1H). |
| 10 | 1H NMR (400 MHz, Methanol-d4) δ 8.54 (t, J = 1.0 Hz, 1H), 8.21 (dd, J = 8.6, 1.4 Hz, 1H), 8.08-8.00 (m, 2H), 7.76 (d, J = 8.6 Hz, 1H), 7.57-7.50 (m, 2H), 7.41-7.33 (m, 2H), 7.33-7.21 (m, 2H), 7.00 (t, J = 7.8 Hz, 1H), 4.85-4.81 (m, 2H), 4.78 (s, 2H), 3.88-3.81 (m, 2H), 3.47 (t, J = 6.4 Hz, 2H), 3.32 (s, 3H), 2.94 (t, J = 6.4 Hz, 2H). |
| 11 | 1H NMR (400 MHz, Methanol-d4) δ 8.52 (dd, J = 1.5, 0.7 Hz, 1H), 8.19 (dd, J = 8.6, 1.4 Hz, 1H), 7.75 (dd, J = 8.6, 0.6 Hz, 1H), 7.72 (d, J = 3.9 Hz, 1H), 7.56 (d, J = 9.0 Hz, 2H), 7.44 (d, J = 3.9 Hz, 1H), 7.25 (dd, J = 8.1, 1.2 Hz, 1H), 7.06 (t, J = 8.0 Hz, 1H), 6.99 (dd, J = 7.8, 1.2 Hz, 1H), 4.82 (t, J = 4.9 Hz, 2H), 4.78 (s, 2H), 3.85 (dd, J = 5.4, 4.4 Hz, 2H), 3.32 (s, 3H), 2.21 (s, 3H). |
| 12 | 1H NMR (400 MHz, Acetonitrile-d3) δ 8.67 (dd, J = 2.5, 0.8 Hz, 1H), 8.32 (s, 1H), 7.95 (d, J = 8.3 Hz, 1H), 7.87 (dd, J = 8.5, 2.5 Hz, 1H), 7.69 (d, J = 8.5, 0.8 Hz, 1H), 7.63 (d, J = 8.4 Hz, 1H), 7.51 (d, J = 8.8 Hz, 2H), 7.20 (dd, J = 7.9, 1.3 Hz, 1H), 7.10-6.88 (m, 2H), 4.61-4.50 (m, 2H), 4.47 (s, 2H), 4.27 (s, 1H), 4.14 (s, 1H), 2.14 (s, 3H), 0.91 (d, J = 5.3 Hz, 2H), 0.83 (d, J = 5.0 Hz, 2H). |
| 13 | 1H NMR (400 MHz, Methanol-d4) δ 8.24 (d, J = 1.2 Hz, 1H), 7.73-7.57 (m, 2H), 7.57-7.46 (m, 2H), 7.32 (dd, J = 10.9, 2.0 Hz, 1H), 7.28-7.15 (m, 2H), 7.06-6.81 (m, 2H), 4.66 (s, 2H), 4.55 (s, 2H), 2.61 (s, 2H), 2.13 (d, J = 1.0 Hz, 3H), 0.98-0.79 (m, 4H). |
| 14 | 1H NMR (400 MHz, MeOD) δ 8.80 (t, J = 1.6 Hz, 1H), 8.63 (dd, J = 2.5, 0.7 Hz, 1H), 8.54 (dd, J = 1.5, 0.7 Hz, 1H), 8.17 (dd, J = 8.6, 1.5 Hz, 1H), 8.08 (dd, J = 10.8, 1.8 Hz, 1H), 7.90 (dd, J = 8.5, 2.4 Hz, 1H), 7.78 (dd, J = 8.6, 0.6 Hz, 1H), 7.69 (dd, J = 8.5, 0.7 Hz, 1H), 7.22 (dd, J = 7.9, 1.4 Hz, 1H), 7.06-6.96 (m, 2H), 5.29-5.19 (m, 1H), 4.96 (dd, J = 15.6, 7.3 Hz, 1H), 4.81 (dd, J = 15.5, 2.6 Hz, 1H), 4.65 (ddd, J = 8.5, 7.4, 5.9 Hz, 1H), 4.48 (dtd, J = 9.2, 5.9, 1.3 Hz, 1H), 2.90-2.77 (m, 1H), 2.61-2.48 (m, 1H), 2.11 (s, 3H). 2H obscured by solvent. |

TABLE 3-continued

| Example | 1H-NMR |
|---|---|
| 15 | 1H NMR (400 MHz, Methanol-d4) δ 8.55 (dd, J = 1.5, 0.7 Hz, 1H), 8.19 (dd, J = 8.6, 1.4 Hz, 1H), 7.79 (dd, J = 8.5, 0.7 Hz, 1H), 7.71-7.49 (m, 2H), 7.38-7.15 (m, 4H), 7.02-6.79 (m, 3H), 5.20 (tt, J = 7.3, 3.9 Hz, 1H), 5.02-4.92 (m, 1H), 4.81-4.74 (m, 3H), 4.69 (td, J = 7.8, 5.9 Hz, 1H), 4.61-4.46 (m, 1H), 3.68 (s, 1H), 3.37 (s, 1H), 2.96-2.74 (m, 1H), 2.56 (ddt, J = 11.5, 9.2, 7.2 Hz, 1H), 2.05 (d, J = 1.1 Hz, 3H). |
| 16 | 1H NMR (400 MHz, DMSO-d6) δ 12.75 (s, 1H), 8.19 (s, 1H), 7.84-7.73 (m, 1H), 7.63 (d, J = 8.4 Hz, 2H), 7.56 (d, J = 8.4 Hz, 1H), 7.49 (dd, J = 8.6, 3.9 Hz, 4H), 7.27-7.15 (m, 1H), 7.08-6.88 (m, 2H), 4.63 (t, J = 5.1 Hz, 2H), 4.42 (s, 2H), 3.72 (t, J = 5.0 Hz, 2H), 3.62 (dt, J = 10.7, 7.4 Hz, 1H), 3.45-3.36 (m, 1H), 3.24 (s, 3H), 2.66 (dt, J = 12.8, 6.1 Hz, 1H), 2.31 (dt, J = 14.4, 7.6 Hz, 1H), 1.93-1.78 (m, 2H). |
| 17 | 1H NMR (400 MHz, Methanol-d4) δ 8.58 (s, 1H), 8.28-8.22 (m, 1H), 8.12-8.01 (m, 2H), 7.78 (d, J = 8.6 Hz, 1H), 7.71 (t, J = 8.6 Hz, 4H), 7.59-7.44 (m, 3H), 4.86-4.83 (m, 4H), 3.87 (t, J = 4.9 Hz, 2H), 3.74 (t, J = 6.6 Hz, 2H), 3.46 (t, J = 6.5 Hz, 2H), 3.32 (s, 3H). |
| 18 | 1H NMR (400 MHz, Methanol-d4) δ 8.47 (d, J = 1.4 Hz, 1H), 8.12 (dd, J = 8.6, 1.5 Hz, 1H), 7.99 (d, J = 7.2 Hz, 1H), 7.76-7.69 (m, 1H), 7.62 (t, J = 8.3 Hz, 1H), 7.48 (d, J = 10.3 Hz, 1H), 7.34-7.18 (m, 2H), 7.09-6.94 (m, 3H), 5.35-5.19 (m, 1H), 4.85-4.56 (m, 4H), 4.50 (dtd, J = 9.2, 6.0, 1.5 Hz, 1H), 3.73-3.62 (m, 2H), 2.86 (dtd, J = 11.4, 8.2, 6.0 Hz, 1H), 2.56 (ddt, J = 11.6, 9.2, 7.2 Hz, 1H), 2.09 (d, J = 1.0 Hz, 3H). |
| 19 | 1H NMR (400 MHz, Methanol-d4) δ 8.55-8.50 (m, 1H), 8.19 (dd, J = 8.6, 1.4 Hz, 1H), 7.75 (d, J = 8.6 Hz, 1H), 7.65-7.57 (m, 3H), 7.34 (dd, J = 11.0, 2.0 Hz, 1H), 7.28-7.19 (m, 2H), 7.05-6.95 (m, 2H), 4.88 (s, 3H), 4.82 (t, J = 5.0 Hz, 2 H), 4.78 (s, 2H), 3.85 (t, J = 4.9 Hz, 2H), 2.14 (s, 3H). |
| 20 | 1H NMR (400 MHz, DMSO-d6) δ 8.26 (d, J = 1.5 Hz, 1H), 7.78 (dd, J = 8.4, 1.6 Hz, 1H), 7.69-7.55 (m, 3H), 7.45-7.30 (m, 2H), 7.11 (dd, J = 7.2, 1.8 Hz, 1H), 7.08-6.96 (m, 2H), 5.13 (qd, J = 6.9, 2.7 Hz, 1H), 4.81 (dd, J = 15.7, 6.8 Hz, 1H), 4.74-4.58 (m, 2H), 4.58-4.45 (m, 2H), 4.34 (dt, J = 9.0, 5.9 Hz, 1H), 2.83-2.65 (m, 1H), 2.39 (ddt, J = 11.3, 9.0, 7.0 Hz, 1H), 2.08 (s, 3H). |
| 21 | 1H NMR (400 MHz, Methanol-d4) δ 8.16 (d, J = 8.3 Hz, 1H), 8.04 (d, J = 8.3 Hz, 1H), 7.62 (t, J = 8.3 Hz, 1H), 7.58-7.50 (m, 2H), 7.33 (dd, J = 10.9, 2.0 Hz, 1H), 7.25 (ddd, J = 8.4, 2.0, 0.8 Hz, 1H), 7.20 (dd, J = 7.9, 1.3 Hz, 1H), 7.03-6.93 (m, 2H), 4.72 (s, 2H), 4.63 (s, 2H), 4.39 (s, 1H), 2.14 (d, J = 1.0 Hz, 3H), 1.23 (dt, J = 6.4, 4.9 Hz, 2H), 0.84-0.72 (m, 2H). |
| 22 | 1H NMR (400 MHz, DMSO) δ 12.79 (s, 1H), 8.27 (s, 1H), 7.79 (dd, J = 8.4, 1.5 Hz, 1H), 7.60 (ddd, J = 13.9, 10.0, 7.3 Hz, 5H), 7.38 (dd, J = 8.4, 2.1 Hz, 1H), 7.31 (d, J = 7.9 Hz, 1H), 7.20-6.92 (m, 2H), 5.12 (dt, J = 9.1, 4.6 Hz, 1H), 4.81 (dd, J = 15.7, 6.8 Hz, 1H), 4.68 (dd, J = 15.7, 2.7 Hz, 1H), 4.61-4.40 (m, 3H), 4.35 (dt, J = 9.0, 6.0 Hz, 1H), 2.75 (dd, J = 12.3, 6.2 Hz, 1H), 2.44-2.32 (m, 1H), 2.12 (s, 3H). |
| 23 | 1H NMR (400 MHz, DMSO-d6) δ 8.31 (d, J = 1.5 Hz, 1H), 7.89 (dd, J = 8.5, 1.5 Hz, 1H), 7.67 (d, J = 8.5 Hz, 1H), 7.65-7.58 (m, 2H), 7.49-7.37 (m, 6H), 7.37-7.31 (m, 1H), 7.28 (dd, J = 7.3, 1.3 Hz, 1H), 7.01 (t, J = 7.6 Hz, 1H), 5.92 (dd, J = 9.4, 8.1 Hz, 1H), 4.64 (t, J = 5.2 Hz, 2H), 4.51 (s, 2H), 3.75 (dd, J = 15.9, 9.4 Hz, 1H), 3.66 (t, J = 5.0 Hz, 2H), 3.25-3.14 (m, 4H). |
| 24 | 1H NMR (400 MHz, MeOD) δ 8.63 (dd, J = 2.5, 0.7 Hz, 1H), 8.57 (d, J = 1.4 Hz, 1H), 8.15 (dd, J = 8.6, 1.4 Hz, 1H), 7.90 (dd, J = 8.5, 2.5 Hz, 1H), 7.71 (d, J = 8.6 Hz, 1H), 7.69 (dd, J = 8.4, 0.8 Hz, 1H), 7.62-7.52 (m, 2H), 7.19 (dd, J = 7.9, 1.4 Hz, 1H), 7.00 (t, J = 7.9 Hz, 1H), 6.95 (dd, J = 7.8, 1.3 Hz, 1H), 4.76 (s, 2H), 4.73 (s, 2H), 2.64 (s, 2H), 2.11 (s, 3H), 1.03-0.96 (m, 2H), 0.96-0.88 (m, 2H). |
| 25 | 1H NMR (400 MHz, MeOD) δ 8.43 (s, 1H), 8.12-8.05 (m, 1H), 7.83 (t, J = 7.7 Hz, 1H), 7.73 (d, J = 8.5 Hz, 1H), 7.67 (dd, J = 10.6, 1.5 Hz, 1H), 7.61 (dd, J = 8.0, 1.6 Hz, 1H), 7.39 (dd, J = 10.0, 6.0 Hz, 1H), 7.27 (dd, J = 10.2, 6.2 Hz, 1H), 7.03-6.94 (m, 3H), 5.23 (d, J = 7.2 Hz, 1H), 4.83 (d, J = 7.2 Hz, 0H), 4.76-4.57 (m, 4H), 4.54-4.42 (m, 1H), 2.83 (q, J = 8.7, 7.8 Hz, 1H), 2.60-2.46 (m, 1H), 1.31 (s, 3H). 1H obscured by solvent. |
| 26 | 1H NMR (400 MHz, MeOD) δ 8.64 (dd, J = 2.4, 0.7 Hz, 1H), 8.40-8.35 (m, 1H), 8.02 (dd, J = 8.5, 1.5 Hz, 1H), 7.95-7.87 (m, 2H), 7.70 (dd, J = 8.5, 2.4 Hz, 2H), 7.21 (dd, J = 7.2, 2.1 Hz, 1H), 7.07 (d, J = 1.9 Hz, 1H), 7.05-6.98 (m, 2H), 6.95 (dd, J = 7.2, 2.0 Hz, 1H), 5.73 (dd, J = 15.9, 2.6 Hz, 1H), 5.55 (dd, J = 15.9, 2.4 Hz, 1H), 5.24 (d, J = 7.7 Hz, 1H), 4.94 (dd, J = 15.7, 6.9 Hz, 1H), 4.79 (d, J = 15.5 Hz, 1H), 4.65 (q, J = 7.3 Hz, 1H), 4.52-4.40 (m, 1H), 2.83 (dt, J = 15.9, 8.0 Hz, 1H), 2.59-2.44 (m, 1H), 2.11 (s, 3H). |
| 27 | 1H NMR (400 MHz, DMSO) δ 12.76 (s, 1H), 8.75 (d, J = 2.4 Hz, 1H), 8.25 (d, J = 1.6 Hz, 1H), 8.04 (dd, J = 8.5, 2.5 Hz, 1H), 7.85-7.63 (m, 2H), 7.56 (t, J = 8.1 Hz, 3H), 7.29 (dd, J = 7.3, 1.9 Hz, 1H), 7.13-6.89 (m, 2H), 5.11 (td, J = 8.5, 6.0 Hz, 1H), 4.80 (dd, J = 15.7, 6.9 Hz, 1H), 4.67 (dd, J = 15.5, 2.7 Hz, 1H), 4.59-4.39 (m, 3H), 4.34 (dt, J = 9.0, 5.9 Hz, 1H), 4.03 (s, 1H), 2.83-2.69 (m, 1H), 2.39 (ddd, J = 11.1, 8.9, 5.2 Hz, 1H), 2.12 (s, 3H). |

TABLE 3-continued

| Example | 1H-NMR |
|---|---|
| 28 | 1H NMR (400 MHz, Methanol-d4) δ 8.61-8.54 (m, 1H), 8.22 (dd, J = 8.6, 1.6 Hz, 1H), 7.79 (d, J = 8.6 Hz, 1H), 7.63 (t, J = 8.3 Hz, 1H), 7.41 (ddd, J = 23.1, 10.0, 6.0 Hz, 2H), 7.31 (dd, J = 10.9, 2.1 Hz, 1H), 7.24 (dd, J = 8.5, 2.0 Hz, 1H), 7.03-6.94 (m, 3H), 5.26 (qd, J = 7.4, 2.4 Hz, 1H), 5.00 (dd, J = 15.5, 7.6 Hz, 1H), 4.88-4.65 (m, 4H), 4.62-4.49 (m, 1H), 2.95-2.79 (m, 1H), 2.64-2.51 (m, 1H), 2.07 (s, 3H). |
| 29 | 1H NMR (400 MHz, Methanol-d4) δ 8.69-8.56 (m, 2H), 8.26-8.18 (m, 1H), 7.92 (dd, J = 8.3, 2.6 Hz, 1H), 7.78 (d, J = 8.5 Hz, 1H), 7.71 (d, J = 8.5 Hz, 1H), 7.45 (dd, J = 10.0, 5.8 Hz, 1H), 7.37 (dd, J = 9.9, 5.9 Hz, 1H), 6.99 (ddt, J = 9.6, 6.7, 4.1 Hz, 3H), 5.34-5.18 (m, 1H), 5.00 (dd, J = 15.5, 7.5 Hz, 1H), 4.87-4.65 (m, 4H), 4.54 (dt, J = 8.9, 5.8 Hz, 1H), 2.95-2.76 (m, 1H), 2.65-2.47 (m, 1H), 2.07 (s, 3H). |
| 30 | 1H NMR (400 MHz, Methanol-d4) δ 8.52 (s, 1H), 8.16 (d, J = 8.5 Hz, 1H), 7.82 (t, J = 7.4 Hz, 1H), 7.78-7.63 (m, 3H), 7.57 (d, J = 9.0 Hz, 2H), 7.49 (s, 1H), 7.27 (d, J = 7.7 Hz, 1H), 7.13-6.97 (m, 2H), 5.27 (d, J = 7.5 Hz, 1H), 4.96 (dd, J = 15.3, 7.4 Hz, 1H), 4.80-4.63 (m, 4H), 4.52 (dd, J = 9.2, 5.5 Hz, 1H), 2.87 (t, J = 9.4 Hz, 1H), 2.58 (d, J = 9.6 Hz, 1H). |
| 31 | 1H NMR (400 MHz, Methanol-d4) δ 8.52 (d, J = 1.4 Hz, 1H), 8.20 (dd, J = 8.6, 1.5 Hz, 1H), 7.82 (t, J = 7.5 Hz, 1H), 7.79-7.64 (m, 3H), 7.50-7.40 (m, 2H), 7.34 (dd, J = 10.0, 6.1 Hz, 1H), 7.12-6.98 (m, 3H), 4.79 (t, J = 5.0 Hz, 2H), 4.73 (s, 2H), 3.82 (t, J = 4.9 Hz, 2H), 3.30 (s, 3H). |
| 32 | 1H NMR (400 MHz, Methanol-d4) δ 8.55 (s, 1H), 8.23 (dd, J = 8.6, 1.4 Hz, 1H), 7.76 (d, J = 8.6 Hz, 1H), 7.74-7.64 (m, 2H), 7.60 (dd, J = 7.4, 2.4 Hz, 2H), 7.56-7.42 (m, 4H), 7.19 (d, J = 8.1 Hz, 1H), 7.13 (s, 1H), 7.01 (t, J = 7.9 Hz, 1H), 6.94 (d, J = 7.7 Hz, 1H), 4.81 (t, J = 5.0 Hz, 2H), 4.76 (s, 2H), 3.80 (t, J = 4.9 Hz, 2H), 3.30 (s, 3H). |
| 33 | 1H NMR (400 MHz, Methanol-d4) δ 8.41 (s, 1H), 8.13-8.06 (m, 1H), 7.84-7.77 (m, 1H), 7.77-7.59 (m, 5H), 7.43 (d, J = 14.0 Hz, 2H), 7.25-7.17 (m, 1H), 7.04 (t, J = 7.9 Hz, 1H), 6.97 (dd, J = 7.6, 1.1 Hz, 1H), 4.67 (t, J = 5.0 Hz, 2H), 4.62 (s, 2H), 3.75 (t, J = 4.9 Hz, 2H), 3.28 (s, 3H). |
| 34 | 1H NMR (400 MHz, Methanol-d4) δ 8.41 (s, 1H), 8.11 (dd, J = 8.6, 1.5 Hz, 1H), 7.80 (t, J = 7.5 Hz, 1H), 7.77-7.57 (m, 5H), 7.43 (d, J = 12.3 Hz, 2H), 7.22 (dd, J = 8.0, 1.2 Hz, 1H), 7.04 (t, J = 7.9 Hz, 1H), 6.97 (dd, J = 7.8, 1.2 Hz, 1H), 4.67 (t, J = 5.0 Hz, 2H), 4.63 (s, 2H), 3.75 (t, J = 5.0 Hz, 2H), 3.28 (s, 3H). |
| 35 | 1H NMR (400 MHz, Methanol-d4) δ 8.52-8.48 (m, 1H), 8.19 (dd, J = 8.6, 1.4 Hz, 1H), 7.75 (d, J = 8.6 Hz, 1H), 7.72-7.64 (m, 2H), 7.64-7.56 (m, 2H), 7.52-7.42 (m, 4H), 7.19 (dd, J = 8.1, 1.2 Hz, 1H), 7.13 (s, 1H), 7.01 (t, J = 7.9 Hz, 1H), 6.93 (dd, J = 7.7, 1.2 Hz, 1H), 4.76 (t, J = 5.0 Hz, 2H), 4.71 (s, 2H), 3.79 (t, J = 4.9 Hz, 2H), 3.29 (s, 3H). |
| 36 | 1H NMR (400 MHz, Methanol-d4) δ 8.50 (t, J = 1.0 Hz, 1H), 8.18 (dd, J = 8.6, 1.4 Hz, 1H), 7.75 (d, J = 8.6 Hz, 1H), 7.71-7.64 (m, 2H), 7.63-7.57 (m, 2H), 7.51-7.40 (m, 4H), 7.19 (dd, J = 8.1, 1.2 Hz, 1H), 7.13 (s, 1H), 7.01 (t, J = 7.9 Hz, 1H), 6.93 (dd, J = 7.7, 1.2 Hz, 1H), 4.76 (t, J = 5.0 Hz, 2H), 4.71 (s, 2H), 3.78 (t, J = 4.9 Hz, 2H), 3.29 (s, 3H). |
| 37 | 1H NMR (400 MHz, Methanol-d4) δ 8.59-8.34 (m, 1H), 8.21-8.02 (m, 1H), 7.93-7.53 (m, 4H), 7.41 (d, J = 8.8 Hz, 2H), 7.37-7.21 (m, 1H), 7.15-6.89 (m, 3H), 4.79-4.71 (m, 2H), 4.67 (s, 2H), 3.86-3.73 (m, 2H), 3.28 (s, 3H). |
| 38 | 1H NMR (400 MHz, Methanol-d4) δ 8.45 (s, 1H), 8.14 (dd, J = 8.4, 1.5 Hz, 1H), 7.81 (t, J = 7.5 Hz, 1H), 7.76-7.70 (m, 2H), 7.67 (dd, J = 8.0, 1.6 Hz, 1H), 7.48-7.37 (m, 2H), 7.28 (dd, J = 10.1, 6.2 Hz, 1H), 7.12-6.97 (m, 3H), 4.73 (t, J = 5.0 Hz, 2H), 4.66 (s, 2H), 3.79 (t, J = 4.9 Hz, 2H), 3.29 (s, 3H). |
| 39 | 1H NMR (400 MHz, Methanol-d4) δ 8.50 (s, 1H), 8.18 (dd, J = 8.6, 1.6 Hz, 1H), 7.82 (t, J = 7.5 Hz, 1H), 7.78-7.64 (m, 3H), 7.49-7.40 (m, 2H), 7.31 (dd, J = 10.1, 6.2 Hz, 1H), 7.10-6.98 (m, 3H), 4.77 (t, J = 5.0 Hz, 2H), 4.70 (s, 2H), 3.81 (t, J = 5.0 Hz, 2H), 3.30 (s, 3H). |
| 40 | 1H NMR (400 MHz, Methanol-d4) δ 8.47 (s, 1H), 8.16 (dd, J = 8.5, 1.5 Hz, 1H), 7.82 (t, J = 7.4 Hz, 1H), 7.77-7.64 (m, 3H), 7.48-7.39 (m, 2H), 7.30 (dd, J = 10.0, 6.0 Hz, 1H), 7.10-6.98 (m, 3H), 4.75 (t, J = 5.1 Hz, 2H), 4.68 (s, 2H), 3.81 (t, J = 5.1 Hz, 2H), 3.29 (s, 3H). |
| 41 | 1H NMR (400 MHz, Methanol-d4) δ 8.44 (s, 1H), 8.09 (d, J = 8.5 Hz, 1H), 7.82 (t, J = 7.4 Hz, 1H), 7.72 (dd, J = 24.1, 9.1 Hz, 3H), 7.55 (d, J = 8.9 Hz, 2H), 7.49 (s, 1H), 7.26 (d, J = 7.8 Hz, 1H), 7.12-6.98 (m, 2H), 5.31-5.21 (m, 1H), 4.93-4.61 (m, 5H), 4.54-4.44 (m, 1H), 2.84 (t, J = 9.4 Hz, 1H), 2.61-2.47 (m, 1H). |
| 42 | 1H NMR (400 MHz, Methanol-d4) δ 8.47 (s, 1H), 8.11 (d, J = 8.5 Hz, 1H), 7.82 (t, J = 7.5 Hz, 1H), 7.77-7.67 (m, 3H), 7.55 (d, J = 8.9 Hz, 2H), 7.48 (s, 1H), 7.26 (d, J = 7.9 Hz, 1H), 7.11-6.98 (m, 2H), 5.26 (qd, J = 7.3, 2.4 Hz, 1H), 4.84-4.62 (m, 5H), 4.50 (dt, J = 9.1, 6.0 Hz, 1H), 2.85 (dq, J = 14.6, 7.7 Hz, 1H), 2.64-2.50 (m, 1H). |
| 43 | 1H NMR (400 MHz, Methanol-d4) δ 8.32 (s, 1H), 7.99 (d, J = 8.5 Hz, 1H), 7.68 (d, J = 8.5 Hz, 1H), 7.62 (t, J = 8.3 Hz, 1H), 7.32 (ddd, J = 19.8, 10.5, 4.0 Hz, 2H), 7.26-7.10 (m, 2H), 7.03-6.86 (m, 3H), 5.24-5.12 (m, 1H), 4.74 (dd, J = 15.7, 6.9 Hz, 1H), 4.69-4.56 (m, 3H), 4.55-4.40 (m, 2H), 2.79 (dq, J = 16.7, 7.8, 5.9 Hz, 1H), 2.58-2.41 (m, 1H), 2.06 (s, 3H). |

TABLE 3-continued

| Example | 1H-NMR |
|---|---|
| 44 | 1H NMR (400 MHz, Methanol-d4) δ 8.31 (dd, J = 1.5, 0.7 Hz, 1H), 7.99 (dd, J = 8.5, 1.5 Hz, 1H), 7.67 (dd, J = 8.5, 0.6 Hz, 1H), 7.61 (t, J = 8.3 Hz, 1H), 7.40-7.26 (m, 2H), 7.26-7.15 (m, 2H), 7.02-6.87 (m, 3H), 5.19 (qd, J = 7.0, 2.6 Hz, 1H), 4.78-4.39 (m, 7H), 2.80 (dtd, J = 11.4, 8.2, 6.1 Hz, 1H), 2.49 (ddt, J = 11.4, 9.2, 7.2 Hz, 1H), 2.06 (d, J = 1.1 Hz, 3H). |
| 45 | 1H NMR (400 MHz, Methanol-d4) δ 8.63 (dd, J = 2.4, 0.7 Hz, 1H), 8.52 (t, J = 1.0 Hz, 1H), 8.17 (dd, J = 8.6, 1.4 Hz, 1H), 7.92 (dd, J = 8.5, 2.4 Hz, 1H), 7.76 (dd, J = 8.6, 0.7 Hz, 1H), 7.71 (dd, J = 8.5, 0.7 Hz, 1H), 7.44 (dd, J = 10.0, 6.0 Hz, 1H), 7.33 (dd, J = 10.0, 6.2 Hz, 1H), 7.04-6.92 (m, 3H), 5.25 (qd, J = 7.4, 2.4 Hz, 1H), 4.99-4.64 (m, 5H), 4.52 (dt, J = 9.1, 5.9 Hz, 1H), 2.95-2.77 (m, 1H), 2.63-2.44 (m, 1H), 2.07 (s, 3H). |
| 46 | 1H NMR (400 MHz, Methanol-d4) δ 8.63 (dd, J = 2.5, 0.7 Hz, 1H), 8.54-8.46 (m, 1H), 8.15 (dd, J = 8.5, 1.4 Hz, 1H), 7.92 (dd, J = 8.5, 2.4 Hz, 1H), 7.75 (d, J = 8.5 Hz, 1H), 7.71 (dd, J = 8.5, 0.7 Hz, 1H), 7.43 (dd, J = 10.0, 6.0 Hz, 1H), 7.31 (dd, J = 10.0, 6.1 Hz, 1H), 7.04-6.93 (m, 3H), 5.23 (dd, J = 8.1, 5.8 Hz, 1H), 4.86-4.64 (m, 5H), 4.51 (dt, J = 9.2, 6.0 Hz, 1H), 2.93-2.76 (m, 1H), 2.64-2.44 (m, 1H), 2.07 (s, 3H). |
| 47 | 1H NMR (400 MHz, DMSO) δ 12.79 (s, 1H), 8.26 (d, J = 1.6 Hz, 1H), 7.78 (dd, J = 8.4, 1.6 Hz, 1H), 7.67-7.47 (m, 5H), 7.39 (dd, J = 8.4, 2.1 Hz, 1H), 7.31 (dd, J = 7.9, 1.4 Hz, 1H), 7.10-6.95 (m, 2H), 5.12 (qd, J = 6.9, 2.7 Hz, 1H), 4.81 (dd, J = 15.6, 6.8 Hz, 1H), 4.68 (dd, J = 15.6, 2.7 Hz, 1H), 4.61-4.39 (m, 3H), 4.35 (dt, J = 9.1, 5.9 Hz, 1H), 2.82-2.71 (m, 1H), 2.44-2.36 (m, 1H), 2.12 (s, 3H). |
| 48 | 1H NMR (400 MHz, DMSO) δ 12.77 (s, 1H), 8.25 (d, J = 1.6 Hz, 1H), 7.77 (dd, J = 8.4, 1.6 Hz, 1H), 7.69-7.50 (m, 5H), 7.39 (dd, J = 8.4, 2.1 Hz, 1H), 7.31 (dd, J = 7.9, 1.4 Hz, 1H), 7.16-6.93 (m, 2H), 5.12 (tt, J = 6.9, 3.3 Hz, 1H), 4.80 (dd, J = 15.7, 6.8 Hz, 1H), 4.67 (dd, J = 15.6, 2.7 Hz, 1H), 4.60-4.39 (m, 3H), 4.35 (dt, J = 9.0, 5.9 Hz, 1H), 2.78-2.71 (m, 1H), 2.45-2.35 (m, 1H), 2.12 (s, 3H). |
| 49 | 1H NMR (400 MHz, DMSO) δ 12.81 (s, 1H), 8.75 (d, J = 2.4 Hz, 1H), 8.27 (d, J = 1.5 Hz, 1H), 8.04 (dd, J = 8.5, 2.5 Hz, 1H), 7.78 (dd, J = 8.5, 1.6 Hz, 1H), 7.71 (d, J = 8.5 Hz, 1H), 7.57 (dd, J = 10.5, 8.5 Hz, 4H), 7.29 (dd, J = 7.4, 1.9 Hz, 1H), 7.22-6.91 (m, 3H), 5.11 (tt, J = 7.1, 3.7 Hz, 1H), 4.81 (dd, J = 15.6, 6.8 Hz, 1H), 4.68 (dd, J = 15.5, 2.7 Hz, 1H), 4.60-4.38 (m, 4H), 4.35 (dt, J = 9.1, 5.9 Hz, 1H), 2.74 (dq, J = 11.1, 7.6 Hz, 1H), 2.45-2.35 (m, 1H), 2.12 (s, 4H). |
| 50 | 1H NMR (400 MHz, DMSO) δ 12.79 (s, 1H), 8.75 (d, J = 2.4 Hz, 1H), 8.26 (d, J = 1.5 Hz, 1H), 8.04 (dd, J = 8.5, 2.5 Hz, 1H), 7.78 (dd, J = 8.5, 1.6 Hz, 1H), 7.71 (d, J = 8.6 Hz, 1H), 7.56 (t, J = 8.9 Hz, 4H), 7.29 (dd, J = 7.4, 2.0 Hz, 1H), 7.16-6.92 (m, 2H), 5.12 (qd, J = 6.9, 2.7 Hz, 1H), 4.81 (dd, J = 15.6, 6.8 Hz, 1H), 4.67 (dd, J = 15.6, 2.7 Hz, 1H), 4.61-4.40 (m, 4H), 4.35 (dt, J = 9.0, 5.9 Hz, 1H), 2.97-2.62 (m, 1H), 2.39 (ddt, J = 11.3, 9.1, 6.9 Hz, 1H), 2.12 (s, 4H). |
| 51 | 1H NMR (400 MHz, Methanol-d4) δ 8.19-8.08 (m, 2H), 8.06-7.95 (m, 1H), 7.78-7.53 (m, 5H), 7.46-7.34 (m, 1H), 7.31 (dd, J = 10.9, 2.1 Hz, 1H), 7.27-7.19 (m, 1H), 7.16 (dd, J = 7.9, 1.3 Hz, 1H), 7.02-6.87 (m, 2H), 5.12 (d, J = 2.1 Hz, 2H), 4.20 (d, J = 2.8 Hz, 2H), 2.10 (d, J = 1.0 Hz, 3H), 1.80-1.65 (m, 2H), 1.65-1.51 (m, 2H). |
| 52 | 1H NMR (400 MHz, DMSO-d6) δ 8.23 (s, 1H), 7.82 (dd, J = 8.4, 1.6 Hz, 1H), 7.77 (d, J = 7.9 Hz, 1H), 7.73 (d, J = 7.8 Hz, 1H), 7.62-7.57 (m, 2H), 7.54 (dd, J = 8.0, 1.8 Hz, 1H), 7.43 (m, 3H), 7.15 (dd, J = 7.6, 1.7 Hz, 1H), 6.99-6.88 (m, 3H), 4.59 (t, J = 5.0 Hz, 2H), 4.44 (s, 2H), 3.95 (s, 3H), 3.67 (t, J = 5.0 Hz, 2H), 3.21 (s, 4H). |
| 53 | 1H NMR (400 MHz, Methanol-d4) δ 8.51 (d, J = 1.3 Hz, 1H), 8.17 (dd, J = 8.6, 1.5 Hz, 1H), 7.74 (d, J = 8.5 Hz, 1H), 7.65-7.55 (m, 3H), 7.32 (dd, J = 11.0, 2.0 Hz, 1H), 7.29-7.16 (m, 2H), 7.03-6.95 (m, 2H), 4.81 (t, J = 5.0 Hz, 2H), 4.76 (s, 2H), 3.89-3.81 (m, 2H), 3.32 (s, 3H), 2.54-2.39 (m, 2H), 1.05 (t, J = 7.4 Hz, 3H). |
| 54 | 1H NMR (400 MHz, Methanol-d4) δ 8.45 (s, 1H), 8.16-8.07 (m, 1H), 7.92-7.83 (m, 1H), 7.82-7.66 (m, 5H), 7.59 (dd, J = 7.6, 1.1 Hz, 1H), 7.52 (s, 1H), 7.38 (t, J = 7.7 Hz, 1H), 7.04-6.92 (m, 2H), 4.80 (t, J = 5.0 Hz, 2H), 4.75 (s, 2H), 3.86 (t, J = 4.9 Hz, 2H), 3.32 (s, 3H). |
| 55 | 1H NMR (400 MHz, DMSO-d6) δ 8.25 (d, J = 1.5 Hz, 1H), 7.82 (dd, J = 8.5, 1.5 Hz, 1H), 7.64-7.55 (m, 3H), 7.52 (d, J = 8.3 Hz, 1H), 7.31 (dd, J = 7.9, 1.3 Hz, 1H), 7.24-7.15 (m, 2H), 7.11-6.97 (m, 2H), 4.67 (t, J = 5.1 Hz, 2H), 4.49 (s, 2H), 4.27-4.12 (m, 2H), 3.72 (t, J = 5.0 Hz, 2H), 3.24 (s, 3H), 2.47 (s, 2H), 2.14 (s, 2H). |
| 56 | 1H NMR (400 MHz, Methanol-d4) δ 8.52 (d, J = 1.7 Hz, 1H), 8.19 (dd, J = 8.6, 1.5 Hz, 1H), 7.73 (d, J = 8.6 Hz, 1H), 7.59-7.52 (m, 2H), 7.50 (d, J = 8.4 Hz, 1H), 7.31-7.14 (m, 3H), 7.03 (t, J = 8.0 Hz, 1H), 6.93 (dd, J = 7.7, 1.2 Hz, 1H), 4.81 (t, J = 5.0 Hz, 2H), 4.76 (s, 2H), 3.88-3.78 (m, 2H), 3.30 (s, 3H), 2.93 (t, J = 6.3 Hz, 2H), 2.39-2.29 (m, 2H), 2.11 (ddt, J = 12.0, 8.7, 4.3 Hz, 2H). |
| 57 | 1H NMR (400 MHz, Methanol-d4) δ 8.52 (d, J = 1.3 Hz, 1H), 8.19 (dd, J = 8.6, 1.4 Hz, 1H), 7.75 (d, J = 8.5 Hz, 1H), 7.67-7.47 (m, 3H), 7.25 (d, J = 2.2 Hz, 1H), 7.22-7.14 (m, 2H), 7.04-6.95 (m, 2H), 4.82 (t, J = 5.0 Hz, 2H), 4.78 (s, 2H), 3.84 (d, J = 5.0 Hz, 2H), 3.32 (s, 3H), 3.19-2.97 (m, 2H), 2.46-2.28 (m, 2H), 2.13 (p, J = 6.3 Hz, 2H), 1.96-1.66 (m, 2H). |

TABLE 3-continued

| Example | 1H-NMR |
|---|---|
| 58 | 1H NMR (400 MHz, Methanol-d4) δ 8.51 (t, J = 0.9 Hz, 1H), 8.18 (dd, J = 8.6, 1.4 Hz, 1H), 7.86 (q, J = 7.8 Hz, 1H), 7.74 (dt, J = 8.6, 1.1 Hz, 1H), 7.66-7.53 (m, 4H), 7.42-7.17 (m, 1H), 7.09-6.93 (m, 2H), 4.86-4.71 (m, 4H), 3.85 (dd, J = 5.3, 4.3 Hz, 2H), 3.32 (s, 3H), 2.21-2.13 (m, 3H). |
| 59 | 1H NMR (400 MHz, DMSO) δ 8.29 (d, J = 1.5 Hz, 1H), 7.89 (dd, J = 8.6, 1.5 Hz, 2H), 7.71 (d, J = 8.5 Hz, 1H), 7.61-7.54 (m, 2H), 7.50 (dd, J = 11.0, 2.0 Hz, 1H), 7.31 (dd, J = 8.4, 2.1 Hz, 1H), 7.23 (dd, J = 6.0, 3.3 Hz, 1H), 6.96-6.88 (m, 2H), 4.71 (s, 2H), 4.62 (t, J = 5.1 Hz, 2H), 3.62 (t, J = 5.1 Hz, 2H), 3.17 (s, 3H), 2.07 (s, 3H). |
| 60 | 1H NMR (400 MHz, DMSO) δ 8.25 (d, J = 1.5 Hz, 1H), 7.81 (dd, J = 8.5, 1.6 Hz, 1H), 7.60 (dd, J = 8.7, 5.5 Hz, 3H), 7.49 (d, J = 8.3 Hz, 1H), 7.28 (dd, J = 8.0, 1.3 Hz, 1H), 7.25 (d, J = 2.0 Hz, 1H), 7.06 (dd, J = 8.4, 2.0 Hz, 1H), 7.02 (dd, J = 7.7, 1.3 Hz, 1H), 6.96 (t, J = 7.9 Hz, 1H), 4.67 (t, J = 5.1 Hz, 2H), 4.49 (s, 2H), 3.92 (s, 3H), 3.73 (t, J = 5.0 Hz, 2H), 3.24 (s, 3H), 2.09 (s, 3H). |
| 61 | 1H NMR (400 MHz, DMSO) δ 8.29 (s, 1H), 8.03-7.79 (m, 1H), 7.70 (d, J = 8.5 Hz, 1H), 7.57-7.51 (m, 2H), 7.50-7.43 (m, 2H), 7.29 (dd, J = 8.4, 2.1 Hz, 1H), 7.21-7.03 (m, 1H), 6.97-6.80 (m, 2H), 4.60 (s, 2H), 4.48 (s, 2H), 3.60 (d, J = 6.8 Hz, 2H), 3.16 (s, 3H), 2.08 (s, 3H). |
| 62 | 1H NMR (400 MHz, DMSO) δ 8.10 (d, J = 1.3 Hz, 1H), 8.07-7.93 (m, 1H), 7.87-7.74 (m, 2H), 7.51 (dd, J = 11.4, 1.3 Hz, 1H), 7.43 (dd, J = 9.9, 6.1 Hz, 1H), 7.38 (dd, J = 10.4, 6.2 Hz, 1H), 7.08 (dd, J = 6.8, 2.2 Hz, 1H), 7.05-6.95 (m, 2H), 4.63 (t, J = 5.1 Hz, 2H), 4.45 (s, 2H), 3.68 (t, J = 5.1 Hz, 2H), 3.21 (s, 3H), 2.08 (s, 3H). |
| 63 | 1H NMR (400 MHz, DMSO) δ 12.82 (s, 1H), 8.29 (d, J = 1.5 Hz, 1H), 7.83 (s, 5H), 7.64 (d, J = 8.5 Hz, 1H), 7.41 (td, J = 10.1, 6.1 Hz, 2H), 7.10-7.02 (m, 1H), 6.99 (d, J = 5.3 Hz, 2H), 5.08 (qd, J = 7.4, 4.4 Hz, 1H), 4.79 (dd, J = 15.6, 7.1 Hz, 1H), 4.65 (dd, J = 15.5, 2.8 Hz, 1H), 4.61-4.41 (m, 3H), 4.36 (dtd, J = 7.9, 5.9, 1.8 Hz, 1H), 2.73 (dtd, J = 11.3, 8.2, 6.2 Hz, 1H), 2.45-2.35 (m, 1H), 2.04 (s, 3H). |
| 64 | 1H NMR (400 MHz, Methanol-d4) δ 8.65 (dd, J = 2.5, 0.7 Hz, 1H), 8.55-8.53 (m, 1H), 8.21 (dd, J = 8.6, 1.4 Hz, 1H), 7.92 (dd, J = 8.5, 2.5 Hz, 1H), 7.78-7.74 (m, 1H), 7.70 (dd, J = 8.5, 0.7 Hz, 1H), 7.62-7.56 (m, 2H), 7.21 (dd, J = 7.9, 1.4 Hz, 1H), 7.03 (t, J = 7.8 Hz, 1H), 6.98 (dd, J = 7.8, 1.4 Hz, 1H), 4.83 (t, J = 4.9 Hz, 2H), 4.79 (s, 2H), 3.85 (dd, J = 5.4, 4.4 Hz, 2H), 2.13 (s, 3H). |
| 65 | 1H NMR (400 MHz, Methanol-d4) δ 8.65 (dd, J = 2.5, 0.7 Hz, 1H), 8.52-8.49 (m, 1H), 8.18 (dd, J = 8.6, 1.4 Hz, 1H), 7.92 (dd, J = 8.5, 2.4 Hz, 1H), 7.76-7.68 (m, 2H), 7.62-7.55 (m, 2H), 7.21 (dd, J = 8.0, 1.4 Hz, 1H), 7.02 (t, J = 7.9 Hz, 1H), 6.97 (dd, J = 7.8, 1.4 Hz, 1H), 4.85 (s, 0H), 4.81 (t, J = 5.0 Hz, 2H), 4.75 (s, 2H), 3.85 (t, J = 4.9 Hz, 2H), 2.13 (s, 3H). |
| 66 | 1H NMR (400 MHz, Methanol-d4) δ 9.01 (dd, J = 2.1, 0.9 Hz, 1H), 8.51 (d, J = 1.1 Hz, 1H), 8.26 (dd, J = 8.2, 2.1 Hz, 1H), 8.18 (dd, J = 8.6, 1.5 Hz, 1H), 7.87 (dd, J = 8.3, 0.9 Hz, 1H), 7.74 (dd, J = 8.6, 0.6 Hz, 1H), 7.64-7.52 (m, 2H), 7.22 (dd, J = 7.9, 1.4 Hz, 1H), 7.07-6.96 (m, 2H), 4.81 (t, J = 5.0 Hz, 2H), 4.75 (s, 2H), 3.85 (t, J = 4.9 Hz, 2H), 3.32 (s, 3H), 2.15 (s, 3H). |
| 67 | 1H NMR (400 MHz, Methanol-d4) δ 9.10 (dd, J = 2.2, 0.9 Hz, 1H), 8.53 (t, J = 1.0 Hz, 1H), 8.31 (dd, J = 8.2, 2.3 Hz, 1H), 8.20 (dd, J = 8.6, 1.4 Hz, 1H), 8.00 (s, 1H), 7.81 (dd, J = 8.2, 0.9 Hz, 1H), 7.75 (dd, J = 8.6, 0.7 Hz, 1H), 7.60 (d, J = 9.1 Hz, 2H), 7.21 (dd, J = 7.7, 1.6 Hz, 1H), 7.09-6.95 (m, 2H), 4.82 (t, J = 5.1 Hz, 2H), 4.77 (s, 2H), 3.85 (t, J = 4.9 Hz, 2H), 3.34 (s, 3H), 3.01 (s, 1H), 2.88 (d, J = 0.7 Hz, 1H), 2.16 (s, 3H). |
| 68 | ¹H NMR (400 MHz, DMSO-d6) δ 8.84 (s, 1H), 8.27 (d, J = 1.4 Hz, 1H), 7.82 (dd, J = 8.4, 1.5 Hz, 1H), 7.74-7.49 (m, 6H), 7.38 (dd, J = 8.4, 2.1 Hz, 1H), 7.30 (dd, J = 7.9, 1.3 Hz, 1H), 7.10-6.94 (m, 2H), 6.05 (s, 2H), 4.44 (s, 2H), 4.19 (q, J = 7.3 Hz, 2H), 2.12 (s, 3H), 1.34 (t, J = 7.3 Hz, 3H). |
| 69 | ¹H NMR (400 MHz, DMSO-d6) δ 8.27 (d, J = 1.5 Hz, 1H), 8.14 (d, J = 0.8 Hz, 1H), 7.81 (dd, J = 8.4, 1.6 Hz, 1H), 7.65-7.51 (m, 5H), 7.38 (dd, J = 8.5, 2.1 Hz, 1H), 7.30 (dd, J = 8.0, 1.3 Hz, 1H), 7.22 (d, J = 0.8 Hz, 1H), 7.11-6.93 (m, 2H), 5.98 (s, 2H), 4.49 (s, 2H), 2.12 (s, 3H). |
| 70 | ¹H NMR (400 MHz, DMSO-d6) δ 8.74 (d, J = 2.4 Hz, 1H), 8.22 (d, J = 1.4 Hz, 1H), 8.06 (dd, J = 8.5, 2.5 Hz, 1H), 7.77 (dd, J = 8.4, 1.6 Hz, 1H), 7.71 (d, J = 8.5 Hz, 1H), 7.57 (d, J = 8.4 Hz, 1H), 7.37 (ddd, J = 9.7, 5.4, 2.0 Hz, 1H), 7.12-6.99 (m, 3H), 5.13 (qd, J = 6.8, 2.6 Hz, 1H), 4.79 (dd, J = 15.6, 6.7 Hz, 1H), 4.71-4.57 (m, 2H), 4.57-4.44 (m, 2H), 4.33 (dt, J = 9.0, 5.9 Hz, 1H), 2.83-2.64 (m, 1H), 2.38 (ddt, J = 11.4, 9.1, 7.1 Hz, 1H), 2.08 (s, 3H). |
| 71 | 1H NMR (400 MHz, DMSO) δ 8.27 (d, J = 1.6 Hz, 1H), 7.82-7.77 (m, 1H), 7.60 (d, J = 8.4 Hz, 1H), 7.47 (d, J = 1.4 Hz, 3H), 7.39 (d, J = 8.1 Hz, 2H), 7.30 (dd, J = 13.9, 2.5 Hz, 1H), 7.19-7.11 (m, 1H), 6.98-6.89 (m, 1H), 5.13 (qd, J = 6.8, 2.7 Hz, 1H), 4.91 (s, 2H), 4.84 (d, J = 2.8 Hz, 2H), 4.80 (d, J = 6.8 Hz, 1H), 4.69 (dd, J = 15.7, 2.8 Hz, 1H), 4.63-4.42 (m, 3H), 4.36 (dt, J = 9.0, 5.9 Hz, 1H), 2.75 (dq, J = 11.1, 7.8 Hz, 1H), 2.40 (ddt, J = 11.2, 8.9, 6.9 Hz, 1H). |

TABLE 3-continued

| Example | 1H-NMR |
|---|---|
| 72 | 1H NMR (400 MHz, DMSO) δ 8.26 (d, J = 1.6 Hz, 1H), 7.84-7.69 (m, 4H), 7.68-7.56 (m, 3H), 7.42 (dd, J = 9.1, 2.3 Hz, 1H), 7.34 (d, J = 8.4 Hz, 2H), 5.11 (td, J = 7.1, 2.7 Hz, 1H), 4.98 (s, 2H), 4.82 (dd, J = 15.6, 6.8 Hz, 1H), 4.68 (dd, J = 15.6, 2.7 Hz, 1H), 4.62-4.42 (m, 3H), 4.35 (dt, J = 9.0, 5.9 Hz, 1H), 2.74 (dtd, J = 11.2, 8.1, 6.1 Hz, 1H), 2.46-2.36 (m, 1H). |
| 73 | 1H NMR (400 MHz, MeOD) δ 8.30 (d, J = 1.5 Hz, 1H), 7.99-7.92 (m, 2H), 7.83 (dd, J = 7.6, 1.1 Hz, 1H), 7.74 (t, J = 7.6 Hz, 1H), 7.67 (t, J = 8.4 Hz, 1H), 7.60 (d, J = 8.5 Hz, 1H), 7.44 (dd, J = 10.4, 2.3 Hz, 1H), 7.40-7.30 (m, 3H), 5.27 (qd, J = 6.8, 2.5 Hz, 1H), 5.12 (s, 2H), 4.85-4.75 (m, 1H), 4.73-4.61 (m, 3H), 4.54 (d, J = 17.0 Hz, 1H), 4.45 (dt, J = 9.2, 5.9 Hz, 1H), 2.90-2.77 (m, 1H), 2.59-2.46 (m, 1H). |
| 74 | 1H NMR (400 MHz, Methanol-d4) δ 8.61 (dd, J = 2.5, 0.7 Hz, 1H), 8.47 (d, J = 1.3 Hz, 1H), 8.12 (dd, J = 8.5, 1.5 Hz, 1H), 7.98 (d, J = 7.2 Hz, 1H), 7.90 (dd, J = 8.5, 2.4 Hz, 1H), 7.73 (dd, J = 8.5, 2.1 Hz, 2H), 7.50 (d, J = 10.2 Hz, 1H), 7.07-7.00 (m, 3H), 5.26 (qt, J = 7.3, 2.4 Hz, 1H), 4.83-4.60 (m, 4H), 4.50 (dt, J = 9.1, 5.9 Hz, 1H), 3.72-3.61 (m, 1H), 2.86 (dtd, J = 11.5, 8.2, 6.1 Hz, 1H), 2.56 (ddt, J = 11.5, 9.1, 7.2 Hz, 1H), 2.09 (s, 3H). |
| 75 | 1H NMR (400 MHz, DMSO) δ 8.11 (d, J = 8.3 Hz, 1H), 7.98 (d, J = 8.2 Hz, 1H), 7.64-7.54 (m, 2H), 7.50-7.40 (m, 2H), 7.36 (dd, J = 8.4, 2.1 Hz, 1H), 7.06 (dd, J = 6.6, 2.3 Hz, 1H), 7.04-6.94 (m, 2H), 4.51 (s, 4H), 2.79 (s, 2H), 2.05 (s, 3H), 1.10-1.02 (m, 2H), 0.72-0.65 (m, 2H). |
| 76 | 1H NMR (400 MHz, DMSO) δ 8.72 (d, J = 2.4 Hz, 1H), 8.20 (d, J = 1.5 Hz, 1H), 8.03 (dd, J = 8.5, 2.5 Hz, 1H), 7.77 (dd, J = 8.4, 1.5 Hz, 1H), 7.69 (d, J = 8.5 Hz, 1H), 7.55 (d, J = 8.4 Hz, 1H), 7.47-7.34 (m, 3H), 6.98 (dd, J = 8.6, 4.2 Hz, 1H), 6.84 (dd, J = 11.3, 8.6 Hz, 1H), 5.22-4.90 (m, 1H), 4.71 (dd, J = 15.5, 7.0 Hz, 1H), 4.58 (dd, J = 15.6, 2.8 Hz, 1H), 4.52-4.21 (m, 4H), 2.78-2.63 (m, 1H), 2.43-2.28 (m, 1H), 2.06 (s, 3H). |
| 77 | 1H NMR (400 MHz, DMSO) δ 8.69 (d, J = 2.3 Hz, 1H), 8.23 (s, 1H), 8.02 (d, J = 8.2 Hz, 1H), 7.87 (dd, J = 8.3, 2.4 Hz, 1H), 7.79 (dd, J = 8.4, 1.6 Hz, 1H), 7.69 (dt, J = 7.9, 1.3 Hz, 1H), 7.65 (t, J = 8.4 Hz, 1H), 7.61-7.54 (m, 2H), 7.35 (dd, J = 8.5, 2.1 Hz, 1H), 7.06-6.94 (m, 2H), 5.07-4.98 (m, 1H), 4.74 (dd, J = 15.5, 7.2 Hz, 1H), 4.60 (dd, J = 15.6, 2.8 Hz, 1H), 4.54-4.41 (m, 3H), 4.41-4.31 (m, 1H), 2.76-2.62 (m, 1H), 2.45-2.34 (m, 1H), 2.11 (s, 3H). |
| 78 | 1H NMR (400 MHz, DMSO-d6) δ 8.59 (d, J = 5.3 Hz, 1H), 8.24 (d, J = 1.5 Hz, 1H), 7.84 (dd, J = 8.4, 1.5 Hz, 1H), 7.67-7.56 (m, 4H), 7.53 (dd, J = 5.3, 2.1 Hz, 1H), 7.46-7.36 (m, 2H), 7.27 (dd, J = 7.3, 1.3 Hz, 1H), 7.01 (t, J = 7.5 Hz, 1H), 5.98 (dd, J = 9.8, 7.0 Hz, 1H), 4.60 (t, J = 5.2 Hz, 2H), 4.46 (s, 2H), 3.75 (dd, J = 16.0, 9.9 Hz, 1H), 3.65 (t, J = 5.1 Hz, 2H), 3.44 (dd, J = 16.1, 7.1 Hz, 1H), 3.19 (s, 3H). |
| 79 | 1H NMR (400 MHz, DMSO-d6) δ 8.32 (d, J = 1.5 Hz, 1H), 7.90 (dd, J = 8.4, 1.5 Hz, 1H), 7.67 (d, J = 8.5 Hz, 1H), 7.64-7.56 (m, 2H), 7.52 (dd, J = 10.6, 2.2 Hz, 1H), 7.49-7.39 (m, 3H), 7.33 (dd, J = 8.3, 2.1 Hz, 1H), 7.28 (dd, J = 7.4, 1.3 Hz, 1H), 7.02 (t, J = 7.5 Hz, 1H), 6.08 (dd, J = 9.7, 7.9 Hz, 1H), 4.65 (t, J = 5.1 Hz, 2H), 4.52 (s, 2H), 3.78 (dd, J = 16.0, 9.8 Hz, 1H), 3.67 (t, J = 5.0 Hz, 2H), 3.28-3.21 (m, 1H), 3.19 (s, 3H). |
| 80 | 1H NMR (400 MHz, MeOD) δ 8.57 (dd, J = 1.5, 0.7 Hz, 1H), 8.24 (dd, J = 8.6, 1.4 Hz, 1H), 7.79 (dd, J = 8.6, 0.7 Hz, 1H), 7.75-7.65 (m, 2H), 7.61 (t, J = 8.3 Hz, 1H), 7.53 (t, J = 8.0 Hz, 1H), 7.32 (dd, J = 10.9, 2.0 Hz, 1H), 7.24 (ddd, J = 8.4, 2.0, 0.8 Hz, 1H), 7.18 (dd, J = 7.9, 1.3 Hz, 1H), 6.99 (t, J = 7.8 Hz, 1H), 6.94 (dd, J = 7.8, 1.3 Hz, 1H), 4.83 (t, J = 5.0 Hz, 2H), 4.78 (s, 2H), 3.83 (dd, J = 5.4, 4.4 Hz, 2H), 3.32 (s, 3H), 2.11 (d, J = 1.0 Hz, 3H). |
| 81 | 1H NMR (400 MHz, MeOD) δ 8.58 (dd, J = 1.5, 0.7 Hz, 1H), 8.24 (dd, J = 8.6, 1.4 Hz, 1H), 7.88-7.76 (m, 2H), 7.67 (dd, J = 10.6, 1.5 Hz, 1H), 7.61 (dd, J = 8.1, 1.6 Hz, 1H), 7.44 (dd, J = 10.1, 6.0 Hz, 1H), 7.38 (dd, J = 10.0, 6.2 Hz, 1H), 7.06-6.97 (m, 3H), 4.87-4.82 (m, 2H), 4.78 (s, 2H), 3.85 (dd, J = 5.4, 4.4 Hz, 2H), 2.10 (d, J = 1.0 Hz, 3H). 3H obscured by solvent |
| 82 | 1H NMR (400 MHz, DMSO-d6) δ 8.25 (d, J = 1.5 Hz, 1H), 7.95-7.86 (m, 2H), 7.83-7.71 (m, 4H), 7.61 (d, J = 8.4 Hz, 1H), 7.53 (dd, J = 7.6, 1.7 Hz, 1H), 7.38 (dd, J = 11.6, 6.1 Hz, 1H), 6.99 (d, J = 8.2 Hz, 1H), 6.65 (t, J = 75.3 Hz, 1H), 5.61 (s, 2H), 4.72 (t, J = 5.1 Hz, 2H), 4.44 (s, 2H), 4.21 (t, J = 5.1 Hz, 2H). |
| 83 | 1H NMR (400 MHz, DMSO-d6) δ 8.27 (d, J = 1.5 Hz, 1H), 7.81 (dd, J = 8.4, 1.6 Hz, 1H), 7.65-7.53 (m, 4H), 7.38 (dd, J = 8.4, 2.1 Hz, 1H), 7.31 (dd, J = 7.9, 1.4 Hz, 1H), 7.10-6.97 (m, 2H), 6.5 (t, J = 48.0 Hz, 1H), 4.79 (t, J = 5.1 Hz, 2H), 4.46 (s, 2H), 4.25 (t, J = 5.0 Hz, 2H), 2.12 (s, 3H). |
| 84 | 1H NMR (400 MHz, DMSO) δ 8.32 (d, J = 1.6 Hz, 1H), 7.84 (dd, J = 8.4, 1.6 Hz, 1H), 7.73 (d, J = 8.4 Hz, 1H), 7.67-7.53 (m, 4H), 7.39 (dd, J = 8.4, 2.1 Hz, 1H), 7.32 (dd, J = 8.0, 1.4 Hz, 1H), 7.10-6.98 (m, 2H), 4.65 (d, J = 5.3 Hz, 2H), 4.47 (d, J = 6.9 Hz, 2H), 3.77 (t, J = 5.1 Hz, 2H), 3.26 (s, 3H), 2.13 (s, 3H). |
| 85 | 1H NMR (400 MHz, DMSO) δ 8.32 (s, 1H), 7.89 (d, J = 8.5 Hz, 1H), 7.78-7.71 (m, 2H), 7.69 (d, J = 7.9 Hz, 1H), 7.65 (d, J = 8.3 Hz, 2H), 7.58 (dd, J = 11.1, 2.0 Hz, 1H), 7.36 (dd, J = 8.4, 2.1 Hz, 1H), 7.07-6.95 (m, 2H), 4.65 (d, J = 5.4 Hz, 2H), 4.41 (s, 2H), 3.96 (s, 3H), 3.69 (t, J = 5.1 Hz, 2H), 3.21 (s, 3H), 2.12 (s, 3H). |

TABLE 3-continued

| Example | 1H-NMR |
|---|---|
| 86 | 1H NMR (400 MHz, DMSO) δ 12.98 (s, 1H), 11.78 (s, 1H), 8.32 (s, 1H), 7.98-7.82 (m, 1H), 7.68 (d, J = 8.5 Hz, 1H), 7.65-7.50 (m, 3H), 7.36 (dd, J = 8.4, 2.1 Hz, 1H), 7.27 (s, 1H), 7.08 (dd, J = 7.8, 1.2 Hz, 1H), 6.98 (t, J = 8.0 Hz, 1H), 6.73 (s, 1H), 4.70 (t, J = 5.2 Hz, 2H), 4.25 (s, 2H), 3.72 (t, J = 5.1 Hz, 2H), 3.21 (s, 3H), 2.09 (s, 3H). |
| 87 | 1H NMR (400 MHz, DMSO) δ 11.76 (s, 1H), 8.33 (s, 1H), 7.91 (d, J = 8.5 Hz, 1H), 7.70 (d, J = 8.5 Hz, 1H), 7.65-7.51 (m, 3H), 7.36 (dd, J = 8.4, 2.1 Hz, 1H), 7.26 (s, 1H), 7.07 (d, J = 7.8 Hz, 1H), 6.98 (t, J = 8.0 Hz, 1H), 6.68 (s, 1H), 4.70 (d, J = 5.9 Hz, 2H), 4.24 (s, 2H), 3.90 (s, 3H), 3.71 (t, J = 5.1 Hz, 2H), 3.21 (s, 3H), 2.09 (s, 3H). |
| 88 | 1H NMR (400 MHz, Methanol-d4) δ 8.51 (d, J = 1.4 Hz, 1H), 8.18 (dd, J = 8.6, 1.4 Hz, 1H), 7.84 (t, J = 7.8 Hz, 1H), 7.75 (d, J = 8.6 Hz, 1H), 7.68 (dd, J = 10.6, 1.5 Hz, 1H), 7.62 (dd, J = 8.1, 1.6 Hz, 1H), 7.30 (ddd, J = 10.0, 5.3, 2.1 Hz, 1H), 7.03 (s, 3H), 4.85-4.77 (m, 4H), 3.87 (t, J = 4.9 Hz, 2H), 3.34 (s, 3H), 2.12 (s, 3H). |
| 89 | 1H NMR (400 MHz, Methanol-d4) δ 8.51 (s, 1H), 8.18 (dd, J = 8.5, 1.5 Hz, 1H), 7.82 (t, J = 7.7 Hz, 1H), 7.77-7.67 (m, 2H), 7.61 (dd, J = 12.0, 8.8 Hz, 3H), 7.23 (dd, J = 7.4, 2.0 Hz, 1H), 7.10-6.98 (m, 2H), 4.82 (t, J = 4.9 Hz, 2H), 4.77 (s, 2H), 3.85 (t, J = 4.9 Hz, 2H), 3.33 (s, 3H), 2.17 (s, 3H). |
| 90 | 1H NMR (400 MHz, Methanol-d4) δ 8.51 (s, 1H), 8.15 (dd, J = 8.7, 1.4 Hz, 1H), 7.84 (t, J = 7.7 Hz, 1H), 7.74 (d, J = 8.6 Hz, 1H), 7.69 (dd, J = 10.6, 1.5 Hz, 1H), 7.63 (dd, J = 8.1, 1.5 Hz, 1H), 7.30 (ddd, J = 10.0, 5.4, 2.1 Hz, 1H), 7.09-6.96 (m, 3H), 5.30 (dt, J = 7.1, 3.6 Hz, 1H), 5.00-4.91 (m, 1H), 4.86-4.65 (m, 4H), 4.51 (dt, J = 10.7, 5.9 Hz, 1H), 2.89 (dq, J = 14.6, 7.6 Hz, 1H), 2.62-2.47 (m, 1H), 2.12 (s, 3H). |
| 91 | 1H NMR (400 MHz, Methanol-d4) δ 8.54 (d, J = 1.4 Hz, 1H), 8.18 (dd, J = 8.5, 1.5 Hz, 1H), 7.82 (t, J = 7.8 Hz, 1H), 7.75 (dd, J = 8.6, 0.6 Hz, 1H), 7.70 (dd, J = 10.6, 1.5 Hz, 1H), 7.65-7.56 (m, 3H), 7.23 (dd, J = 7.3, 1.9 Hz, 1H), 7.06-6.97 (m, 2H), 5.28 (qd, J = 7.2, 2.5 Hz, 1H), 4.98 (dd, J = 15.5, 7.3 Hz, 1H), 4.86-4.65 (m, 4H), 4.53 (dt, J = 9.0, 5.9 Hz, 1H), 2.97-2.77 (m, 1H), 2.58 (ddt, J = 11.6, 9.1, 7.2 Hz, 1H), 2.17 (d, J = 1.0 Hz, 3H). |
| 92 | 1H NMR (400 MHz, Methanol-d4) δ 8.48 (t, J = 1.0 Hz, 1H), 8.12 (dd, J = 8.6, 1.5 Hz, 1H), 7.82 (t, J = 7.8 Hz, 1H), 7.75-7.66 (m, 2H), 7.66-7.52 (m, 3H), 7.23 (dd, J = 7.5, 1.7 Hz, 1H), 7.06-6.94 (m, 2H), 5.27 (tt, J = 7.1, 3.7 Hz, 1H), 5.00-4.90 (m, 2H), 4.82-4.44 (m, 4H), 2.95-2.81 (m, 1H), 2.56 (dd, J = 11.6, 8.9 Hz, 1H), 2.17 (s, 3H). |
| 93 | 1H NMR (400 MHz, Methanol-d4) δ 8.48 (t, J = 1.0 Hz, 1H), 8.12 (dd, J = 8.5, 1.5 Hz, 1H), 7.82 (t, J = 7.8 Hz, 1H), 7.75-7.66 (m, 2H), 7.65-7.54 (m, 3H), 7.23 (dd, J = 7.6, 1.7 Hz, 1H), 7.08-6.95 (m, 2H), 5.27 (tt, J = 7.2, 3.7 Hz, 1H), 4.97-4.91 (m, 1H), 4.84-4.64 (m, 4H), 4.51 (dt, J = 9.2, 6.0 Hz, 1H), 2.93-2.81 (m, 1H), 2.64-2.50 (m, 1H), 2.17 (s, 3H). |
| 94 | 1H NMR (400 MHz, Methanol-d4) δ 8.51 (dd, J = 1.4, 0.7 Hz, 1H), 8.15 (dd, J = 8.6, 1.5 Hz, 1H), 7.84 (t, J = 7.8 Hz, 1H), 7.77-7.66 (m, 2H), 7.63 (dd, J = 8.0, 1.6 Hz, 1H), 7.30 (ddd, J = 9.8, 5.3, 2.1 Hz, 1H), 7.04 (d, J = 1.7 Hz, 3H), 5.30 (td, J = 7.2, 4.7 Hz, 1H), 5.04-4.92 (m, 1H), 4.87-4.63 (m, 4H), 4.51 (dt, J = 9.2, 6.0 Hz, 1H), 2.98-2.81 (m, 1H), 2.69-2.50 (m, 1H), 2.12 (s, 3H). |
| 95 | 1H NMR (400 MHz, Methanol-d4) δ 8.50 (t, J = 1.0 Hz, 1H), 8.15 (dd, J = 8.5, 1.5 Hz, 1H), 7.84 (t, J = 7.7 Hz, 1H), 7.77-7.66 (m, 2H), 7.63 (dd, J = 8.1, 1.6 Hz, 1H), 7.30 (ddd, J = 9.9, 5.3, 2.1 Hz, 1H), 7.04 (d, J = 1.7 Hz, 3H), 5.30 (qd, J = 7.1, 2.5 Hz, 1H), 5.03-4.91 (m, 1H), 4.87-4.67 (m, 4H), 4.51 (dt, J = 9.2, 6.0 Hz, 1H), 2.97-2.82 (m, 1H), 2.57 (ddd, J = 16.2, 11.5, 7.3 Hz, 1H), 2.12 (s, 3H). |
| 96 | 1H NMR (400 MHz, Methanol-d4) δ 8.45 (d, J = 1.4 Hz, 1H), 8.12 (dd, J = 8.5, 1.5 Hz, 1H), 7.84 (t, J = 7.8 Hz, 1H), 7.75-7.66 (m, 2H), 7.62 (dd, J = 8.1, 1.5 Hz, 1H), 7.28 (ddd, J = 9.9, 5.3, 2.1 Hz, 1H), 7.08-6.95 (m, 3H), 4.82-4.69 (m, 4H), 3.85 (t, J = 4.9 Hz, 2H), 3.33 (s, 3H), 2.14-2.09 (m, 3H). |
| 97 | 1H NMR (400 MHz, Methanol-d4) δ 8.51 (d, J = 1.4 Hz, 1H), 8.18 (dd, J = 8.6, 1.5 Hz, 1H), 7.84 (t, J = 7.8 Hz, 1H), 7.75 (d, J = 8.6 Hz, 1H), 7.69 (dd, J = 10.6, 1.5 Hz, 1H), 7.63 (dd, J = 8.1, 1.6 Hz, 1H), 7.31 (ddd, J = 9.9, 5.3, 2.2 Hz, 1H), 7.08-7.02 (m, 3H), 4.85-4.78 (m, 4H), 3.91-3.83 (m, 2H), 3.32 (s, 3H), 2.15-2.09 (m, 3H). |
| 98 | 1H NMR (400 MHz, Methanol-d4) δ 8.46-8.41 (m, 1H), 8.12 (dd, J = 8.6, 1.5 Hz, 1H), 7.82 (t, J = 7.8 Hz, 1H), 7.74-7.67 (m, 2H), 7.62 (dd, J = 8.0, 1.5 Hz, 1H), 7.57 (d, J = 9.0 Hz, 2H), 7.23 (dd, J = 7.6, 1.7 Hz, 1H), 7.06-6.97 (m, 2H), 4.76 (t, J = 5.0 Hz, 2H), 4.69 (s, 2H), 3.84 (t, J = 4.9 Hz, 2H), 3.32 (s, 3H), 2.17 (d, J = 1.0 Hz, 3H). |
| 99 | 1H NMR (400 MHz, Methanol-d4) δ 8.45-8.38 (m, 1H), 8.09 (dd, J = 8.5, 1.5 Hz, 1H), 7.82 (t, J = 7.8 Hz, 1H), 7.74-7.66 (m, 2H), 7.62 (dd, J = 8.0, 1.5 Hz, 1H), 7.56 (d, J = 9.0 Hz, 2H), 7.23 (dd, J = 7.6, 1.7 Hz, 1H), 7.08-6.94 (m, 2H), 4.75 (t, J = 5.0 Hz, 2H), 4.67 (s, 2H), 3.83 (t, J = 4.9 Hz, 2H), 3.32 (s, 3H), 2.22-2.09 (m, 3H). |
| 100 | 1H NMR (400 MHz, DMSO) δ 8.74 (d, J = 2.1 Hz, 1H), 8.22 (d, J = 1.6 Hz, 1H), 8.05 (dd, J = 8.5, 2.5 Hz, 1H), 7.78 (dd, J = 8.4, 1.6 Hz, 1H), 7.72 (d, J = 8.7 Hz, 1H), 7.60 (d, J = 8.5 Hz, 1H), 7.39-7.33 (m, 2H), 7.03 (dd, J = 8.6, 4.2 Hz, 1H), 6.88 (dd, J = 11.4, 8.6 Hz, 1H), 4.65 (t, J = 5.0 Hz, 2H), 4.47 (s, 2H), 3.71 (t, J = 5.0 Hz, 2H), 3.22 (s, 3H), 2.09 (s, 3H). |

TABLE 3-continued

| Example | 1H-NMR |
|---|---|
| 101 | 1H NMR (400 MHz, DMSO) δ 8.72 (d, J = 2.4 Hz, 1H), 8.24 (d, J = 1.5 Hz, 1H), 8.05 (dd, J = 8.5, 2.5 Hz, 1H), 7.82 (dd, J = 8.4, 1.6 Hz, 1H), 7.67 (dd, J = 12.5, 8.5 Hz, 2H), 7.49-7.37 (m, 2H), 7.05 (dd, J = 8.6, 4.3 Hz, 1H), 6.86 (dd, J = 10.6, 8.6 Hz, 1H), 4.62 (t, J = 5.1 Hz, 2H), 4.47 (s, 2H), 3.67 (t, J = 5.0 Hz, 2H), 3.19 (s, 3H), 2.05 (s, 3H). |
| 102 | 1H NMR (400 MHz, Methanol-d4) δ 8.50 (t, J = 1.0 Hz, 1H), 8.17 (dd, J = 8.6, 1.5 Hz, 1H), 7.73 (d, J = 8.6 Hz, 1H), 7.65-7.56 (m, 3H), 7.34 (dd, J = 10.9, 2.0 Hz, 1H), 7.28-7.19 (m, 2H), 7.01 (t, J = 7.8 Hz, 1H), 6.97 (dd, J = 7.8, 1.5 Hz, 1H), 4.80 (t, J = 5.0 Hz, 2H), 4.75 (s, 2H), 3.85 (t, J = 4.9 Hz, 2H), 2.14 (s, 3H). |
| 103 | 1H NMR (400 MHz, Methanol-d4) δ 8.49 (t, J = 1.0 Hz, 1H), 8.16 (dd, J = 8.5, 1.5 Hz, 1H), 7.73 (d, J = 8.5 Hz, 1H), 7.66-7.55 (m, 3H), 7.34 (dd, J = 10.9, 2.0 Hz, 1H), 7.28-7.19 (m, 2H), 7.01 (t, J = 7.8 Hz, 1H), 6.97 (dd, J = 7.8, 1.5 Hz, 1H), 4.80 (t, J = 5.0 Hz, 2H), 4.74 (s, 2H), 3.84 (t, J = 4.9 Hz, 2H), 2.14 (s, 3H). |
| 104 | 1H NMR (400 MHz, Methanol-d4) δ 8.60 (dd, J = 2.4, 0.7 Hz, 1H), 8.53 (s, 1H), 8.39 (s, 1H), 8.06 (dd, J = 8.5, 1.5 Hz, 1H), 7.88 (dd, J = 8.5, 2.4 Hz, 1H), 7.81-7.68 (m, 2H), 7.60 (dd, J = 8.1, 1.2 Hz, 1H), 6.99 (t, J = 7.9 Hz, 1H), 6.89 (dd, J = 7.8, 1.1 Hz, 1H), 6.19 (s, 2H), 4.76 (t, J = 5.0 Hz, 2H), 3.75 (t, J = 4.9 Hz, 2H), 3.28 (s, 3H), 2.10 (s, 3H). |
| 105 | 1H NMR (400 MHz, Methanol-d4) δ 8.19 (s, 1H), 7.71-7.56 (m, 2H), 7.52 (d, J = 9.0 Hz, 2H), 7.33 (dd, J = 10.9, 2.1 Hz, 1H), 7.28-7.15 (m, 2H), 7.05-6.82 (m, 2H), 4.64 (s, 2H), 4.52 (s, 2H), 2.13 (s, 3H), 0.87 (s, 4H). |
| 106 | 1H NMR (400 MHz, Methanol-d4) δ 8.19 (s, 1H), 7.71-7.56 (m, 2H), 7.52 (d, J = 9.0 Hz, 2H), 7.33 (dd, J = 10.9, 2.1 Hz, 1H), 7.28-7.15 (m, 2H), 7.05-6.82 (m, 2H), 4.64 (s, 2H), 4.52 (s, 2H), 2.13 (s, 3H), 0.87 (s, 4H). |
| 107 | 1H NMR (400 MHz, Methanol-d4) δ 8.62 (d, J = 1.7 Hz, 1H), 8.45-8.33 (m, 1H), 8.16 (dd, J = 8.5, 1.5 Hz, 1H), 7.79 (d, J = 8.6 Hz, 1H), 7.67-7.55 (m, 4H), 7.46 (t, J = 8.0 Hz, 1H), 7.32 (dd, J = 10.9, 2.0 Hz, 1H), 7.28-7.19 (m, 1H), 7.14 (dd, J = 8.0, 1.3 Hz, 1H), 7.05-6.87 (m, 2H), 6.39 (d, J = 1.8 Hz, 1H), 5.91 (s, 2H), 4.69 (s, 2H), 2.11 (d, J = 1.0 Hz, 3H). |
| 108 | 1H NMR (400 MHz, Methanol-d4) δ 8.67-8.58 (m, 1H), 8.23 (dd, J = 8.6, 1.4 Hz, 1H), 7.81-7.74 (m, 1H), 7.74-7.65 (m, 2H), 7.65-7.53 (m, 2H), 7.36-7.27 (m, 1H), 7.23 (dd, J = 8.4, 2.1 Hz, 1H), 7.17 (dd, J = 7.9, 1.4 Hz, 1H), 7.08-6.87 (m, 2H), 5.04 (dd, J = 15.5, 9.6 Hz, 1H), 4.74 (d, J = 22.7 Hz, 1H), 4.26-4.05 (m, 2H), 2.70-2.48 (m, 1H), 2.24 (dq, J = 15.4, 6.1 Hz, 1H), 2.10 (s, 3H), 1.67 (s, 2H). |
| 109 | 1H NMR (400 MHz, Methanol-d4) δ 8.19-8.08 (m, 2H), 8.06-7.95 (m, 1H), 7.78-7.53 (m, 5H), 7.46-7.34 (m, 1H), 7.31 (dd, J = 10.9, 2.1 Hz, 1H), 7.27-7.19 (m, 1H), 7.16 (d, J = 7.9, 1.3 Hz, 1H), 7.02-6.87 (m, 2H), 5.12 (d, J = 2.1 Hz, 2H), 4.20 (d, J = 2.8 Hz, 2H), 2.10 (d, J = 1.0 Hz, 3H), 1.80-1.65 (m, 2H), 1.65-1.51 (m, 2H). |
| 110 | ¹H NMR (400 MHz, Acetonitrile-d3) δ 8.42 (dd, J = 1.5, 0.7 Hz, 1H), 8.06 (dd, J = 8.6, 1.5 Hz, 1H), 7.72 (dd, J = 8.6, 0.7 Hz, 1H), 7.61 (td, J = 8.4, 1.3 Hz, 1H), 7.56-7.46 (m, 2H), 7.32 (ddd, J = 11.0, 2.0, 1.0 Hz, 1H), 7.25 (dt, J = 8.4, 1.3 Hz, 1H), 7.17-7.07 (m, 1H), 7.06-6.92 (m, 2H), 4.70-4.59 (m, 3H), 4.44 (dd, J = 15.1, 8.7 Hz, 1H), 4.33-4.21 (m, 1H), 3.87 (dtd, J = 7.9, 6.7, 1.1 Hz, 1H), 3.71 (dt, J = 7.8, 6.6 Hz, 1H), 2.27-2.14 (m, 1H), 2.13 (d, J = 1.1 Hz, 3H), 1.98-1.84 (m, 2H), 1.72 (ddt, J = 12.4, 8.5, 7.3 Hz, 1H). |
| 111 | ¹H NMR (400 MHz, Acetonitrile-d3) δ 8.21 (d, J = 1.6 Hz, 1H), 7.85 (dd, J = 8.4, 1.6 Hz, 1H), 7.62 (t, J = 8.4 Hz, 1H), 7.54 (d, J = 8.5 Hz, 1H), 7.49 (d, J = 8.8 Hz, 2H), 7.32 (dd, J = 11.0, 2.0 Hz, 1H), 7.25 (ddd, J = 8.4, 2.0, 0.8 Hz, 1H), 7.16 (dd, J = 7.4, 1.9 Hz, 1H), 7.03-6.91 (m, 2H), 4.50 (dd, J = 15.0, 2.6 Hz, 1H), 4.46-4.43 (m, 2H), 4.39-4.23 (m, 2H), 3.87 (dt, J = 8.3, 6.8 Hz, 1H), 3.72 (dt, J = 8.2, 6.7 Hz, 1H), 2.22-2.09 (m, 4H), 1.94-1.85 (m, 2H), 1.68 (dq, J = 12.3, 7.7 Hz, 1H). |
| 112 | ¹H NMR (400 MHz, Acetonitrile-d3) δ 8.21 (d, J = 1.6 Hz, 1H), 7.85 (dd, J = 8.4, 1.6 Hz, 1H), 7.62 (t, J = 8.4 Hz, 1H), 7.54 (d, J = 8.5 Hz, 1H), 7.49 (d, J = 8.8 Hz, 2H), 7.32 (dd, J = 11.0, 2.0 Hz, 1H), 7.25 (ddd, J = 8.4, 2.0, 0.8 Hz, 1H), 7.16 (dd, J = 7.4, 1.9 Hz, 1H), 7.03-6.91 (m, 2H), 4.50 (dd, J = 15.0, 2.6 Hz, 1H), 4.46-4.43 (m, 2H), 4.39-4.23 (m, 2H), 3.87 (dt, J = 8.3, 6.8 Hz, 1H), 3.72 (dt, J = 8.2, 6.7 Hz, 1H), 2.22-2.09 (m, 4H), 1.94-1.85 (m, 2H), 1.68 (dq, J = 12.3, 7.7 Hz, 1H). |
| 113 | 1H NMR (400 MHz, Acetonitrile-d3) δ 8.41 (dd, J = 1.5, 0.7 Hz, 1H), 8.10 (dd, J = 8.6, 1.5 Hz, 1H), 7.81 (dd, J = 8.5, 0.7 Hz, 1H), 7.62 (t, J = 8.4 Hz, 1H), 7.39 (dd, J = 10.2, 6.1 Hz, 1H), 7.35-7.21 (m, 3H), 6.99 (s, 3H), 4.68-4.59 (m, 4H), 3.79-3.71 (m, 2H), 3.25 (s, 3H), 2.08 (d, J = 1.0 Hz, 3H). |
| 114 | 1H NMR (400 MHz, Acetonitrile-d3) δ 8.64 (dd, J = 2.5, 0.7 Hz, 1H), 8.46 (dd, J = 1.5, 0.7 Hz, 1H), 8.15 (dd, J = 8.6, 1.5 Hz, 1H), 7.89-7.78 (m, 2H), 7.67 (dd, J = 8.5, 0.7 Hz, 1H), 7.42 (dd, J = 10.2, 6.1 Hz, 1H), 7.31 (dd, J = 10.2, 6.2 Hz, 1H), 7.05-6.94 (m, 3H), 4.80-4.52 (m, 4H), 3.77 (dd, J = 5.4, 4.4 Hz, 2H), 3.25 (s, 3H), 2.07 (s, 3H). |

C. Biological Data

GLP-1R Activation

GLP-1R activation by a compound of the present disclosure was quantified by measuring cAMP increase in CHO cells stably expressing GLP-1R (MultiSpan product #C1267-1a). The cells were harvested and plated in growth medium (DMEM/F-12 (Corning product #10-090-CV) supplemented with 10% FBS (HyClone product #SH30071-03), penicillin/streptomycin (Corning product #30-002CI') and 10 μg/ml puromycin (Gibco product #A11138-03)) at 1,000 cells/well in a 384-well plate (Greiner product #781080). The cells were then incubated overnight at 37° C., 5% $CO_2$. The next day, the medium was removed and the cells were washed with DPBS (Corning product #21-031-CM) before adding the assay medium (HBSS, Corning product #21-023-CV) with 20 mM Hepes (Gibco product #15630-080) and 0.1% BSA (Rockland Immunochemicals product #BSA-1000)). Following the medium change, the cells were incubated for 1 hour at 37° C., 5% $CO_2$. The tested GLP-1 compound was added to the cells in a 10 point dose response followed by a 30 minutes incubation at 37° C., 5% $CO_2$. cAMP concentration increase was then detected using Cisbio's cAMP Gs Dynamic Kit (product #62AM4PEC) according to the manufacturer's protocol. The response was plotted against the log of the agonist concentration and fitted to a sigmoidal equation to determine the $EC_{50}$. The following Table 4 shows exemplary data for GLP-1 compounds of the disclosure.

TABLE 4

| Example | $EC_{50}$ (nM) |
| --- | --- |
| 1 | 0.51 |
| 2 | 0.17 |
| 3 | 78 |
| 4 | 103 |
| 5 | 161 |
| 6 | 219 |
| 7 | 530 |
| 8 | 78 |
| 9 | 8.6 |
| 10 | 130 |
| 11 | 34 |
| 12 | 2.4 |
| 13 | 0.41 |
| 14 | 4.5 |
| 15 | 0.015 |
| 16 | 6916 |
| 17 | 10000 |
| 18 | 0.14 |
| 19 | 0.97 |
| 20 | 0.089 |
| 21 | 0.86 |
| 22 | 0.024 |
| 23 | 0.49 |
| 24 | 1.7 |
| 25 | 0.30 |
| 26 | 37 |
| 27 | 0.53 |
| 28 | 0.034 |
| 29 | 0.076 |
| 30 | 1.9 |
| 31 | 89 |
| 32 | 1919 |
| 33 | 53 |
| 34 | 350 |
| 35 | 646 |
| 36 | 242 |
| 37 | 1000 |
| 38 | 37 |
| 39 | 49 |
| 40 | 1234 |
| 41 | 438 |
| 42 | 1.1 |
| 43 | 7.4 |
| 44 | 0.033 |
| 45 | 0.19 |
| 46 | 17 |
| 47 | 0.070 |
| 48 | 1.2 |
| 49 | 0.31 |
| 50 | 16 |
| 51 | 9.1 |
| 52 | 2269 |
| 53 | 1288 |
| 54 | 628 |
| 55 | 1273 |
| 56 | 3746 |
| 57 | 347 |
| 58 | 6.3 |
| 59 | 1624 |
| 60 | 3.8 |
| 61 | 639 |
| 62 | 2.5 |
| 63 | 0.62 |
| 64 | 111 |
| 65 | 10 |
| 66 | 21 |
| 67 | 20 |
| 68 | 12 |
| 69 | 2.5 |
| 70 | 0.78 |
| 71 | 10000 |
| 72 | 10000 |
| 73 | 10000 |
| 74 | 1.7 |
| 75 | 0.7 |
| 76 | 4.3 |
| 77 | 72 |
| 78 | 1782 |
| 79 | 738 |
| 80 | 11 |
| 81 | 26 |
| 82 | 20 |
| 83 | 13 |
| 84 | 49 |
| 85 | 168 |
| 86 | 13 |
| 87 | 1152 |
| 88 | 12 |
| 89 | 15 |
| 90 | 0.23 |
| 91 | 0.69 |
| 92 | 3.3 |
| 93 | 0.52 |
| 94 | 0.32 |
| 95 | 21 |
| 96 | 57 |
| 97 | 1.9 |
| 98 | 67 |
| 99 | 2.4 |
| 100 | 14 |
| 101 | 160 |
| 102 | 65 |
| 103 | 8.2 |
| 104 | 3033 |
| 105 | 2.6 |
| 106 | 0.64 |
| 107 | 1.9 |
| 108 | 4.3 |
| 109 | 9.1 |
| 110 | 7.1 |
| 111 | 377 |
| 112 | 3.3 |
| 113 | 2.8 |
| 114 | 11 |

Microsomal Stability

Metabolic stability of compounds was assessed using human or rat liver microsomal assays (Corning). In these assays, 10 nL of each analyte at a concentration of 1 mM in 100% DMSO was dispensed into a well of a polypropylene plates using the Echo 550 acoustic liquid dispenser (Labcyte®). Each plate contained 384 wells with a single analyte in each well.

A solution of human (Corning® Gentest™ Human Mixed Pooled Microsomes or rat (Corning® Gentest™ Rat [Sprague-Dawley] Pooled Liver Microsomes) liver microsomes at 2 mg/ml in 100 mM $K_2HPO_4/KH_2PO_4$ at pH 7.4 was combined with alamethicin from *Trichoderma viride* (Sigma-Aldrich) 0.0225 mg/ml. The mixture was incubated on ice for 15 minutes. 5 µL of this mixture was added to individual wells following a 15 minute incubation at room temperature and supplemented with 5 µL NADPH Regenerating Solution of cofactors (Corning® Gentest™ UGT Reaction Mix) containing 100 mM $K_2HPO_4/KH_2PO_4$ at pH 7.4, 2.6 mM NADP+, 6.6 mM glucose-6-phosphate, 6.6 mM $MgCl_2$, 0.8 U/mL glucose-6-phosphate dehydrogenase, 0.1 mM sodium citrate, and 6.8 mM uridine diphosphate-glucuronic acid. The final concentration of each analyte compound at the beginning of the reaction was 1 µM. The reactions were incubated at 37° C. and samples were collected at time points of 0, 5, 15, 30, 40, 50, 60, and 70 minutes for further analysis. Background data were collected using reactions without analyte compounds.

Upon collection of the sample time points, samples were quenched with 30 µL of a solution of 72% acetonitrile, 8% methanol, 0.1% formic acid, 19.9% water, and internal standard (IS). Reaction plates were spun in a centrifuge at speed of 4,000 rcf for 30 minutes at 4° C., following a dilution of the 10 µL quenched reaction into 40 µL deionized water, yielding assay plates.

Assay plates were analyzed using solid-state extraction coupled with quadrupole time-of-flight mass spectrometer, using Agilent QToF 6530 RapidFire 360 system, with C4 type A solid state cartridges. Analysis was performed in either positive or negative ionization modes. Mobile phases contained 0.1% formic acid in water for loading analytes onto solid state extraction cartridges and 0.1% formic acid in acetonitrile for elution into a mass spectrometer in positive ionization mode, or 0.1% acetic acid in water for loading and 0.1% acetic acid in acetonitrile for extraction in negative ionization mode. Peak-area ratios of integrated counts for individual compounds to IS were plotted as semi-logarithmic chart of log vs time. The initial linear portion of decay was fitted to a linear regression equation to derive the half-time of analyte decay.

Pharmacological parameters for an analyte compound metabolism were calculated using the following equations:

| Parameter | Equation |
|---|---|
| Half Life | $T_{1/2} = \dfrac{\log_{10} 2}{-1 * \text{Slope}}$ |
| Intrinsic Clearance (in vitro) | $Cl_{int,\,in\,vitro} = \dfrac{\ln 2}{T_{1/2} * Conc}$ |
| Intrinsic Clearance | $Cl_{int} = \dfrac{Cl_{int,\,in\,vitro} * \text{Liver Mass} * \text{Yield}}{\text{Body Weight}}$ |
| Predicted Hepatic Clearance | $Cl = \dfrac{Cl_{int} * Q_H}{Cl_{int} + Q_H}$ |
| Hepatic Extraction | $E = \dfrac{Cl}{Q_H} * 100\%$ |

Where:
Calculation of In Vitro Intrinsic Clearance $$CL_{int,\,in\,vitro} = \frac{\ln 2}{\text{Half-life} * \text{Concentration}}$$

wherein concentration refers to the protein concentration (mg/ml) in the reaction.

| System | Concentration |
|---|---|
| "Mixed cofactor" Hepatic microsomes (+UDPGA +NADPH) | 1.0 mg protein/mL |

Calculation of In Vivo Intrinsic Clearance

This scales the in vitro intrinsic clearance up to the value that would be predicted for the entire mass of liver tissue (but with no restriction by blood flow). The value depends upon the size of the liver (species-dependent) and the yield of microsomal protein as appropriate (assumed to be species-independent).

$$CL_{int} = \frac{CL_{int,\,in\,vitro} * \text{Liver Mass} * \text{Yield}}{\text{Body weight}}$$

| Matrix | Yield |
|---|---|
| Microsomal fraction | 45 mg/g liver |

| Species | Body weight kg | Liver weight g |
|---|---|---|
| Huan | 70 | 1800 |

Calculation of Predicted Clearance

Hepatic clearance will depend upon the inter-relationship of intrinsic clearance and hepatic blood flow and was predicted from in vitro data using a variety of approaches.

$$CL = \frac{CL_{int} * Q_H}{CL_{int} + Q_H}$$

| Species | Hepatic blood flow L/hr/kg |
|---|---|
| Human | 1.3 |

Calculation of Hepatic Extraction

The hepatic extraction is reported as the predicted clearance expressed as a proportion of hepatic blood flow.

$$E = CL/Q_H * 100\%$$

The Predicted Hepatic Clearance is reported in Table 5 below.

TABLE 5

| Example | Predicted Hepatic Clearance (Pred. Cl.) (L/h/kg) |
|---|---|
| 1 | <0.11 |
| 2 | <0.11 |
| 3 | 0.12 |
| 4 | 0.25 |
| 5 | <0.11 |
| 6 | 0.29 |
| 7 | 0.45 |
| 8 | 0.47 |
| 9 | 0.15 |
| 10 | 0.76 |
| 11 | 0.43 |
| 12 | 0.24 |
| 13 | <0.11 |
| 14 | 0.15 |
| 15 | 0.27 |
| 16 | 0.54 |
| 17 | 0.44 |
| 18 | 0.48 |
| 19 | 0.15 |
| 20 | 0.15 |
| 21 | <0.11 |
| 22 | <0.11 |
| 23 | 0.14 |
| 24 | 0.16 |
| 25 | 0.26 |
| 26 | <0.11 |
| 27 | 0.14 |
| 28 | 0.23 |
| 29 | 0.28 |
| 30 | 0.21 |
| 31 | 0.19 |
| 32 | 0.38 |
| 33 | 0.16 |
| 34 | 0.25 |
| 35 | 0.17 |
| 36 | 0.52 |
| 37 | 0.23 |
| 38 | 0.24 |
| 39 | 0.19 |
| 40 | 0.30 |
| 41 | 0.17 |
| 42 | 0.23 |
| 43 | 0.28 |
| 44 | 0.29 |
| 45 | 0.30 |
| 46 | 0.26 |
| 47 | 0.19 |
| 48 | 0.12 |
| 49 | 0.20 |
| 50 | 0.19 |
| 51 | 0.15 |
| 52 | 1.07 |
| 53 | 0.8 |
| 54 | 0.18 |
| 55 | 0.5 |
| 56 | 0.35 |
| 57 | 0.55 |
| 58 | 0.19 |
| 59 | N/A |
| 60 | 0.21 |
| 61 | 0.8 |
| 62 | 0.53 |
| 63 | 0.21 |
| 64 | 0.22 |
| 65 | 0.2 |
| 66 | 0.43 |
| 67 | 0.43 |
| 68 | 0.17 |
| 69 | 0.15 |
| 70 | 0.21 |
| 71 | 0.23 |
| 72 | 0.22 |
| 73 | 0.15 |
| 74 | 0.46 |
| 75 | 0.29 |
| 76 | 0.48 |
| 77 | 0.26 |
| 78 | 0.43 |
| 79 | 0.14 |
| 80 | 0.24 |
| 81 | 0.52 |
| 82 | N/A |
| 83 | 0.2 |
| 84 | 0.17 |
| 85 | 0.18 |
| 86 | 0.12 |
| 87 | 0.54 |
| 88 | 0.48 |
| 89 | 0.37 |
| 90 | 0.28 |
| 91 | 0.23 |
| 92 | 0.16 |
| 93 | 0.36 |
| 94 | 0.42 |
| 95 | 0.17 |
| 96 | 0.21 |
| 97 | 0.91 |
| 98 | 0.21 |
| 99 | 0.68 |
| 100 | 0.62 |
| 101 | 0.71 |
| 102 | 0.19 |
| 103 | 0.25 |
| 104 | 0.8 |
| 105 | 0.11 |
| 106 | 0.91 |
| 107 | 0.26 |
| 108 | 0.12 |
| 109 | 0.15 |
| 110 | 0.18 |
| 111 | 0.11 |
| 112 | 0.11 |
| 113 | 0.35 |
| 114 | 0.46 |

Although the foregoing has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of Formula (I):

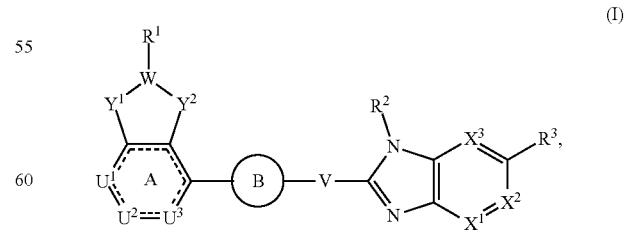

or a pharmaceutically acceptable salt thereof, wherein $R^1$ is $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{6-10}$ aryl, heteroaryl, —C(O)N($R^{1b}$)($R^{1c}$), —C(O)$R^{1b}$, or —C(O)O$R^{1c}$, wherein the alkyl, haloalkyl, cycloalkyl, aryl, heteroaryl, or heterocyclyl is each optionally substituted with one to four $Z^1$;

ring A is an aromatic ring in which $U^1$, $U^2$, $U^3$, are each independently —C(H)=, —C($Z^{1a}$)=, or —N=;

ring B is $C_{6-10}$ aryl or heteroaryl, which is each optionally substituted with one to four $R^4$;

$R^2$ is H, $C_{1-6}$ alkyl, $C_{1-6}$ haloalkyl, $C_{2-6}$ alkenyl, $C_{2-6}$ alkynyl, $C_{3-10}$ cycloalkyl, heterocyclyl, $C_{6-10}$ aryl, heteroaryl, —S—$R^{2a}$, —S(O)$R^{2a}$, —S(O)(NH)$R^{2a}$, —S(O)$_2R^{2a}$, —S(O)$_2$N($R^{2a}$)($R^{2b}$), or —S(O)(N$R^{2a}$)$R^{2b}$, wherein the alkyl, cycloalkyl, heterocyclyl, aryl, or heteroaryl is each optionally substituted with one to four $Z^1$;

$X^1$, $X^2$, and $X^3$ are each independently —N=, —C(H)=, or —C($R^8$)=;

$Y^1$ and $Y^2$ are each —C($R^{y1}$)($R^{y2}$)—, —N($R^{y1}$)—, —O—, —S—, —S(O)$_2$—, or —C(O)—;

W is —C($R^5$)—, or —N—, wherein when W is —N, one of $Y^1$ and $Y^2$ is —C($R^{y1}$)($R^{y2}$)— or —C(O)— and the other of $Y^1$ and $Y^2$ is —C($R^{y1}$)($R^{y2}$)—, —C(O)—, or —S(O)$_2$—;

$R^3$ is H, $C_{1-6}$ alkyl, $C_{1-6}$ haloalkyl, $C_{2-6}$ alkenyl, $C_{2-6}$ alkynyl, halogen, $C_{3-10}$ cycloalkyl, heterocyclyl, $C_{6-10}$ aryl, heteroaryl, —CN, —NO$_2$, —O$R^{3a}$, —C(O)$R^{3a}$, —C(O)O$R^{3a}$, —C(O)N($R^{3a}$)($R^{3b}$), —N($R^{3a}$)C(O)$R^{3b}$, —N($R^{3a}$)C(O)O$R^{3b}$, —N($R^{3a}$)C(O)N($R^{3b}$)$_2$, —C(O)NHS(O)$_2R^{3a}$, —C(O)N$R^{3a}$S(O)$_2R^{3b}$, —C(O)N$R^{3a}$S(O)$_2$N$R^{3b}R^{3c}$, —S(O)$_2$O$R^{3a}$, —S(O)$_2$N($R^{3a}$)($R^{3b}$), —N($R^{3a}$)S(O)$_2R^{3b}$, —S(O)$_2$NHC(O)$R^{3a}$, —S(O)(=N$R^{3a}$)$R^{3b}$, —S(=N$R^{3a}$)(=N$R^{3b}$)$R^{3c}$, —P(O)(O$R^{3a}$)($R^{3b}$), —P(O)(O$R^{3a}$)(O$R^{3b}$), or —B(O$R^{3a}$)(O$R^{3b}$), wherein the alkyl, haloalkyl, alkenyl, alkynyl, cycloalkyl, heterocyclyl, aryl, or heteroaryl is each optionally substituted with one to four $R^{3d}$;

each $R^{3a}$, $R^{3b}$, and $R^{3c}$ is independently H, $C_{1-6}$ alkyl, $C_{1-6}$ haloalkyl, $C_{2-8}$ alkoxyalkyl, —$C_{1-4}$ alkyl-N($R^{9a}$)($R^{9b}$), —$C_{1-4}$ alkyl-C(O)N($R^{9a}$) ($R^{9b}$), —$C_{1-4}$ alkyl-O—C(O)—$C_{1-4}$ alkyl, —$C_{1-4}$ alkyl-O—C(O)—O—$C_{1-4}$ alkyl, —$C_{1-4}$ alkyl-O—C(O)—$C_{1-4}$ alkyl-N($R^{9a}$) ($R^{9b}$), —$C_{1-4}$ alkyl-$C_{3-8}$ cycloalkyl, —$C_{1-4}$ alkyl-heterocyclyl, $C_{2-6}$ alkenyl, $C_{2-6}$ alkynyl, $C_{3-10}$ cycloalkyl, heterocyclyl, $C_{6-10}$ aryl, heteroaryl, —P(O)(O$R^{9c}$)$_2$, —OP(O)(O$R^{9c}$)$_2$, —CH$_2$P(O)(O$R^{9c}$)$_2$, —OCH$_2$P(O) (O$R^{9c}$)$_2$, —C(O)OCH$_2$P(O)(O$R^{9c}$)$_2$, —P(O)(O$R^{9c}$) (O$R^{9d}$), —OP(O)($R^{9c}$)(O$R^{9d}$), —CH$_2$P(O)($R^{9c}$) (O$R^{9d}$), —OCH$_2$P(O)($R^{9c}$)(O$R^{9d}$), —C(O)OCH$_2$P(O) ($R^{9c}$)(O$R^{9d}$), —P(O)(N($R^{9c}$)$_2$)$_2$, —OP(O)(N($R^{9c}$)$_2$)$_2$, —CH$_2$P(O)(N($R^{9c}$)$_2$)$_2$, —OCH$_2$P(O)(N($R^{9c}$)$_2$)$_2$, —C(O)OCH$_2$P(O)(N($R^{9c}$)$_2$)$_2$, —P(O)(N($R^{9c}$)$_2$) (O$R^{9d}$), —OP(O)(N($R^{9c}$)$_2$)(O$R^{9d}$), —CH$_2$P(O)(N ($R^{9c}$)$_2$)(O$R^{9d}$), —OCH$_2$P(O)(N($R^{9c}$)$_2$)(O$R^{9d}$), —C(O)OCH$_2$P(O)(N($R^{9c}$)$_2$)(O$R^{9d}$), —P(O)($R^{9c}$)(N($R^{9d}$)$_2$), —OP(O)($R^{9c}$)(N($R^{9d}$)$_2$), —CH$_2$P(O)($R^{9c}$)(N($R^{9d}$)$_2$), —OCH$_2$P(O)($R^{9c}$)(N($R^{9d}$)$_2$), or —C(O)OCH$_2$P(O) ($R^{9c}$)(N($R^{9d}$)$_2$);

wherein the alkyl, alkenyl, cycloalkyl, heterocyclyl, aryl, or heteroaryl is each optionally substituted with one to four $Z^{1b}$, each $R^4$ is independently $C_{1-9}$ alkyl, $C_{1-8}$ haloalkyl, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—$R^{4a}$, —C(O)$R^{4a}$, —C(O)O—$R^{4a}$, —C(O)N($R^{4a}$) ($R^{4b}$), —N($R^{4a}$) ($R^{4b}$), —N($R^{4a}$)$_2$($R^{4b}$)$^+$, —N($R^{4a}$)—C(O) $R^{4b}$, —N($R^{4a}$)C(O)O($R^{4b}$), —N($R^{4a}$)C(O)N($R^{4b}$) ($R^{4c}$), —N($R^{4a}$)S(O)$_2$($R^{4b}$), —N($R^{4a}$)S(O)$_2$—N($R^{4b}$) ($R^{4c}$), —N($R^{4a}$)S(O)$_2$O($R^{4b}$), —OC(O)$R^{4a}$, —OC(O) O$R^{4a}$, —OC(O)—N($R^{4a}$) ($R^{4b}$), —S—$R^{4a}$, —S(O) $R^{4a}$, —S(O)(NH)$R^{4a}$, —S(O)$_2R^{4a}$, —S(O)$_2$N($R^{4a}$) ($R^{4b}$), —S(O)(N$R^{4a}$)$R^{4b}$, or —Si($R^{4a}$)$_3$;

wherein the alkyl, haloalkyl, alkenyl, alkynyl, cycloalkyl, heterocyclyl, aryl, or heteroaryl is each optionally substituted with one to four $Z^{1b}$;

or two $R^4$ groups attached to adjacent ring atoms are combined with the atoms to which they are attached to form a $C_{5-10}$ cycloalkyl or heterocyclyl, which is each optionally substituted with one to four $Z^{1b}$;

$R^5$ is H, cyclopropyl, or $C_{1-3}$alkyl, wherein the $C_{1-3}$alkyl is optionally substituted with one, two or three groups selected from halogen, —OH, —OCH$_3$, —CN, oxo, and —N($R^{x1}$)($R^{x2}$);

or $R^5$ and $R^{y1}$ are combined with the atoms to which they are attached to form a $C_{3-10}$ cycloalkyl or heterocyclyl optionally substituted with oxo;

$R^{x1}$ and $R^{x2}$ are each independently H, $C_{1-6}$ alkyl, $C_{3-10}$ cycloalkyl, heterocyclyl, —S(O)$_2R^{6a1}$, or —S(O)$_2$N ($R^{6a1}$)(N$R^{6a2}$), wherein the $C_{1-6}$ alkyl, cycloalkyl or heterocyclyl is each optionally substituted with F, —CN, oxo, or $C_{3-6}$ cycloalkyl;

or $R^{x1}$ and $R^{x2}$ are combined with the atom to which they are attached to form a heterocyclyl, which is optionally substituted with one to four $R^{6b1}$;

V is —C(O)—, —O—, —N($R^{6a}$)—, or —C($R^{6b}$)($R^{6c}$)—;

$R^{6a}$ is H, $C_{1-6}$ alkyl, $C_{3-10}$ cycloalkyl, heterocyclyl, —S(O)$_2R^{6a1}$, or —S(O)$_2$N($R^{6a1}$)(N$R^{6a2}$), wherein the cycloalkyl or heterocyclyl is each optionally substituted with $C_{1-6}$ alkyl, F, or —CN;

each $R^{6b}$ and $R^{6c}$ is independently H, $C_{1-6}$ alkyl, $C_{1-6}$ haloalkyl, $C_{2-6}$ alkoxyalkyl, halogen, $C_{3-10}$ cycloalkyl, heterocyclyl, —$C_{1-6}$ alkyl-N($R^{9a}$) ($R^{9b}$), —CN, —O$R^{6c1}$, or —N($R^{6c2}$) ($R^{6c3}$), wherein the alkyl, cycloalkyl, or heterocyclyl is each optionally substituted with one to four $R^{6b1}$;

or $R^{6b}$ and $R^{6c}$ are combined with the atom to which they are attached to form $C_{3-10}$ cycloalkyl or heterocyclyl, which is each optionally substituted with one to four $R^{6b1}$;

or $R^{6a}$ or $R^{6c}$ is combined with one $R^4$ group and the atoms to which they are attached to form a $C_{5-10}$ cycloalkyl or heterocyclyl, which is each optionally substituted with one to four $R^{10}$;

each $R^{y1}$ and $R^{y2}$ is independently H, halo, $C_{1-6}$ alkyl, $C_{1-6}$ haloalkyl, wherein the alkyl and haloalkyl are each optionally substituted with oxo;

each $R^{3d}$, $R^{6b1}$, and $R^{10}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —OH, —CN, —NO$_2$, or —C(O)N($R^{2a}$)($R^{2b}$), wherein the heterocyclyl or heteroaryl is optionally substituted with $C_{1-6}$ alkyl, $C_{1-6}$ haloalkyl, or $C_{1-6}$ haloalkoxy; and each $R^{6a1}$, $R^{6a2}$, $R^{6c1}$, $R^{6c2}$, and $R^{6c3}$ is independently H, $C_{1-6}$ alkyl or $C_{3-10}$ cycloalkyl;

each $R^{9a}$ and $R^{9b}$ is independently H, $C_{1-6}$ alkyl, or $C_{1-6}$ haloalkyl;

each $Z^1$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —N$_3$, —CN, —O—$R^{12a}$, —C(O)—$R^{12a}$, —C(O)O—$R^{12a}$, —C(O)—N($R^{12a}$)($R^{12b}$), —N($R^{12a}$)($R^{12b}$), —N($R^{12a}$)$_2$($R^{12b}$)$^+$, —N($R^{12a}$)C(O)—$R^{12b}$, —N($R^{12a}$)C(O)O—$R^{12b}$, —N($R^{12a}$)C(O)N($R^{12b}$)($R^{12c}$), —N($R^{12a}$)S(O)$_2$($R^{12b}$), —N$R^{12a}$S(O)$_2$N($R^{12b}$)($R^{12c}$), —N$R^{12a}$S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$$R^{12a}$, —S(O)$_2$N($R^{12a}$)($R^{12b}$), —S(O)(N$R^{12a}$)$R^{12b}$, or —Si($R^{12a}$)$_3$;

wherein the alkyl, haloalkyl, alkenyl, alkynyl, cycloalkyl, heterocyclyl, aryl, or heteroaryl is each optionally substituted with one to four $Z^{1a}$;

each $Z^{1a}$ is independently $C_{1-9}$ alkyl, $C_{1-8}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —NO$_2$, —CN, —N$_3$, —O—$R^{12a}$, —C(O)$R^{12a}$, —C(O)O—$R^{12a}$, —C(O)N($R^{12a}$)($R^{12b}$), —N($R^{12a}$)($R^{12b}$), —N($R^{12a}$)$_2$($R^{12b}$)$^+$, —N($R^{12a}$)—C(O)$R^{12b}$, —N($R^{12a}$)C(O)O($R^{12b}$), —N($R^{12a}$)C(O)N($R^{12b}$)($R^{12c}$), —N($R^{12a}$)S(O)$_2$($R^{12b}$), —N($R^{12a}$)S(O)$_2$—N($R^{12b}$)($R^{12c}$), —N($R^{12a}$)S(O)$_2$O($R^{12b}$), —OC(O)$R^{12a}$, —OC(O)O$R^{12a}$, —OC(O)—N($R^{12a}$)($R^{12b}$), —S—$R^{12a}$, —S(O)$R^{12a}$, —S(O)(NH)$R^{12a}$, —S(O)$_2$$R^{12a}$, —S(O)$_2$N($R^{12a}$)($R^{12b}$), —S(O)(N$R^{12a}$)$R^{12b}$, or —Si ($R^{12a}$)$_3$;

wherein the alkyl, haloalkyl, alkenyl, alkynyl, cycloalkyl, heterocyclyl, aryl, or heteroaryl is each optionally substituted with one to four $Z^{1b}$;

each $R^8$ or $Z^{1b}$ is independently $C_{1-9}$ alkyl, $C_{1-8}$ haloalkyl, $C_{2-6}$ alkenyl, $C_{2-6}$ alkynyl, halogen, $C_{3-15}$ cycloalkyl, heterocyclyl, $C_{6-10}$ aryl, heteroaryl, oxo, —OH, —CN, —NO$_2$, —NH$_2$, —N$_3$, —SH, —O($C_{1-9}$ alkyl), —O($C_{1-8}$ haloalkyl), —O($C_{2-6}$ alkenyl), —O($C_{2-6}$ alkynyl), —O($C_{3-15}$ cycloalkyl), —O(heterocyclyl), —O($C_{6-10}$ aryl), —O(heteroaryl), —NH($C_{1-9}$ alkyl), —NH($C_{1-8}$ haloalkyl), —NH($C_{2-6}$ alkenyl), —NH($C_{2-6}$ alkynyl), —NH($C_{3-15}$ cycloalkyl), —NH(heterocyclyl), —NH($C_{6-10}$ aryl), —NH(heteroaryl), —N($C_{1-9}$ alkyl)$_2$, —N($C_{1-8}$ haloalkyl)$_2$, —N($C_{2-6}$ alkenyl)$_2$, —N($C_{2-6}$ alkynyl)$_2$, —N($C_{3-15}$ cycloalkyl)$_2$, —N(heterocyclyl)$_2$, —N($C_{6-10}$ aryl)$_2$, —N(heteroaryl)$_2$, —N($C_{1-9}$ alkyl)($C_{1-8}$ haloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)(heterocyclyl), —N($C_{1-9}$ alkyl)($C_{6-10}$ aryl), —N($C_{1-9}$ alkyl)(heteroaryl), —C(O)($C_{1-9}$ alkyl), —C(O)($C_{1-8}$ haloalkyl), —C(O)($C_{2-6}$ alkenyl), —C(O)($C_{2-6}$ alkynyl), —C(O) ($C_{3-15}$ cycloalkyl), —C(O)(heterocyclyl), —C(O) ($C_{6-10}$ aryl), —C(O)(heteroaryl), —C(O)O($C_{1-9}$ alkyl), —C(O)O($C_{1-8}$ haloalkyl), —C(O)O($C_{2-6}$ alkenyl), —C(O)O($C_{2-6}$ alkynyl), —C(O)O($C_{3-15}$ cycloalkyl), —C(O)O(heterocyclyl), —C(O)O($C_{6-10}$ aryl), —C(O)O(heteroaryl), —C(O)NH$_2$, —C(O)NH($C_{1-9}$ alkyl), —C(O)NH($C_{1-8}$ haloalkyl), —C(O)NH($C_{2-6}$ alkenyl), —C(O)NH($C_{2-6}$ alkynyl), —C(O)NH($C_{3-15}$ cycloalkyl), —C(O)NH(heterocyclyl), —C(O)NH($C_{6-10}$ aryl), —C(O)NH(heteroaryl), —C(O)N($C_{1-9}$ alkyl)$_2$, —C(O)N($C_{1-8}$ haloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N(heterocyclyl)$_2$, —C(O)N($C_{6-10}$ aryl)$_2$, —C(O)N(heteroaryl)$_2$, —NHC(O)($C_{1-9}$ alkyl), —NHC(O)($C_{1-8}$ haloalkyl), —NHC(O)($C_{2-6}$ alkenyl), —NHC(O)($C_{2-6}$ alkynyl), —NHC(O)($C_{3-15}$ cycloalkyl), —NHC(O)(heterocyclyl), —NHC(O)($C_{6-10}$ aryl), —NHC(O)(heteroaryl), —NHC(O)O($C_{1-9}$ alkyl), —NHC(O)O($C_{1-8}$ haloalkyl), —NHC(O)O($C_{2-6}$ alkenyl), —NHC(O)O($C_{2-6}$ alkynyl), —NHC(O)O($C_{3-15}$ cycloalkyl), —NHC(O)O(heterocyclyl), —NHC(O)O($C_{6-10}$ aryl), —NHC(O)O(heteroaryl), —NHC(O)NH($C_{1-9}$ alkyl), —NHC(O)NH($C_{1-8}$ haloalkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH(heterocyclyl), —NHC(O)NH($C_{6-10}$ aryl), —NHC(O)NH(heteroaryl), —NHS(O) ($C_{1-9}$ alkyl), —N($C_{1-9}$ alkyl)S(O)($C_{1-9}$ alkyl), —S($C_{1-9}$ alkyl), —S($C_{1-8}$ haloalkyl), —S($C_{2-6}$ alkenyl), —S($C_{2-6}$ alkynyl), —S($C_{3-15}$ cycloalkyl), —S(heterocyclyl), —S($C_{6-10}$ aryl), —S(heteroaryl), —S(O)N ($C_{1-9}$ alkyl)$_2$, —S(O)($C_{1-9}$ alkyl), —S(O)($C_{1-8}$ haloalkyl), —S(O)($C_{2-6}$ alkenyl), —S(O)($C_{2-6}$ alkynyl), —S(O)($C_{3-15}$ cycloalkyl), —S(O)(heterocyclyl), —S(O)($C_{6-10}$ aryl), —S(O)(heteroaryl), —S(O)$_2$($C_{1-9}$ alkyl), —S(O)$_2$($C_{1-8}$ haloalkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$ (heterocyclyl), —S(O)$_2$($C_{6-10}$ aryl), —S(O)$_2$ (heteroaryl), —S(O)(NH) ($C_{1-9}$ alkyl), —S(O)$_2$NH ($C_{1-9}$ alkyl), or —S(O)$_2$N($C_{1-9}$ alkyl)$_2$;

wherein the alkyl, cycloalkyl, heterocyclyl, aryl, or heteroaryl in each instance is optionally substituted with one to three $C_{1-9}$ alkyl, $C_{1-8}$ haloalkyl, halogen, —OH, —NH$_2$, —O($C_{1-9}$ alkyl), —O($C_{1-8}$ haloalkyl), —O($C_{3-15}$ cycloalkyl), —O(heterocyclyl), —O(aryl), —O(heteroaryl), —NH($C_{1-9}$ alkyl), —NH($C_{1-8}$ haloalkyl), —NH($C_{3-15}$ cycloalkyl), —NH(heterocyclyl), —NH(aryl), —NH(heteroaryl), —N($C_{1-9}$ alkyl)$_2$, —N($C_{3-15}$ cycloalkyl)$_2$, —NHC(O)($C_{1-8}$ haloalkyl), —NHC(O)($C_{3-15}$ cycloalkyl), —NHC(O)(heterocyclyl), —NHC(O) (aryl), —NHC(O)(heteroaryl), —NHC(O)O($C_{1-9}$ alkyl), —NHC(O)O($C_{1-8}$ haloalkyl), —NHC(O)O ($C_{2-6}$ alkynyl), —NHC(O)O($C_{3-15}$ cycloalkyl), —NHC(O)O(heterocyclyl), —NHC(O)O(aryl), —NHC(O)O(heteroaryl), —NHC(O)NH($C_{1-9}$ alkyl), S(O)$_2$($C_{1-9}$ alkyl), —S(O)$_2$($C_{1-8}$ haloalkyl), —S(O)$_2$($C_{3-15}$ cycloalkyl), —S(O)$_2$ (heterocyclyl), —S(O)$_2$ (aryl), —S(O)$_2$ (heteroaryl), —S(O)(NH) ($C_{1-9}$ alkyl), —S(O)$_2$NH($C_{1-9}$ alkyl), or —S(O)$_2$N ($C_{1-9}$ alkyl)$_2$; and each $R^{1b}$, $R^{1c}$, $R^{2a}$, $R^{2b}$, $R^{4a}$, $R^{4b}$, $R^{4c}$, $R^{9c}$, $R^{9d}$, $R^{12a}$, $R^{12b}$, and $R^{12c}$ is independently H, $C_{1-9}$ alkyl, $C_{2-6}$ alkenyl, $C_{2-6}$ alkynyl, $C_{3-15}$ cycloalkyl, heterocyclyl, $C_{6-10}$ aryl, or heteroaryl wherein the alkyl, alkenyl, alkynyl, cycloalkyl, heterocyclyl, aryl, or heteroaryl is each optionally substituted with one to four $Z^{1b}$;

wherein each heteroaryl has 5 to 12 ring members and has one to four heteroatoms each independently N, O, or S; and wherein each heterocyclyl has 3 to 12 ring members and has one to four heteroatoms each independently N, O, or S.

2. The compound of claim 1, or a pharmaceutically acceptable salt thereof, wherein
$R^1$ is $C_{1-6}$ alkyl, $C_{1-6}$ haloalkyl, $C_{3-10}$ cycloalkyl, heterocyclyl, $C_{6-10}$ aryl, or heteroaryl; wherein the alkyl, haloalkyl, cycloalkyl, aryl, heteroaryl, or heterocyclyl is each optionally substituted with one to four $Z^1$.

3. The compound of claim 2, or a pharmaceutically acceptable salt thereof, wherein
$R^1$ is $C_{6-10}$ aryl, or heteroaryl, which is each optionally substituted with one to three $Z^1$.

4. The compound of claim 3, or a pharmaceutically acceptable salt thereof, wherein
$R^1$ is a 6-membered aryl or a 5- or 6-membered heteroaryl substituted with one, two, or three groups selected from $C_{1-8}$ haloalkyl, halogen, $C_{1-6}$ alkoxy, —CN, and —C(O)—N($R^{12a}$)($R^{12b}$).

5. The compound of claim 4, or a pharmaceutically acceptable salt thereof, wherein
$R^1$ is a 6-membered aryl or a 5- or 6-membered heteroaryl substituted with one or two —Cl, —F, or —CN.

6. The compound of claim 1, or a pharmaceutically acceptable salt thereof, wherein
$R^5$ is hydrogen or methyl.

7. The compound of claim 1, or a pharmaceutically acceptable salt thereof, wherein
$Y^1$ and $Y^2$ are both —O—.

8. The compound of claim 1, or a pharmaceutically acceptable salt thereof, wherein
each $Z^{1a}$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, oxo, —OH, —CN, —$NO_2$, —$OR^{12a}$, or —$C(O)N(R^{12a})(R^{12b})$, wherein the alkyl, haloalkyl, alkenyl, alkynyl, cycloalkyl, heterocyclyl, aryl, and heteroaryl is optionally substituted with $Z^{1b}$.

9. The compound of claim 1, or a pharmaceutically acceptable salt thereof, wherein
ring B is phenyl or 5- to 6-membered heteroaryl, wherein the phenyl or heteroaryl is optionally substituted with one to four $R^4$.

10. The compound of claim 1, or a pharmaceutically acceptable salt thereof, wherein
ring B is

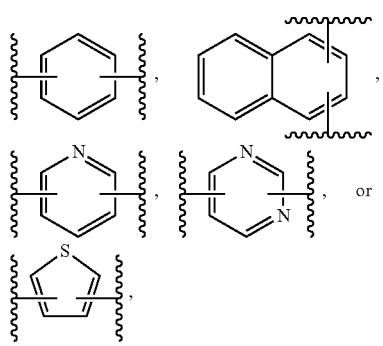

which are each optionally substituted with one to three $R^4$.

11. The compound of claim 10, or a pharmaceutically acceptable salt thereof, wherein
ring B is

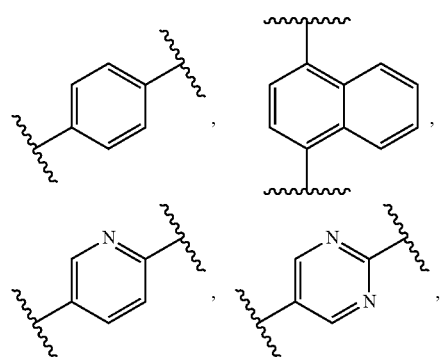

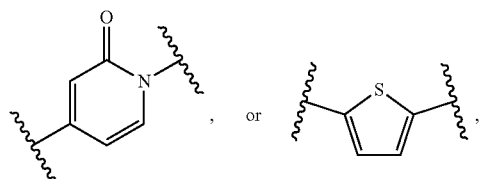

which are each optionally substituted with one or two $R^4$.

12. The compound of claim 1, or a pharmaceutically acceptable salt thereof, having the structure of Formula (Ic) or (Id):

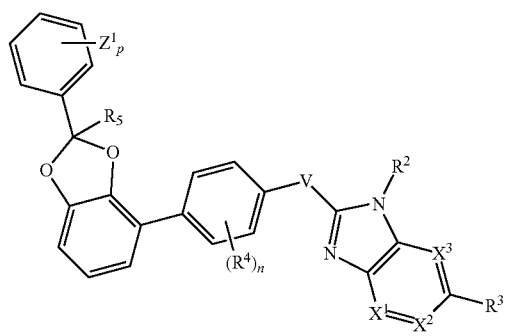

or

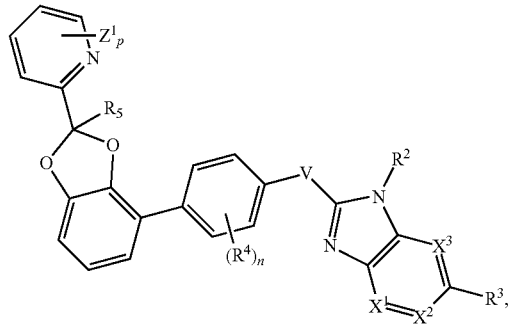

wherein
subscript n is 0, 1, 2, or 3; and
subscript p is 1, 2, or 3.

13. The compound of claim 1, or a pharmaceutically acceptable salt thereof, wherein
$X^1$, $X^2$, and $X^3$ are each independently —CH=, —C(F)=, —C(Cl)=, —C(Br)=, or —C(CN)=.

14. The compound of claim 1, or a pharmaceutically acceptable salt thereof, wherein
V is —O—, —NH—, or —$CH_2$—.

15. The compound of claim 12, or a pharmaceutically acceptable salt thereof, having the structure of Formula (Ie) or (If):

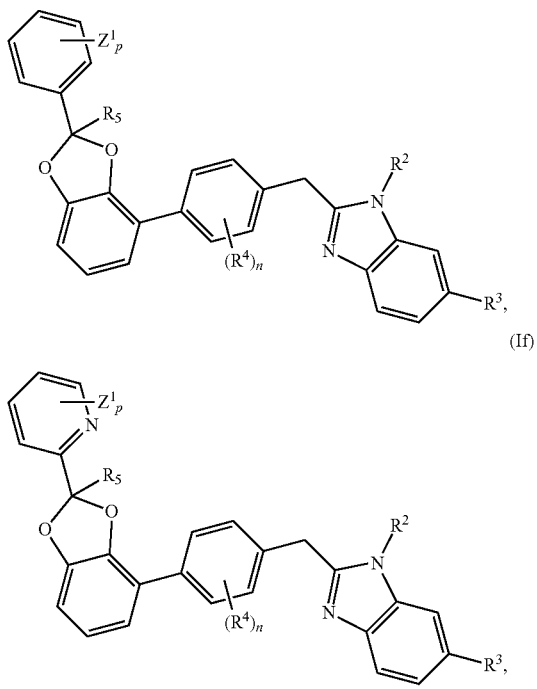

(Ie)

(If)

wherein
subscript n is 0, 1, 2, or 3; and
subscript p is 1, 2, or 3.

16. The compound of claim 12, or a pharmaceutically acceptable salt thereof, having the structure of Formula (Ig):

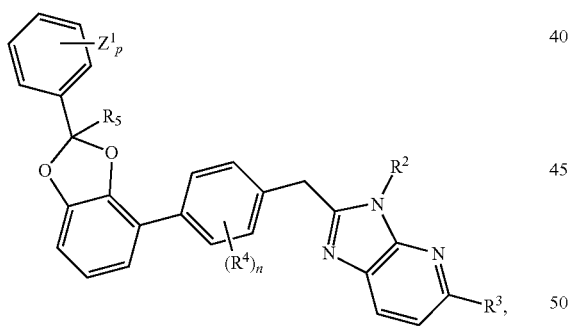

(Ig)

wherein
subscript n is 0, 1, 2, or 3; and
subscript p is 1, 2, or 3.

17. The compound of claim 1, or a pharmaceutically acceptable salt thereof, wherein
each $Z^1$ is independently $C_{1-6}$ alkyl, $C_{1-6}$ haloalkyl, $C_{1-6}$ alkoxy, $C_{1-6}$ haloalkoxy, $C_{2-6}$ alkoxyalkyl, $C_{2-6}$ alkenyl, $C_{2-6}$ alkynyl, halogen, $C_{3-10}$ cycloalkyl, heterocyclyl, $C_{6-10}$ aryl, heteroaryl, heterocyclyl-$C_{1-6}$ alkyl, heterocyclyl-$C_{1-6}$ haloalkyl, heteroaryl-$C_{1-6}$ alkyl, heteroaryl-$C_{1-6}$ haloalkyl, oxo, —OH, —CN, —NO$_2$, or —C(O)N($R^{12a}$)($R^{12b}$), wherein the heteroaryl or heterocyclyl is each optionally substituted with one to four halogen, $C_{1-6}$ haloalkyl, $C_{3-6}$ cycloalkyl, 4-6 membered heterocyclyl, or —CN.

18. The compound of claim 17, or a pharmaceutically acceptable salt thereof, wherein
each $Z^1$ is independently $C_{1-6}$ alkyl, $C_{1-6}$ haloalkyl, $C_{1-6}$ alkoxy, $C_{1-6}$ haloalkoxy, halogen, oxo, —OH, —CN, or —NO$_2$, $C_{3-10}$ cycloalkyl, 3 to 12 membered heterocyclyl having one to three heteroatoms, or 5 to 10 membered heteroaryl having one to three heteroatoms.

19. The compound of claim 18, or a pharmaceutically acceptable salt thereof, wherein
each $Z^1$ is independently $C_{1-6}$ haloalkyl, $C_{1-6}$ haloalkoxy, halogen, —CN, or 5 to 6 membered heteroaryl having one to three heteroatoms.

20. The compound of claim 18, or a pharmaceutically acceptable salt thereof, wherein
each $Z^1$ is independently halogen, $C_{1-6}$ haloalkyl, $C_{1-3}$ alkoxy, $C_{3-10}$ cycloalkyl, or —CN.

21. The compound of claim 1, or a pharmaceutically acceptable salt thereof, wherein
$R^2$ is:

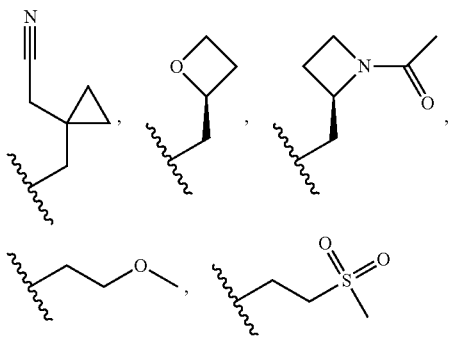

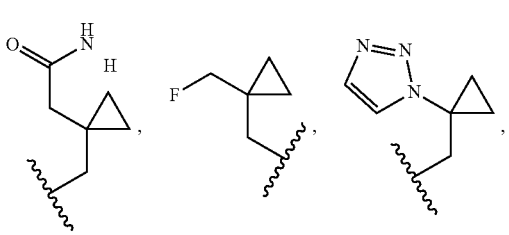

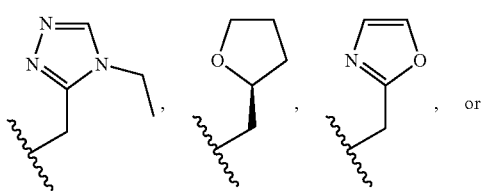

or

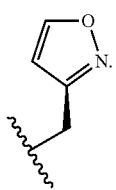

22. The compound of claim 1, or a pharmaceutically acceptable salt thereof, wherein R² is:

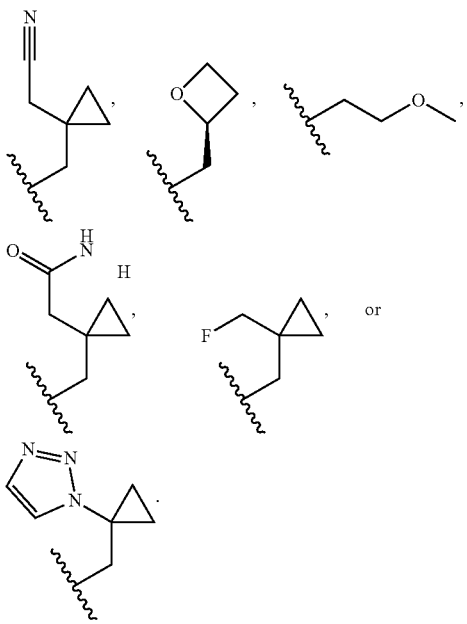

23. The compound of claim 1, or a pharmaceutically acceptable salt thereof, wherein
R³ is heteroaryl, —C(O)OH, —C(O)OR$^{3a}$, —C(O)N(R$^{3a}$)S(O)$_2$(R$^{3b}$), —S(O)$_2$NHC(O)R$^{3a}$, or —C(O)N(R$^{3a}$)S(O)$_2$N(R$^{3b}$)(R$^{3c}$), wherein the heteroaryl is optionally substituted with one to four R$^{3d}$.

24. The compound of claim 23, or a pharmaceutically acceptable salt thereof, wherein
R³ is 5- to 6-membered heteroaryl, optionally substituted with one to four R$^{3d}$.

25. The compound of claim 23, or a pharmaceutically acceptable salt thereof, wherein
R³ is —C(O)OR$^{3a}$.

26. The compound of claim 25, or a pharmaceutically acceptable salt thereof, wherein
R³ is —C(O)OH.

27. The compound of claim 1, or a pharmaceutically acceptable salt thereof, wherein
each R⁴ is independently C$_{1-6}$ alkyl, C$_{1-6}$ haloalkoxy, C$_{2-6}$ alkoxyalkyl, halogen, oxo, —CN, or —OR$^{4a}$.

28. The compound of claim 27, or a pharmaceutically acceptable salt thereof, wherein
each R⁴ is independently C$_{1-6}$ alkyl, halogen, oxo, —CN, or —OR$^{4a}$.

29. The compound of claim 28, or a pharmaceutically acceptable salt thereof, wherein
each R⁴ is independently C$_{1-6}$ alkyl, halogen, oxo, —OH, or —CN.

30. The compound of claim 29, or a pharmaceutically acceptable salt thereof, wherein
each R⁴ is independently F, oxo, or —CN.

31. The compound of claim 1, or a pharmaceutically acceptable salt thereof, wherein
R$^{6a}$ is H, C$_{1-6}$ alkyl, C$_{3-10}$ cycloalkyl, or heterocyclyl.

32. The compound of claim 1, or a pharmaceutically acceptable salt thereof, wherein
each R$^{6b}$ and R$^{6c}$ is independently H, C$_{1-3}$ alkyl, F, Cl, or —CN.

33. The compound of claim 12, or a pharmaceutically acceptable salt thereof, wherein
subscript n is 0, 1, or 2.

34. The compound of claim 12, or a pharmaceutically acceptable salt thereof, wherein
subscript p is 1 or 2.

35. The compound of claim 1, or a pharmaceutically acceptable salt thereof, having the structure:

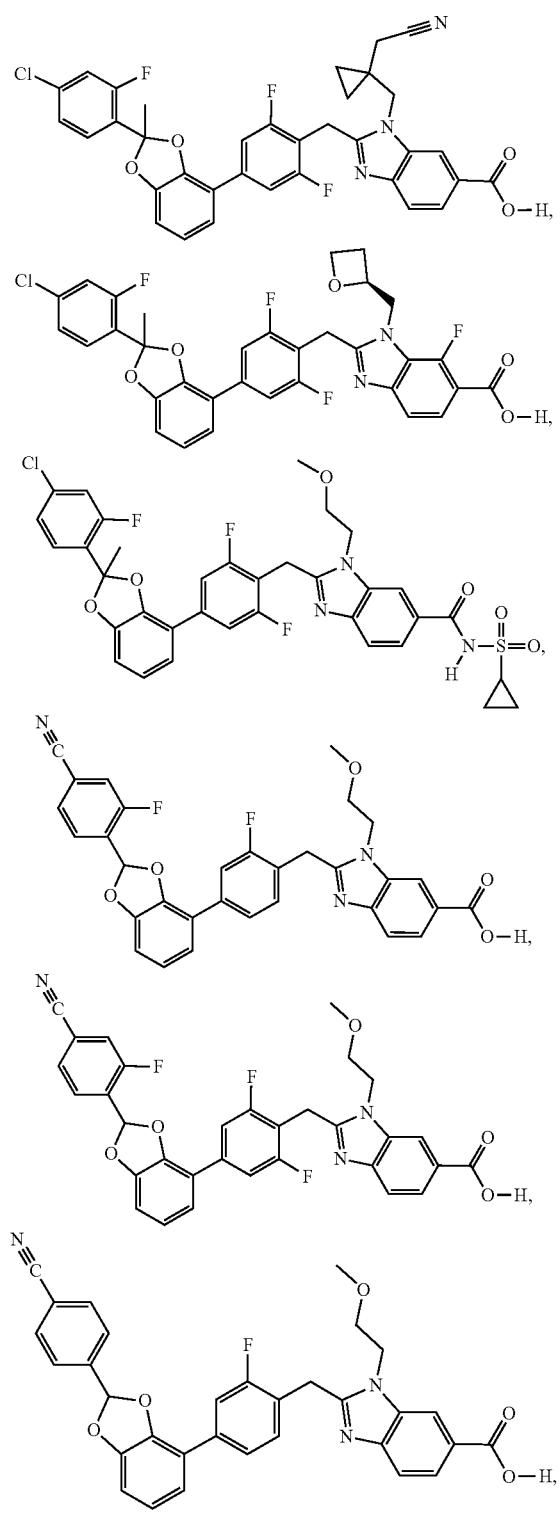

221
-continued
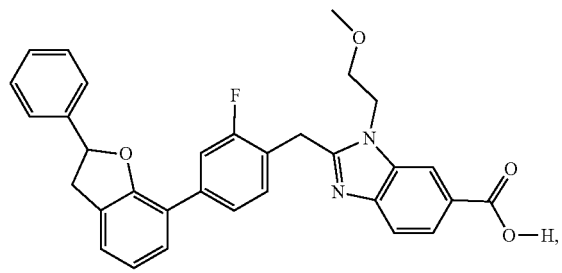
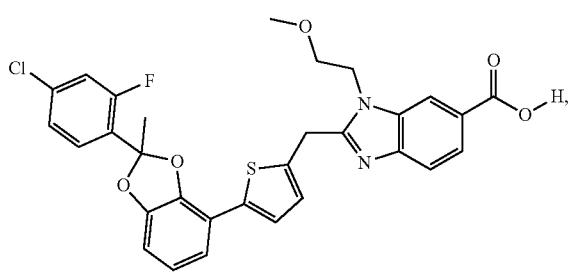
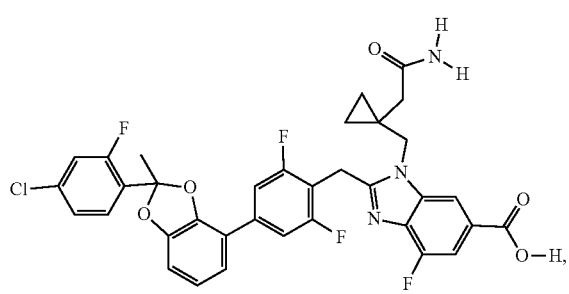
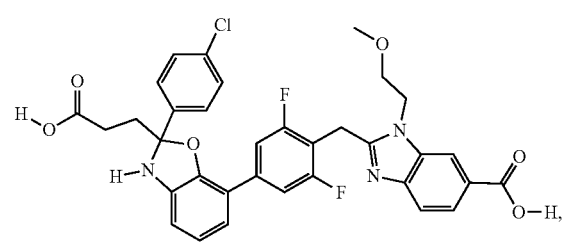
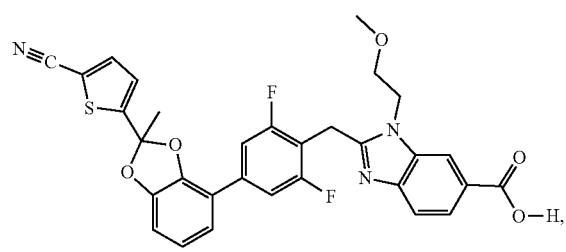
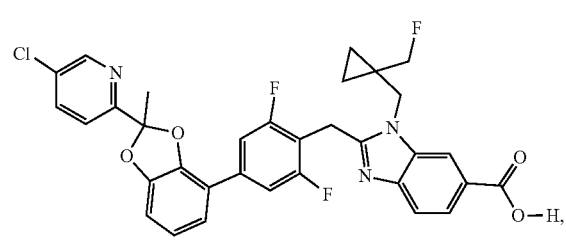
222
-continued
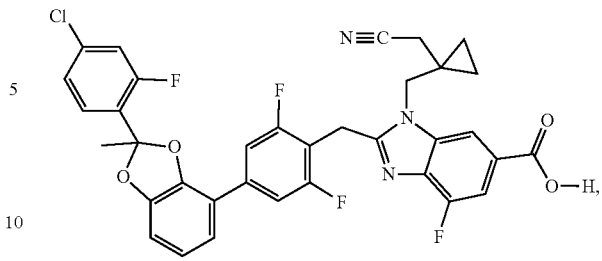
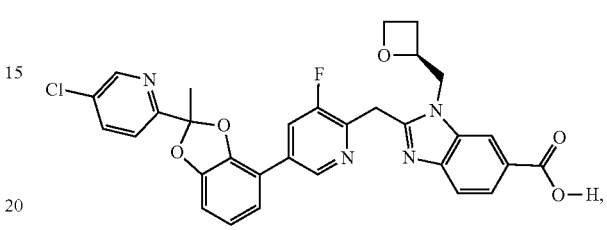
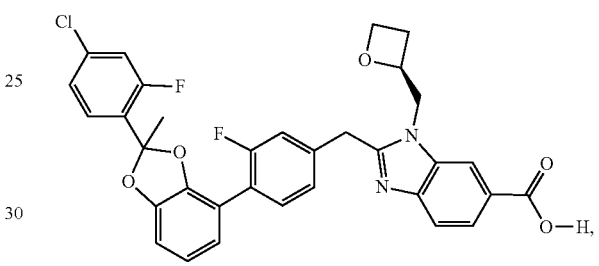
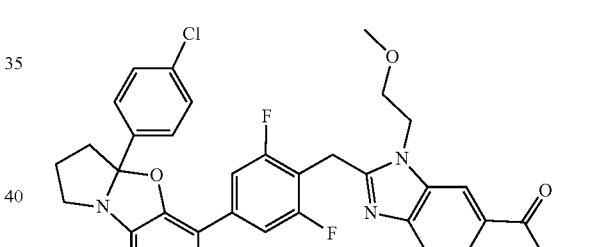
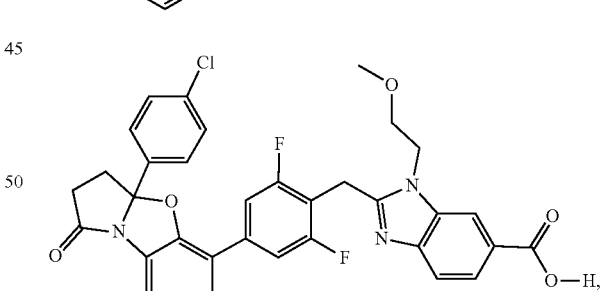
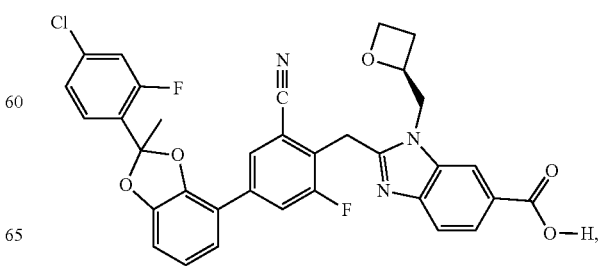

223
-continued
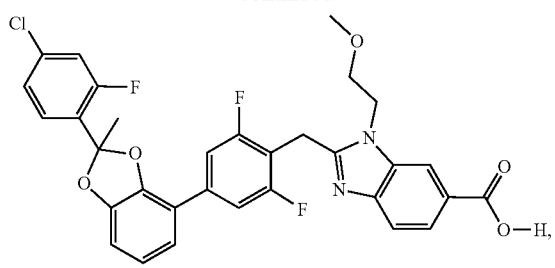
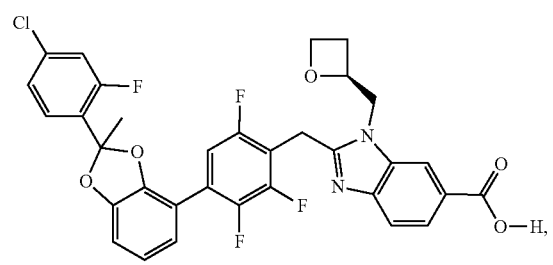
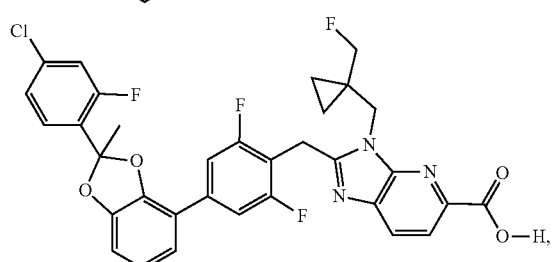
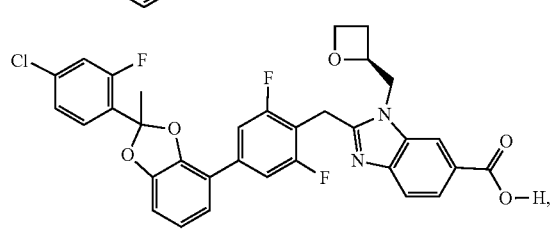
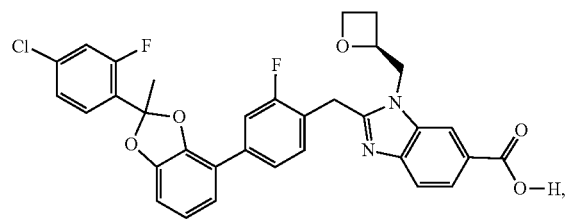
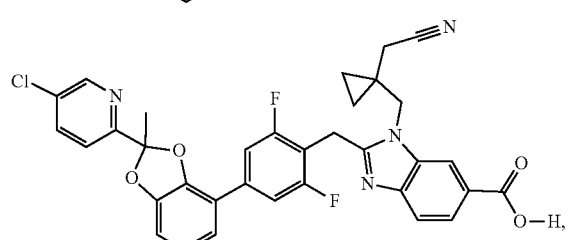
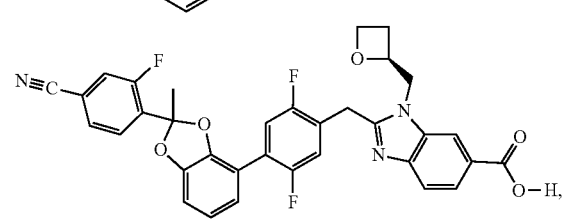
224
-continued
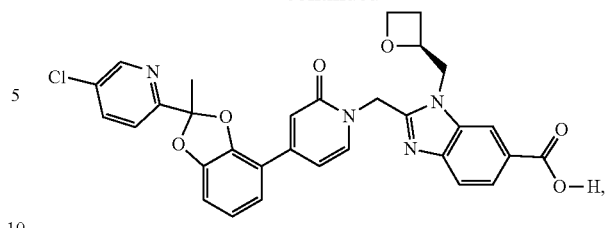
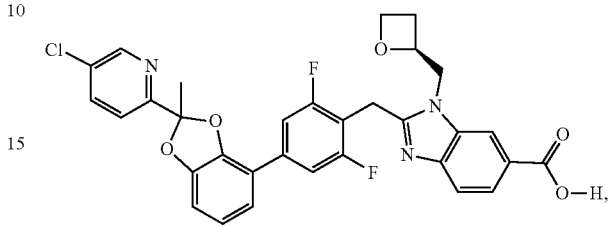
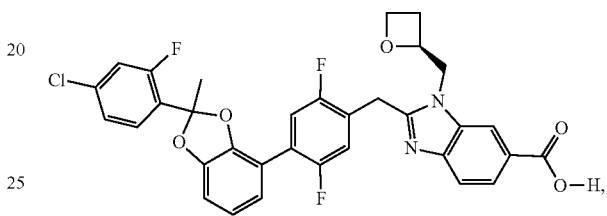
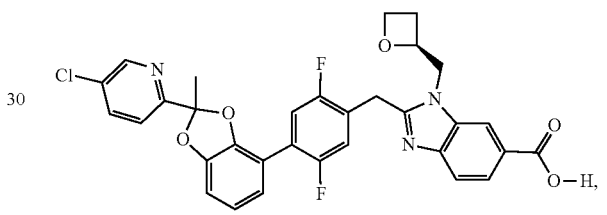
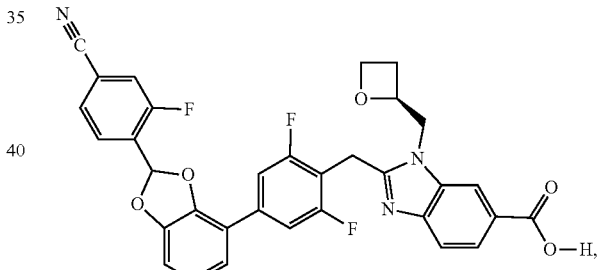
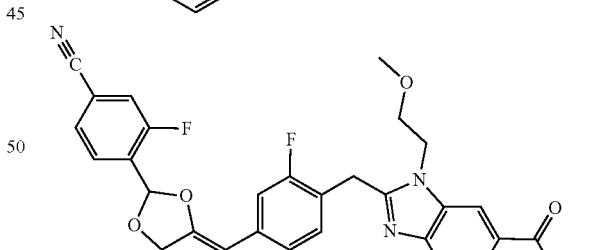
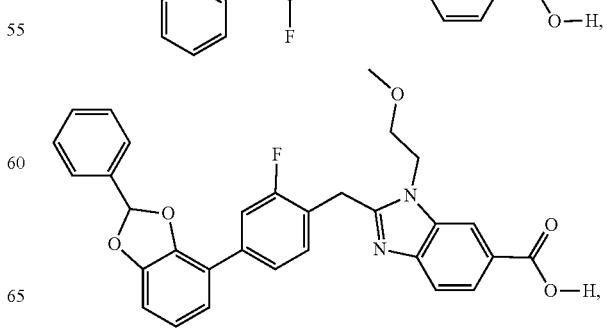

225
-continued
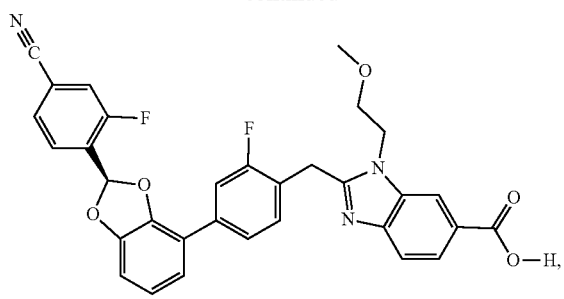
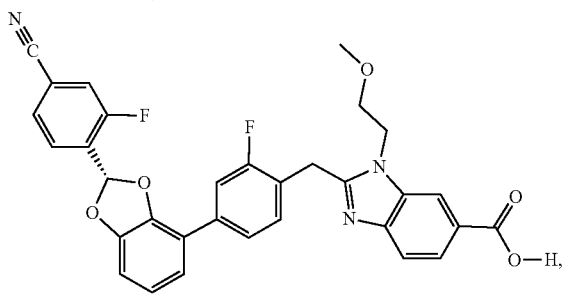
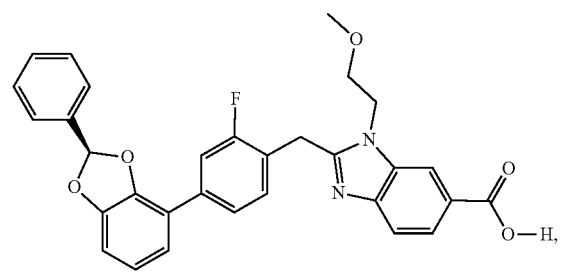
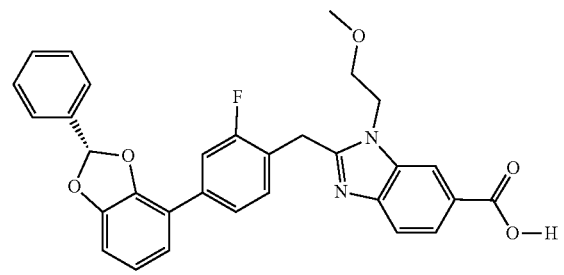
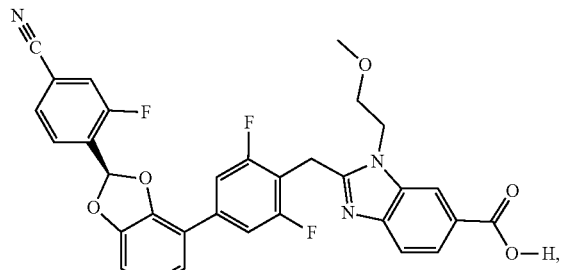
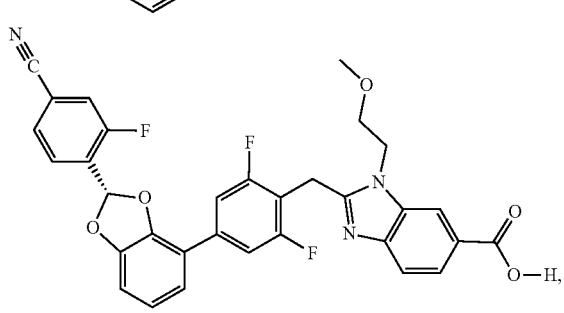
226
-continued
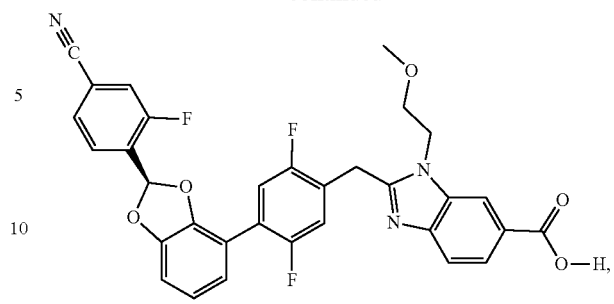
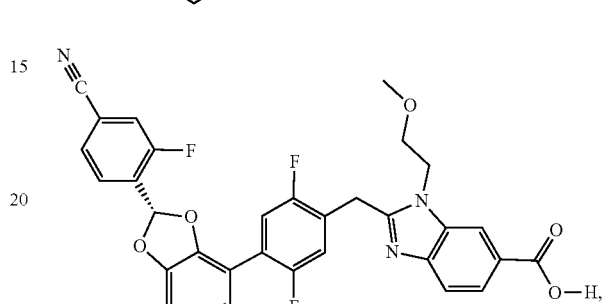
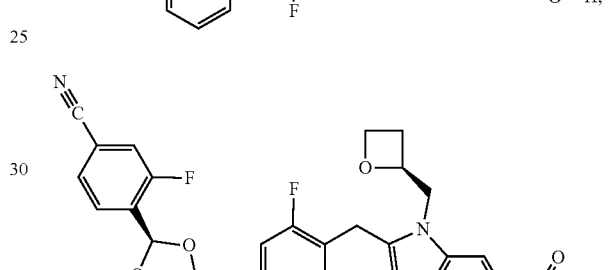
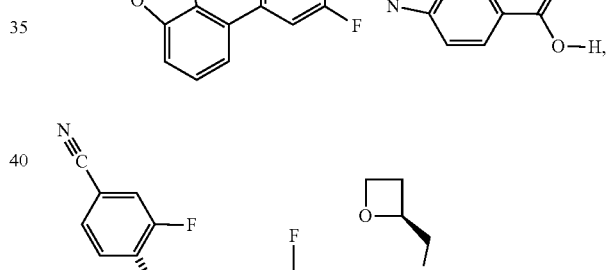
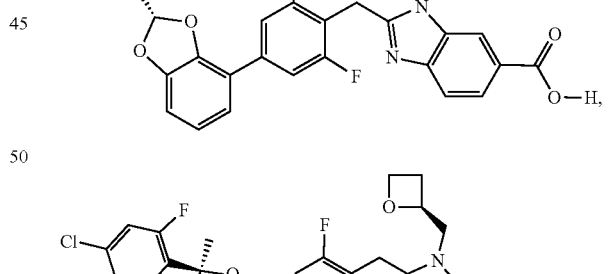
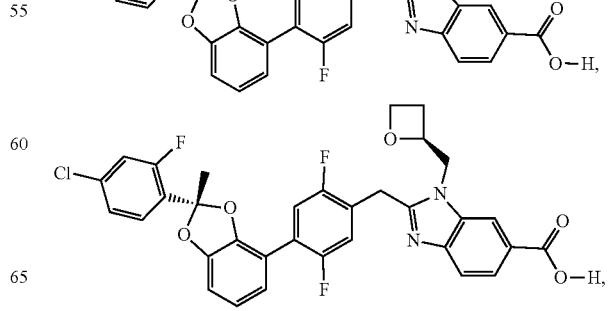

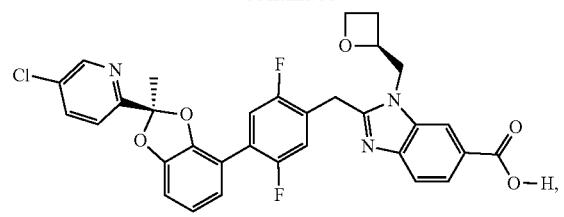
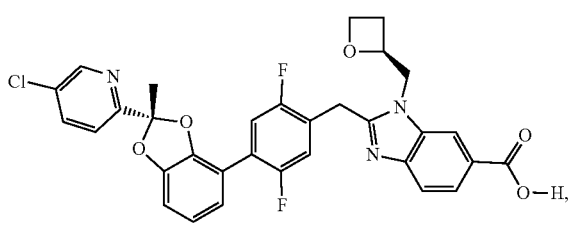
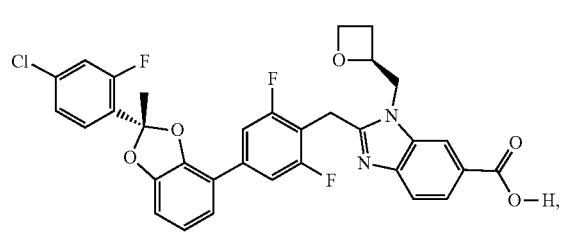
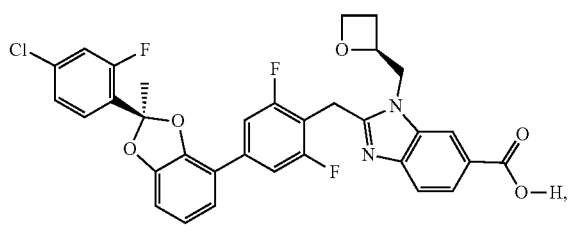
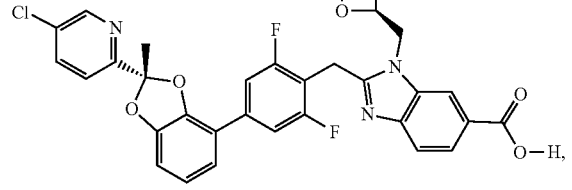
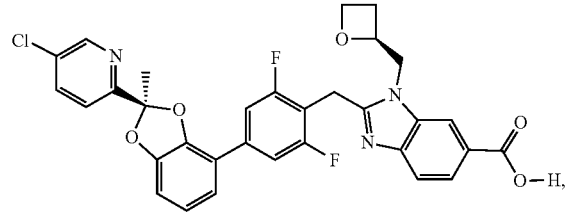
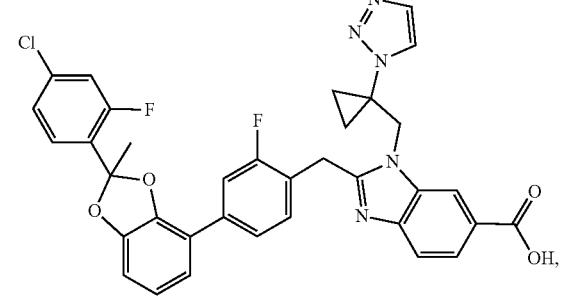
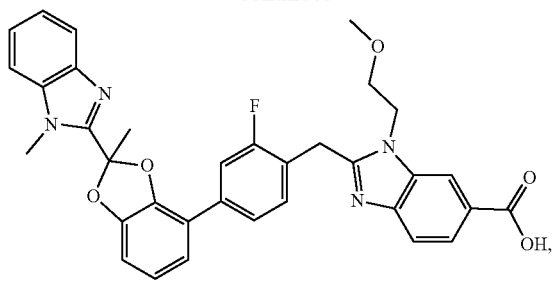
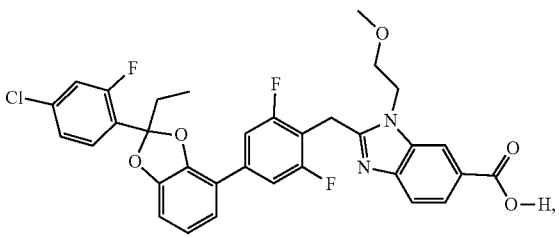
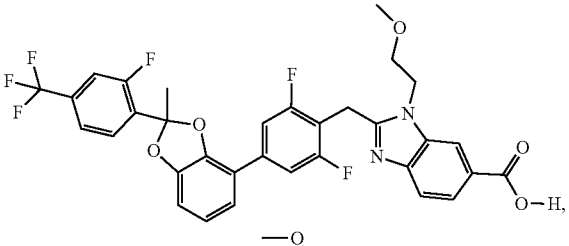
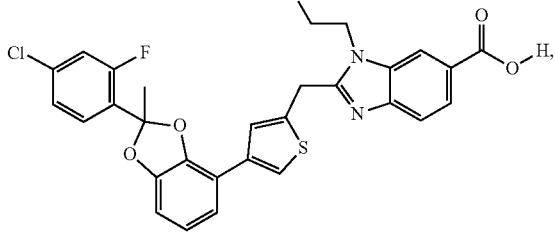
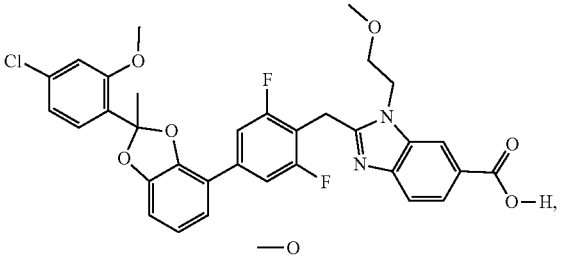
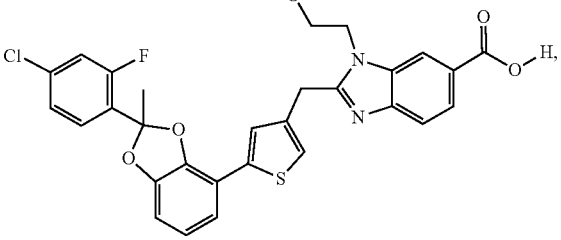
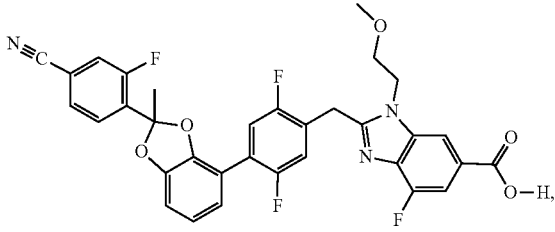

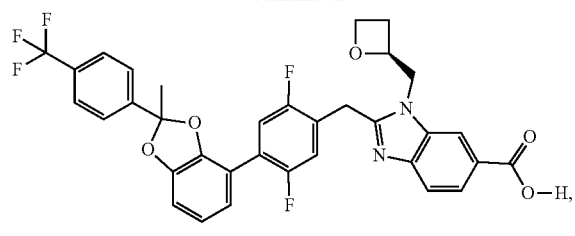
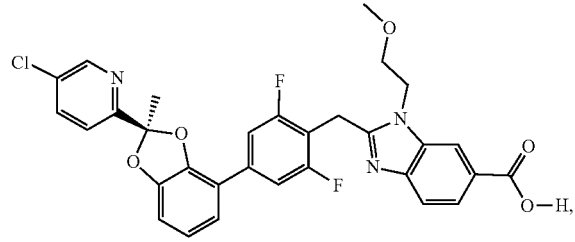
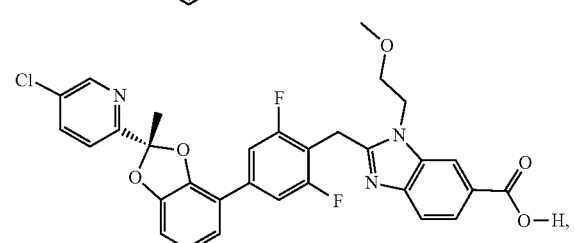
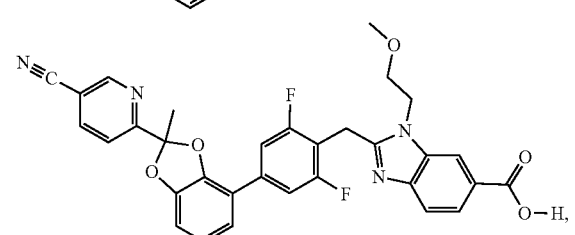
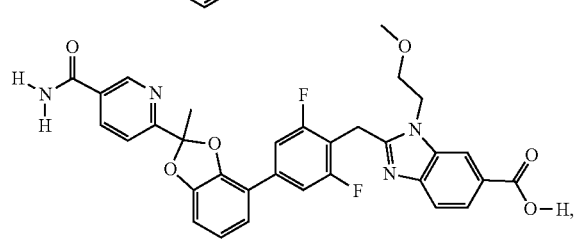
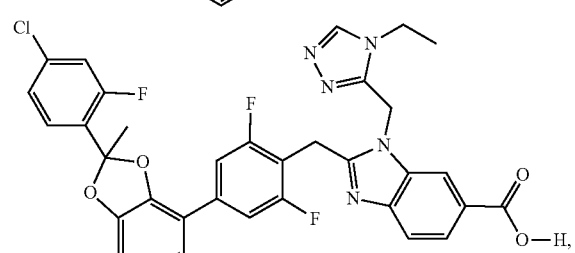
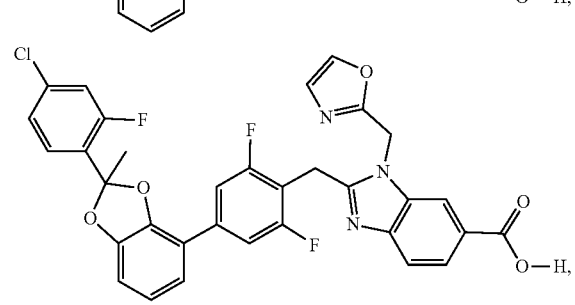
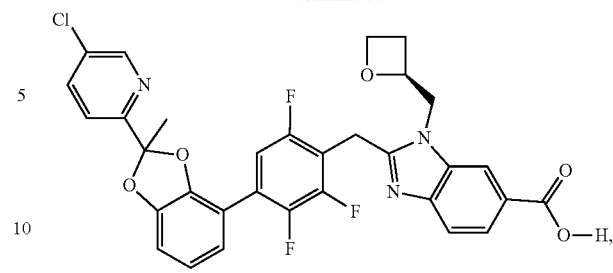
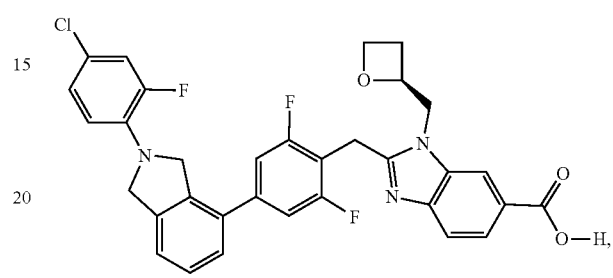
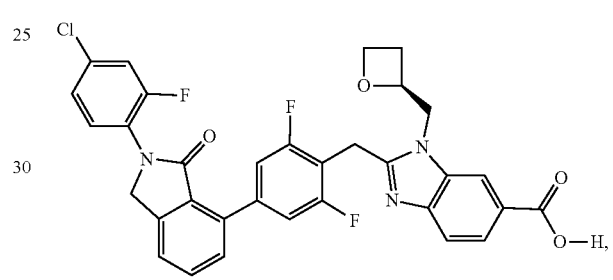
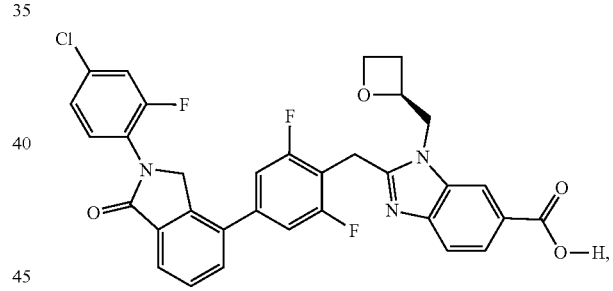
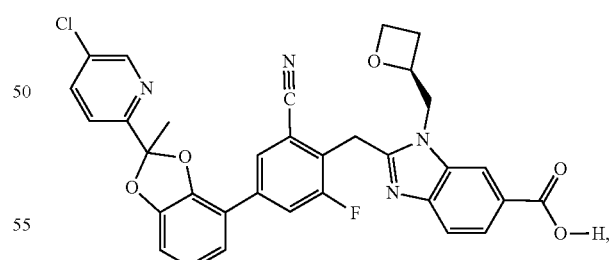
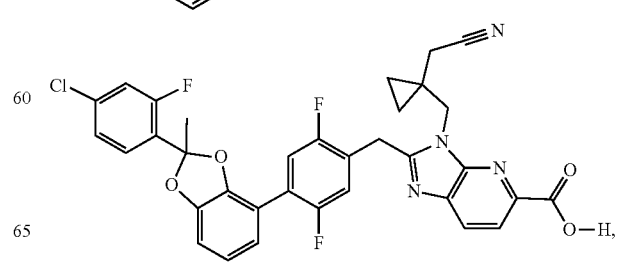

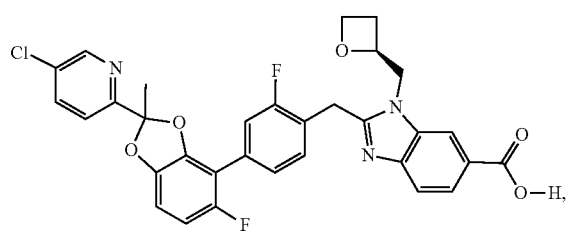
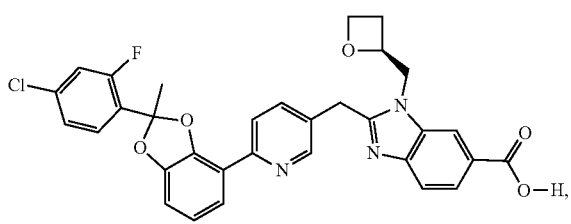
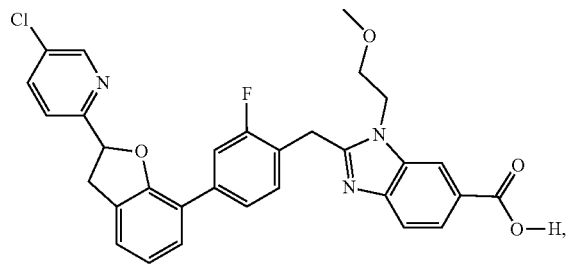
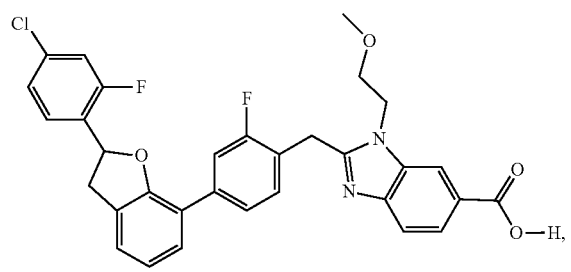
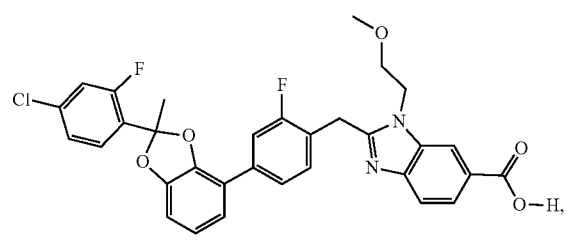
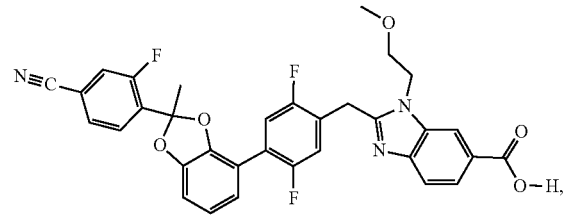
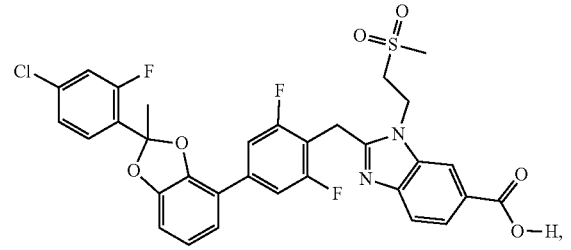
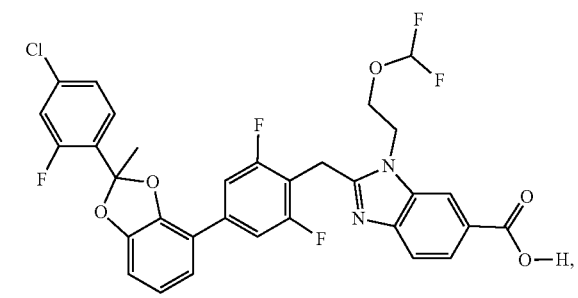
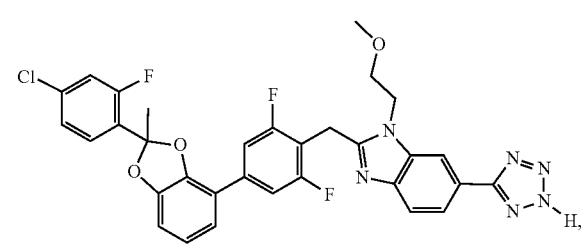
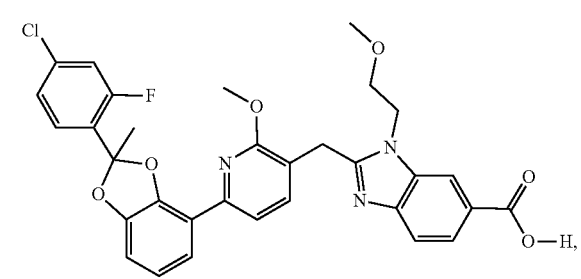
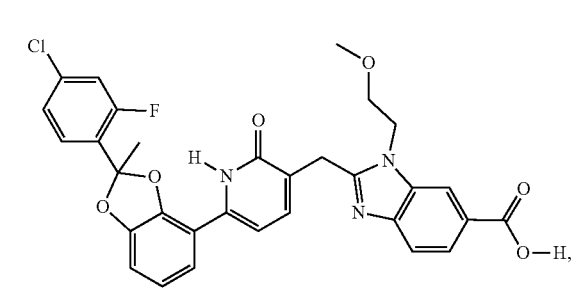
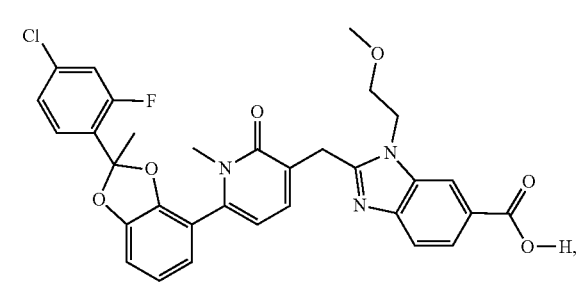
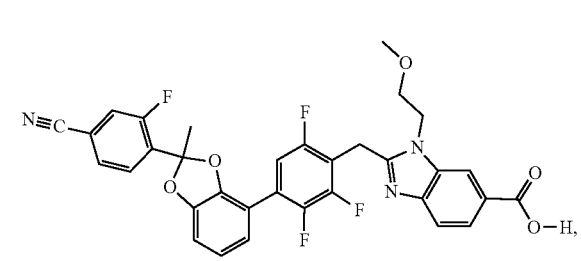

233
-continued
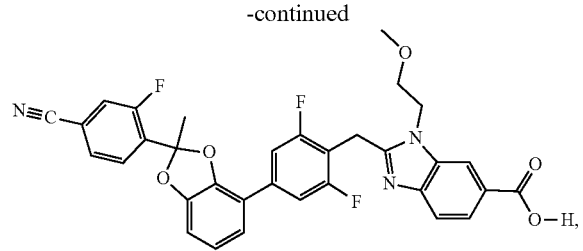
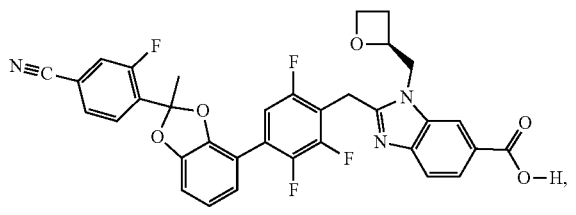
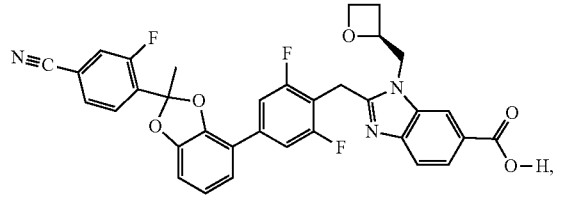
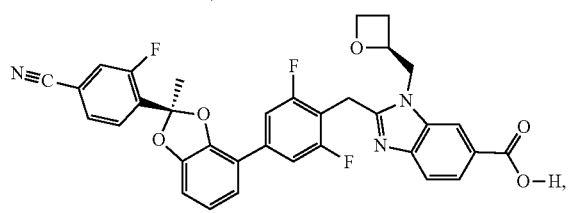
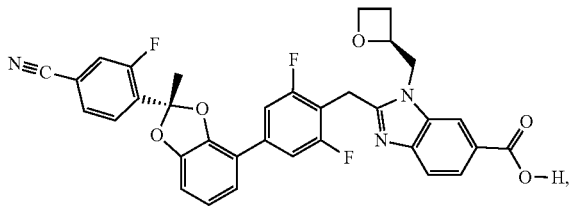
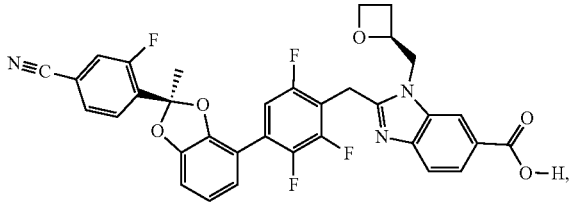
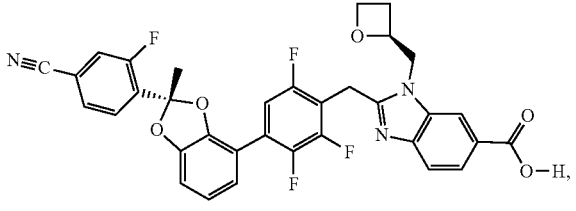
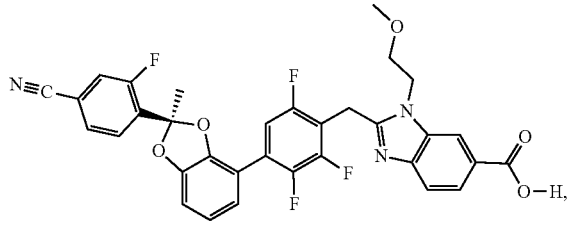
234
-continued
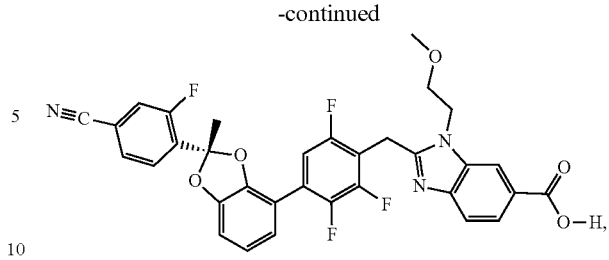
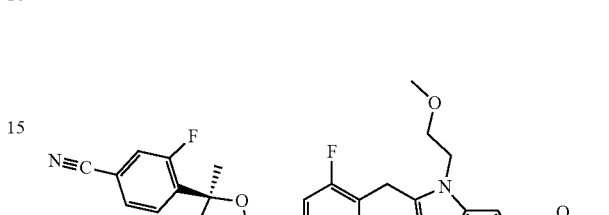
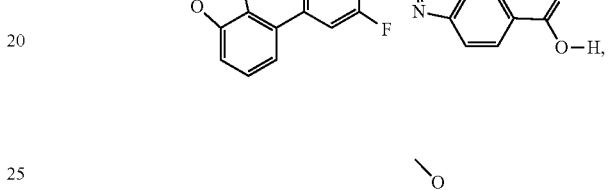
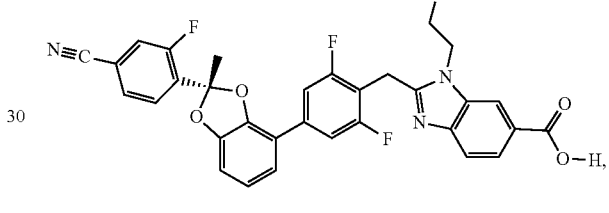
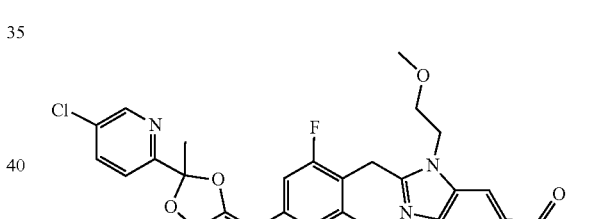
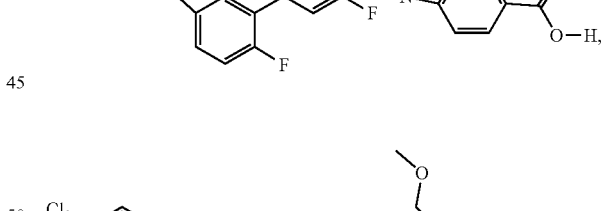
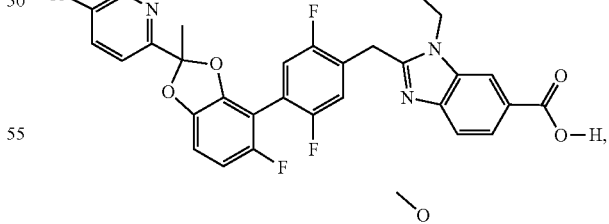
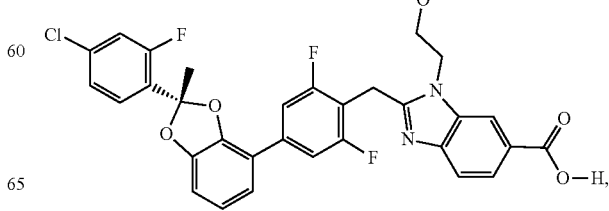

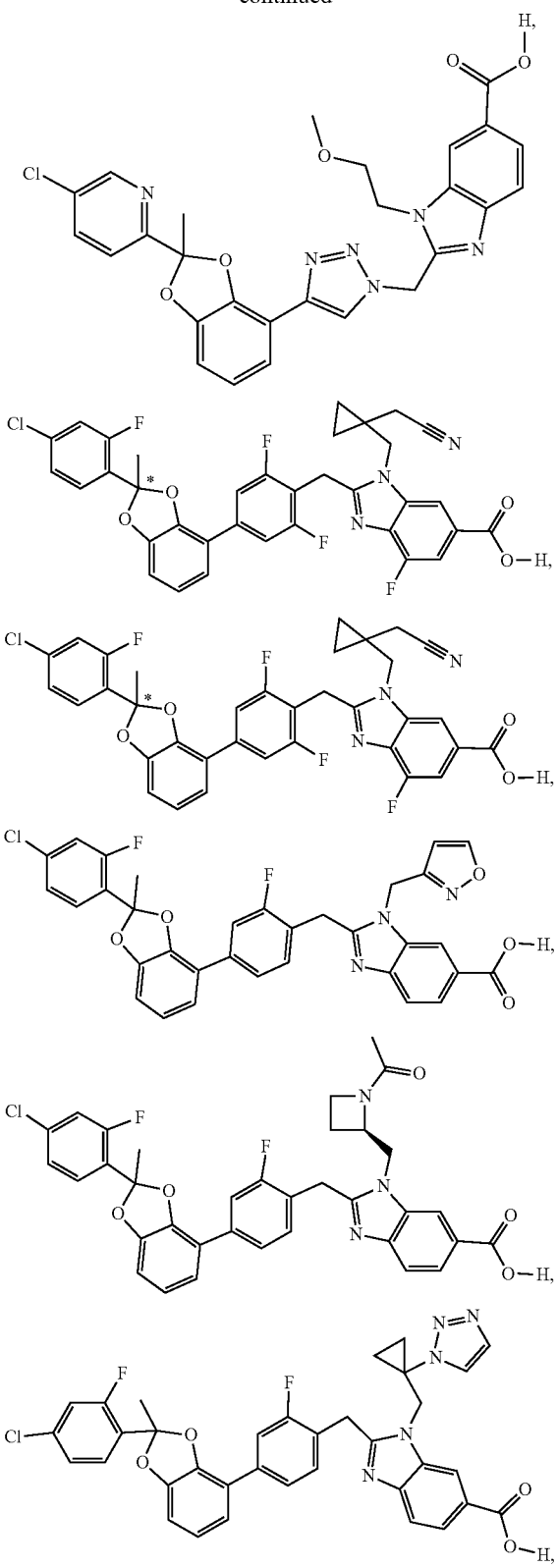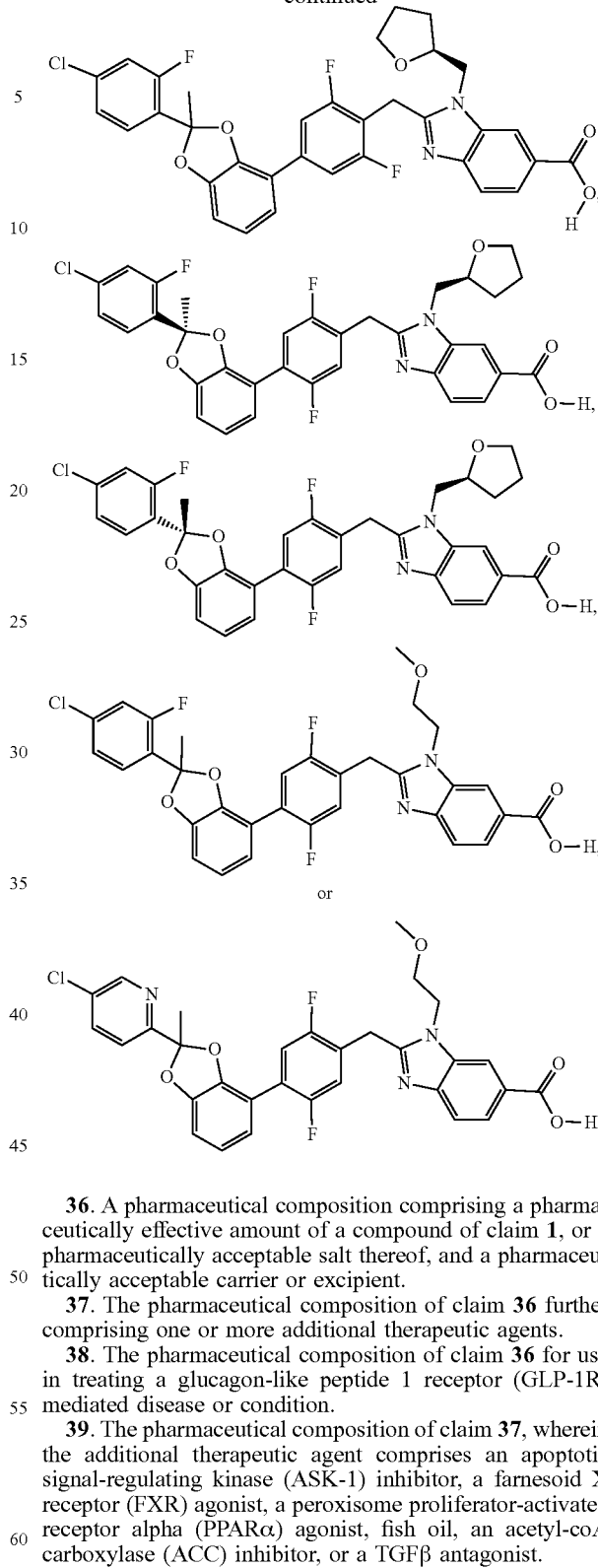

36. A pharmaceutical composition comprising a pharmaceutically effective amount of a compound of claim 1, or a pharmaceutically acceptable salt thereof, and a pharmaceutically acceptable carrier or excipient.

37. The pharmaceutical composition of claim 36 further comprising one or more additional therapeutic agents.

38. The pharmaceutical composition of claim 36 for use in treating a glucagon-like peptide 1 receptor (GLP-1R) mediated disease or condition.

39. The pharmaceutical composition of claim 37, wherein the additional therapeutic agent comprises an apoptotic signal-regulating kinase (ASK-1) inhibitor, a farnesoid X receptor (FXR) agonist, a peroxisome proliferator-activated receptor alpha (PPARα) agonist, fish oil, an acetyl-coA carboxylase (ACC) inhibitor, or a TGFβ antagonist.

* * * * *

UNITED STATES PATENT AND TRADEMARK OFFICE
CERTIFICATE OF CORRECTION

| | | |
|---|---|---|
| PATENT NO. | : 12,121,511 B2 | Page 1 of 1 |
| APPLICATION NO. | : 17/159485 | |
| DATED | : October 22, 2024 | |
| INVENTOR(S) | : Ammann et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 99 days.

Signed and Sealed this
Tenth Day of June, 2025

Coke Morgan Stewart
*Acting Director of the United States Patent and Trademark Office*